(12) United States Patent
Ruckh et al.

(10) Patent No.: US 11,905,377 B2
(45) Date of Patent: Feb. 20, 2024

(54) FACTORS CONTROLLING DRUG RELEASE IN CROSS-LINKED POLY(VALEROLACTONE) BASED MATRICES

(71) Applicant: Pendant Biosciences, Inc., Nashville, TN (US)

(72) Inventors: Timothy Tordella Ruckh, Mountain View, CA (US); Carl Eric Elmquist, Franklin, TN (US); David Michael Stevens, Frederick, MD (US); Frantz Le Dévédec, Toronto (CA); Hilary Boucher, Toronto (CA); Christine Allen, Toronto (CA)

(73) Assignees: Pendant Biosciences, Inc., Nashville, TN (US); The Governing Council of the University of Toronto, Toronto (CA)

( * ) Notice: Subject to any disclaimer, the term of this patent is extended or adjusted under 35 U.S.C. 154(b) by 37 days.

(21) Appl. No.: 16/746,596

(22) Filed: Jan. 17, 2020

(65) Prior Publication Data
US 2020/0407514 A1    Dec. 31, 2020

Related U.S. Application Data

(60) Provisional application No. 62/793,744, filed on Jan. 17, 2019.

(51) Int. Cl.
*C08G 81/02* (2006.01)
*A61K 47/34* (2017.01)
(Continued)

(52) U.S. Cl.
CPC .............. *C08G 81/02* (2013.01); *A61K 31/12* (2013.01); *A61K 31/167* (2013.01);
(Continued)

(58) Field of Classification Search
CPC ....................................................... C08G 81/02
See application file for complete search history.

(56) References Cited

U.S. PATENT DOCUMENTS 10,258,578 B2   4/2019   Le et al.
11,426,356 B2   8/2022   Le Devedec et al.
(Continued)

FOREIGN PATENT DOCUMENTS

WO   WO-2013169938 A2   11/2013
WO   WO-2013169938 A3   12/2013
WO   WO-2016174116 A1   11/2016

OTHER PUBLICATIONS

Le Devedec et al, Factors Controlling Drug Release in Cross-Linked Poly(valerolactone) Based Matrices, Molecular Pharmaceutics, 15(4). (Year: 2018).*
(Continued)

*Primary Examiner* — Carlos A Azpuru
(74) *Attorney, Agent, or Firm* — COOLEY LLP

(57) ABSTRACT

The present disclosure relates to controlling drug release in cross-linked poly(valerolactone) based matrices. In one aspect, the compounds or pharmaceutically acceptable salts thereof include a poly(valerolactone)-co-poly(allylvalerolactone)-co-polyethylene glycol (PEG) copolymer. In some embodiments, at least a portion of allylvalerolactone residues within the copolymer are crosslinked with a crosslinker. In some embodiments, the compound has a polydispersity index of less than or equal to 1.5. In one aspect, a method is described herein, comprising: (a) polymerizing valerolactone residues, allylvalerolactone, and polyethylene glycol residues in the presence of a non-metal catalyst via a ring opening polymerization to produce a poly(valerolactone)-co-poly(allylvalerolactone)-co-polyethylene glycol copolymer; (b) crosslinking the poly(valerolactone)-co-poly(allylvalerolactone)-co-polyethylene glycol copolymer with
(Continued)

a crosslinker; and (c) loading a drug into the crosslinked copolymer. In some embodiments, the compound can comprise amorphous networks. In some embodiments, the compound can include semi-crystalline networks.

10 Claims, 204 Drawing Sheets

(51) Int. Cl.
    *A61K 31/58*     (2006.01)
    *A61K 31/167*     (2006.01)
    *A61K 31/12*     (2006.01)
    *A61K 31/337*     (2006.01)

(52) U.S. Cl.
    CPC ............ *A61K 31/337* (2013.01); *A61K 31/58* (2013.01); *A61K 47/34* (2013.01)

(56) References Cited

U.S. PATENT DOCUMENTS

| | | |
|---|---|---|
| 2005/0020734 A1 | 1/2005 | Asgarzadeh et al. |
| 2006/0239924 A1 | 10/2006 | Bolotin |
| 2008/0145338 A1 | 6/2008 | Anderson et al. |
| 2011/0257343 A1 | 10/2011 | Harth et al. |
| 2013/0142733 A1 | 6/2013 | Harth et al. |
| 2019/0262274 A1 | 8/2019 | Le Devedec et al. |

OTHER PUBLICATIONS

Athanasiou, et al. "Sterilization, toxicity, biocompatibility and clinical applications of polylactic acid/ polyglycolic acid copolymers." Biomaterials 1996, 17, 2, 93-102.
Attenello, et al. "Use of Gliadel (BCNU) Wafer in the Surgical Treatment of Malignant Glioma: A 10-Year Institutional Experience." Annals of Surgical Oncology 2008, 15, (10), 2887.
Aubin, M. and Prud'homme, R. E. "Preparation and properties of poly(valerolactone)." Polymer 1981, 22, (9), 1223-1226.
Baek, et al., "Evaluation of the Extraction Method for the Cytotoxicity Testing of Latex Gloves." Yonsei Medical Journal 2005, 46, (4), 579-583.
Barra, et al. "The Expanded Hansen Approach to Solubility Parameters. Paracetamol and Citric Acid in Individual Solvents." Journal of Pharmacy and Pharmacology 1997;49:644-51.
Boire, et al. "Pendant allyl crosslinking as a tunable shape memory actuator for vascular applications." Acta Biomaterialia 2015, 24, 53-63.
Citrin, et al. "A comparison of Zoladex® and DES in the treatment of advanced prostate cancer: Results of a randomized, multicenter trial." The Prostate 1991, 18, 2, 139-146.
Cheng, et al. "Characterization and in vitro release of praziquantel from poly(ε-caprolactone) implants." International Journal of Pharmaceutics 2009, 377, (1-2), 112 119.
Coombes, et al. "Precipitation casting of polycaprolactone for applications in tissue engineering and drag delivery." Biomaterials 2004, 25, 2, 315-325.
Crotts, G. and Park, T. G. "Protein delivery from poly(lactic-co-glycolic acid) biodegradable microspheres: Release kinetics and stability issues." Journal of Microencapsulation 1998, 15, (6), 699-713.
D'Souza, et al. "Methods to Assess in vitro Drag Release from Injectable Polymeric Particulate Systems." Pharmaceutical Research 2006, 23, 3, 460-474.
Da Silva-Junior, et al. "Thermal behavior arid stability of biodegradable spray-dried microparticles containing triamcinolone." International journal of Pharmaceutics 2009, 368, 1, 45-55.
Darcos, et al. "Cationic polyesters bearing pendent amino groups prepared by thiol-ene chemistry." Polymer Chemistry 2012, 3, 2, 362-368.
Dordunoo, et al. "Release of taxol from poly(ε-caprolactone) pastes: effect of water-soluble additives." Journal of Controlled Release 1997, 44, 1, 87-94.
Doty, et al. "Validation of a cage implant system for assessing in vivo performance of long-acting release microspheres." Biomaterials 2016, 109, 88-96.
Du, et al. "Functionalized Pluronic-b-poly(ε-caprolactone) based nanocarriers of paclitaxel: solubilization, antiproliferative efficacy and in vivo pharmaceutic kinetics." Journal of Materials Chemistry B 2015;3:3685-94.
Egawa, et al. "Solubility Parameter and Dissolution Behavior of Cefalexin Powders with Different Crystallinity." Chemical & Pharmaceutical Bulletin 1992, 40, 3, 819-820.
Elzein, et al., "FTIR study of polycaprolactone chain organization at interfaces." Journal of Colloid and Interface Science 2004, 273, 2, 381-387.
Faisant, et al. "PLGA-based microparticles: elucidation of mechanisms and a new, simple mathematical model quantifying drag release." European Journal of Pharmaceutical Sciences 2002, 15, (4), 355-366.
FDA. Guidance for Industry: Dissolution Testing of Immediate Release Solid Oral Dosage Forms, Office of Training and Communications, Rockville, MD, 1997, pp. A1-A2. 1997.
Fetters, et al. "Connection between Polymer Molecular Weight, Density, Chain Dimensions, and Melt Viscoelastic Properties." Macromolecules 1994, 27, (17), 4639-4647.
Fialho, et al. "Dexamethasone-loaded poly(ε-caprolactone) intravitreal implants: A pilot study." European Journal of Pharmaceutics and Biopharmaceutics 2008, 68, 3, 637-646.
Fialho, et al. (2007). "Biodegradable implants for ocular delivery of anti-inflammatory drag." Journal of Drag Delivery Science and Technology 171: 93- 97.
Folkman and Long. "The use of silicone rubber as a carrier for prolonged drug therapy." Journal of Surgical Research 1964, 4, 3, 139-142.
Greenhalgh, et al. "Solubility parameters as predictors of miscibility in solid dispersions." Journal of Pharmaceutical Sciences 1999, 88, (11), 1182-1190.
Guse, et al. J. "Drug release from lipid-based implants: Elucidation of the underlying mass transport mechanisms." International Journal of Pharmaceutics 2006, 314, 2, 137-144.
Hancock, et al. "The use of solubility parameters in pharmaceutical dosage form design." International journal of Pharmaceutics 1997, 148, 1, 1-21.
Heya, et al. "Factors influencing the profiles of TRH release from copoly(d,l-lactic/glycolic acid) microspheres." International Journal of Pharmaceutics 1991, 72, 3, 199-205.
Higuchi, T. "Rate of Release of Medicaments from Ointment Bases Containing Drugs in Suspension," Journal of Pharmaceutical Sciences 1961, 50, (10), 874-875.
Huang, et al. "Study of crosslinking of polyphosphazene with allyl pendant groups initiated by benzoyl peroxide." Journal of Applied Polymer Science 2009, 113, (4), 2353-2360.
Jain, R. A. "The manufacturing techniques of various dmg loaded biodegradable poly(lactide-co-glycolide) (PLGA) devices." Biomaterials 2000, 21, (23), 2475-2490.
Jenkins, M. J. and Harrison, K. L. "The effect of molecular weight on the crystallization kinetics of polycaprolactone." Polymers for Advanced Technologies 2006, 17, (6), 474-478.
Jeong, et al. "Effects of crystalline microstructure on drug release behavior of poly(ε-caprolactone) microspheres." Journal of Controlled Release 2003, 92, 3, 249-258.
Jones, et al. and Buckton, G. "Comparison of the cohesion-adhesion balance approach to colloidal probe atomic force microscopy and the measurement of Hansen partial solubility parameters by inverse gas chromatography for the prediction of dry powder inhalation performance." International Journal of Pharmaceutics 2016;509:419-30.
Kazumichi, et al. "A new biodegradable implant consisting of waxy-type poly(ε caprolactone-co-δ-valerolactone) and estramustine." International Journal of Pharmaceutics 1991, 68, 1, 87-95.
Keroack, et al. "Molecular orientation in crystalline miscible blends." Polymer 1999, 40, 1, 243-251.

(56) References Cited

OTHER PUBLICATIONS

Khor, et al. "Poly(ε-caprolactone) films as a potential substrate for tissue engineering an epidermal equivalent." Materials Science and Engineering: C 2002, 20, (1-2), 71-75.
Kleiner, et al. "Evolution of implantable and insertable drug delivery systems." Journal of Controlled Release 2014, 181, 1-10.
Klose, et al. "How porosity and size affect the drag release mechanisms from PLGA-based microparticles." International Journal of Pharmaceutics 2006, 314, 2, 198-206.
Kohane, D. S. "Microparticles and nanoparticles for drug delivery." Biotechnology and Bioengineering 2007, 96, 2, 203-209.
Korsmeyer, et al. "Mechanisms of solute release from porous hydrophilic polymers." International Journal of Pharmaceutics 1983, 15, 1, 25-35.
Kulkarni, et al. "Polylactic acid for surgical implants." Archives of Surgery 1966, 93, (5), 839-843.
Lee, et al. "Methoxy Poly(ethylene glycol)-block-Poly(δ valerolactone) Copolymer Micelles for Formulation of Hydrophobic Drugs." Biomacromolecules 2005, 6, (6), 3119-3128.
Liu, et al. "Polymer-drag compatibility: A guide to the development of delivery systems for the anticancer agent, ellipticine." Journal of Pharmaceutical Sciences 2004, 93, 1, 132-143.
Lofgren, et al. "Recent Advances in Ring-Opening Polymerization of Lactones and Related Compounds." Journal of Macromolecular Science, Part C 1995, 35, 3, 379-418.
Lou, et al.. "Living Cationic Polymerization of δ Valerolactone and Synthesis of High Molecular Weight Homopolymer and Asymmetric Telechelic and Block Copolymer." Macromolecules 2002, 35, (4), 1190-1195.
Lyu, S. and Untereker, D. "Degradability of Polymers for Implantable Biomedical Devices." International Journal of Molecular Sciences 2009, 10, (9), 4033-4065.
Ma, et al. "A biodegradable levonorgestrel-releasing implant made of PCL/F68 compound as tested in rats and dogs." Contraception 2006, 74, 2, 141-147.
Marsac, et al. "Theoretical and Practical Approaches for Prediction of Drug-Polymer Miscibility and Solubility." Pharmaceutical Research 2006, 23, (10), 2417.
Mecerreyes, et al. "Ring-opening polymerization of 6-hydroxynon-8-enoic acid lactone: Novel biodegradable copolymers containing allyl pendent groups." Journal of Polymer Science Part A: Polymer Chemistry 2000, 38, (5), 870-875.
Miyajima, et al. "Effect of polymer crystallinity on papaverine release from poly (1-lactic acid) matrix." Journal of Controlled Release 1997, 49, (2-3), 207-215.
Murphy, et al. "A Comparison of the use of FTIR spectroscopy with DSC in the characterisation of melting and crystallisation in polycaprolactone." Journal of Thermal Analysis and Calorimetry 2012, 107, 2, 669-674.
Nair, et al. "Influence of various drugs on the glass transition temperature of poly (vinylpyrrolidone): a thermodynamic and spectroscopic investigation." International Journal of Pharmaceutics 2001, 225, 1, 83-96.
Nishi, et al. "In vitro evaluation of diepoxy compounds used for biomaterial modification." Journal of Biomedical Materials Research 1995, 29, 829-834.
Nsereko, et al. "Localized delivery of paclitaxel in solid tumors from biodegradable chitin microparticle formulations." Biomaterials 2002, 23, (13), 2723-2731.
OECD. Guidelines for Testing of Chemicals. Section 1, Physical Chemical properties. 1995, 107.
Omelczuk, M.O. and McGinity, J. W. "The influence of Polymer Glass Transition Temperature and Molecular Weight on Drag Release from Tablets Containing Poly(PL lactic Acid)." Pharmaceutical Research 1992, 9, 1, 26-32.
Parrish, et al. "Functional polyesters prepared by polymerization of α-allyl(valerolactone) and its copolymerization with ε-caprolactone and δ valerolactone." Journal of Polymer Science Part A: Polymer Chemistiy 2002, 40, (12), 1983-1990.

Peeling, W. B. "Phase III studies to compare goserelin (zoladex) with orchiectomy and with diethylstilbestrol in treatment of prostatic carcinoma." Urology 1989, 33, (5, Supplement), 45-52.
Peppas, N. A. and Sahlin, J. J. "A simple equation for the description of solute release. III. Coupling of diffusion and relaxation," International Journal of Pharmaceutics 1989, 57, 2, 169-172.
Pinto, et al. "Controlled release of triamcinolone acetonide from polyurethane implantable devices: application for inhibition of inflammatory-angiogenesis." Journal of Materials Science: Materials in Medicine 2012, 23, (6), 1431-1445.
Ramchandani, M and Robinson, D. "In vitro and in vivo release of ciprofloxacin from PLGA 50:50 implants." Journal of Controlled Release 1998, 54, 2, 167-175.
Ritger, P. L. and Peppas, N. A. "A simple equation for description of solute release 1. Fickian and non-fickian release from non-swellable devices in the form of slabs, spheres, cylinders or discs." Journal of Controlled Release 1987, 5, 1, 23-36.
Salaun. IV. "Curcumin loaded nanocapsules: formulation and Influence of the nanoencapsulation processes variables on the physicochemical characteristics of the particles." Int J Chem Reactor Eng 2009;7:A55.
Samaha, M. W. and Naggar, V. F. "Micellar properties of non-ionic surfactants in relation to their solubility parameters." International Journal of Pharmaceutics 1988, 42, 1, 1-9.
Serrano, et al. "In vitro biocompatibility assessment of poly(epsilon-caprolactone) films using L929 mouse fibroblasts." Biomaterials 2004, 25 (25), 5603-11.
Siepmann, J. and Siepmann, F. "Mathematical modeling of drug delivery." International Journal of Pharmaceutics 2008, 364, 2, 328-343.
Silva, et al. "Implants as drug delivery devices for the treatment of eye diseases." Brazilian Journal of Pharmaceutical Sciences 2010, 46, 585-595.
Silvers, et al. "Functional aliphatic polyesters and nanoparticles prepared by organocatalysis and orthogonal grafting chemistry." Journal of Polymer Science Part A: Polymer Chemistry 2012, 50, (17), 3517-3529.
Suh, et al. "Regulation of smooth muscle cell proliferation using paclitaxel-loaded poly(ethylene oxide)-poly(lactide/glycolide) nanospheres." Journal of Biomedical Materials Research 1998, 42, 2, 331-338.
Sun, et al. "The in vivo degradation, absorption and excretion of PCL-based implant." Biomaterials 2006, 27, (9), 1735-1740.
Sung, et al. "The effect of scaffold degradation rate on three-dimensional cell growth and angiogenesis." Biomaterials 2004, 25, (26), 5735-5742.
Toncheva, et al. "Synthesis and environmental degradation of polyesters based on poly (ε-caprolactone)." Journal of environmental polymer degradation 1996, 4, 2, 71-83.
Van Krevelen, D. W. and Te Nijenhuis, K., Chapter 7—"Cohesive Properties and Solubility." In Properties of Polymers (Fourth Edition), Elsevier: Amsterdam, 2009; pp. 189-227.
Varshochian, et al. (2013). "The protective effect of albumin on bevacizumab activity and stability in PLGA nanoparticles intended for retinal and choroidal neovascularization treatments." European Journal of Pharmaceutical Sciences 503: 341-352.
Varshochian, et al. (2015). "Albuminated PLGA nanoparticles containing bevacizumab intended for ocular neovascularization treatment." Journal of Biomedical Materials Research Part A 103(10): 3148-3156.
Wang, et al. "Drug Delivery Implants in the Treatment of Vitreous Inflammation." Mediators of Inflammation 2013, 2013, 8.
Woodruff, M. A. and Hutmacher, D. W. "The return of a forgotten polymer—Polycaprolactonc in the 21st century." Progress in Polymer Science 2010, 35, (10), 1217-1256.
Yandrapu, et al. (2013). "Nanoparticles in Porous Microparticles Prepared by Supercritical Infusion and Pressure Quench Technology for Sustained Delivery of Bevacizumab." Molecular Pharmaceutics 10(12): 4676-4686.
Yang, et al. "Applicability of a Newly Developed Bioassay for Determining Bioactivity of Anti-Inflammatory Compounds in Release

(56) References Cited

OTHER PUBLICATIONS

Studies—Celecoxib and Triamcinolone Acetonide Released from Novel PLGA-Based Microspheres." Pharmaceutical Research 2015, 32, 2, 680-690.

Yeo, et al. "Fabrication, characterisation and biological activity of phlorotannin-conjugated PCL/βTCP composite scaffolds for bone tissue regeneration." Journal of Materials Chemistry 2012, 22, (8), 3568-3577.

Yerragunta, et al. "Development of a novel 3-month drag releasing risperidone microspheres." Journal of Pharmacy And Bioallied Sciences 2015, 7, 1, 37-44.

Zange, R. and Kissel, T. "Comparative in vitro biocompatibility testing of polycyanoacrylates and poly(d,l-lactide-co-glycolide) using different mouse fibroblast (L929) biocompatibility test models." European Journal of Pharmaceutics and Biopharmaceutics 1997, 44, 2, 149-157.

Zeng, et al. "Synthesis and Characterization of Six-Arm Star Poly(δ-valerolactone)-block-Methoxy Poly(ethylene glycol) Copolymers." Biomacromolecules 2005, 6, (4), 2140-2149.

Zeng, et al. "Epidermal Growth Factor-Conjugated Poly(ethylene glycol)-block- Poly(δ-valerolactone) Copolymer Micelles for Targeted Delivery of Chemotherapeutics." Bioconjugate Chemistry 2006, 17, 2, 399-409.

Zhang, et al. "DD Solver: An Add-In Program for Modeling and Comparison of Drag Dissolution Profiles." The AAPS Journal 2010, 12, 3, 263-271.

Zoladex. <https://http://www.zoladex.com/>. Zoladex 10.8 and 3.6 mg implants.

Australian Office Action for Application No. AU2021202965 dated Jul. 6, 2022, 3 pages.

Chinese Office Action for Application No. CN20168072252 dated Dec. 30, 2021, 16 pages.

Extended European Search Report dated Apr. 29, 2019, for EP Application No. 16 854 494.8, filed on Oct. 7, 2016, 10 pages.

Extended European Search Report dated May 13, 2022, for EP Application No. 21211254, 5 pages.

International Search Report and Written Opinion dated Feb. 27, 2017, for International Application No. PCT/US2016/056135, filed on Oct. 7, 2016, 21 pages.

Jaszcz, K. "Photocrosslinked poly(ester-anhydride) microspheres with macroporous structure," Polym. Adv. Technol., 2013, 24:873-880.

Lowe, A.B. "Thiol-ene "click" reactions and recent applications in polymer and materials synthesis: a first update", Polymer Chemistry, 2014, 5:4820-4870.

Notice of Acceptance for Australian Patent Application No. 2016335866, dated Jan. 19, 2021, 3 pages.

Van Der Ende, A.E. et al., "Click" Reactions: Novel Chemistries for Forming Well-defined Polyester Nanoparticles, Macromolecules, 2010, 43:5665-5671.

Wu, C., et al., "Pure paclitaxel nanoparticles: preparation, characterization, and antitumor effect for human liver cancer SMMC-7721 cells," Internal Journal of Nanomedicine, 2018, 13:6189-6198.

Zou, et al. "Clicking well-defined biodegradable nanoparticles and nanocapsules by UV-induced thiol-ene cross-linking in transparent miniemulsions." Adv Mater. 2011, 23(37):4274-7.

Tasdelen, M.A. et al. "Externally stimulated click reactions for macromolecular syntheses," Progress in Polymer Science, Jan. 2016, 52:19-78.

* cited by examiner

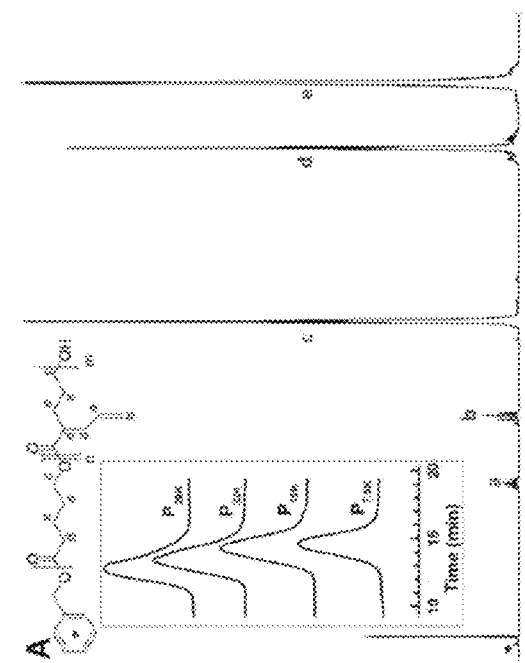
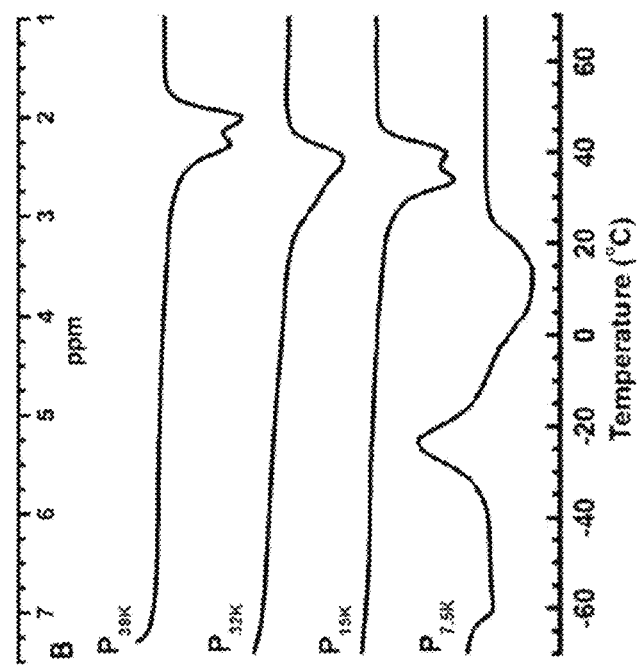
FIGURE 2A
FIGURE 2B

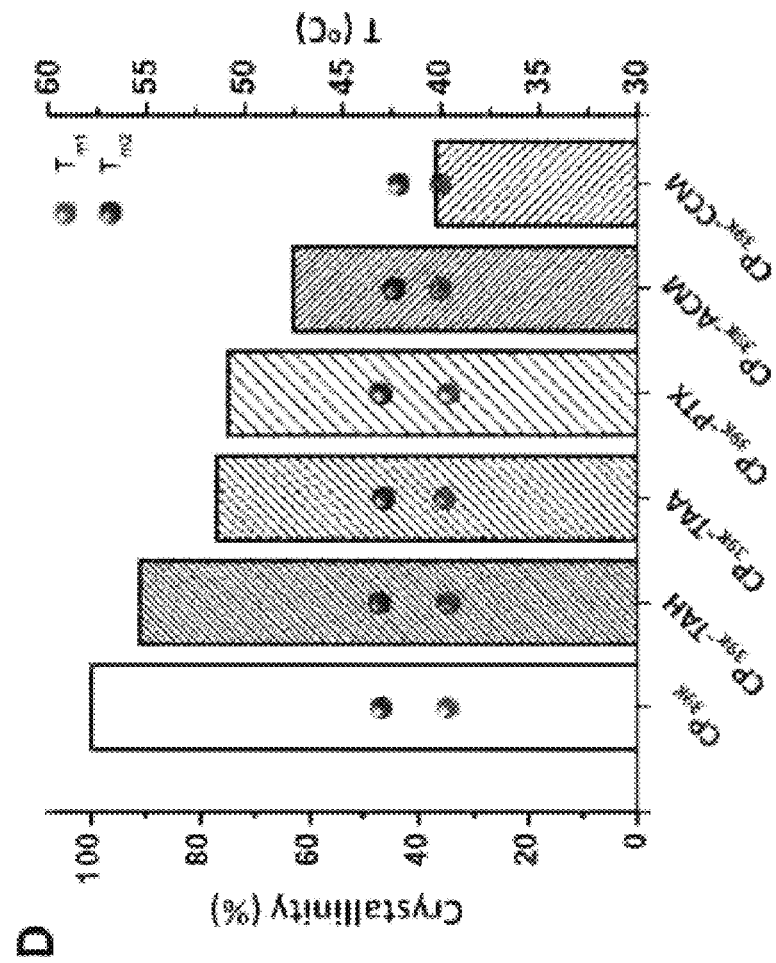
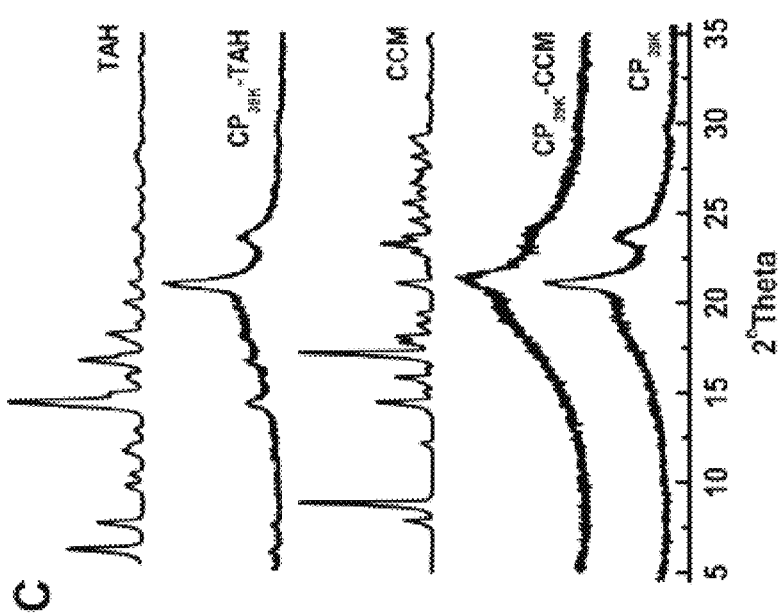
FIGURE 7D
FIGURE 7C

| | First Order $\log C = \log C_0 - kt/2.303$ | Higuchi $M_t/M_\infty = k_H t^{1/2}$ | Korsmeyer-Peppas $M_t/M_\infty = k_{KP} t^n$ | | Peppas-Sahlin $M_t/M_\infty = k_1 t^m + k_2 t^{2m}$ | |
|---|---|---|---|---|---|---|
| | $R^2$ | $R^2$ | n | $R^2$ | m | $R^2$ |
| $CP_{10x}$-ACM | 0.9431 | 0.3685 | | 0.8675 | | 0.9886 |
| $CP_{10x}$-PTX | 0.9865 | 0.9556 | | 0.9818 | | 0.9993 |
| $CP_{10x}$-CCM | 0.9627 | 0.9077 | $0.78 < n < 0.80$ | 0.9616 | $0.78 < m < 0.80$ | 0.9994 |
| $CP_{1x}$-TAA | 0.8903 | 0.9337 | | 0.9342 | | 0.9990 |
| $CP_{1x}$-TAH | 0.9344 | 0.9975 | | 0.9983 | | 0.9983 |

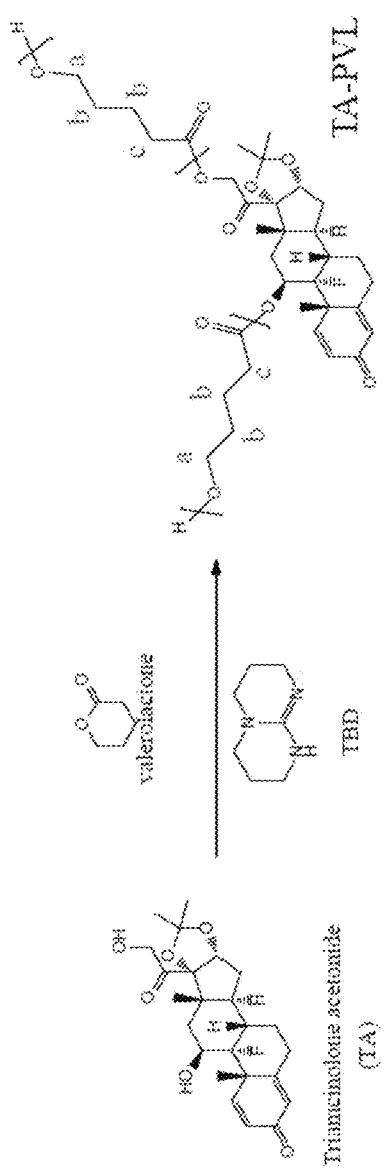 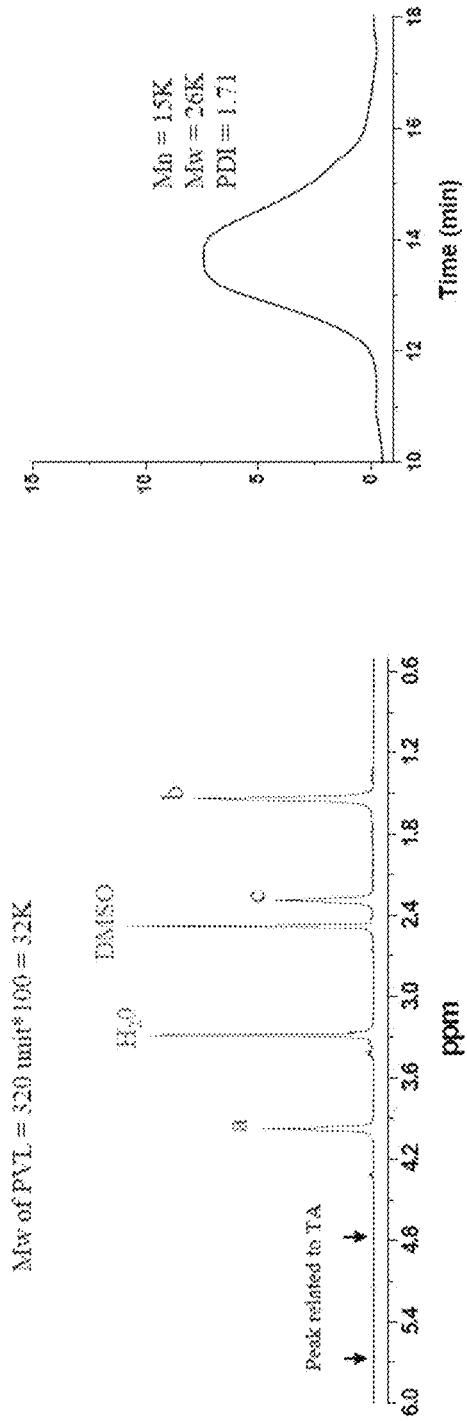
FIGURE 19

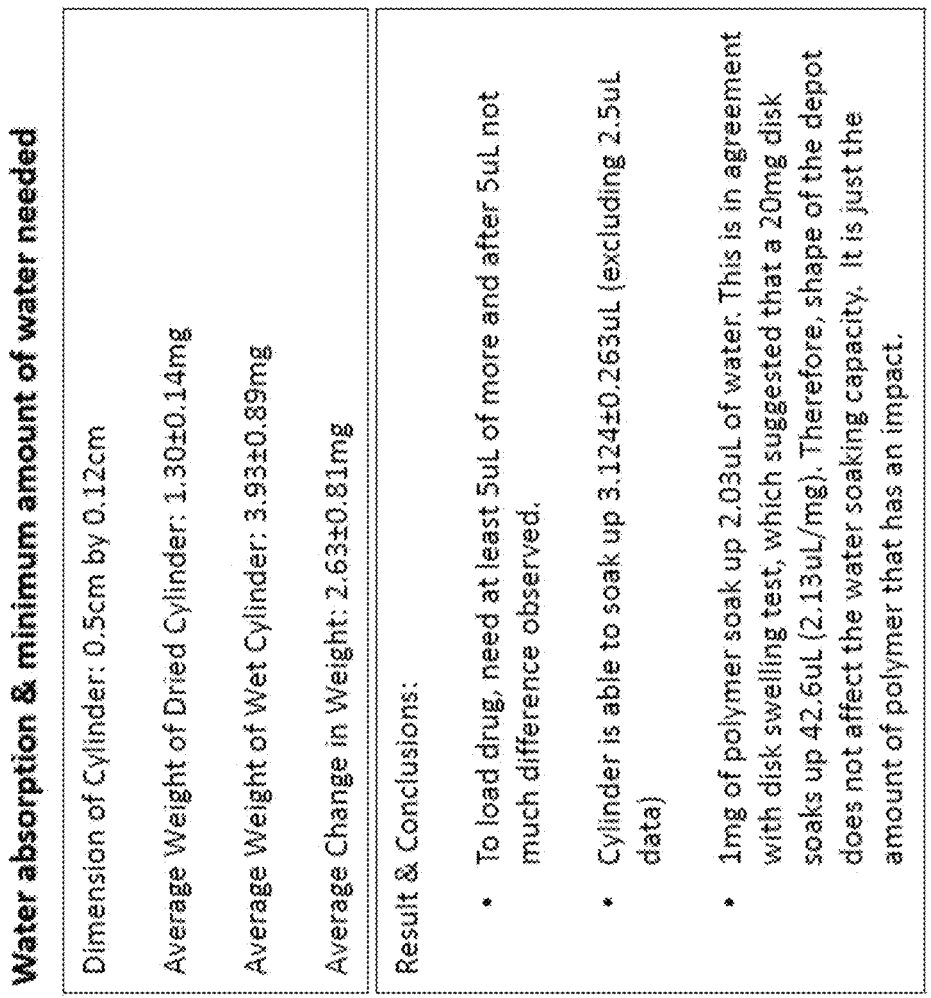
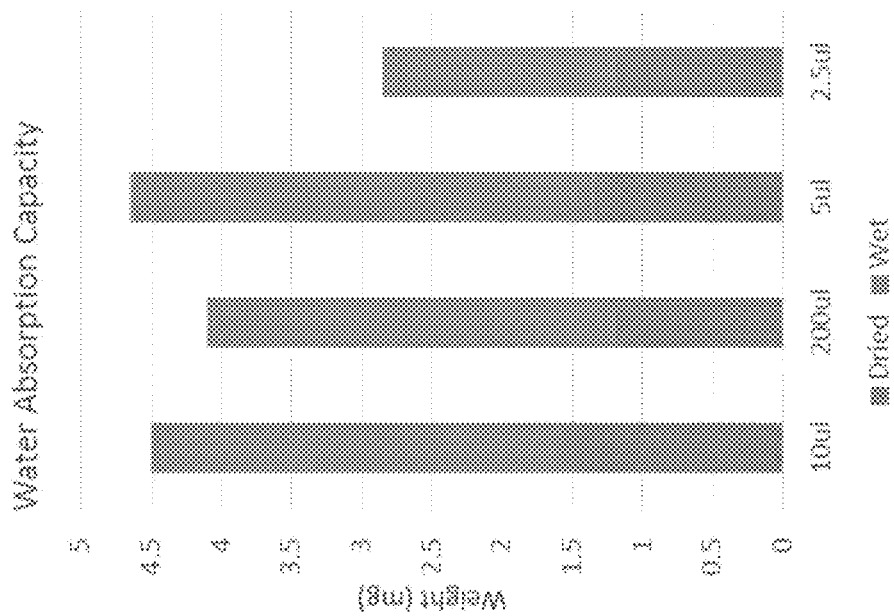
FIGURE 47

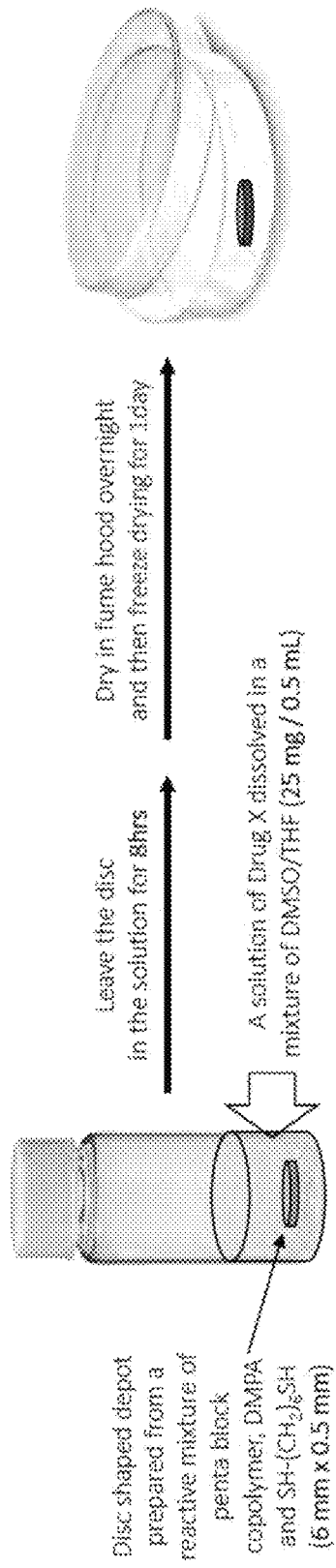

➤ Drug X loaded disc shaped depot

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP1-Drug X-1 | 22.9 | 25.0 | 27.1 | 4.2 | 15.5 | 16.8 | 1/0.18 |
| SJP1-Drug X-2 | 24.3 | 25.0 | 29.2 | 4.9 | 16.8 | 19.6 | 1/0.2 |
| | Disc (mg) | Drug (mg) | Disc Loaded (mg) | Drug content (mg) | DLC (%) | DLE (%) | Depot/Drug (w/w) |
| SJP2-Drug X-1 | 21.5 | 25.0 | 30.0 | 8.5 | 28.3 | 34.0 | 1/0.4 |
| SJP2-Drug X-2 | 24.1 | 25.0 | 32.6 | 8.5 | 26.1 | 34.0 | 1/0.35 |
| | Disc (mg) | Drug (mg) | Disc Loaded (mg) | Drug content (mg) | DLC (%) | DLE (%) | Depot/Drug (w/w) |
| SJP3-Drug X-1 | 22.0 | 25.0 | 34.3 | 12.3 | 35.9 | 49.2 | 1/0.56 |
| SJP3-Drug X-2 | 25.4 | 25.0 | 37.9 | 12.5 | 33.0 | 50.0 | 1/0.49 |

❖ In addition to freeze drying for 1 day, I have done freeze drying once again to confirm removal of DMSO from depot. However, there is no weight change meaning that residue DMSO is completely removed by freeze drying for 1 day.

FIGURE 52

Drug X loaded dis shaped depot

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP1-Drug X-1 | 22.9 | 25.0 | 27.1 | 4.2 | 15.5 | 16.8 | 1/0.18 |
| SJP1-Drug X-2 | 24.3 | 25.0 | 29.2 | 4.9 | 16.8 | 19.6 | 1/0.2 |
| SJP2-Drug X-1 | 21.5 | 25.0 | 30.0 | 8.5 | 28.3 | 34.0 | 1/0.4 |
| SJP2-Drug X-2 | 24.1 | 25.0 | 32.6 | 8.5 | 26.1 | 34.0 | 1/0.35 |
| SJP3-Drug X-1 | 22.0 | 25.0 | 34.3 | 12.3 | 35.9 | 49.2 | 1/0.56 |
| SJP3-Drug X-2 | 25.4 | 25.0 | 37.9 | 12.5 | 33.0 | 50.0 | 1/0.49 |
| SJP7-Drug X-1 | 26.1 | 25.0 | 30.1 | 4.0 | 13.3 | 16.0 | 1/0.56 |
| SJP7-Drug X-2 | 25.2 | 25.0 | 29.8 | 3.6 | 12.5 | 14.4 | 1/0.49 |

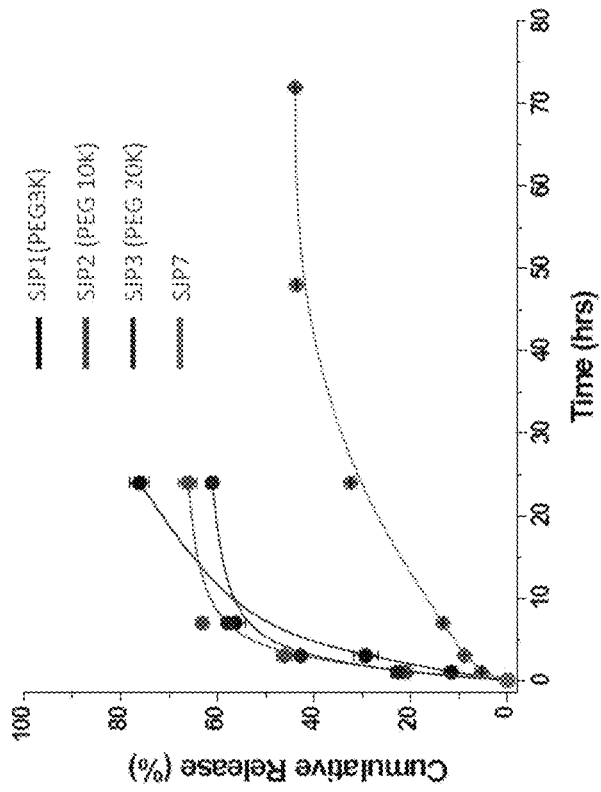
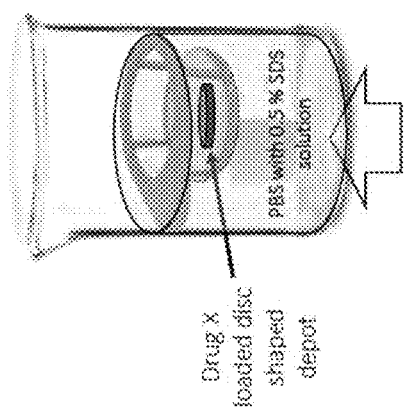
Drug X release profile.
FIGURE 54

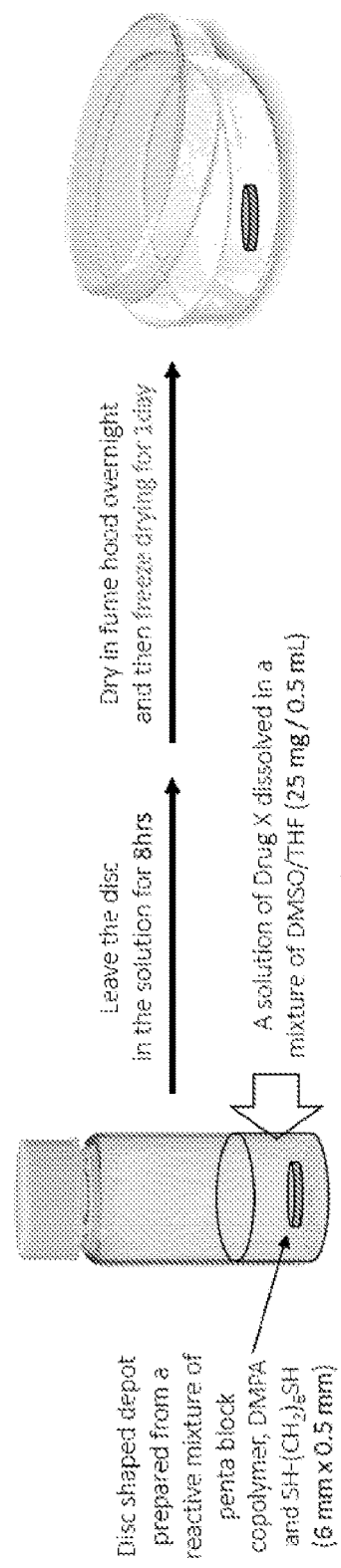

Drug X loaded the depot

| | Disc (mg) | Drug (mg) | Disc loaded (mg) | Drug content (mg) | DLC (%) | DLE (%) | Depot/Drug (w/w) |
|---|---|---|---|---|---|---|---|
| SJP1-Drug X-1 | 22.9 | 25.0 | 27.1 | 4.2 | 15.5 | 16.8 | 1/0.18 |
| SJP1-Drug X-2 | 24.3 | 25.0 | 29.2 | 4.9 | 16.8 | 19.6 | 1/0.2 |
| SJP2-Drug X-1 | 21.5 | 25.0 | 30.0 | 8.5 | 28.3 | 34.0 | 1/0.4 |
| SJP2-Drug X-2 | 24.1 | 25.0 | 32.6 | 8.5 | 26.1 | 34.0 | 1/0.35 |
| SJP3-Drug X-1 | 22.0 | 25.0 | 34.3 | 12.3 | 35.9 | 49.2 | 1/0.56 |
| SJP3-Drug X-2 | 25.4 | 25.0 | 37.9 | 12.5 | 33.0 | 50.0 | 1/0.49 |
| SJP7-Drug X-1 | 26.1 | 25.0 | 30.1 | 4.0 | 13.3 | 16.0 | 1/0.15 |
| SJP7-Drug X-2 | 25.2 | 25.0 | 28.8 | 3.6 | 12.5 | 14.4 | 1/0.14 |

❖ In addition to freeze drying for 1day, I have done freeze drying once again to confirm removal of DMSO from depot. However, there is no weight change meaning that residue DMSO is completely removed by freeze drying for 1 day.

FIGURE 56

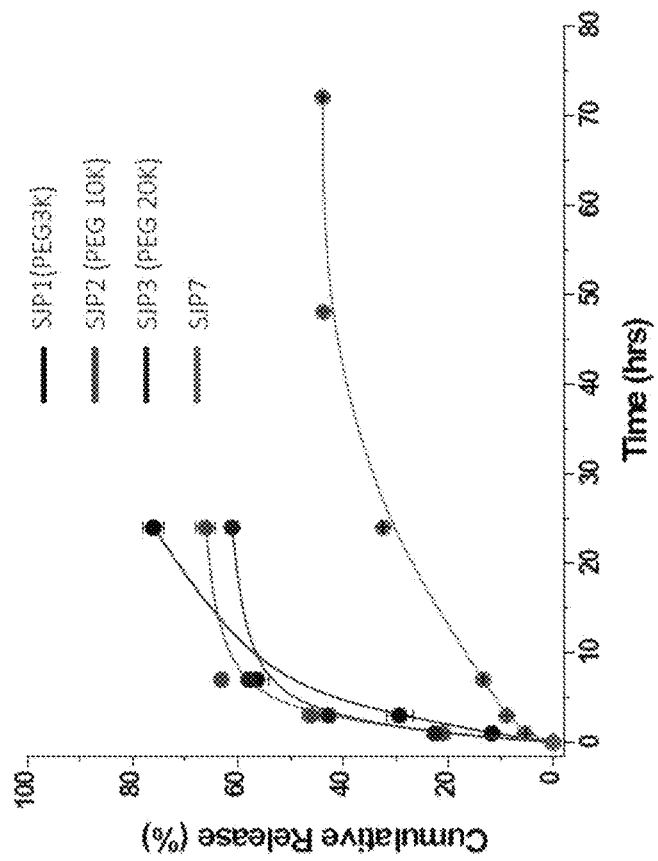
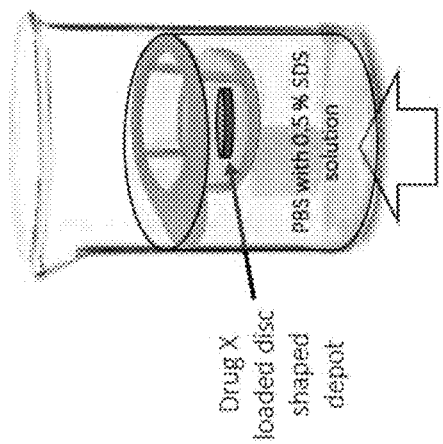
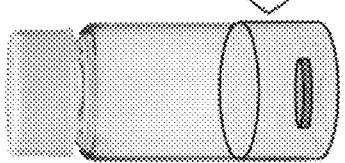
FIGURE 57

➢ Drug X freebase loaded disc shaped depot

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP1-Drug X-1 | 20.40 | 25.00 | 22.68 | 2.28 | 10.05 | 9.12 | 1/0.11 |
| SJP1-Drug X-2 | 18.68 | 25.00 | 20.07 | 1.39 | 6.93 | 5.56 | 1/0.07 |
| SJP2-Drug X-1 | 20.76 | 25.00 | 25.85 | 5.09 | 19.69 | 20.36 | 1/0.25 |
| SJP2-Drug X-2 | 19.80 | 25.00 | 24.79 | 4.99 | 20.13 | 19.96 | 1/0.25 |
| SJP3-Drug X-1 | 21.29 | 25.00 | 30.23 | 8.94 | 29.57 | 35.76 | 1/0.42 |
| SJP3-Drug X-2 | 19.45 | 25.00 | 27.44 | 7.99 | 29.12 | 31.96 | 1/0.41 |
| SJP7-Drug X-1 | 25.66 | 25.00 | 30.53 | 4.87 | 15.95 | 19.48 | 1/0.19 |
| SJP7-Drug X-2 | 26.96 | 25.00 | 31.08 | 4.12 | 13.26 | 16.48 | 1/0.15 |

▶ Drug X freebase loading

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP1-Drug X-1 | 20.40 | 25.00 | 23.52 | 3.12 | 13.27 | 12.48 | 1/0.15 |
| SJP1-Drug X-2 | 18.68 | 25.00 | 21.02 | 2.34 | 11.13 | 9.36 | 1/0.13 |
| SJP2-Drug X-1 | 20.76 | 25.00 | 25.12 | 4.36 | 17.36 | 17.44 | 1/0.21 |
| SJP2-Drug X-2 | 19.80 | 25.00 | 24.04 | 4.24 | 17.64 | 16.96 | 1/0.21 |
| SJP3-Drug X-1 | 21.29 | 25.00 | 29.13 | 7.84 | 26.91 | 31.36 | 1/0.37 |
| SJP3-Drug X-2 | 19.45 | 25.00 | 26.40 | 6.95 | 26.33 | 27.80 | 1/0.36 |
| SJP7-Drug X-1 | 25.66 | 25.00 | 29.69 | 4.03 | 13.57 | 16.12 | 1/0.16 |
| SJP7-Drug X-2 | 26.96 | 25.00 | 30.25 | 3.29 | 10.88 | 13.16 | 1/0.12 |

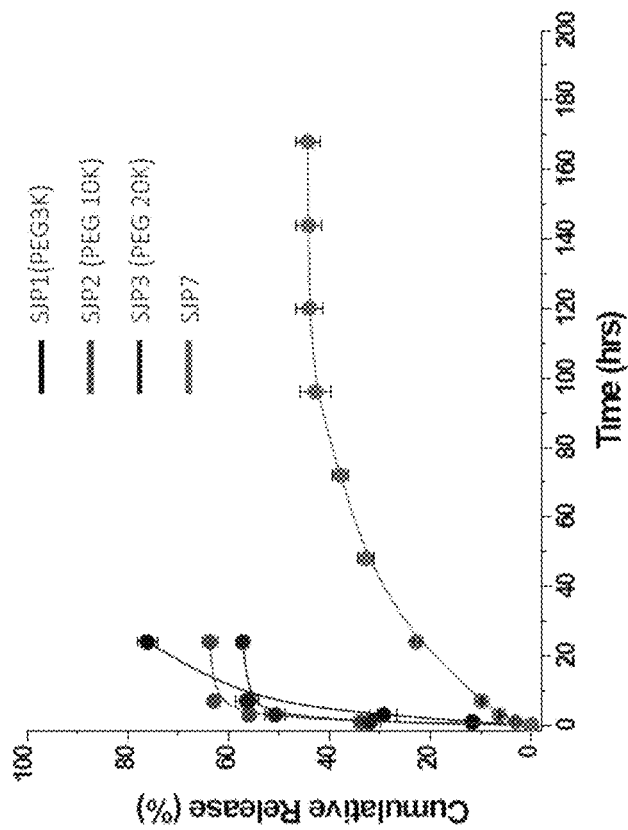
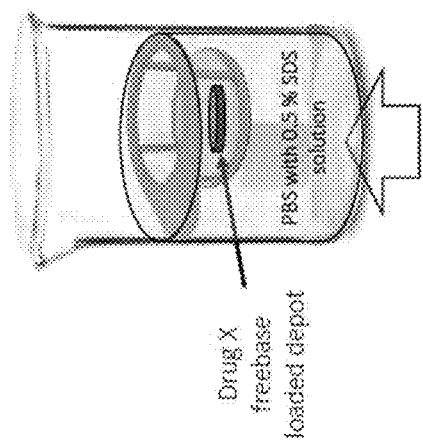
FIGURE 60

| X-linker | | Disc (mg) | Drug (mg) | Disc Loaded (mg) | Drug content (mg) | DLC (%) | DLE (%) | Depot/Drug (w/w) |
|---|---|---|---|---|---|---|---|---|
| SH-(CH₂)₆-SH | SJP3-1-rt | 21.29 | 25.00 | 29.13 | 7.84 | 26.91 | 31.36 | 1/0.37 |
| | SJP3-2-rt | 19.45 | 25.00 | 26.40 | 6.95 | 26.33 | 27.80 | 1/0.36 |
| | SJP3-1-rt | 27.01 | 50.00 | 41.80 | 14.79 | 35.38 | 29.58 | 1/0.55 |
| | SJP3-2-rt | 27.39 | 50.00 | 42.37 | 14.98 | 35.36 | 29.96 | 1/0.55 |
| | SJP3-1-37.5°C | 27.13 | 50.00 | 48.79 | 21.66 | 44.39 | 43.32 | 1/0.79 |
| | SJP3-2-37.5°C | 26.04 | 50.00 | 44.53 | 18.49 | 41.52 | 36.98 | 1/0.71 |
| SH-(OCH₂)₅-SH | SJP3-1-rt | 26.47 | 50.00 | 49.42 | 22.95 | 46.44 | 45.90 | 1/0.87 |
| | SJP3-2-rt | 26.46 | 50.00 | 49.68 | 23.22 | 46.74 | 46.44 | 1/0.88 |
| | SJP3-1-37.5°C | 26.73 | 50.00 | 51.96 | 25.23 | 48.56 | 50.46 | 1/0.94 |
| | SJP3-2-37.5°C | 27.33 | 50.00 | 55.76 | 28.43 | 50.99 | 56.86 | 1/1.04 |

| Entry No | Polymer structure | X-linker | 1H-NMR | | | GPC | |
|---|---|---|---|---|---|---|---|
| | | | $M_n$ | DP (PEG/PVL/PAVL) | PAVL (%) | $M_n$ | PDI |
| SJP3 | PAVL-b-PVL-b-20KPEG-b-PVL-b-PAVL | HS~O(O=)~SH | 34.5K | 475/100/26 | 10 | 35.7K | 1.14 |
| SJP7 | PVL-co-PAVL | | 32K | 0/235/45 | 20 | 24K | 1.48 |

FIGURE 69 (Continued)

Protocol
- [polymer (25 mg)]/[DCM (125 μL)] = 0.2M
- [polymer (25 mg)]/[DMPA (4 mg)] = 1/0.4
- [polymer (25 mg)]/[SH(CH$_2$)$_6$SH (3 μL)] = 1/0.5
- PVA (polyvinyl alcohol) = 2.5mL
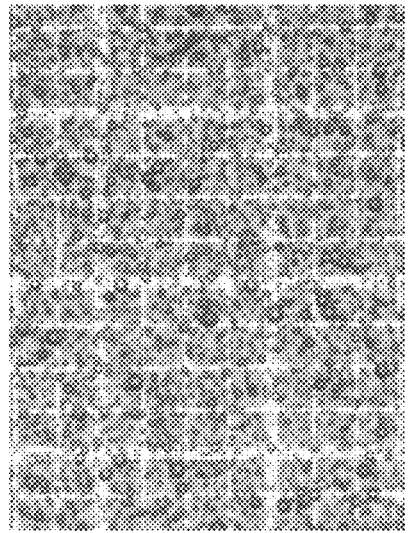
Crosslinked Microparticles in PVA
Size = 5 - 25 μm
Protocol
- [polymer (25 mg)]/[DCM (125 μL)] = 0.2M
- [polymer (25 mg)]/[DMPA (4 mg)] = 1/0.4
- [polymer (25 mg)]/[SH(CH$_2$)$_6$SH (3 μL)] = 1/0.5
- PVA (polyvinyl alcohol) = 5mL
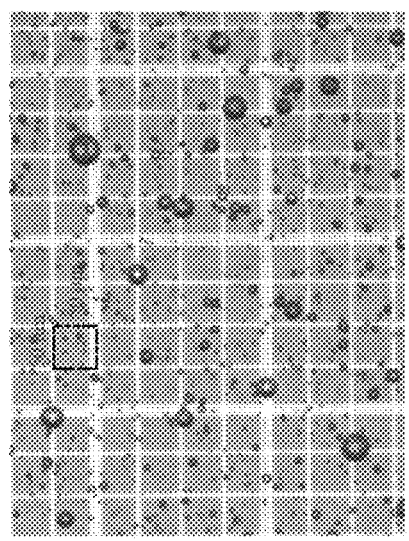
Crosslinked Microparticles in PVA
Size = 5 - 30 μm
FIGURE 77

1. Increase concentration of polymer

Protocol
- [polymer (25 mg)]/[DCM (125 μL)] = 0.2M
- [polymer (25 mg)]/[DMPA (4 mg)] = 1/0.4
- [polymer (25 mg)]/[SH(CH$_2$)$_6$SH (3 μL)] = 1/0.5
- PVA (polyvinyl alcohol) = 5mL
- RPM = 25K

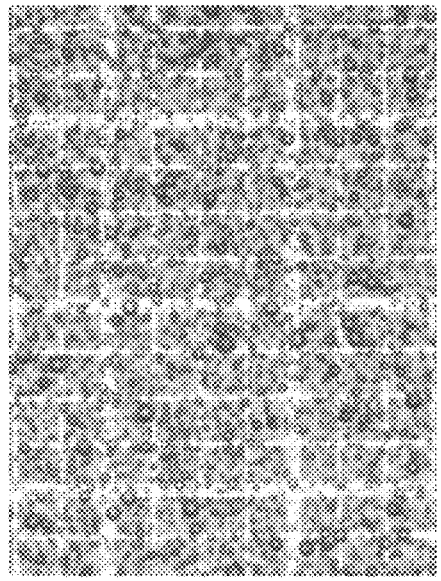

Crosslinked Microparticles in PVA
Size = 5- 25 μm

2. Reduce amount of PVA

Protocol
- [polymer (25 mg)]/[DCM (125 μL)] = 0.2M
- [polymer (25 mg)]/[DMPA (4 mg)] = 1/0.4
- [polymer (25 mg)]/[SH(CH$_2$)$_6$SH (3 μL)] = 1/0.5
- PVA (polyvinyl alcohol) = 2.5mL
- RPM = 25K

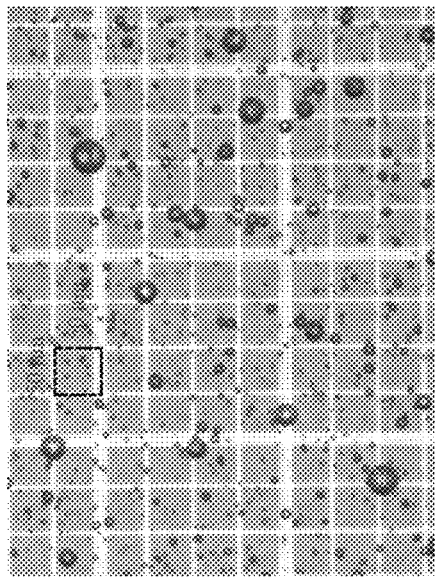

Crosslinked Microparticles in PVA
Size = 5- 30 μm

FIGURE 82

- However, Release profile shows difference between 10-50% and 1-5%
- Same as release of Drug X, amount of PEGylated copolymer can be a factor to control drug release.

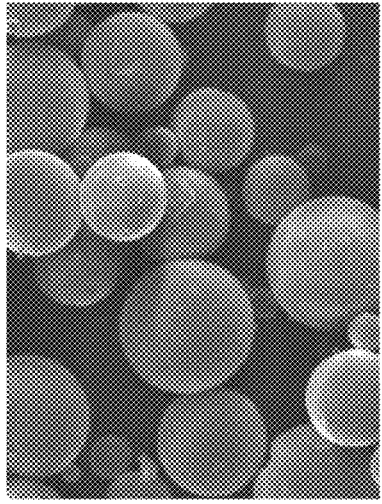
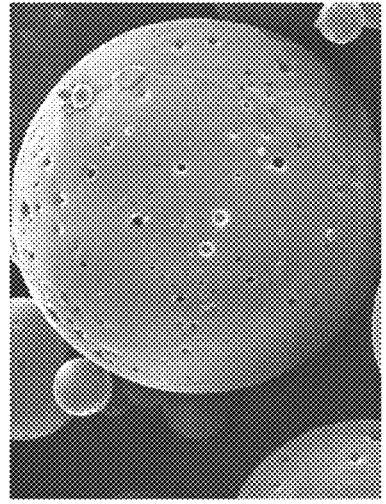
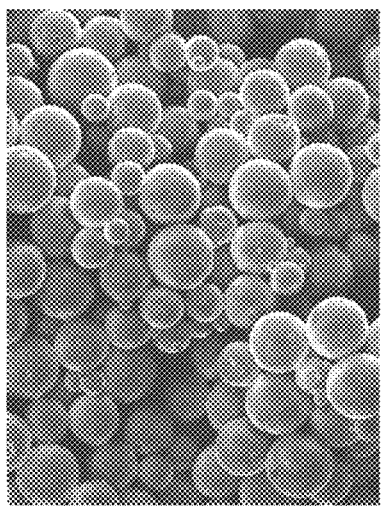
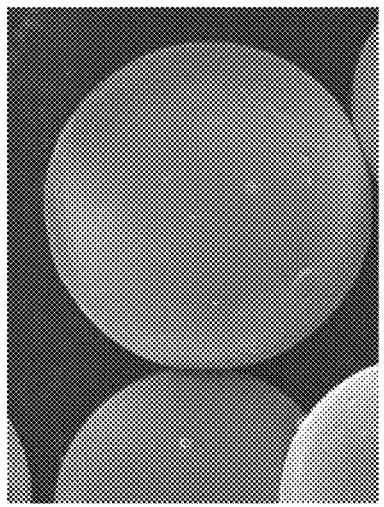
FIGURE 103

➢ Conclusion:

1. No great different based on NaCl concentration between NaCl MP and EtOH MP

2. Slightly trend of decreasing intensity as NaCl concentration increases (0.05M being the brightest)

3. Might be better to use Normal MP

• Release profile shows difference relied on amount of PEGylated copolymer

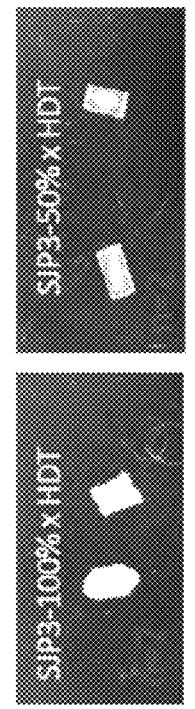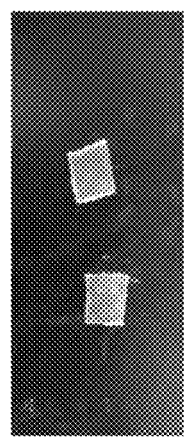
FIGURE 118

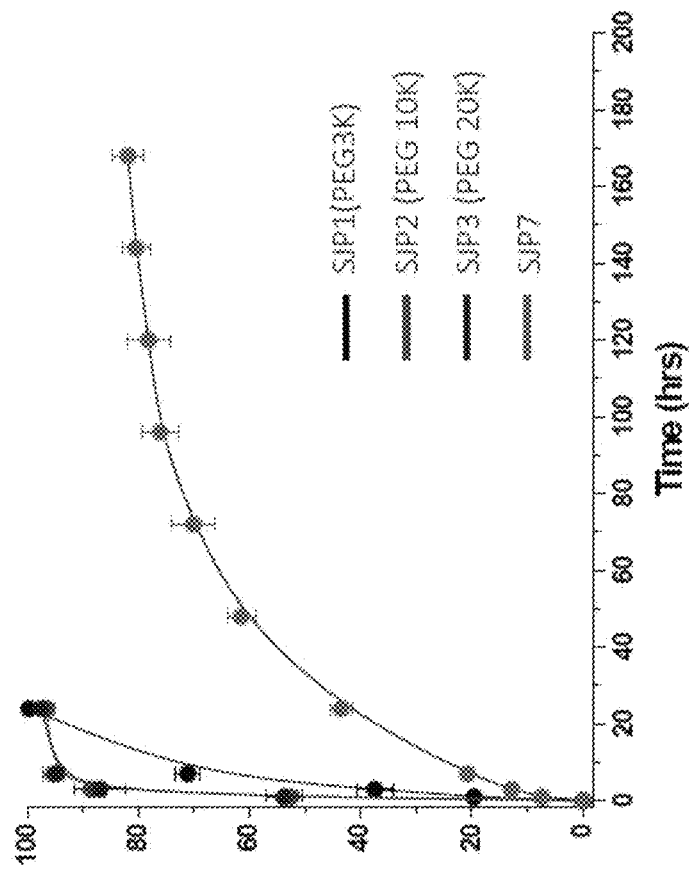
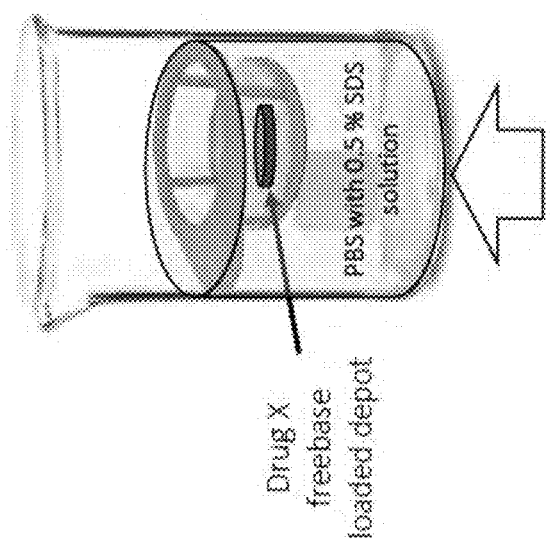
FIGURE 121

Blend system demonstrates different Drug X release depending on amount of PEGylated copolymer (SJP3).

1-1. Approach to eliminate centrifugation: Microparticle mesh washing

✓ Advantages
- Narrow PDI of microparticles
- Scalable

✓ Challenges
- Loss of Microparticle to surface adherence
- Aggregation may prevent proper filtration

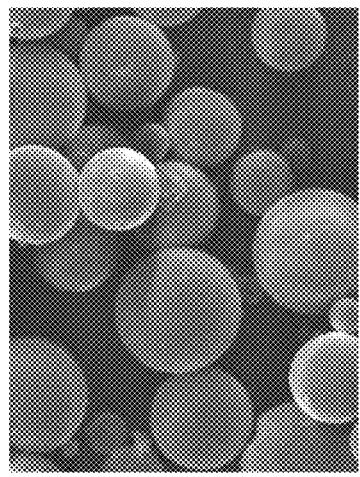
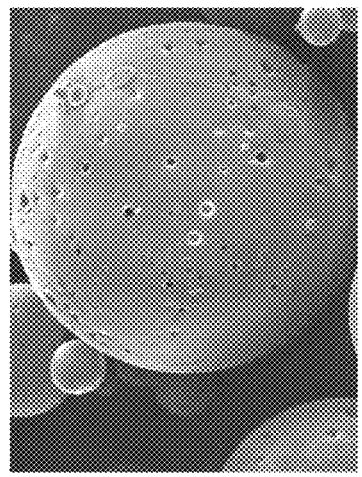
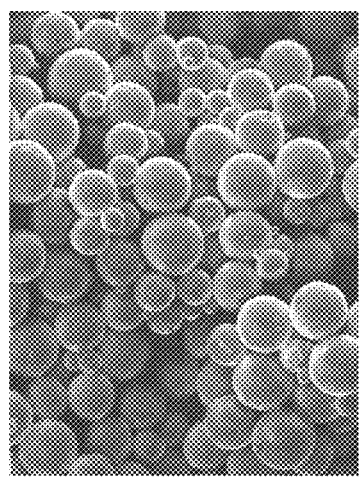
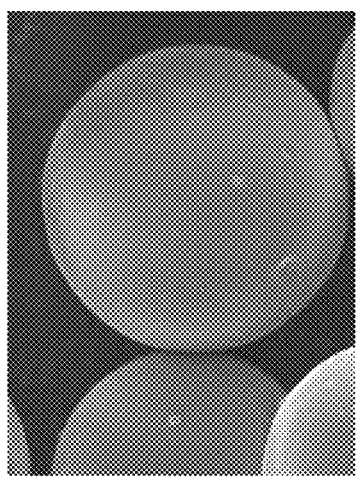
Normal MPs after filtration with mesh
Normal MPs having smooth surface
MPs using NaCl after filtration with mesh
Normal MPs having pore on the surface
- NaCl and EtOH does not have a significant effect on surface morphology of MPs.
- MPs including smooth surface and pores exist more randomly.
FIGURE 130

* There is no issue of saturation as concentration with 60mL of release media shows half concentration of 30mL and the same amount of Drug X release.

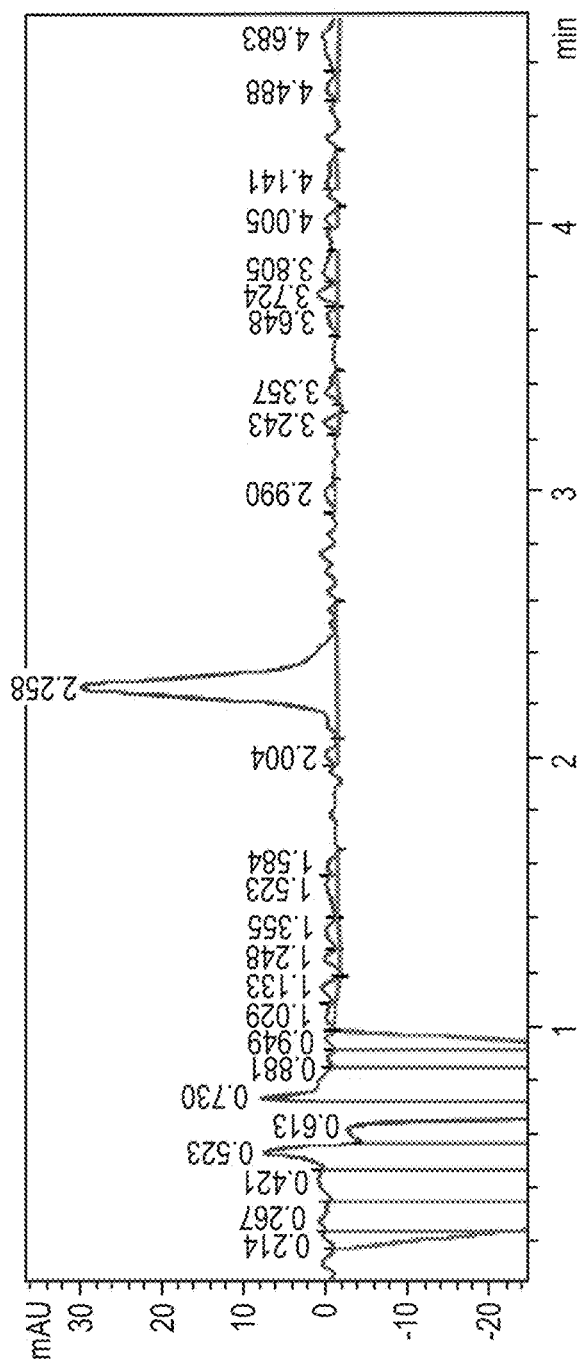
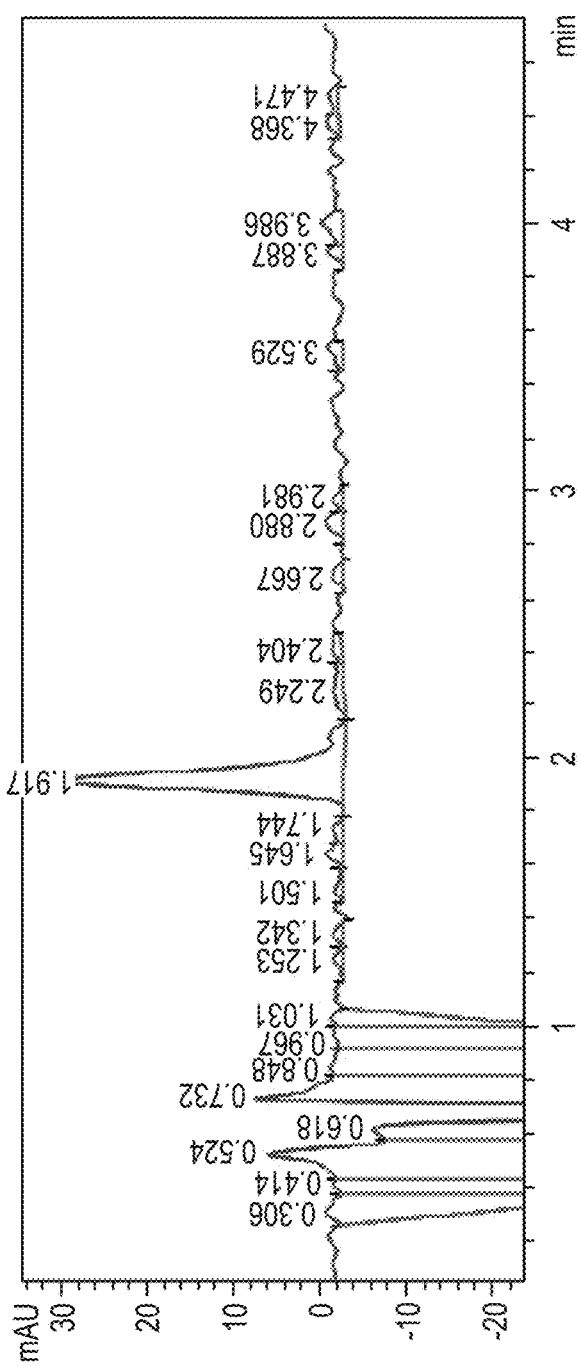
FIG. 141A
FIG. 141B

Peak #4: This is the drug peak. Only 0.5% SDS shows a significant decrease. The other three SDS concentration show slower decrease rate.

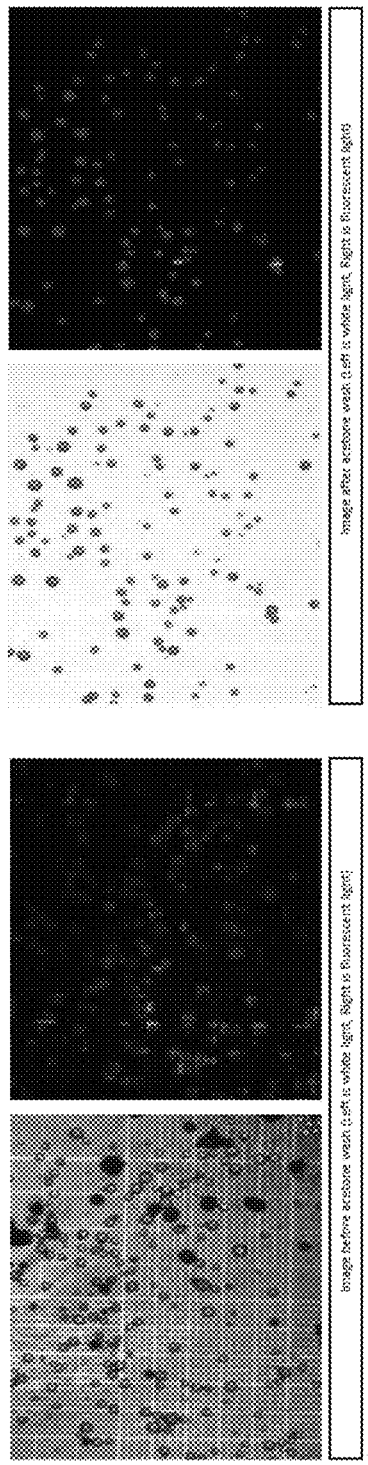

Conclusion:
1. There is no difference between before and after washing in terms of fluorescent. The microparticles still retained curcumin even after acetone wash. This suggests that drug is staying inside the microparticle even with organic solvent wash. However, we still cannot determine how much of drug remained inside the microparticle based on the fluorescent image

FIGURE 151

Figure. Swelling of a series of discs prepared from blends at different weight ratios of CoPAVL/PEG-PAVL = 99/1, 97.5/2.5, 95/5, 90/10, 75/25, and 50/50 in a mixture of DMSO/THF (50/50) at room temperature (a) and PBS with 0.5% SDS (pH 7.5) at 37 °C (b).

FACTORS CONTROLLING DRUG RELEASE IN CROSS-LINKED POLY(VALEROLACTONE) BASED MATRICES

RELATED APPLICATIONS

This application claims the benefit under 35 U.S.C. § 119(e) of U.S. Provisional Patent Application Ser. No. 62/239,758, filed Jan. 17, 2019, the disclosure of which is incorporated herein by reference in its entirety.

FIELD OF THE INVENTION

The present disclosure relates to controlling drug release in cross-linked poly(valerolactone) based matrices.

BACKGROUND OF THE INVENTION

Over the past 50 years, numerous platforms have been approved, marketed, and used clinically for the delivery of a broad range of drugs for distinct clinical indications. Athanasiou, K. A.; Niederauer, G. G.; Agrawal, C. M. Sterilization, toxicity, biocompatibility and clinical applications of polylactic acid/polyglycolic acid copolymers. Biomaterials 1996, 17, 2, 93-102.; Wang, J.; Jiang, A.; Joshi, M.; Christoforidis, J. Drug Delivery Implants in the Treatment of Vitreous Inflammation. Mediators of Inflammation 2013, 2013, 8.; Kohane, D. S. Microparticles and nanoparticles for drug delivery. Biotechnology and Bioengineering 2007, 96, 2, 203-209.; Pinto, F. C. H.; Da Silva-Cunha Junior, A.; Oréfice, R. L.; Ayres, E.; Andrade, S. P.; Lima, L. D. C.; Lima Moura, S. A.; Da Silva, G. R. Controlled release of triamcinolone acetonide from polyurethane implantable devices: application for inhibition of inflammatory-angiogenesis. Journal of Materials Science: Materials in Medicine 2012, 23, (6), 1431-1445.; Silva, G. R. d.; Fialho, S. L.; Siqueira, R. C.; Jorge, R.; Cunha Junior, A. d. S. Implants as drug delivery devices for the treatment of eye diseases. Brazilian Journal of Pharmaceutical Sciences 2010, 46, 585-595. In the 1960s, pioneers Folkman and Long investigated the potential of implantable drug delivery systems (IDDS) based on silicone rubber capsules (Silastic®) as a method for long term therapy for either local or systemic drug delivery. Folkman, J.; Long, D. M. The use of silicone rubber as a carrier for prolonged drug therapy. Journal of Surgical Research 1964, 4, 3, 139-142. Since the Norplant® contraceptive implant was approved by the FDA in 1990, the number of published articles and commercialized products based on polymeric drug delivery devices has grown exponentially. Kleiner, L. W.; Wright, J. C.; Wang, Y. Evolution of implantable and insertable drug delivery systems. Journal of Controlled Release 2014, 181, 1-10. Several types of non-degradable IDDS are commercially available for birth control, ocular, and vascular applications (e.g Norplant®; Implanon™, Vitraset® or Cypher®). They are mostly formed from silicones, acrylates and their copolymers, ethylene vinyl acetate copolymers, vinylidene fluoride copolymers, and urethanes. Kleiner, L. W.; Wright, J. C.; Wang, Y. Evolution of implantable and insertable drug delivery systems. Journal of Controlled Release 2014, 181, 1-10. There is keen interest in the substitution of non-degradable polymers with those that degrade once the drug has been released to avoid the need for surgical removal of the implant. Among the biodegradable materials used to prepare implantable matrix-based delivery systems, aliphatic polyesters including poly(glycolic acid) (PGA), poly(lactic acid) (PLA), poly(lactic-co-glycolic acid) (PLGA), and poly(caprolactone) (PCL) are the most commonly used (co)polymers owing to their high biocompatibility. Athanasiou, K. A.; Niederauer, G. G.; Agrawal, C. M. Sterilization, toxicity, biocompatibility and clinical applications of polylactic acid/polyglycolic acid copolymers. Biomaterials 1996, 17, 2, 93-102.; Kulkarni., R. K.; Pani, K. C.; Neuman, C. C.; Leonard, F. F. Polylactic acid for surgical implants. Archives of Surgery 1966, 93, (5), 839-843.; Sun, H.; Mei, L.; Song, C.; Cui, X.; Wang., P. The in vivo degradation, absorption and excretion of PCL-based implant. Biomaterials 2006, 27, (9), 1735-1740.

In the case of PLGA-based delivery systems, drug release is a collective process of bulk and surface diffusion as well as bulk and surface erosion. Faisant, N.; Siepmann, J.; Benoit, J. P. PLGA-based microparticles: elucidation of mechanisms and a new, simple mathematical model quantifying drug release. European Journal of Pharmaceutical Sciences 2002, 15, (4), 355-366.; Preparation of drug-loaded PLGA-based implants has been reported by many groups. Jain, R. A. The manufacturing techniques of various drug loaded biodegradable poly(lactide-co-glycolide) (PLGA) devices. Biomaterials 2000, 21, (23), 2475-2490. The rates of degradation and drug release from PLGA matrices are dependent on the lactide:glycolide ratio, total molecular weight, crystallinity, and thermal properties (e.g. $T_g$ and $T_m$) of the copolymer, and can therefore be tailored to suit the application of interest. Ramchandani, M.; Robinson, D. In vitro and in vivo release of ciprofloxacin from PLGA 50:50 implants. Journal of Controlled Release 1998, 54, 2, 167-175.; Yerragunta, B.; Jogala, S.; Chinnala, K.; Aukunuru, J. Development of a novel 3-month drug releasing risperidone microspheres. Journal of Pharmacy And Bioallied Sciences 2015, 7, 1, 37-44. Since the first FDA approval of a drug depot system in 1989 (Lupron Depot®), other PLA and PLGA based-formulations were approved and commercialized for the treatment of several diseases (Atridox®, Decapeptyl®, Nutropin Depot®, Trelstar®, Sandostatin®). Approved by the FDA in 1996 and 1997, Gliadel® (14 mm×1 mm disc) and Zoladex® (1.5 mm diameter cylinder) are polyanhydride and PLGA implants surgically or subcutaneously implanted for the treatment of brain cancer or advanced prostate carcinoma and breast cancer, respectively. Citrin, D. L.; Resnick, M. I.; Guinan, P.; Al-Bussam, N.; Scott, M.; Gau, T. C.; Kennealey, G. T. A comparison of Zoladex® and DES in the treatment of advanced prostate cancer: Results of a randomized, multicenter trial. The Prostate 1991, 18, 2, 139-146.; Peeling, W. B. Phase III studies to compare goserelin (zoladex) with orchiectomy and with diethylstilbestrol in treatment of prostatic carcinoma. Urology 1989, 33, (5, Supplement), 45-52.; https://http://www.zoladex.com/ Zoladex 10.8 and 3.6 mg implants.; Attenello, F. J.; Mukherjee, D.; Datoo, G.; McGirt, M. J.; Bohan, E.; Weingart, J. D.; Olivi, A.; Quinones-Hinojosa, A.; Brem, L I. Use of Gliadel (BCNU) Wafer in the Surgical Treatment of Malignant Glioma: A 10-Year Institutional Experience. Annals of Surgical Oncology 2008, 15, (10), 2887.

PCL also has great potential for tissue engineering and IDDS applications. Dordunoo, S. K.; Oktaba, A. M. C.; Hunter, W.; Min, W.; Cruz, T.; Burt, H. M. Release of taxol from poly(ε-caprolactone) pastes: effect of water-soluble additives. Journal of Controlled Release 1997, 44, 1, 87-94.; Coombes, A. G. A.; Rizzi, S. C.; Williamson, M.; Barralet, J. E.; Downes, S.; Wallace, W. A. Precipitation casting of polycaprolactone for applications in tissue engineering and drug delivery. Biomaterials 2004, 25, 2, 315-325.; Fialho, S.

L.; Behar-Cohen, F.; Silva-Cunha, A. Dexamethasone-loaded poly(ε-caprolactone) intravitreal implants: A pilot study. *European Journal of Pharmaceutics and Biopharmaceutics* 2008, 68, 3, 637-646.; Khor, H. L; Ng, K. W.; Schantz, J. T.; Phan, T.-T.; Lim, T. C.; Teoh, S. H.; Hutmacher., D. W. Poly(ε-caprolactone) films as a potential substrate for tissue engineering an epidermal equivalent. *Materials Science and Engineering: C* 2002, 20, (1-2), 71-75.; Cheng, L.; Guo, S.; Wu, W. Characterization and in vitro release of praziquantel from poly(ε-caprolactone) implants. *International Journal of Pharmaceutics* 2009, 377, (1-2), 112-119.; Woodruff, M. A.; Hutmacher, D. W. The return of a forgotten polymer-Polycaprolactone in the 21st century. *Progress in Polymer Science* 2010, 35, (10), 1217-1256. PCL is a promising biomaterial given its thermal and mechanical properties (e.g. low $T_g$ and $T_m$), high permeability, and good compatibility with a wide range of drugs. Woodruff, M. A.; Hutmacher, D. W. The return of a forgotten polymer—Polycaprolactone in the 21st century. *Progress in Polymer Science* 2010, 35, (10), 1217-1256. Compared to PLGA, the lower degradation rate of PCL makes it suitable for sustained release of drugs over years, similar to non-degradable IDDS. Capronor, a PCL-based contraceptive implant containing levonorgestrel (LNG), was clinically evaluated in the 1980s as a method of birth control. Capronor® showed good pharmacological results in Phase I and II clinical trials but did not reach Phase III due to self-oxidation of an additive, ethyl oleate, that had been included in the formulation in order to disperse the contraceptive drug within the polymer matrix. C. G. Pitt, A. S., *Capronor—a biodegradable delivery system for levonorgestrel*. Philadelphia, 1984; Vol. Long-acting contraceptive delivery systems, Harper and Row. Ma and colleagues (2006) reported preclinical studies of a similar implant (e.g. PCL/Pluronic©-F68/LNG) and demonstrated good stability and efficacy of the treatment over two years. Ma, G.; Song, C.; Sun, H.; Yang, J.; Leng, X. A biodegradable levonorgestrel-releasing implant made of PCL/F68 compound as tested in rats and dogs. *Contraception* 2006, 74, 2, 141-147.

Polyester (co)polymers are most commonly prepared by ring-opening polymerization (ROP) according to a variety of mechanisms (i.e. cationic, anionic, coordinative) and are propagated by active hydrogen or zwitterionic species. Löfgren, A.; Albertsson, A.-C.; Dubois, P.; Jěrôme, R. Recent Advances in Ring-Opening Polymerization of Lactones and Related Compounds. *Journal of Macromolecular Science, Part C* 1995, 35, 3, 379-418. Traditionally, aliphatic polyesters have been prepared by ROP using metal catalysts, such as tin and aluminum salts. Unlike the use of the common catalysts $Sn(Oct)_2$ and $Sc(OTf)_3$, compounds such as 1,5,7-triazabicyclo[4.4.0]dec-5-ene (TBD) afford rapid polymerization kinetics of lactones (e.g. valerolactone and caprolactone) in a metal-free environment at ambient temperature and result in polymer products with a low polydispersity (PDI). Silvers, A. L.; Chang, C.-C.; Emrick, T. Functional aliphatic polyesters and nanoparticles prepared by organocatalysis and orthogonal grafting chemistry. *Journal of Polymer Science Part A: Polymer Chemistry* 2012, 50, (17), 3517-3529.; Parrish, B.; Quansah, J. K.; Emrick, T. Functional polyesters prepared by polymerization of α-allyl (valerolactone) and its copolymerization with ε-caprolactone and δ-valerolactone. *Journal of Polymer Science Part A: Polymer Chemistry* 2002, 40, (12), 1983-1990. Incorporation of alkene-substituted lactones in polyesters enables integration of new chemical functionalities and results in tunable materials with a broad range of properties. Huang, Y.; Pan, Y.; Fu, J.; Huang, X.; Tang, X. Study of crosslinking of polyphosphazene with allyl pendant groups initiated by benzoyl peroxide. *Journal of Applied Polymer Science* 2009, 113, (4), 2353-2360.; Mecerreyes, D.; Miller, R. D.; Hedrick, J. L.; Detrembleur, C.; Jérôme, R. Ring-opening polymerization of 6-hydroxynon-8-enoic acid lactone: Novel biodegradable copolymers containing allyl pendent groups. *Journal of Polymer Science Part A: Polymer Chemistry* 2000, 38, (5), 870-875. Preparation of allyl-ε-caprolactone in good yield (≈50%) remains problematic and polymerization has been shown to yield polymers of high PDI. Whereas, the allyl-6-valerolactone (AVL) monomer can be produced in good yield (≥70% yield) and is associated with high polymerizability. Silvers, A. L.; Chang, C.-C.; Emrick, T. Functional aliphatic polyesters and nanoparticles prepared by organocatalysis and orthogonal grafting chemistry. *Journal of Polymer Science Part A: Polymer Chemistry* 2012, 50, (17), 3517-3529.; Darcos, V.; Antoniacomi, S.; Paniagua, C.; Coudane, J. Cationic polyesters hearing pendent amino groups prepared by thiol-ene chemistry. *Polymer Chemistry* 2012, 3, 2, 362-368. TBD-catalyzed ROP of lactones has been used to prepare the copolymers poly(valerolactone)-co-poly(allyl-valerolactone) (PVL-co-PAVL) and PCL-co-poly(allyl-valerolactone) (PCL-co-PAVL) in excellent yield and with low PDI. PVL is similar to PCL in terms of physicochemical properties with a slightly faster rate of degradation, yet remains relatively unexplored as a material for use in biomedical applications. Lou, X.; Detrembleur, C.; Jérôme, R. Living Cationic Polymerization of 6-Valerolactone and Synthesis of High Molecular Weight Homopolymer and Asymmetric Telechelic and Block Copolymer. *Macromolecules* 2002, 35, (4), 1190-1195.; Lee, H.; Zeng, F.; Dunne, M.; Allen, C. Methoxy Poly(ethylene glycol)-block-Poly(δ-valerolactone) Copolymer Micelles for Formulation of Hydrophobic Drugs. *Biomacromolecules* 2005, 6, (6), 3119-3128.; Zeng, F.; Lee, H.; Chidiac, M.; Allen, C. Synthesis and Characterization of Six-Arm Star Poly(δ-valerolactone)-block-Methoxy Poly(ethylene glycol) Copolymers. *Biomacromolecules* 2005, 6, (4), 2140-2149.; Zeng, F.; Lee, H.; Allen, C. Epidermal Growth Factor-Conjugated Poly(ethylene glycol)-block-Poly(δ-valerolactone) Copolymer Micelles for Targeted Delivery of Chemotherapeutics. *Bioconjugate Chemistry* 2006, 17, 2, 399-409.

SUMMARY OF THE INVENTION

The present disclosure relates to controlling drug release in cross-linked poly(valerolactone) based matrices. In one aspect, the compounds or pharmaceutically acceptable salts thereof include a poly(valerolactone)-co-poly(allylvalerolactone)-co-polyethylene glycol (PEG) copolymer. In some embodiments, at least a portion of allylvalerolactone residues within the copolymer are crosslinked with a crosslinker. In some embodiments, the compound has a polydispersity index of less than or equal to 1.5.

In some embodiments, the compound can comprise amorphous networks.

In some embodiments, the compound can include semicrystalline networks.

In some embodiments, the copolymer can comprise poly (allylvalerolactone)-b-allylvalerolactone-b-3K-polyethylene glycol-b-poly(valerolactone)-b-poly(allylvalerolactone).

In some embodiments, the copolymer can comprise poly (allylvalerolactone)-b-allylvalerolactone-b-10K-polyethylene glycol-b-poly(valerolactone)-b-poly(allylvalerolactone). In some embodiments, the copolymer can have a number average molecular weight of 25.5 kDa.

In some embodiments, the crosslinker can comprise a dithiol moiety. In some embodiments, the crosslinker can be 1,6-hexanedithiol.

In some embodiments, the compound can be loaded with a drug.

In some embodiments, the drug can include at least one of paclitaxel, triamcinolone acetonide, triamcinolone hexacetonide, acetaminophen, and curcumin.

In one aspect, a method is described herein, comprising: (a) polymerizing valerolactone residues, allylvalerolactone, and polyethylene glycol residues in the presence of a non-metal catalyst via a ring opening polymerization to produce a poly(valerolactone)-co-poly(allylvalerolactone)-co-polyethylene glycol copolymer; (b) crosslinking the poly(valerolactone)-co-poly(allylvalerolactone)-co-polyethylene glycol copolymer with a crosslinker; and (c) loading a drug into the crosslinked copolymer.

In some embodiments, the catalyst can comprise 1,5,7-triazabicyclo[4.4.0]dec-5-ene.

In some embodiments, the crosslinker can comprise a dithiol moiety. In some embodiments, the crosslinker can be 1,6-hexanedithiol.

In some embodiments, the crosslinking can comprise exposing the poly(valerolactone)-co-poly(allylvalerolactone) to UV light.

In some embodiments, the drug can include at least one of paclitaxel, triamcinolone acetonide, triamcinolone hexacetonide, acetaminophen, and curcumin.

In some embodiments, loading the drug into the crosslinked copolymer can comprise swelling and equilibration of the crosslinked copolymer in a saturated solution of the drug. In some embodiments, the solution can be a tetrahydrofuran solution.

In some embodiments, the copolymer comprises poly (allylvalerolactone)-b-allylvalerolactone-b-3K-polyethylene glycol-b-poly(valerolactone)-b-poly(allylvalerolactone). In some embodiments, the copolymer comprises poly(allylvalerolactone)-b-allylvalerolactone-b-10K-polyethylene glycol-b-poly(valerolactone)-b-poly(allylvalerolactone). In some embodiments, the copolymer can have a number average molecular weight of 25.5 kDa.

In one aspect, a method of releasing a drug from a crosslinked polymer is described herein, comprising: (a) polymerizing valerolactone residues, allylvalerolactone, and polyethylene glycol residues in the presence of a non-metal catalyst via a ring opening polymerization to produce a poly(valerolactone)-co-poly(allylvalerolactone)-co-polyethylene glycol copolymer; (b) crosslinking the poly(valerolactone)-co-poly(allylvalerolactone)-co-polyethylene glycol copolymer with a crosslinker; (c) loading a drug into the crosslinked copolymer, the drug comprising at least one of paclitaxel, triamcinolone acetonide, triamcinolone hexacetonide, acetaminophen, and curcumin; and (d) releasing the drug from the drug-loaded crosslinked copolymer.

In some embodiments, the drug can be triamcinolone hexacetonide and cumulative release of triamcinolone hexacetonide from the drug-loaded crosslinked copolymer is about 42 wt % after 34 days.

In some embodiments, the drug can be paclitaxel and cumulative release of paclitaxel from the drug-loaded crosslinked copolymer is about 58 wt % after 35 days. In some embodiments, releasing the drug from the drug-loaded crosslinked copolymer can take place in phosphate-buffer saline. In some embodiments, the phosphate-buffer saline can take place in 0.5% (w/v) sodium dodecyl sulfate.

In some embodiments, the copolymer can be poly(allylvalerolactone)-b-allylvalerolactone-b-3K-polyethylene glycol-b-poly(valerolactone)-b-poly(allylvalerolactone).

In some embodiments, the copolymer can be poly(allylvalerolactone)-b-allylvalerolactone-b-10K-polyethylene glycol-b-poly(valerolactone)-b-poly(allylvalerolactone). In some embodiments, the copolymer has a number average molecular weight of 25.5 kDa.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows $^1$H NMR spectra of one random block copolymer PVL-co-PAVL ($P_{39K}$) in CDCl$_3$. Inset includes the gel permeation chromatograms for the four copolymers $P_{7.5K}$, $P_{15K}$, $P_{32K}$ and $P_{39K}$.

FIG. 2B shows thermograms for the four copolymers obtained by DSC at 10° C./min ($2^{nd}$ cycle).

FIG. 7C shows comparison of the XRD patterns of the $CP_{39K}$ matrices loaded with TAH and CCM.

FIG. 7D shows the percent crystallinity (left axis) and the melting transition temperatures ($T_m$, right axis) for the $CP_{39K}$ matrices after drug incorporation (red dots indicate the first transition temperature $T_{m1}$ and blue indicate the second transition temperature $T_{m2}$).

FIG. 8C shows a table of the different fittings applied on the release experiments presented in A) with the $R^2_{adjusted}$ ($R^2$).

FIG. 19 shows a homopolymer with TA as initiator—PVL reaction scheme with data, according to an embodiment.

FIG. 47 shows a water adsorption capacity study.

FIG. 52 shows drug loading in disc shaped depot formed from SJP1, SJP2, and SJP3.

FIG. 54 shows a drug release from disc shaped depot formed from SJP1, SJP2, SJP3 and SJP7.

FIG. 56 shows Drug X fumarate loading in the depot formed from SJP1, SJP2, SJP3, and SJP7.

FIG. 57 shows Drug X fumarate release from the depot formed from SJP1, SJP2, SJP3 and SJP7.

FIG. 60 shows Drug X freebase release from the depot formed from SJP1, SJP2, SJP3 and SJP7.

FIG. 77 shows a plan of preparation of controlled microparticle by adjusting concentration, according to an embodiment.

FIG. 103 shows SEM images of MPs before drug loading.

FIG. 105 shows Drug X Loading and release using Mesh washed MPs, NaCl MPs and EtOH MPs.

FIG. 106 shows pre-loading of Drug X into a microparticle, according to an embodiment.

FIG. 107 shows PTX loading and release using MPs.

FIG. 108 shows curcumin post-loading protocol for NaCl MP and EtOH MP.

FIG. 109 shows fluorescent Image of Curcumin loaded MP (0.25M NaCl) Different incubation time.

FIG. 110 shows fluorescent image of curcumin loaded MP Different concentration of NaCl and EtOH MP (after 24 hour incubation).

FIG. 111 shows a fluorescent image of curcumin loaded MP before and after wash.

FIG. 112 shows a fluorescent image of curcumin loaded MP before and after wash.

FIG. 113 shows a fluorescent image of curcumin loaded MP before washing.

FIG. 114 shows a blend system of SJP7 and SJP3 with hexanedithiol.

FIG. 115 shows release of Paclitaxel varying amount of PEGylated copolymer.

FIG. 116 shows release of Paclitaxel varying amount of PEGylated copolymer.

Figure 117:
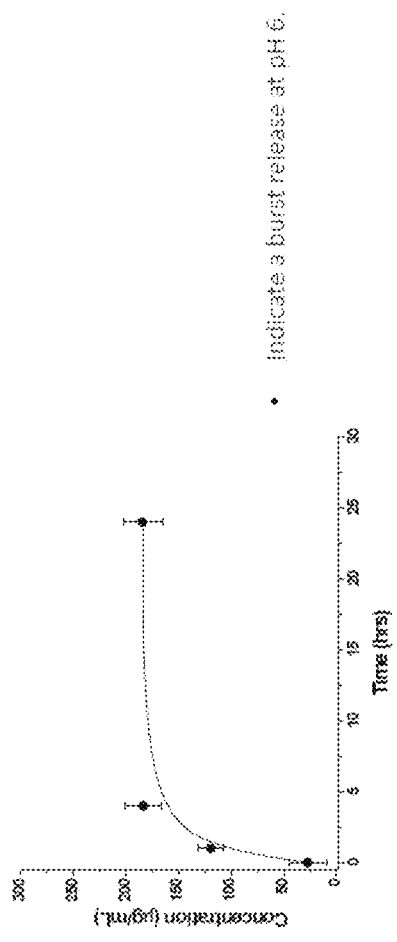

FIG. 117 shows Drug X loading and release in release media at pH 6.

FIG. 118 shows enzymatic degradation of blended disc.

Figure 119:
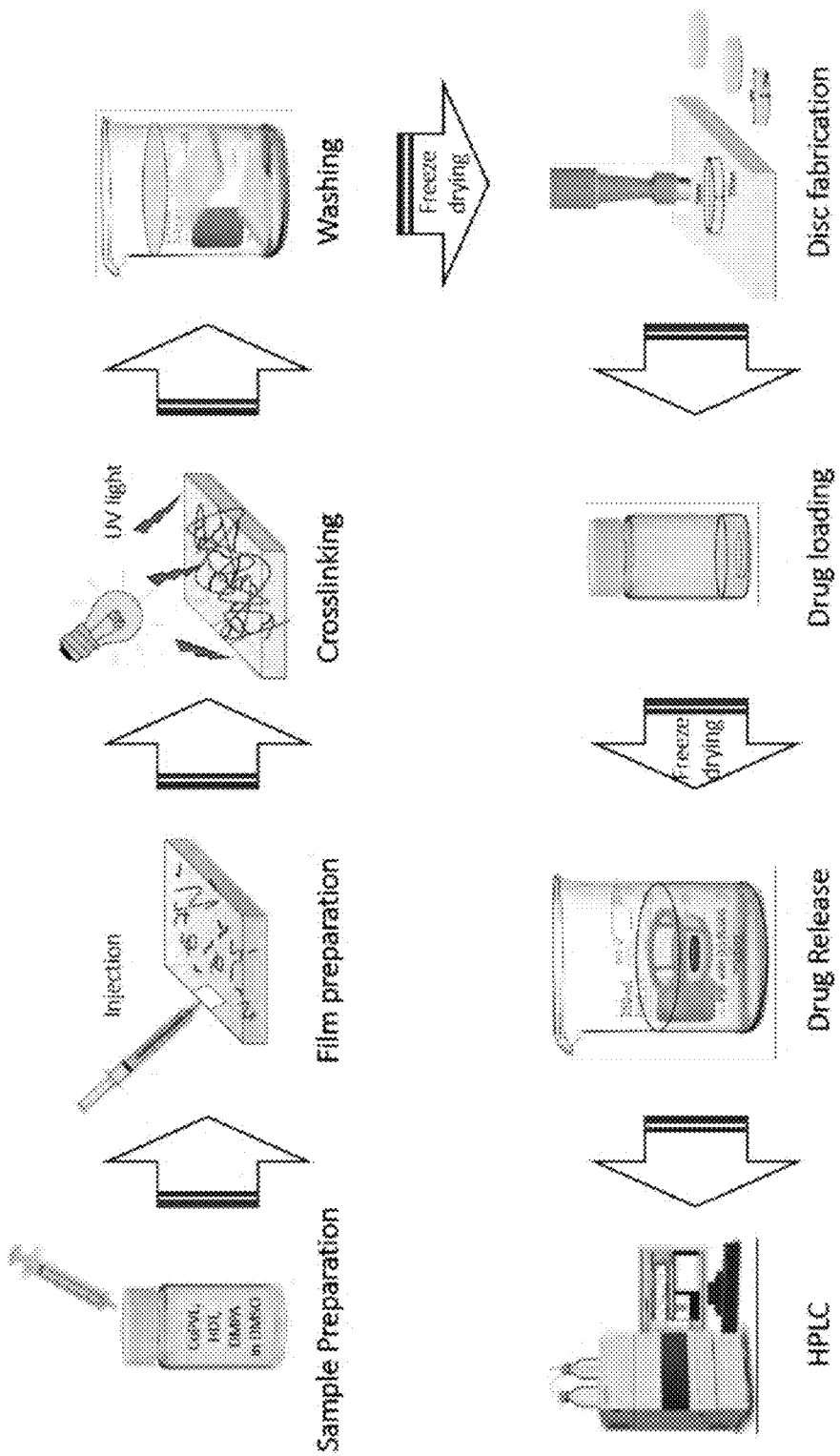

FIG. 119 shows an overall procedure used for preparation of disc and Drug X loading and release, according to an embodiment.

Figure 120:
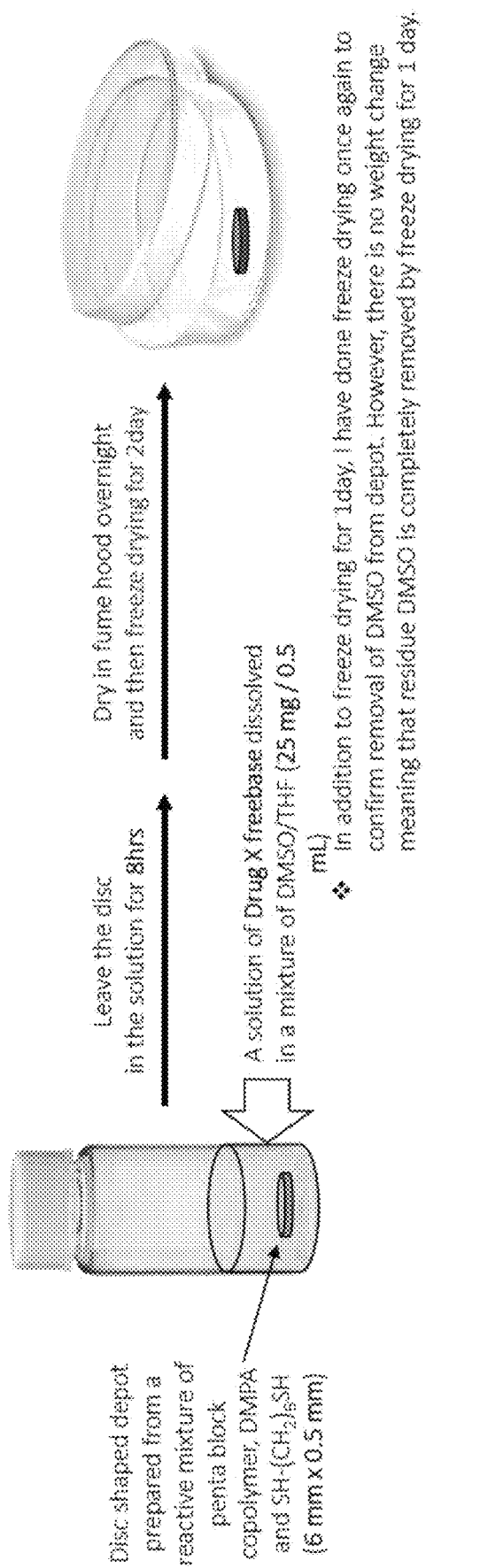

FIG. 120 shows a Drug X freebase loading in disc shaped depot formed from SJP1, SJP2, SJP3, and SJP7.

FIG. 121 shows Drug X release of the depot formed from SJP1, SJP2, SJP3 and SJP7.

Figure 122:
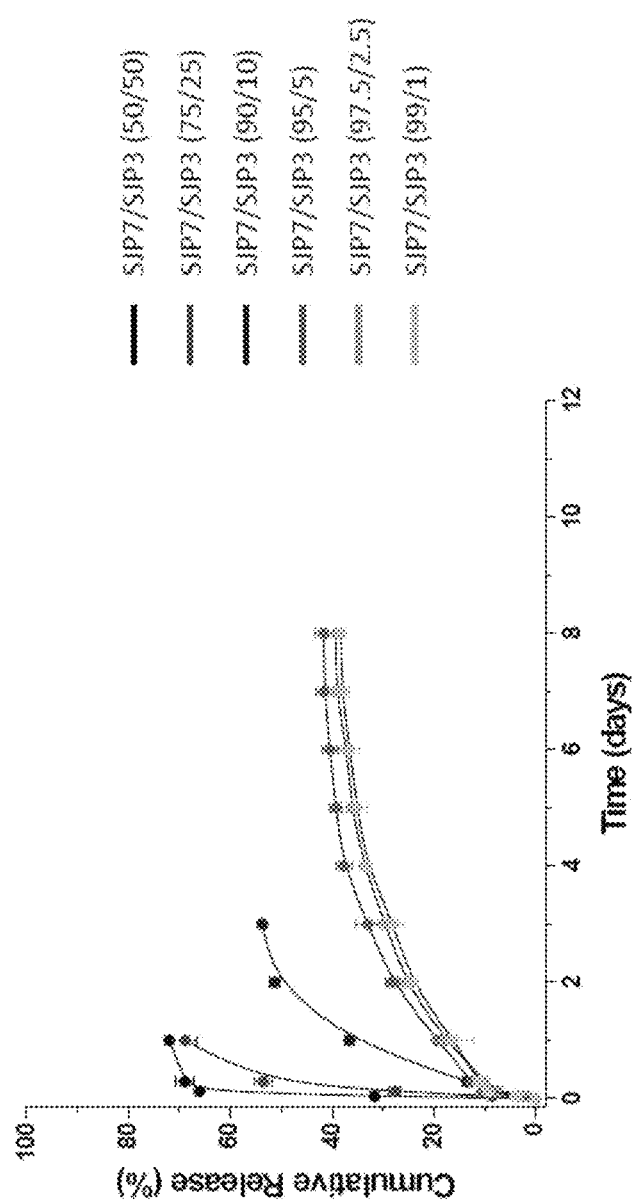

FIG. 122 shows Drug X release profile for a blend system of SJP7 and SJP3 with hexanedithiol.

Figure 123:
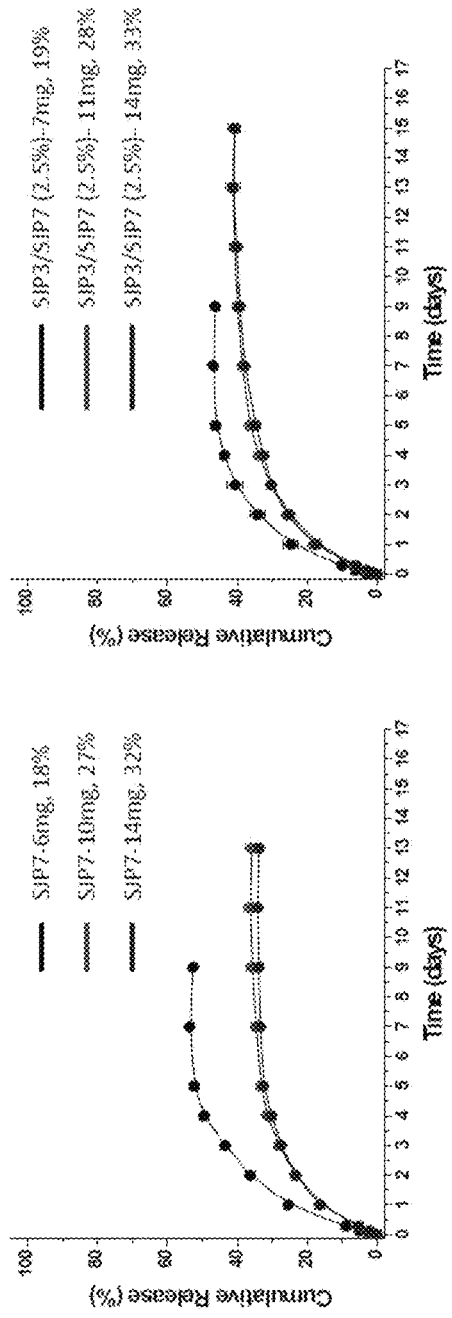

FIG. 123 shows Drug X release of disc prepared from SJP7 and its blend system with SJP3 (2.5%).

Figure 124:
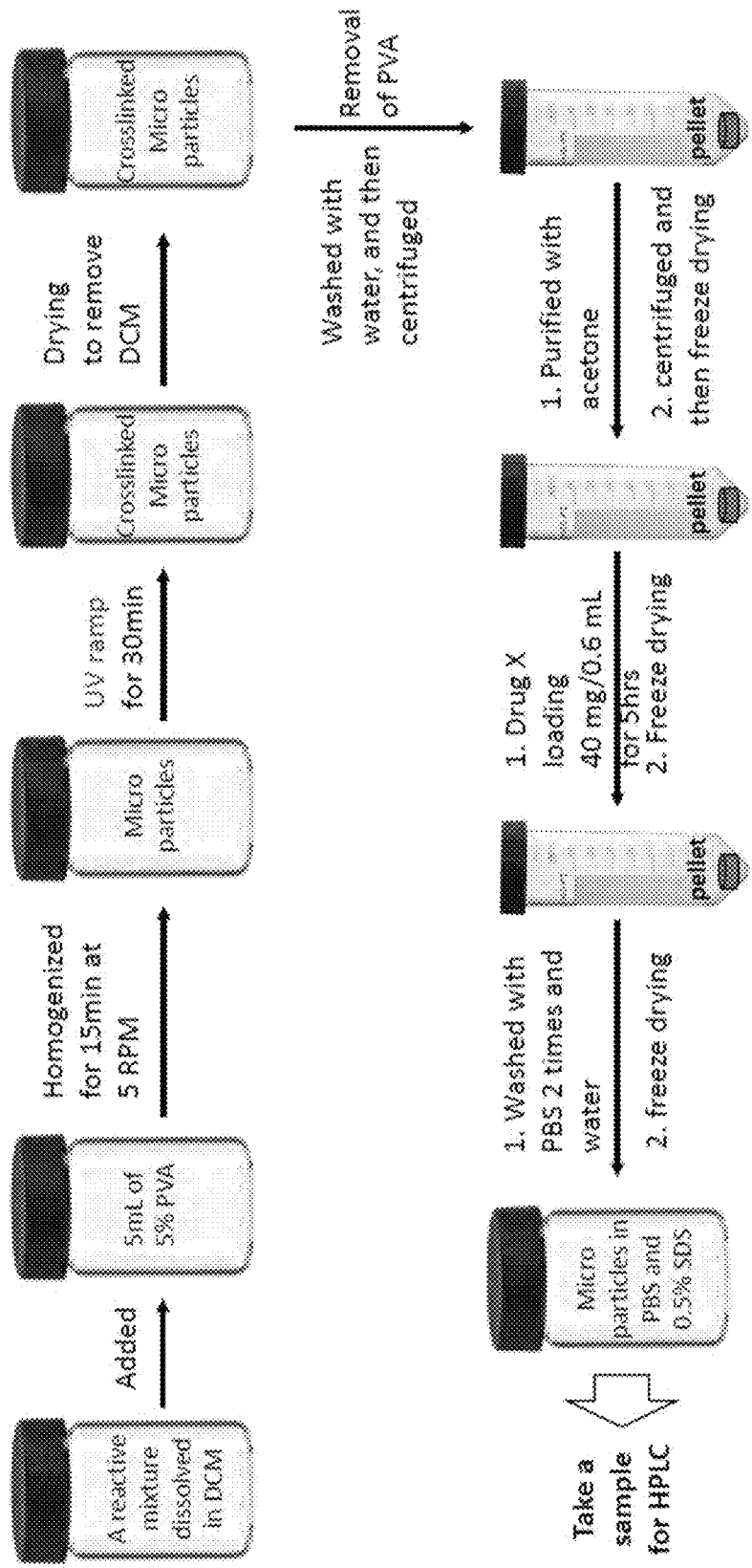

FIG. 124 shows an overall procedure for preparation of a microparticle and post-loading, according to an embodiment.

Figure 125:
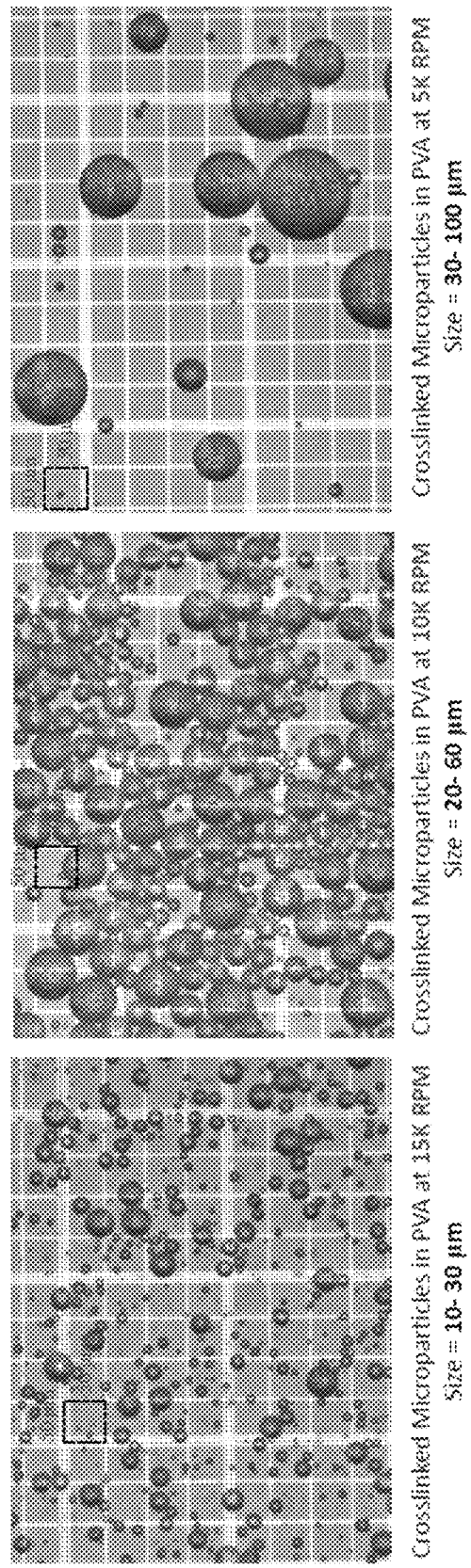

FIG. 125 shows preparation of a well-controlled microparticle, according to an embodiment.

Figure 126:
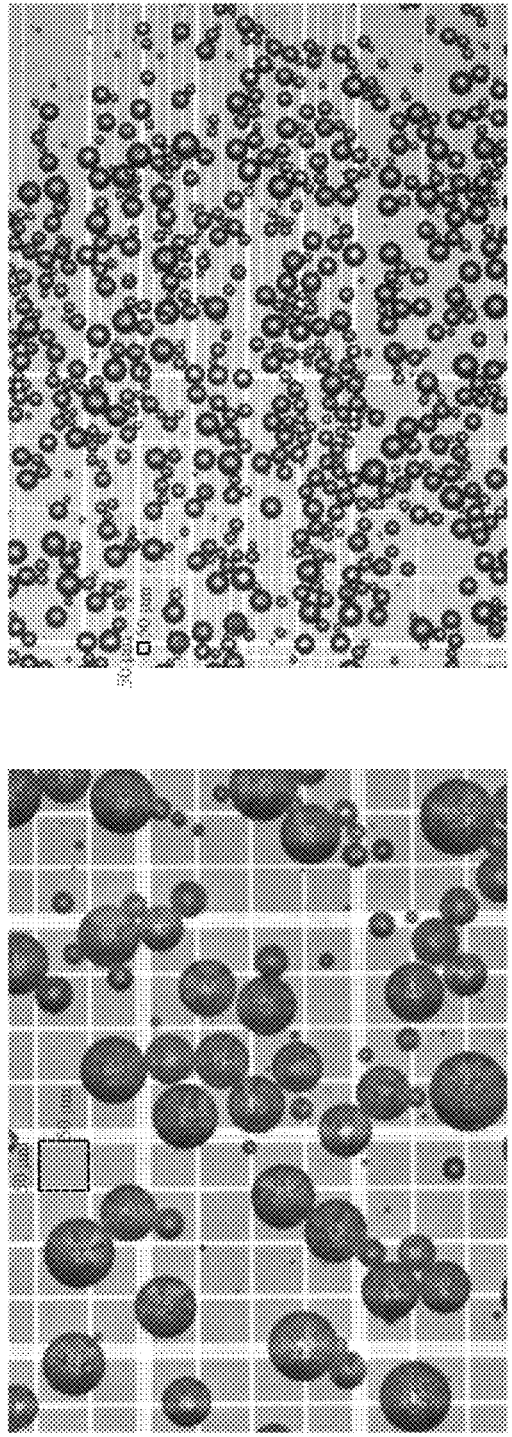

FIG. 126 shows preparation of a microparticle, according to an embodiment.

Figure 127:
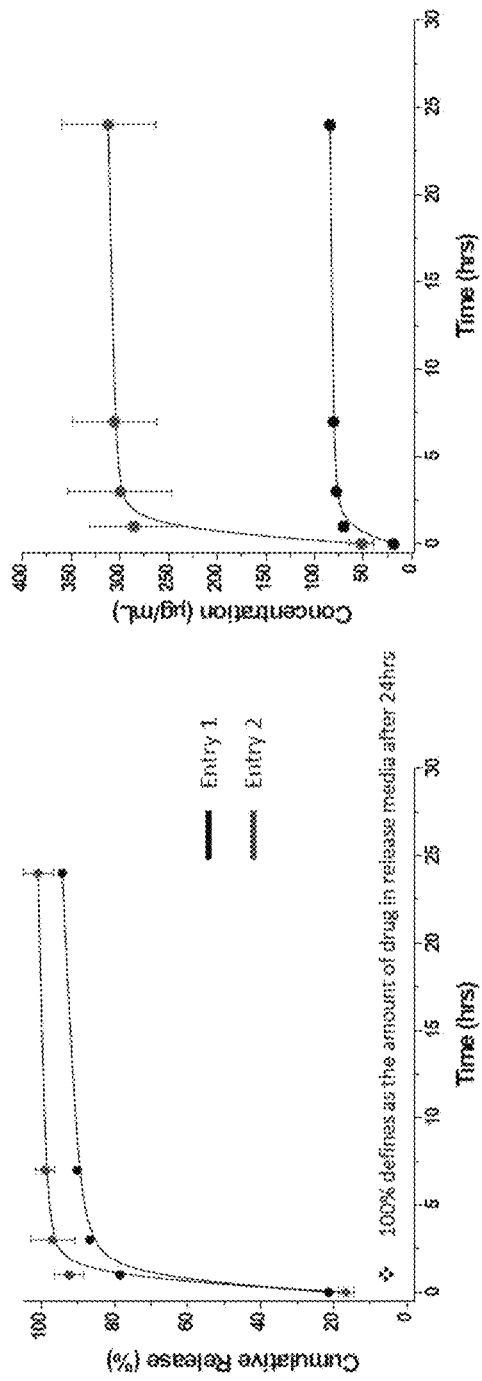

FIG. 127 shows loading and release of Drug X freebase.

Figure 128:
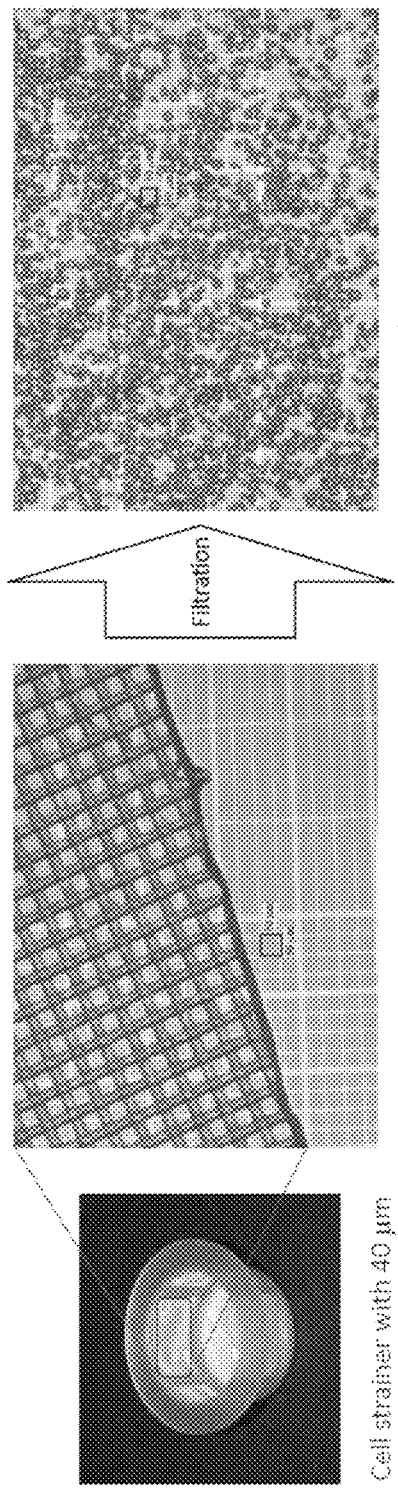

FIG. 128 shows filtration using mesh to remove small particles.

Figure 129:
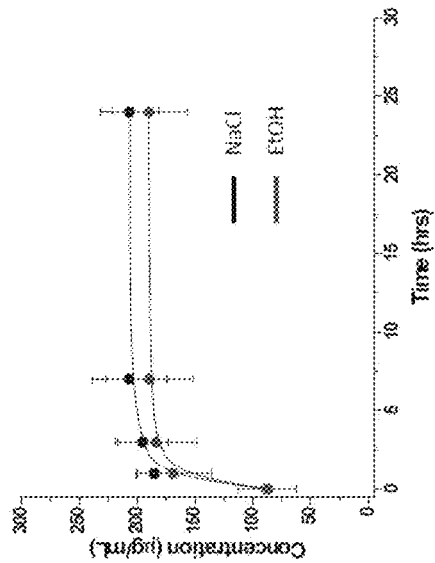

FIG. 129 shows Drug X Loading and release using NaCl MPs and EtOH MPs.

FIG. 130 shows SEM images of MPs before drug loading.

Figure 131:
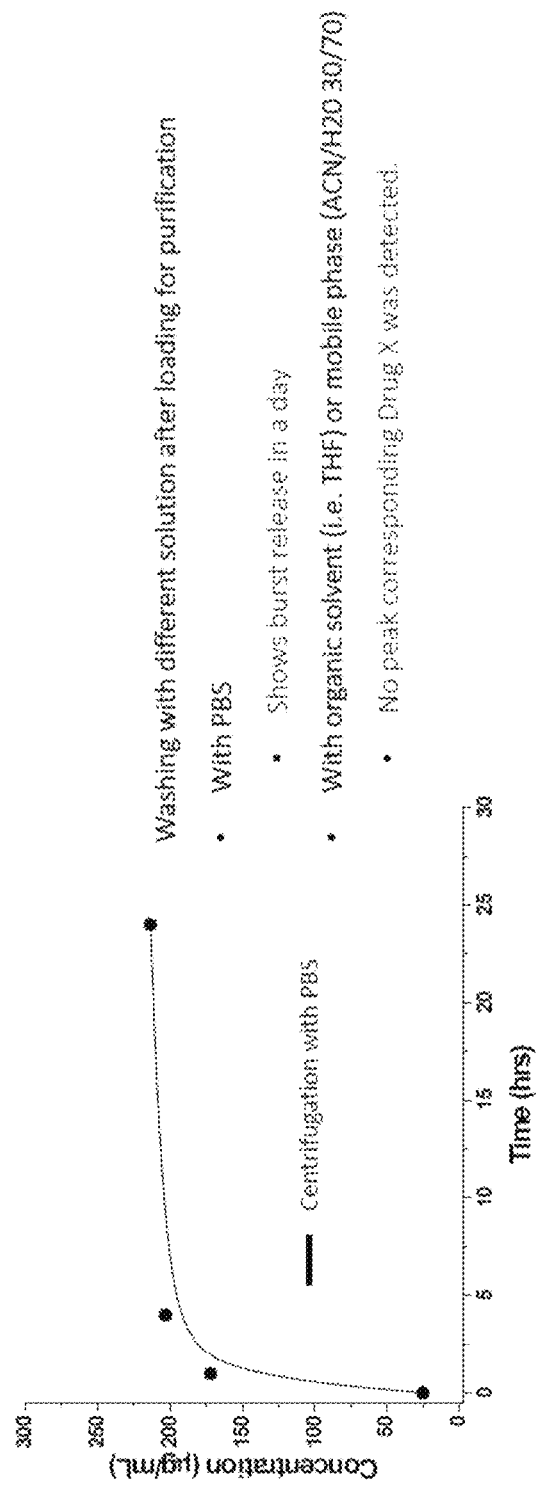

FIG. 131 shows Drug X loading and release of MPs after washing out with different solution.

Figure 132:
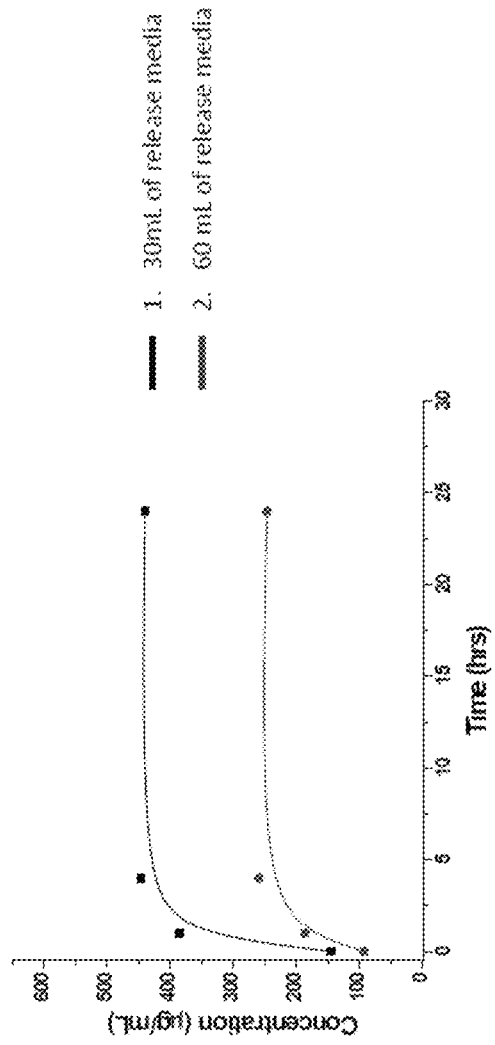

FIG. 132 shows Drug X loading and release for ruling out a saturation issue.

Figure 133:
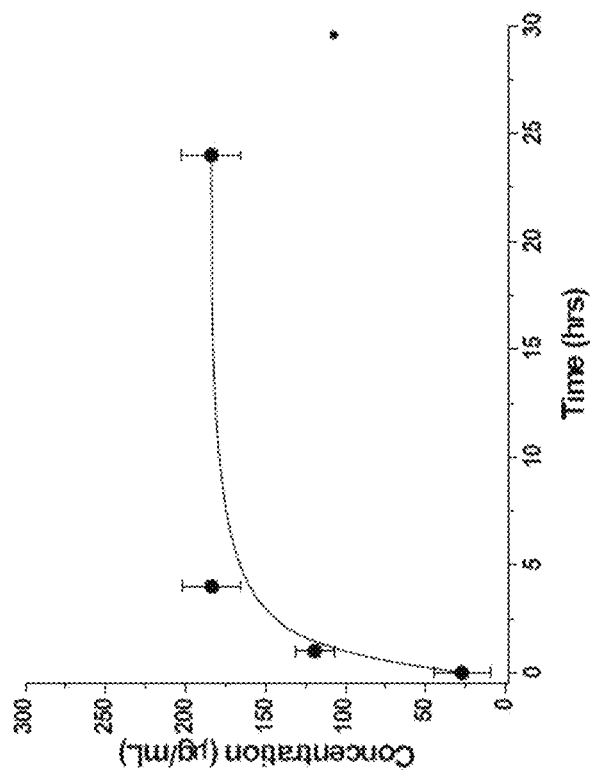
Figure 134A:
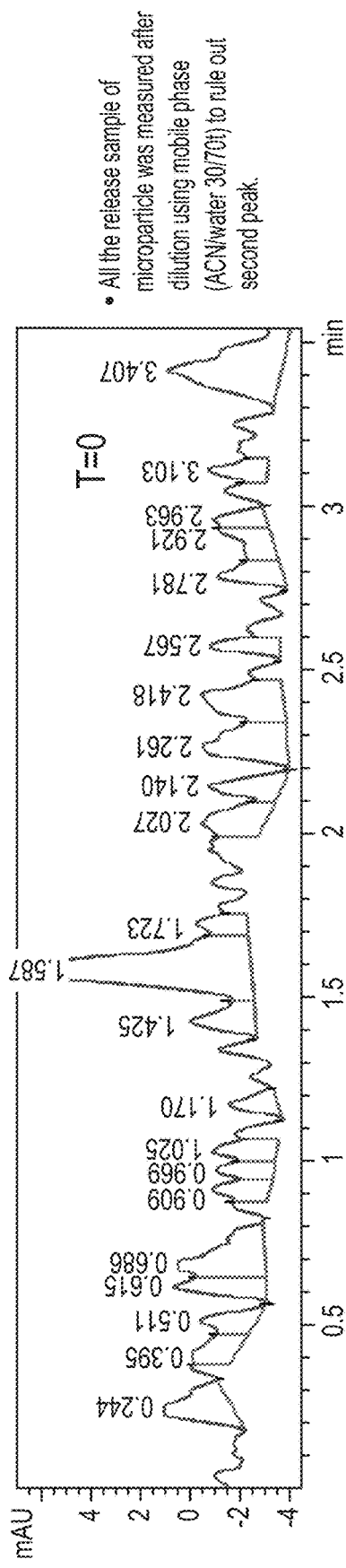
Figure 134B:
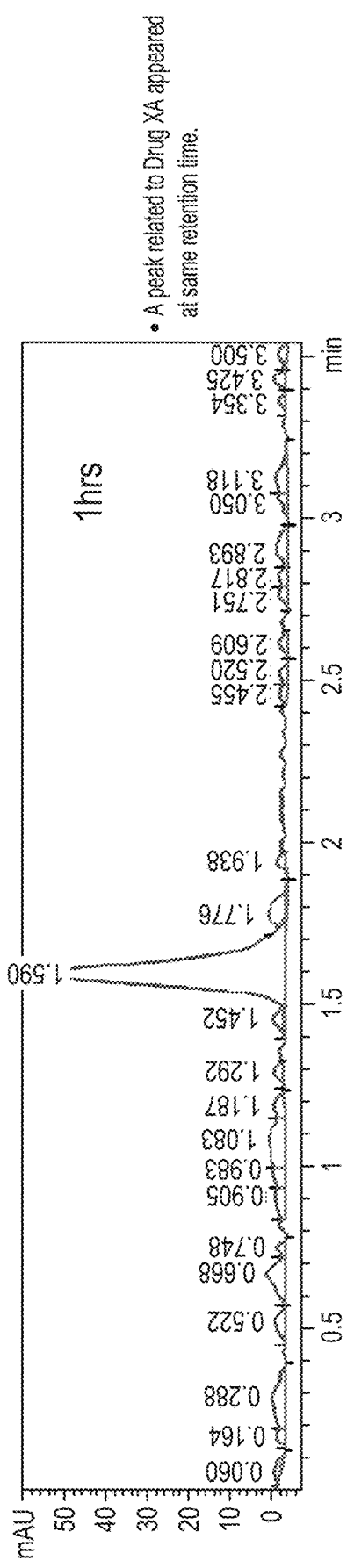
Figure 134C:
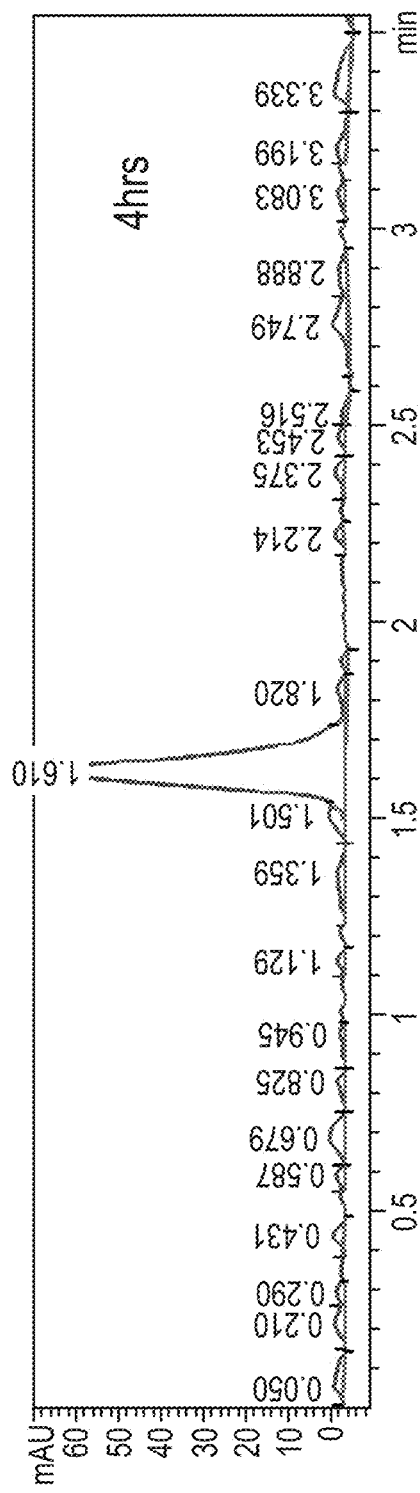
Figure 134D:
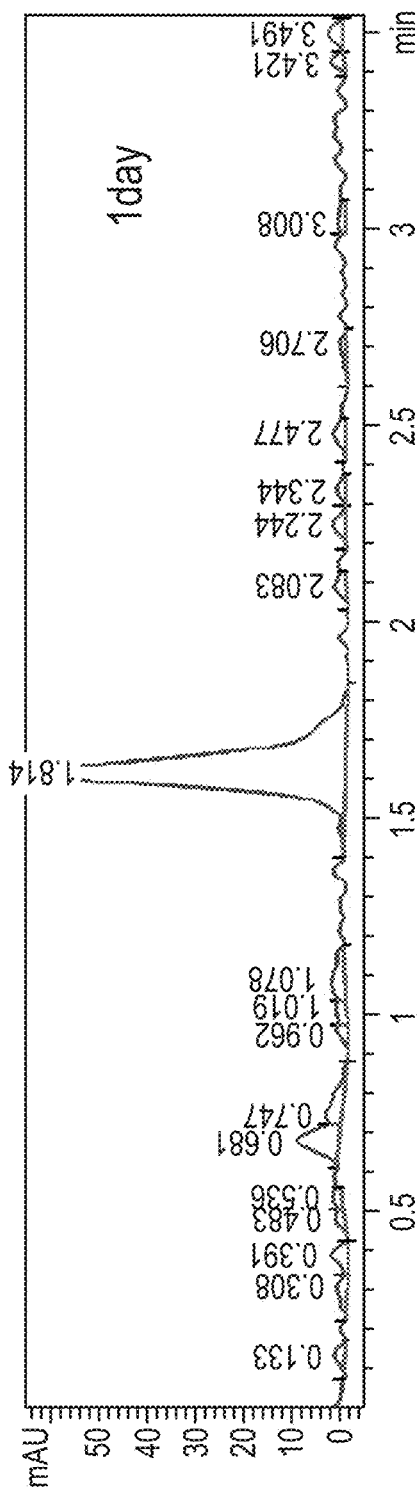
Figure 134E:
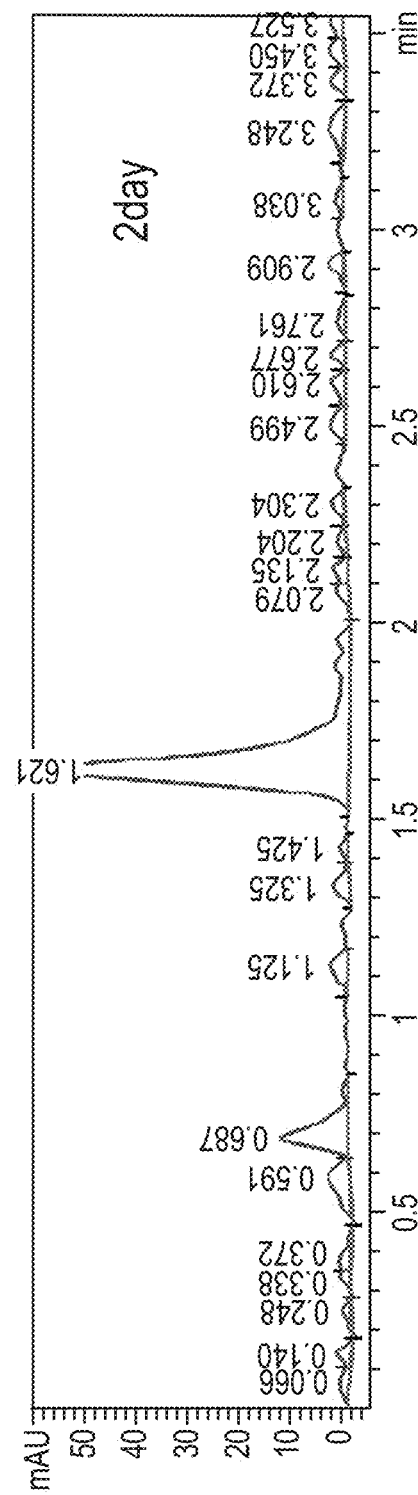
Figure 135A:
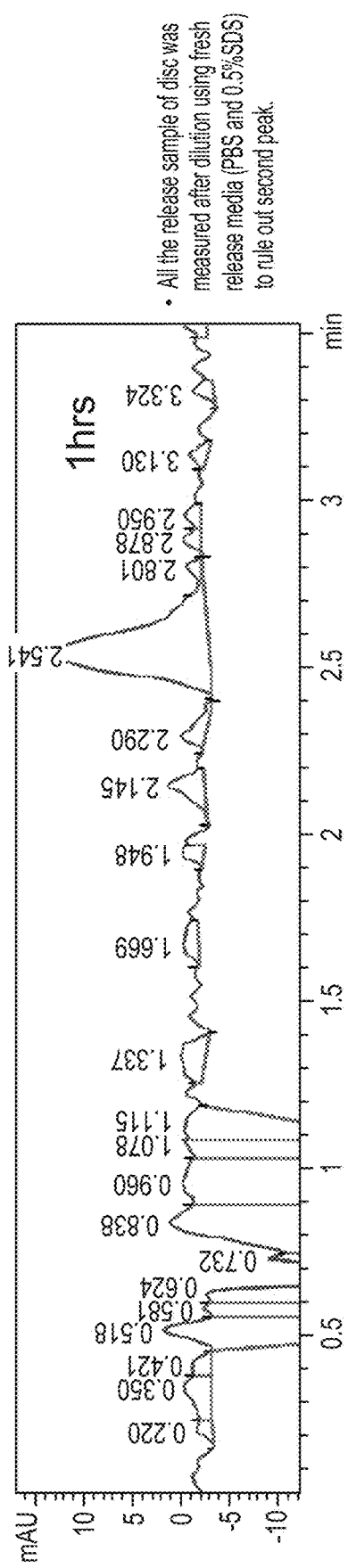
Figure 135B:
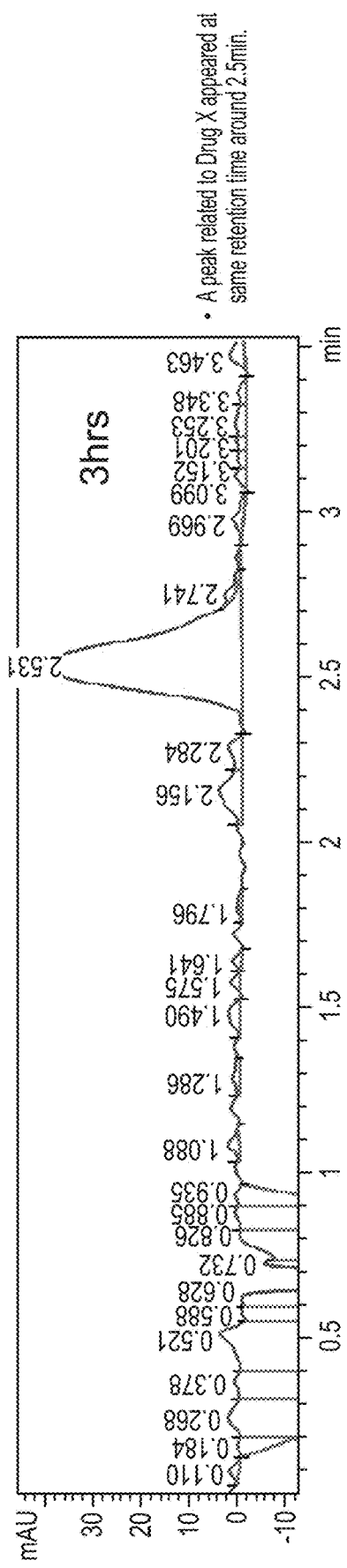
Figure 135C:
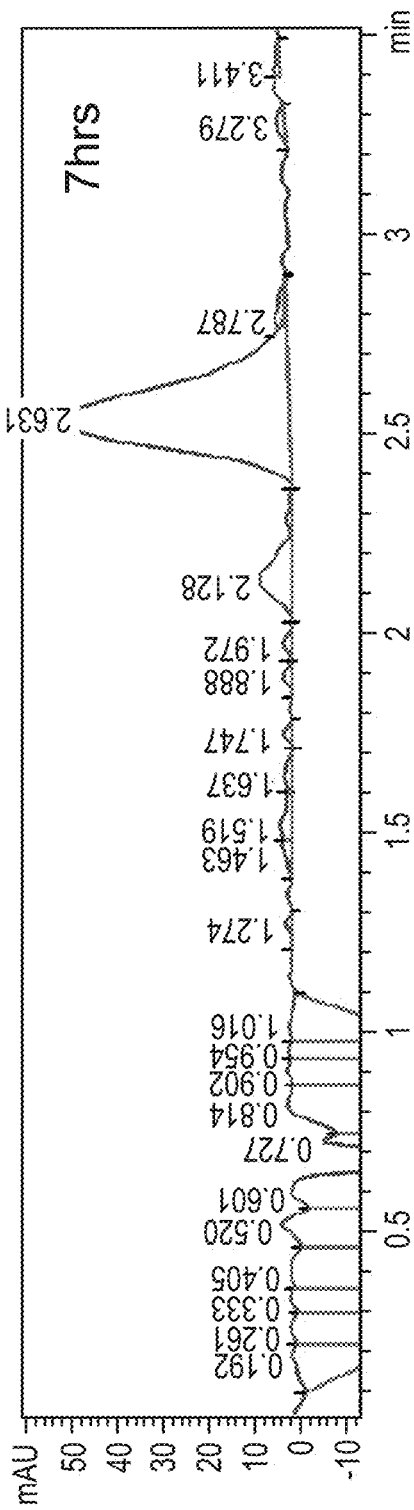
Figure 135D:
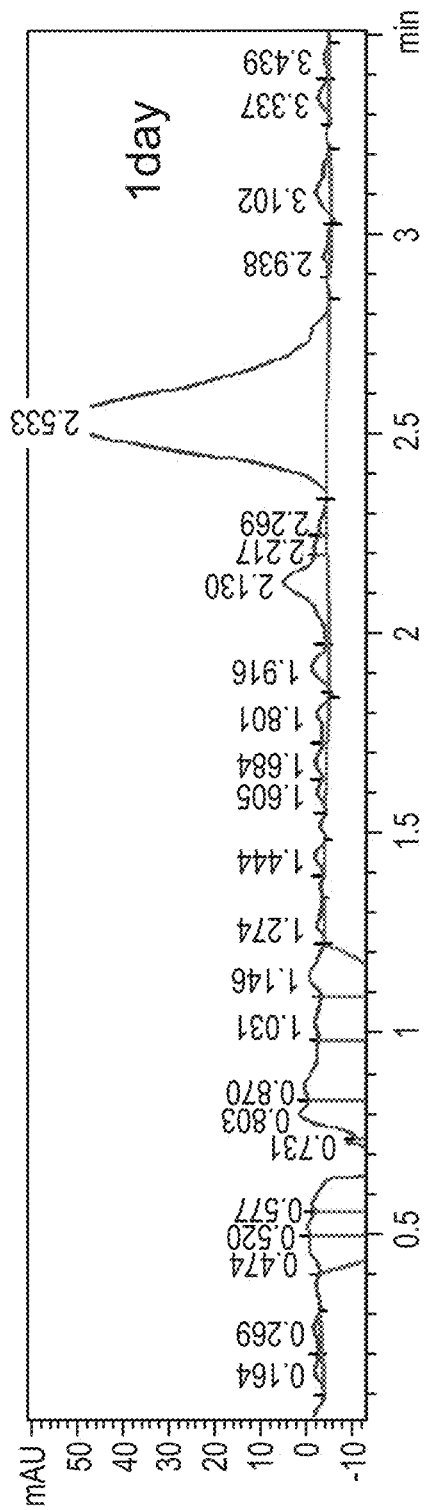
Figure 135E:
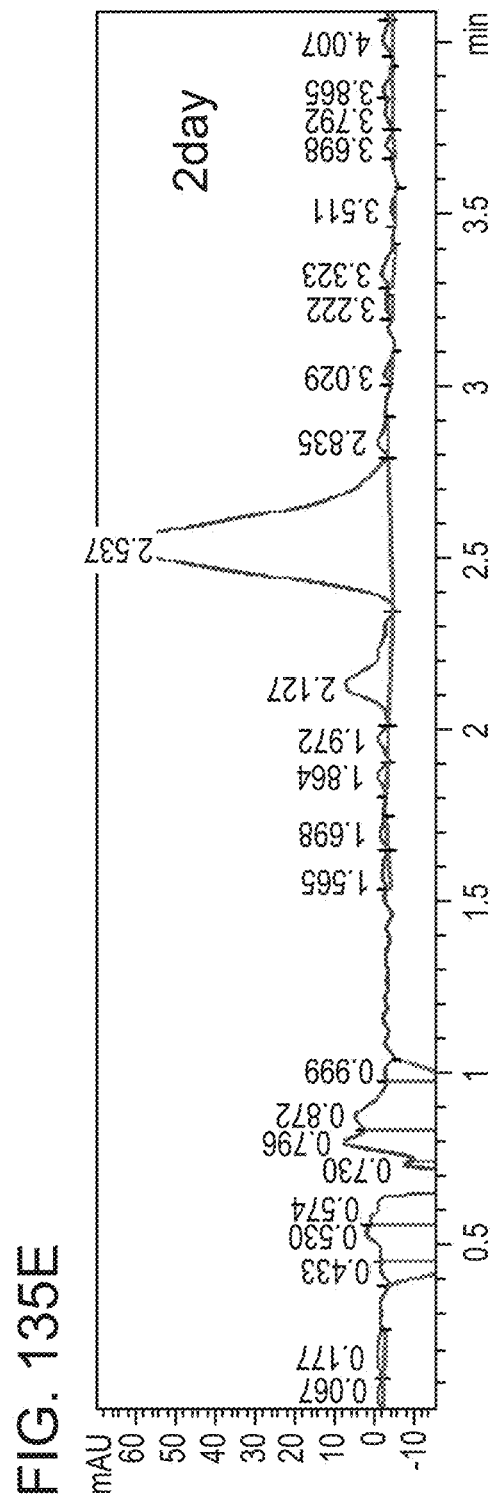
Figures 136A, 136B:
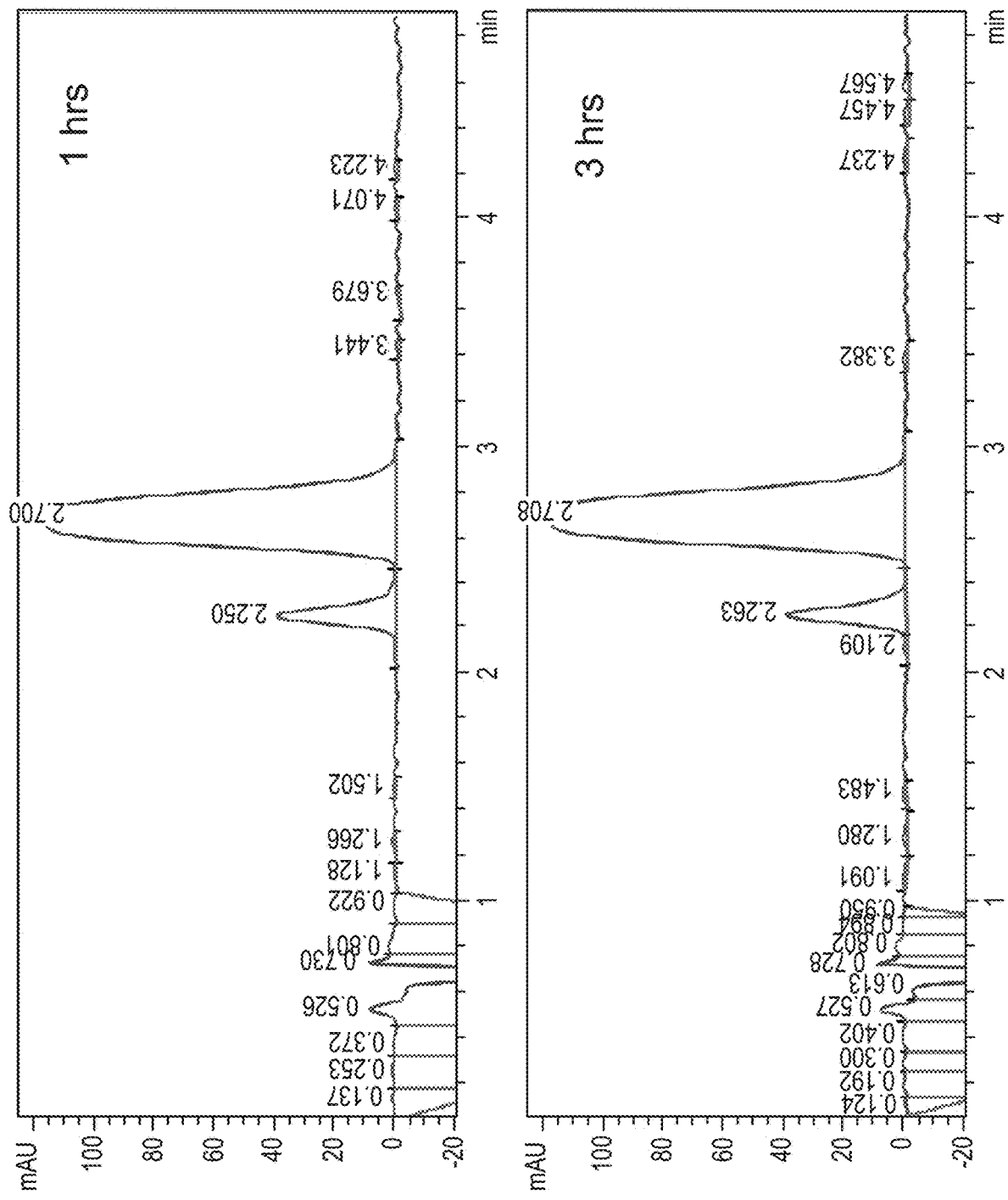
Figure 136C:
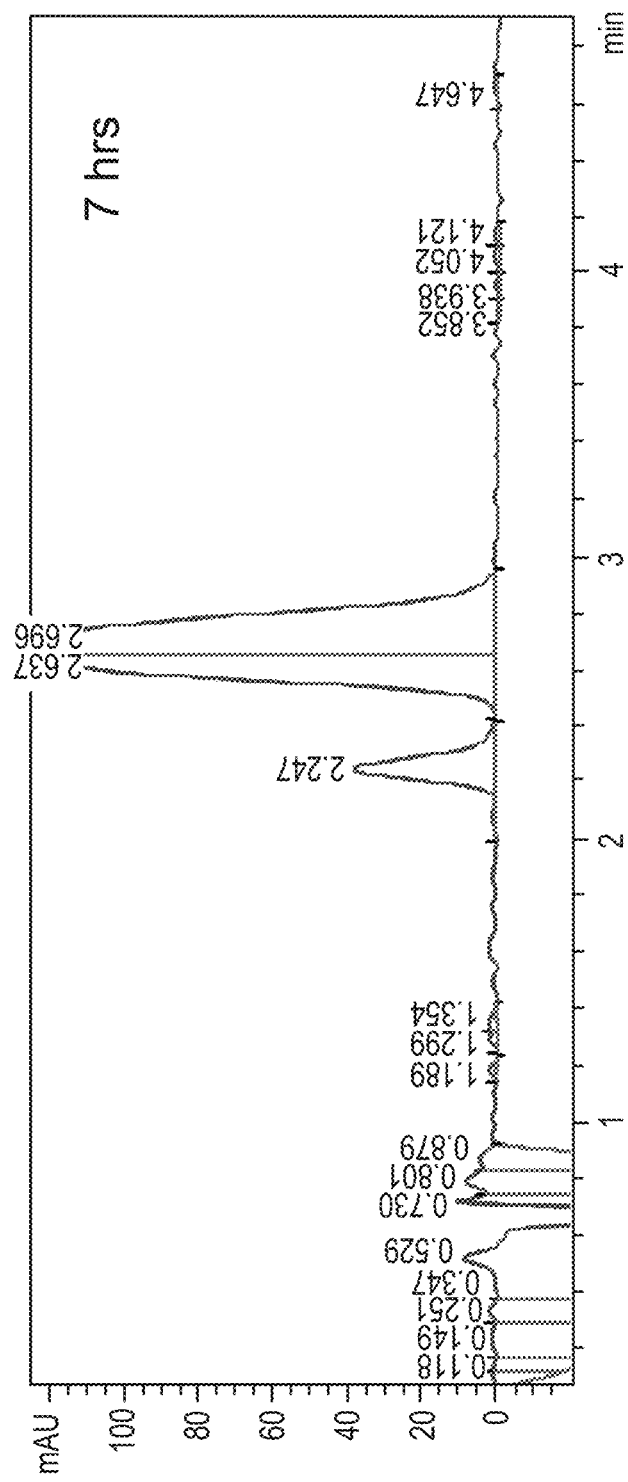
Figures 136D, 136E:
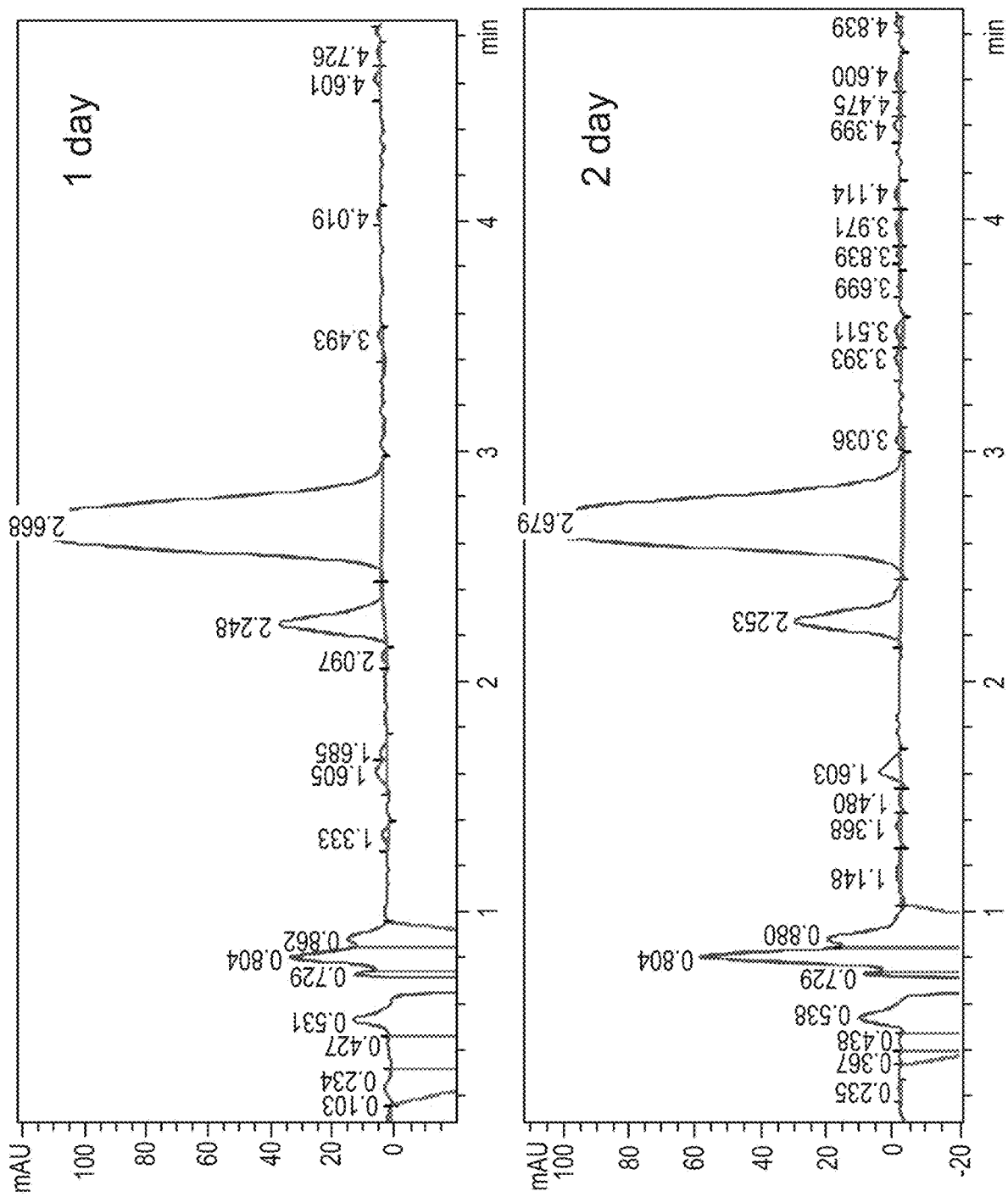
Figures 136F, 136G:
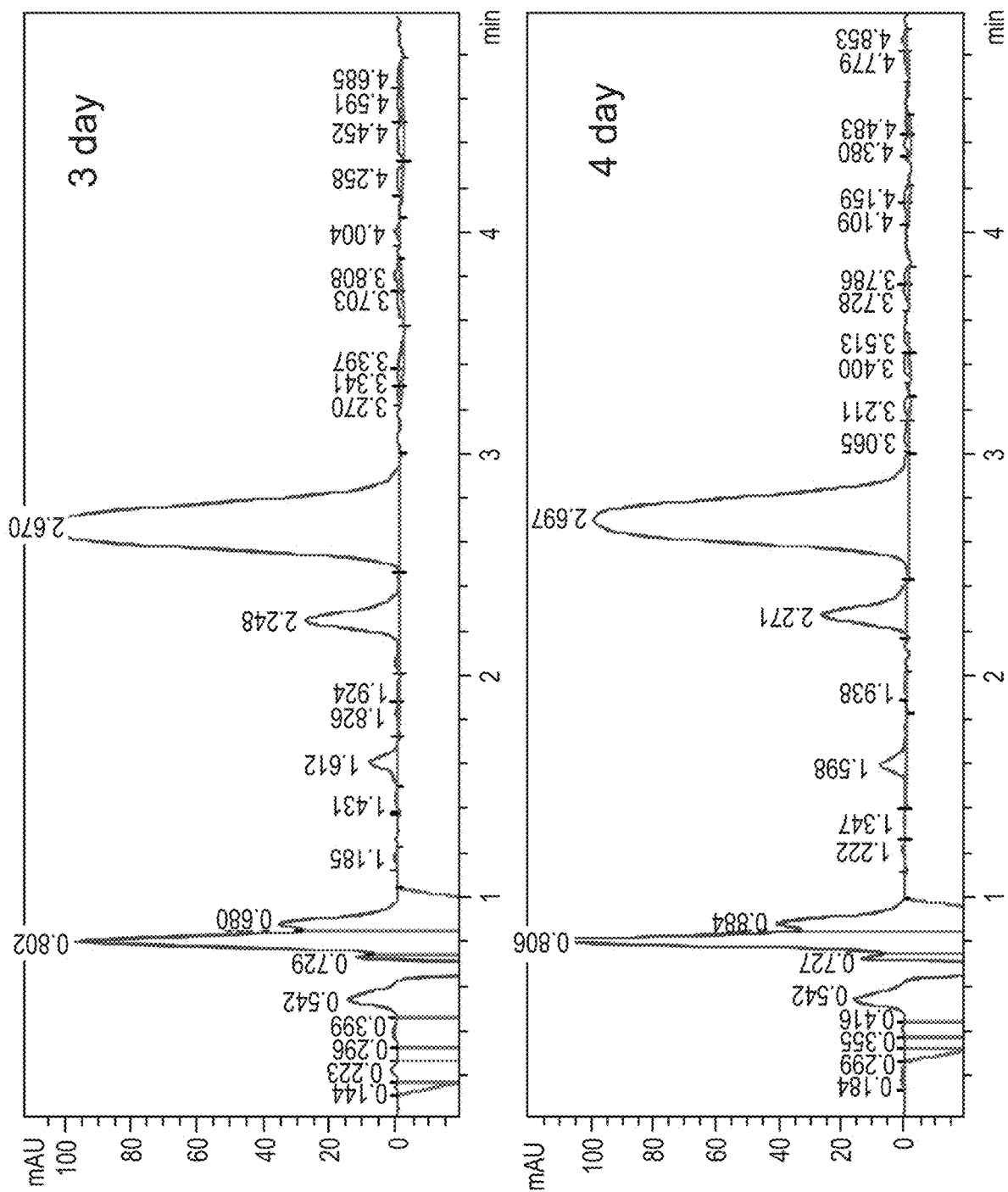
Figures 137A, 137B:
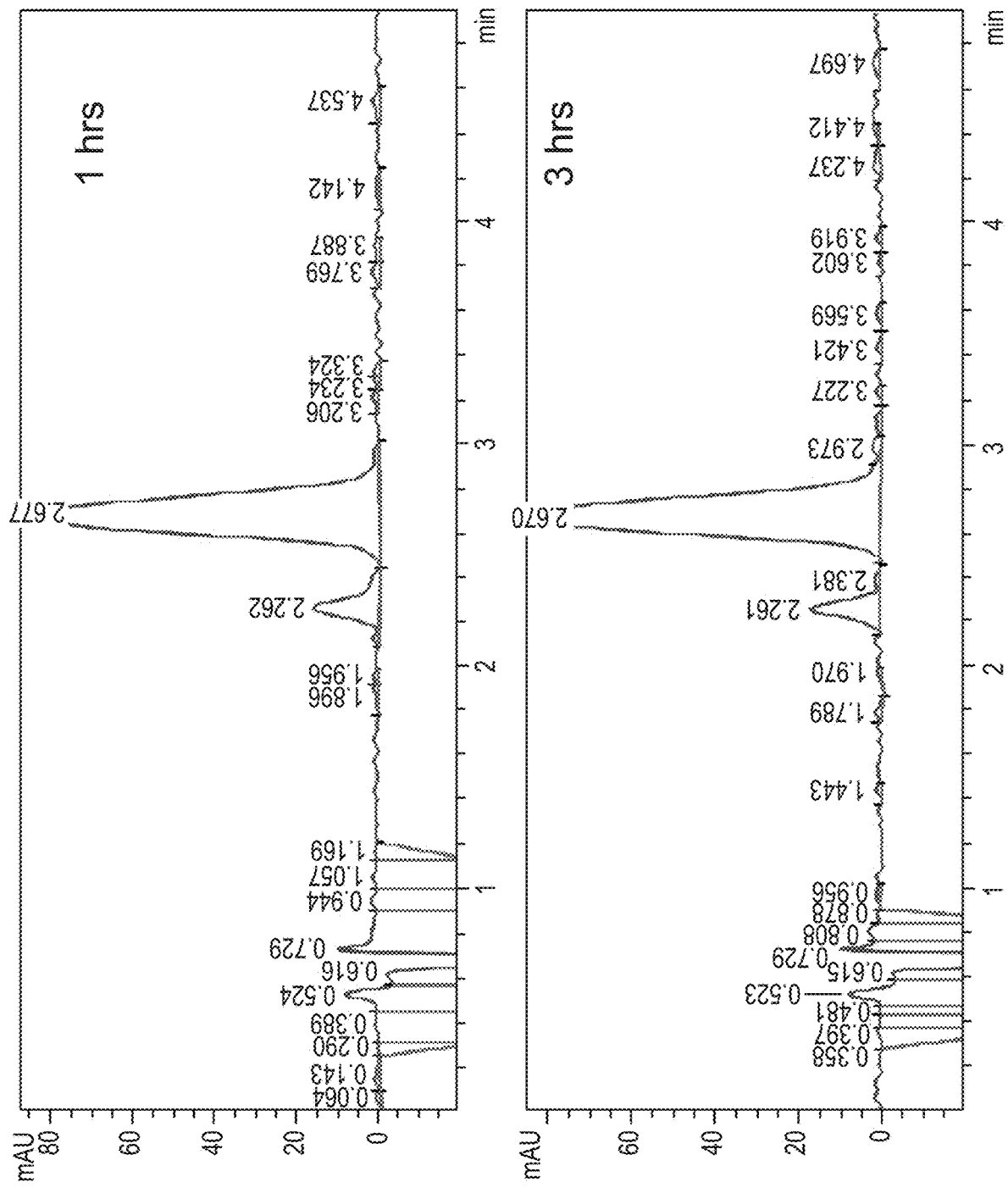
Figures 137C, 137D:
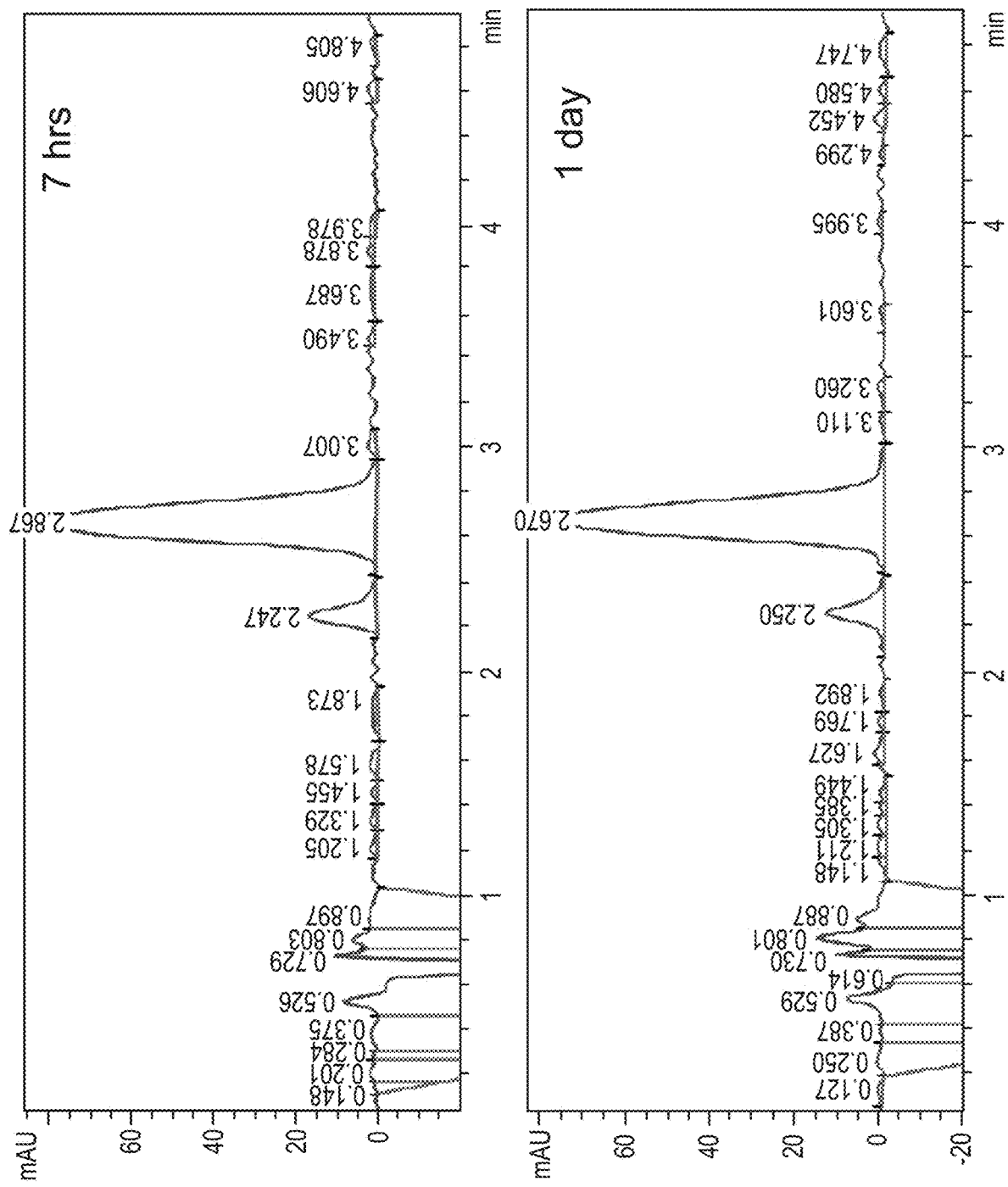
Figures 137E, 137F:
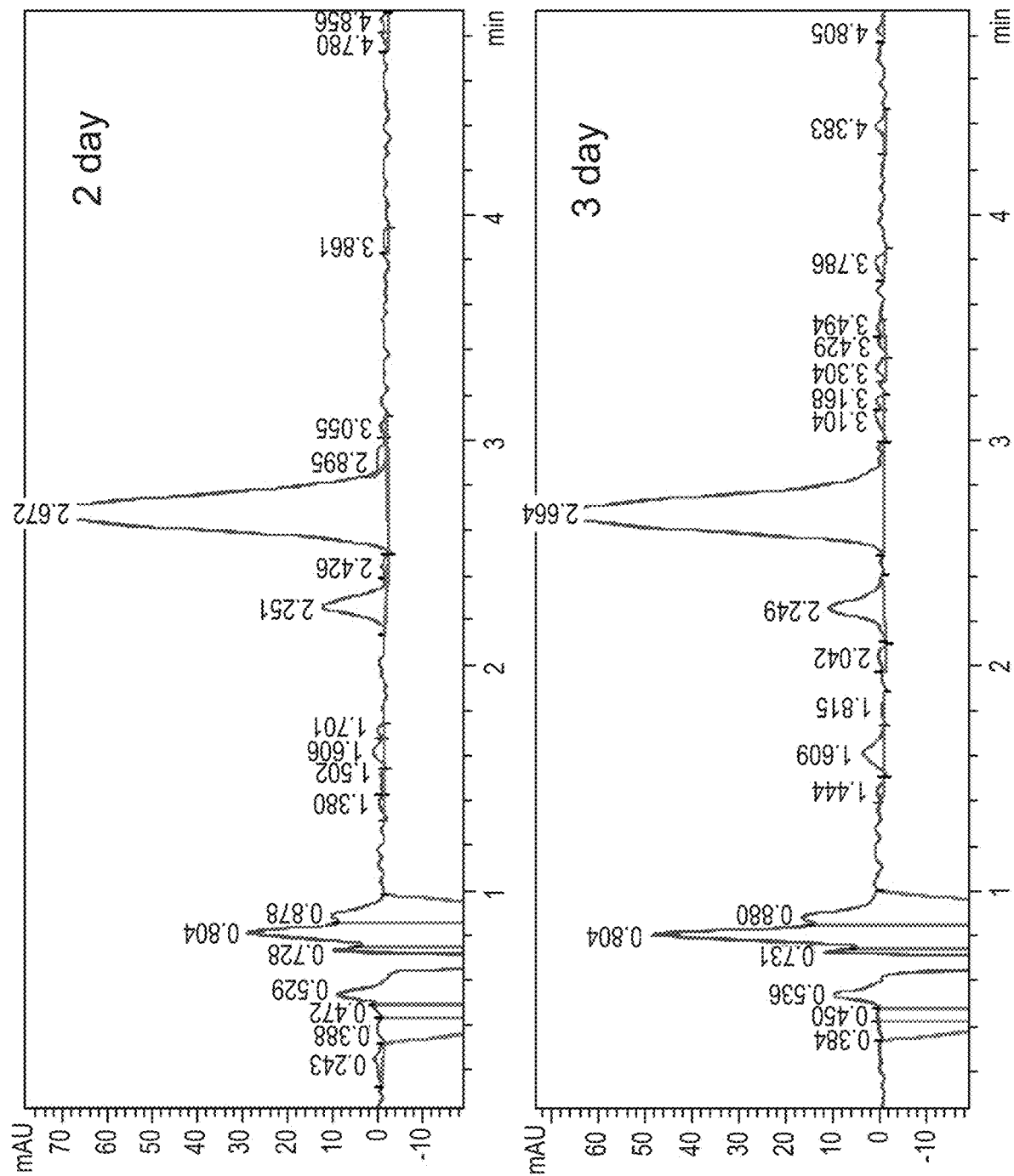
Figure 137G:
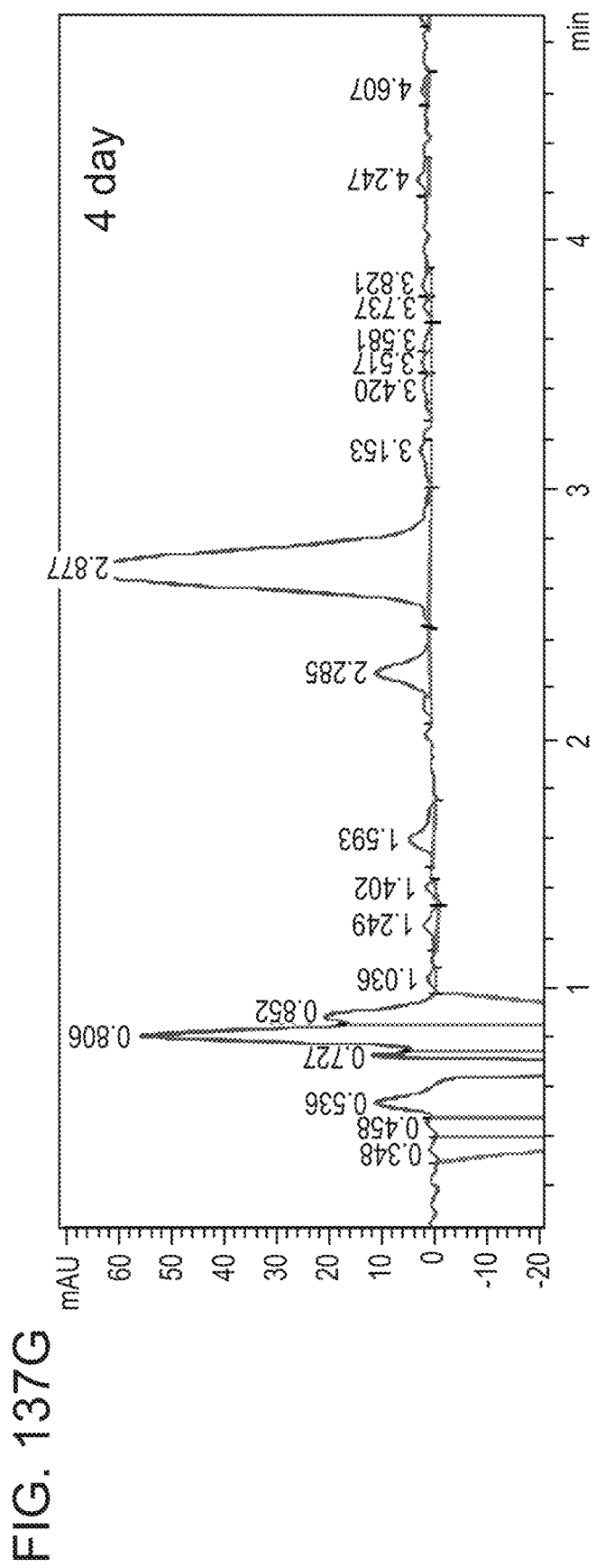
Figures 138A, 138B:
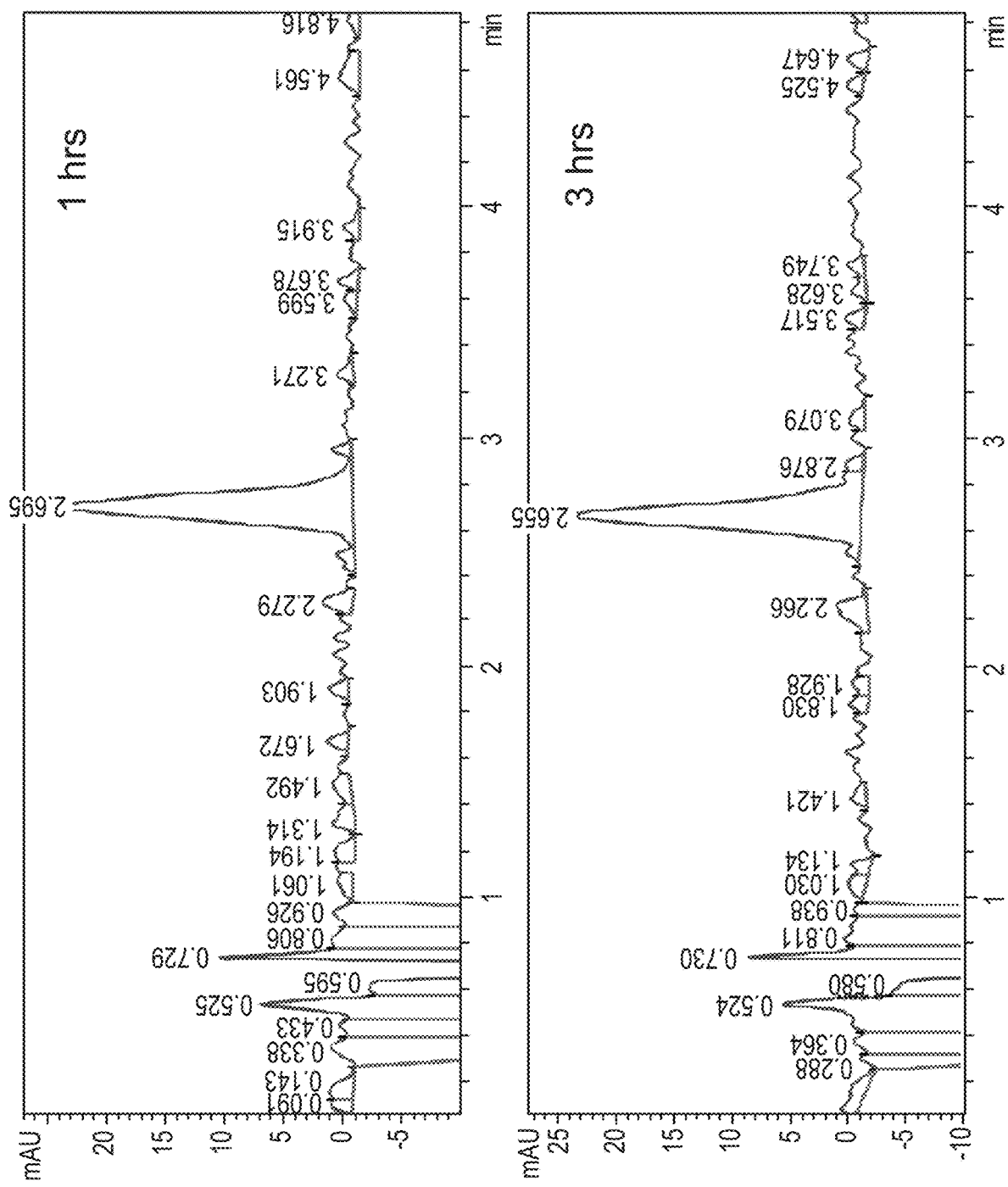
Figures 138C, 138D:
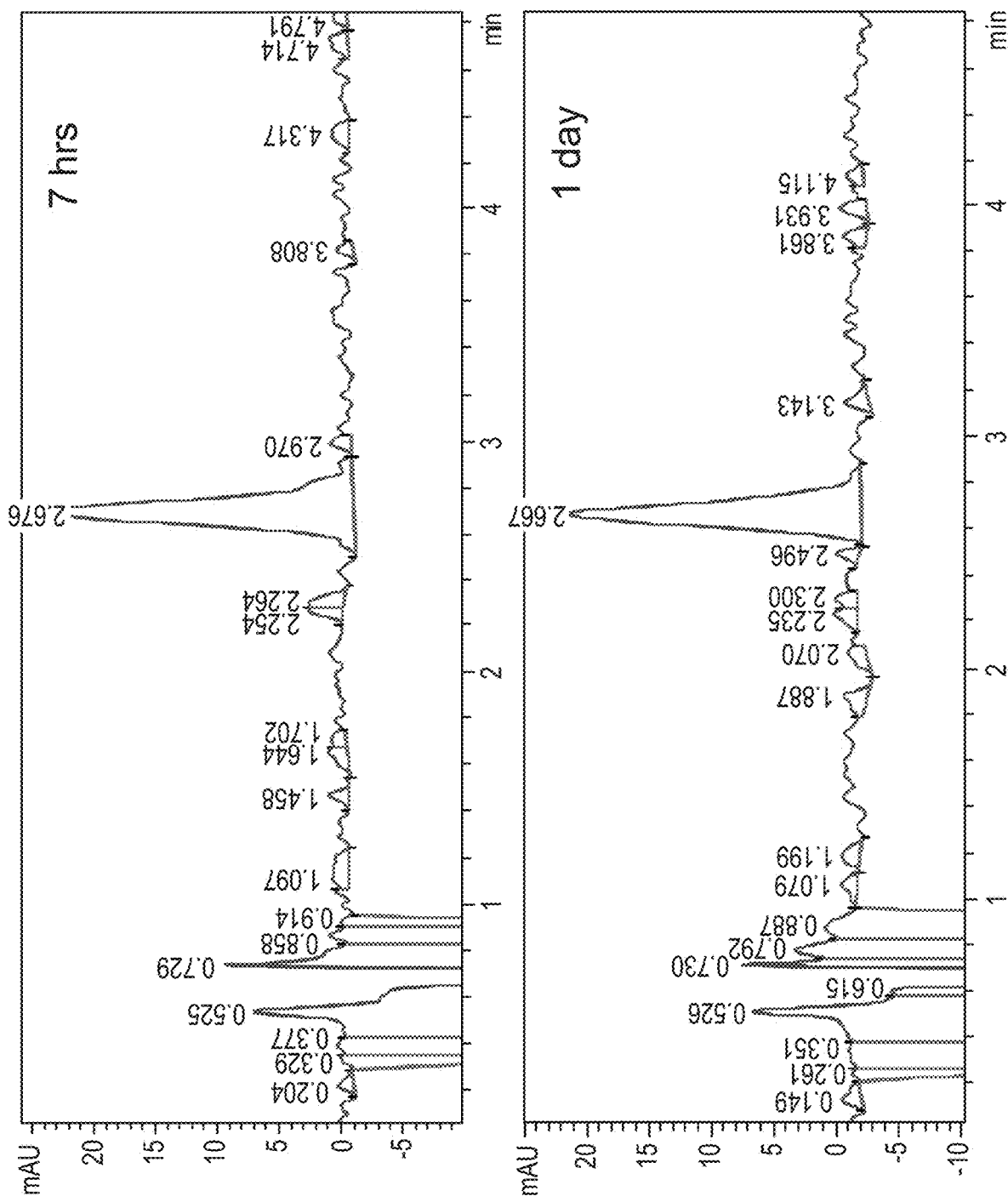
Figures 138E, 138F:
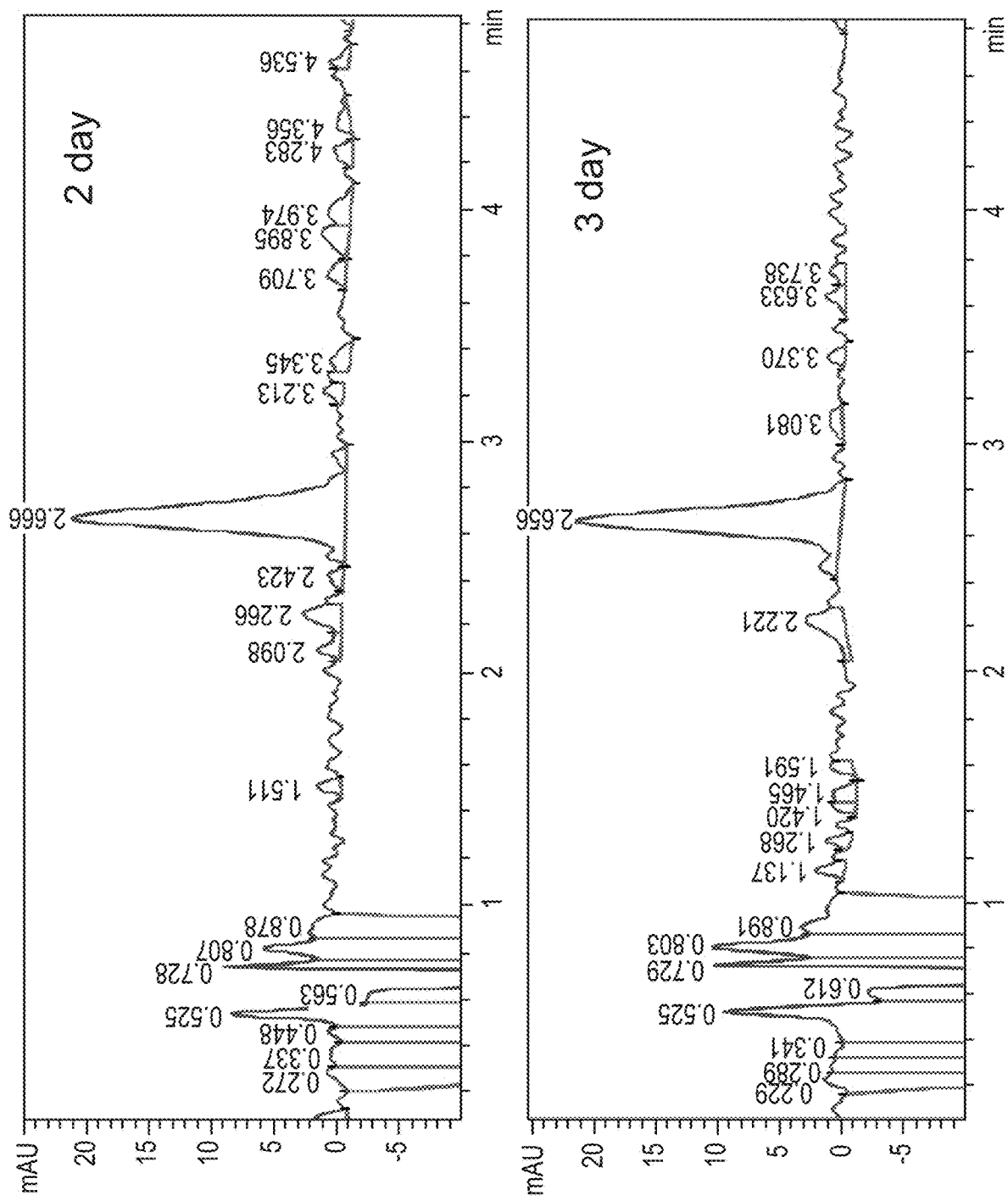
Figure 138G:
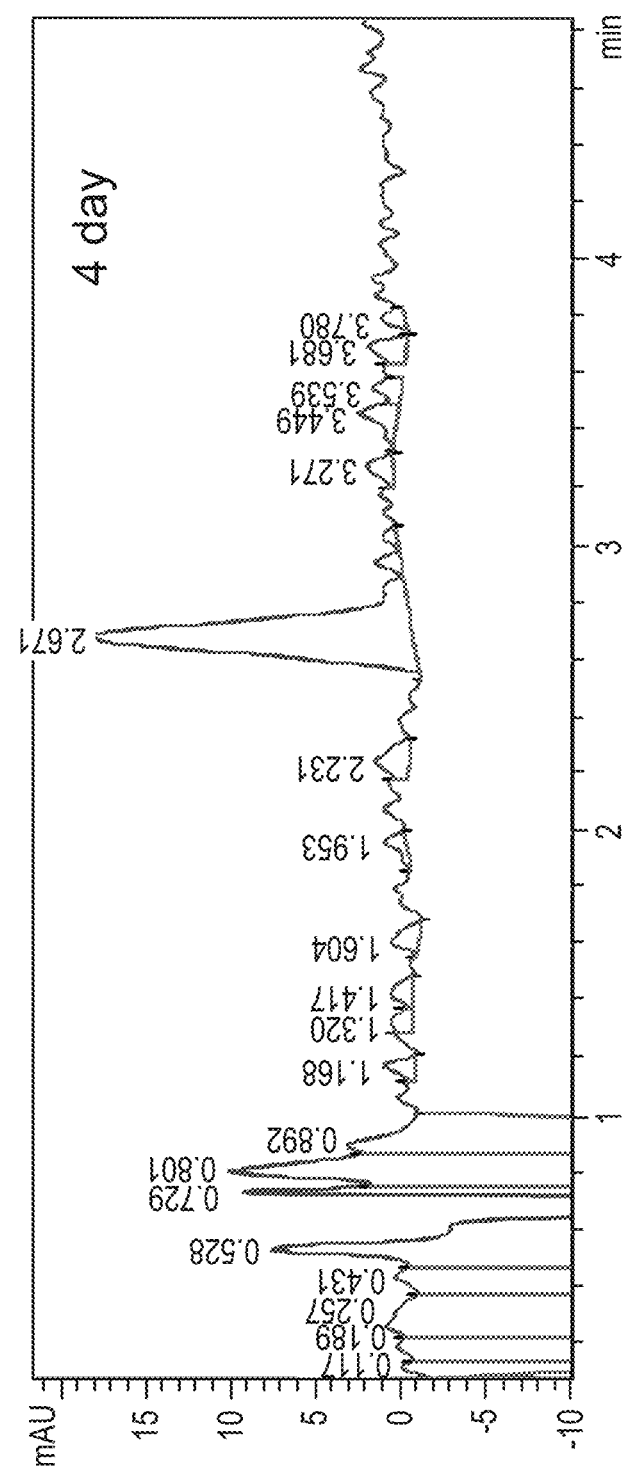
Figures 139A, 139B:
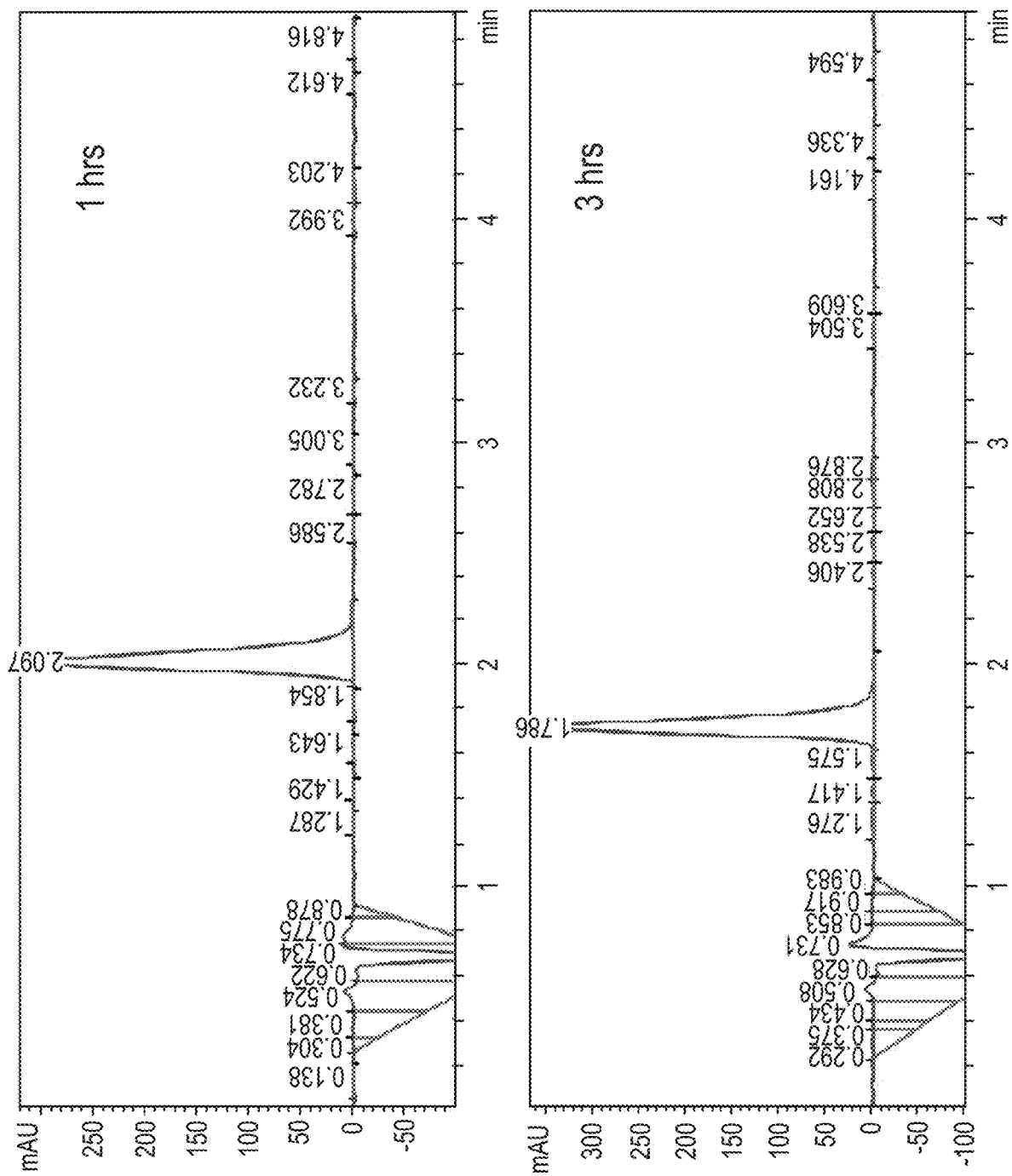
Figures 139C, 139D:
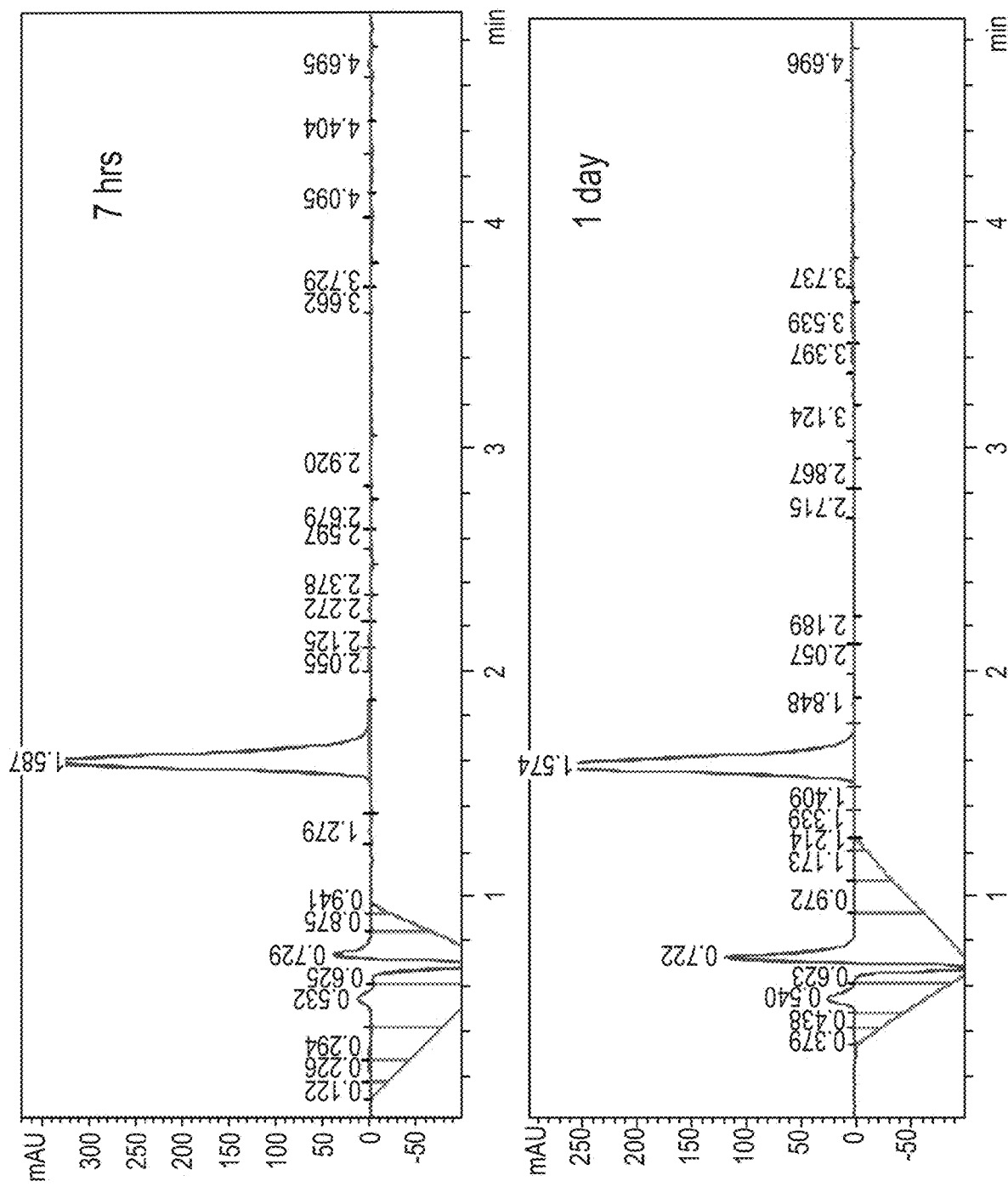
Figure 139E:
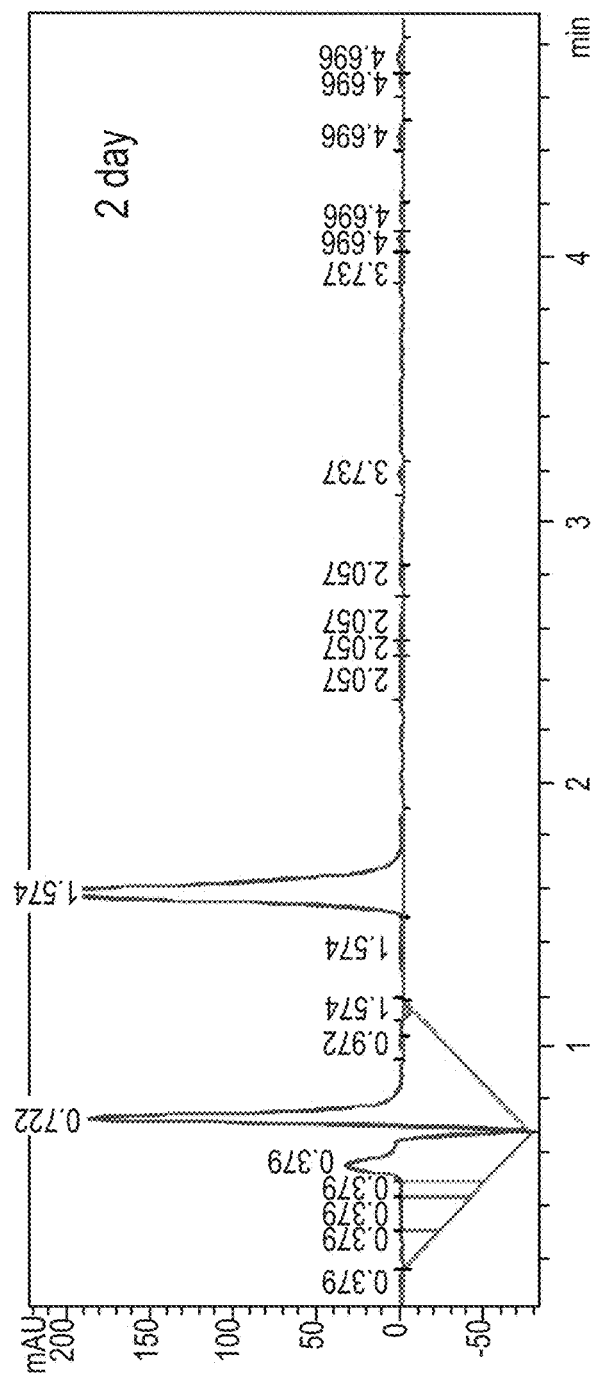
Figure 139F:
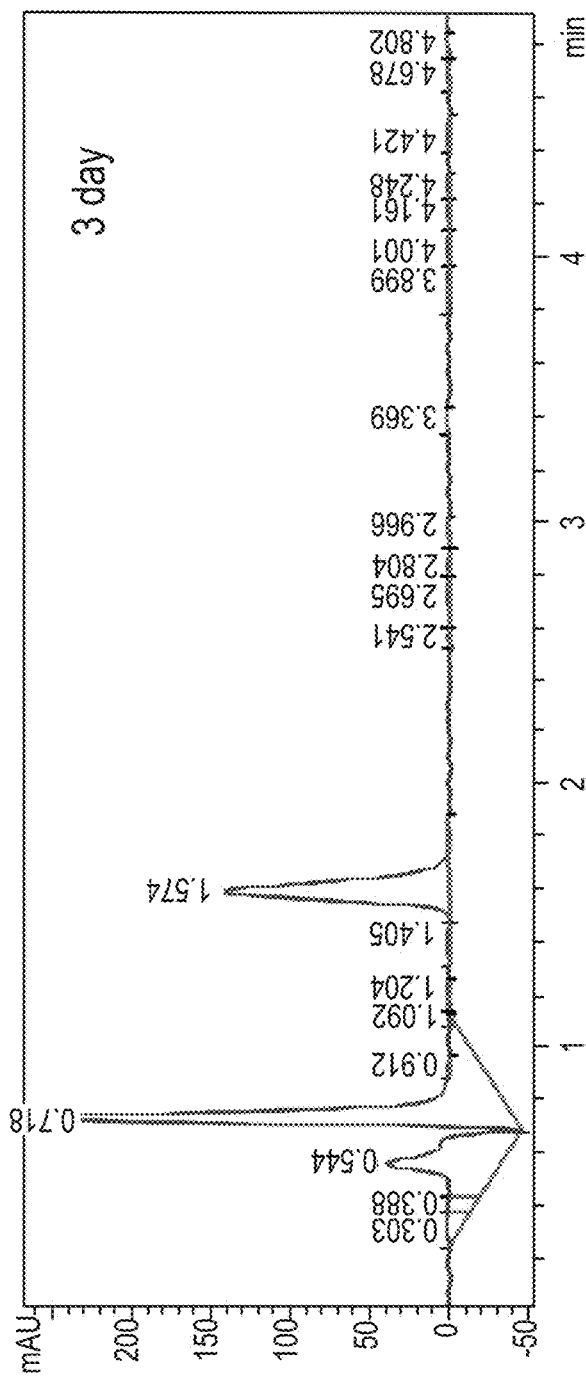
Figure 139G:
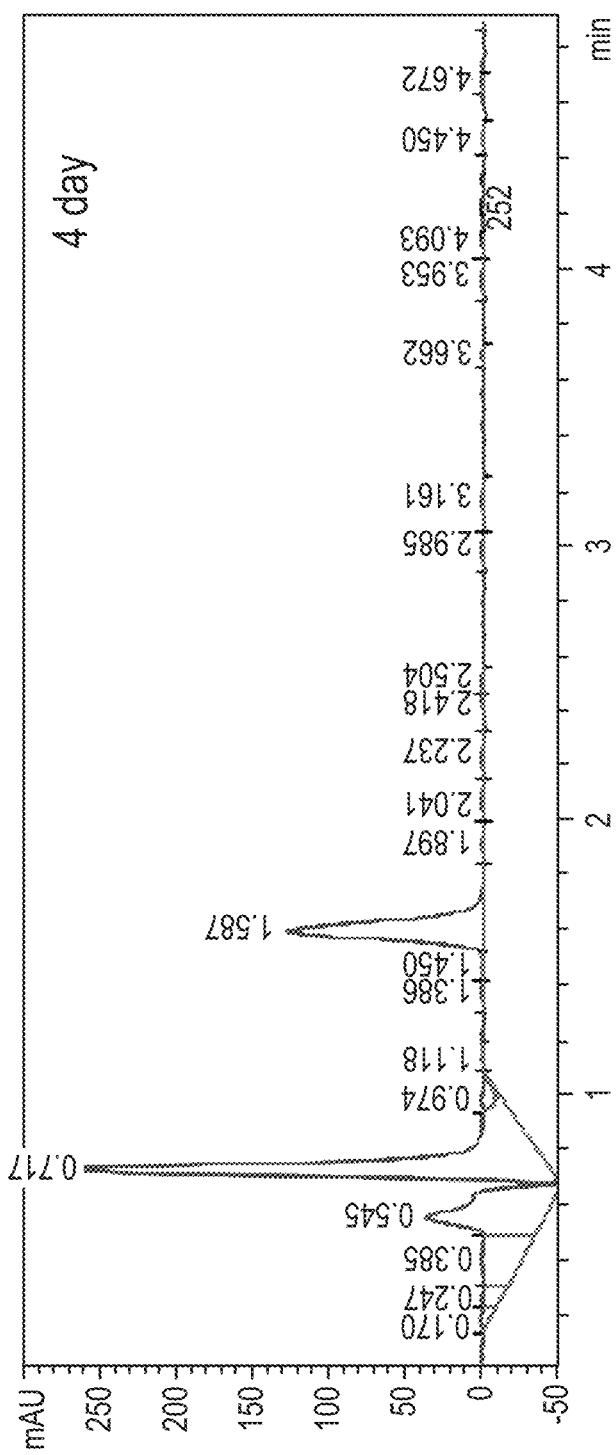
Figure 140A:
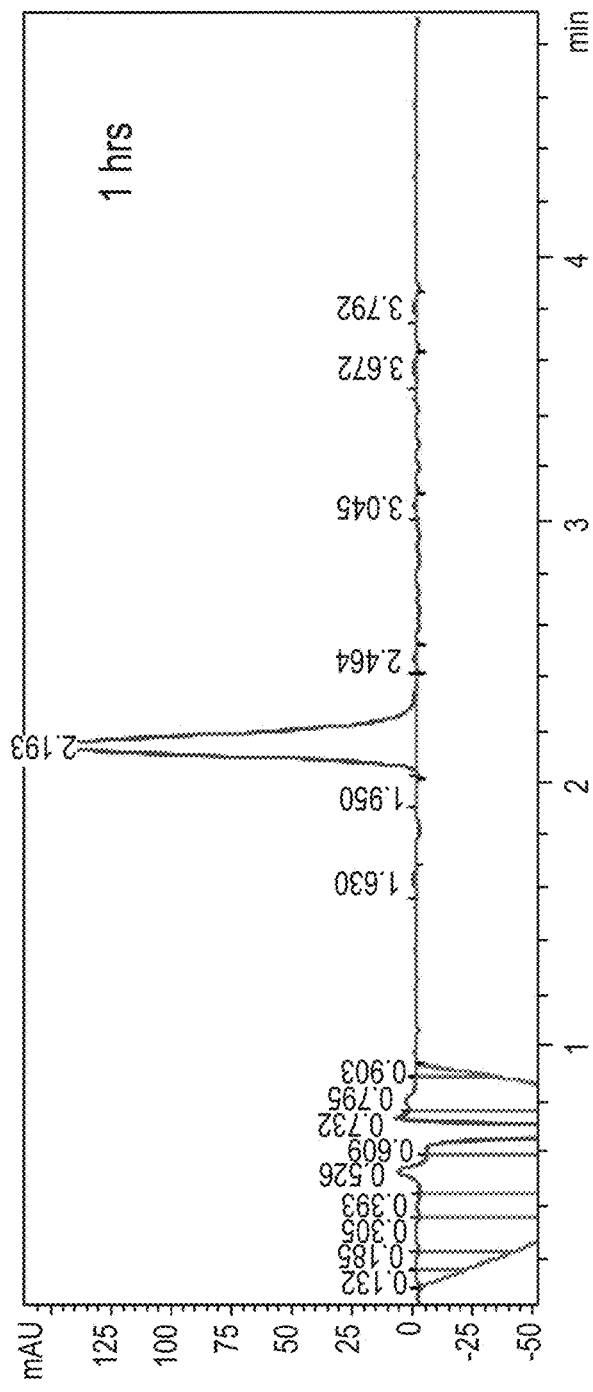
Figure 140B:
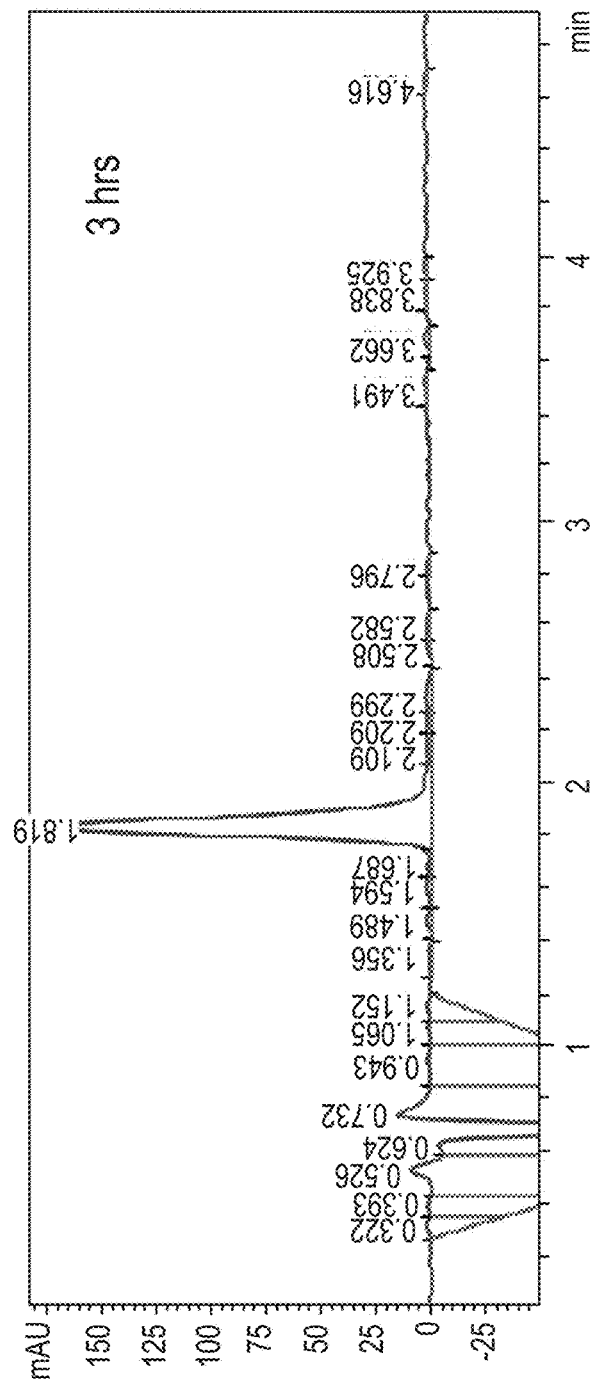
Figures 140C, 140D:
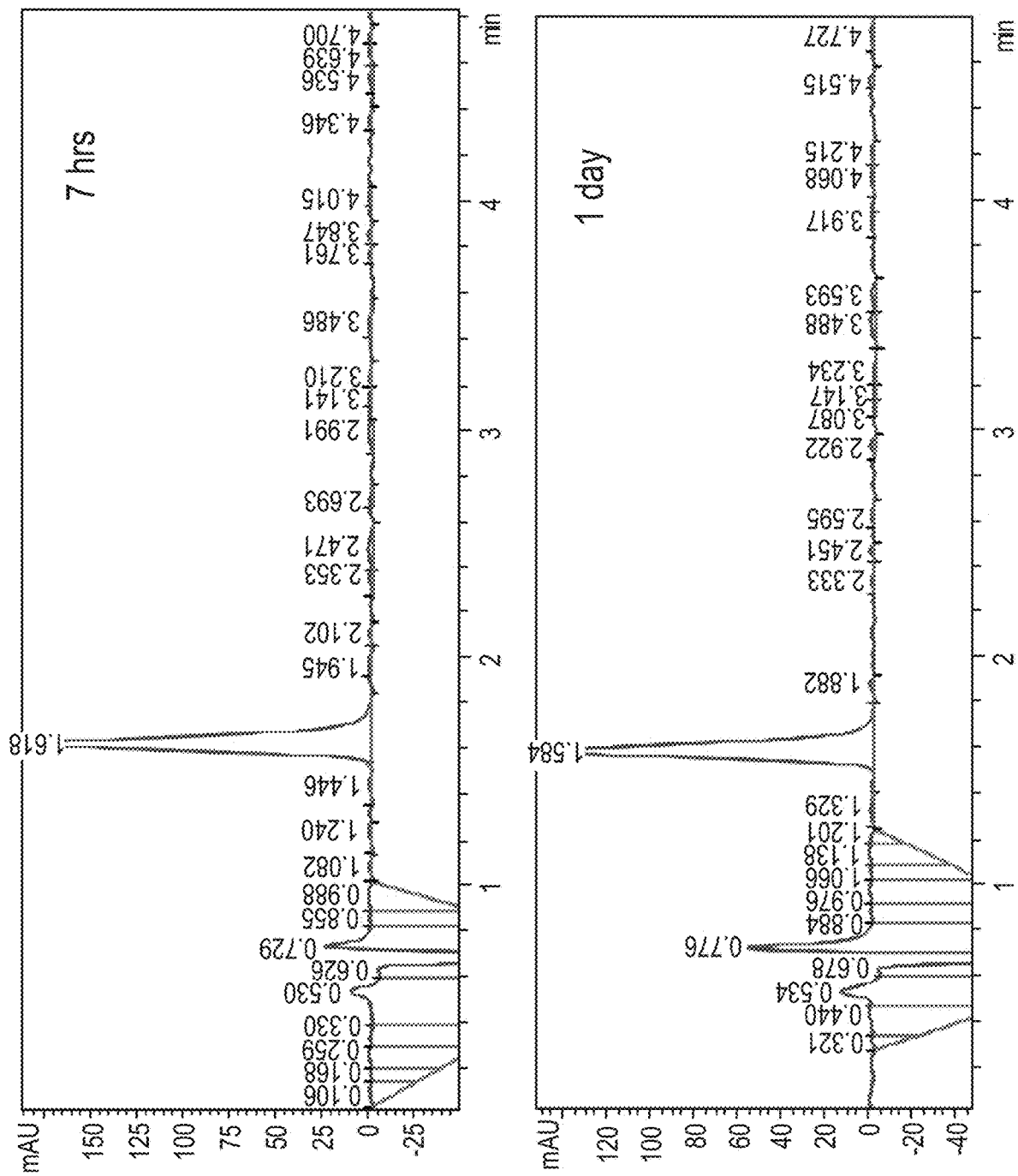
Figure 140E:
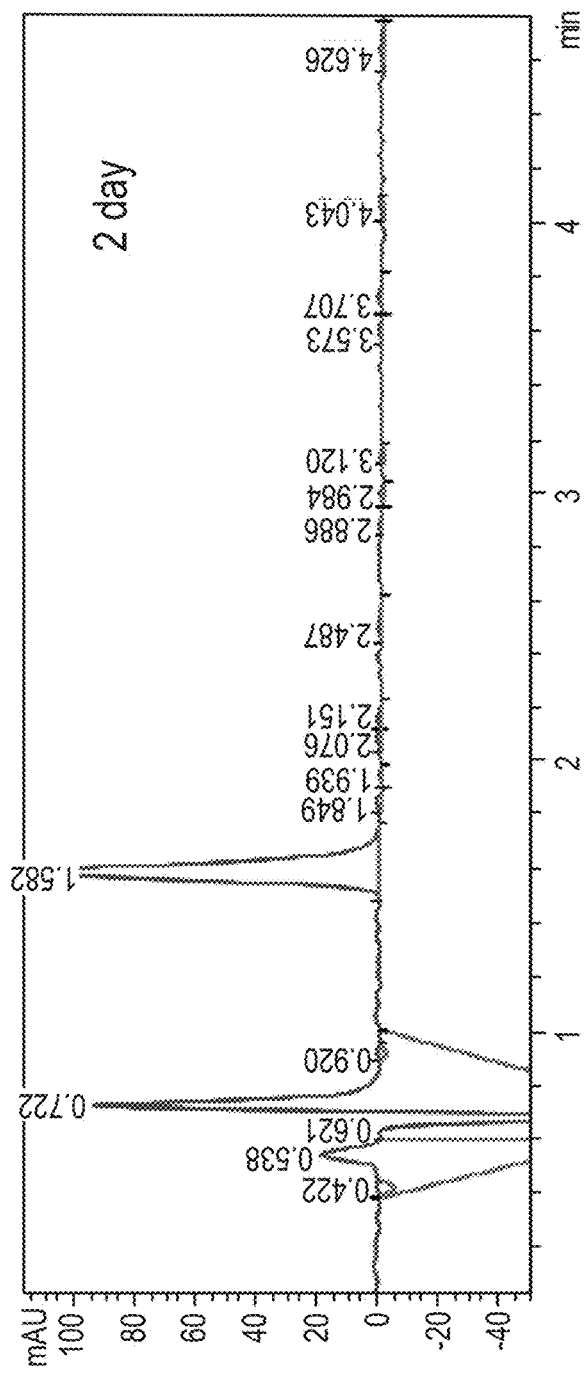
Figure 140F:
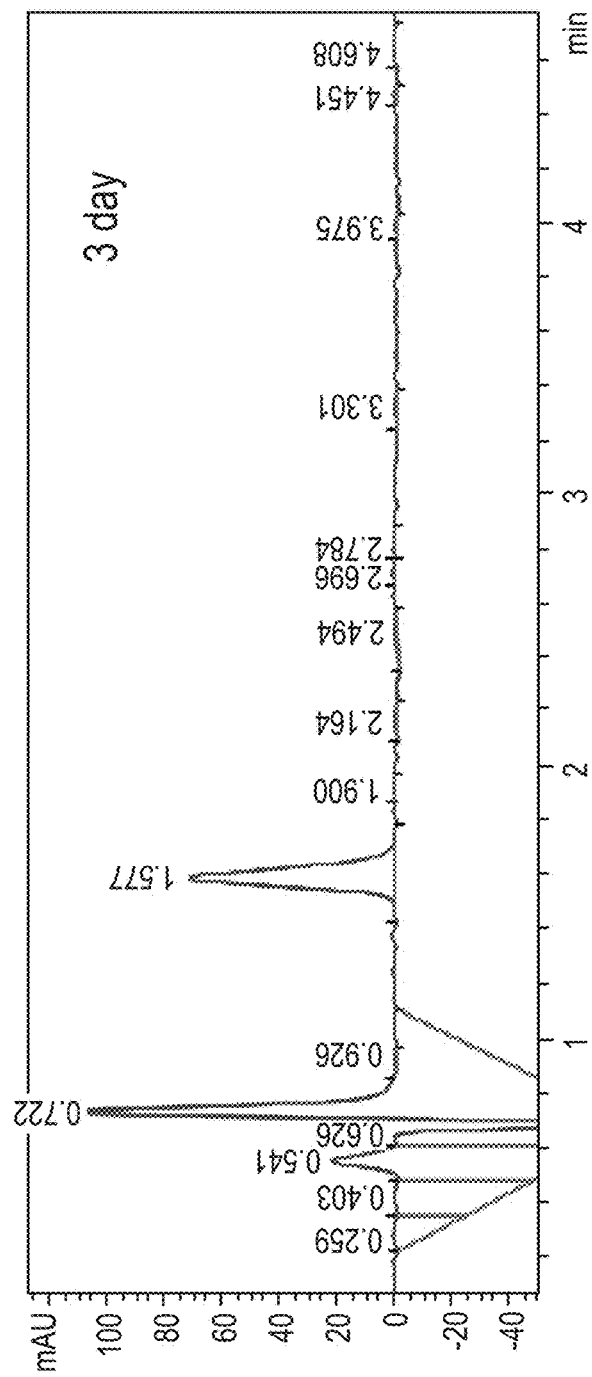
Figure 140G:
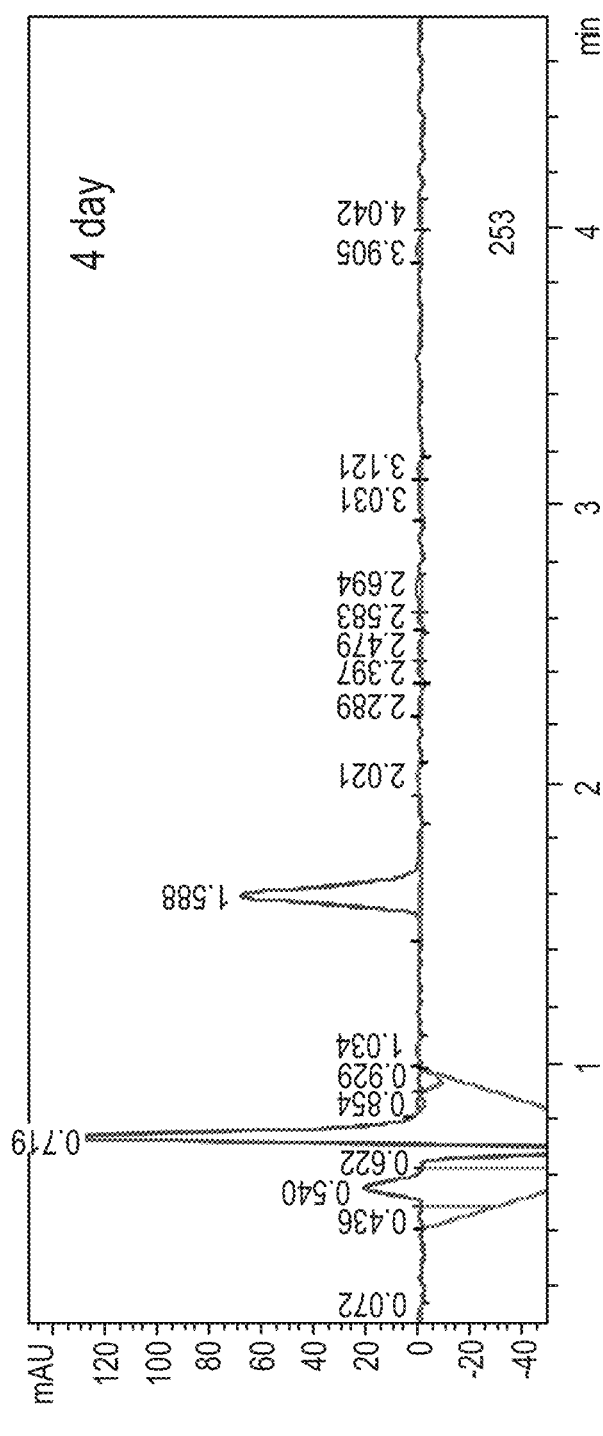
Figure 141C:
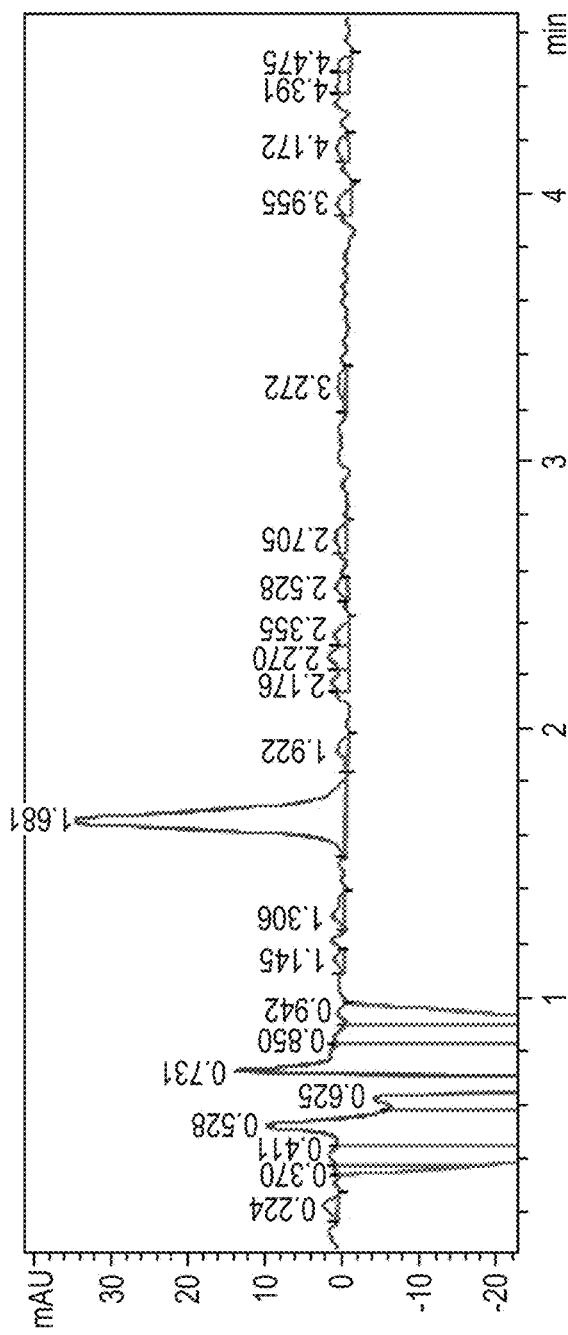
Figure 141D:
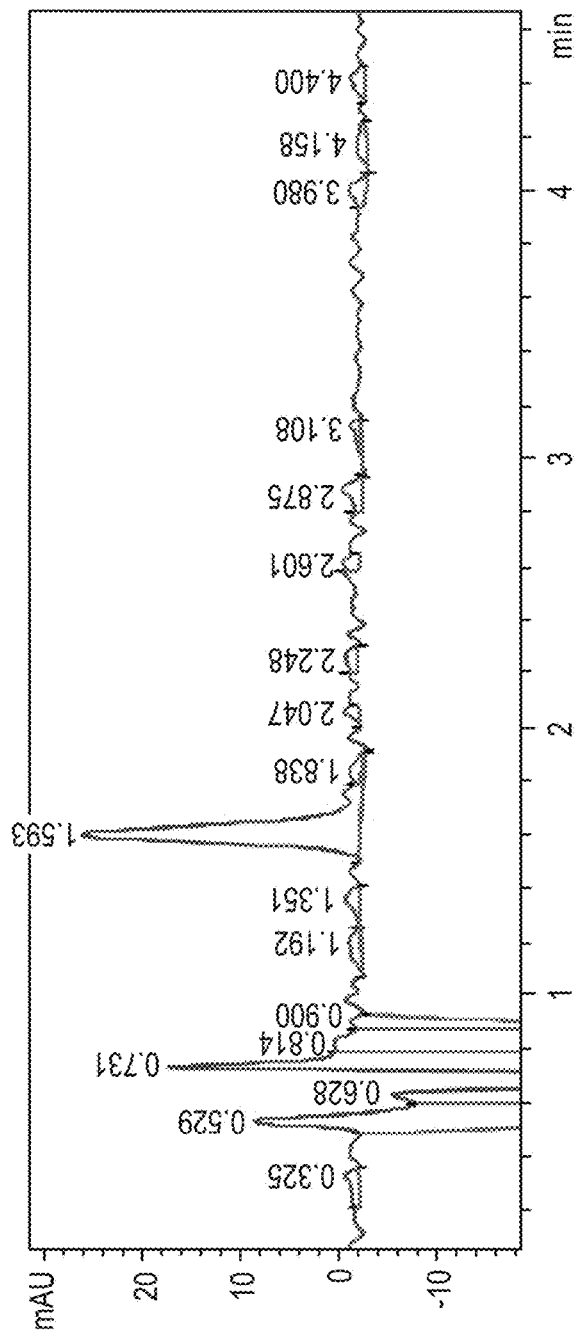
Figure 141E:
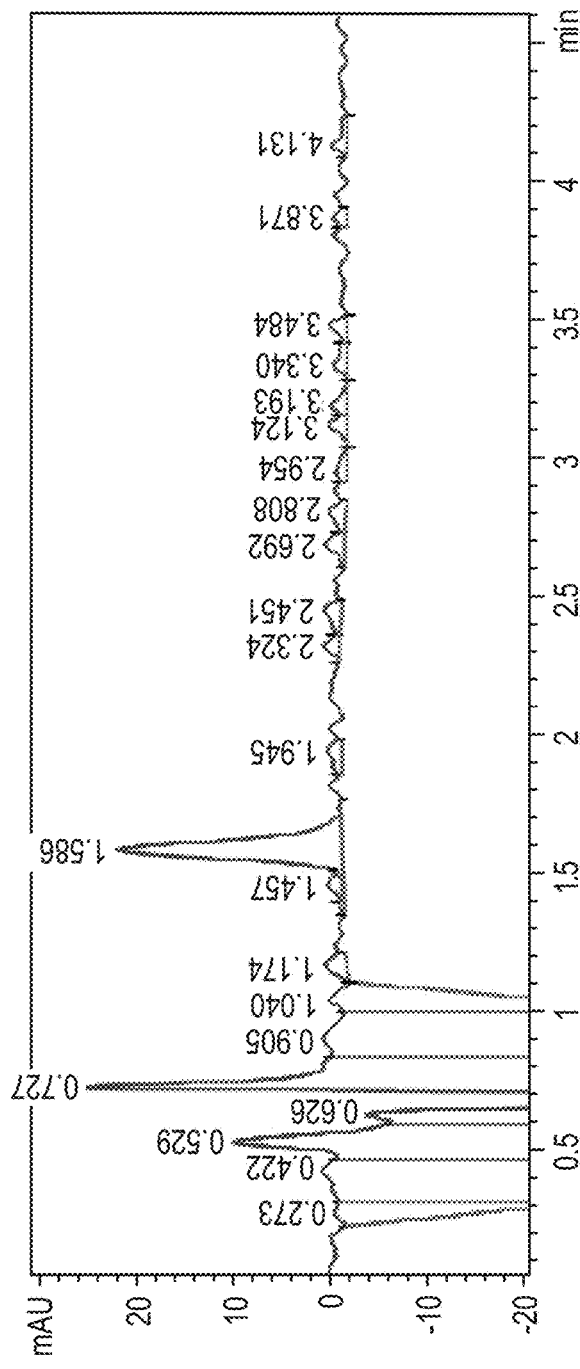
Figure 141F:
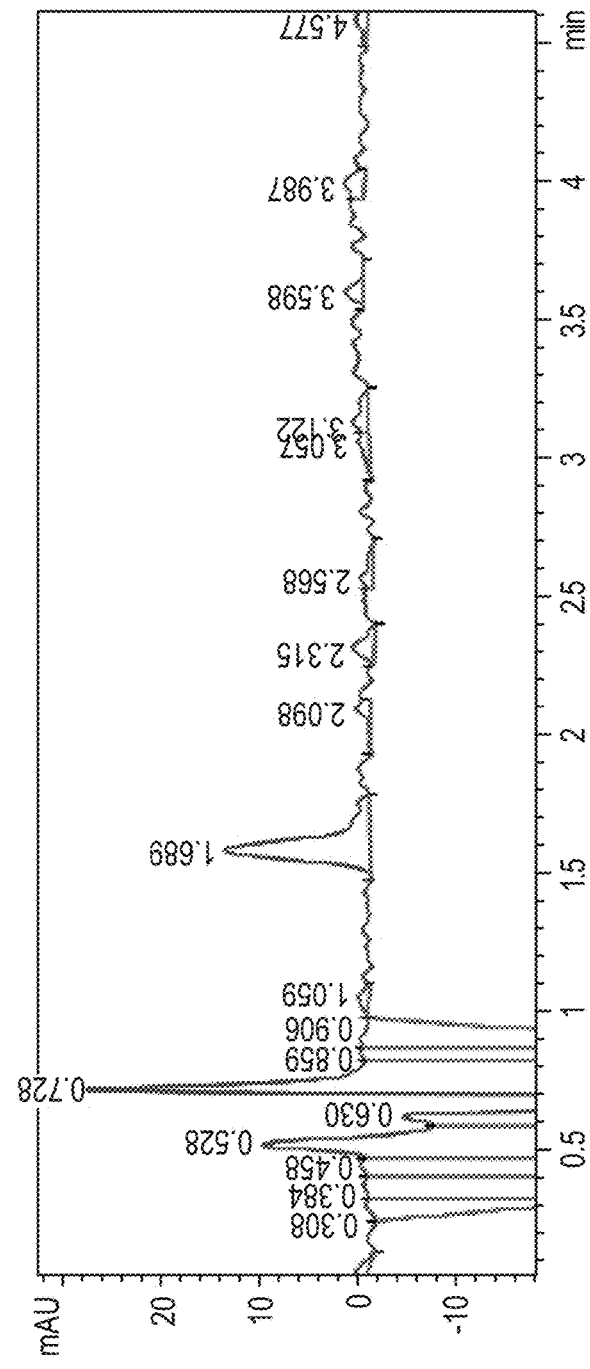
Figure 141G:
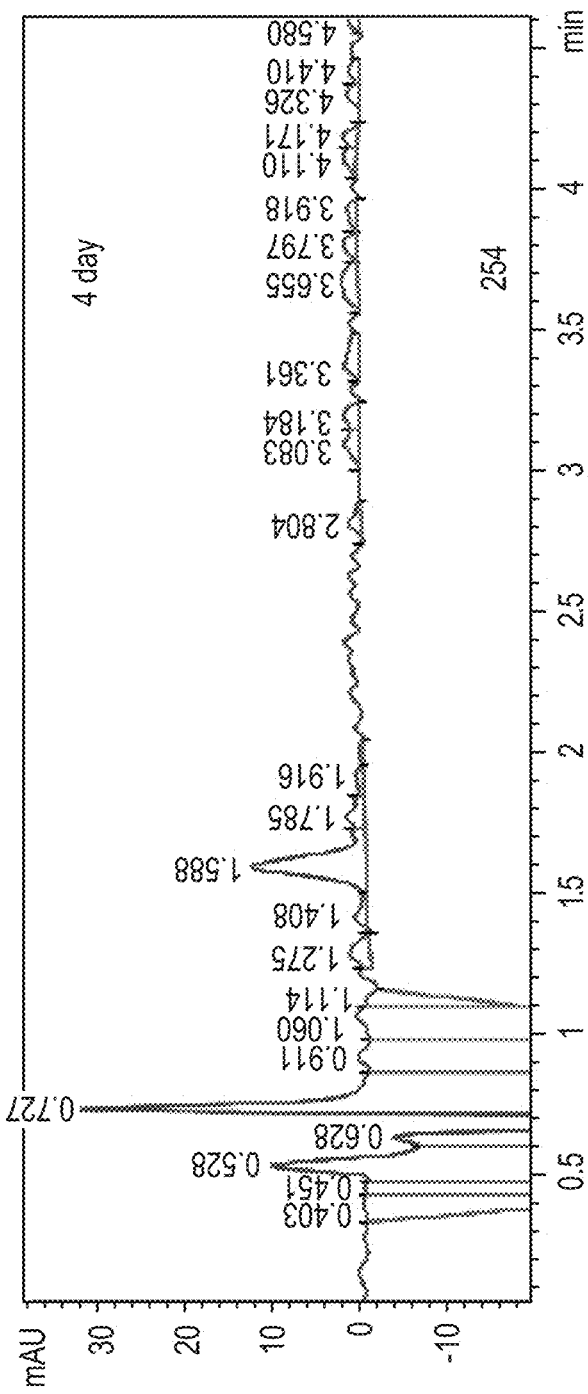

FIG. 133 shows Drug X loading and release in release media at pH 6.

FIG. 134 shows microparticle release in PBS with SDS.

FIG. 135 shows disc release in PBS with SDS.

FIG. 136 shows release in PBS with SDS at 120 μg/1 mL.

FIG. 137 shows release in PBS with SDS at 60 μg/1 mL.

FIG. 138 shows release in PBS with SDS at 12 μg/1 mL.

FIG. 139 shows release in PBS without SDS at 120 μg/1 mL.

FIG. 140 shows release in PBS without SDS at 60 μg/1 mL.

FIG. 141 shows release in PBS without SDS at 12 μg/1 mL.

Figure 142:
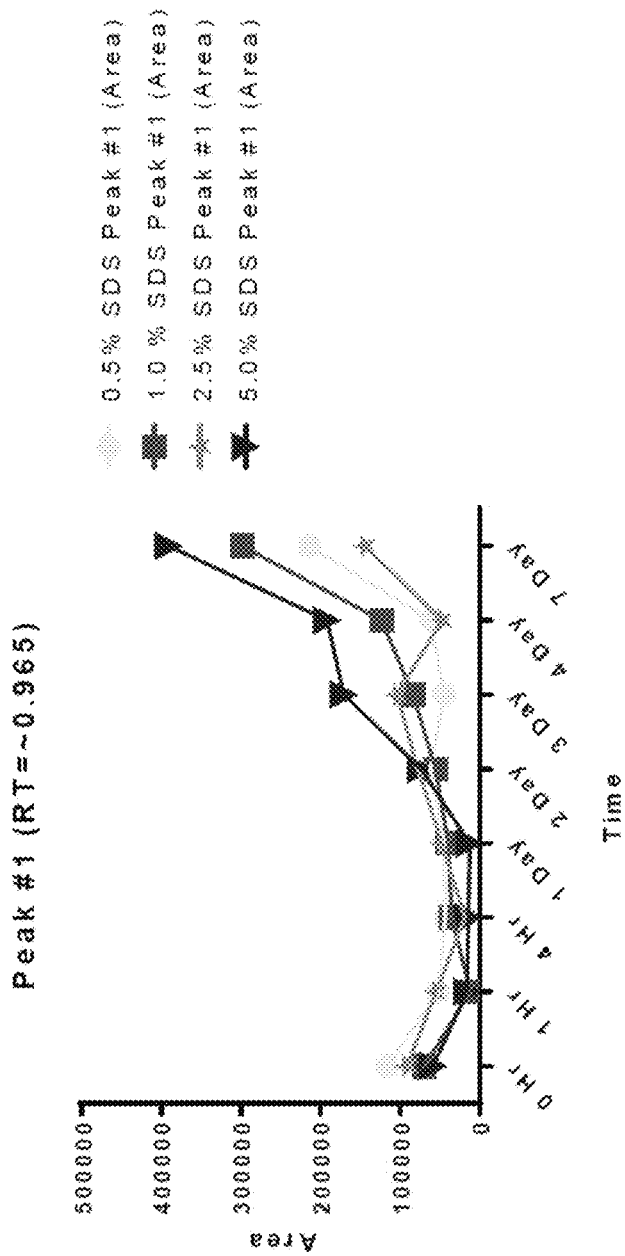

FIG. 142 shows Drug X stability in aqueous solution at different concentration of SDS (i.e., 0.5%, 1%, 2.5%, 5% at pH 7.45)—Peak #1 (RT~0.965).

Figure 143:
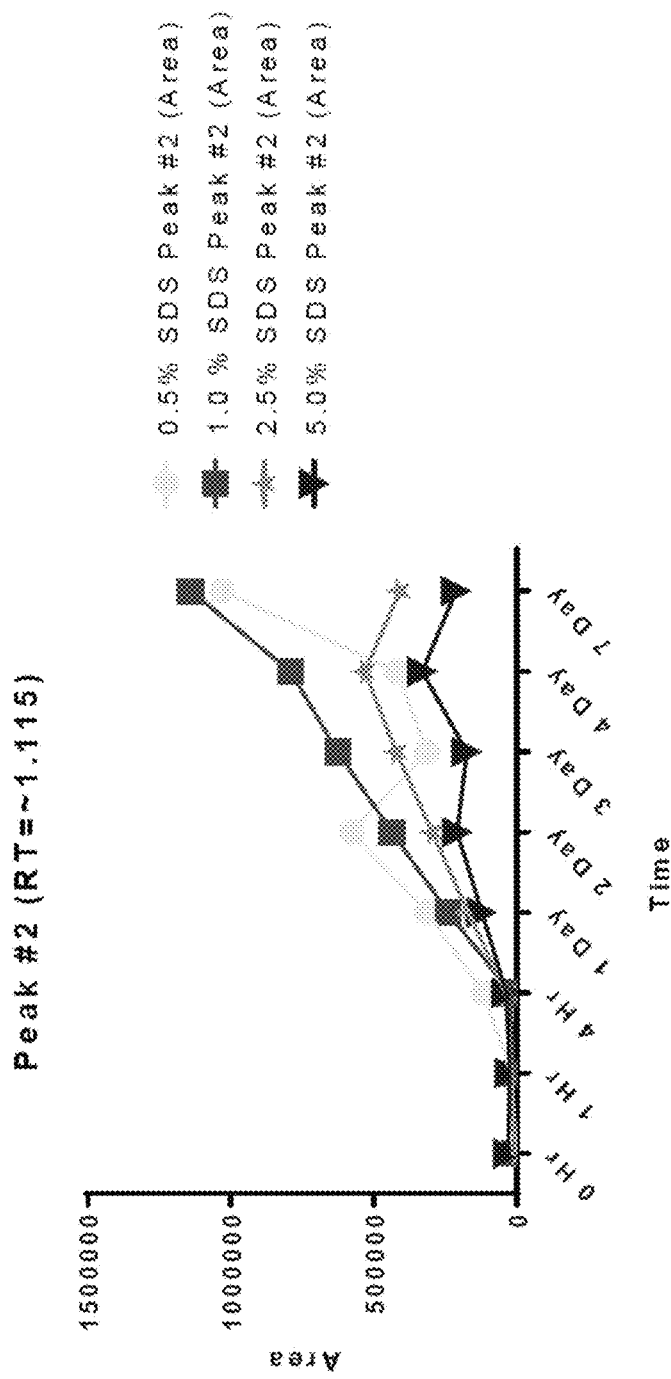

FIG. 143 shows Drug X stability in aqueous solution at different concentration of SDS (i.e., 0.5%, 1%, 2.5%, 5% at pH 7.45)—Peak #2 (RT~1.115).

Figure 144:
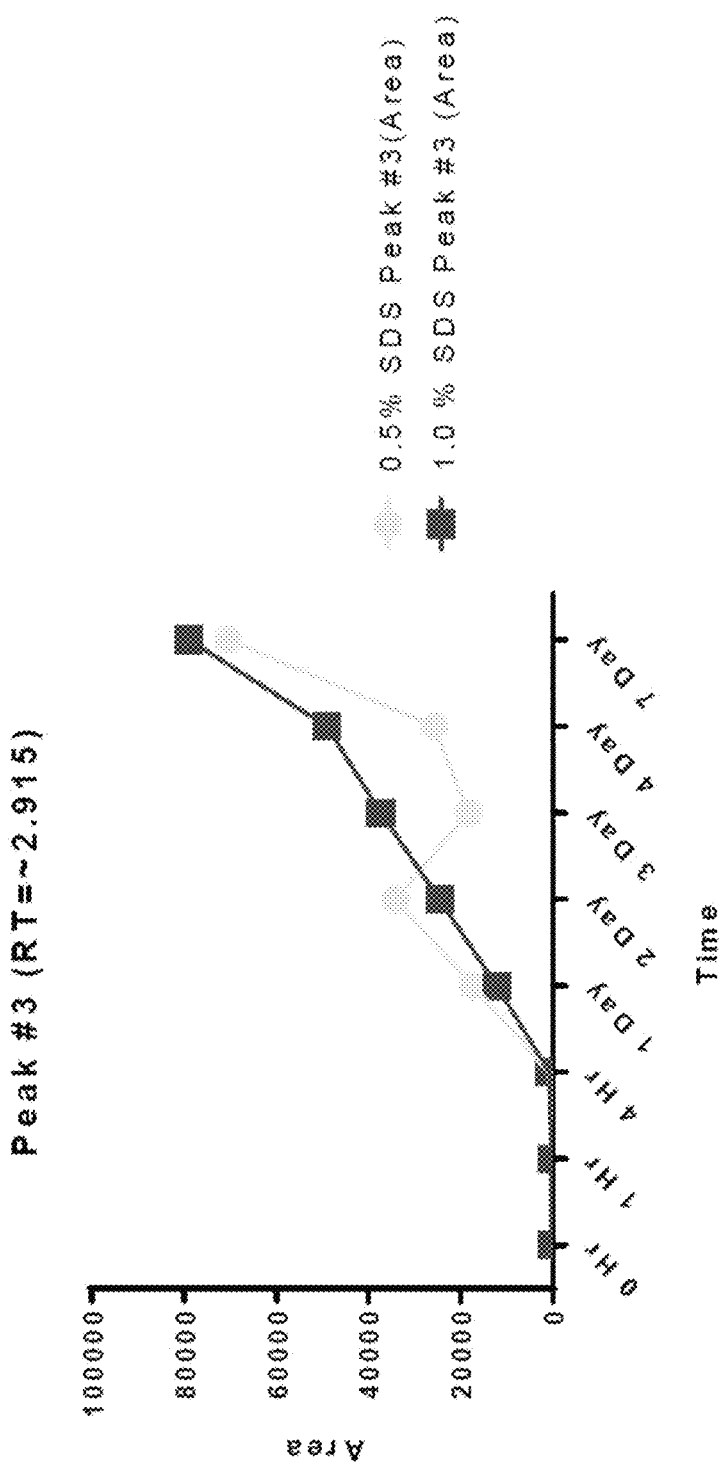

FIG. 144 shows Drug X stability in aqueous solution at different concentration of SDS (i.e., 0.5%, 1%, 2.5%, 5% at pH 7.45)—Peak #3 (RT~2.915).

Figure 145:
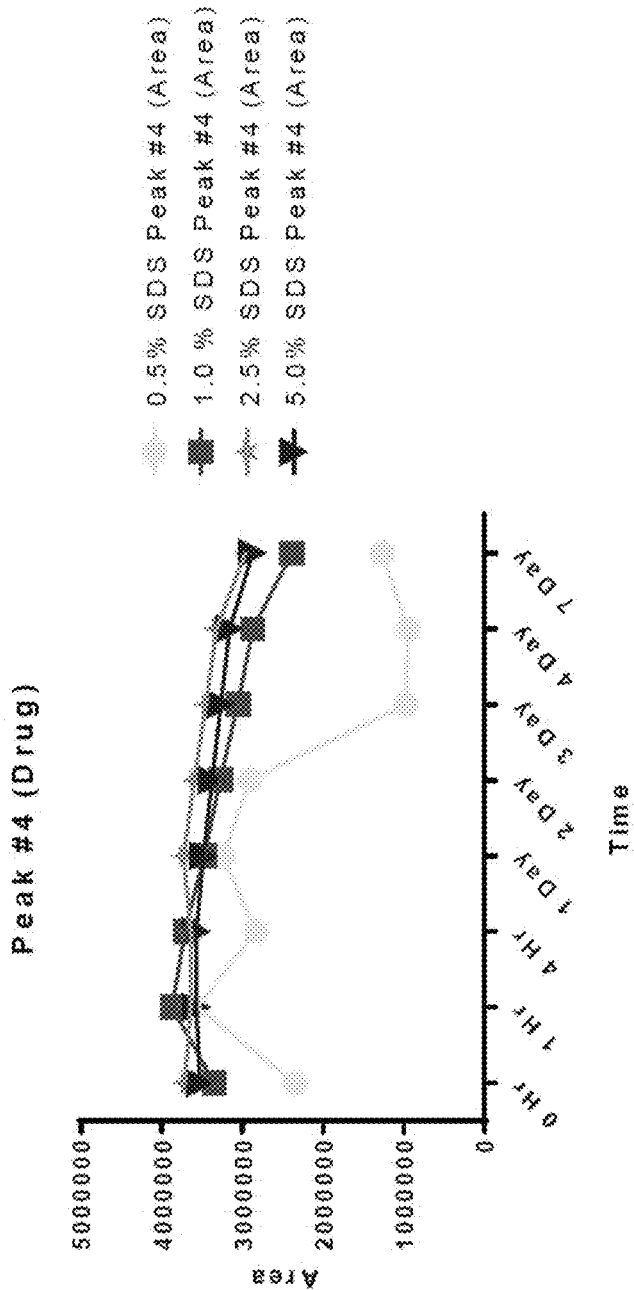

FIG. 145 shows Drug X stability in aqueous solution at different concentration of SDS (i.e., 0.5%, 1%, 2.5%, 5% at pH 7.45)—Peak #4 (Drug).

Figure 146:
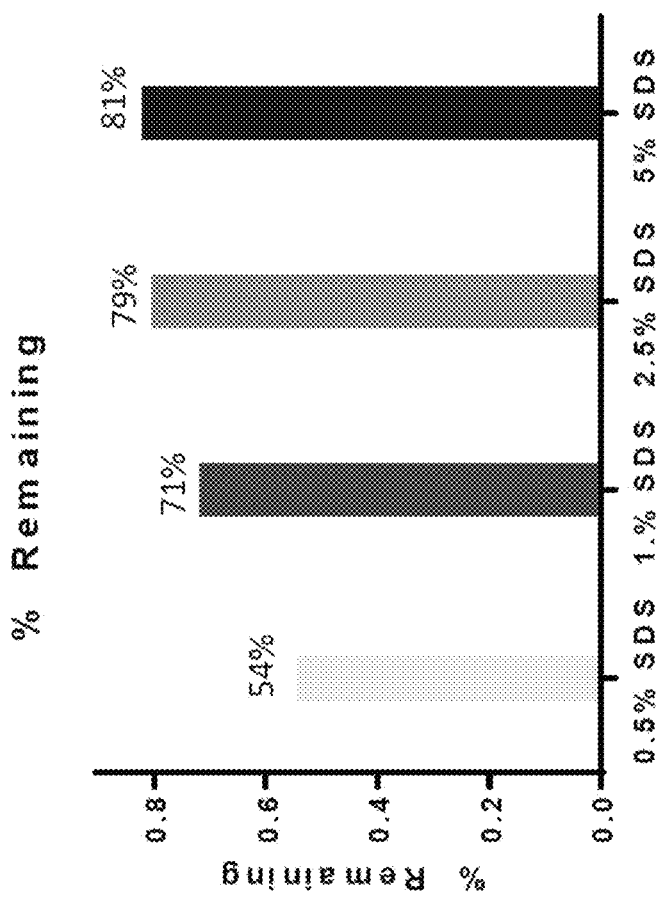
Figure 147A:
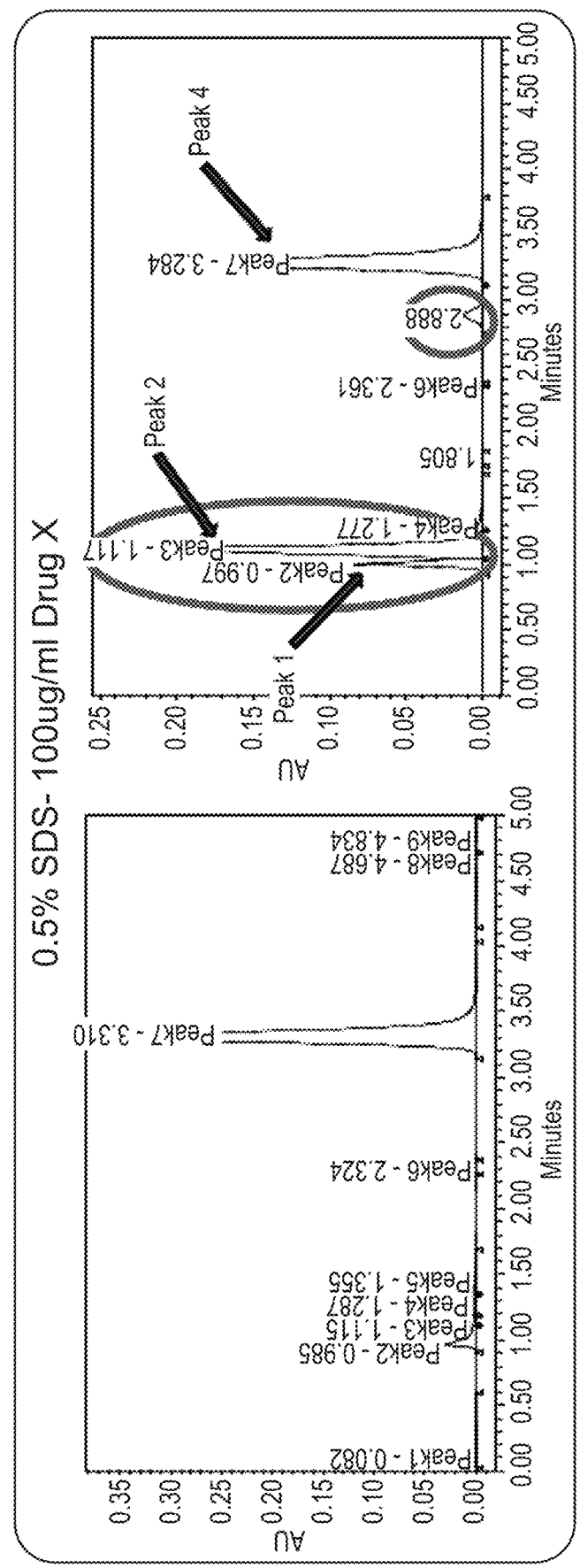
Figure 147B:
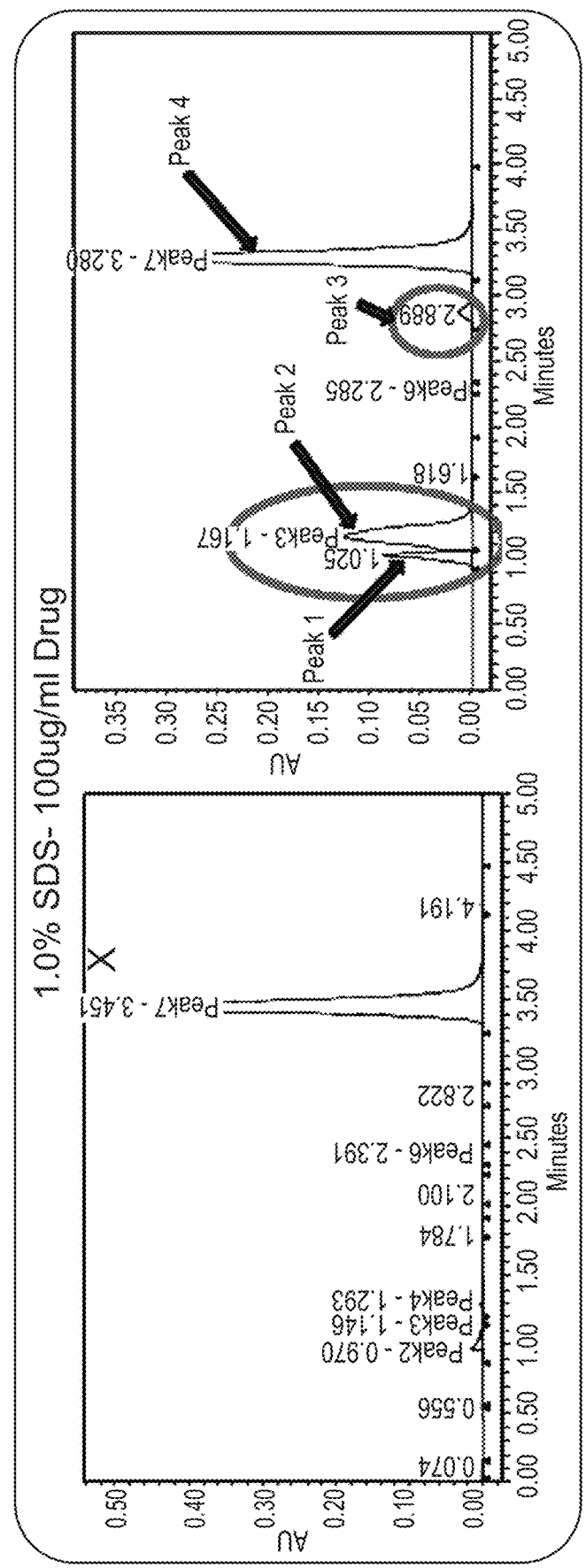
Figure 147C:
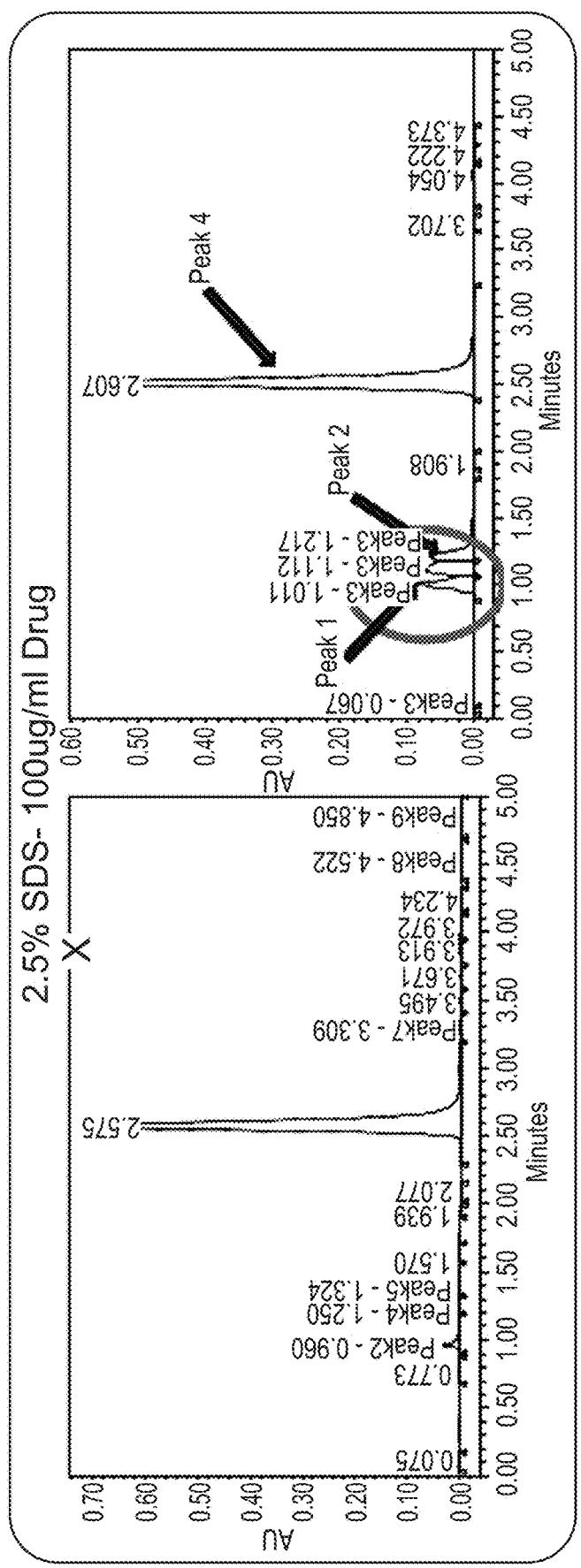
Figure 147D:
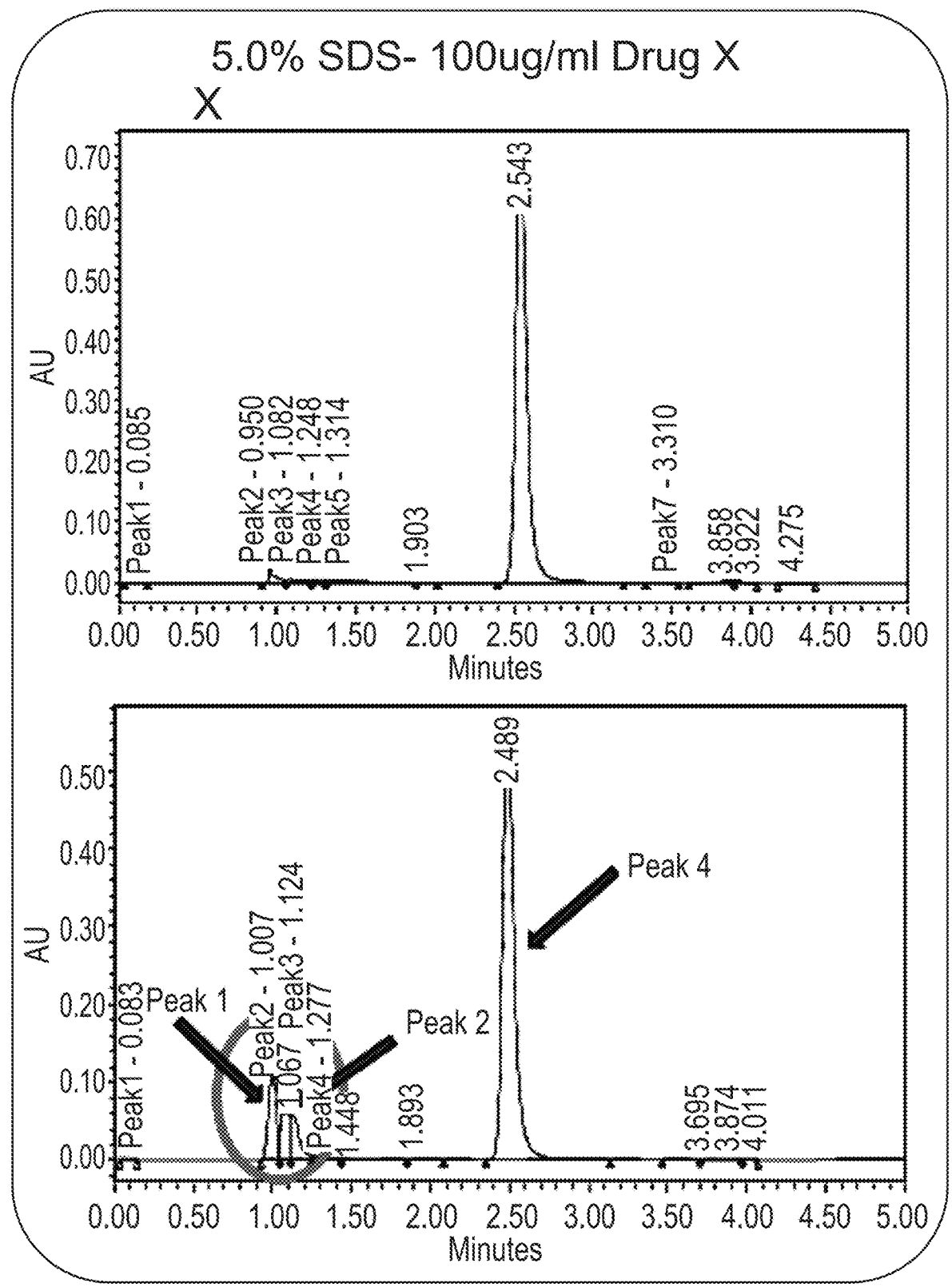

FIG. 146 shows the change in area of drug peak from T=0 to T=7 days.

FIG. 147 shows peaks associated with various mixes of Drug X in SDS.

Figure 148:
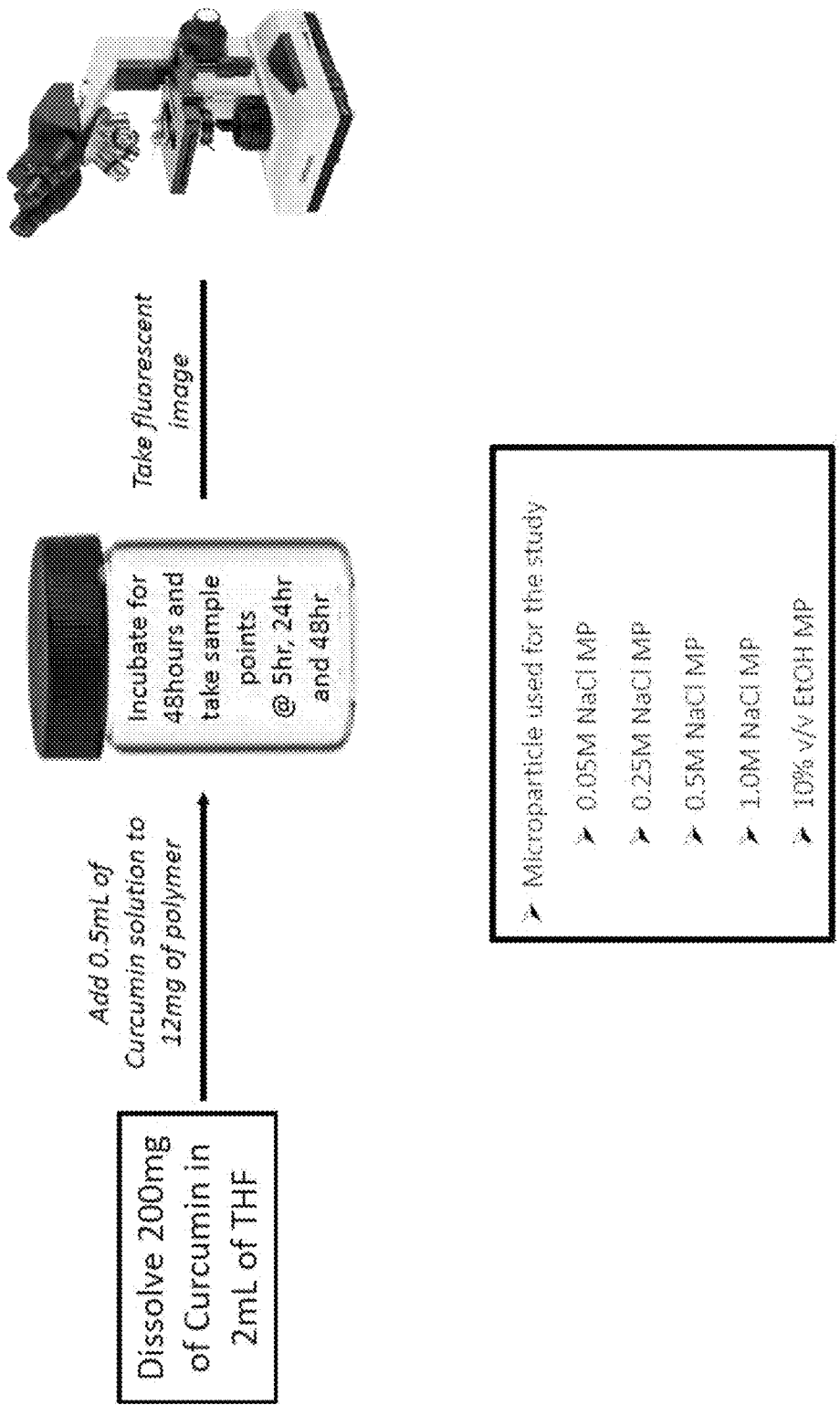

FIG. 148 shows curcumin post-loading protocol for NaCl MP and EtOH MP.

Figure 149:
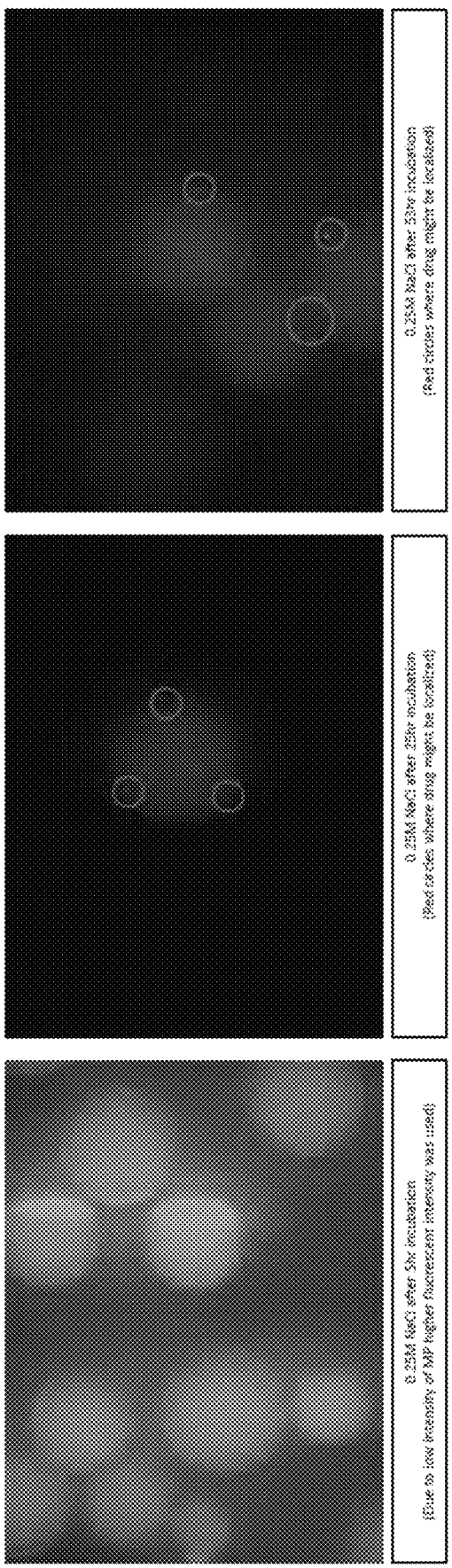

FIG. 149 shows fluorescent images of curcumin loaded MP (0.25M NaCl) with different incubation times.

Figure 150:
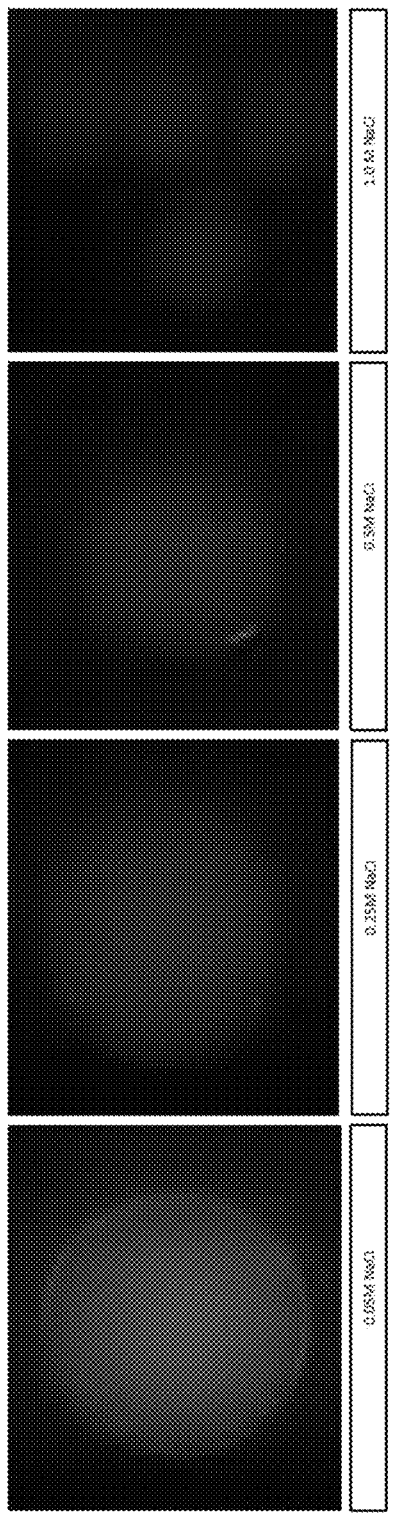

FIG. 150 shows fluorescent images of curcumin loaded MP at different concentrations of NaCl and EtOH MP (after 24 hour incubation).

FIG. 151 shows fluorescent images of curcumin loaded MP before and after wash.

Figure 152:
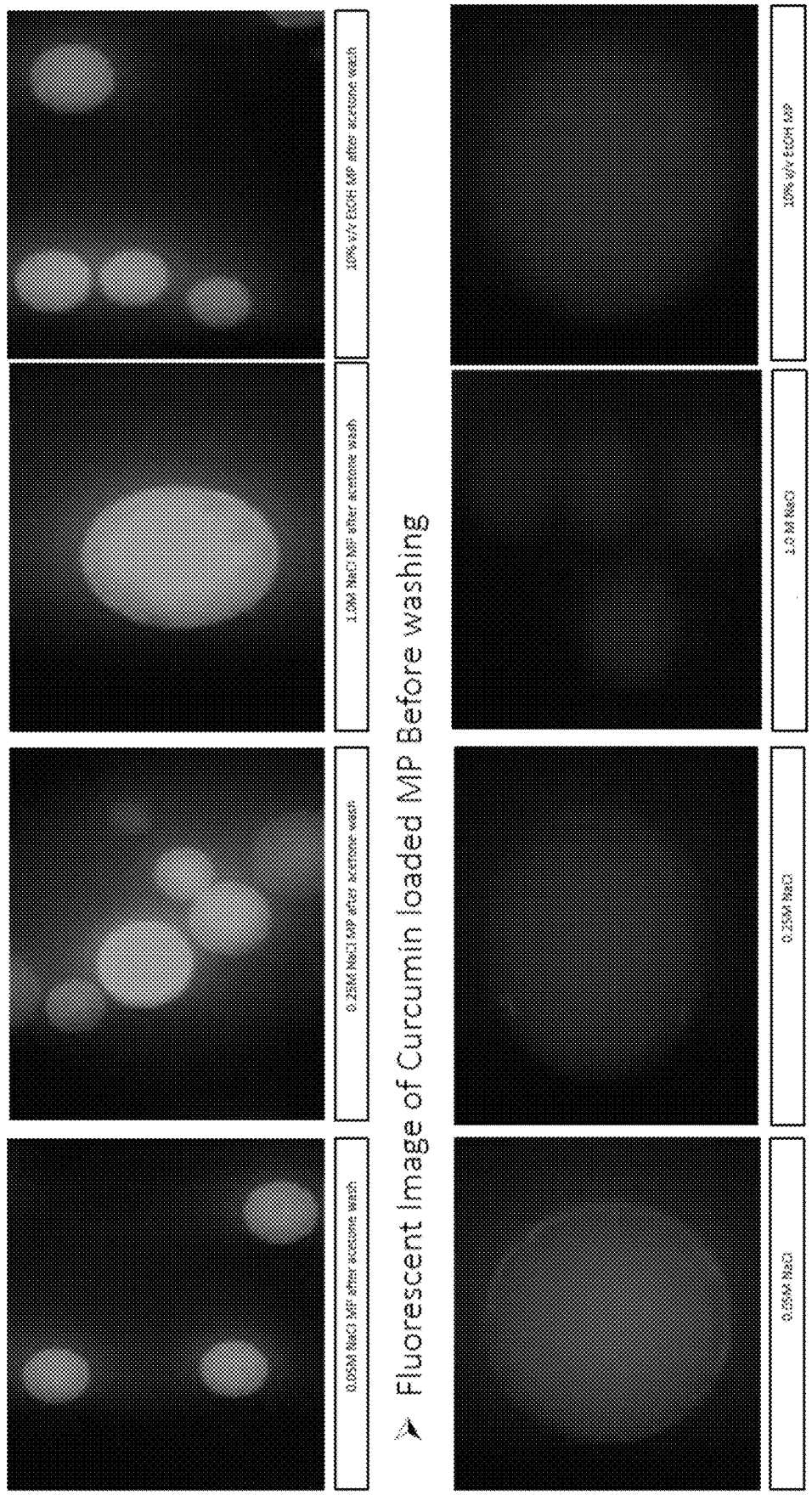

FIG. 152 shows fluorescent images of curcumin loaded MP before and after wash.

Figure 153:
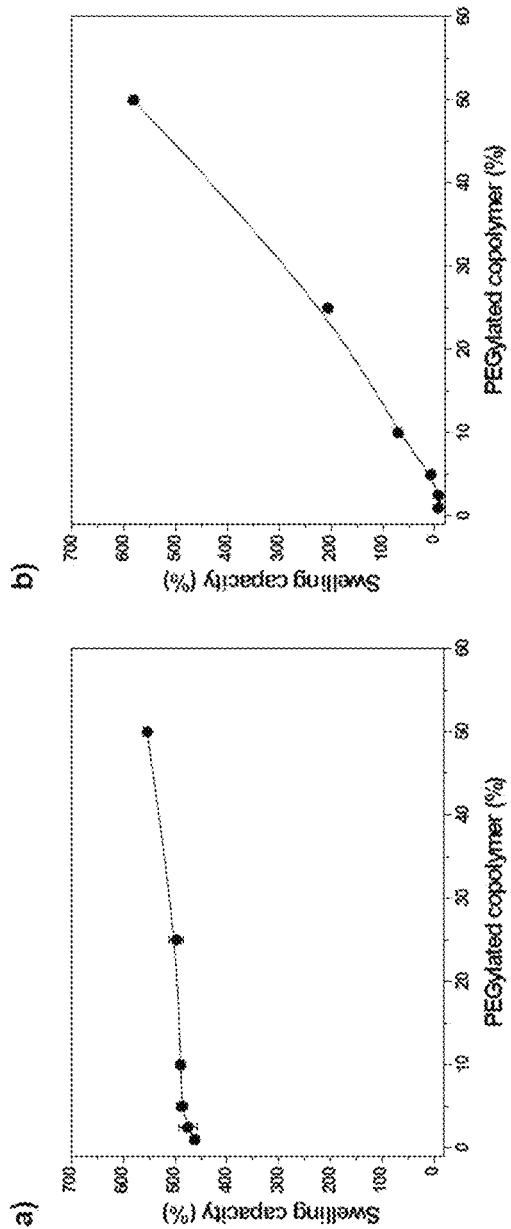

FIG. 153 shows extent of swelling in organic solvent and PBS.

Figure 154:
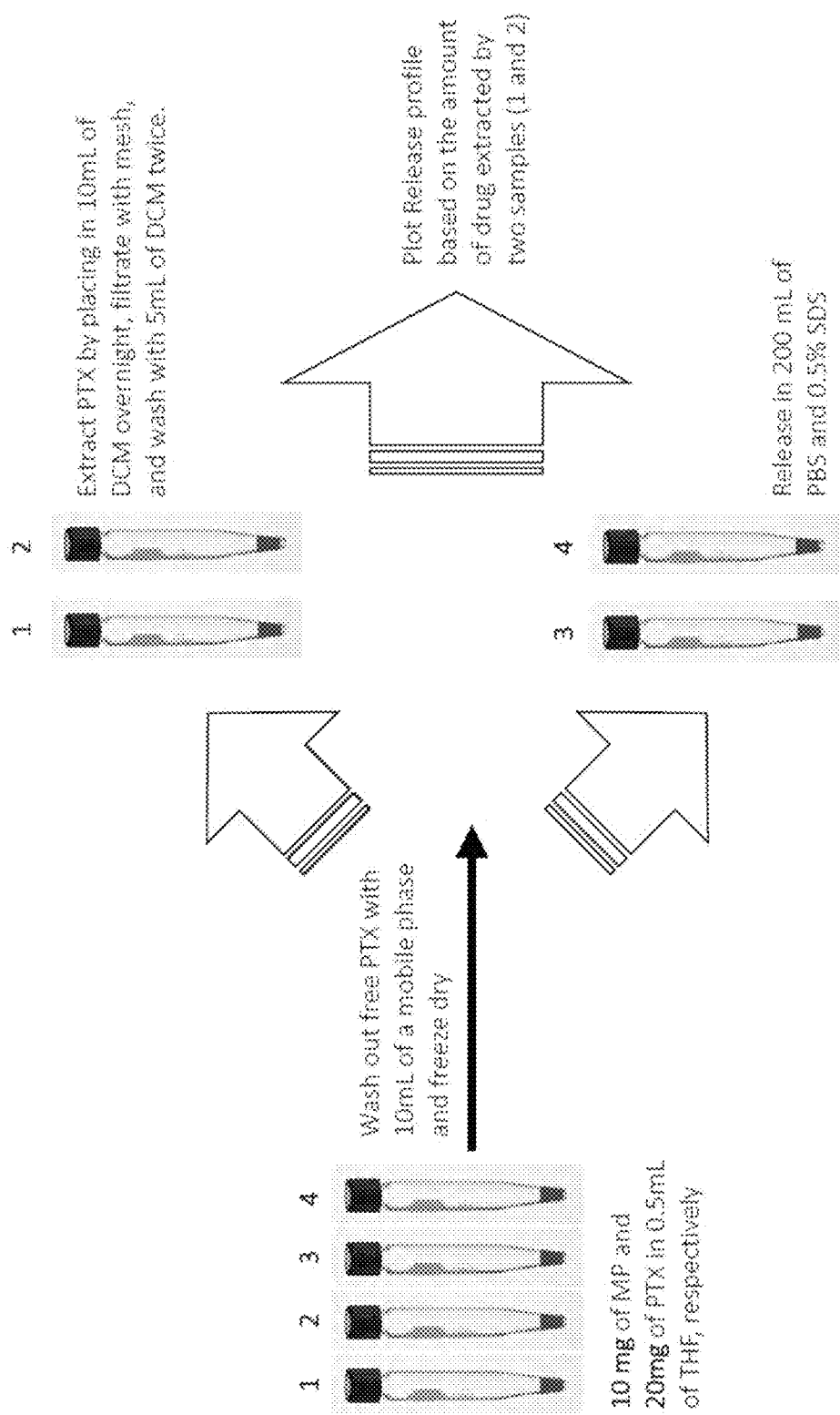

FIG. 154 shows protocol 1 for PTX loading and release of MPs.

Figure 155:
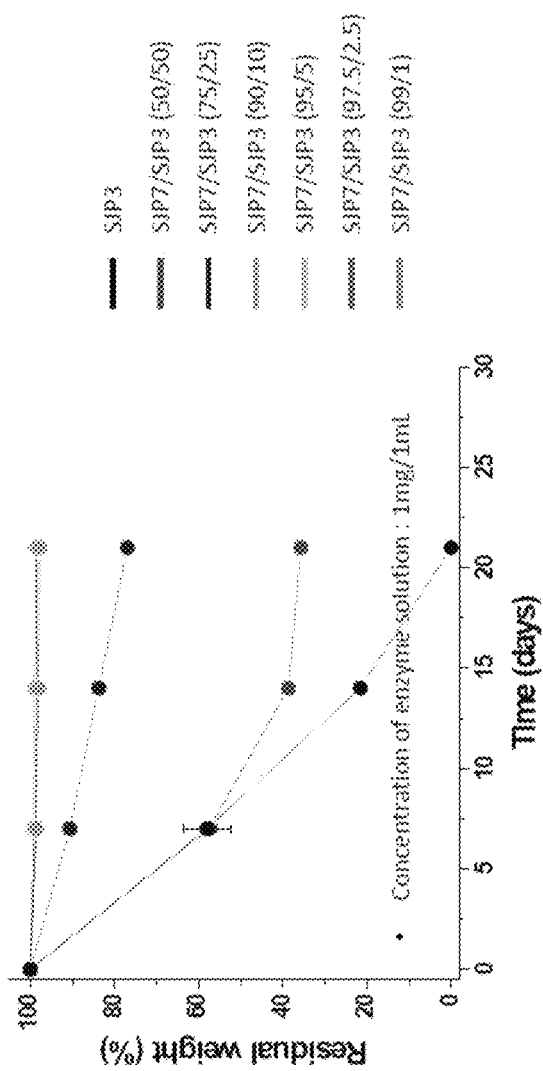

FIG. 155 shows mass change by enzymatic degradation.

Figure 156:
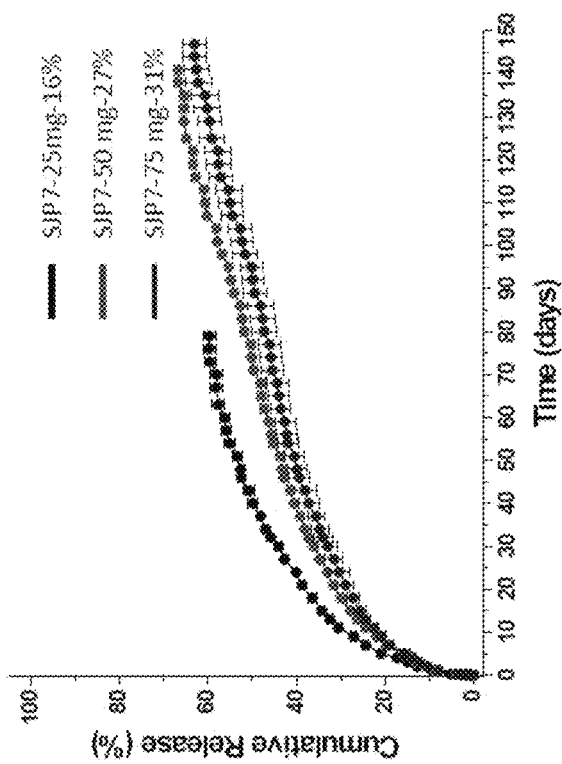

FIG. 156 shows release of Paclitaxel varying amount of PEGylated copolymer.

Figure 157:
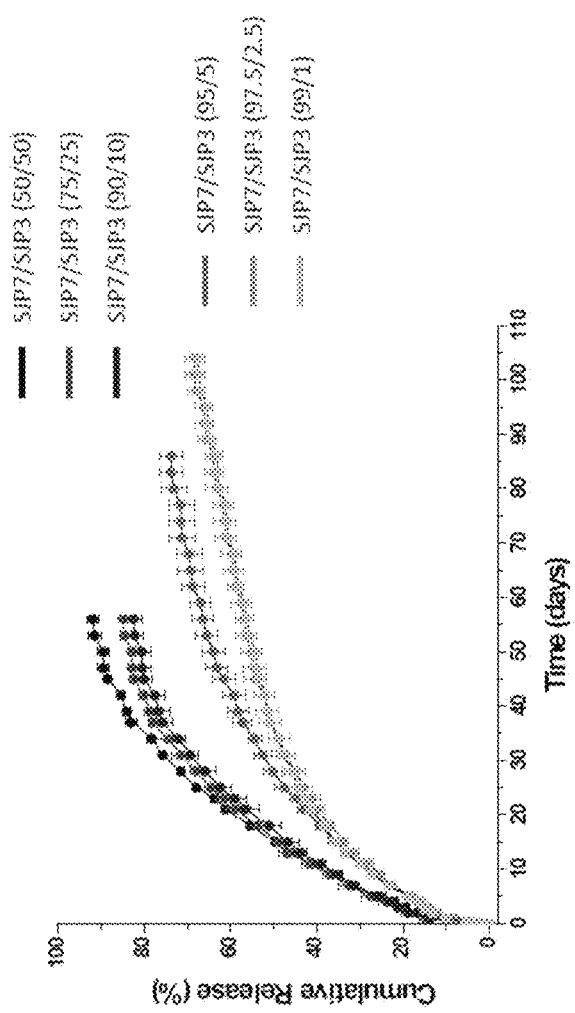

FIG. 157 shows release of Paclitaxel varying amount of PEGylated copolymer.

Figure 158:
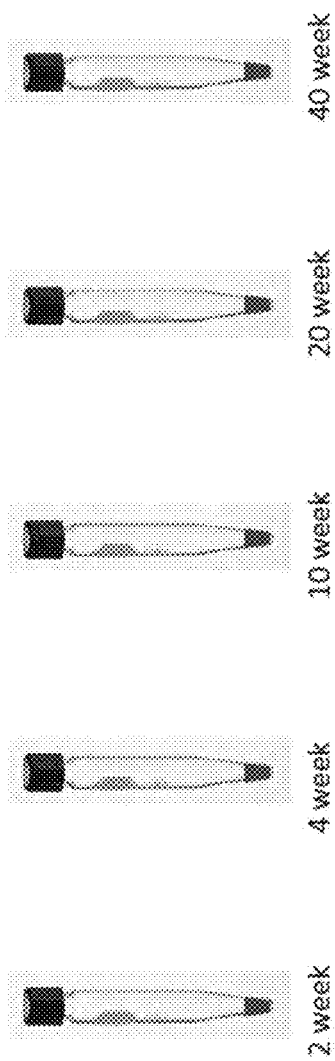

FIG. 158 shows a protocol for degradation of a microparticle (SJP7).

Figure 159:
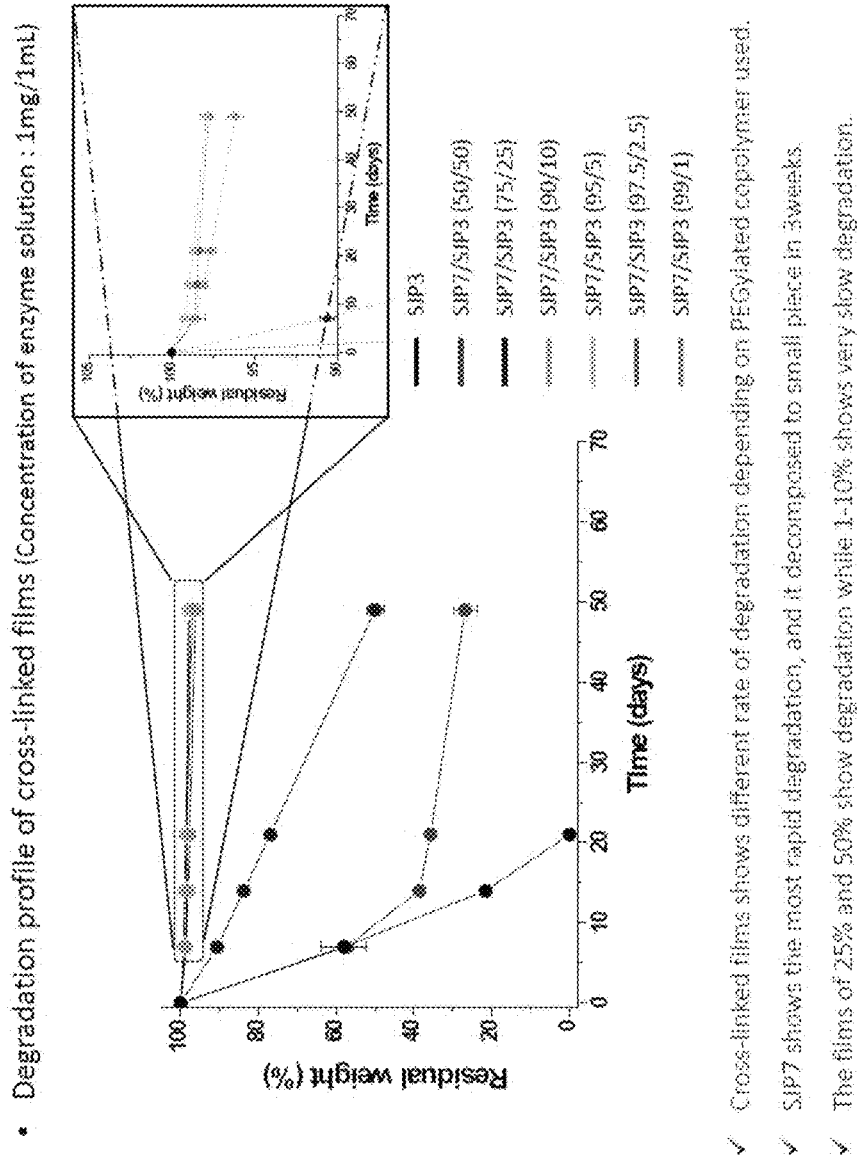

FIG. 159 shows mass change by enzymatic degradation.

Figure 160:
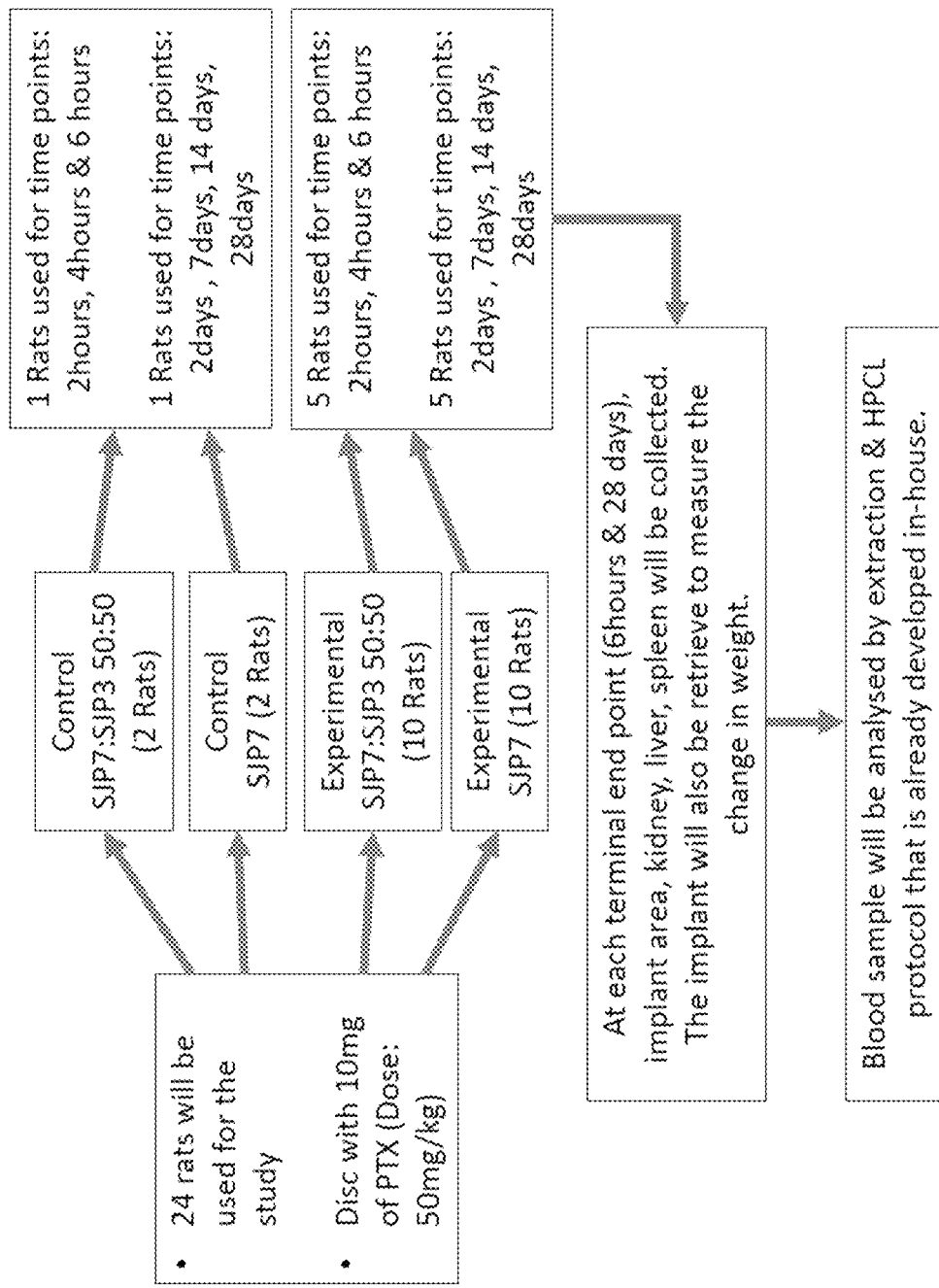

FIG. 160 shows a PTX-Discs PK study outline.

Figure 161:
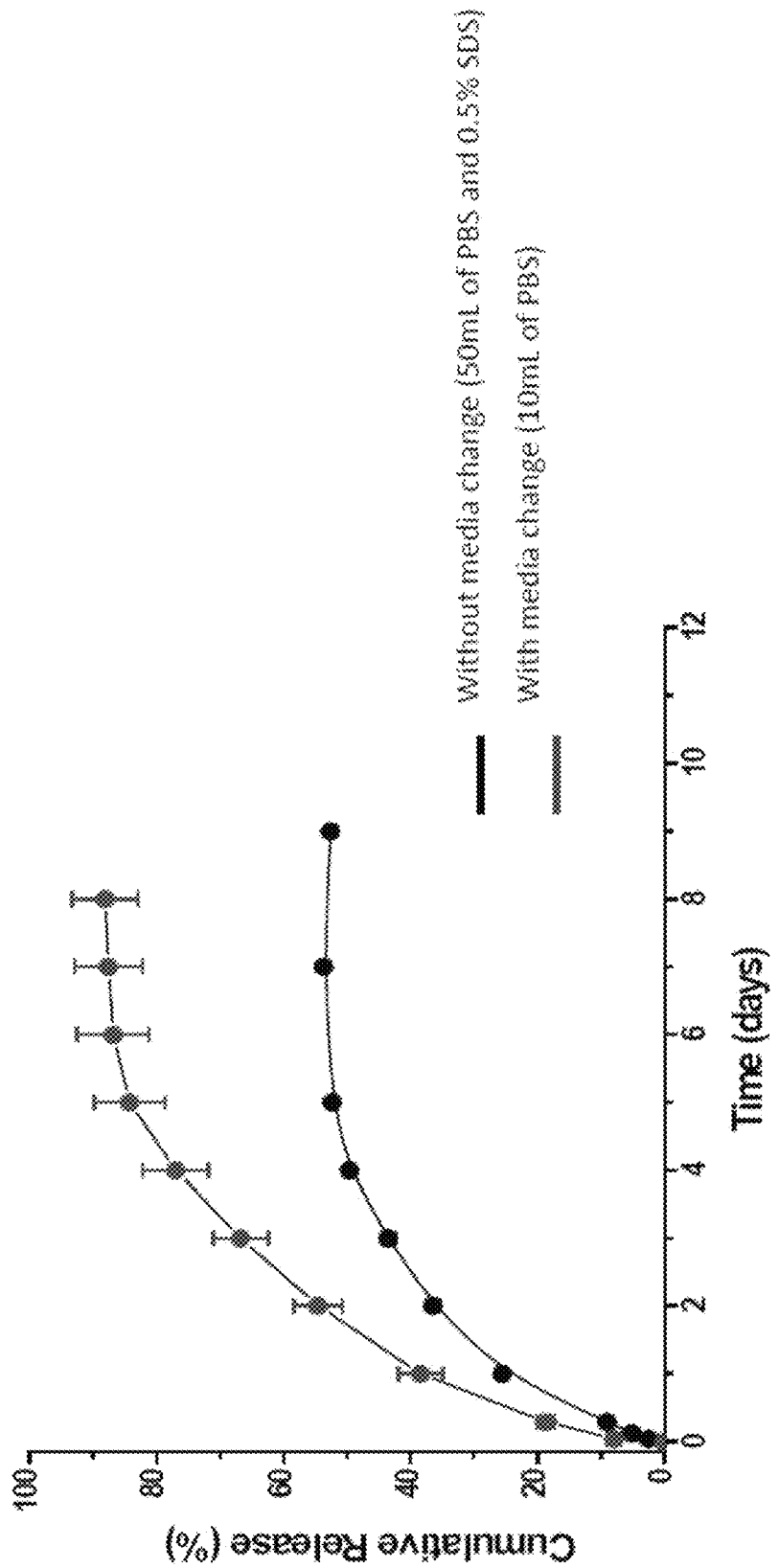

FIG. 161 shows Drug X release with and without release media exchange.

Figure 162:
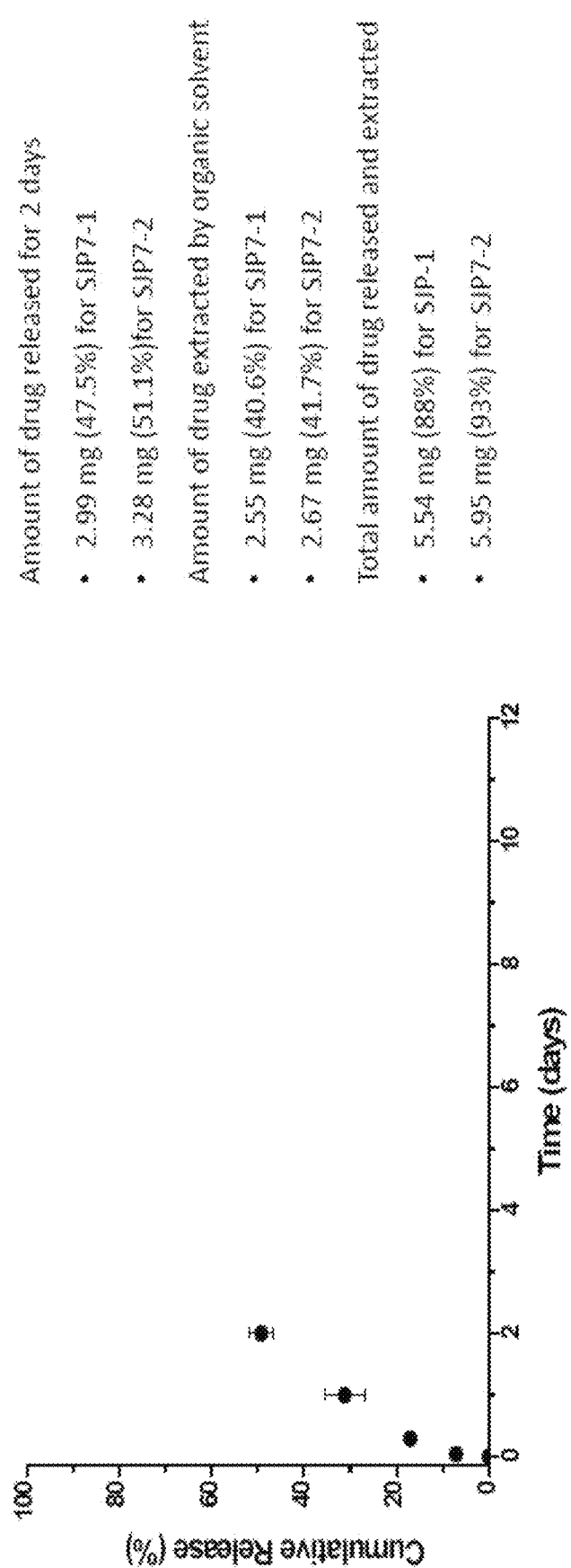

FIG. 162 shows Drug X stability in polymer matrix.

Figure 163:
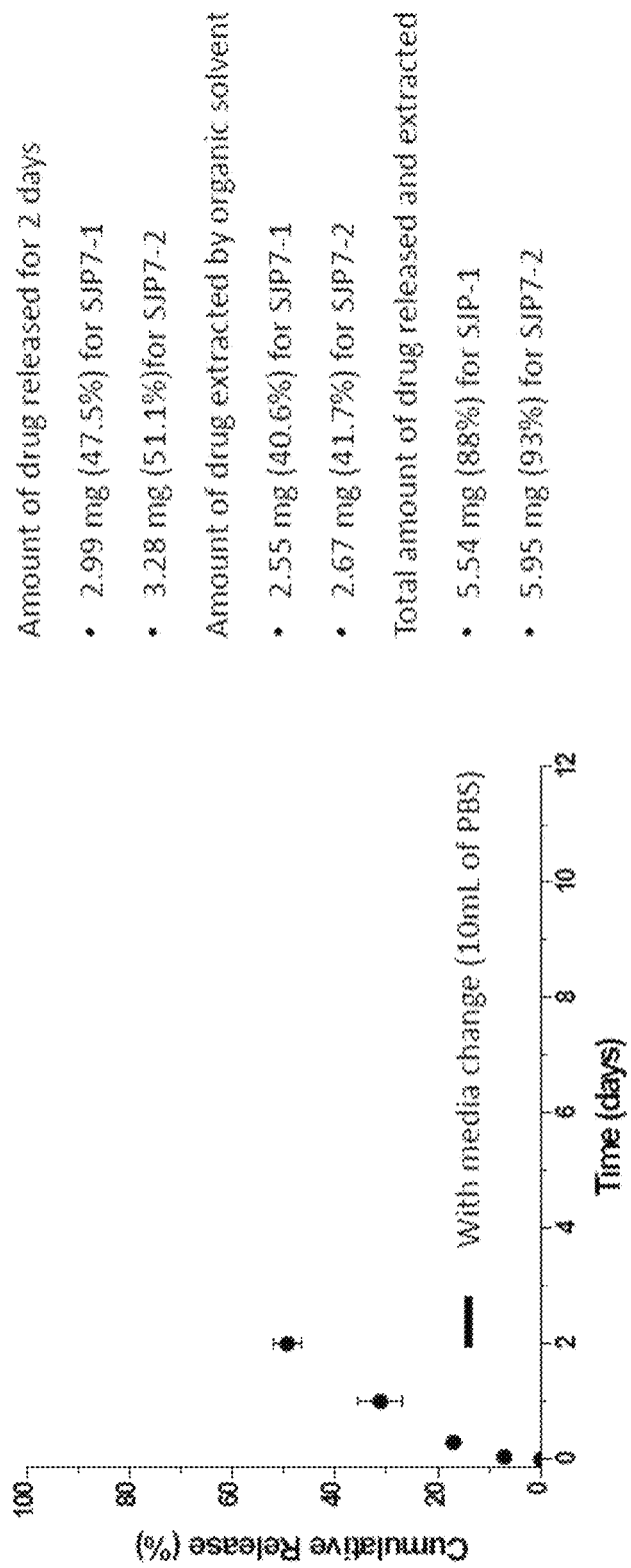

FIG. 163 shows Drug X stability in a disc after 2 weeks of release in PBS.

Figure 164:
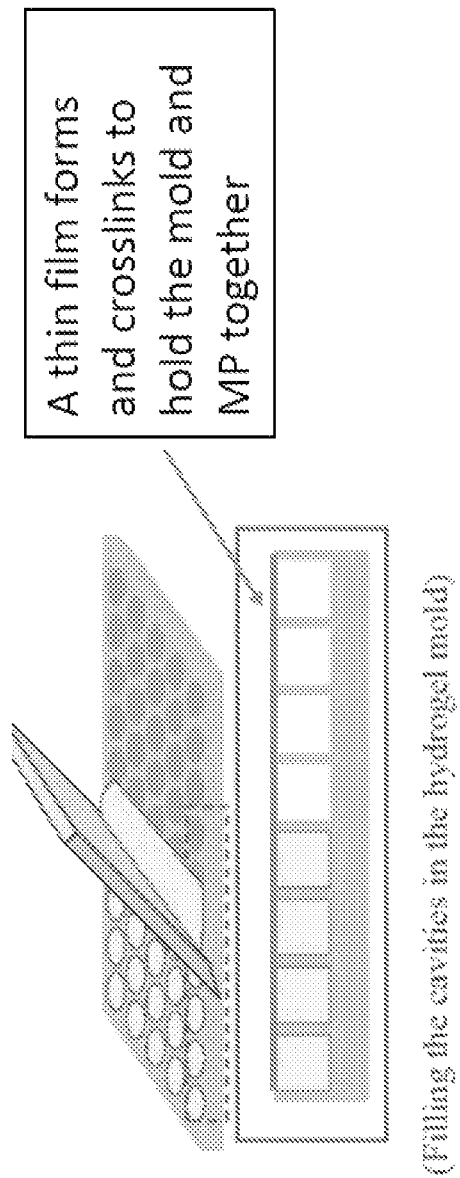

FIG. 164 shows Drug X related experiments.

Figure 165:
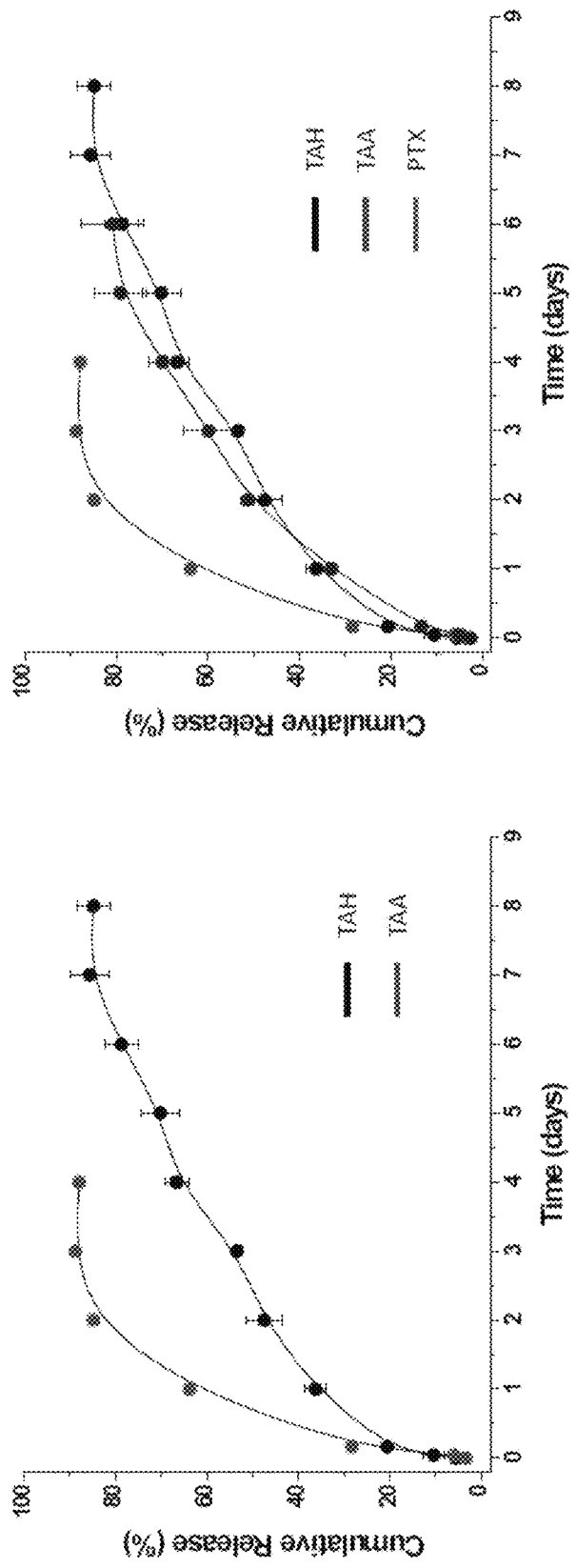

FIG. 165 shows TAA and TAH release using blend system with protocol.

Figure 166:
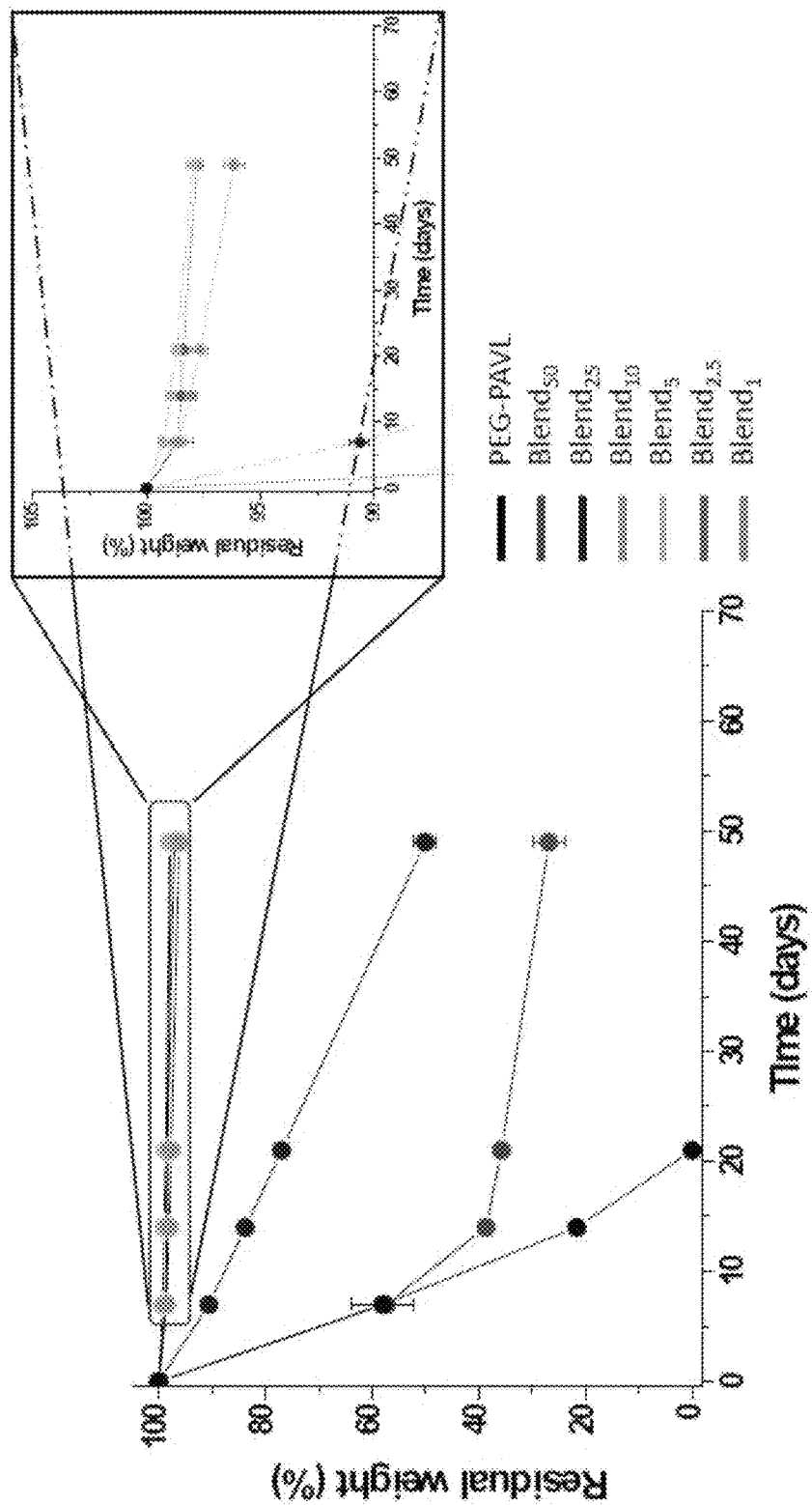

FIG. 166 shows results from degradation of cross-linked film in enzyme solution at 37.5°.

Figure 167:
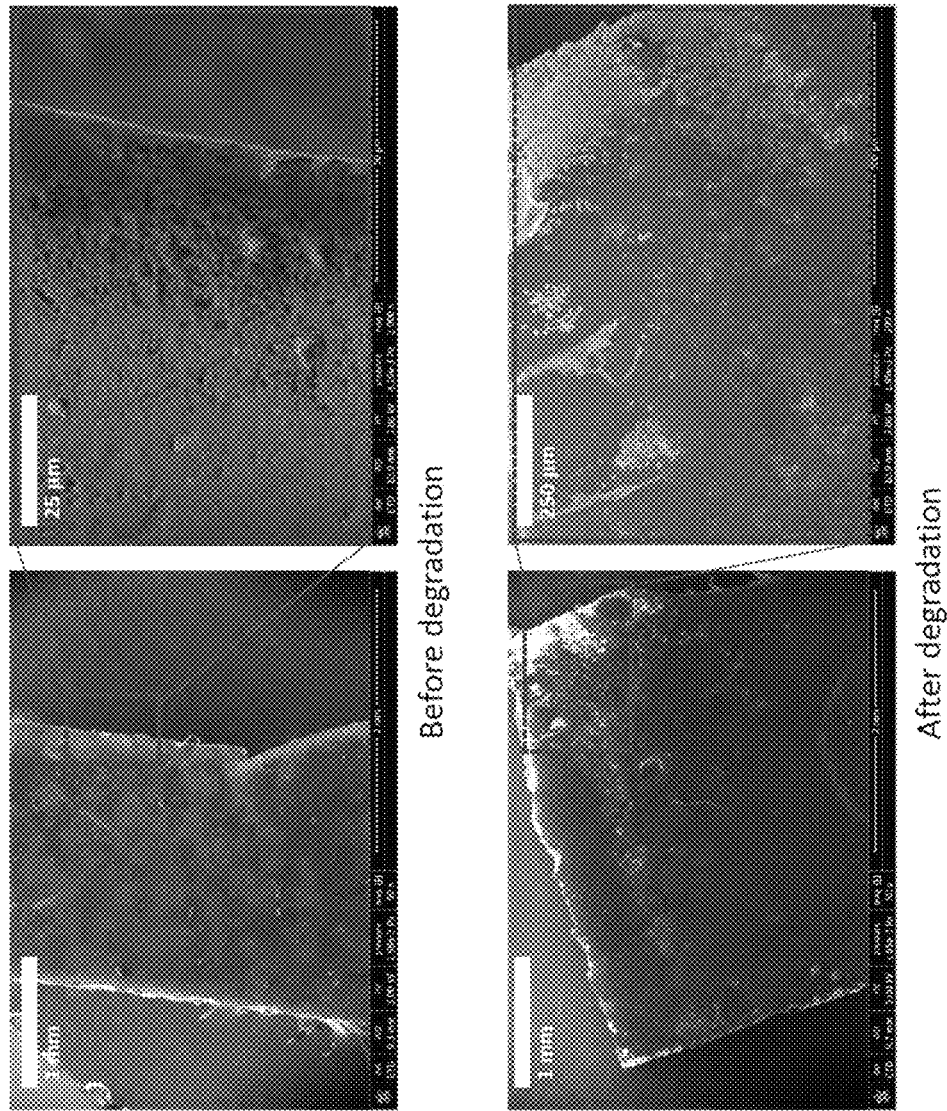

FIG. 167 shows SEM images of crosslinked films—CoPAVL.

Figure 168:
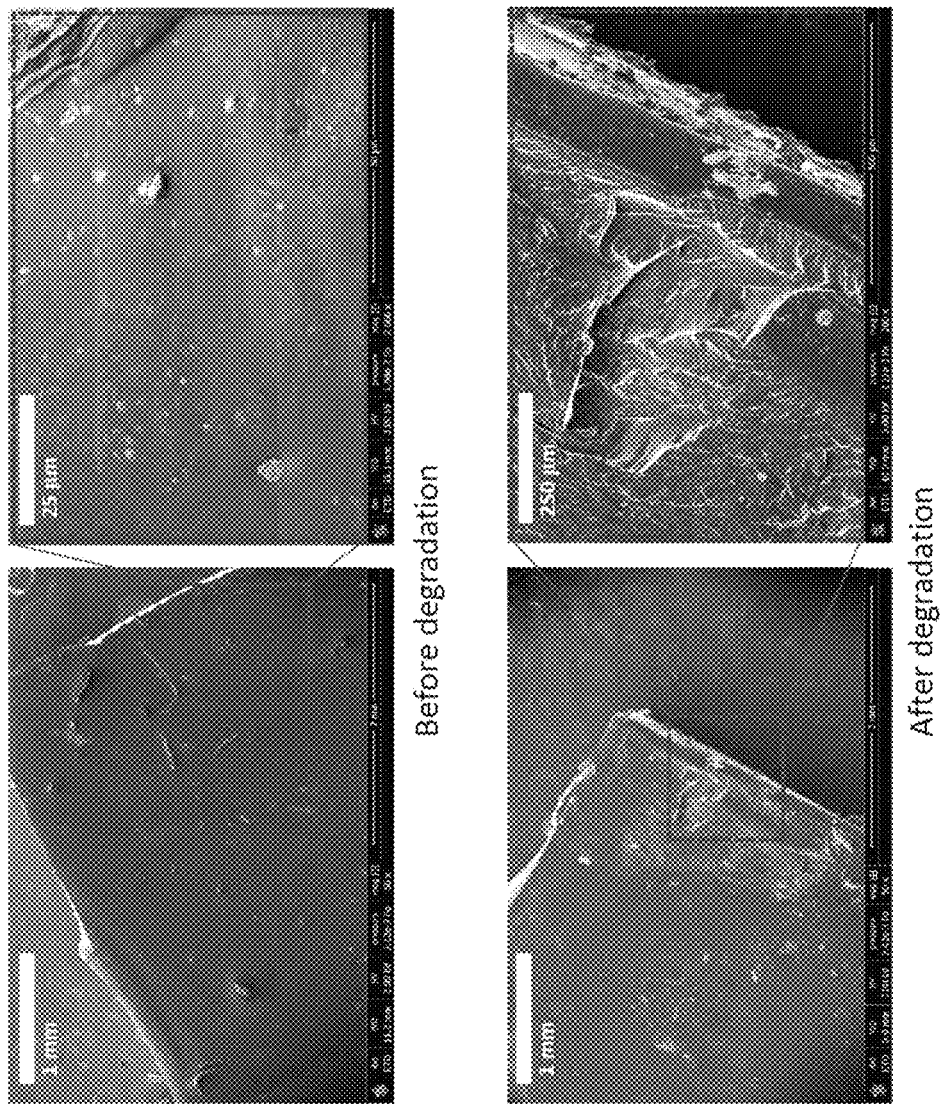

FIG. 168 shows SEM images of $blend_{25}$—CoPAVL/PEG-PAVL (75/25).

Figure 169:
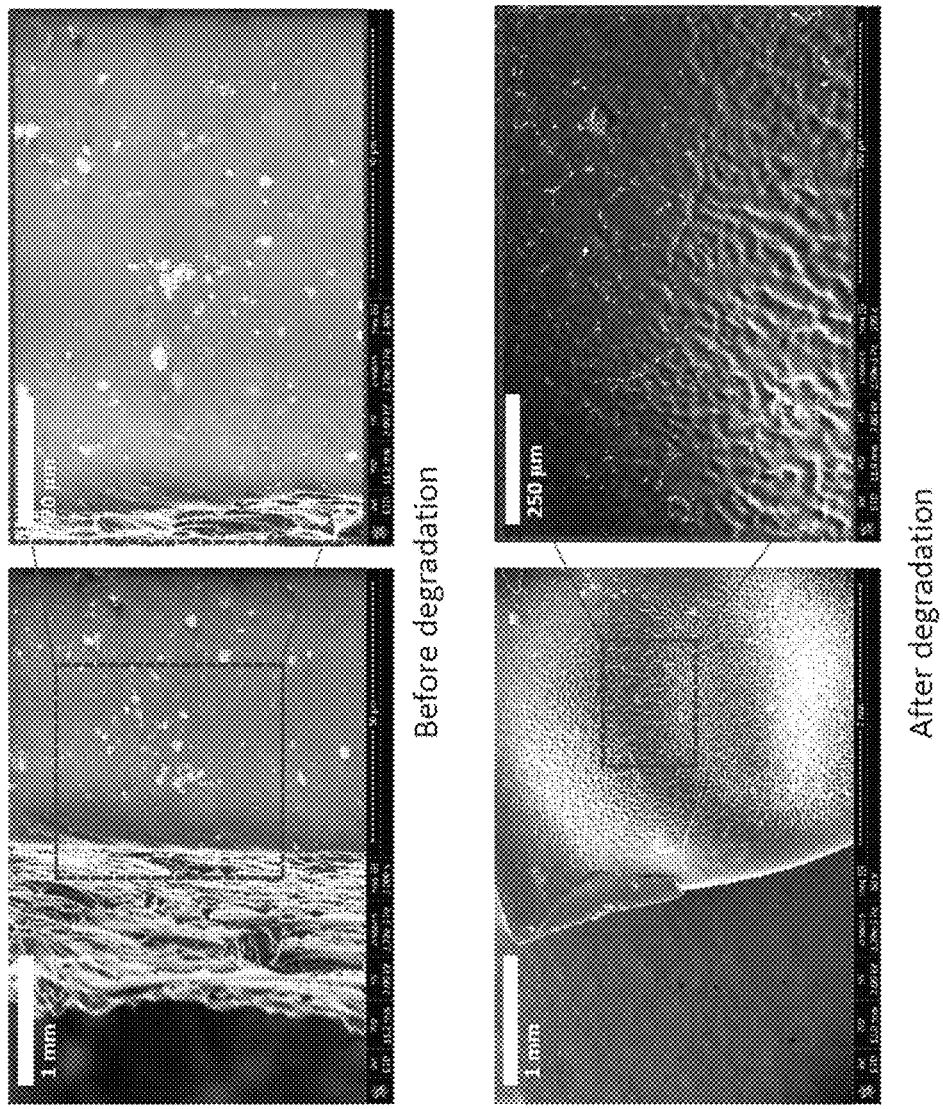

FIG. 169 shows SEM images of $blend_{25}$—CoPAVL/PEG-PAVL (50/50).

DETAILED DESCRIPTION OF THE INVENTION

Herein, we present an IDDS based on poly(valerolactone)-co-poly(allyl-valerolactone) (PVL-co-PAVL) copolymers, cross-linked with 1,6-hexanedithiol by thiolene click chemistry to yield amorphous or semi-crystalline networks. The PVL-co-PAVL system has been evaluated as a universal platform for delivery of a series of drugs that vary in terms of their physicochemical properties (see FIG. 1). The purpose of this study was to evaluate the underlying factors and mechanisms that control the release of drugs from the cross-linked matrices. In particular, to determine the extent to which polymer-drug interactions and in vitro release conditions play a role.

There is keen interest in the development of biocompatible and biodegradable implantable delivery systems (IDDS) that provide sustained drug release for prolonged periods in humans. These systems have the potential to enhance therapeutic outcomes, reduce systemic toxicity and improve patient compliance. Herein, we report the preparation and physico-chemical characterization of cross-linked polymeric matrices from poly(valerolactone)-co-poly(allyl-δ-valerolactone) (PVL-co-PAVL) copolymers for use in drug delivery. A series of well-defined PVL-co-PAVL, copolymers (PDI<1.5), that vary in terms of M.W and AVL content were prepared by ring opening polymerization catalyzed by 1,5,7-triazabicyclo[4.4.0]dec-5-ene (TBD). A subsequent cross-linking reaction using 1,6 hexanedithiol lead to solid cylindrical amorphous or semi-crystalline matrices as potential IDDS. High loading levels (up to 20% (w/w)) of several model drugs that vary in physicochemical properties, including paclitaxel, triamcinolone acetonide and hexacetonide, curcumin and acetaminophen, was achieved using a post-loading method in organic solvent. Drugs-IDDS interactions were evaluated via the group contribution method, X-ray diffraction as well as calorimetric, spectroscopic and microscopic techniques. Results indicate superior drug-matrix compatibility for drugs bearing phenyl groups. In vitro release studies under distinct sink conditions highlight the key factors (i.e. state and loading level of drug, solubility of drug in external media, composition of release media) that impact drug release.

Results and Discussion

Copolymer characterization (PVL-co-PAVL): Four random copolymers based on poly(valerolactone)-co-poly(allyl)valerolactone ($P_{7.5K}$, $P_{32K}$, $P_{39K}$) were prepared by metal-free ROP catalyzed by TBD. Gel permeation chromatography revealed a monomodal distribution for the copolymers and polydispersity index of ≤1.5 (Table 1 and FIG. 2A). $^1$H NMR spectroscopy confirmed the degree of polymerization (DP) and the % AVL in the resulting copolymers. The terminal phenyl group was used as an internal reference (m, phenyl δ=7.33 ppm), 5.70 ppm (m. $CH_2$=CH), 5.03 ppm (m, $CH_2$=CH), 4.08 ppm (m, $CH_2$—OC—O), 2.38 (m, —$CH_2$—CH—, and —O=C—$CH_2$—), 1.68 ppm (m, —$CH_2$—$CH_2$— VL, AVL) (FIG. 2A). After precipitation in ether and methanol, the polymers were dried under vacuum at room temperature with a yield of 80% (~10 g). The four copolymers have molecular weights ($M_n$) of 7500, 15000, 32000 and 39000 g·mol$^{-1}$ and contain 28, 23, 20 and 9% AVL.

the other copolymers showed only recrystallization during the cooling process. Incorporation of 20 units of AVL per polymer chain decreased the % crystallinity (xc) to values as low as 25% for $P_{7.5K}$. The $\chi_c$ values for $P_{15K}$ and $P_{32K}$ were found to be 53% and 40% respectively while that for $P_{39K}$ increased to 61% when AVL content decreased at 9% (Table 1). Overall, the melting transitions ($T_m$) increased from 12.6° C. to 47.6° C. with an increase in M.W (e.g VL content) of the copolymer and a decrease in % AVL content. Zeng, F.; Lee, H.; Chidiac, M.; Allen, C. Synthesis and Characterization of Six-Arm Star Poly(δ-valerolactone)-block-Methoxy Poly(ethylene glycol) Copolymers. *Biomacromolecules* 2005, 6, (4), 2140-2149.; Elzein, T.; Nasser-Eddine, M.; Delaite., C.; Bistac, S.; Dumas, P. FTIR study of polycaprolactone chain organization at interfaces. *Journal of Colloid and Interface Science* 2004, 273, 2, 381-387.; Kazumichi, I.; Masaru, Y.; Hironobu, F.; Masaharu, A.; Minoru, K.; Tohoru, M.; Hidetoshi, Y.; Tsuneji, N. A new biodegradable implant consisting of waxy-type poly(ε-caprolactone-co-δ-valerolactone) and estramustine. *International Journal of Pharmaceutics* 1991, 68, 1, 87-95.

TABLE 1

Characteristics of the copolymers.

| PVL-co-PAVL[1] | $M_n$ (g/mol) | | nb allyl groups[2] | % AVL[3] | $T_m$ (° C.)[4] | $\Delta^D H_m$ (J/g)[g] | $\chi_c$ (%) |
|---|---|---|---|---|---|---|---|
| | GPC[5] | PDI | $^1$H NMR[6] | | | | |
| $P_{7.5K}$ | 9300 | 1.45 | 7500 | 15 | 28 | 12.6 | 36 | 25 |
| $P_{15K}$ | 12000 | 1.45 | 15000 | 25 | 23 | 34/39.3 | 76 | 53 |
| $P_{32K}$ | 24000 | 1.47 | 32000 | 45 | 20 | 38.2 | 58 | 40 |
| $P_{39K}$ | 33000 | 1.52 | 39000 | 25 | 9 | 41.6/47.6 | 88 | 61 |

[1]$P_{7.5K}$, $P_{15K}$ $P_{32K}$ and $P_{39K}$ refer to the different PVL-co-PA VL copolymers.
[2]Number percentage (% M. Wt) of allyl valerolactone in the copolymer (% AVL) based on the total molecular weight determined by 1H NMR spectroscopy.
[3]Weight percentage (% M. Wt) of allyl valerolactone in the copolymer (% AVL) based on the total molecular weight determined by $^1$H NMR spectroscopy.
[4]Melting temperatures ($T_m$) and $^g$ enthalpy of melting ($H_m$) were determined by DSC analysis (2$^{nd}$ cycle). The degree of crystallinity $\chi_c$ (%) of the copolymers was calculated as described in supplementary materials.
[5]Number-average molecular weight (g/mol) obtained from GPC analysis. (Polydispersity index = PDI).
[6]Number-average molecular weight (g/mol) obtained by $^1$H NMR spectroscopy.

Figure 11:
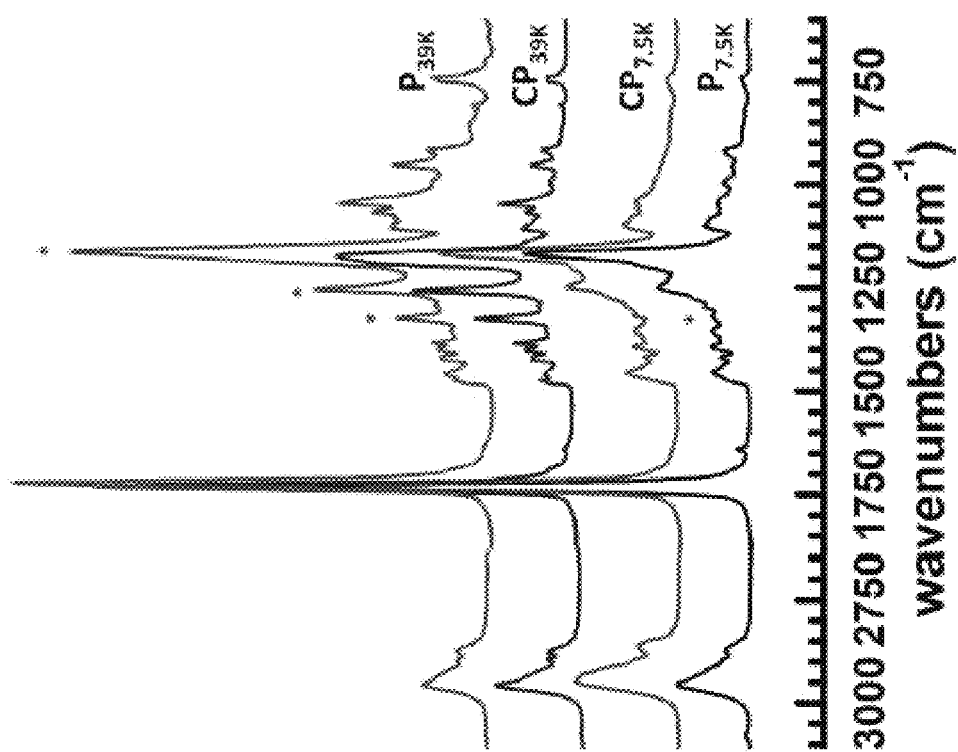
FIG. 11 shows ATR-FTIR spectroscopy of the copolymer (bulk) and the resulting cross-linked copolymer matrices: $P_{7.5K}$ (black), $CP_{7.5K}$ (red), $P_{39K}$ (blue) and $CP_{39K}$ (green). Normalization has been done at 1730 cm$^{-1}$. (64 scans at 2 cm$^{-1}$).

The thermal properties of the copolymers (FIG. 2B) are summarized in Table 1. In bulk, $P_{7.5K}$ is waxy while $P_{15K}$, $P_{32K}$ and $P_{39K}$ are powders. The glass transition temperatures ($T_g$) for $P_{7.5K}$, $P_{32K}$ and $P_{15K}$ were observed at ≈−62° C. whereas no $T_g$ was detected for $P_{39K}$. Aubin, M.; Prud'homme, R. E. Preparation and properties of poly (valerolactone). *Polymer* 1981, 22, (9), 1223-1226.; Keroack, D.; Zhao, Y.; Prud'homme, R. E. Molecular orientation in crystalline miscible blends. *Polymer* 1999, 40, 1, 243-251. Homopolymers (i.e. PVT, and PCL) of equivalent molecular weight were found to have higher degrees of crystallinity (Table 1). As shown in Table 1, for copolymers with similar AVL content, an increase in the molecular weight leads to a decrease in crystallinity due to a higher melt viscosity and chain entanglement (e.g. $CP_{15K}$ vs $CP_{32K}$). The overall effect is a higher level of stress in the amorphous layer that hinders the reputation process and prevents the thickening of the lamellae. Jenkins, M. J.; Harrison, K. L. The effect of molecular weight on the crystallization kinetics of polycaprolactone. Polymers for Advanced Technologies 2006, 17, (6), 474-478. In comparison to PVL homopolymer, copolymerization of AVL with VL was found to have a significant impact on the thermal properties of the resulting random copolymers (e.g. $T_m$ and $x_c$). The low M.W copolymer, $P_{7.5K}$, containing 28% AVL revealed a crystallization transition (Tc at −24° C. whereas The isotropic state of the copolymers was investigated in the infrared spectral region from 1800 cm$^{-1}$ to 1100 cm$^{-1}$ (FIG. 11). The strongest band observed at ~1730 cm$^{-1}$ is attributed to the carbonyl stretching modes of the copolymer backbone (vc=0). Three other bands of interest (e.g. 1325, 1250, 1170-1190 cm$^{-1}$), attributed to $v_{crystalline\ (C-O)\ \&\ (C-C)}$, $v_{s(COC)}$, $v_{as(COC)}-v_{amorphous}$, respectively, confirmed the relative degree of crystallinity of the polyesters.42 In comparison to $P_{7.5K}$, the copolymers with higher M.W (e.g. $P_{15K}$, $P_{32K}$ (data not shown) and $P_{39K}$) demonstrated more definite bands (orientation) and the appearance of a new band at 1325 cm$^{-1}$ ($v_{crystalline\ (C-O)\ \&\ (C-C)}$) (FIG. 11). In comparison to the amorphous $P_{7.5K}$, a shift to higher wavenumbers for the $v_{s(COC)}$, $v_{as(COC)}-v_{amorphous}$ bands (e.g. +10 cm$^{-1}$) and a significant enlargement of this band relative to vc=o (e.g. band at 1730-1711 cm$^{-1}$) confirmed a higher degree of crystallinity for copolymers with higher M.W or lower AVL content (i.e. $P_{15K}$ vs $P_{32K}$ vs $P_{39K}$). Keroack, D.; Zhao, Y.; Prud'homme, R. E. Molecular orientation in crystalline miscible blends. *Polymer* 1999, 40, 1, 243-251.; Murphy, S. H.; Leeke, G. A.; Jenkins, M. J. A Comparison of the use of FTIR spectroscopy with DSC in the characterisation of melting and crystallisation in polycaprolactone. *Journal of Thermal Analysis and Calorimetry* 2012, 107, 2, 669-674.

FIG. 2A shows $^1$H NMR spectra of one random block copolymer PVL-co-PAVL ($P_{39K}$) in CDCl$_3$. Inset includes the gel permeation chromatograms for the four copolymers $P_{7.5K}$, $P_{15K}$, $P_{32K}$ and $P_{39K}$. FIG. 2B shows thermograms for the four copolymers obtained by DSC at 10° C./min ($2^{nd}$ cycle).

Figure 1:
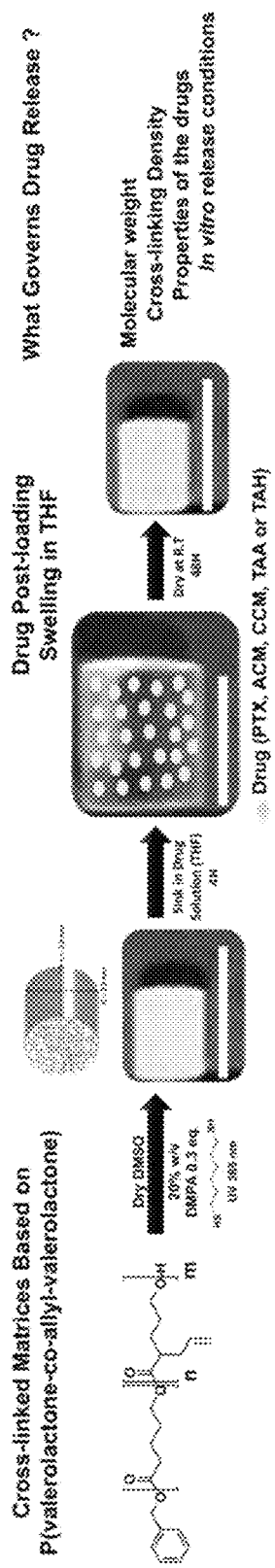
FIG. 1 shows a schematic of the formation of the cross-linked polymer network and post-drug loading procedure in organic solvent of the IDDS.
Figure 12:
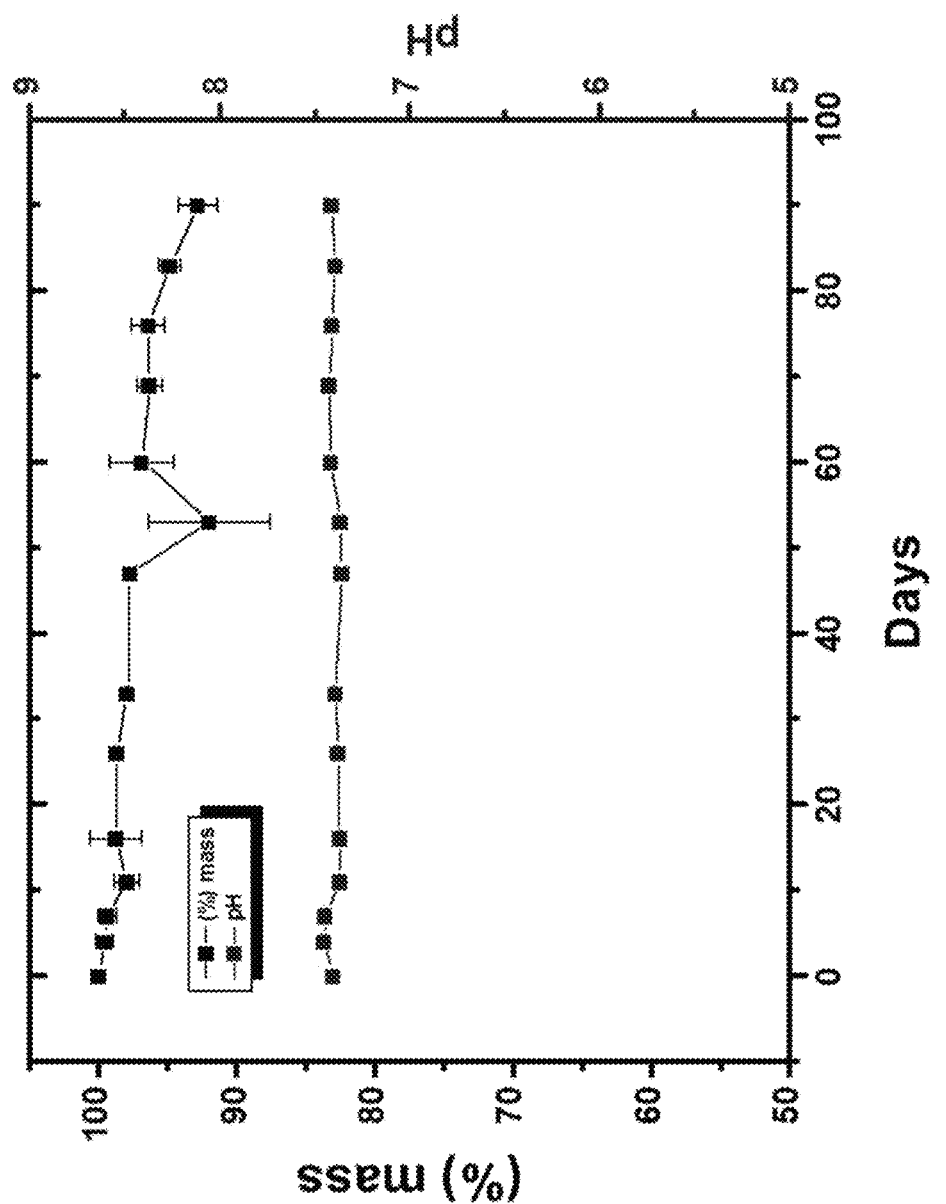
FIG. 12 shows stability of the $CP_{15K}$ in PBS pH 7.4. Evaluation of the weight loss (%) of $CP_{15K}$ matrix over a period of 90 days (n=3).
Figure 13:
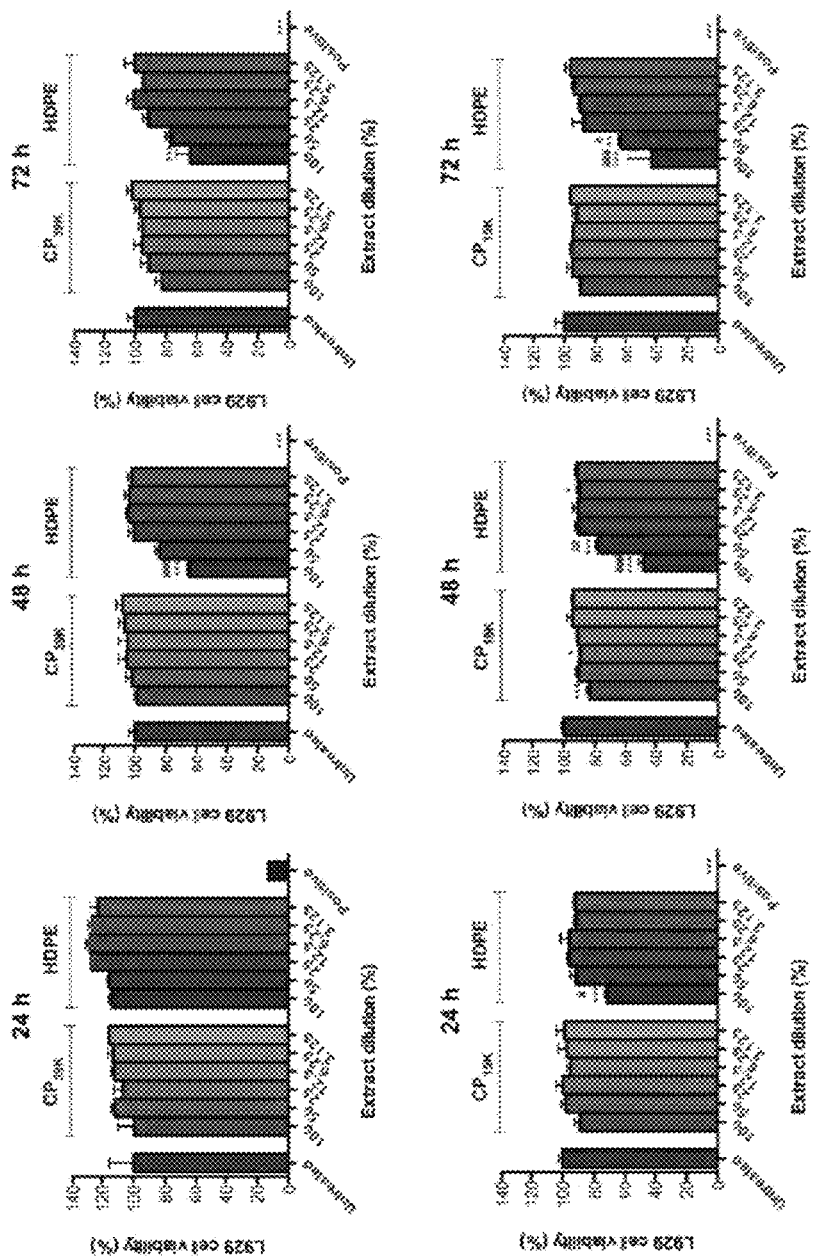
FIG. 13 shows in vitro cytotoxicity of the applied extract dilution of $CP_{39K}$ and $CP_{15K}$ cylinders (green) or high density polyethylene (HDPE) (purple) to L929 mouse fibroblast cells. Cells incubated with media alone were employed as a control and considered as 100% cell viability. (*, , and *) indicates lesser viability relative to untreated ($p<0.0001$, 0.01, and 0.05, respectively); (###, ##, and #) indicates lesser viability relative to treatment group ($CP_{39K}$) of same extract dilution concentration ($p<0.0001$, 0.01, and 0.05, respectively).

Characterization of the cross-linked matrices: Formation of the cross-linked polymer networks (CPs) was successfully achieved by thiolene click chemistry between pendant allyl groups on the copolymers and 1,6-hexanedithiol (FIG. 1). $UV_{365\ nm}$, curing of copolymer in a syringe followed by removal from the scaffold (syringe) and extensive washing in organic solvent (i.e. THF) resulted in a solid, transparent cylinder. Once dried, the CPs were characterized by FT-IR spectroscopy (FIG. 11), x-ray diffraction (XRD), DSC, and scanning electron microscopy (SEM) (FIG. 3 and FIG. 4). The stability of the cross-linked networks was evaluated by measuring weight loss as a function of time (FIG. 12) whereas the in vitro biocompatibility was assessed using the extract dilution method (FIG. 13). Baek, H. S.; Yoo, J. Y.; Rah, D. K.; Han, D.-W.; Lee, D. H.; Kwon, O.-H.; Park, J.-C. Evaluation of the Extraction Method for the Cytotoxicity Testing of Latex Gloves. *Yonsei Medical Journal* 2005, 46, (4), 579-583.; Zange, R.; Kissel, T. Comparative in vitro biocompatibility testing of polycyanoacrylates and -poly(d, l-lactide-co-glycolide) using different mouse fibroblast (L929) biocompatibility test models. *European Journal of Pharmaceutics and Biopharmaceutics* 1997, 44, 2, 149-157. Macroscopically, the cross-linked networks formed from the copolymers of different M.W were found to have distinct properties. With 28% allyl content, $CP_{7.5K}$ was found to be amorphous (flexible and transparent) with a $T_g$ at −47° C., whereas the networks formed from $P_{15K}$, $P_{32K}$ and $P_{39K}$ remained semi-crystalline (rigid and semi-opaque).

Figures 3A, 3B:
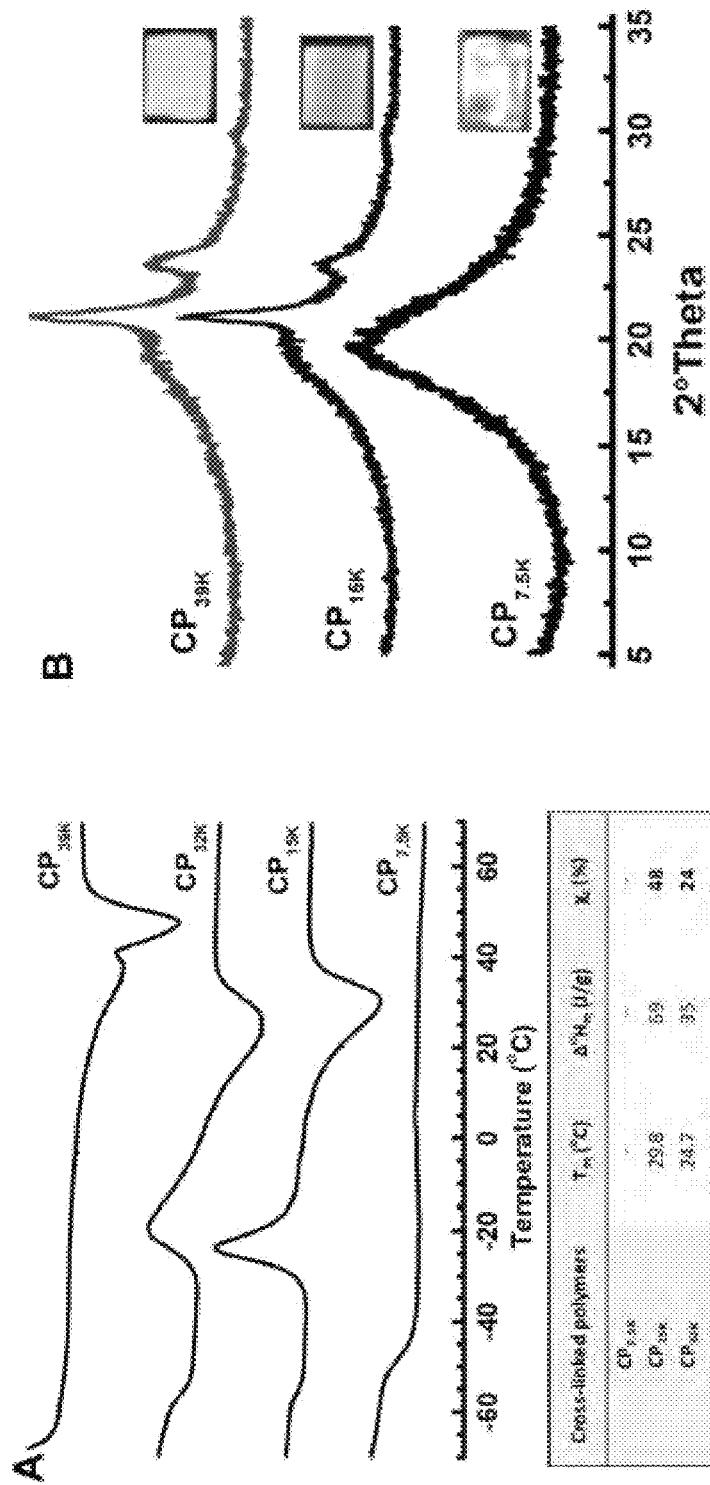
FIG. 3A shows representative DSC thermograms; Inset: table of the thermal properties of the different cross-linked matrices.
FIG. 3B shows representative x-ray diffraction patterns of the cross-linked materials.
Figure 4B:
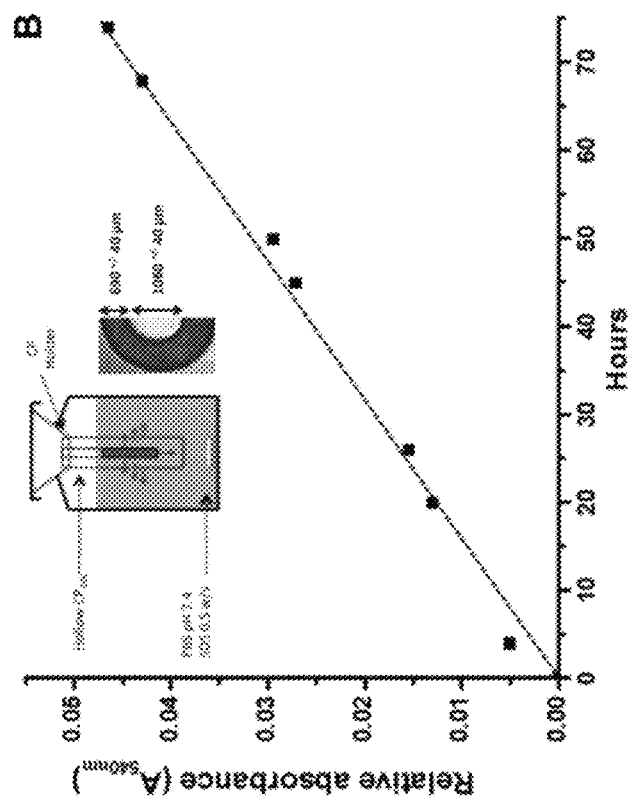
FIG. 4B shows Indirect evaluation of water diffusion across a hollow cylinder formed from the cross-linked polymer (CP39K). Transport of the hydrophilic probe sulforhodamine (A540 nm) was evaluated across the polymer matrix from the internal to the external media (PBS pH=7.4 with 0.5% w/v SDS).
Figure 4A:
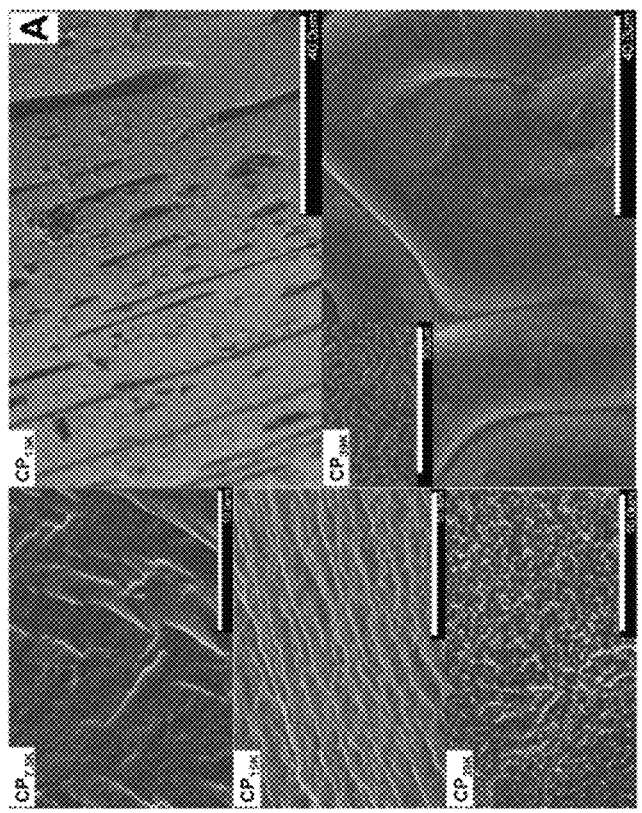
FIG. 4A shows SEM images of cross-sections of freeze dried matrices (left, scale bars represent 10 μm) and the surface morphology (right) of the cross-linked networks of CP7.5K, 15K and 39K (scale bar represents 40 μm and inset 300 μm).
Figure 14A:
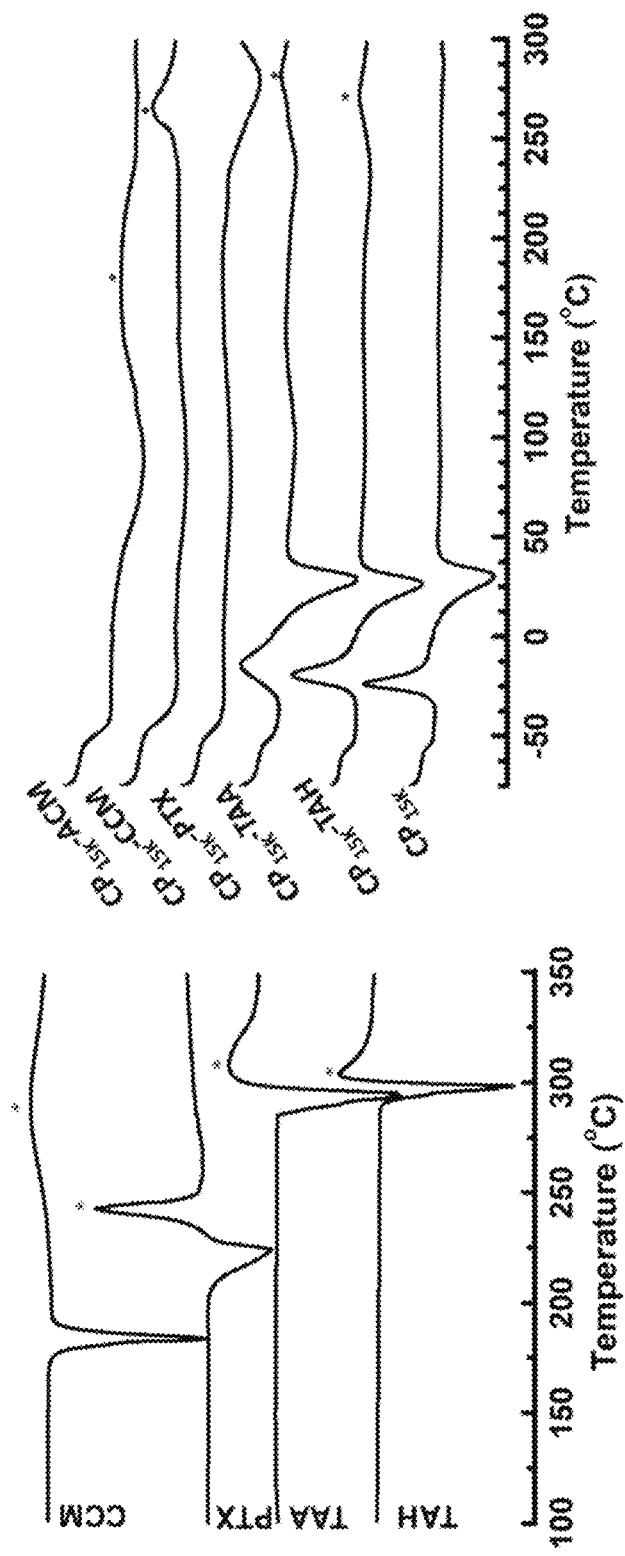
FIG. 14A shows DSC thermograms (left) of the drugs (e.i. TAH, TAA, PTX, CCM and ACM) and (right) full DSC thermograms of $CP_{15K}$ loaded at 10% w/w of drug analyzed at 10° C./min (1$^{st}$ cycle). Stars indicate degradation of drug.

At similar AVL content (i.e. ≈20%), the $T_m$ and degree of crystallinity of $CP_{15K}$ were found to be higher following crosslinking compared to $CP_{32K}$, whereas lowering the AVL content (e.g. $CP_{32K}$≈20% vs $CP_{39K}$≈9%) increased the $\chi_c$ of the cross-linked polymer (FIG. 3A, FIG. 3C and FIG. 14A). Boire et al., prepared similar polyester materials based on PCL-co-(allyl-carboxylate-caprolactone) (PCL-ACPCL) using a self-crosslinking reaction, and observed similar trends in thermal properties. Boire, T. C.; Gupta, M. K.; Zachman, A. L.; Lee, S. H.; Balikov, D. A.; Kim, K.; Bellan, L. M.; Sung, H.-J. Pendant allyl crosslinking as a tunable shape memory actuator for vascular applications. *Acta Biomaterialia* 2015, 24, 53-63. In agreement, $CP_{7.5K}$ exhibited a typical amorphous XRD pattern whereas cross-linked matrices with higher M.W. or lower AVL content (i.e. $CP_{15K}$, $CP_{32K}$ and $CP_{39K}$) demonstrated crystalline domains with the appearance of two characteristic peaks at 2θ=21.4° and 23.8° (FIG. 3B). Yeo, M.; Jung, W.-K.; Kim, G. Fabrication, characterisation and biological activity of phlorotannin-conjugated PCL/[small beta]-TCP composite scaffolds for bone tissue regeneration. *Journal of Materials Chemistry* 2012, 22, (8), 3568-3577. FIG. 4A shows SEM images of cross-sections of freeze dried matrices (left, scale bars represent 10 μm) and the surface morphology (right) of the cross-linked networks of $CP_{7.5K,\ 15K\ and\ 39K}$ (scale bar represents 40 μm and inset 300 μm). FIG. 4B Indirect evaluation of water diffusion across a hollow cylinder formed from the cross-linked polymer ($CP_{39K}$). Transport of the hydrophilic probe sulfo-rhodamine ($A_{540\ nm}$) was evaluated across the polymer matrix from the internal to the external media (PBS pH=7.4 with 0.5% w/v SDS).

As shown in FIG. 11, the intensity of the $v_{crystalline\ (C-O)\ \&\ (C-C)}$ bands in the FTIR spectra of crystalline copolymers (i.e. $P_{15K}$, $P_{32K}$ and $P_{39K}$) is maintained after crosslinking (i.e. $CP_{15K}$, $CP_{32K}$ and $CP_{39K}$ and the amorphous state of $P_{7.5K}$ remained after the reaction (i.e. $CP_{7.5K}$). SEM microscopy was used to evaluate the cross-section and surface (wall) morphologies of the four matrices (FIG. 4A). Microscopic analysis revealed that the morphology varies with the M.W of the copolymers used for preparation. CP cross-sections demonstrated an increase in roughness with increasing M.W and crystallinity of the copolymers.

Regardless of copolymer M.W. and cross-linking density, significant porosity was not apparent at the magnifications employed on the freeze-dried samples. A coral-like, heterogeneous surface morphology with densely packed folds was observed for $CP_{39K}$, whereas a smooth surface with uniform ridges was observed for $CP_{32K}$, $CP_{15K}$ and $CP_{7.5K}$ (FIG. 4A). As described for latex-based matrices, water can diffuse within the matrix. Folkman, J.; Long, D. M. The use of silicone rubber as a carrier for prolonged drug therapy. *Journal of Surgical Research* 1964, 4, 3, 139-142. In the present study, the diffusion of water into the polymer matrix was evaluated using a hollow cylinder (FIG. 4B). An aqueous solution containing the hydrophilic probe sulfo-rhodamine was filled into the cavity of the cylinder, sealed at the top and diffusion through the cross-linked polymer material (wall thickness=640 μm) was monitored by measurement of probe content in the external media over a 72-hour period. As shown in FIG. 4B, even at early time-points there is linear transport (diffusion) of the probe across the polymer matrix. Based on optical and SEM microscopy (data not shown) and measurement of weight loss, the cross-linked matrices remained unchanged over three months in 0.1 M PBS (pH 7.4) at 37° C. (FIG. 12). However, this study only comprise preliminary assessment of the stability and degradation of this system. In the future, studies examining the kinetics of bulk erosion will include cross-sectional analysis of morphology as a function of time. The degradation rates of PCL and PVL polymers are known to be slower than that for PGA or PLA polymers of similar molecular weight. Lyu, S.; Untereker, D. Degradability of Polymers for Implantable Biomedical Devices. *International Journal of Molecular Sciences* 2009, 10, (9), 4033-4065.; Sung, H.-J.; Meredith, C.; Johnson, C.; Galis, Z. S. The effect of scaffold degradation rate on three-dimensional cell growth and angiogenesis. *Biomaterials* 2004, 25, (26), 5735-5742. Similar cylindrical IDDS (e.g. $PCL_{66k}$-F68) inserted subcutaneously in rats showed a linear rate of degradation over three years with less than 10% weight loss after three months and 77% weight loss after 30 months. Sun, H.; Mei, L.; Song, C.; Cui, X.; Wang., P. The in vivo degradation, absorption and excretion of PCL-based implant. *Biomaterials* 2006, 27, (9), 1735-1740. As described by Toncheva et al. (1996), hydrolytic degradation of discs composed of PVL and PCL (21.5 mm×1.3 mm) revealed minor water uptake (≤3%), low weight loss (≤4%), and no change in M.W over a period of 20 weeks. Toncheva, V.; Van Den Bulcke, A.; Schacht, E.; Mergaert., J.; Swings, J. Synthesis and environmental degradation of polyesters based on poly (ε-caprolactone). *Journal of environmental polymer degradation* 1996, 4, 2, 71-83. Herein, even if selective degradation of the amorphous regions can occur prior to degradation of the crystalline regions of the PVL matrix, the chemical cross-linking, which leads to formation of the CP matrices, provides good stability over time under neutral conditions.

Figures 5A, 5B:
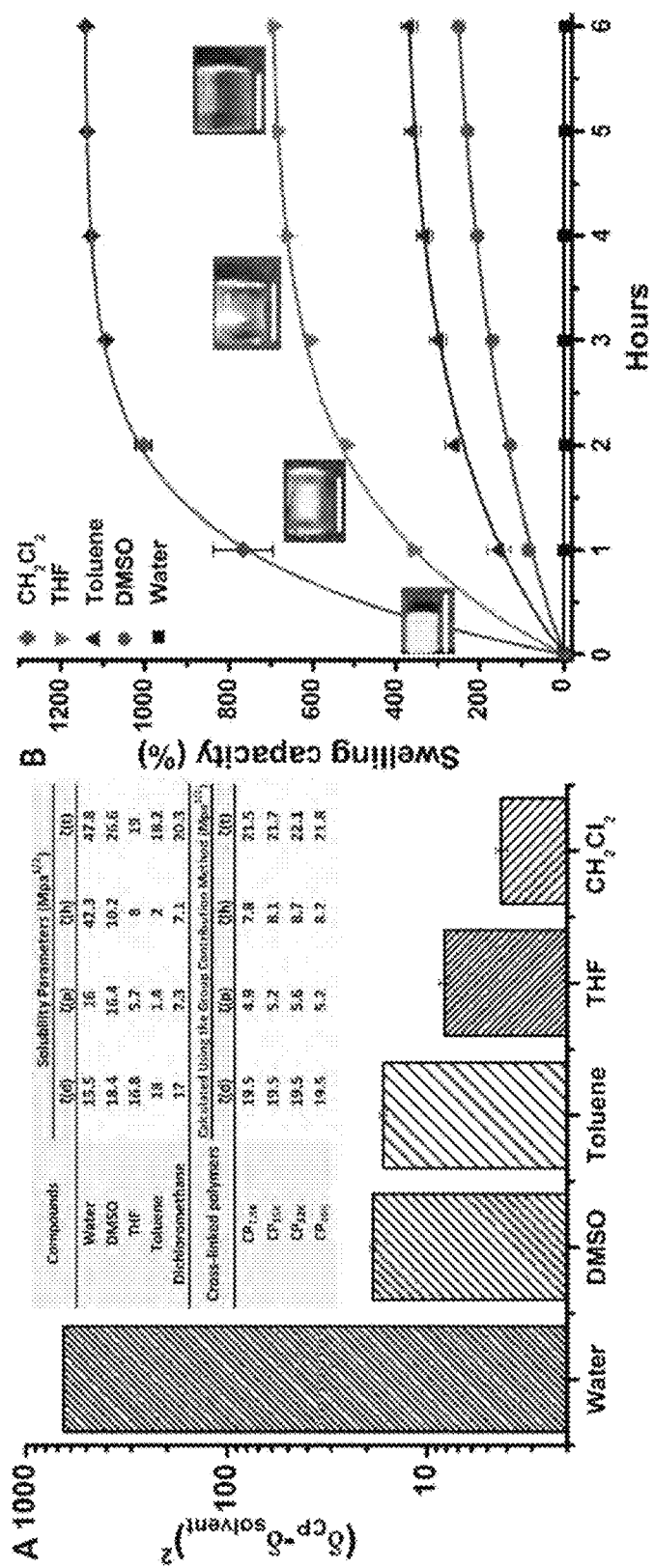
FIG. 5A shows a plot of the calculated $(\delta_{CP}-\delta_{sol})^2$ and solubility parameters of the solvents and of the $CP_{7.5K\to39K}$ matrices using the group contribution method (MPa$^{1/2}$). Jenkins, M. J.; Harrison, K. L. The effect of molecular weight on the crystallization kinetics of polycaprolactone. *Polymers for Advanced Technologies* 2006, 17, (6), 474-478. Jouyban., A., *Handbook of Solubility Data for Pharmaceuticals*. CRC Press: 2009.
FIG. 5B shows swelling capacity of the cylinders $CP_{39K}$) in distinct solvents as a function of time (n=2). Inset pictures of $CP_{39K}$ swollen in THF ($t_{0h}$, $t_{1.5h}$, $t_{3h}$, $t_{4h}$). Scale bar represents 0.5 cm.

Solubility parameters and swelling capacity: To determine the compatibility between solvent, copolymer, cross-linked materials and the selected drugs, partial ($\delta_{d,p,h}$) and total (St) solubility parameters of all components were calculated using the group contribution method (GCM). The calculated solubility parameters obtained for both $\delta_{pavl}$ and $\delta_{pvl}$ are close to the solubility parameters of the aprotic and nonpolar solvents used for post-loading of drugs (FIG. 5A). The smaller the difference between the values for δ(t) of the solute and solvent, the greater the solubility of the solute in the solvent (i.e. Δδ(t)≤7.5 MPa$^{1/2}$ for a solute-solvent pair). Van Krevelen, D. W.; Te Nijenhuis, K., Chapter 7—Cohesive Properties and Solubility. In *Properties of Polymers* (*Fourth Edition*), Elsevier: Amsterdam, 2009; pp 189-227. Solubility parameter values ($δ_{d,p,h,t}$) have been calculated for the four cross-linked matrices (including Sa contribution for 1,6-hexanedithiol) and compared to values for the partial solubility parameters of select drug loading solvents (FIG. 5A). Liu, J.; Xiao, Y.; Allen, C. Polymer-drug compatibility: A guide to the development of delivery systems for the anticancer agent, ellipticine. *Journal of Pharmaceutical Sciences* 2004, 93, 1, 132-143. Swelling occurs in a polymer-solvent system when the free energy of mixing is favorable, (e.g. $ΔG_m$<0). The swelling is maximal when $(δ_{CP}-δ_{sol})^2$ is 0, where $δ_{pol}$ and $δ_{sol}$ are the solubility parameters of the polymer and solvent, respectively (FIG. 5A). The degree of swelling observed for the four copolymer matrices (CPs) in the various solvents was in good agreement with the solvent-network compatibility as predicted by values obtained using the GCM method (i.e. $CH_2Cl_2$>THF>Toluene>DMSO>$H_2O$) (FIG. 5B). The same trend was observed for all copolymer systems (i.e. $CP_{7.5K}→CP_{39K}$). While $CP_{39K}$ and $CP_{32K}$ implants swelled well in $CH_2Cl_2$ (e.g. swelling >1100%), $CP_{7.5K}$ and $CP_{15K}$ broke into pieces after two hours. This is likely due to the relatively low M.W of PVL-co-PAVL copolymers that comprised the $CP_{7.5K}$ and $CP_{15K}$ matrices. Due to the high degree of implant swelling and drug solubility in THF, this solvent was chosen as the solvent for drug loading. In terms of geometry, following four hours of equilibration in THF, the four-copolymer matrices swelled more in diameter than in length i.e. 2.5 vs 1.3 times, respectively.

FIG. 5A shows a plot of the calculated $(δcp-δ_{sol})^2$ and solubility parameters of the solvents and of the $CP_{7.5K→39K}$ matrices using the group contribution method (MPa$^{1/2}$). Jenkins, M. J.; Harrison, K. L. The effect of molecular weight on the crystallization kinetics of polycaprolactone. *Polymers for Advanced Technologies* 2006, 17, (6), 474-478.; Jouyban., A., *Handbook of Solubility Data for Pharmaceuticals*. CRC Press: 2009. FIG. 5B shows swelling capacity of the cylinders ($CP_{39K}$) in distinct solvents as a function of time (n=2). Inset pictures of $CP_{39K}$ swollen in THF ($t_{0h}$, $t_{1.5h}$, $t_{3h}$, $t_{4h}$). Scale bar represents 0.5 cm.

Figure 6B:
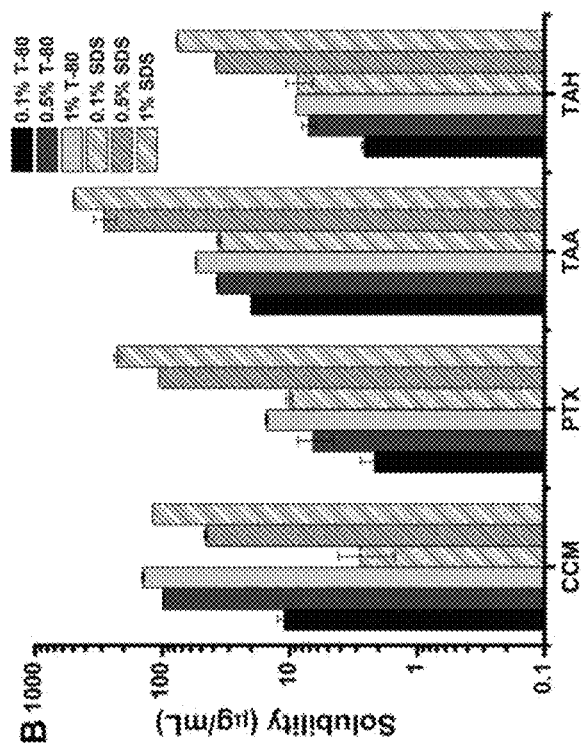
FIG. 6B shows solubility of the hydrophobic drugs in PBS (pH=7.4) containing 0.1%, 0.5%, or 1% (w/v) Tween 80 (T-80) or SDS (n=3).
Figure 6A:
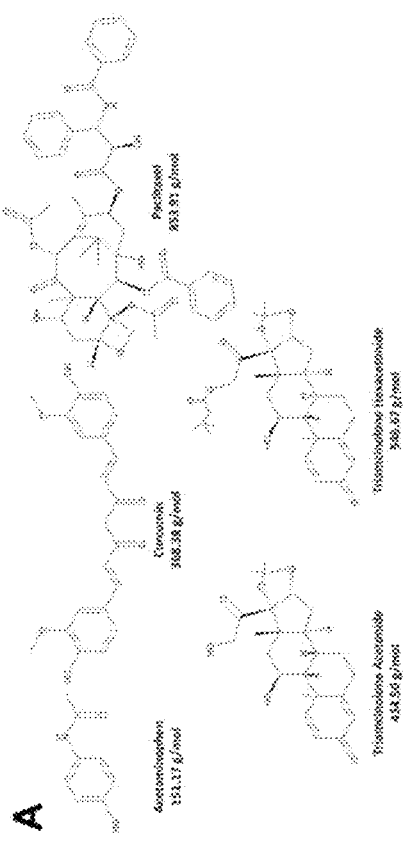
FIG. 6A shows chemical structures of drugs selected for loading into the CP matrices.

Evaluation of the physiochemical properties of the drugs: Five drugs that vary in terms of physicochemical properties, such as M.W, log P, and water solubility were selected as model drugs for incorporation into the four matrices (FIG. 6A). The drugs chosen include acetaminophen (ACM), a simple analgesic; curcumin (CCM) a natural hydrophobic compound with anti-inflammatory activity; paclitaxel (PTX), a chemotherapeutic agent; triamcinolone acetonide (TAA) and triamcinolone hexacetonide (TAH), two commonly used corticosteroids for the treatment of osteoarthritis.

TABLE 2

Solubility parameters, molar volumes and LogP values for the drugs loaded into the polymer matrices.

| Drugs | Calculated Solubility Parameter by GCM (MPa)$^{1/2}$ | | | | | Calculated V (cm$^2$/mol) | Predicted * V (cm$^3$/mol) | Calculated LogP | Predicted * LogP | M.W. (g/mol) |
|---|---|---|---|---|---|---|---|---|---|---|
| | ζ(d) | ζ(p) | ζ(h) | ζ(t) | ζ(E/V) | | | | | |
| Acetaminophen | 20.6 | 6.3 | 14.8 | 26.7 | 28.7 | 111 | 121 | 0.7 | 3.5-3.9 | 151.1 |
| Paclitaxel | 20.8 | 6.2 | 13.0 | 24.9 | 28.3 | 590 | 611 | 2.7 | 2.5-3.5 | 853.9 |
| Curcumin | 20.8 | 8.9 | 14.8 | 21.0 | 23.2 | 300 | 288 | 3 | 3.2-3.7 | 368.4 |
| Triamcinolone acetonide | 18.0 | 3.3 | 11.8 | 21.8 | 23.2 | 328 | 325 | 2.3 | 1.9-2.5 | 434.5 |
| Triamcinolone hexacetonide | 18.3 | 4.4 | 9.0 | 20.8 | 20.8 | 417.7 | 427 | N.D | 4.1-4.8 | 532.6 |

* Values have been determined using ACD/Lab and Chemaxon softwares.

In order to evaluate the influence that the physico-chemical properties of the drugs have on their respective release profiles from the cross-linked matrices, the limit of solubility in different media, the logarithm of the octanol-water partition coefficient (i.e. log P (=Log ([c]octanol/[c]water)), and the solubility parameters of the different drugs were determined. The log P of four of the drugs was determined by the shake tube method with log P values between −2 to 4 obtained for all drugs. The log P value for TAH was estimated using softwares* (Table 2). OECD. Guidelines for Testing of Chemicals. Section 1, Physical Chemical properties. 1995, 107.

FIG. 6A shows chemical structures of drugs selected for loading into the CP matrices. FIG. 6B shows solubility of the hydrophobic drugs in PBS (pH=7.4) containing 0.1%, 0.5%, or 1% (w/v) Tween 80 (T-80) or SDS (n=3).

To ensure that sink conditions were maintained in the drug release study, two common surfactants, Tween 80 and SDS, were included in the release media. According to the GCM (e.g. $(δ_{drug}-δ_{surfactant})^2$), both surfactants were found to have good compatibility with all drugs (i.e. δ(t)=21.1 MPa$^{1/2}$ and 28.7 MPa$^{1/2}$ for Tween 80 and SDS, respectively) and improved their aqueous solubility when surfactant concentrations were higher than 0.5% w/v ($δ(t)_{drugs}$ in Table 2 and FIG. 6B). Mikkelsen, L. M., Enzyme solubility in liquid detergent and use of detergent composition. Google Patents: 2014.; Samaha, M. W.; Naggar, V. F. Micellar properties of non-ionic surfactants in relation to their solubility parameters. *International Journal of Pharmaceutics* 1988, 42, 1, 1-9. SDS (0.5% (w/v)) was employed as the surfactant for the majority of the release studies given that it resulted in the highest increase in aqueous solubility of the drugs. It has also been reported that SDS can minimize non-specific drug adsorption at the surface of polymer matrices and promotes the dissociation of non-covalent drug-drug aggregates. Crotts, G.; Park, T. G. Protein delivery from poly(lactic-co-glycolic acid) biodegradable microspheres: Release kinetics and stability issues. *Journal of Microencapsulation* 1998, 15, (6), 699-713. The FDA guidance for dissolution studies include use of SDS for water-insoluble or sparingly water-soluble drugs. FDA. Guidance for Industry: Dissolution Testing of Immediate Release Solid Oral Dosage Forms, Office of Training and Communications, Rockville, Md., 1997, pp. A1-A2. 1997.

Figure 7B:
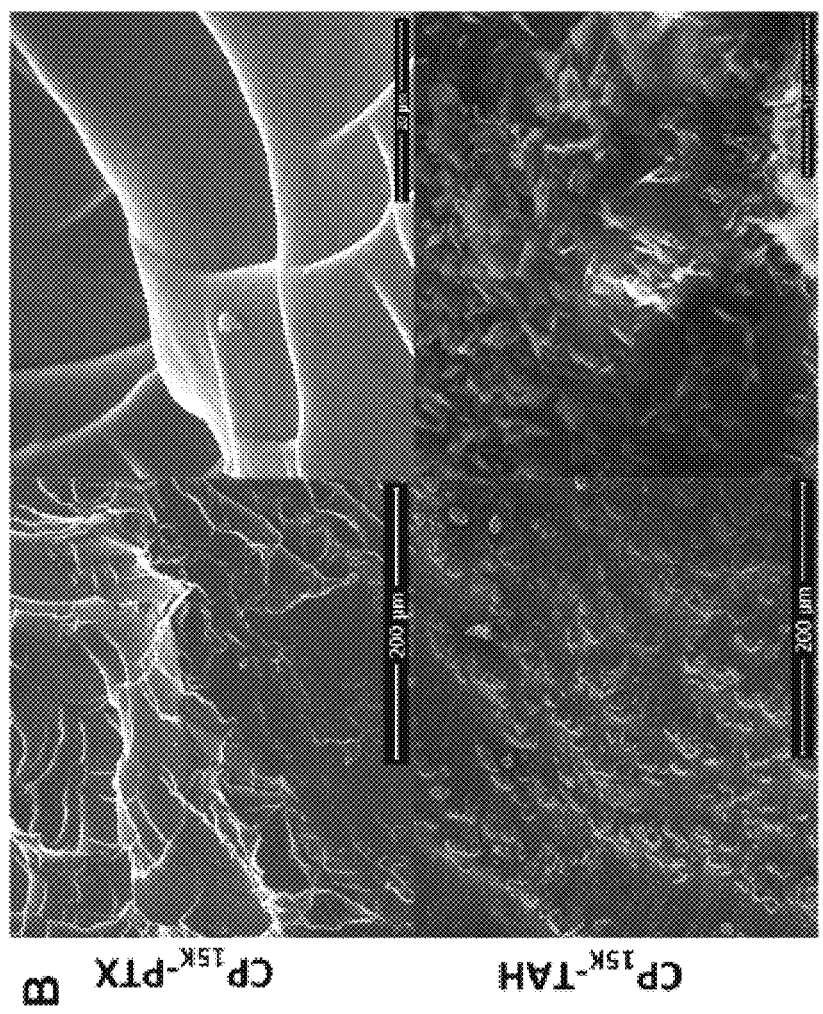
FIG. 7B shows representative SEM micrographs of matrices loaded with PTX (upper) and with TAH (lower).
Figure 7A:
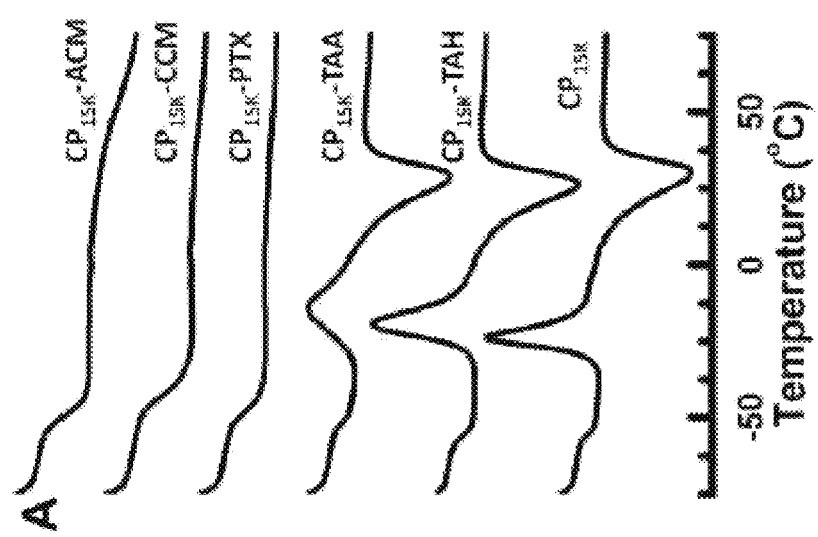
FIG. 7A shows DSC thermograms (exothermic up) of the $CP_{15K}$ matrices loaded with the five model drugs (10% w/w).
Figure 15:
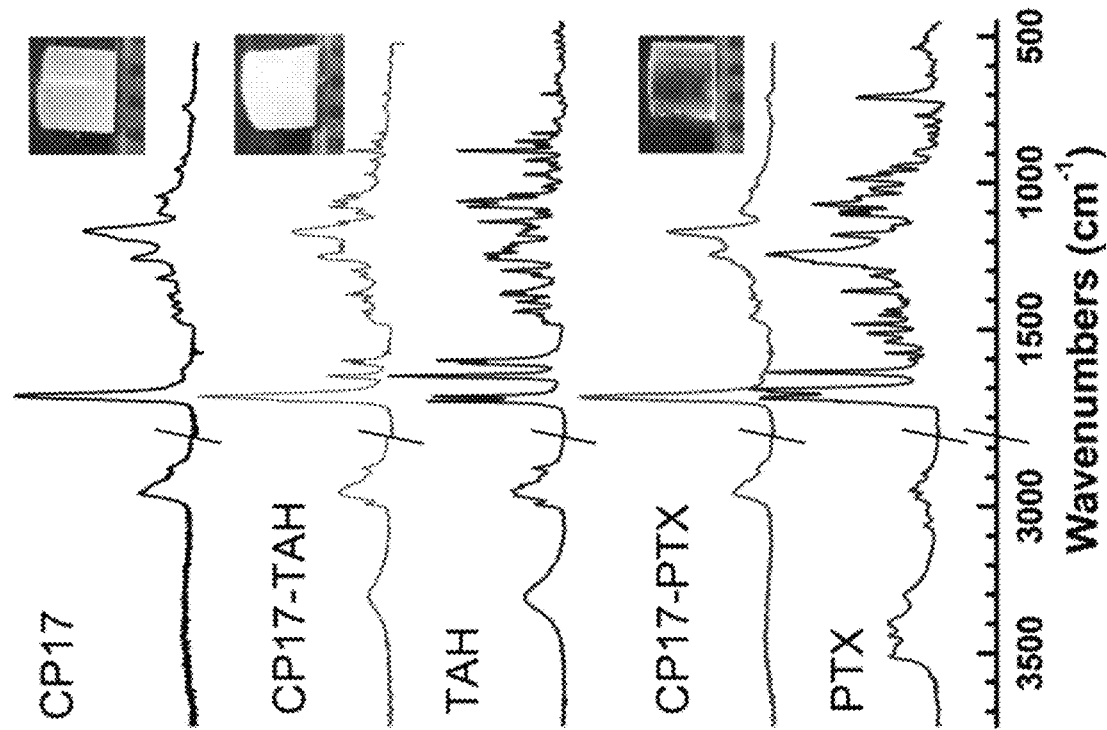
FIG. 15 shows FTIR spectra of $CP_{15K}$ loaded with TAH and PTX as well as the FTIR spectra of the drugs. Insets include images of the drug free and drug loaded cylindrical cross-linked materials.

Loading and state of the drugs in the cross-linked matrices: The drug-loaded matrices were characterized by several methods including DSC, XRD, FTIR, and SEM. Depending to the amount of drug dissolved in the THF solution, the drug loading content (DLC) of the matrices for all drugs ranged from 10 to 20% (±4%) with drug loading efficiencies between 10 to 17%. Macroscopically, CP-ACM, CP-PTX, and CP-CCM loaded at 10% and 20% drug content, were transparent, similar to the unloaded $CP_{7.5K}$, whereas CP-TAA and CP-TAH were opaque (FIG. 15). DSC revealed the presence of crystalline drug within the CP-TAA and CP-TAH systems, but not within the CP-ACM, CP-CCM, or CP-PTX polymer-drug matrices (FIG. 7A). In solid dispersions, drug and polymer can be completely miscible in their liquid state (i.e. post-loading step), but upon solidification (i.e. evaporation step), the drug can take on different forms, such as the supersaturated solid solution phase, a distinct amorphous phase, crystalline phase(s) (i.e. polymorphism) or a combination of two or more of these phases. Drug stabilization in polymeric matrices is known to be maintained by minimizing the molecular mobility of drugs (e.g. incorporating in a polymeric matrix with high $T_g$), decreasing the free volume within the matrix (e.g. increasing the cross-linking density) and by favorable drug-polymer interactions which may disrupt drug-drug interactions. M. Vasanthavada; W.-Q. Tong; Serajuddin, A., *Water-Insoluble Drug Formulation, Second Edition*. CRC press: 2008.; Egawa, H.; Maeda, S.; Yonemochi, E.; Oguchi, T.; Yamamoto, K.; Nakai, Y. Solubility Parameter and Dissolution Behavior of Cefalexin Powders with Different Crystallinity. *CHEMICAL & PHARMACEUTICAL BULLETIN* 1992, 40, 3, 819-820.

FIG. 7A shows DSC thermograms (exothermic up) of the $CP_{15K}$ matrices loaded with the five model drugs (10% w/w). FIG. 7B shows representative SEM micrographs of matrices loaded with PTX (upper) and with TAH (lower). FIG. 7C shows comparison of the XRD patterns of the $CP_{39K}$ matrices loaded with TAH and CCM. FIG. 7D shows the percent crystallinity (left axis) and the melting transition temperatures ($T_m$, right axis) for the $CP_{39K}$ matrices after drug incorporation (red dots indicate the first transition temperature $T_{m1}$ and blue indicate the second transition temperature $T_{m2}$).

Figure 14B:
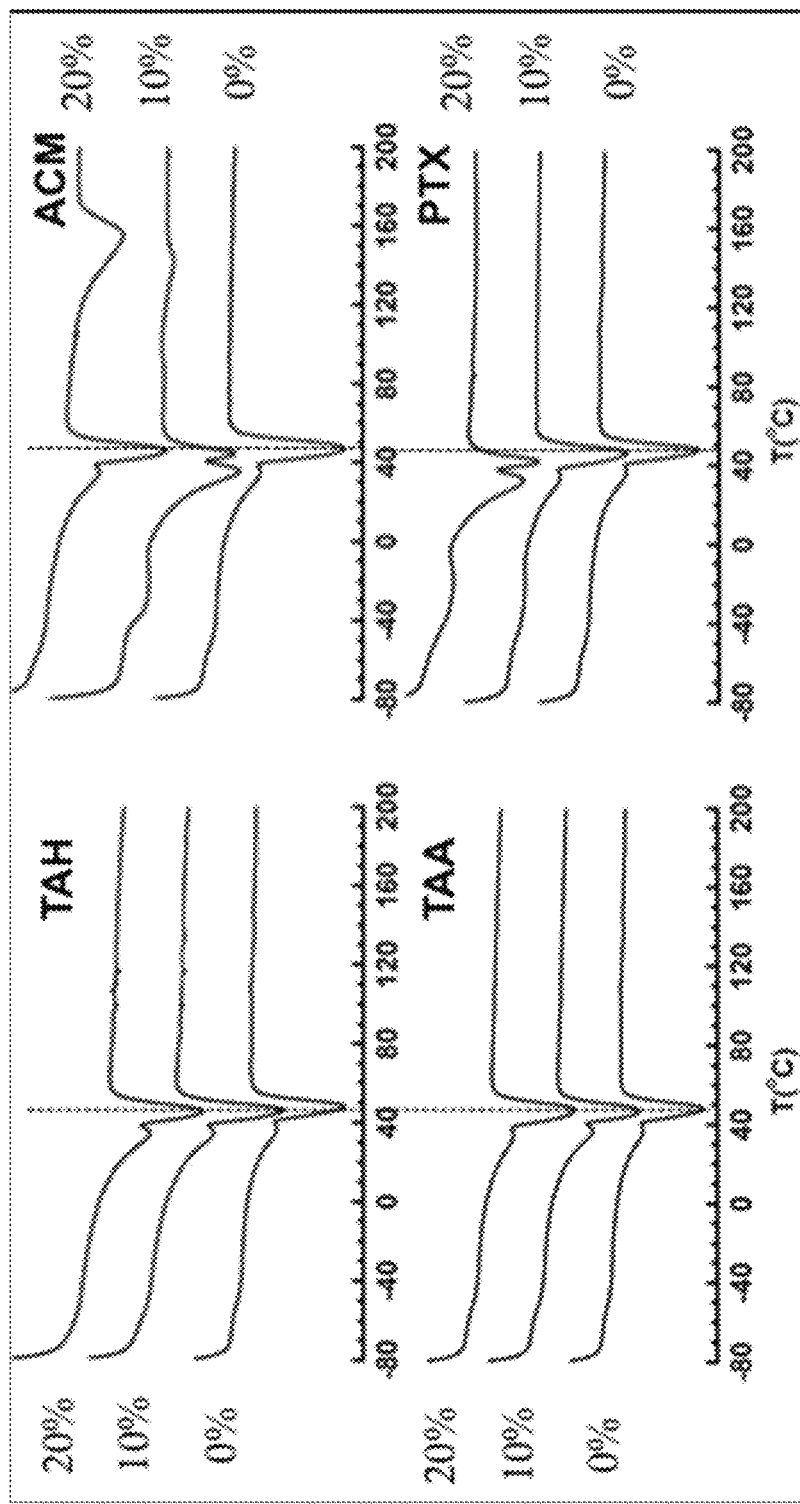
FIG. 14B shows an example of thermograms of $CP_{39K}$ loaded with the drugs at 10 and 20% (±4%) w/w.

According to the DSC thermograms, incorporation of ACM, PTX and CCM in the $CP_{15K}$, and $CP_{32K}$ lead to a loss in the crystallinity of the matrices ($CP_{7.5K}$ remained amorphous) with no sharp melting transitions related to the drugs (FIG. 7A, FIG. 7D, & FIG. 14A). The amorphous state of the matrices (i.e. $CP_{15K}$ and $CP_{32K}$) loaded with ACM, CCM, or PTX suggests that the drugs are molecularly dispersed throughout the matrices and this may be attributed to favorable polymer-drug interactions. Drug incorporation within the $CP_{39K}$ matrix had a significant impact on the degree of crystallinity of the cross-linked material (FIG. 7D & FIG. 14B).

Depending on the drug and the drug loading content, it appears that there are different degrees of interaction between the drug and the polymers. Miscible or partially miscible drugs in CPs result in melting point depression or no melting point depression of the drug (FIG. 14B). ACM in $CP_{15K}$ showed a broad depressed melting transition whereas loaded in $CP_{39K}$, $T_m$ temperature remained at similar values observed for the free ACM. In comparison, melting transitions of PTX and CCM loaded in $CP_{15K}$ were similar to those observed to their crystalline form whereas no detectable melting transitions were observed when loaded in $CP_{32K}$ or $CP_{39K}$. As shown in FIG. 13, the broad melting transitions at 240-260° C. can be explained by characteristic polymorphic transitions of TAH and TAA within the matrices. da Silva-Junior, A. A.; de Matos, J. R.; Formariz, T. P.; Rossanezi, G.; Scarpa, M. V.; do Egito, E. S. T.; de Oliveira, A. G. Thermal behavior arid stability of biodegradable spray-dried microparticles containing triamcinolone. *International journal of Pharmaceutics* 2009, 368, 1, 45-55. XRD and FTIR spectroscopy analyses confirmed the presence of defined crystalline structures of TAA and TAH within the matrices (FIG. 7C & FIG. 15). Drugs having high melting points (i.e. TAH and TAA, $T_m \approx 300°$ C.) demonstrate low miscibility in polymers (FIG. 14A). Marsac, P. J.; Shamblin, S. L.; Taylor, L. S. Theoretical and Practical Approaches for Prediction of Drug-Polymer Miscibility and Solubility. *Pharmaceutical Research* 2006, 23, (10), 2417. According to Greenhalgh et al., based on the magnitude of the differences in solubility parameters for the CPs and drugs, which ranged from 0.6-4.5 $MPa^{1/2}$ ($\Delta\delta$<7 $MPa^{1/2}$), polymer-drug miscibility is expected for all systems (Table 2, Table 5 and FIG. 5A). Greenhalgh, D. J.; Williams, A. C.; Timmins, P.; York, P. Solubility parameters as predictors of miscibility in solid dispersions. *Journal of Pharmaceutical Sciences* 1999, 88, (11), 1182-1190. Despite the expected favorable interaction between polymer and drug, the adhesive and cohesive interactions (i.e. van der Waals, Debye, Hydrogen, charge transfer interaction) differ experimentally in strength and directionality. Marsac, P. J.; Shamblin, S. L.; Taylor, L. S. Theoretical and Practical Approaches for Prediction of Drug-Polymer Miscibility and Solubility. *Pharmaceutical Research* 2006, 23, (10), 2417. Indeed, halogenated drugs such as TAH and TAA with low polarity $\delta_p$ and/or low capacity for hydrogen bonds formation 8 h (with the matrices), resulted in adhesive interactions rather than cohesive interactions within the polymer matrices. Marsac, P. J.; Shamblin, S. L.; Taylor, L. S. Theoretical and Practical Approaches for Prediction of Drug-Polymer Miscibility and Solubility. *Pharmaceutical Research* 2006, 23, (10), 2417. Favorable conditions (i.e. cohesive interactions), leading to molecular dispersions (e.g. ACM, CCM, and PTX) seemed to be present when aromatic drugs are loaded into the matrices (FIG. 7A and FIGS. 14A-B and FIG. 15). To confirm these observations, two other steroids with lower fusion temperatures, cholesterol ($\delta_f$=20.7 $MPa^{1/2}$) and hydrocortisone ($\delta_f$=25.4 $MPa^{1/2}$), with $T_m$=148° C., and 220° C., respectively, were loaded (10% w/w) within the cross-linked matrix (e.g. $CP_{39K}$ data not shown). TAH and TAA only decreased the $\chi_{CP39K}$ to 90 and 75%, respectively, and cholesterol and hydrocortisone decreased the crystallinity of the matrix to values as low as 60 to 55%, indicating a higher degree of drug-matrix interaction (i.e. transparent matrices). The analysis hints that molecular dispersion of select drugs within the cross-linked matrices is largely dependent on the $T_m$ of the drugs. Marsac, P. J.; Shamblin, S. L.; Taylor, L. S. Theoretical and Practical Approaches for Prediction of Drug-Polymer Miscibility and Solubility. *Pharmaceutical Research* 2006, 23, (10), 2417. Unlike polymers that have a high $T_g$ (e.g. PLGA or PVP), the cross-linked materials in this study (i.e. CPs) have a low $T_g$ ($\approx$−55° C.) and may allow for crystallization of TAA and TAH due to their higher degrees of freedom and mobility within the polymeric matrices. Marsac, P. J.; Shamblin, S. L.; Taylor, L. S. Theoretical and Practical Approaches for Prediction of Drug-Polymer Miscibility and Solubility. *Pharmaceutical Research* 2006, 23, (10), 2417. Although, it appears that cross-linked density does not play a predominant role in the crystallization or the miscibility of the drugs within the matrices but rather depends on the chemical properties of the drugs (e.g. $f_m$ of the drug Vs free volume within the matrix).

Evaluation of in vitro drug release: impact of the nature of the drug, polymer and release media: In the in vitro release studies the impact of a number of variables was evaluated including nature of the drug, compatibility between the drug and the polymer matrix, degree of crystallinity of the matrix, M.W. of the copolymer, cross-linking density and the composition of the release media. The commonly used, sample-and-separate method was employed to evaluate drug release from the cross-linked matrices. D'Souza, S. S.; DeLuca, P. P. Methods to Assess in vitro Drug Release from Injectable Polymeric Particulate Systems. *Pharmaceutical Research* 2006, 23, 3, 460-474. To compare drug release from the matrices (i.e. $CP_{7.5K}$, $CP_{15K}$, $CP_{32K}$ and $CP_{39K}$) under similar conditions, SDS at 0.5% (w/v) was chosen to maintain sink conditions.

Drug release mechanism from cross-linked matrices: Mathematical modeling of drug release is a highly useful tool in pre-clinical formulation optimization. Firstly, it enables quantitative prediction of the effects of changes in formulation and processing parameters on the resulting drug release kinetics. Secondly, it can provide insight into the underlying mechanisms controlling drug release from the particular dosage form. Siepmann, J.; Siepmann, F. Mathematical modeling of drug delivery. *International Journal of Pharmaceutics* 2008, 364, 2, 328-343. However, no universal mathematical model is applicable for release kinetics from all polymeric matrices due to the many variables that must be taken into account to model solute transport. Under perfect sink conditions, diffusion of drug within the matrices will depend on the physical structure of the matrix (i.e. porosity, crystallinity, cross-linking density), the diffusion of water, the aqueous solubility of the drug, state of the drug (i.e. amorphous vs crystalline) and drug content (i.e. DIX) within the matrix, as well as the relative interaction(s) between the polymer matrix and drug. To gain an understanding of the mechanism(s) controlling drug release from the polymeric matrices, different commonly used mathematical models (FIG. 8C), were applied to the experimental data (i.e. First order, Higuchi, Korsemayer-Peppas and Peppas-Sahlin models). Zhang, Y.; Huo, M.; Zhou, J.; Zou, A.; Li, W.; Yao, C.; Xie, S. DDSolver: An Add-In Program for Modeling and Comparison of Drug Dissolution Profiles. *The AAPS Journal* 2010, 12, 3, 263-271. The first order model describes mainly a linear relationship of drug dissolution (i.e concentration dependent) over time from pharmaceutical dosage. The Higuchi model describes the release of a drug from an insoluble matrix as the square root of a time-dependent process based on Fickian diffusion (i.e. penetration of the solvent within the matrix, dissolution and leaching out of the drug). In addition to these assumptions, models such as Korsemayer-Peppas and Peppas-Sahlin take into consideration the geometry of the matrix and other drug transport parameters. Peppas, N. A.; Sahlin, J. J. A simple equation for the description of solute release. III. Coupling of diffusion and relaxation. *International Journal of Pharmaceutics* 1989, 57, 2, 169-172.; Higuchi, T. Rate of Release of Medicaments from Ointment Bases Containing Drugs in Suspension. *Journal of Pharmaceutical Sciences* 1961, 50, (10), 874-875.; Korsmeyer, R. W.; Gurny, R.; Doelker, E.; Burl, P.; Peppas, N. A. Mechanisms of solute release from porous hydrophilic polymers. *International Journal of Pharmaceutics* 1983, 15, 1, 25-35.; Ritger, P. L.; Peppas, N. A. A simple equation for description of solute release 1. Fickian and non-fickian release from non-swellable devices in the form of slabs, spheres, cylinders or discs. *Journal of Controlled Release* 1987, 5, 1, 23-36.

Figures 8A, 8B:
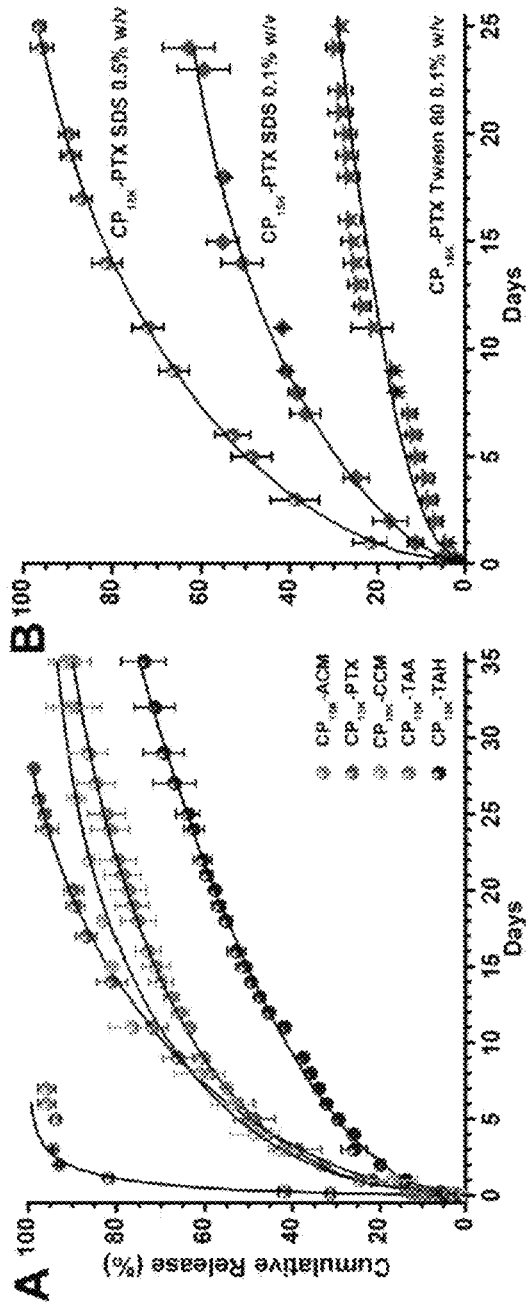
FIG. 8A shows the in vitro release profiles for ACM, PTX, CCM, TAA and TAH from the $CP_{15K}$ matrix (DLC≈10% w/w) in PBS containing 0.5% (w/v) SDS at 37° C.
FIG. 8B shows the release profiles for PTX from $CP_{15K}$ matrix (DLC≈10% w/w) in PBS containing 0.5, 0.1% (w/v) SDS or 0.1% of Tween 0.1% at 37° C. (n=3 individual experiments).

FIG. 8A shows the in vitro release profiles for ACM, PTX, CCM, TAA and TAH from the $CP_{15K}$ matrix (DLC≈10% w/w) in PBS containing 0.5% (w/v) SDS at 37° C. FIG. 8B shows the release profiles for PTX from $CP_{15K}$ matrix (DLC≈10% w/w) in PBS containing 0.5, 0.1% (w/v) SDS or 0.1% of Tween 0.1% at 37° C. (n=3 individual experiments). FIG. 8C shows a table of the different fittings applied on the release experiments presented in A) with the $R^2_{adjusted}$ ($R^2$).

The fittings were applied to the release data obtained for all drugs from the matrices in PBS 7.4 with SDS 0.5%. The Peppas-Sahlin model, where diffusion and polymer relaxation are known to be the underlying drivers of drug release provided the best fit in terms of $R^2$ adjusted (FIGS. 8A and 8C) For cylindrical shaped matrices, Fickian diffusion is considered to be operative when the ratio of diameter to thickness (n or m) of the matrix is equal to or less than 0.45. If the value is <0.85, the drug release mechanism is considered non-Fickian; whereas, if n is 0.89 drug release is considered to be case II transport. Herein, the dimension and the geometry of the matrices evaluated have a value of 0.78<n<0.80. Based on the fitting of the data, $k_2$ is negligible (i.e. contribution of the relaxational mechanism of drug release) and non-fickian diffusion ($k_1$) is the main mechanism of drug release. Since drug diffusion through the implant is the dominant mass transport step in the cross-linked polyester-based matrices, data were modeled based on the following analytical solution to Fick's second law of diffusion ( Table 3). Vergnaud, J. M., Controlled drug release of oral dosage forms. E. Horwood: New York:, 1993.; Guse, C.; Koennings, S.; Kreye, F.; Siepmann, F.; Goepferich, A.; Siepmann, J. Drug release from lipid-based implants: Elucidation of the underlying mass transport mechanisms. *International Journal of Pharmaceutics* 2006, 314, 2, 137-144.

TABLE 3

Comparison of diffusion coefficients and $R_{adjusted}^2$ ($R_2$) of drugs through the cross-linked matrices under different experimental conditions (e.g. release buffer).

$$\frac{M_t}{M_\infty} = 1 - \frac{32}{\pi^2} \cdot \sum_{n=1}^{\infty} \frac{\exp\left(-\frac{q_n^2 Dt}{R^2}\right)}{q_n^2} \cdot \sum_{p=0}^{\infty} \frac{\exp(-(2p+1)^2 \pi^2 Dt / H^2)}{(2p+1)^2}$$

| Evaluations | Cross-linked Matrices-Drug (30% w/w) | Media | $R^2$ | Diffusion Coefficient (m²/s) |
|---|---|---|---|---|
| Amorphous (State of the Drugs) | $CP_{15K}$-ACM | SDS 0.5% | 0.9767 | $1.8 \times 10^{-12}$ |
|  | $CP_{15K}$-FTX |  | 0.9519 | $1.6 \times 10^{-13}$ |
|  | $CP_{15K}$-CCM |  | 0.9762 | $1.4 \times 10^{-13}$ |
|  | $CP_{15K}$-TAA |  | 0.9978 | $1.1 \times 10^{-13}$ |
| Semi-crystalline (Drugs) | $CP_{15K}$-TAH |  | 0.9885 | $4.3 \times 10^{-14}$ |
| Drug Vs M.W and | $CP_{7.515K}$-TAA | SDS 0.5% | 0.9891 | $1.5 \times 10^{-13}$ |
|  | $CP_{32K}$-TAA |  | 0.9937 | $2.2 \times 10^{-13}$ |

TABLE 3-continued

Comparison of diffusion coefficients and $R_{adjusted}^2$ ($R_2$) of drugs through the cross-linked matrices under different experimental conditions (e.g. release buffer).

$$\frac{M_t}{M_\infty} = 1 - \frac{32}{\pi^2} \cdot \sum_{n=1}^{\infty} \frac{\exp\left(-\frac{q_n^2 Dt}{R^2}\right)}{q_n^2} \cdot \sum_{p=0}^{\infty} \frac{\exp(-(2p+1)^2 \pi^2 Dt/H^2)}{(2p+1)^2}$$

Cross-linked Matrices-Drug

| Evaluations | (30% w/w) | Media | $R^2$ | Diffusion Coefficient (m²/s) |
|---|---|---|---|---|
| Cross-linked Density | $CP_{39K}$-TAA | | 0.9939 | $6.5 \times 10^{-13}$ |
| Sink Conditions ([C] and type of surfactant) | $CP_{15X}$-FTX | SDS 0.1% | 0.9790 | $4.0 \times 10^{-14}$ |
| | $CP_{15X}$-PTX | Tween-80 0.1% | 0.9656 | $1.2 \times 10^{-14}$ |
| | $CP_{15X}$-CCM | | 0.9723 | $5.7 \times 10^{-12}$ |
| Impact of Drug Loading (w/w) | $CP_{32K}$-PTX-10% | SDS 0.5% | 0.9860 | $1.6 \times 10^{-13}$ |
| | $CP_{32K}$-PTX-20% | | 0.9814 | $9.9 \times 10^{-14}$ |
| | $CP_{39K}$-PTX-10% | | 0.9830 | $3.2 \times 10^{-13}$ |
| | $CP_{39K}$-PTX-20% | | 0.9777 | $3.9 \times 10^{-14}$ |

As described earlier, contributions of axial as well as radial mass transfer in the cylinders remain similar (i.e. 0.78<n<0.80). For the implementation of the mathematical model, R Studio (Version 3.3.3) was used. D was fitted into equation using enough experimentally determined data points to characterize the shape of the curve, and the resulting diffusion coefficients for each of the five drugs through the system. Though these assumptions may hold true for ACM, CCM, and PTX, assumption three is challenged by TAA and TAH. The crystalline drug diffraction peaks in the XRD spectrum and the melting and recrystallization thermal events in the DSC thermograms indicate crystalline dispersions of TAA and TAH are present within the matrices, suggesting the possibility of two phases: an amorphous drug-polymer phase and a crystalline drug only phase. Nair, R.; Nyamweya, N.; Gönen, S.; Martinez-Miranda, L. J.; Hoag, S. W. Influence of various drugs on the glass transition temperature of poly(vinylpyrrolidone): a thermodynamic and spectroscopic investigation. *International Journal of Pharmaceutics* 2001, 225, 1, 83-96. Linear buffer penetration and diffusion into the matrix observed at an early stage FIG. 4B), and the dissolution of crystalline drug aggregates serve to create a homogenous distribution. Klose, D.; Siepmann, F.; Elkharraz, K.; Krenzlin, S.; Siepmann, J. How porosity and size affect the drug release mechanisms from PLGA-based microparticles. *International Journal of Pharmaceutics* 2006, 314, 2, 198-206. Therefore, the good agreement observed between experiment and theory suggests the chosen model is appropriate for TAA and TAH under these conditions. Overall, the presented mathematical theory allowed to quantitatively predict the effect of changes in implant geometry on the resulting drug release kinetics (e.g. diffusion coefficient).

Figure 9:
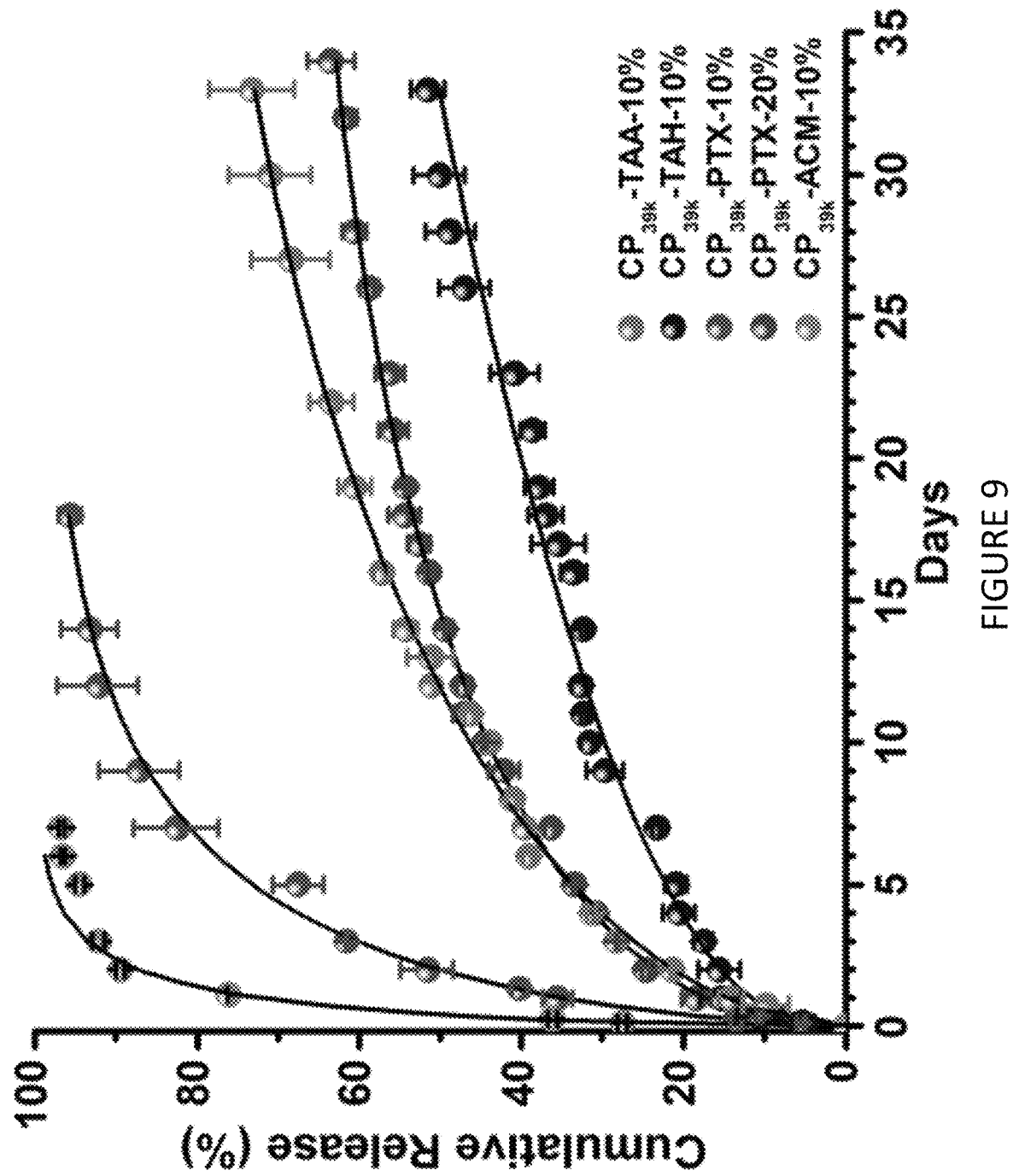
FIG. 9 shows release of ACM, TAA and TAH from $CP_{39K}$ at 10% drug content (w/w) and at 10 and 20% drug content for PTX in PBS pH 7.4 in 0.5% (w/v) SDS (n=2 individual experiments).
Figure 16A:
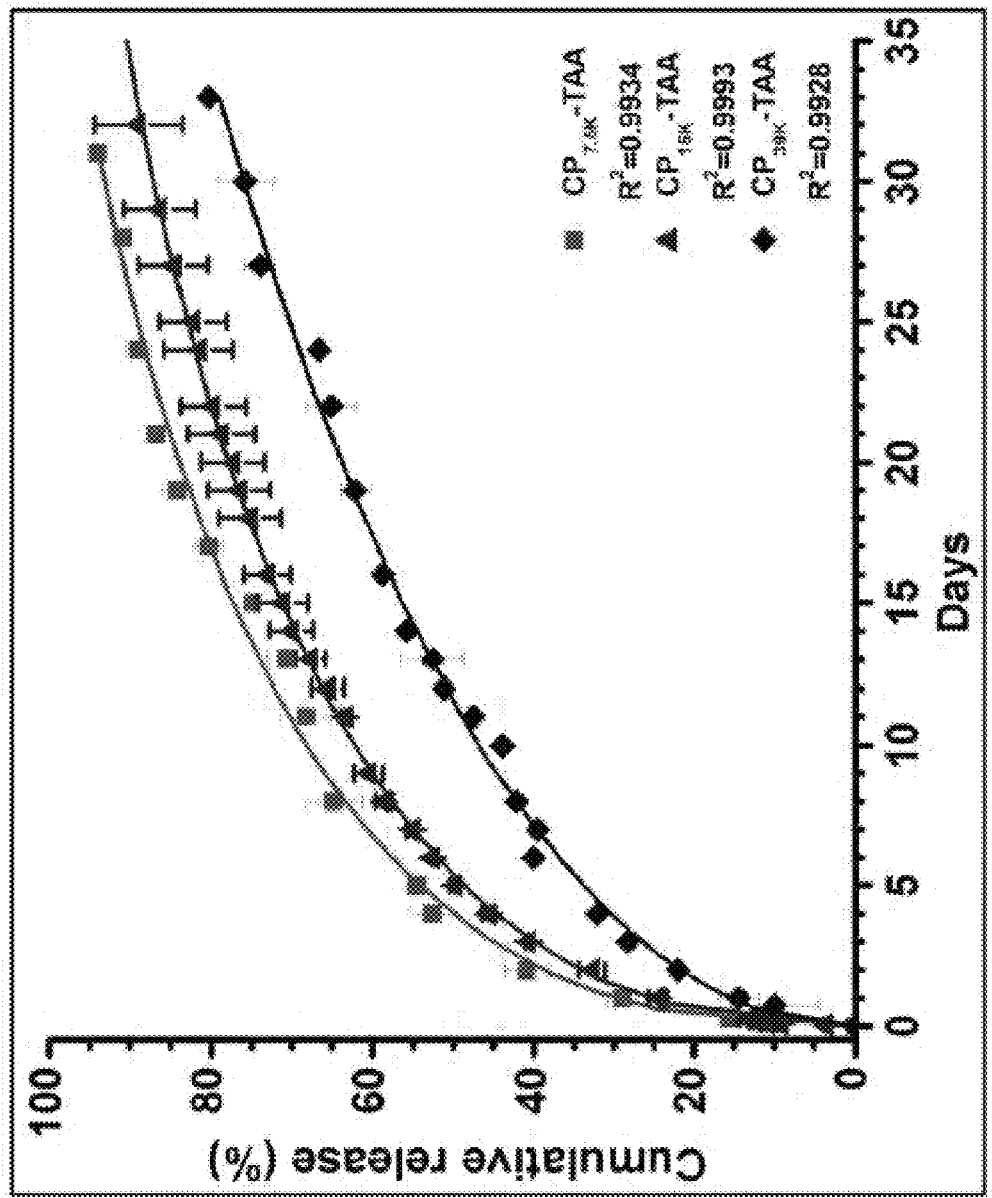
FIG. 16A shows release profiles for TAA 10% from $CP_{7.5K}$ (red), $CP_{15K}$ (blue) and $CP_{39K}$ (black) matrices in PBS containing 0.5% (w/v) SDS at 37° C. (n=3 individual experiments).

Influence of matrix and drug composition: Drug containing polymer matrices can be classified as either monolithic solutions or monolithic dispersions. FDA. Guidance for Industry: Dissolution Testing of Immediate Release Solid Oral Dosage Forms, Office of Training and Communications, Rockville, Md., 1997, pp. A1- A2. 1997. Based on characterization of the drug loaded in the polymeric systems by DSC, XRD, and FUR, it is indicated that ACM, CCM, and PTX are dissolved in the matrix as monolithic solutions, while TAA and TAH are dissolved and dispersed in the matrix as monolithic dispersions. With the smallest partial molar volume and the highest aqueous solubility, ACM exhibited a rapid release over a period of less than a week from all matrices (FIG. 8A and FIG. 9). At 37° C., the release of ACM from the amorphous matrices (i.e. $CP_{7.5K}$ and $CP_{15K}$ or semi-crystalline matrix (e.g. $CP_{39K}$) was similar. However, the release of TAA was found to proceed much more slowly in comparison to ACM. It is reported that the influx of water into the matrix is accelerated by the presence of hydrophilic drugs, which explains the rapid release observed for ACM. Guse, C.; Koennings, S.; Kreye, F.; Siepmann, F.; Goepferich, A.; Siepmann, J. Drug release from lipid-based implants: Elucidation of the underlying mass transport mechanisms. *International Journal of Pharmaceutics* 2006, 314, 2, 137-144. Where $CP_{7.5K}$-TAA, $CP_{32K}$-TAA and $CP_{15K}$-TAA reached 50% drug release at a $T_{50\%}$ between four and six days, $T_{50\%}$ release from the semi-crystalline matrix (i.e. $CP_{39K}$) was not reached until 12 days (FIG. 16A). Release from $CP_{39K}$-TAA ($T_{80\%}$=50 days) was sustained for at least an additional two weeks compared to $CP_{15K}$-TAA ($T_{80\%}$=30 days). Diffusion of the molecularly dispersed fraction vs crystalline TAA cannot be distinguished during the release experiment. Thus, the molecularly dissolved and crystalline drugs co-exist within the system, yet it is established that only the dissolved drug is available for diffusion within the amorphous regions of the matrices. Complete release of TAA and TAH from the matrices suggests a conversion of crystalline forms of the drugs to amorphous state. Overall, the data revealed that at similar cross-linking density (i.e. $CP_{15K}$ vs $CP_{32K}$) and drug loading level (i.e. PTX), an increase in the M.W of the polymer decreased the drug release rate (FIG. 8A and FIG. 16B), which is in agreement with the literature. Miyajima., M.; Koshika, A.; Okada, J. i.; Ikeda, M.; Nishimura, K. Effect of polymer crystallinity on papaverine release from poly (l-lactic acid) matrix. *Journal of Controlled Release* 1997, 49, (2-3), 207-215. Jeong, J.-C.; Lee, J.; Cho, K. Effects of crystalline microstructure on drug release behavior of poly(ε-caprolactone) microspheres. *Journal of Controlled Release* 2003, 92, 3, 249-258. Fetters, L. J.; Lohse, D. J.; Richter, D.; Witten, T. A.; Zirkel, A. Connection between Polymer Molecular Weight, Density, Chain Dimensions, and Melt Viscoelastic Properties. *Macromolecules* 1994, 27, (17), 4639-4647. When comparing polymer-drug systems within the same category (i.e. monolithic solutions or dispersions), drug release is expected to be governed primarily by the solubility and diffusion of the drug within the system. As observed in FIG. 8A, the state of the drug is considered as one of the rate-limiting step to the diffusion of drug from the system and explains the observed order of release wherein the amorphous drug-loaded matrices release at a faster rate in comparison to those containing crystalline drug but still with excellent reproducibility (e.g. TAA and TAH). The release of CCM and PTX can be understood on the basis of their aqueous solubilities: 105.98±0.57 µg/ml for PTX vs. 45.63±1.05 µg/ml for CCM, which leads to a rapid solubilization and a faster rate of diffusion from the matrix. For the steroid-loaded matrices that contain both dissolved and non-dissolved drug, TAA releases faster than TAH due to its higher aqueous solubility (i.e. 287.04±56.86 µg/ml compared to 37.89±0.40 µg/ml for TAH) and its relatively higher interaction within the matrices. In a report by Pinto et al., release of TAA from a polyurethane-PCL matrix under sink conditions in pure PBS pH 7.4 (TAA solubility 2.1 µg/mL) revealed a linear TAA release of up to 64% over 8 months, whereas in vivo, it was found that almost 81% of TAA was released in only 45 days. Pinto, F. C. H.; Da Silva-Cunha Junior, A.; Oréfice, R. L.; Ayres, E.; Andrade, S. P.; Lima, L. D. C.; Lima Moura, S. A.; Da Silva, G. R. Controlled release of triamcinolone acetonide from polyurethane implantable devices: application for inhibition of inflammatory-angiogenesis. *Journal of Materials Science: Materials in Medicine* 2012, 23, (6), 1431-1445. Overall, the data suggests that the solubility of the drug in the release media needs to be carefully considered given that it is a key determinant of release kinetics. Then, the impact of the nature and the concentration of the release media on the release profile of PTX were also investigated (FIG. 8B). Tween 80 (0.1% w/v) is commonly used to improve the solubility/stability of PTX in aqueous media. OECD. Guidelines for Testing of Chemicals. Section 1, Physical Chemical properties. 1995, 107. Mikkelsen, L. M., Enzyme solubility in liquid detergent and use of detergent composition. Google Patents: 2014. SDS has been used to effectively enhance the aqueous solubility of TAA and TAH. Nsereko, S.; Amiji, N I. Localized delivery of paclitaxel in solid tumors from biodegradable chitin microparticle formulations. *Biomaterials* 2002, 23, (13), 2723-2731. Suh, H.; Jeong, B.; Rathi, R.; Kim, S. W. Regulation of smooth muscle cell proliferation using paclitaxel-loaded poly(ethylene oxide)-poly(lactide/glycolide) nanospheres. *Journal of Biomedical Materials Research* 1998, 42, 2, 331-338. Doty, A. C.; Hirota, K.; Olsen, K. F.; Sakamoto, N.; Ackermann, R.; Feng, M. R.; Wang, Y.; Choi, S.; Qu, W.; Schwendeman, A.; Schwendeman, S. P. Validation of a cage implant system for assessing in vivo performance of long-acting release microspheres. *Biomaterials* 2016, 109, 88-96. Yang, H.-y.; van Dijk, M.; Licht, R.; Beekhuizen, M.; van Rijen, M.; Janstil, M. K.; Oner, F. C.; Dhert, W. J. A.; Schumann, D.; Creemers, L. B. Applicability of a Newly Developed Bioassay for Determining Bioactivity of Anti-Inflammatory Compounds in Release Studies—Celecoxib and Triamcinolone Acetonide Released from Novel PLGA-Based Microspheres. *Pharmaceutical Research* 2015, 32, 2, 680-690. It can be seen that the release rate depends greatly on the solubility of the drug in the aqueous media (FIG. 6B, FIG. 8B and Table 3). The solubility of PTX is 10 and 50 times greater in 0.5% SDS than it is in 0.1% SDS and 0.1% Tween 80, respectively, and for CCM this increase in solubility is four times greater in SDS than in Tween 80. An increase in the solubility of the drug leads to an increase in its dissolution rate and a higher degree of partitioning between the matrix and the external media (micellization/solubilization by the surfactant), thereby increasing the driving force for drug release and the diffusion coefficient ( Table 3). Yang, H.-y.; van Dijk, M.; Licht, R.; Beekhuizen, M.; van Rijen, M.; Janstçl, M. K.; Oner, F. C.; Dhert, W. J. A.; Schumann, D.; Creemers, L. B. Applicability of a Newly Developed Bioassay for Determining Bioactivity of Anti-Inflammatory Compounds in Release Studies—Celecoxib and Triamcinolone Acetonide Released from Novel PLGA-Based Microspheres. *Pharmaceutical Research* 2015, 32, 2, 680-690.

FIG. 9 shows release of ACM, TAA and TAH from $CP_{39K}$ at 10% drug content (w/w) and at 10 and 20% drug content for PTX in PBS pH 7.4 in 0.5% (w/v) SDS (n=2 individual experiments).

Figure 16B:
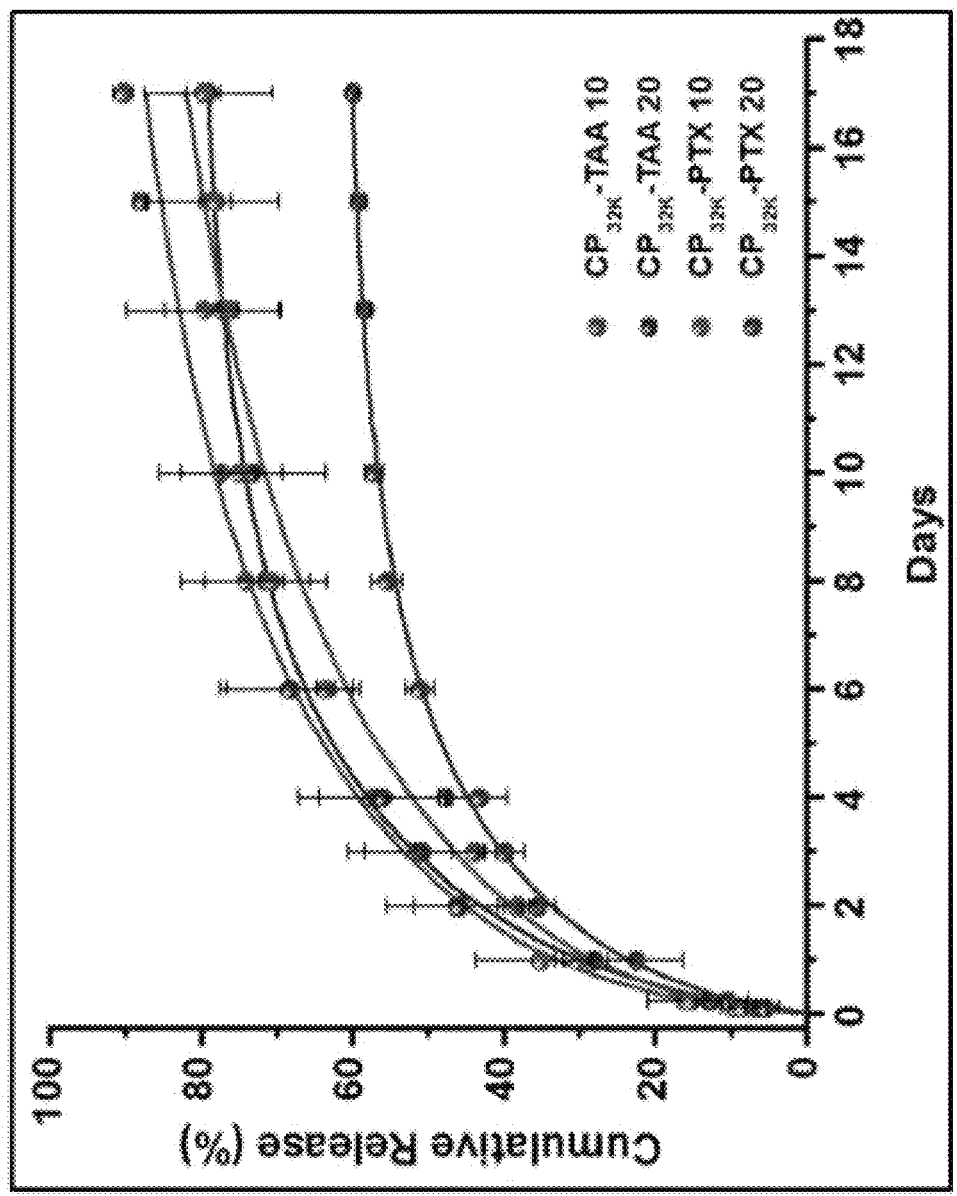
FIG. 16B shows a release profile from $CP_{32K}$ of PTX and TAA loaded at 10 and 20% in PBS containing 0.5% (w/v) SDS at 37° C. (n=3 individual experiments).

Release of TAA and/or PTX from the four cross-linked matrices was conducted to determine the impact of matrix composition (e.g. M.W vs cross-linking density) on drug release (FIG. 8A, FIG. 9, and FIG. 16B). Globally, as polymer M.W increases and cross-linked density decreases, the drug release rate and the diffusion coefficient decrease. It is put forward that the cross-linking density does not play a direct role in influencing the drug release profile rather an increase in the crosslinking density decreases the degree of crystallinity within the matrix which in turn makes it more amenable for diffusion of drug.

This result is in agreement with many reports of slow release from high molecular weight polymers. Guse, C.; Koennings, S.; Kreye, F.; Siepmann, F.; Goepferich, A.; Siepmann, J. Drug release from lipid-based implants: Elucidation of the underlying mass transport mechanisms. *International Journal of Pharmaceutics* 2006, 314, 2, 137-144. Toshiro, H.; Hiroaki, O.; Yasuaki, O.; Hajime, T. Factors influencing the profiles of TRH release from copoly (d,l-lactic/glycolic acid) microspheres. *International Journal of Pharmaceutics* 1991, 72, 3, 199-205. Omelezuk, M. O.; McGinity, J. W. The influence of Polymer Glass Transition Temperature and Molecular Weight on Drug Release from Tablets Containing Poly(PL-lactic Acid). *Pharmaceutical Research* 1992, 9, 1, 26-32. Drug diffusion (e.g. ACM, PTX and CCM) through the amorphous implants (i.e $CP_{7.5k \rightarrow 32K}$) is the most rapid since there are no crystalline domains acting as barriers to diffusion( Table 3). Interestingly, at a drug loading level of 10% for matrices formed from copolymers of similar M.W. (i.e. $CP_{32K}$ vs $CP_{39K}$) a decrease in the cross-linking density of the matrix results in faster drug release. However, at higher drug loading content (i.e. 20% w/w PTX in $CP_{32K}$ and $CP_{39K}$) sustained release is much more pronounced for $CP_{39K}$-PTX (FIG. 9 and FIG. 16B). In contrast, loading drugs that are present in the matrices in crystalline form, TAA or TAH, at higher levels (i.e. 20% vs 10%) did not significantly impact the release rate (FIG. 16B). This indicates that the crystalline state of the drug in the matrix is the main limiting factor that controls drug release. These observations suggest that the cross-linking density indirectly impacts the release profile since an increase in the cross-linking density was found to decrease the crystallinity of the polymer matrix. Overall, a combination of drug-drug interaction at high drug content (i.e. 20%) and the crystalline domains within the matrix control and afford sustained release profiles.

There is an unmet need to develop polymer materials that can be functionalized in good yield to produce customizable biodegradable drug delivery systems. We have developed one such system based on PVL-co-PAVL, cross-linked with 1,6-hexanedithiol, which possesses several advantages including high drug loading with a post-loading method, sustained and reproducible diffusion-controlled release kinetics, and good in vitro biocompatibility. Furthermore, we have shown the importance of a thoroughly conducted investigation into the underlying mechanisms controlling drug release from these new materials and addressed factors secondary to diffusion, including polymer-drug interactions and solubility parameters that play a role. We have demonstrated the potential of this new IDDS based on PVL-co-PAVL, as a universal drug delivery system for numerous therapies since the pendant allyl functionality provides a versatile backbone for improving polymer-drug compatibility and tailoring release profiles to meet clinical demands.

Figure 10:
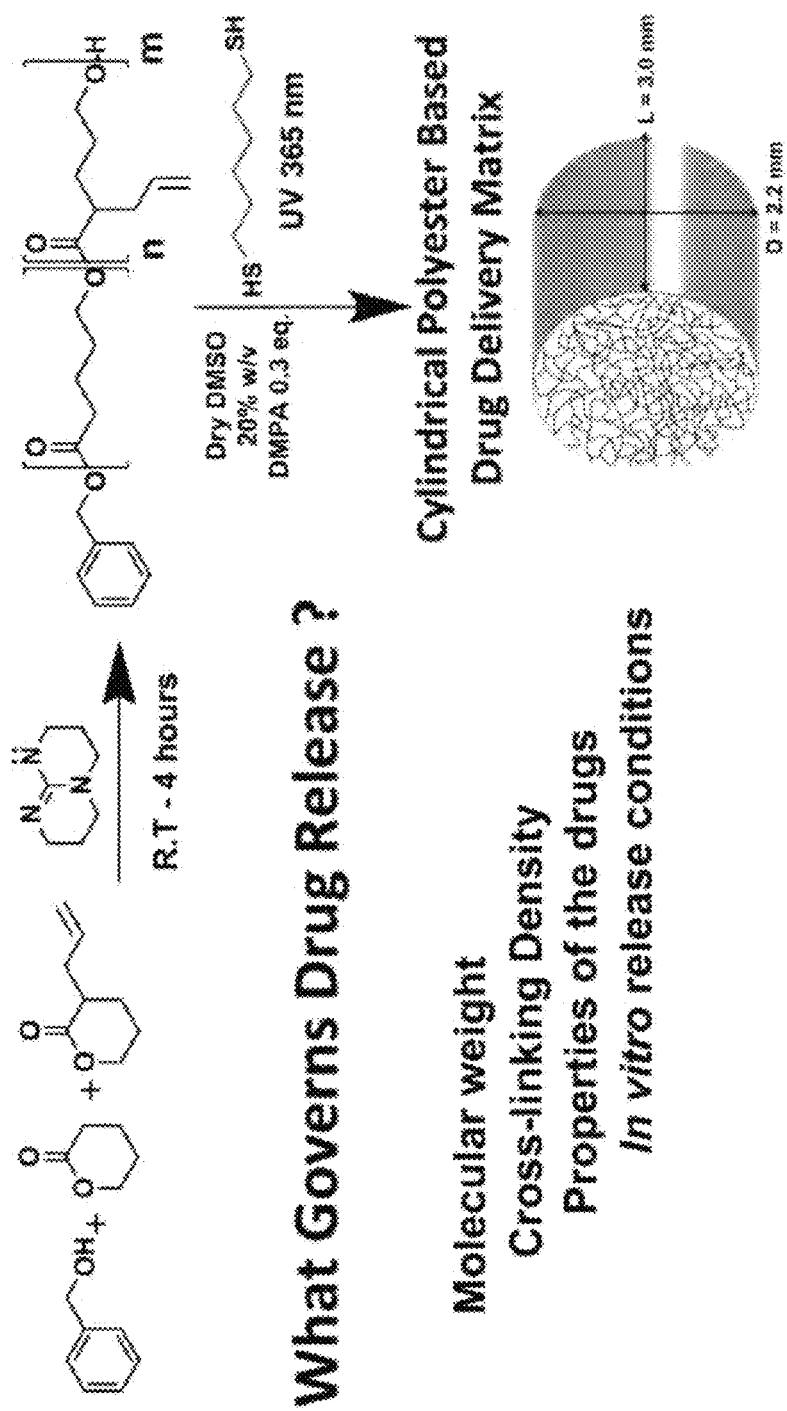
FIG. 10 shows a schematic of the formation of the cylindrical polyester based drug delivery matrix.

FIG. 10 shows a schematic of the formation of the cylindrical polyester based drug delivery matrix.

Protocols for drug analysis by HPLC and cytotoxicity evaluation of the cross-linked matrices: The drug release was analyzed by reverse phase HPLC using an Agilent 1200 HPLC system with Agilent ChemStation software, an XDB C18 column (150×4.6 mm i.d+guard column) and UV detection. For PTX, the mobile phase consisted of 55:45 acetonitrile:water with a flowrate of 1 ml/min and UV detection at 227 nm. For TAA, the mobile phase consisted of 80:20 methanol:water (0.1% acetic acid) with a flow rate of 1.2 ml/min and UV detection at 240 nm. For TAH, the mobile phase consisted of 90:10 MeOH:H$_2$O (0.1% acetic acid) with a flow rate of 1.2 ml/min and UV detection at 240 nm. For CCM, the mobile phase consisted of 55:45 ACN:H$_2$O (0.1% acetic acid) with a flow rate of 1 ml/min and UV detection at 420 nm. For ACM, the mobile phase consisted of 80:20 MeOH:H$_2$O with a flow rate of 1 ml/min with UV detection at 250 nm. Drug concentrations were quantified using calibration curves using standards that ranged in concentration from 1 to 100 µg/ml (0.9986<R$^2$≤1).

Cytotoxicity evaluation: CPs were incubated in culture media at a surface area to volume ratio of 1.25 cm$^2$/mL for 48 h. Then, the media was serial diluted two-fold to the following concentrations: 50, 25, 12.5, 6.25, and 3.125%. The L929 fibroblast cells were cultured and routinely maintained in Dulbecco's modified Eagle's medium (DMEM) supplemented with 10% fetal bovine serum (FBS) and 1% penicillin-streptomycin. The cells were grown in a monolayer in tissue culture flasks incubated at 37° C. and 5% C02 at 90% relative humidity. Cells were counted and seeded in 96-well plates at a density of 2000 cells/well, which was determined to be the optimum cell density. After 24 h incubation, growth media was aspirated and replaced with either 150 µL CPs extracts at a surface area to volume ratio of 1.25 cm$^2$/mL or the same volume of extraction media that had been serially diluted to the above concentrations. Following 24, 48, and 72 h incubation periods, cell viability was evaluated using the MTS assay. Specifically, the extraction media was aspirated and replaced with 200 µL of fresh media followed by 20 µL of MTS reagent, and the cells were incubated at 37° C. for 1.5 h. Cell viability was measured by optical absorbance at λ=490 nm using a Cytation™ 5 Cell Imaging Multi-Mode Reader (BioTek, Vt.). Cells incubated with media were employed as control and this was considered 100% cell viability. 100 µM cadmium chloride (CdCl$_2$) was used as a positive control. All experiments were conducted in triplicate (FIG. 16A and FIG. 16B). This method eliminates confounding factors resulting from physical trauma to the cells due to sample weight and it has been reported that toxicities resulting from polymeric biomaterials are likely a result of their leachables. Nishi, C.; Nakajima, N.; Ikada, Y., In vitro evaluation of diepoxy compounds used for biomaterial modification. Journal of Biomedical Materials Research 1995, 29, 829-834. Serrano, M. C.; Pagani, R.; Vallet-Regi, M.; Pena, J.; Ramila, A.; Izquierdo, I.; Portoles, M. T., In vitro biocompatibility assessment of poly(epsilon-caprolactone) films using L929 mouse fibroblasts. Biomaterials 2004, 25 (25), 5603-11.

NMR $^1$H calculation: Using the integration of the internal reference (5H*), the number of AVL units is obtained by considering the integrations of peak "a" (i.e. 5.70 ppm (m. CH$_2$=CH)), peak b (i.e. 5.03 ppm (m, CH$_2$=CH)) and c (i.e. 1.68 ppm (m, —CH$_2$—CH$_2$— VL, AVL)) with the following equations:

The number of VL units=integration of peak c–integration of peak a     1.

The number of VL units=(integration of peak e)/4–integration of peak a     2.

The number of VL units=(integration of peak e)/4–(integration of peak b/2)     3.

The % AVL content in the copolymers was determined by the ratio of the calculated PAVL mass fraction over the total M.Wt of PVL-co-PAVL.

TABLE 4

Differential calorimetry analysis of synthetized polyvalerolactone (PVL) and commercial polycaprolactone (PCL) homopolymers.

| Homopolymers | M (g/mol) | | | $T_m$ | $\Delta°H_m$ | $x_c$ |
| --- | --- | --- | --- | --- | --- | --- |
| | GPC$^b$ | PDI | $^3$H NMR$^t$ | (° C.)$^t$ | (J/g)$^g$ | (%) |
| PVL | 6200 | 1.21 | 7000 | 56 | 144 | 100 |
| PCL 14K | 10000 | 1.40 | N.D. | 55.1/58.2 | 116 | 80 |
| PCL 50K | 48000 | >2.5 | N.D. | 56.1 | 106 | 75 |

The degree of crystallinity was estimated by DSC using the following equation:

$$\chi_c = 100 \times \frac{\Delta°H_m}{\Delta°H_m^{100\%}}$$

where $\Delta° H_m$ is the melt enthalpy, determined as the area under the melt endotherm, and $\Delta° H^{100\%}_m$ is the melt enthalpy $\Delta H^{100\%}m$=144 J/g of a completely crystalline sample (e.g PVL—Table 4).

FIG. 11 shows ATR-FTIR spectroscopy of the copolymer (bulk) and the resulting cross-linked copolymer matrices: P$_{7.5K}$ (black), CP$_{7.5K}$ (red), P$_{39K}$ (blue) and CP$_{39K}$ (green). Normalization has been done at 1730 cm$^{-1}$. (64 scans at 2 cm$^{-1}$).

Compared to the bulk materials, the cross-linked copolymers (e.g. CP$_{15K}$ and CP$_{39K}$) led to an enlargement of the v$_{(C=O)}$, and v$_{s(COC)}$ bands at 1168 and 1253 cm$^{-1}$, respectively. The methylene stretching and rocking bands attributed to the copolymer backbone at 2960-2865 cm$^{-1}$ (V$_{asym}$, V$_{sym}$) and 750 cm$^{-1}$ shifted to shorter wavenumbers and increased in intensity (e.g. —S—(CH$_2$)$_6$—S—). Similar shifts of the carbonyl stretching bands to higher energetic wavenumbers were also observed. The carbonyl bands of the copolymer demonstrate a crystalline band (1730 cm$^{-1}$) and an amorphous band (1710 cm$^{-1}$) whereas after cross-linking, only one broad band was observed. Murphy, S. H.; Leeke, G. A.; Jenkins, M. J. A Comparison of the use of FTIR spectroscopy with DSC in the characterisation of melting and crystallisation in polycaprolactone. *Journal of Thermal Analysis and Calorimetry* 2012, 107, 2, 669-674.

FIG. 12 shows stability of the CP$_{15K}$ in PBS pH 7.4. Evaluation of the weight loss (%) of CP$_{15K}$ matrix over a period of 90 days (n=3).

FIG. 13 shows in vitro cytotoxicity of the applied extract dilution of CP$_{39K}$ and CP$_{15K}$ cylinders (green) or high density polyethylene (HDPE) (purple) to L929 mouse fibroblast cells. Cells incubated with media alone were employed as a control and considered as 100% cell viability. (*, , and *) indicates lesser viability relative to untreated ($p<0.0001$, 0.01, and 0.05, respectively); (###, ##, and #) indicates lesser viability relative to treatment group ($CP_{39K}$) of same extract dilution concentration ($p<0.0001$, 0.01, and 0.05, respectively).

The CP matrices demonstrated excellent in vitro biocompatibility at all extract concentrations and time points studied. Interestingly, high-density polyethylene (HDPE), the negative control, resulted in a significant ($p<0.0001$) decrease in cell viability (approximately 66%) relative to the untreated control at the highest extract concentration studied. Cell viability was significantly lower ($p<0.0001$) for HDPE relative to the $CP_{39K}$ materials at 48 h post-treatment, suggesting a high degree of in vitro biocompatibility of the PVL-co-PAVL delivery system.

FIG. 14A shows DSC thermograms (left) of the drugs (e.i. TAH, TAA, PTX, CCM and ACM) and (right) full DSC thermograms of $CP_{15K}$ loaded at 10% w/w of drug analyzed at 10° C./min ($1^{st}$ cycle). Stars indicate degradation of drug.

FIG. 14B shows an example of thermograms of $CP_{39K}$ loaded with the drugs at 10 and 20% (±4%) w/w.

FIG. 15 shows FTIR spectra of $CP_{15K}$ loaded with TAH and PTX as well as the FTIR spectra of the drugs. Insets include images of the drug free and drug loaded cylindrical cross-linked materials.

FIG. 16A shows release profiles for TAA 10% from $CP_{7.5K}$ (red), $CP_{15K}$ (blue) and $CP_{39K}$ (black) matrices in PBS containing 0.5% (w/v) SDS at 37° C. (n=3 individual experiments).

FIG. 16B shows a release profile from $CP_{32K}$ of PTX and TAA loaded at 10 and 20% in PBS containing 0.5% (w/v) SDS at 37° C. (n=3 individual experiments).

TABLE 5

Solubility parameter values of the drugs obtained from the literature.

| Drugs | Solubility Parameter (MPa)$^{1/2}$ (literature) | | | |
|---|---|---|---|---|
| | $\zeta(d)$ | $\zeta(p)$ | $\zeta(h)$ | $\zeta(t)$ |
| Acetaminophen | 17.8 | 10.5 | 13.9 | 25.77 |
| Paclitaxel | 21.61 | 2.92 | 12.57 | 25.18 |
| Curcumin | 17.4 | 6 | 10.9 | 21.4 |
| Triamcinolone acetonide | 18.5 | 3 | 25.6 | 31.7 |
| Triamcinolone hexacetonide | N.D | N.D | N.D | N.D |

The group contribution method (GCM) was used to determine the partial solubility parameters of the drugs. Values for ACM, CCM and PTX were found to be in agreement with values reported in the literature. However, to our knowledge, only one study has evaluated $\delta(t)$ values for TAA and this was determined by inverse gas chromatography method (IGCM) and no studies have reported a value for TAH. Our estimation of the partial solubility parameters for Sa and $\delta_p$ were similar but $\delta_h$ and consequently $\delta(t)$ values were much lower than previously report. IGCM gives precise and reproducible solubility parameters, but experimental evaluation is affected by a heterogeneous distribution of active sites on the stationary phase, altering cohesive energy density. Du Z, Zhang Y, Xu H, Lang M. Functionalized Pluronic-b-poly(ε-caprolactone) based nanocarriers of paclitaxel solubilization, antiproliferative efficacy and in vivo pharmaceutic kinetics. Journal of Materials Chemistry B 2015; 3:3685-94. Barra J, Lescure F, Doetker E, Bustarnante P. The Expanded Hansen Approach to Solubility Parameters. Paracetamol and Citric Acid in Individual Solvents. Journal of Pharmacy and Pharmacology 1997; 49:644-51. Jones M D, Buckton G. Comparison of the cohesion-adhesion balance approach to colloidal probe atomic force microscopy and the measurement of Hansen partial solubility parameters by inverse gas chromatography for the prediction of dry powder inhalation performance. International Journal of Pharmaceutics 2016; 509:419-30. F. Salaün IV. Curcumin loaded nanocapsules: formulation and Influence of the nano-encapsulation processes variables on the physico-chemical characteristics of the particles. Int J Chem Reactor Eng 2009; 7:A55. Despite similar partial solubility values, the nature and the structure of these steroids (e.g. molecular recognition, orientational and directional interactions) as well as themodynatnic and kinetic factors may influence experimental values.

Purification of monomer: VL (δ-valerolactone) and AVL (allyl δ-valerolactone) monomers were distilled over $CaH_2$ under reduced pressure and stored under argon before use.

Synthesis of pentablock copolymer: A series of pentablock copolymers was prepared via ring opening polymerization of VL and AVL in the presence of PEG (polyethylene glycol) as the macroinitiator and TBD (1, 5, 7-triazabicyclo[4.4.0]dec-5-ene) as the catalyst. For the synthesis of PAVL-b-AVL-b-PEG 20K-b-PVL-b-PAVL as a typical example, PEG 20K (1 g, 0.1 mmol of OH group) in round two-neck flask was carefully flame-dried to melt PEG down and remove residue water under vacuum. After cooling down to room temperature, TBD (25 mg, 0.18 mmol) was added and dried again under vacuum. The reaction mixture was dissolved in anhydrous toluene (20 mL) and stirred at room temperature for 30 min. Then, purified VL (0.5 mL, 5.0 mmol, target repeating unit=100) was transfer to the reaction mixture by cannulation to start polymerization and followed by stirring at room temperature for 3 hrs. For block copolymerization, AVL (0.17 mL, 1.25 mmol, target repeating unit is 25) as second monomer was injected into the reactive mixture by cannulation, and the resulting mixture was further stirred at room temperature for 4 hrs. The as-synthesized polymer solution was precipitated from a mixture of Ethyl ether and Hexane (70/30 v/v) for purification, and residues were dried in a vacuum oven at room temperature overnight.

TABLE 6

Characteristics of synthesized polymers

| Entry | | | $^1$H-NMR | | GPC | |
|---|---|---|---|---|---|---|
| No. | Polymer structure | $M_n$ | DP (PEG/PVL/PAVL) | PAVL (%) | $M_n$ | PDI |
| SJP1 | PAVL-b-PVL-b-3KPEG-b-PVL-b-PAVL | 28K | 85/214/22 | 11 | 17.6K | 1.26 |

TABLE 6-continued

Characteristics of synthesized polymers

| Entry No. | Polymer structure | $M_n$ | ¹H-NMR DP (PEG/PVL/PAVL) | PAVL (%) | GPC $M_n$ | PDI |
|---|---|---|---|---|---|---|
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-35KPEG-b-PVL-b-PAVL | 51.4K | 812/134/14 | 4 | 51.8K | 1.04 |
| SJP4 | PAVL-b-3KPEG-b-PAVL | 6.2K | 85/0/18 | 40 | 7.7K | 1.07 |
| SJP5 | (PAVL-co-PVL)-3KPEG-(PAVL-co-PVL) | 8.5K | 85/36/8 | 15 | 7.4K | 1.39 |
| SJP6 | PVL-co-PAVL | 30K | 0/235/42 | 20 | 24K | 1.37 |

Figure 17:
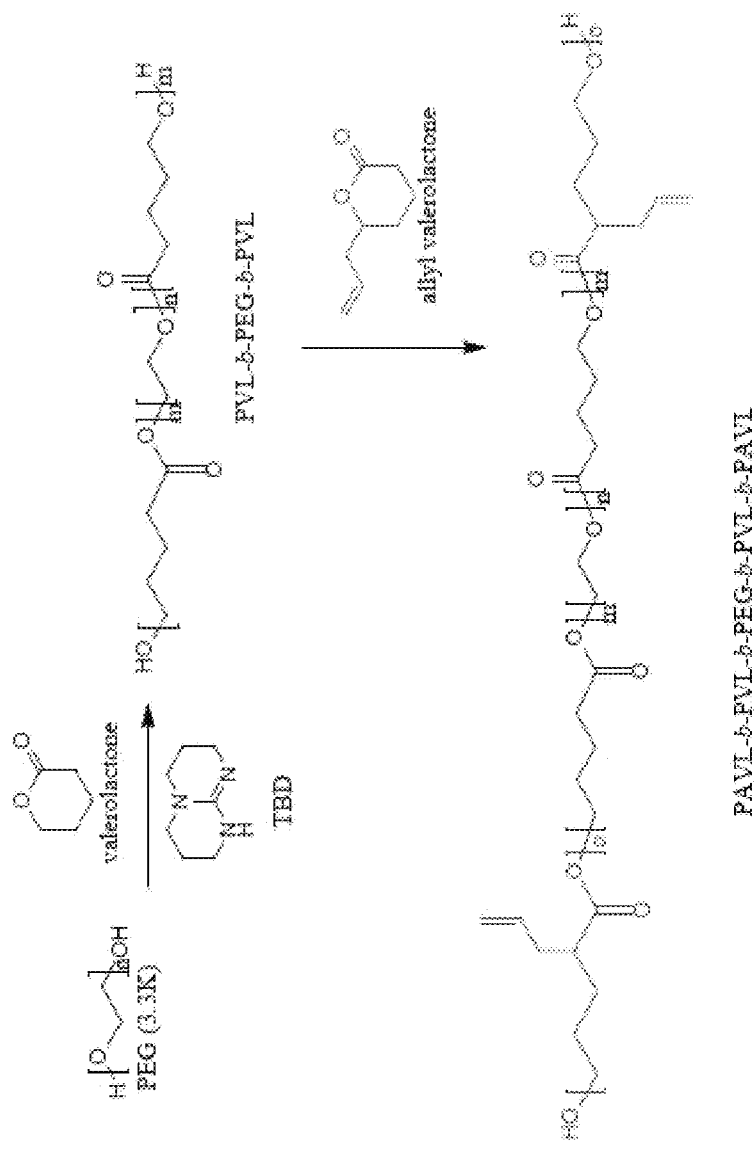
FIG. 17 shows a pentablock copolymer—PAVL-b-PVL-3KPEG-b-PVL-b-PAVL reaction scheme, according to an embodiment.

FIG. 17 shows a pentablock copolymer—PAVL-b-PVL-3KPEG-b-PVL-b-PAVL reaction scheme, according to an embodiment.

Figure 18:
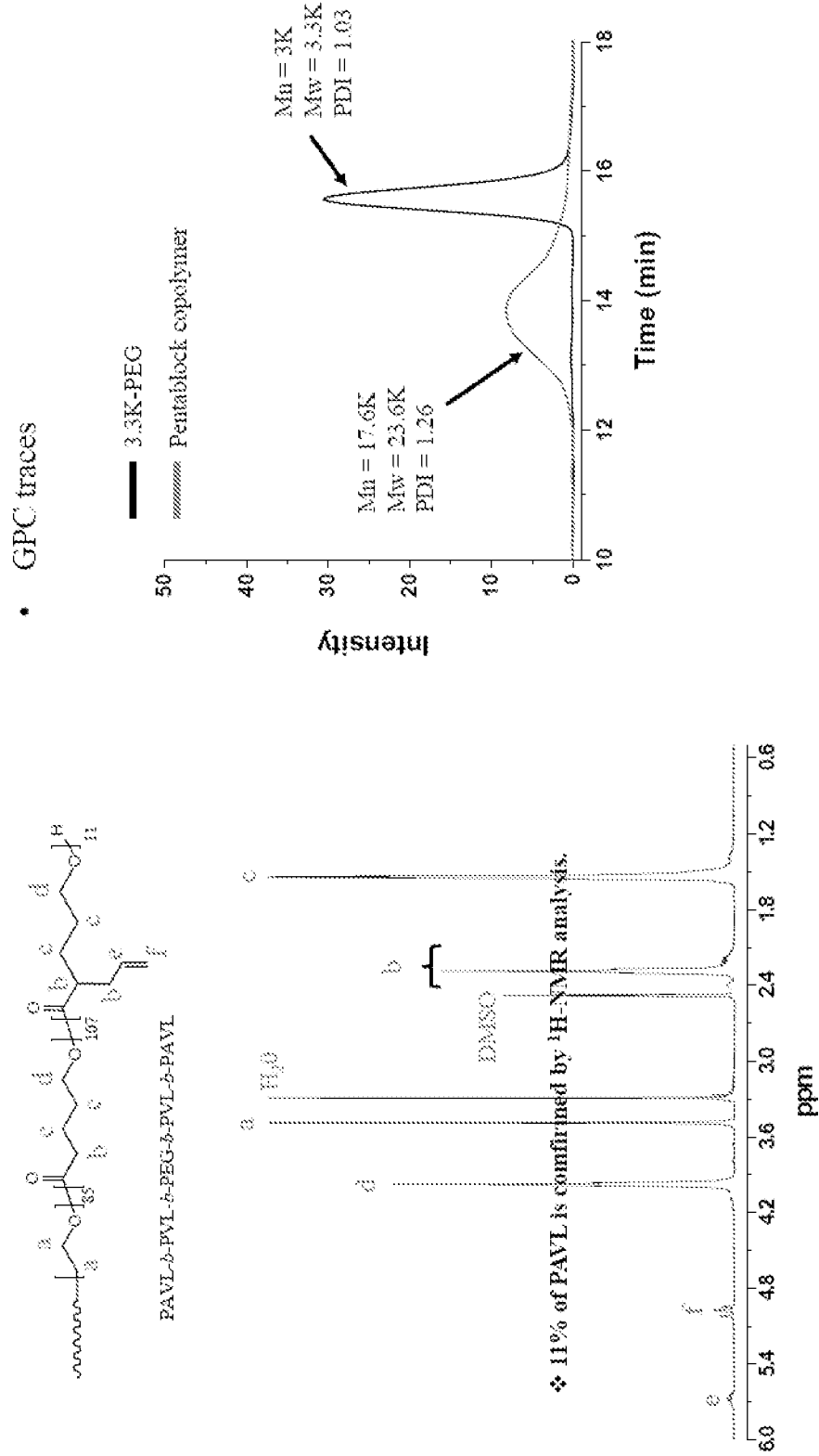
FIG. 18 shows a pentablock copolymer—PAVL-b-PVL-3KPEG-b-PVL-b-PAVL reaction scheme with data, according to an embodiment.

FIG. 18 shows a pentablock copolymer—PAVL-b-PVL-3KPEG-b-PVL-b-PAVL reaction scheme with data, according to an embodiment.

FIG. 19 shows a homopolymer with TA as initiator—PVL reaction scheme with data, according to an embodiment.

TABLE 7

Polymers used to Prepare Microparticles

| Entry No. | Polymer structure | $M_n$ | ¹H-NMR DP (PEG/PVL/PAVL) | PAVL (%) | GPC $M_n$ | PDI |
|---|---|---|---|---|---|---|
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-35KPEG-b-PVL-b-PAVL | 51.4K | 812/134/14 | 4 | 51.8K | 1.04 |
| SJP4 | PAVL-b-3KPEG-b-PAVL | 6.2K | 85/0/18 | 40 | 7.7K | 1.07 |
| SJP5 | (PAVL-co-PVL)-3KPEG-(PAVL-co-PVL) | 8.5K | 85/36/8 | 15 | 7.4K | 1.39 |
| SJP6 | PVL-co-PAVL | 30K | 0/235/42 | 20 | 24K | 1.37 |

Figure 20:
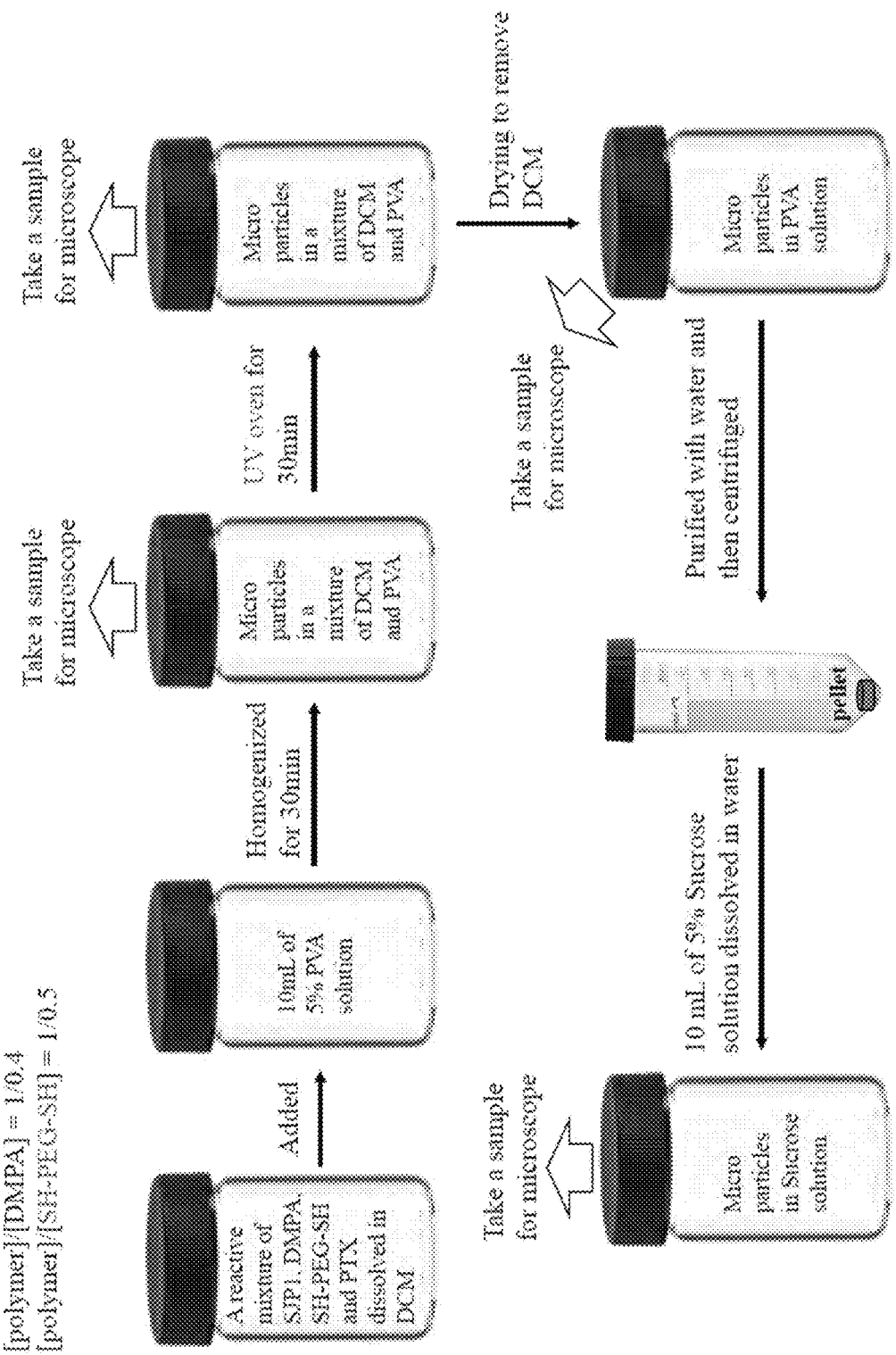
FIG. 20 shows a procedure to prepare microparticles, according to an embodiment.

FIG. 20 shows a procedure to prepare microparticles, according to an embodiment.

Figure 21A:
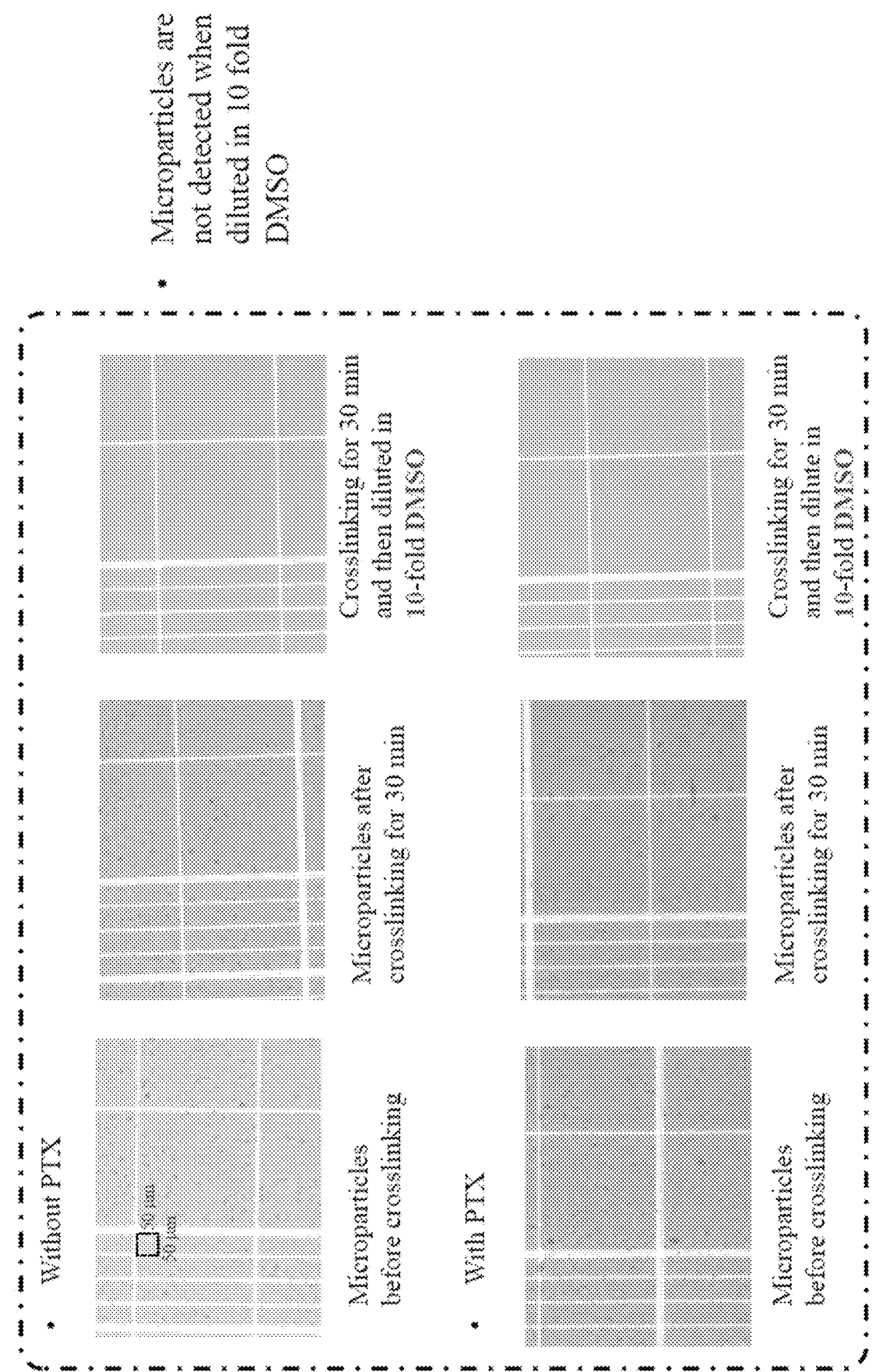
FIG. 21A shows a Polymer (SJP1), DMPA, SH-PEG-SH and PTX dissolved in DCM mixed with 5% PVA using a homogenizer for 30 min before evaporation of DCM.

FIG. 21A shows a Polymer (SJP1), DMPA, SH-PEG-SH and PTX dissolved in DCM mixed with 5% PVA using a homogenizer for 30 min before evaporation of DCM. Microparticles are not detected when diluted in 10 fold DMSO.

Figure 21B:
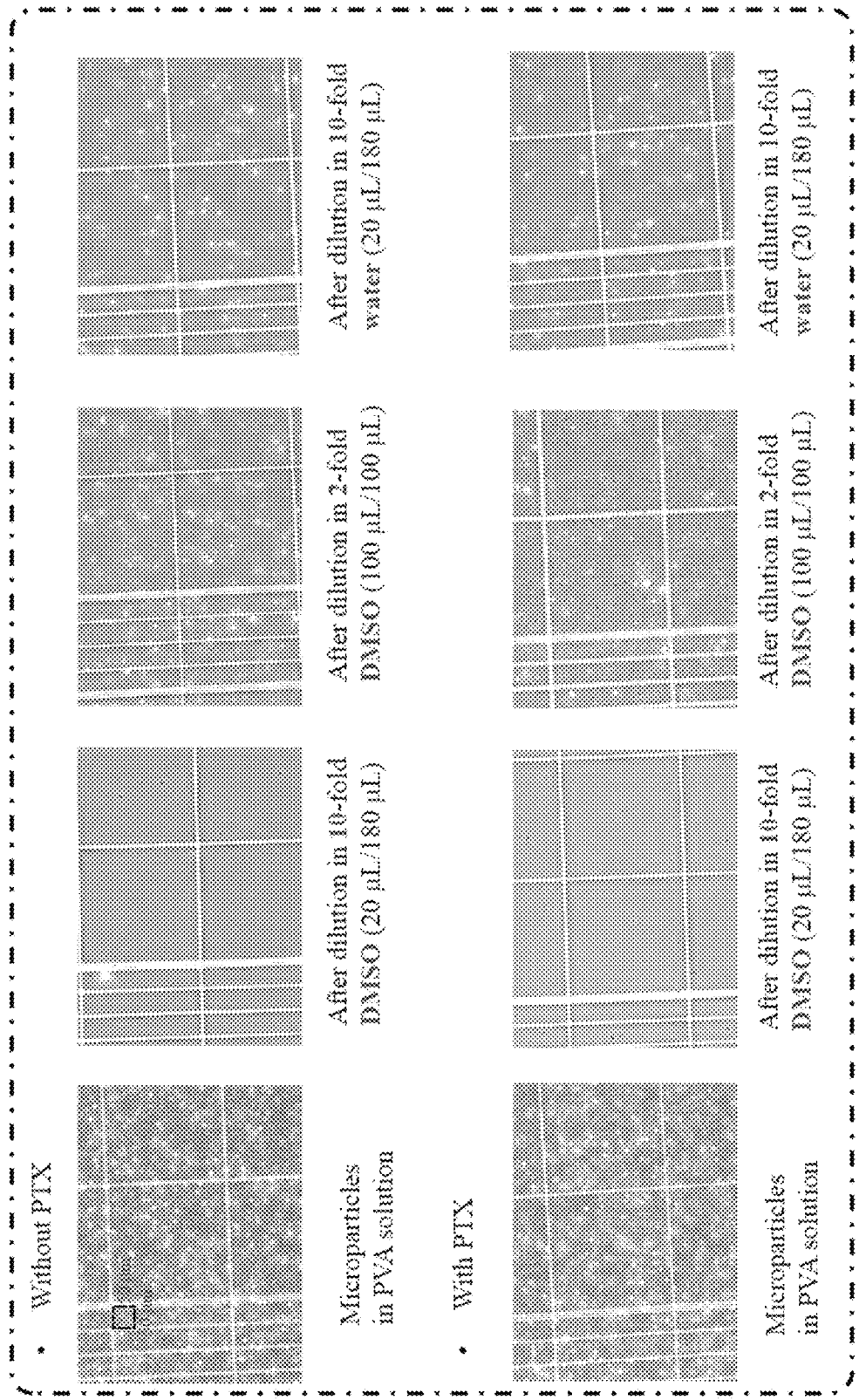
FIG. 21B shows a Polymer (SJP1), DMPA, SH-PEG-SH and PTX dissolved in DCM were mixed with 5% PVA using a homogenizer for 30 min after evaporation of DCM overnight in fume hood.

FIG. 21B shows a Polymer (SJP1), DMPA, SH-PEG-SH and PTX dissolved in DCM were mixed with 5% PVA using a homogenizer for 30 min after evaporation of DCM overnight in fume hood.

Figure 21C:
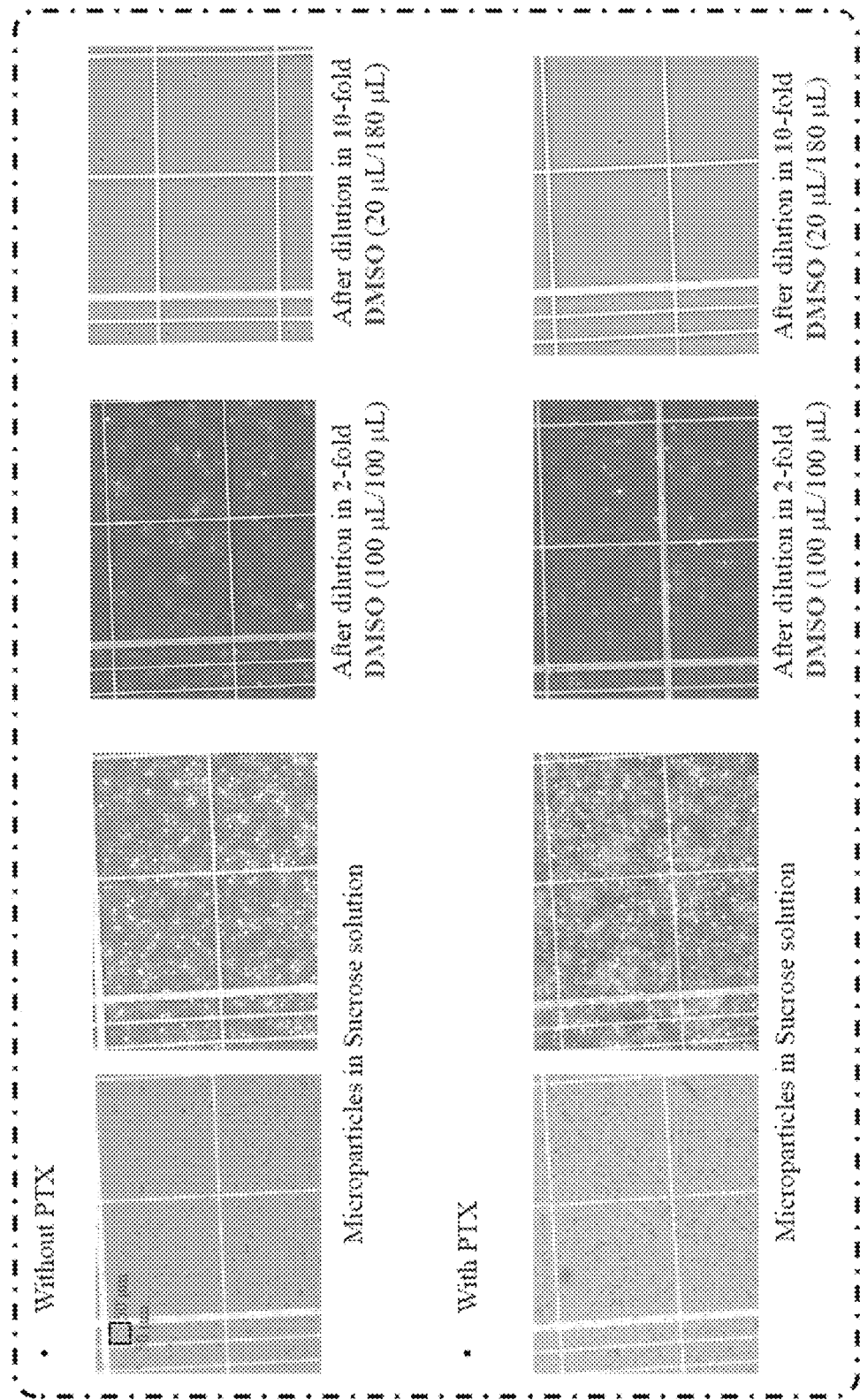
FIG. 21C shows a Polymer (SJP1), DMPA, SH-PEG-SH and PTX dissolved in DCM mixed with 5% PVA using a homogenizer for 30 min purified using water three times and then mixed with 5% of Sucrose solution.

FIG. 21C shows a Polymer (SJP1), DMPA, SH-PEG-SH and PTX dissolved in DCM mixed with 5% PVA using a homogenizer for 30 min purified using water three times and then mixed with 5% of Sucrose solution.

Summary for microparticles: We can make non-crosslinked microparticles with SJP1 polymer, SH-PEG-SH as crosslinker and PTX. The microparticles are stable in water, but not in 10 fold DMSO and therefore are not crosslinked. 1,6-hexanedithiol as a crosslinker and uses s stir bar during crosslinking.

Figure 22A:
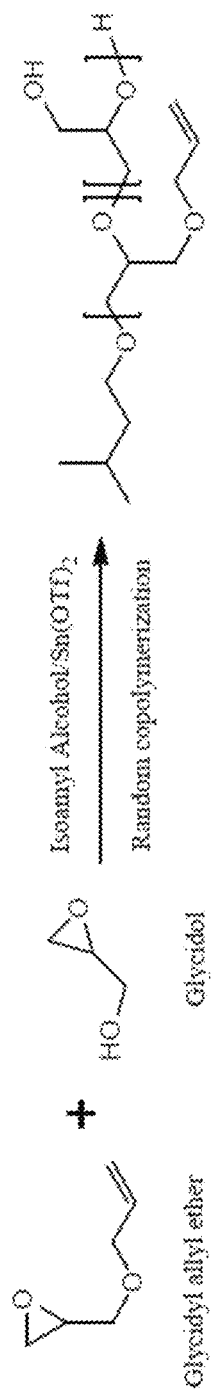
FIG. 22A shows a reaction scheme for Synthesis of PAGE-co-PGLY, according to an embodiment.

FIG. 22A shows a reaction scheme for Synthesis of PAGE-co-PGLY, according to an embodiment.

Figure 22B:
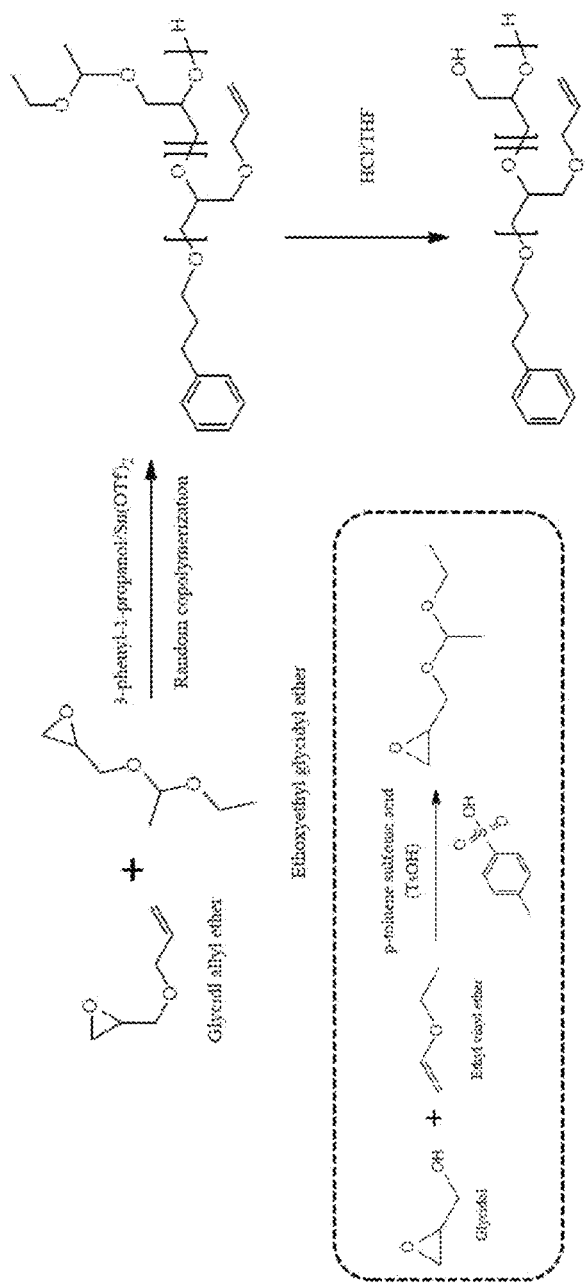
FIG. 22B shows a reaction scheme for Synthesis of PAGE-co-PGLY, according to an embodiment.

FIG. 22B shows a reaction scheme for Synthesis of PAGE-co-PGLY, according to an embodiment.

Figure 23:
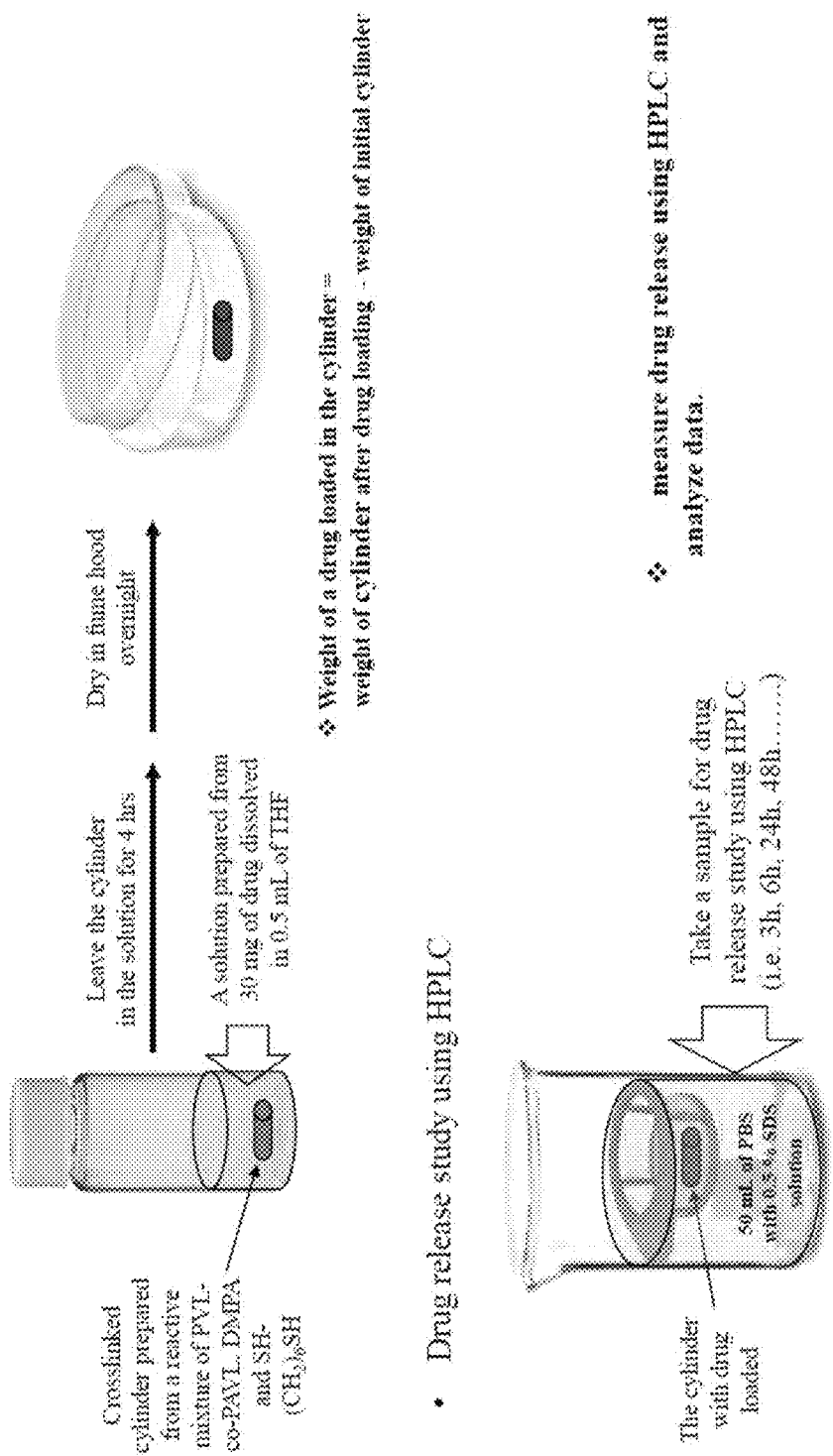
FIG. 23 shows a drug loading and release study with HPLC.

FIG. 23 shows a drug loading and release study with HPLC.

TABLE 8

Characteristics of Synthesized Polymers

| Drug | Molecular Weight (g/mol) | Molecular formula | Log P | pKa | Water solubility |
|---|---|---|---|---|---|
| Lucentis (ranibizumab) | 48349.611 | $C_{2158}H_{3282}N_{562}O_{681}S_{12}$ | less than 0 | | Soluble in water |
| Penicillin G | 334.39 | $C_{16}H_{18}N_2O_4S$ | 1.83 | 3.96 | Slightly soluble in water (0.21 mg/mL) |

TABLE 8-continued

Characteristics of Synthesized Polymers

| Drug | Molecular Weight (g/mol) | Molecular formula | Log P | pKa | Water solubility |
|---|---|---|---|---|---|
| Drug X | 476.47 | $C_{21}H_{29}N_6O_5P$ | 1.6 | 2.74 | Soluble in water (4.86 mg/mL) |

Figure 24:
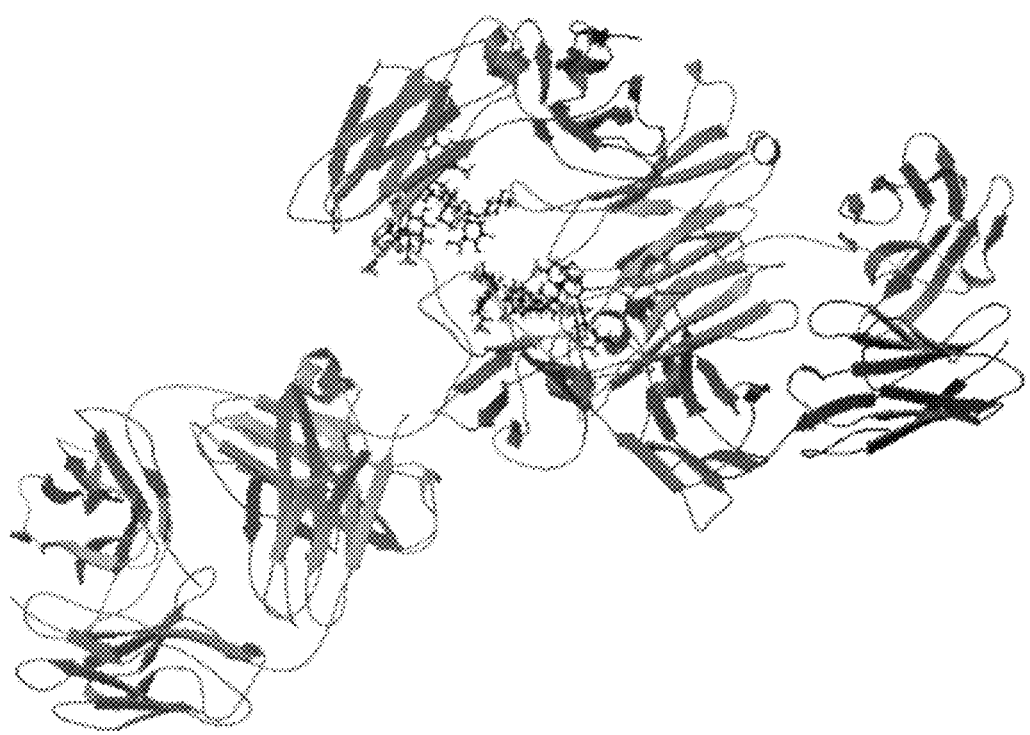
FIG. 24 shows a Lucentis® molecule.

FIG. 24 shows a Lucentis® molecule.

Figure 25:
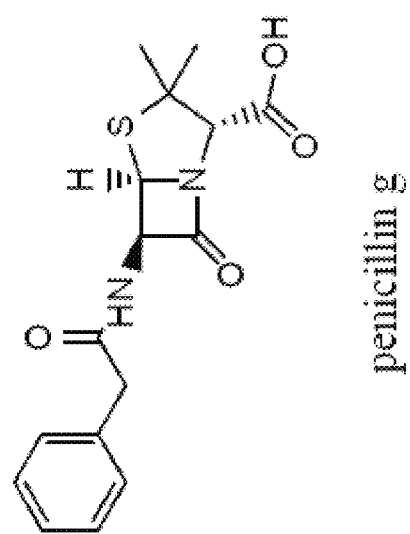
FIG. 25 shows a penicillin g molecule.

FIG. 25 shows a penicillin g molecule.

Figure 26:
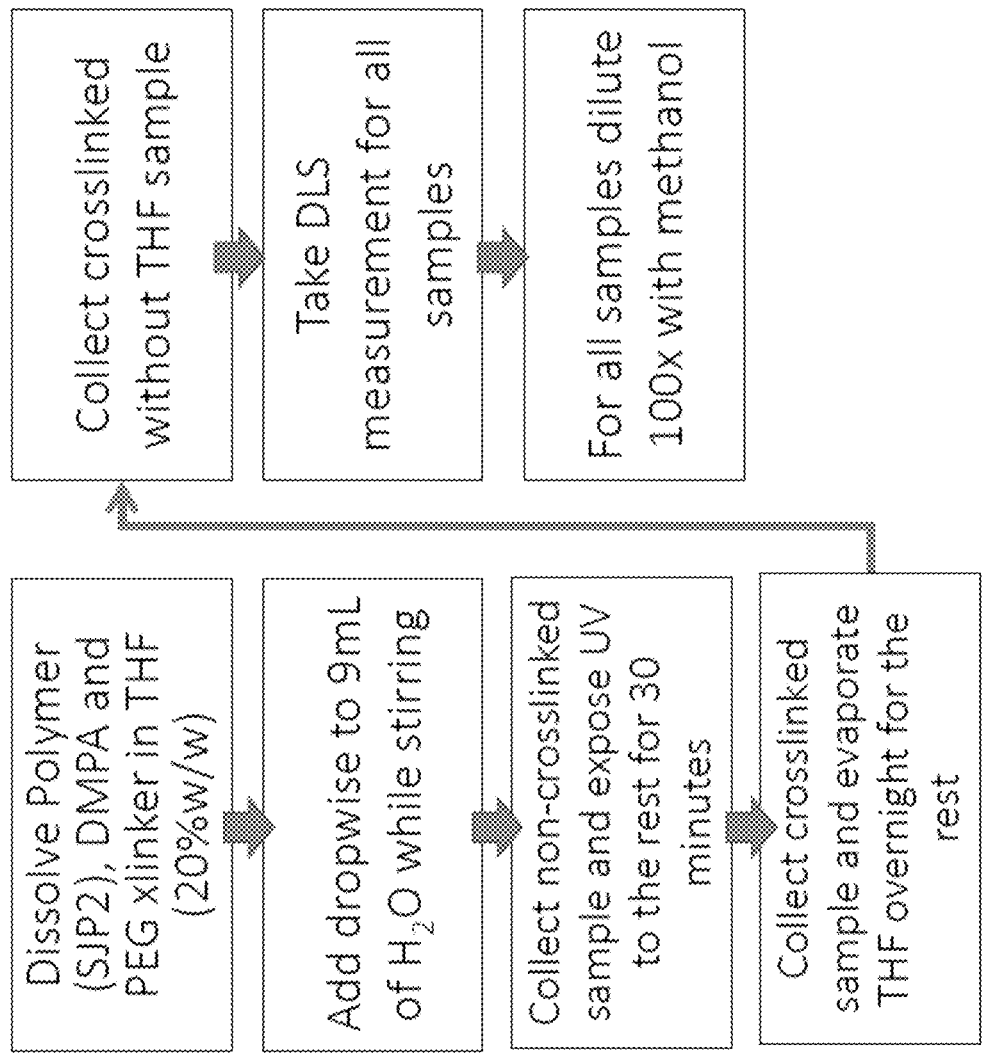
FIG. 26 shows a nanoparticle profile, according to an embodiment.

FIG. 26 shows a nanoparticle profile, according to an embodiment.

Figure 27:
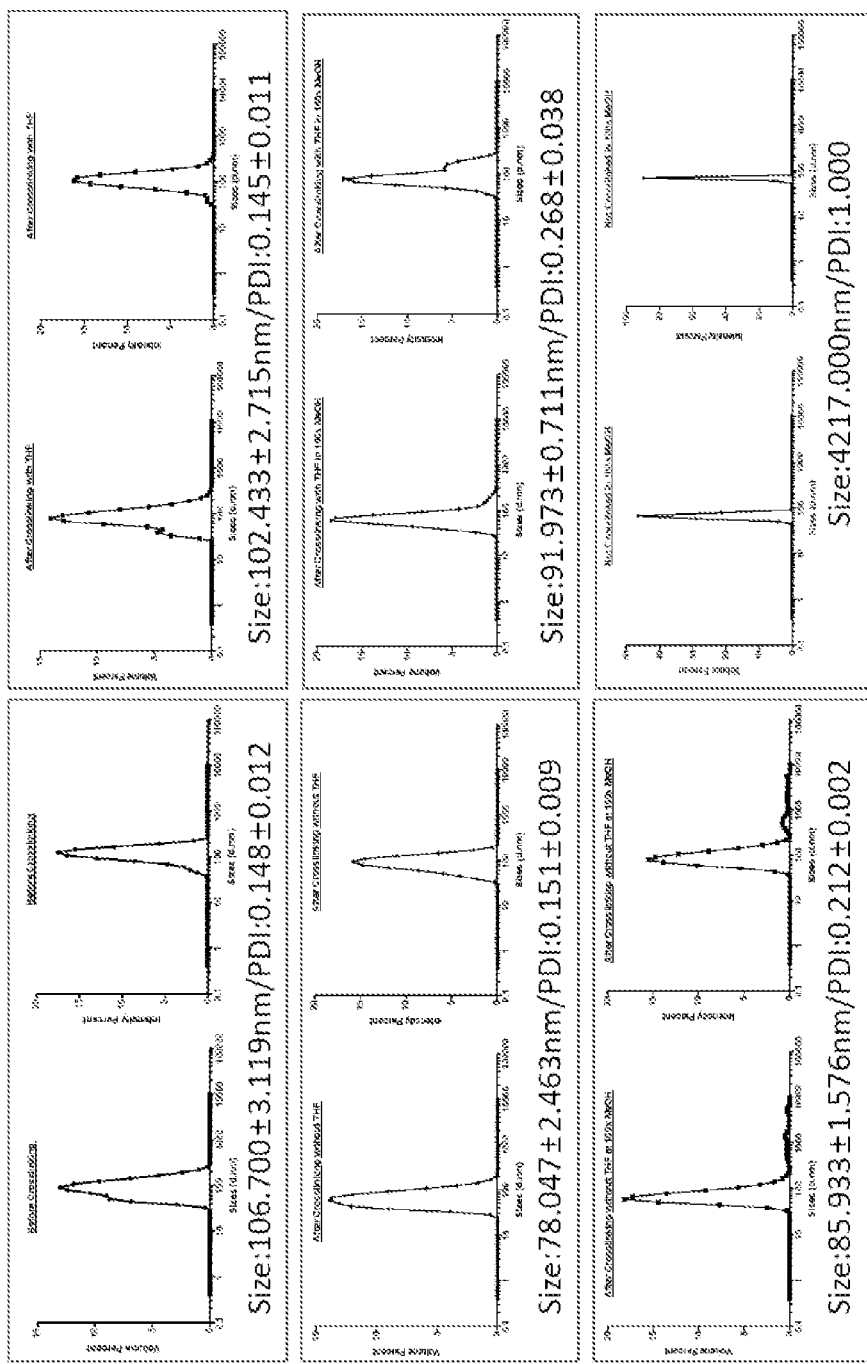
FIG. 27 shows DLS results.

FIG. 27 shows DLS results.

Figure 28:
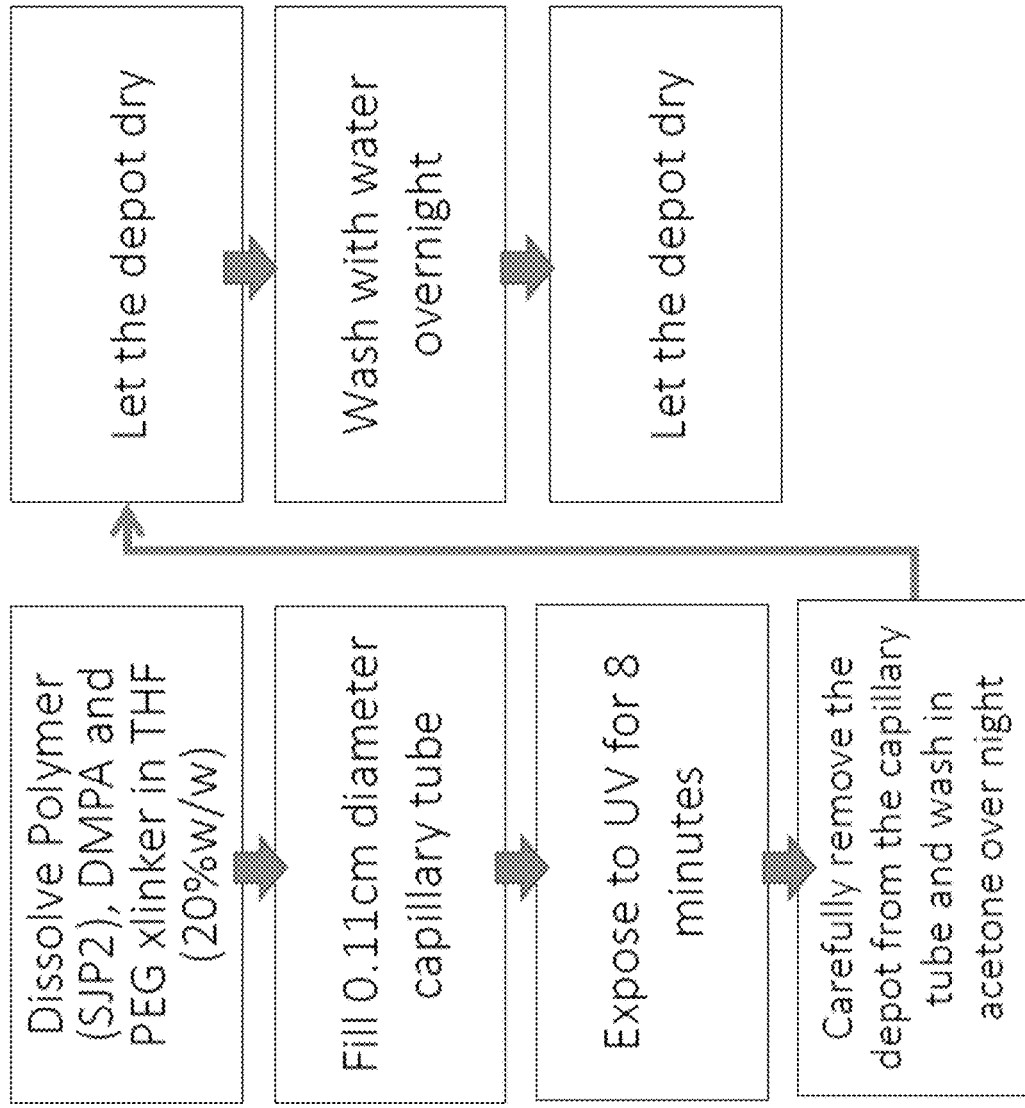
FIG. 28 shows a depot protocol, according to an embodiment.

FIG. 28 shows a depot protocol, according to an embodiment.

Figure 29:
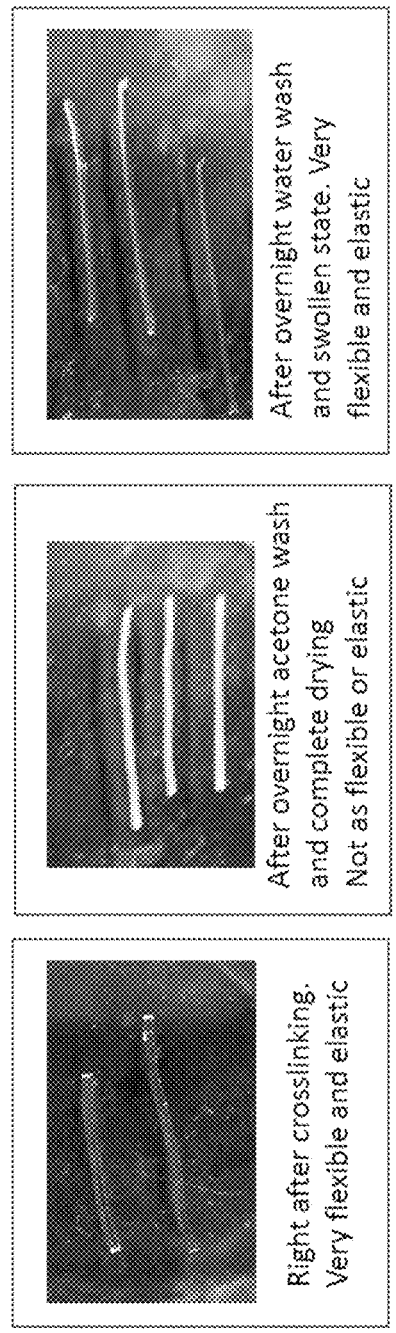
FIG. 29 shows depot images.

FIG. 29 shows depot images.

Based on these studies, we have confirmed that cross-linked nanoparticles can be produced with SJP2, giving a platform for a sustainable release system. Nanoparticle has been shown to be successful in achieving sustain release of bevacizumab. Varshochian, R., et al. (2013). "The protective effect of albumin on bevacizumab activity and stability in PLGA nanoparticles intended for retinal and choroidal neovascularization treatments." *European Journal of Pharmaceutical Sciences* 503: 341-352. Varshochian, R., et al. (2015). "Albuminated PLGA nanoparticles containing bevacizumab intended for ocular neovascularization treatment." *Journal of Biomedical Materials Research Part A* 103(10): 3148-3156. Combination of nanoparticles and microparticles also has been used, which can be another platform for a sustainable release system. Yandrapu, S. K., et al. (2013). "Nanoparticles in Porous Microparticles Prepared by Supercritical Infusion and Pressure Quench Technology for Sustained Delivery of Bevacizumab." *Molecular Pharmaceutics* 10(12): 4676-4686. Nanoparticle formation with albumin post loading albumin to nanoparticle. We have also made a depot with diameter of 0.11 cm. The material is very flexible and elastic when swollen. It swell in organic solvents and water. When dried, it loses its flexibility and elasticity and becomes firm but stretches. Having firmness is useful because it will be easier to penetrate the ocular layer. The material swells fair quickly, which is another advantage. The diameter is ideal for insertion into the eye based. Fialho, S. L., et al. (2007). "Biodegradable implants for ocular delivery of anti-inflammatory drug." *Journal of Drug Delivery Science and Technology* 171: 93-97. Loading albumin into the depot loading FITC labelled albumin. The depot has highly elastic property.

TABLE 9

Characteristics of Synthesized Polymers

| Entry. | | | $^1$H-NMR | | GPC | |
|---|---|---|---|---|---|---|
| No | Polymer structure | $M_n$ | DP (PEG/ PVL/PAVL) | PAVL (%) | $M_n$ | PDI |
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP4 | PAVL-b-PVL-b-35KPEG-b-PVL-b-PAVL | 47.0K | 812/86/17 | 6 | 50.4K | 1.06 |
| SJP5 | PAVL-b-3KPEG-b-PAVL | 6.2K | 85/0/18 | 40 | 7.7K | 1.07 |
| SJP6 | (PAVL-co-PVL)-3KPEG-(PAVL-co-PVL) | 8.5K | 85/36/8 | 15 | 7.4k | 1.39 |
| SJP7 | PVL-co-PAVL | 32K | 0/235/42 | 20 | 24K | 1.37 |

TABLE 10

Polymers used to Form Depots and Microparticles

| Entry. | | | $^1$H-NMR | | GPC | |
|---|---|---|---|---|---|---|
| No | Polymer structure | $M_n$ | DP (PEG/ PVL/PAVL) | PAVL (%) | $M_n$ | PDI |
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP4 | PAVL-b-PVL-b-35KPEG-b-PVL-b-PAVL | 47.0K | 812/86/17 | 5 | 50.4K | 1.06 |
| SJP5 | PAVL-b-3KPEG-b-PAVL | 6.2K | 85/0/18 | 40 | 7.7K | 1.07 |
| SJP6 | (PAVL-co-PVL)-3KPEG-(PAVL-co-PVL) | 8.5K | 85/36/8 | 15 | 7.4k | 1.39 |
| SJP7 | PVL-co-PAVL | 32K | 0/235/42 | 20 | 24K | 1.37 |

Figure 30:
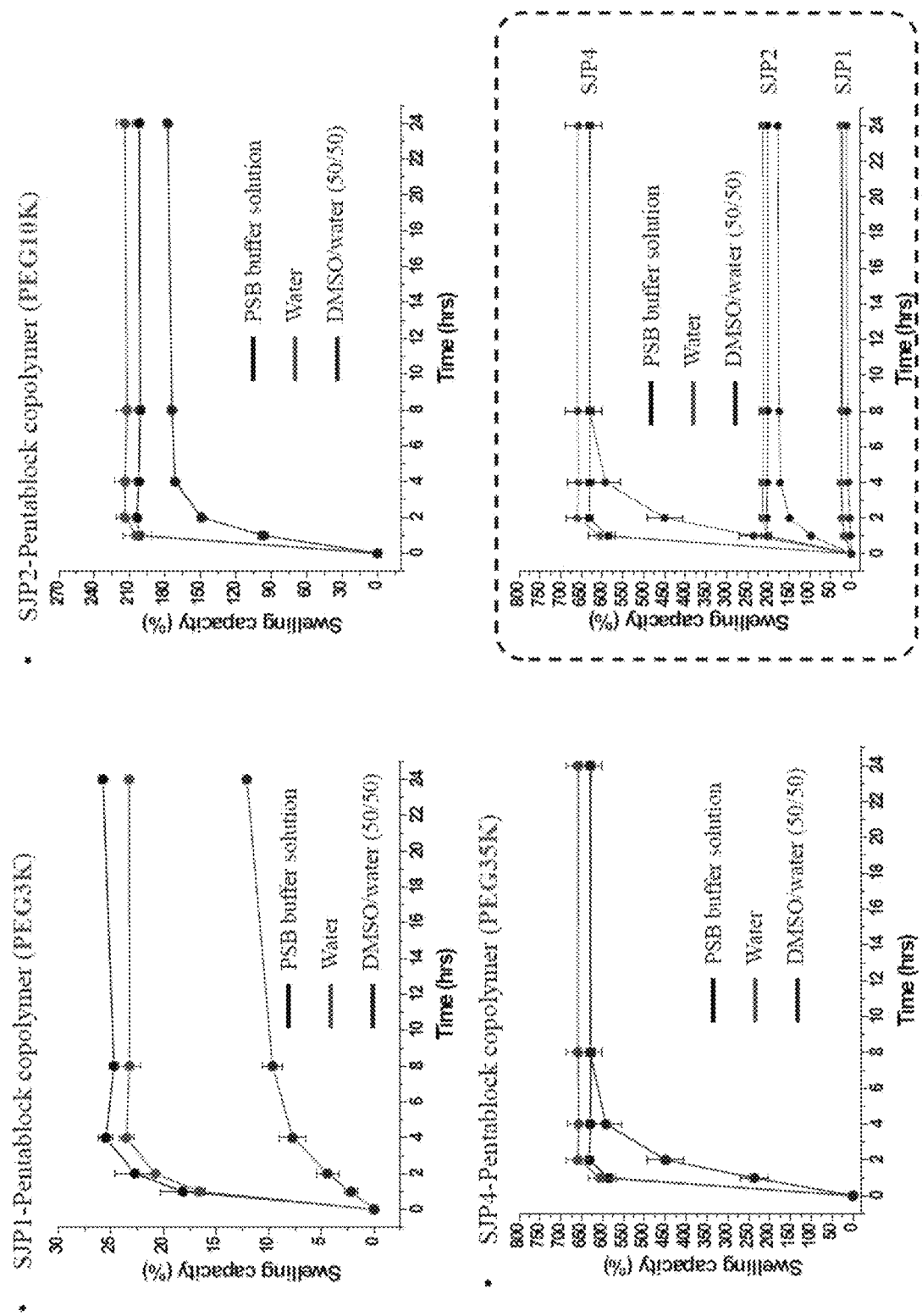
FIG. 30 shows results of a swelling study.

FIG. 30 shows results of a swelling study.

Figure 31:
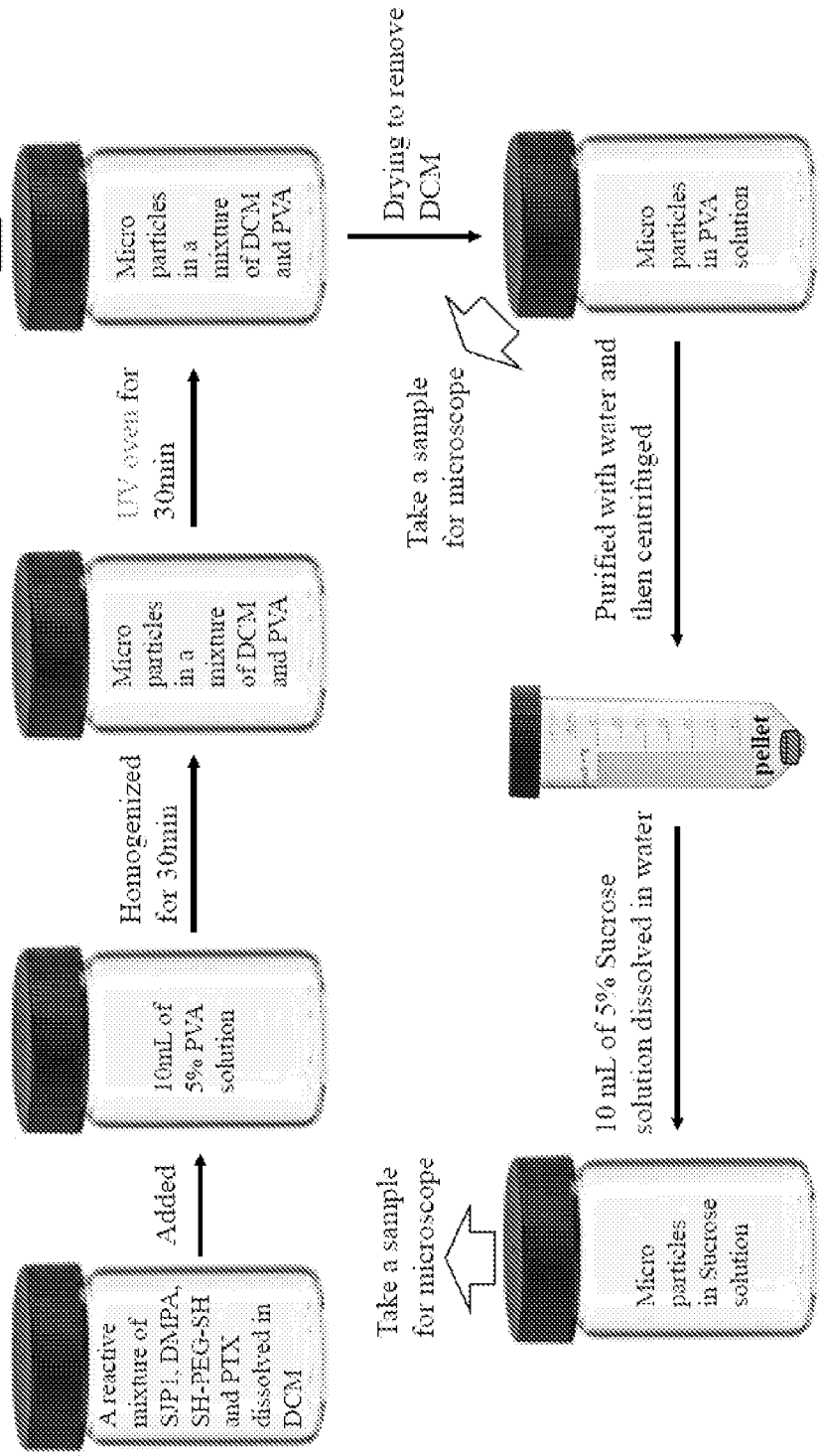
FIG. 31 shows a procedure to prepare microparticles, according to an embodiment.

FIG. 31 shows a procedure to prepare microparticles, according to an embodiment.

Figure 32:
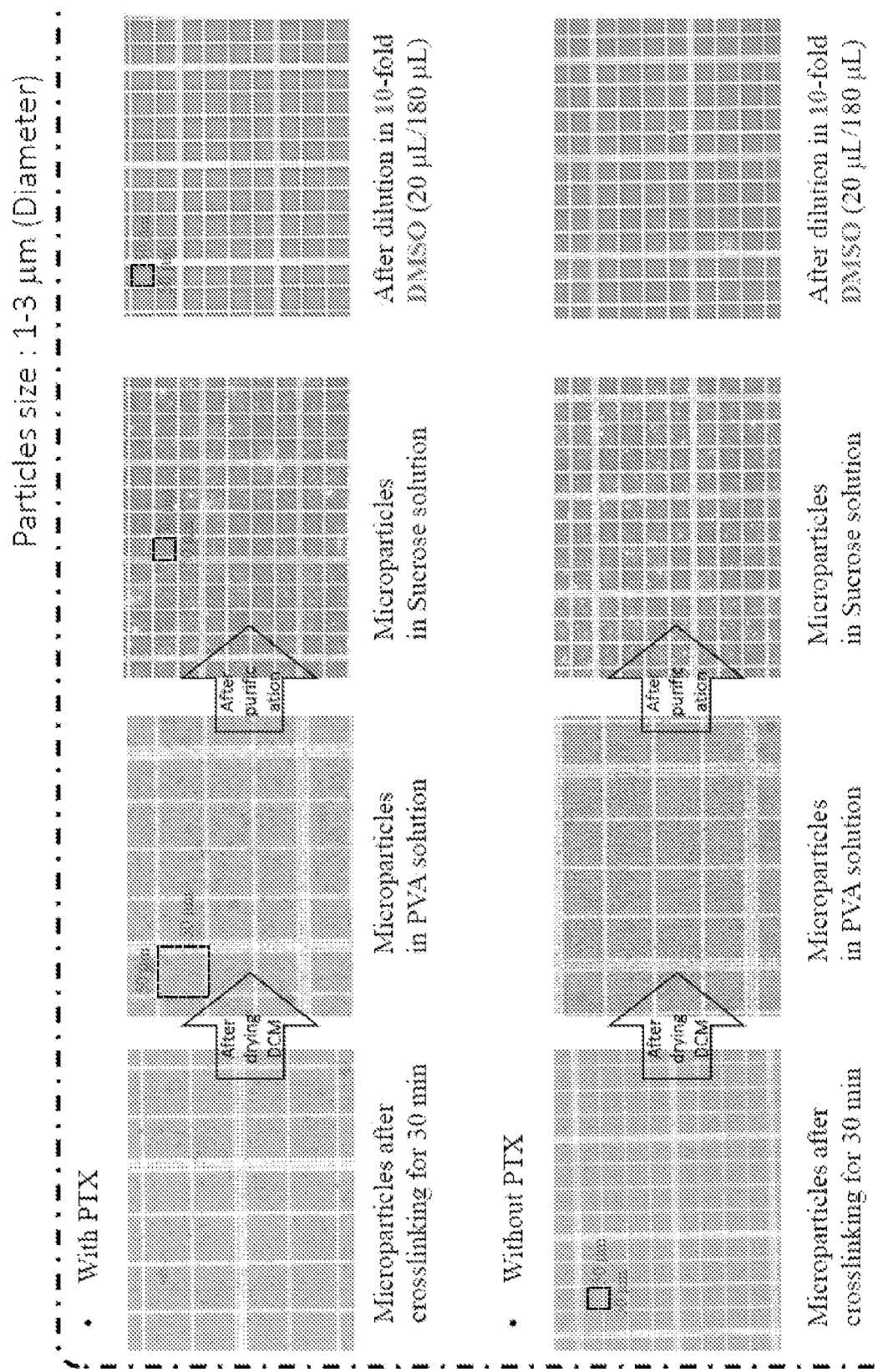
FIG. 32 shows a polymer (SJP2), DMPA, SH—(CH$_2$)$_6$—SH and PTX dissolved in DCM mixed with 5% PVA using a homogenizer for 30 min (particle size 1-3 µm).

FIG. 32 shows a polymer (SJP1), DMPA, SH—$(CH_2)_6$—SH and PTX dissolved in DCM mixed with 5% PVA using a homogenizer for 30 min (particle size 1-3 µm).

Figure 33:
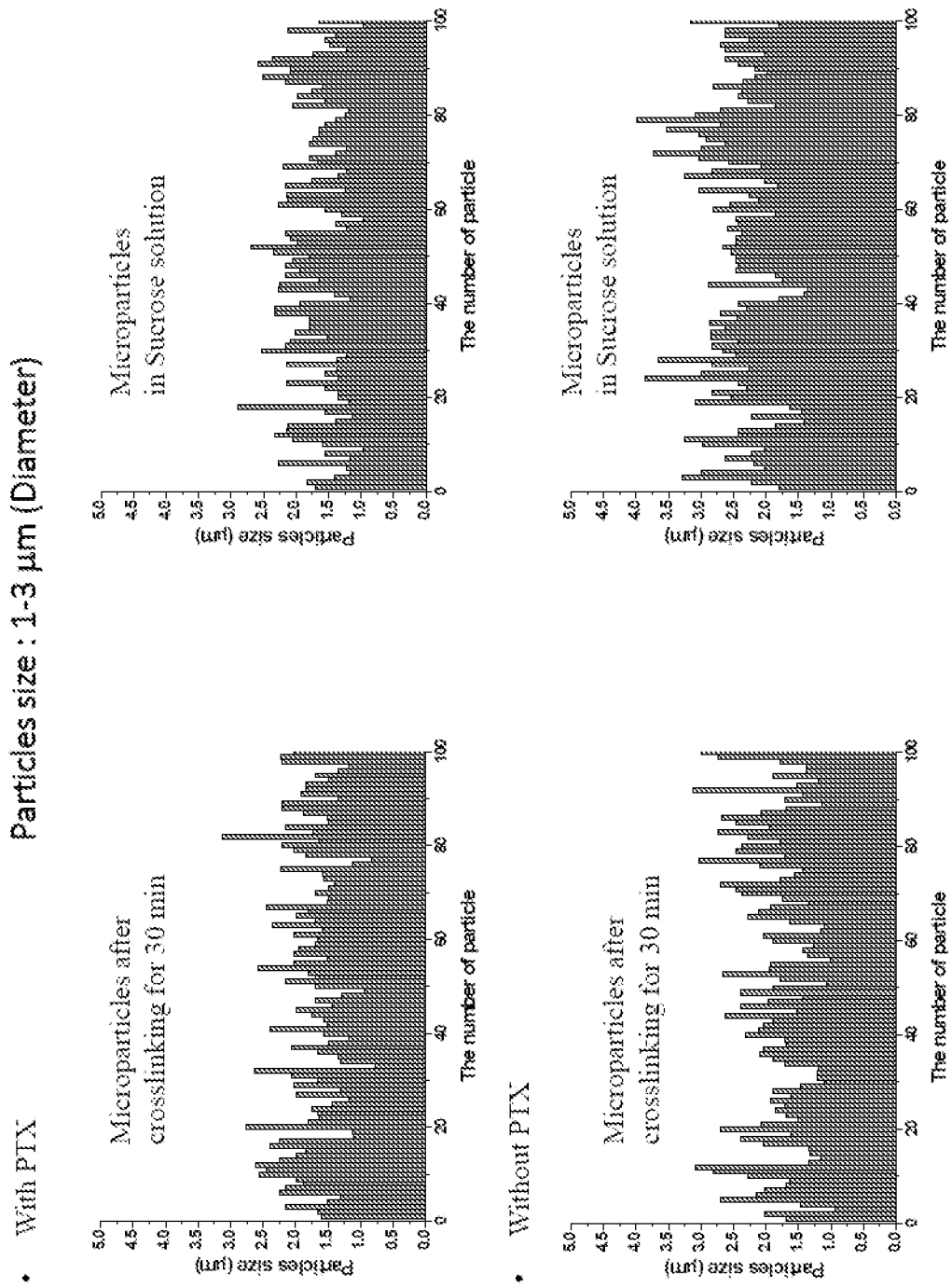
FIG. 33 shows particle size distribution of a polymer (SJP2), DMPA, SH—(CH$_2$)$_6$—SH and PTX dissolved in DCM mixed with 5% PVA using a homogenizer for 30 min (particle size 1-3 µm).

FIG. 33 shows particle size distribution of a polymer (SJP1), DMPA, SH—$(CH_2)_6$—SH and PTX dissolved in DCM mixed with 5% PVA using a homogenizer for 30 min (particle size 1-3 µm).

Figure 34:
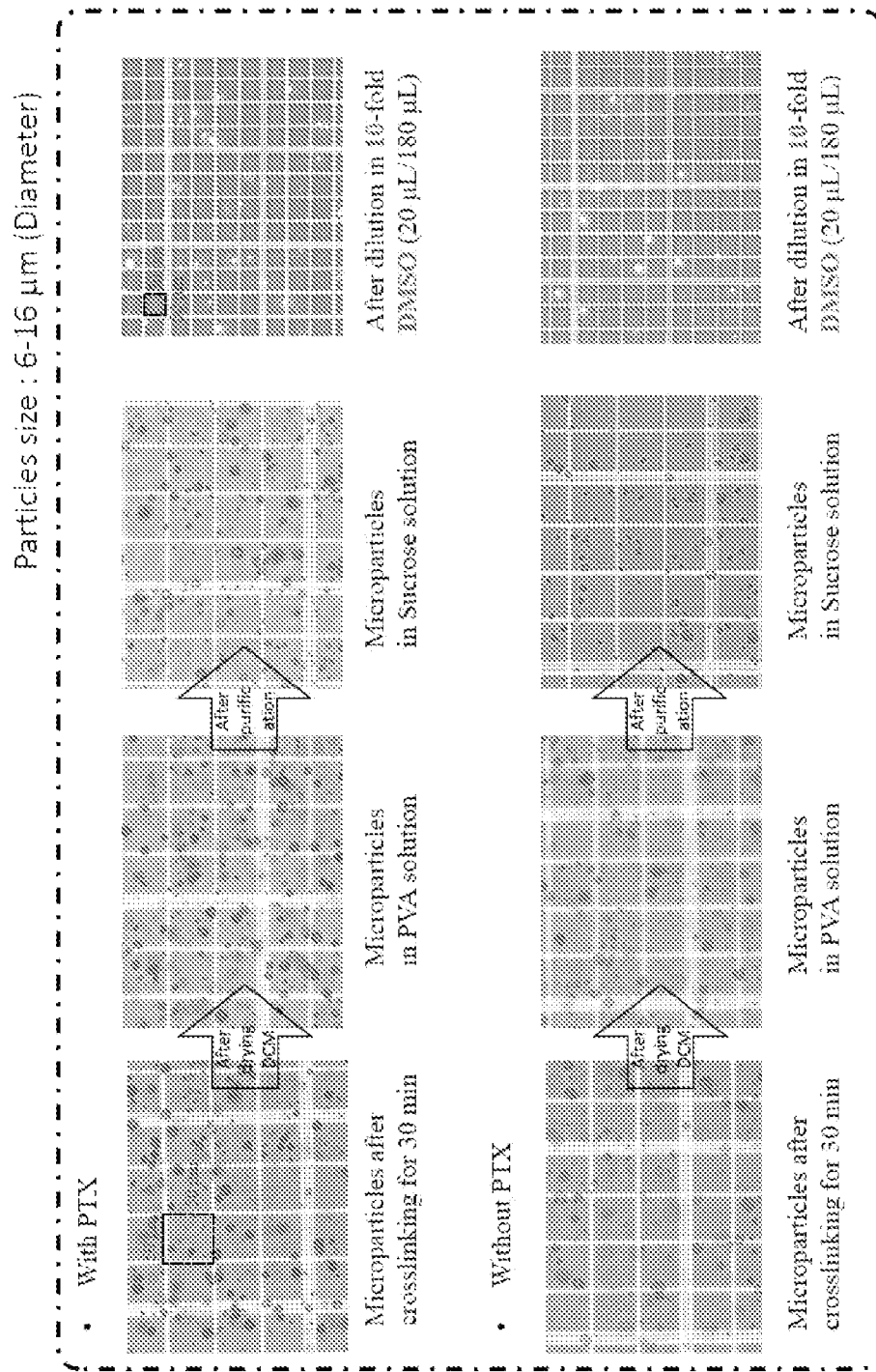
FIG. 34 shows a polymer (SJP2), DMPA, SH—(CH$_2$)$_6$—SH and PTX dissolved in DCM mixed with 5% PVA using a homogenizer for 30 min (particle size 6-16 µm).

FIG. 34 shows a polymer (SJP2), DMPA, SH—$(CH_2)_6$—SH and PTX dissolved in DCM mixed with 5% PVA using a homogenizer for 30 min (particle size 6-16 µm).

Figure 35:
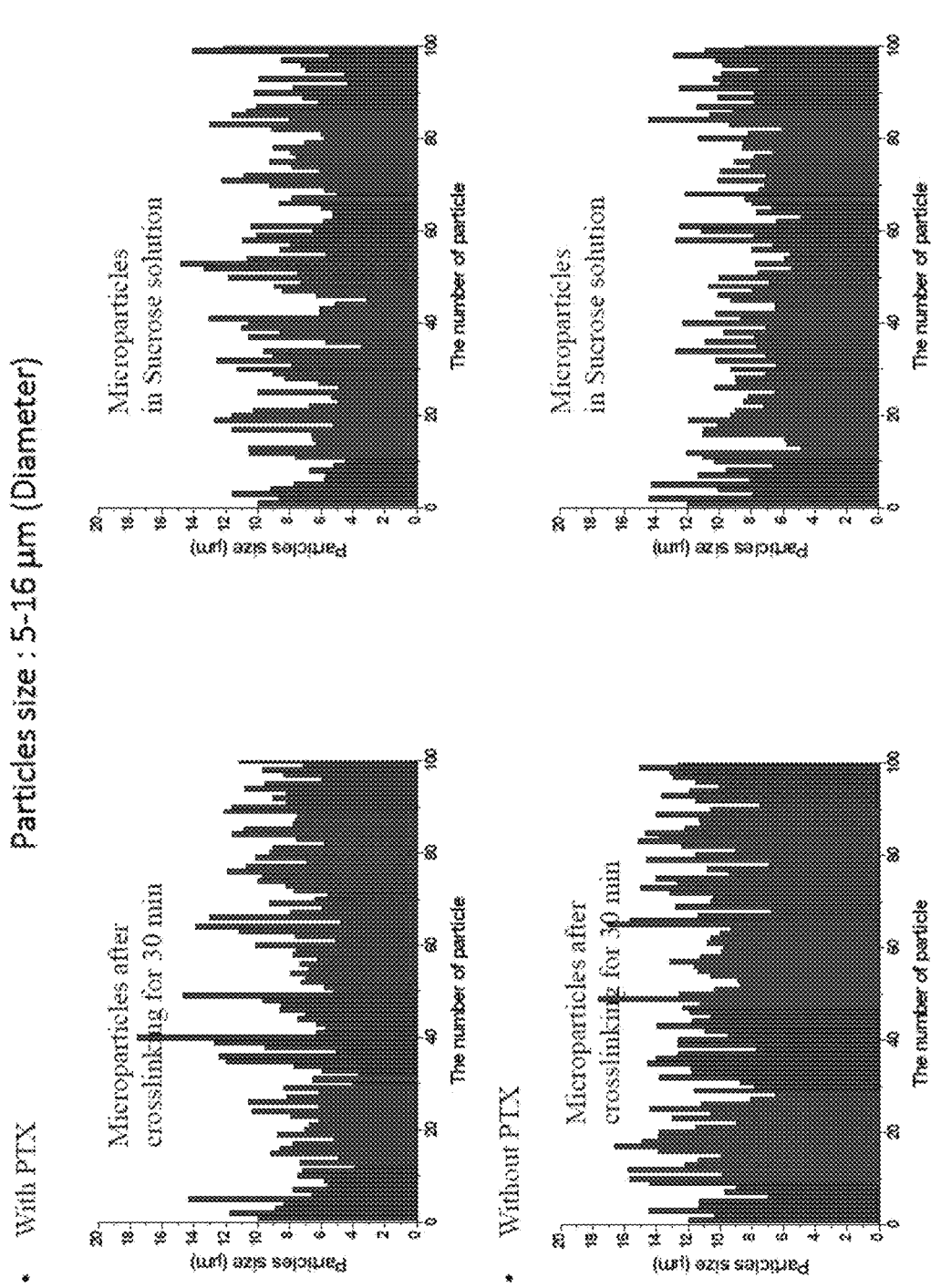
FIG. 35 shows particle size distribution of a polymer (SJP2), DMPA, SH—(CH$_2$)$_6$—SH and PTX dissolved in DCM mixed with 5% PVA using a homogenizer for 30 min (particle size 6-16 µm).

FIG. 35 shows particle size distribution of a polymer (SJP2), DMPA, SH—(CH$_2$)$_6$—SH and PTX dissolved in DCM mixed with 5% PVA using a homogenizer for 30 min (particle size 6-16 μm).

Figure 36:
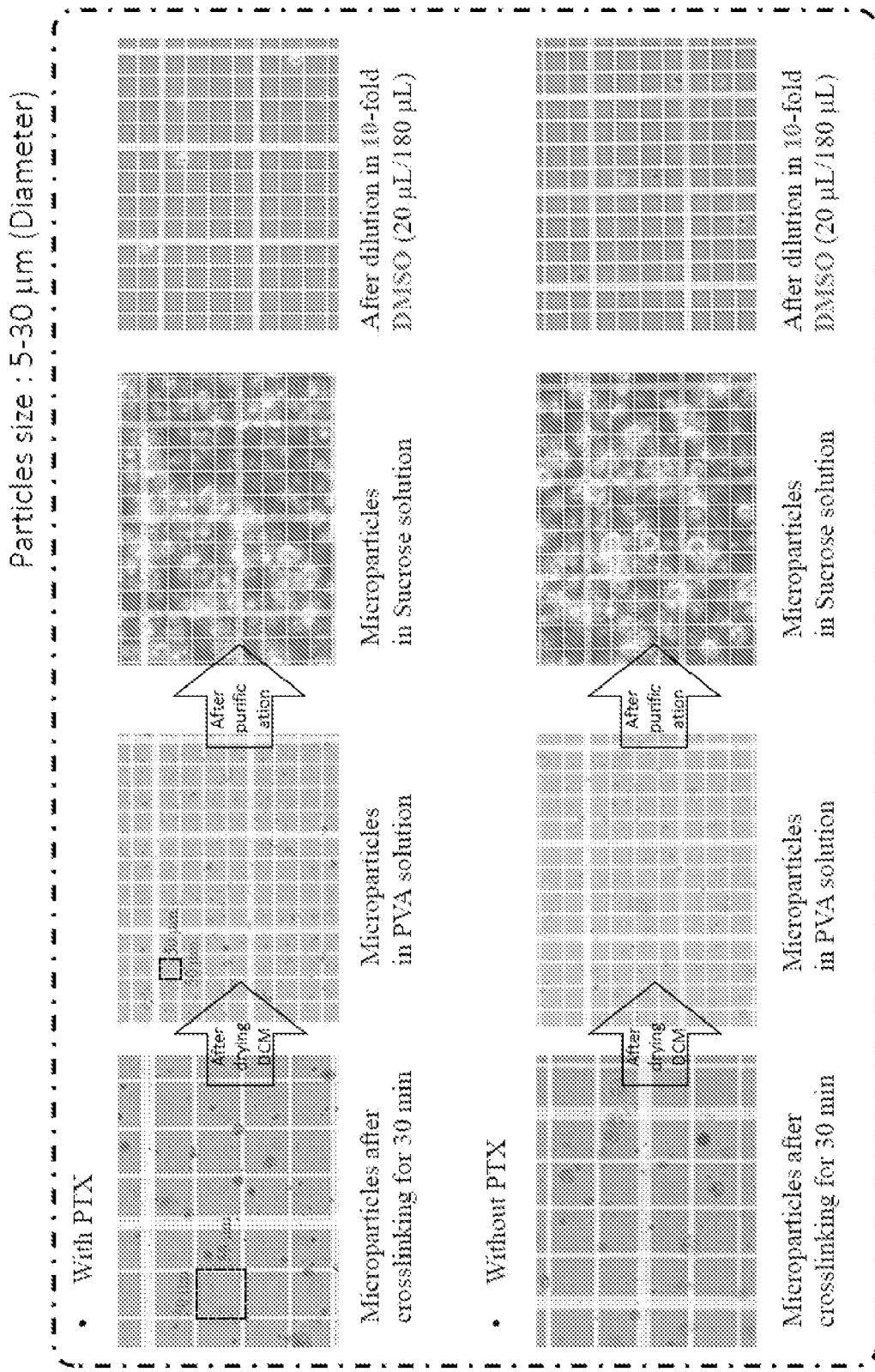
FIG. 36 shows a polymer (SJP2), DMPA, SH—(CH$_2$)$_6$—SH and PTX dissolved in DCM mixed with 5% PVA using a homogenizer for 30 min (particle size 5-30 µm).

FIG. 36 shows a polymer (SJP4), DMPA, SH—(CH$_2$)$_6$—SH and PTX dissolved in DCM mixed with 5% PVA using a homogenizer for 30 min (particle size 5-30 μm).

Figure 37:
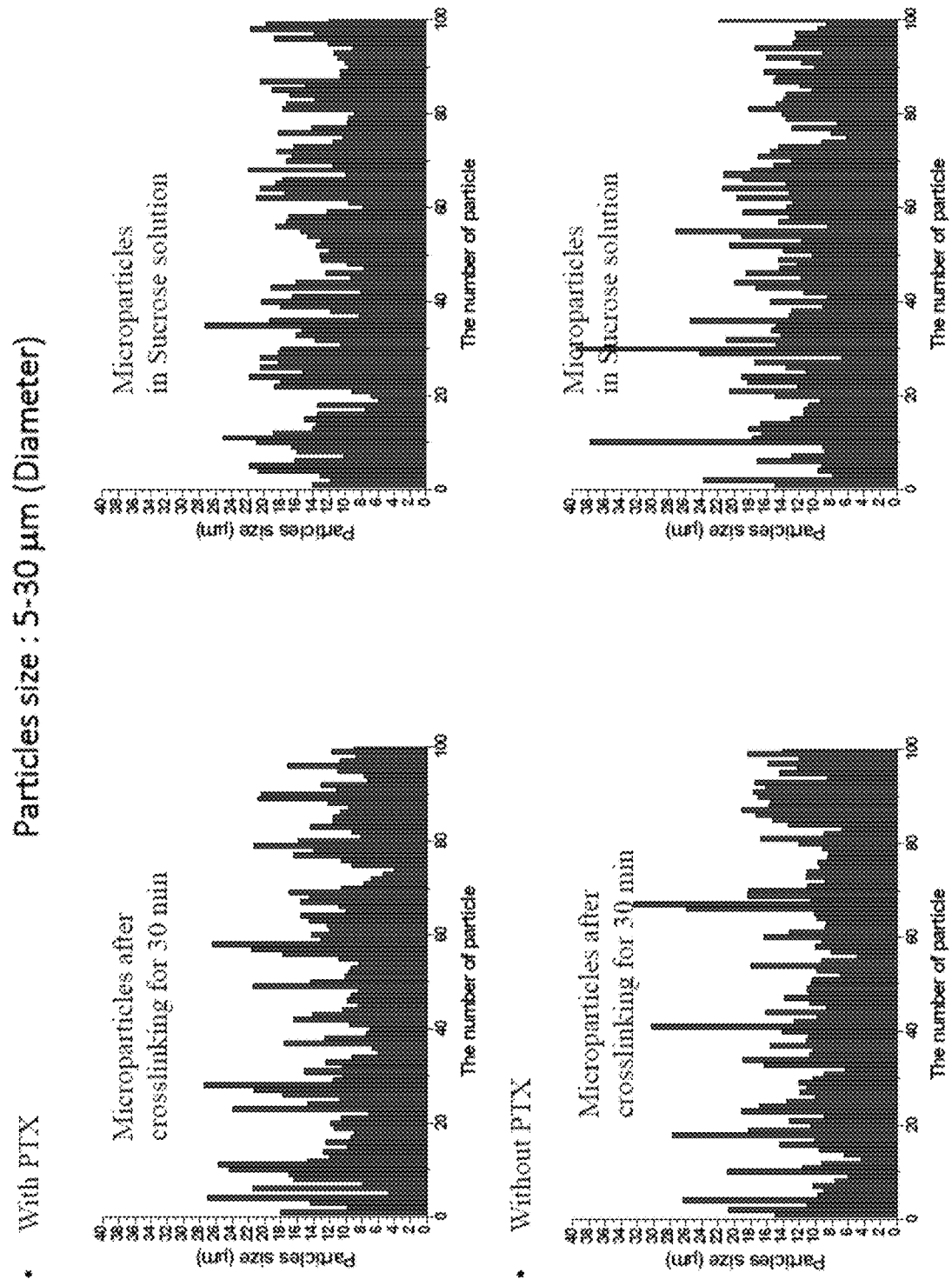
FIG. 37 shows particle size distribution of a polymer (SJP2), DMPA, SH—(CH$_2$)$_6$—SH and PTX dissolved in DCM mixed with 5% PVA using a homogenizer for 30 min (particle size 5-30 µm).

FIG. 37 shows particle size distribution of a polymer (SJP4), DMPA, SH—(CH$_2$)$_6$—SH and PTX dissolved in DCM mixed with 5% PVA using a homogenizer for 30 min (particle size 5-30 μm).

Summary for Microparticles: We can make crosslinked microparticles with pentablock copolymer (SJP1, SJP2 and SJP4), SH—(CH$_2$)$_6$—SH as crosslinker and PTX. The microparticles are stable in 10 fold DMSO meaning are crosslinked. The size of Microparticles is increased as molecular weight of PEG is increased.

Strategy on biologic delivery: Two forms of delivery system for the biologics delivery→Inserted Depot and Injectable Nano/MicroParticles.

Potential biomaterial→Penta-Block copolymer synthesized release, degradation and biocompatibility.

Model Biologics→Albumin.

Purpose & Target→For treatment of age-related macular degeneration. Target is the back of the eye and to release for 90 days.

Loading Method→Post-loading (swelling & drying method), if not pre-loading; however protein stability under UV exposure.

Method of detection→Micro BCA assay.

Figure 38:
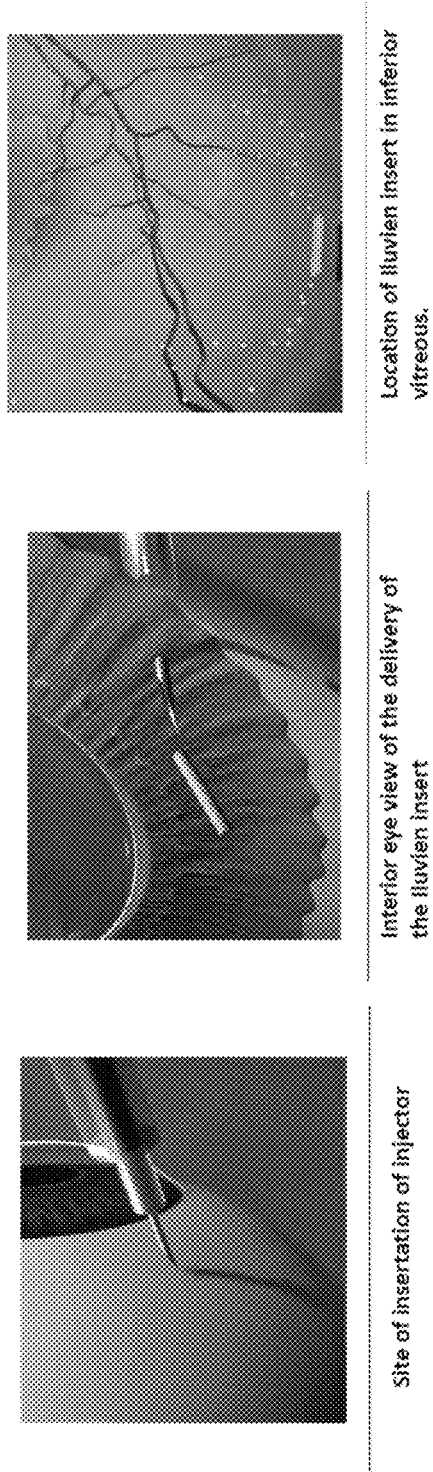
FIG. 38 shows biologic delivery, according to an embodiment.

FIG. 38 shows biologic delivery, according to an embodiment.

Figure 39:
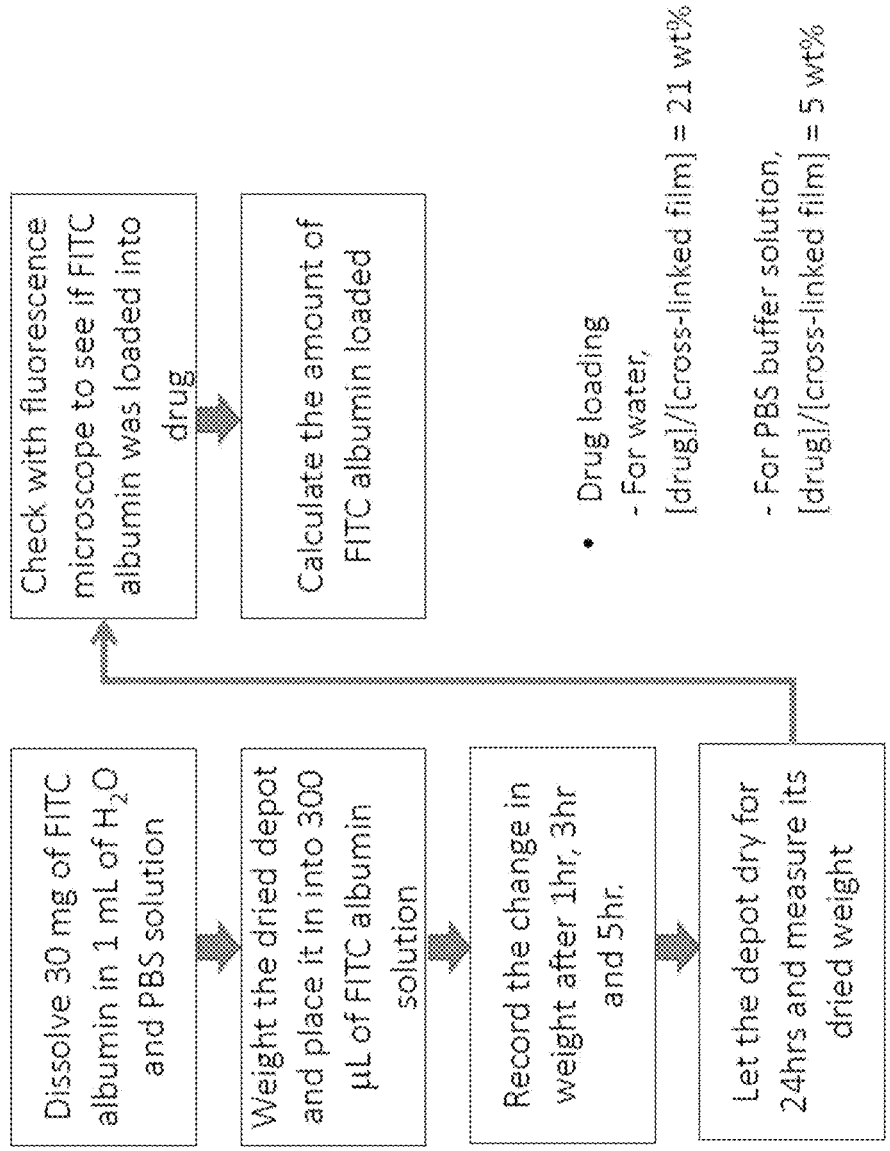
FIG. 39 shows loading albumin as model biologic into a depot, according to an embodiment.

FIG. 39 shows loading albumin as model biologic into a depot, according to an embodiment.

Figure 40:
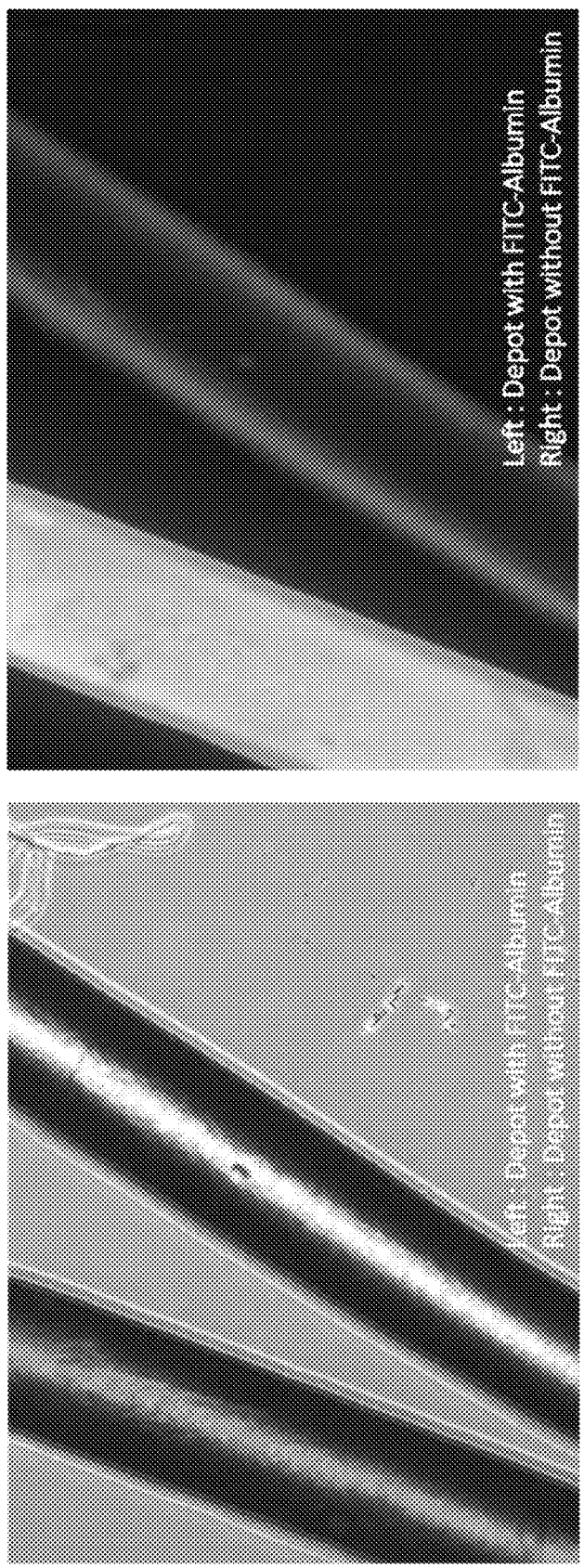
FIG. 40 shows swelling and loading results.

FIG. 40 shows swelling and loading results.

Figure 41:
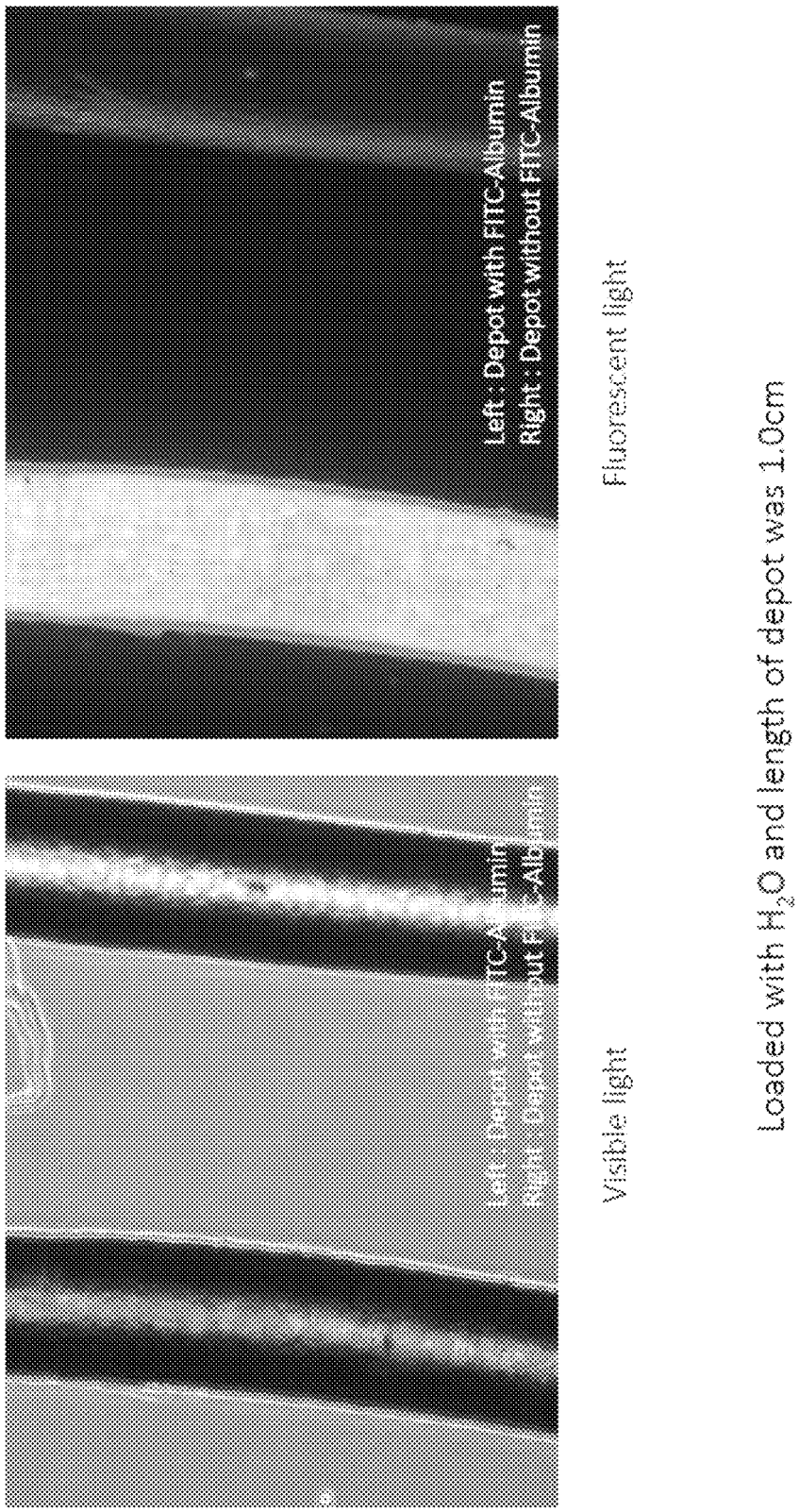
FIG. 41 shows swelling and loading results.

FIG. 41 shows swelling and loading results.

Loading Drug X into a depot:

Disc shaped depot to characterize the drug (Drug X) loading capacity and the release rate Drug loaded via swelling & evaporation methods An appropriate size of a depo determined based on results of disc experiment Release for at least 1 month, ideally 2 months Release rate is 1-3 mg per day.

Target amount of drug is 180 mg (for 2 months release), ideally at least 200 mg of drug.

TABLE 11

Library of Synthesized Copolymer Materials

| Entry. No | Polymer structure | $^1$H-NMR $M_n$ | DP (PEG/ PVL/PAVL) | PAVL (%) | GPC $M_n$ | PDI |
|---|---|---|---|---|---|---|
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP4 | PAVL-b-PVL-b-35KPEG-b-PVL-b-PAVL | 47.0K | 812/86/17 | 6 | 50.4K | 1.06 |
| SJP5 | PAVL-b-3KPEG-b-PAVL | 6.2K | 85/0/18 | 40 | 7.7K | 1.07 |
| SJP6 | (PAVL-co-PVL)-3KPEG-(PAVL-co-PVL) | 8.5K | 85/36/8 | 15 | 7.4k | 1.39 |
| SJP7 | PVL-co-PAVL | 32K | 0/235/42 | 20 | 24K | 1.48 |

Figure 42:
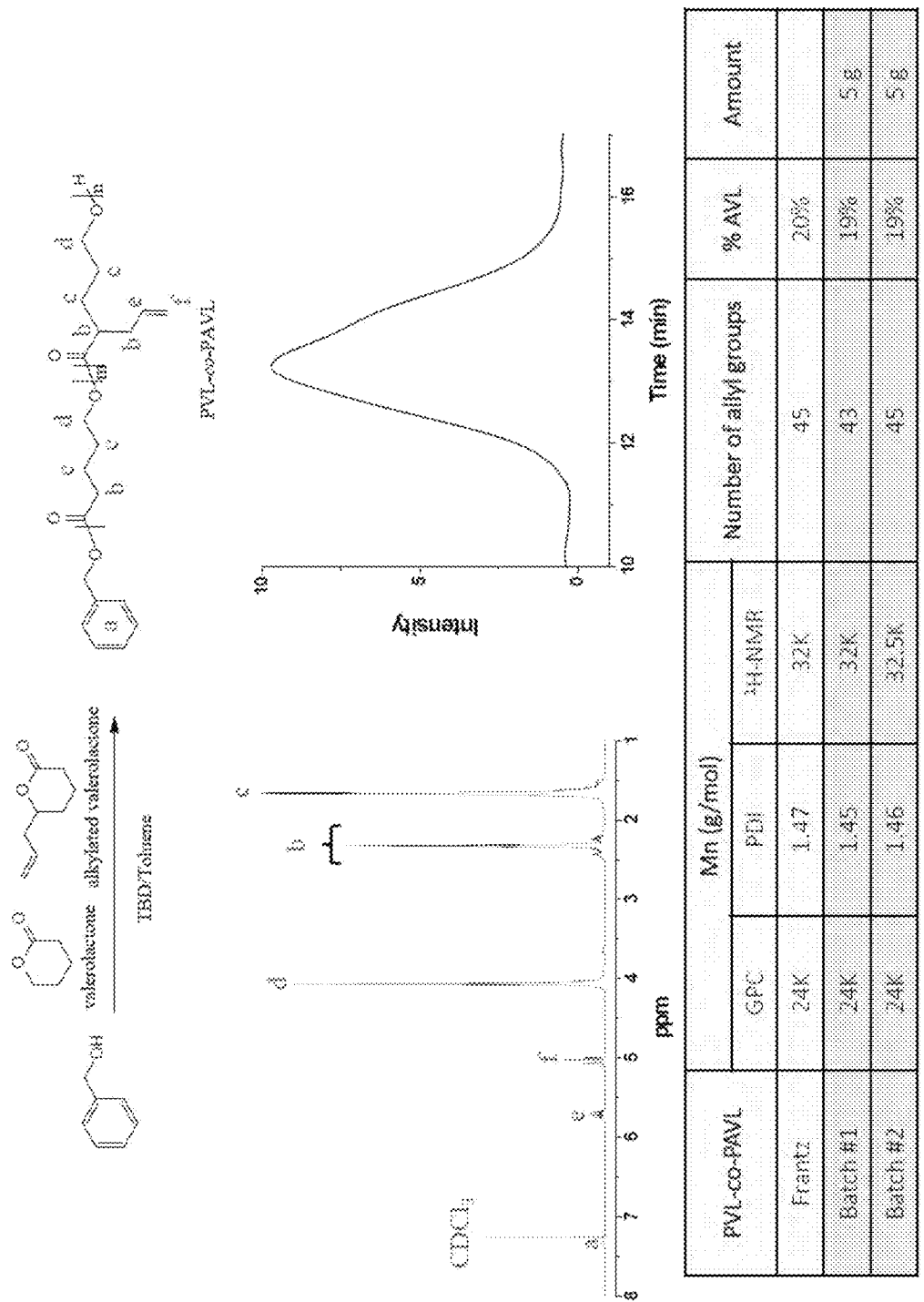
FIG. 42 shows Synthesis of PVL-co-PAVL (SJP7) to be sent to PSI.

FIG. 42 shows Synthesis of PVL-co-PAVL (SJP7) to be sent to PSI.

Figure 43:
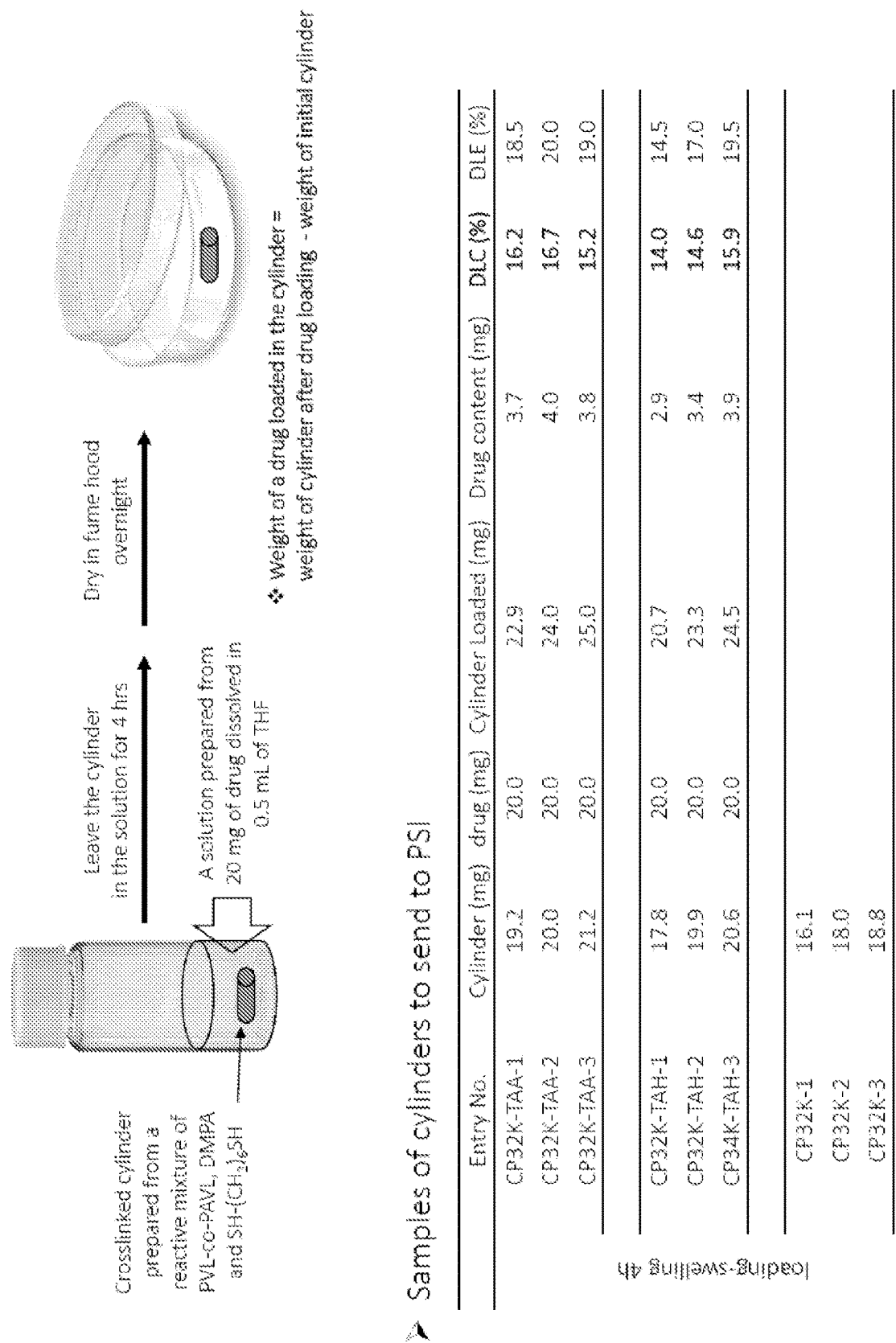
FIG. 43 shows drug loading in crosslinked cylinder formed from SJP7, according to an embodiment.

FIG. 43 shows drug loading in crosslinked cylinder formed from SJP7, according to an embodiment. Preparation of disc shaped depots (6 mm×0.5 mm) formed from a series of pentablock copolymer (SJP1, SJP2, SJP3, SJP4).

Measure swelling of depot in common organic solvents (DMSO, THF, DMSO/THF).

Evaluate solubility of Drug X in solvents to be used for drug loading (Soluble in DMSO as well as a mixture of DMSO/THF and DMSO/EtOH) (Not fully soluble in THF)

Load Drug X using swelling and equilibration methods with mixture of DMSO/THF

Get HPLC assay for Drug X from company and validate in our own hands.

Determine solubility limit of Drug X in PBS +0.5% SDS (in preparation for release study).

Evaluate in vitro release of Drug X from depots (using HPLC to assess drug levels in release samples.

Figure 44:
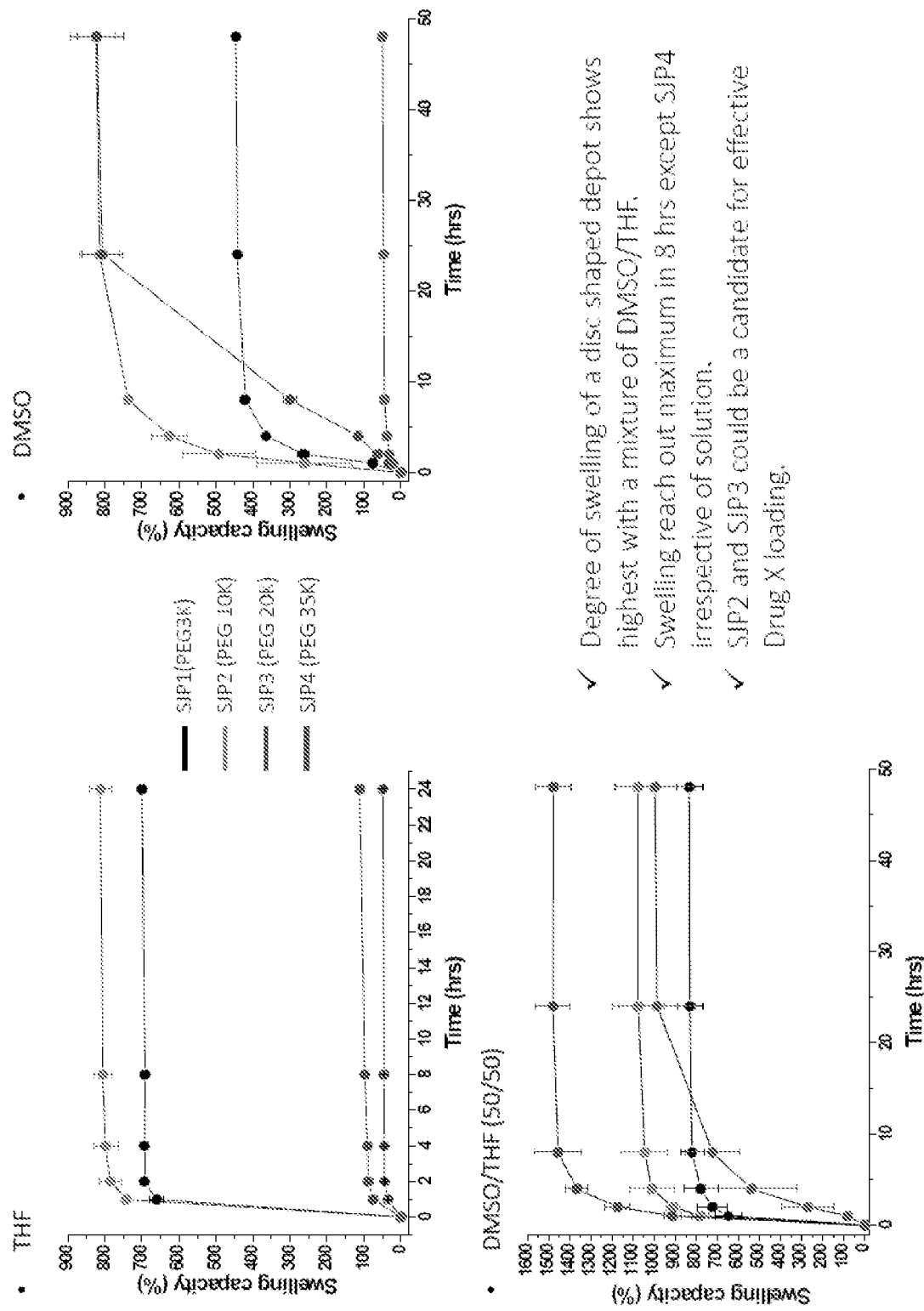
FIG. 44 shows the degree of swelling with disc shaped depots.

FIG. 44 shows the degree of swelling with disc shaped depots.

TABLE 12

Solubility of Drug X.

| | THF | EtOH | DMSO | THF/DMSO (50/50) | EtOH/DMSO (50/50) | DMSO/Water (50/50) | Water |
|---|---|---|---|---|---|---|---|
| Drug X | Soluble, but insoluble species exist (5 mg/200 mL) | Soluble, but insoluble species exist (5 mg/200 mL) | Soluble, and transparent (5 mg/100 mL) | Soluble, and transparent (5 mg/100 mL) | Soluble, and transparent (5 mg/100 mL) | Insoluble (5 mg/200 mL) | Insoluble (5 mg/200 mL) |

Preparation of Drug X solution and loading in a disc shaped depot:
A solution of Drug X (25 mg) dissolved in a mixture of DMSO/THF (50/50) or DMSO (0.5 mL).
Swelling and equilibration approach with the prepared solution for Drug X loading.
Measurement of Drug X loading capacity and release study to be conducted.

Figure 45:
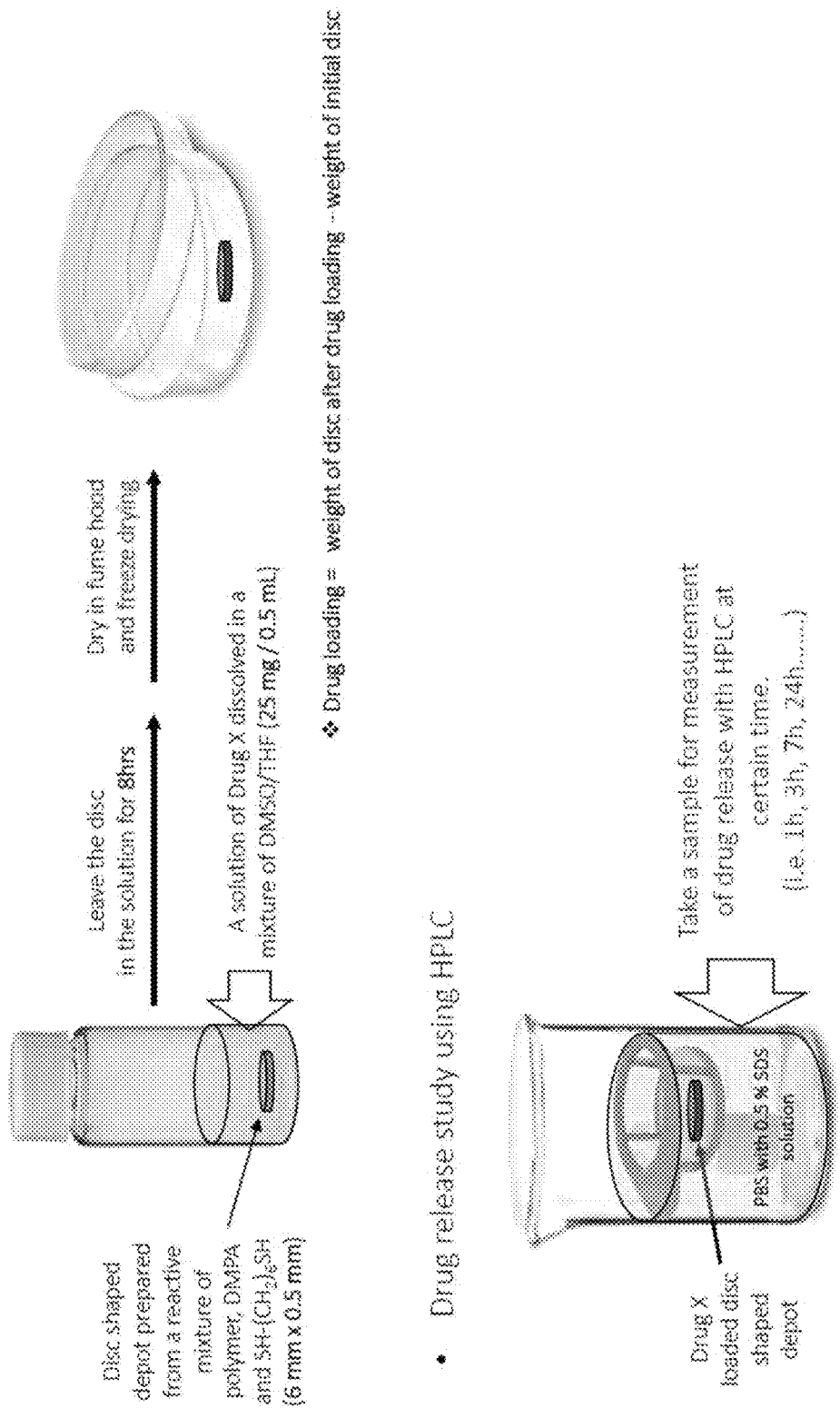
FIG. 45 shows a drug loading and release study to be conducted.

FIG. 45 shows a drug loading and release study to be conducted.

Figure 46:
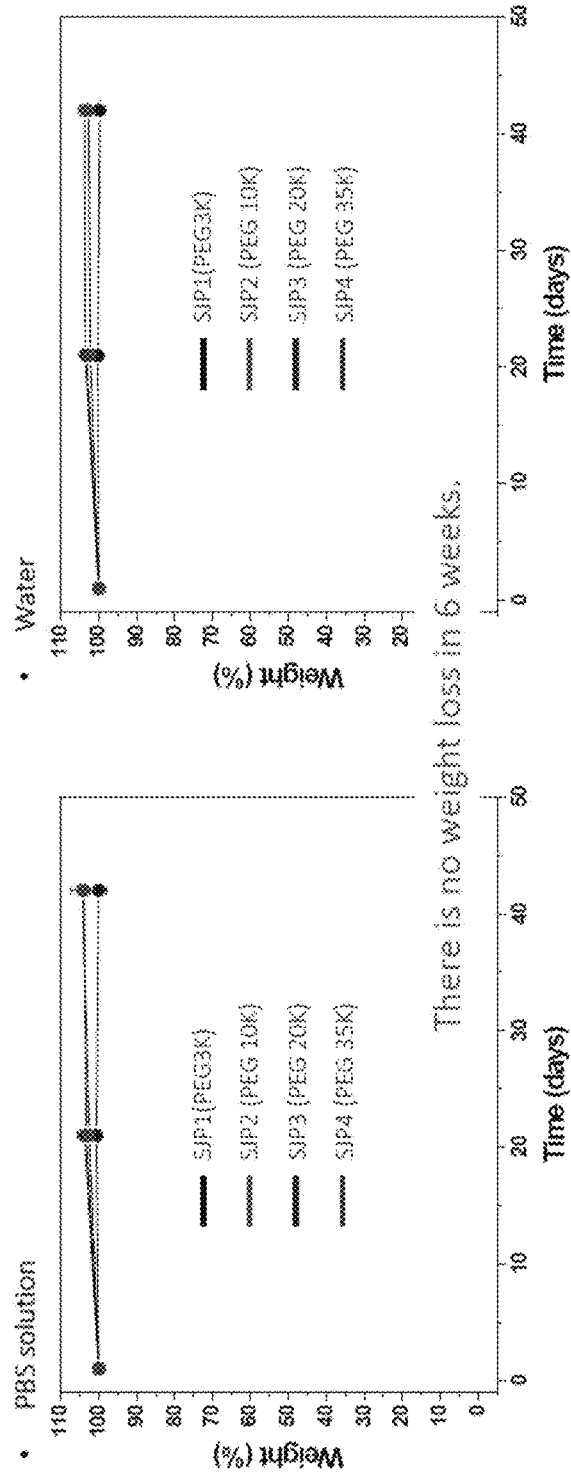
FIG. 46 shows a degradation study of disc shaped depots.

FIG. 46 shows a degradation study of disc shaped depots.

FIG. 47 shows a water adsorption capacity study.

Figure 48:
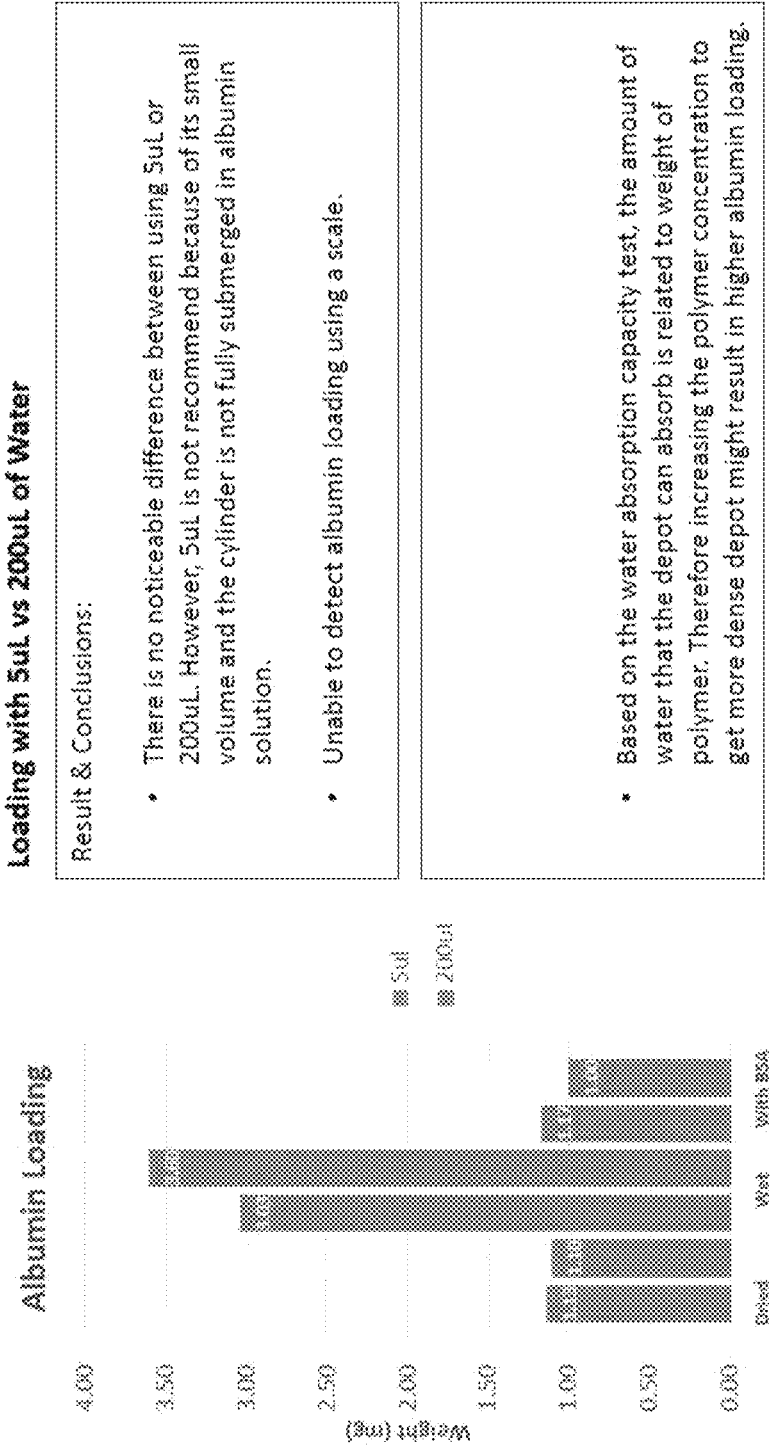
FIG. 48 shows an albumin loading study.

FIG. 48 shows an albumin loading study.

The following are experiments with depots formed from higher Concentration of copolymer Procedure:
SJP2 with concentration listed below was used to make the depot
  300 mg/ml (30% w/v)
  400 mg/ml (40% w/v)
  500 mg/ml (4% w/v)
  All depots were crosslinked for 8 minutes and washed with acetone (24 hr)→water (24 hr)→Lyophilized (24 hr)
  Depot with dimension of 0.5 cm by 0.12 cm were pre-weighted and placed in to 100 uL of 200 mg/ml Albumin solution (5% FITC-albumin) for 4 hrs and 24 hrs. Their swollen weight was recorded.
  The swollen depots were lyophilized overnight and the dried weight was recorded to determined the albumin loading.

Figure 49:
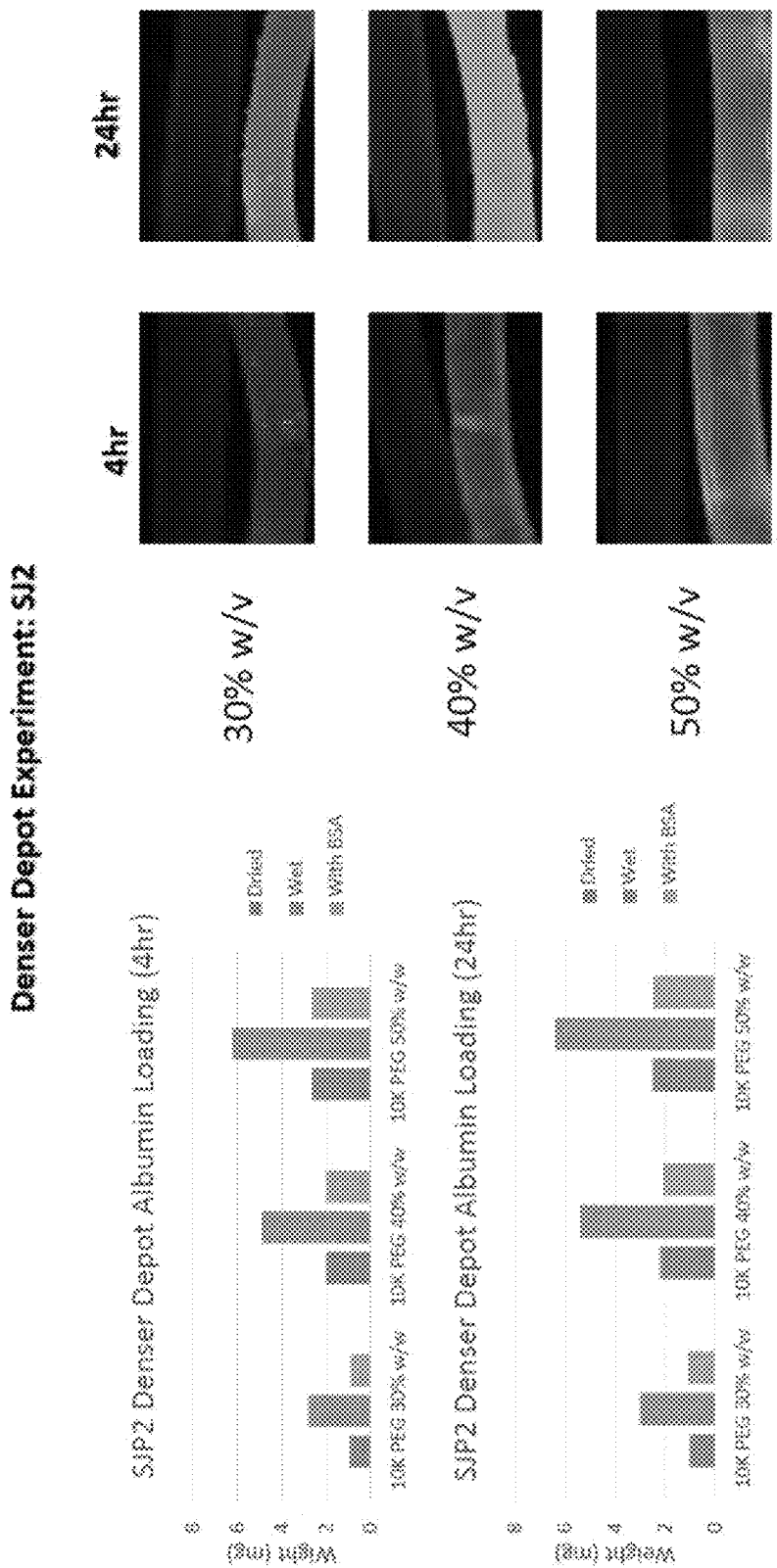
FIG. 49 shows a denser depot experiment: SJ2.

FIG. 49 shows a denser depot experiment: SJ2. The following results and conclusions are developed from the denser depot experiment. As the concentration of polymer increases, the amount of water absorbed increases. Albumin is loading in to the depot and as you increase the polymer concentration you get more loading. Using weight measurements to assess loading is not sensitive enough to get accurate results. Will start to use microBCA assay and fluorescence (measure BSA concentration before and after depot incubation). Increasing the incubation time of the depot in the albumin solution results in higher albumin loading (based on fluorescence intensity measurements). From 35K PEG PVL-PAVL (SJP4), when the depot absorbs more water it absorbs more albumin, therefore try loading into deport formed from SJP4 which has been shown to well 600% in water. Depot formed from SJP4 copolymer of different concentration.

The following describes experiments with depots formed from higher concentrations of SJP4 copolymer.
Procedure:
SJP 4 with concentration listed below was used to make the depot
  300 mg/ml (30% w/v)
  400 mg/ml (40% w/v)
  500 mg/ml (4% w/v)
  All depots were crosslinked for 8 minutes and washed with acetone (24 hr) water (24 hr) Lyophilized (24 hr)
  Depot with dimension of 0.5 cm by 0.12 cm were pre-weighted and placed in to 100 uL of 200 mg/ml Albumin solution (5% FITC-albumin) for 4 hrs and 24 hrs. Their swollen weight was recorded.
  The swollen depots were lyophilized overnight and the dried weight was recorded to determined the albumin loading.

Figure 50:
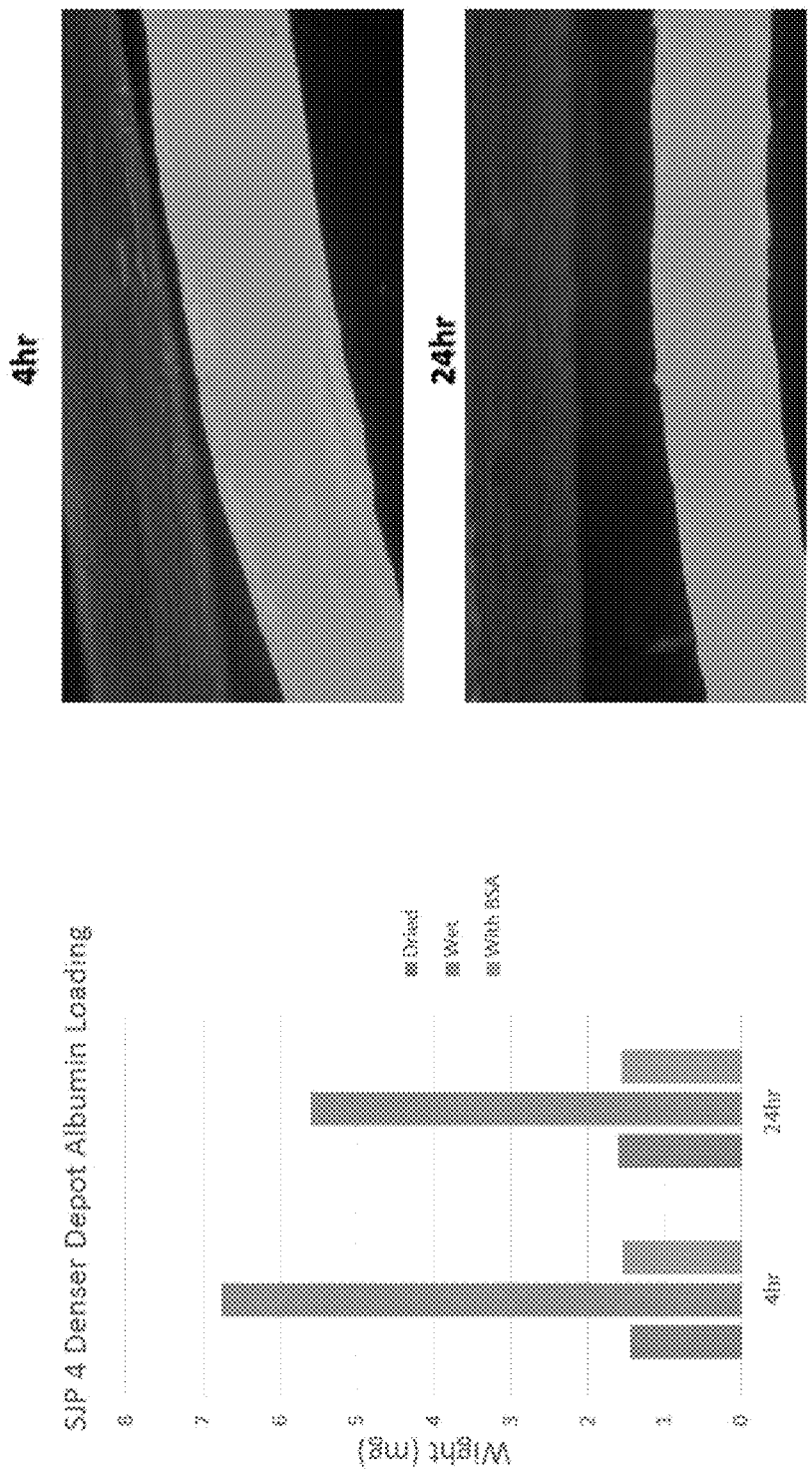
FIG. 50 shows a denser depot experiment: SJP4.
Figure 50:
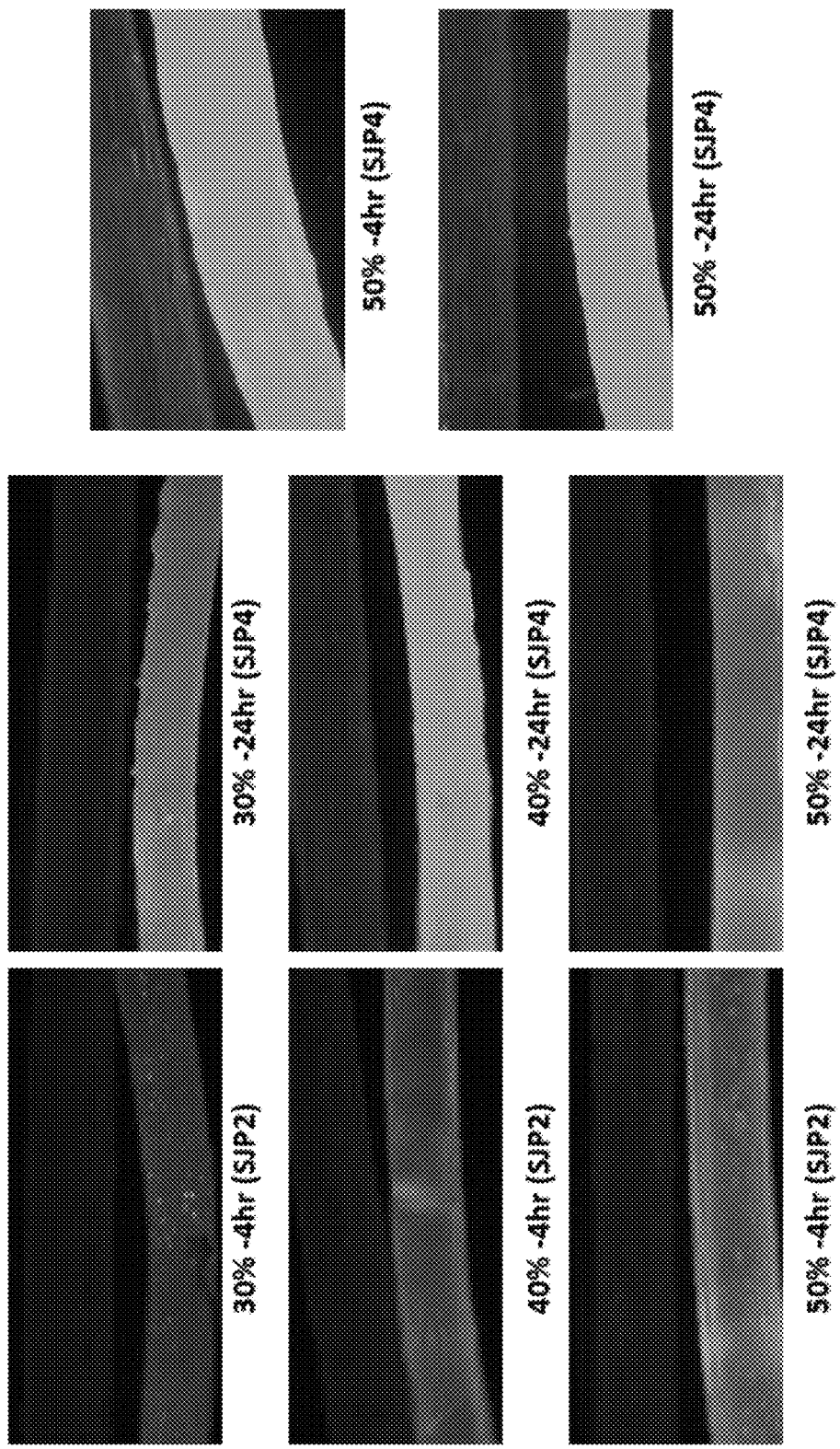

FIG. 50 shows a denser depot experiment: SJP4.
The following results and conclusions were derived from the denser depot experiment. 30% w/v and 40% v of copolymer form gels that are too fragile and cannot be removed from the mold. As predicted SJP4 showed the largest swelling that translated into strongest intensity of the fluorescence, indicating highest albumin loading. Still unable to detect the albumin loading accurately by weight. Cylinder formed from 32K PVL-co-PAVL has been prepared.

Loading Drug X into a depot: Disc shaped depot to characterize the drug (Drug X) loading capacity and the release rate. Drug will be loaded via swelling & evaporation methods. An appropriate size of a depot determined based on results of disc experiment. Release for at least 1 month, ideally 2 months. Release rate is 1-3 mg per day. Target amount of drug is 180 mg (for 2 months release), ideally at least 200 mg of drug.

TABLE 13

Library of Synthesized Copolymer Materials

| Entry. No | Polymer structure | $^1$H-NMR | | PAVL (%) | GPC | |
| --- | --- | --- | --- | --- | --- | --- |
| | | $M_n$ | DP (PEG/ PVL/PAVL) | | $M_n$ | PDI |
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP4 | PAVL-b-PVL-b-35KPEG-b-PVL-b-PAVL | 47.0K | 812/86/17 | 6 | 50.4K | 1.06 |
| SJP5 | PAVL-b-3KPEG-b-PAVL | 6.2K | 85/0/18 | 40 | 7.7K | 1.07 |
| SJP6 | (PAVL-co-PVL)-3KPEG-(PAVL-co-PVL) | 8.5K | 85/36/8 | 15 | 7.4k | 1.39 |
| SJP7 | PVL-co-PAVL | 32K | 0/235/42 | 20 | 24K | 1.37 |

Figure 51:
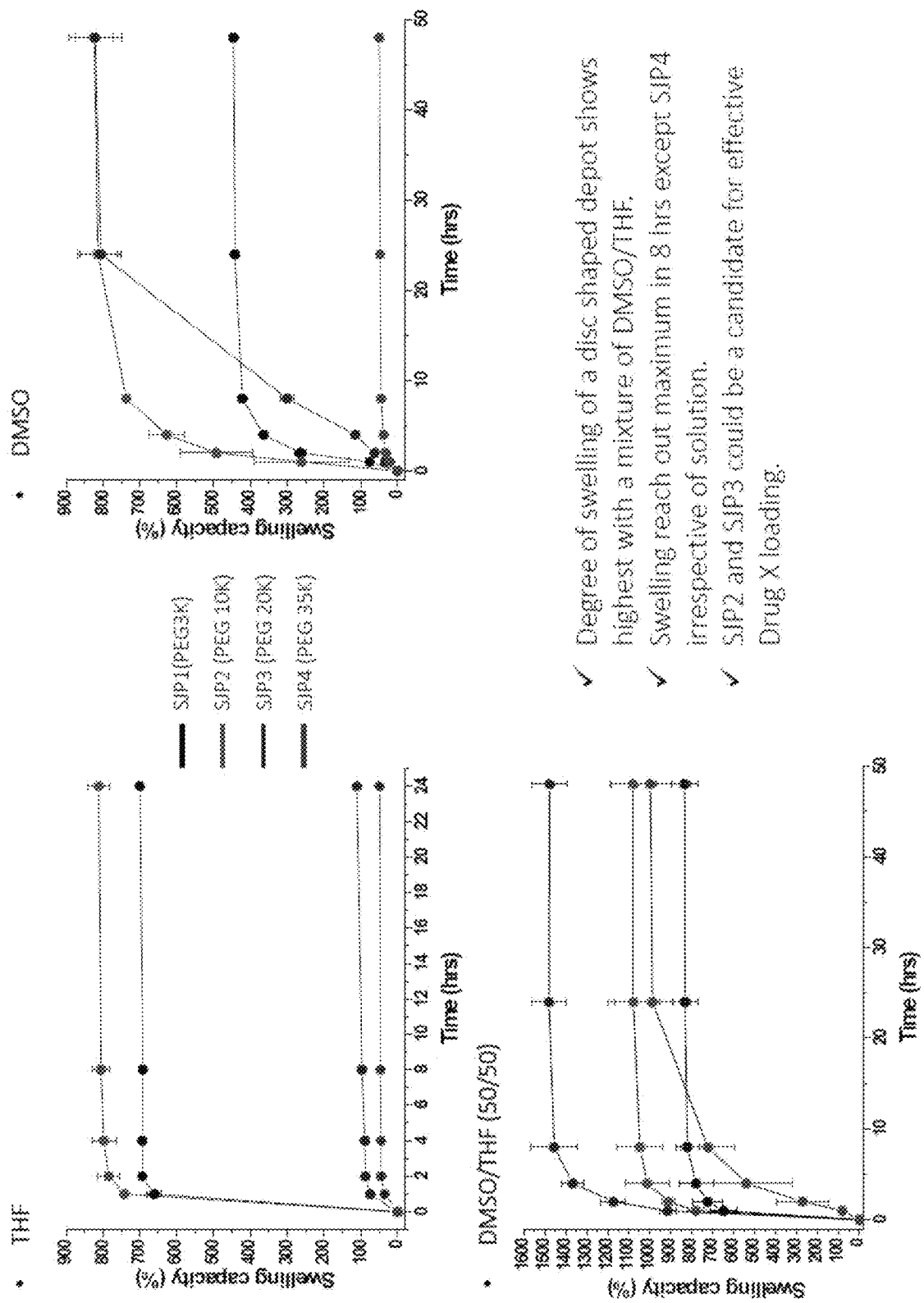
FIG. 51 shows a degree of swelling with disc shaped depots.

FIG. 51 shows a degree of swelling with disc shaped depots.

TABLE 14

Solubility of Drug X

| | THF | EtOH | DMSO | THF/ DMSO (50/50) | EtOH/ DMSO (50/50) | DMSO/ Water (50/50) | Water |
| --- | --- | --- | --- | --- | --- | --- | --- |
| Drug X | Soluble, but insoluble | Soluble, but insoluble | Soluble, and | Soluble, and | Soluble, and | Insoluble (5 mg/ | Insoluble (5 mg/ |

TABLE 14-continued

Solubility of Drug X

| | | | THF/ | EtOH/ | DMSO/ | |
| | | | DMSO | DMSO | Water | |
| THF | EtOH | DMSO | (50/50) | (50/50) | (50/50) | Water |
|---|---|---|---|---|---|---|
| species exist (5 mg/ 200 mL) | species exist (5 mg/ 200 mL) | transparent (5 mg/ 100 mL) | transparent (5 mg/ 100 mL) | transparent (5 mg/ 100 mL) | 200 mL) | 200 mL) |

Preparation of Drug X solution and loading in a disc shaped depot

A solution of Drug X (25 mg) dissolved in a mixture of DMSO/THF (50/50) or DMSO (0.5 mL)

Swelling and equilibration approach with the prepared solution for Drug X loading Measurement of Drug X loading capacity and release study to be conducted FIG. 52 shows drug loading in disc shaped depot formed from SJP1, SJP2, and SJP3.

TABLE 15

Drug loading in disc shaped depot formed from SJP1, SJP2, SJP3, and SJP7

| Entry. No | Polymer structure | $M_n$ | DP (PEG/ PVL/PAVL) | PAVL (%) | GPC $M_n$ | PDI |
|---|---|---|---|---|---|---|
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP4 | PAVL-b-PVL-b-35KPEG-b-PVL-b-PAVL | 47.0K | 812/86/17 | 6 | 50.4K | 1.06 |
| SJP5 | PAVL-b-3KPEG-b-PAVL | 6.2K | 85/0/18 | 40 | 7.7K | 1.07 |
| SJP6 | (PAVL-co-PVL)-3KPEG-(PAVL-co-PVL) | 8.5K | 85/36/8 | 15 | 7.4k | 1.39 |
| SJP7 | PVL-co-PAVL | 32K | 0/235/45 | 20 | 24K | 1.48 |

In some embodiments, the crosslinker can be SH—$(CH_2)_6$—SH. In some embodiments, the crosslinker can be SH—$(OCH_2)_3$-SH. In some embodiments, the crosslinker can be 4- and 8-arm star PEG-SH ($M_n$=10K).

TABLE 16

Solubility of Drug X

| | THF | EtOH | DMSO | DCM | THF/ DMSO (50/50) | EtOH/ DMSO (50/50) | DMSO/ Water (50/50) | Water |
|---|---|---|---|---|---|---|---|---|
| Drug X fumarate | Soluble, but insoluble species exist (5 mg/ 200 μL) | Soluble, but insoluble species exist (5 mg/200 μL) | Soluble, and transparent (5 mg/ 100 μL) | N/A | Soluble, and transparent (5 mg/ 100 μL) | Soluble, and transparent (5 mg/ 100 μL) | Insoluble (5 mg/ 200 μL) | Insoluble (5 mg/ 200 μL) |
| Drug X freebase | Soluble, and transparent (5 mg/ 100 μL) | Soluble, and transparent (5 mg/ 100 μL) | Soluble, and transparent (5 mg/ 100 μL) | Soluble, and transparent (5 mg/ 100 μL) | Soluble, and transparent (5 mg/ 100 μL) | | | |

Figure 53:
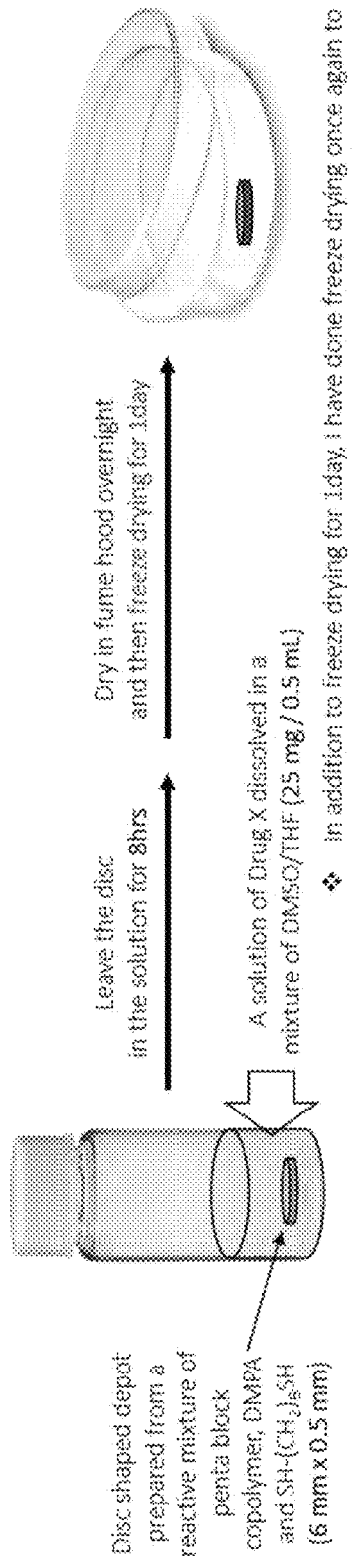
FIG. 53 shows a drug loading in disc shaped depot formed from SJP1, SJP2, SJP3, and SJP7.

FIG. 53 shows a drug loading in disc shaped depot formed from SJP1, SJP2, SJP3, and SJP7.

FIG. 54 shows a drug release from disc shaped depot formed from SJP1, SJP2, SJP3 and SJP7.

TABLE 17

Sustainable Drug X Release—Copolymer Materials

| Entry. No | Polymer structure | $^1$H-NMR | | PAVL (%) | GPC | |
|---|---|---|---|---|---|---|
| | | $M_n$ | DP (PEG/ PVL/PAVL) | | $M_n$ | PDI |
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP7 | PVL-co-PAVL | 32K | 0/235/45 | 20 | 24K | 1.48 |

In some embodiments, the crosslinker can be SH—(CH$_2$)$_6$—SH. In some embodiments, the crosslinker can be SH—(OCH$_2$)$_3$-SH. In some embodiments, the crosslinker can be 4- and 8-arm star PEG-SH ($M_n$=10K). Denser crosslinking density and more complex network could prevent fast Drug X release from the depot.

Figure 55:
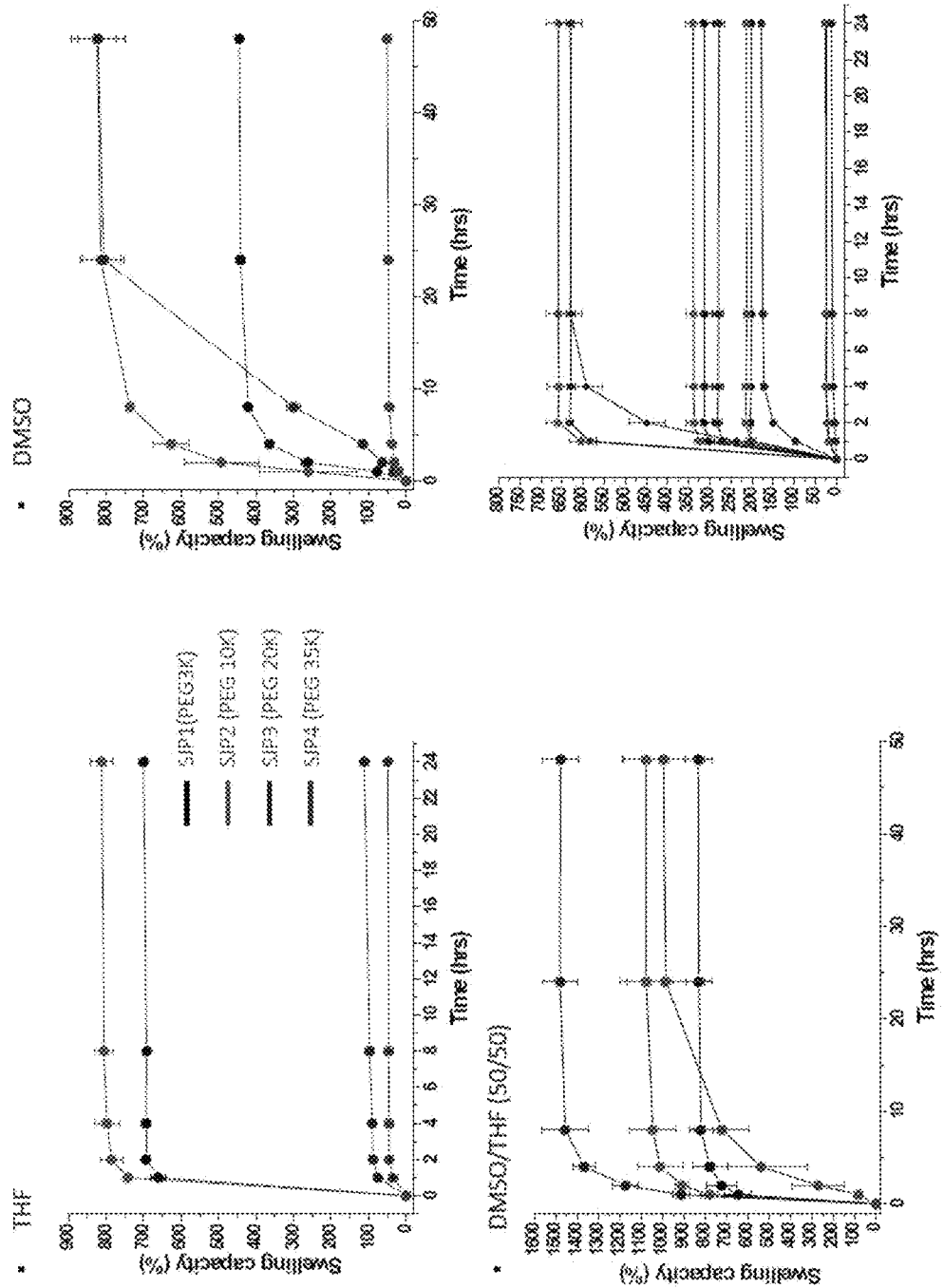
FIG. 55 shows a degree of swelling with disc shaped depots.

FIG. 55 shows a degree of swelling with disc shaped depots.

FIG. 57 shows Drug X fumarate release from the depot formed from SJP1, SJP2, SJP3 and SJP7.

Figure 58:
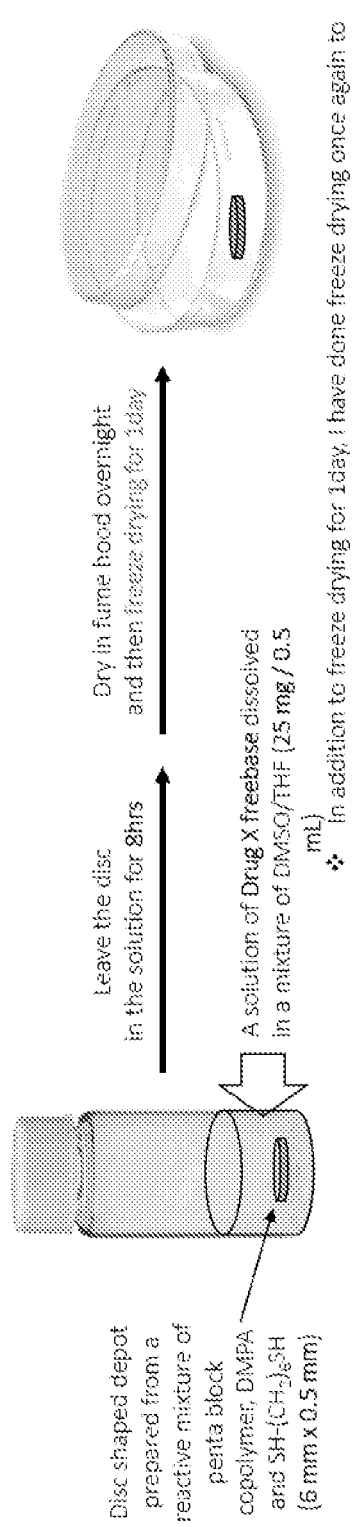
FIG. 58 shows Drug X freebase loading in disc shaped depot formed from SJP1, SJP2, SJP3 and SJP7.

FIG. 58 shows Drug X freebase loading in disc shaped depot formed from SJP1, SJP2, SJP3 and SJP7.

Figure 59:
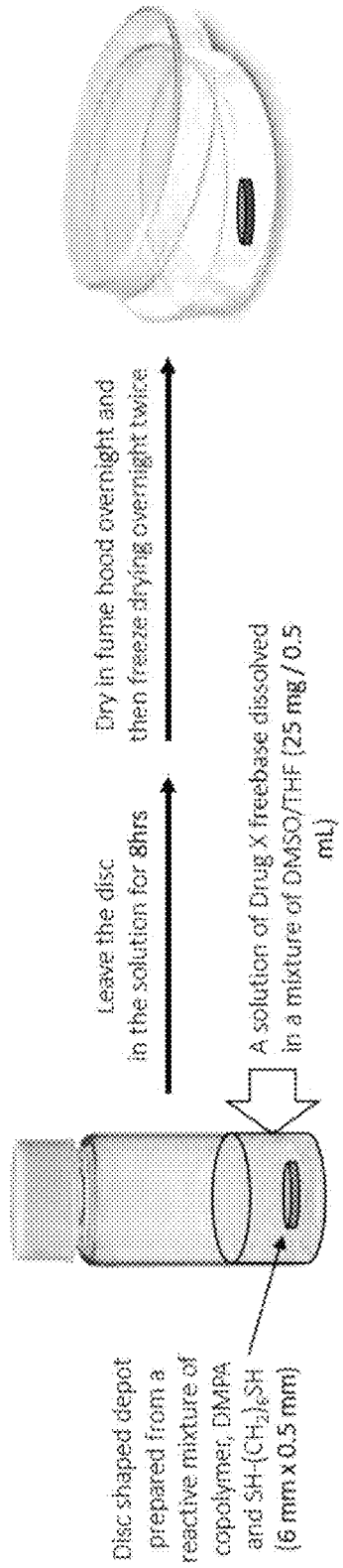
FIG. 59 shows Drug X freebase loading in disc shaped depot formed from SJP1, SJP2, SJP3 and SJP7.

FIG. 59 shows Drug X freebase loading in disc shaped depot formed from SJP1, SJP2, SJP3 and SJP7.

FIG. 60 shows Drug X freebase release from the depot formed from SJP1, SJP2, SJP3 and SJP7.

TABLE 18

Drug X Fumarate loaded disc shaped depot

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP1-Drug X-1 | 21.50 | 25.0 | 25.14 | 3.64 | 14.48 | 14.56 | 1/0.17 |
| SJP1-Drug X-2 | 20.60 | 25.0 | 24.59 | 3.99 | 16.23 | 15.96 | 1/0.19 |
| SJP2-Drug X-1 | 24.40 | 25.0 | 32.66 | 8.26 | 25.29 | 33.04 | 1/0.34 |
| SJP2-Drug X-2 | 23.60 | 25.0 | 31.75 | 8.15 | 25.67 | 32.60 | 1/0.35 |
| SJP3-Drug X-1 | 22.10 | 25.0 | 34.11 | 12.01 | 35.21 | 48.04 | 1/0.54 |
| SJP3-Drug X-2 | 20.60 | 25.0 | 31.28 | 10.68 | 34.14 | 42.72 | 1/0.52 |
| SJP7-Drug X-1 | 25.10 | 25.0 | 29.89 | 4.79 | 16.03 | 19.16 | 1/0.19 |
| SJP7-Drug X-2 | 24.90 | 25.0 | 29.45 | 4.55 | 15.45 | 18.20 | 1/0.18 |

Drug X fumarate release with 70/30 (v/v) of 0.1% trifluoroacetic acid and acetonitrile solution. The extract residue of Drug X fumarate from the depot with THF twice.

Figure 61:
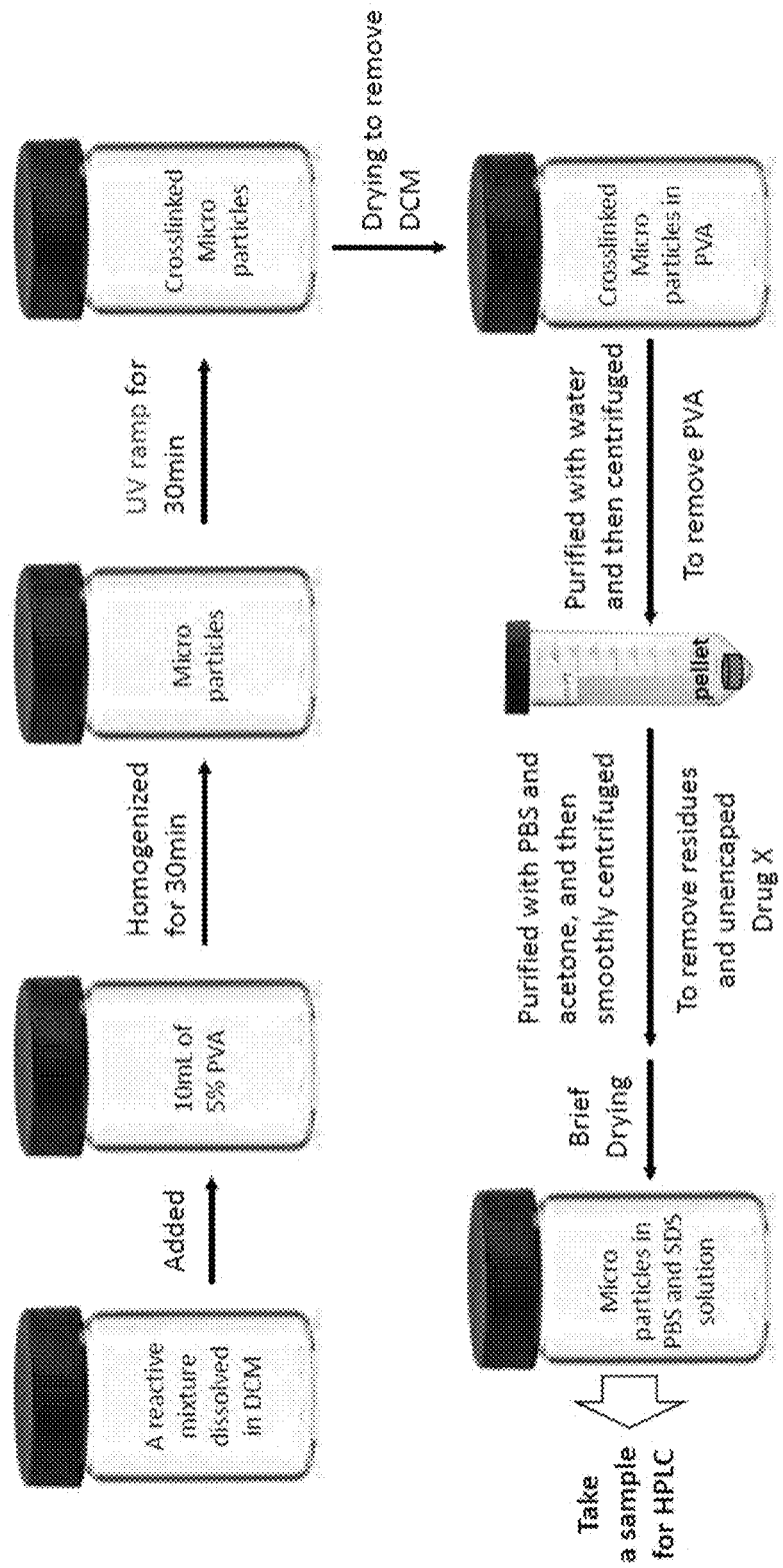
FIG. 61 shows a plan of preloading microparticles via an emulsion method, according to an embodiment.

FIG. 61 shows a plan of preloading microparticles via an emulsion method, according to an embodiment.

Figure 62:
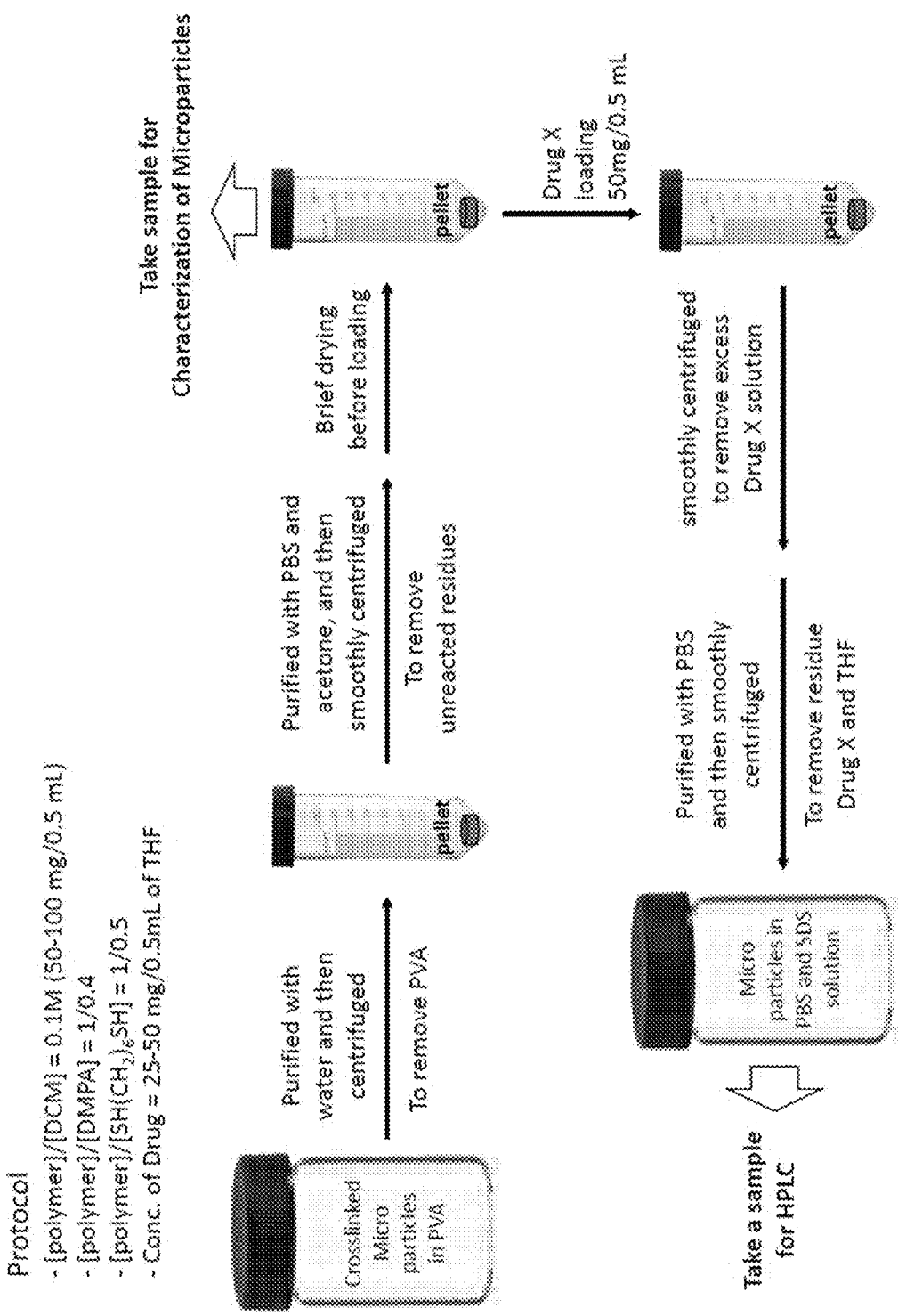
FIG. 62 shows a plan of postloading microparticles via an emulsion method, according to an embodiment.

FIG. 62 shows a plan of postloading microparticles via an emulsion method, according to an embodiment.

Figure 63:
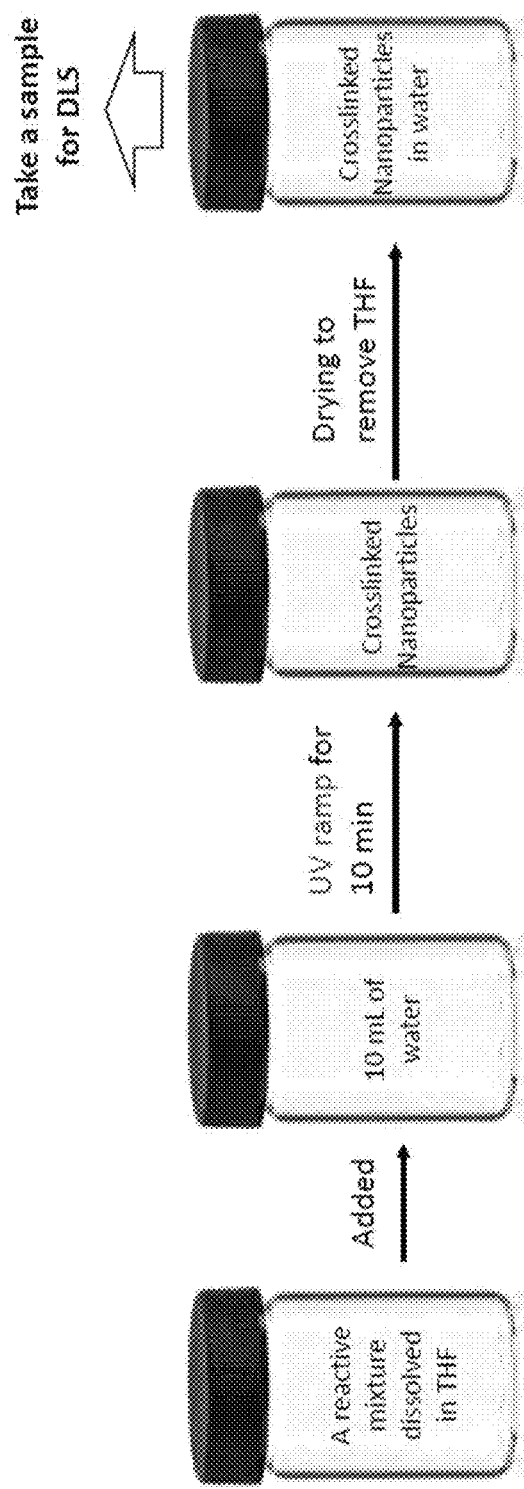
FIG. 63 shows a plan for preparation of nanoparticles via solvent evaporation method, according to an embodiment.

FIG. 63 shows a plan for preparation of nanoparticles via solvent evaporation method, according to an embodiment.

Figure 64:
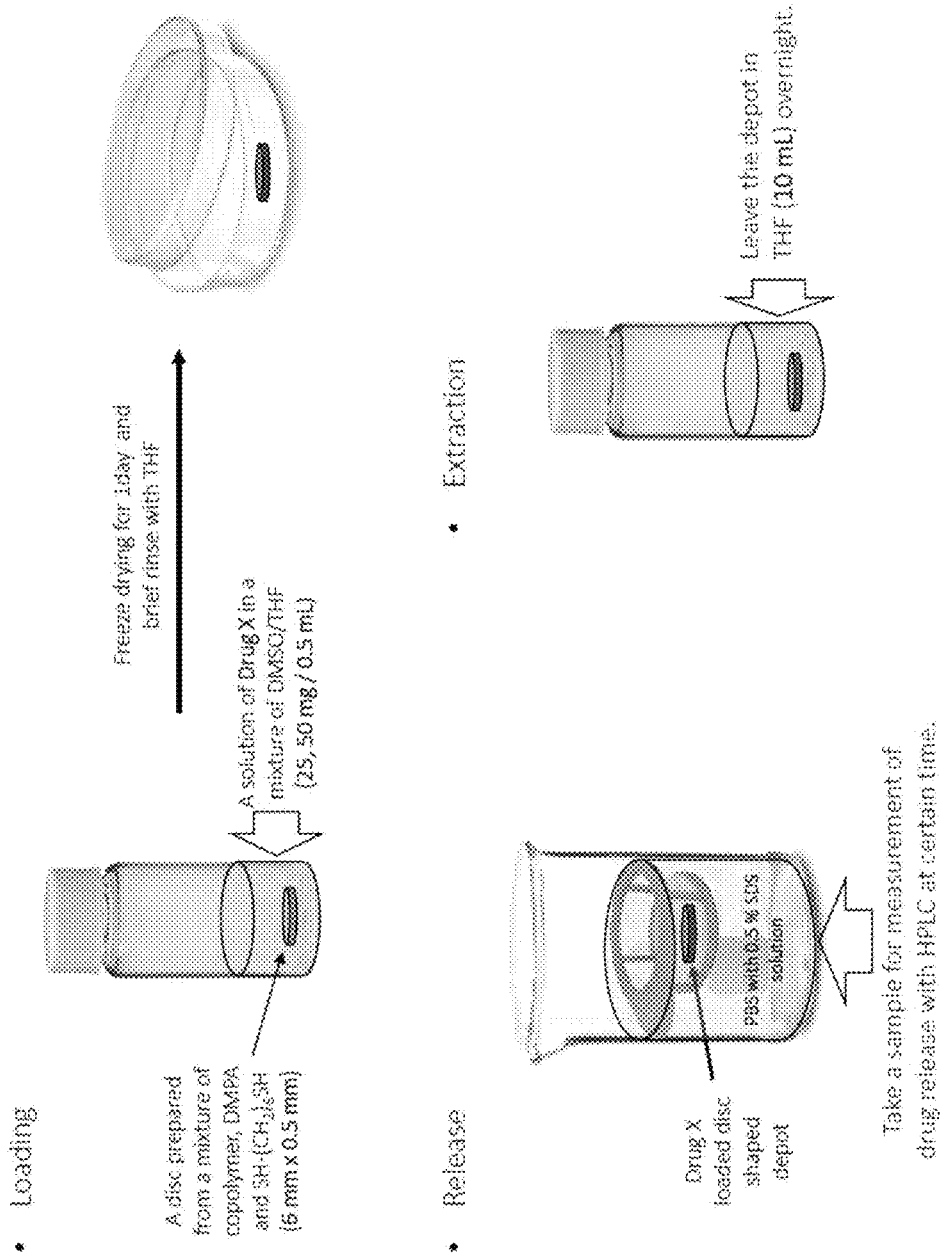
FIG. 64 shows Drug X loading and release of a depot formed from SJP1, SJP2, SJP3 and SJP7.

FIG. 64 shows Drug X loading and release of a depot formed from SJP1, SJP2, SJP3 and SJP7.

Figure 65:
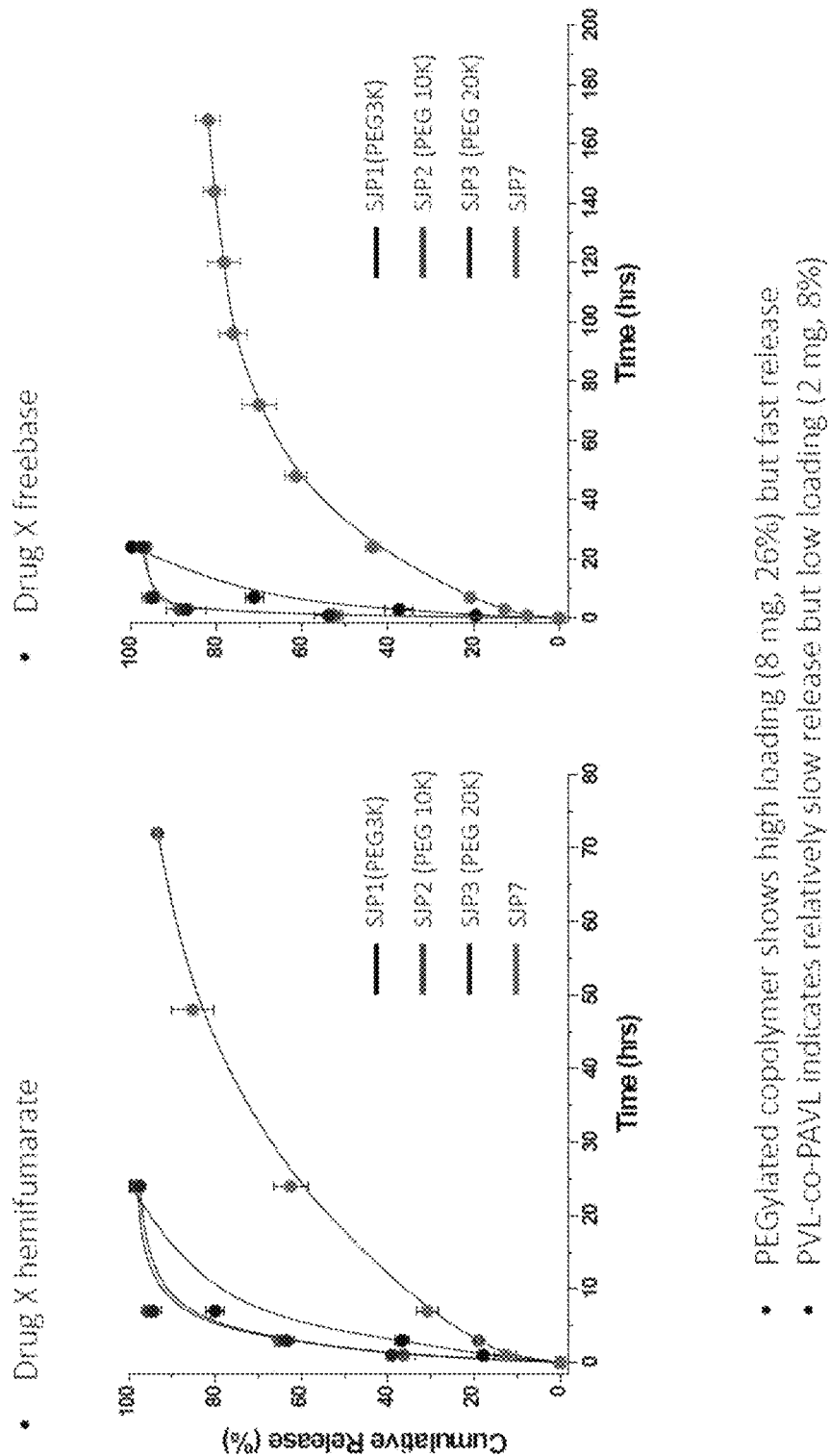
FIG. 65 shows Drug X release of the depot formed from SJP1, SJP2, SJP3 and SJP7.

FIG. 65 shows Drug X release of the depot formed from SJP1, SJP2, SJP3 and SJP7.

TABLE 19

Drug X freebase loaded disc shaped depot

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP1-Drug X-1 | 20.40 | 25.0 | 22.68 | 2.28 | 10.05 | 9.12 | 1/0.11 |
| SJP1-Drug X-2 | 18.68 | 25.0 | 20.07 | 1.39 | 6.93 | 5.56 | 1/0.07 |
| SJP2-Drug X-1 | 20.76 | 25.0 | 25.85 | 5.09 | 19.69 | 20.36 | 1/0.25 |
| SJP2-Drug X-2 | 19.80 | 25.0 | 24.79 | 4.99 | 20.13 | 19.96 | 1/0.25 |
| SJP3-Drug X-1 | 21.29 | 25.0 | 30.23 | 8.94 | 29.57 | 35.76 | 1/0.42 |
| SJP3-Drug X-2 | 19.45 | 25.0 | 27.44 | 7.99 | 29.12 | 31.96 | 1/0.41 |
| SJP7-Drug X-1 | 25.66 | 25.0 | 30.53 | 4.87 | 15.95 | 19.48 | 1/0.19 |
| SJP7-Drug X-2 | 26.96 | 25.0 | 31.08 | 4.12 | 13.26 | 16.48 | 1/0.15 |

Figure 66:
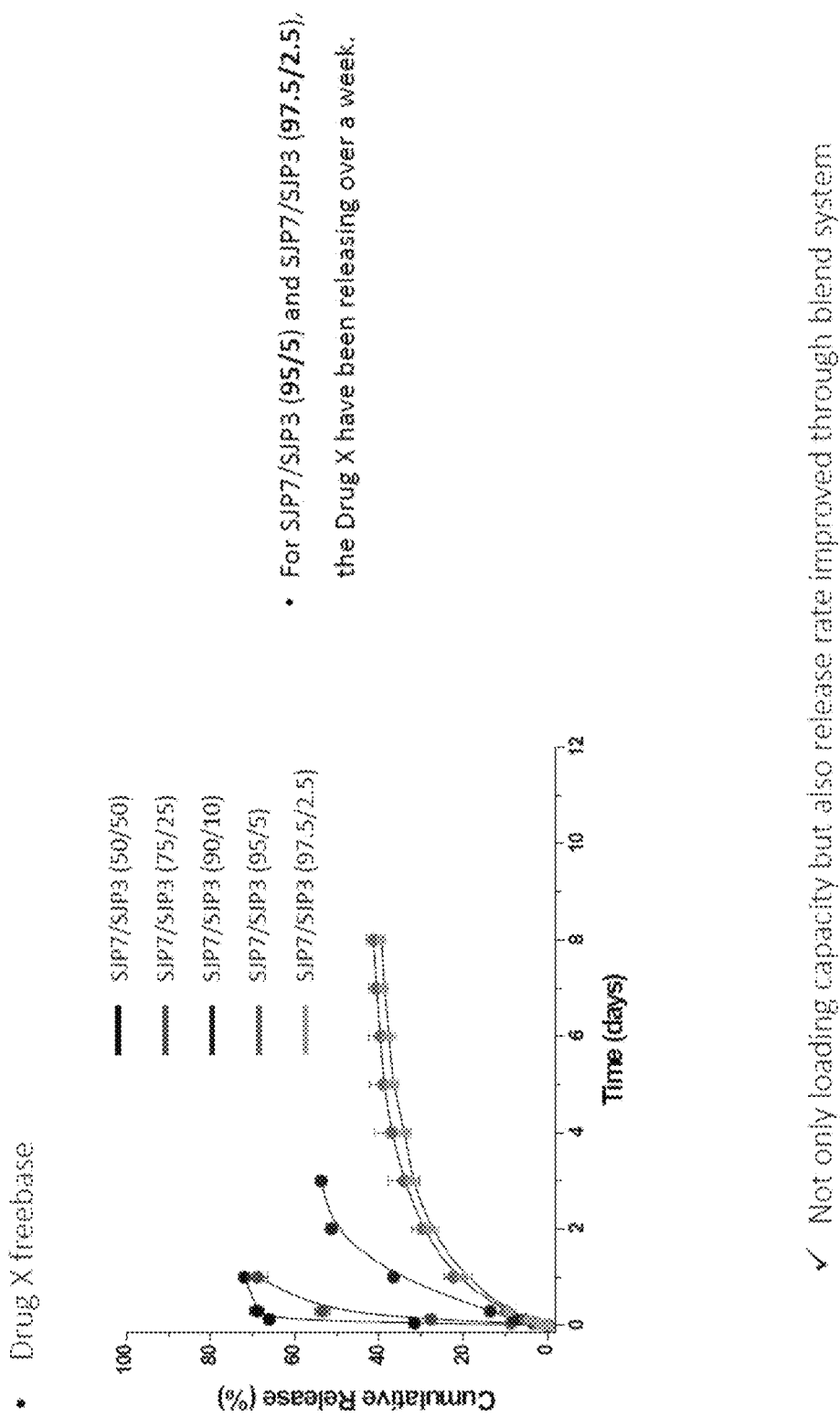
FIG. 66 shows Drug X release of the depot formed from a blend.

FIG. 66 shows Drug X release of the depot formed from a blend.

Figure 67:
FIG. 67 shows high loading of Drug X.

FIG. 67 shows high loading of Drug X.

Figure 68:
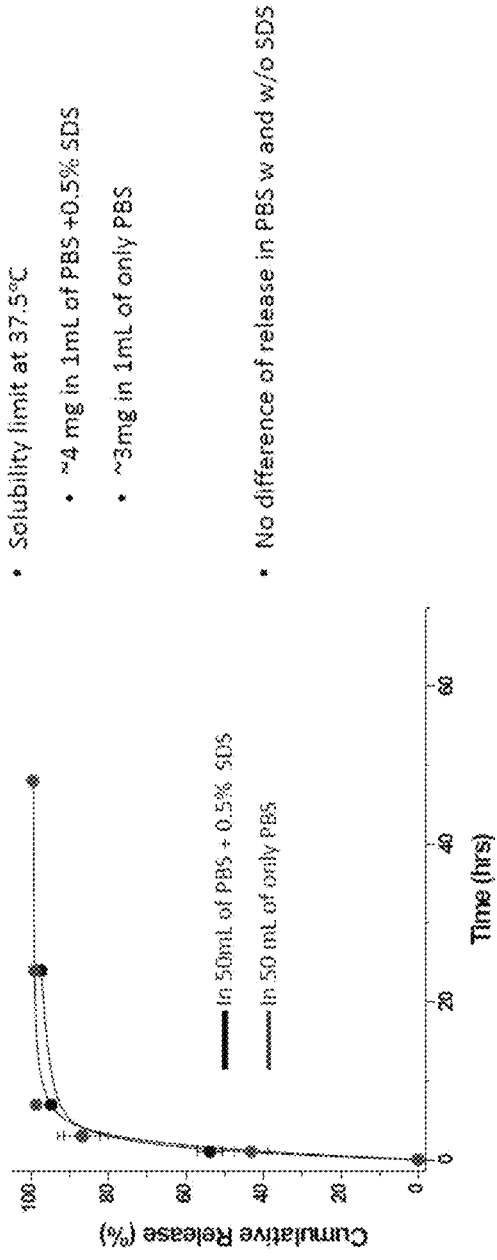
FIG. 68 shows Drug X release in PBS with and without SDS.

FIG. 68 shows Drug X release in PBS with and without SDS.

Figure 69:
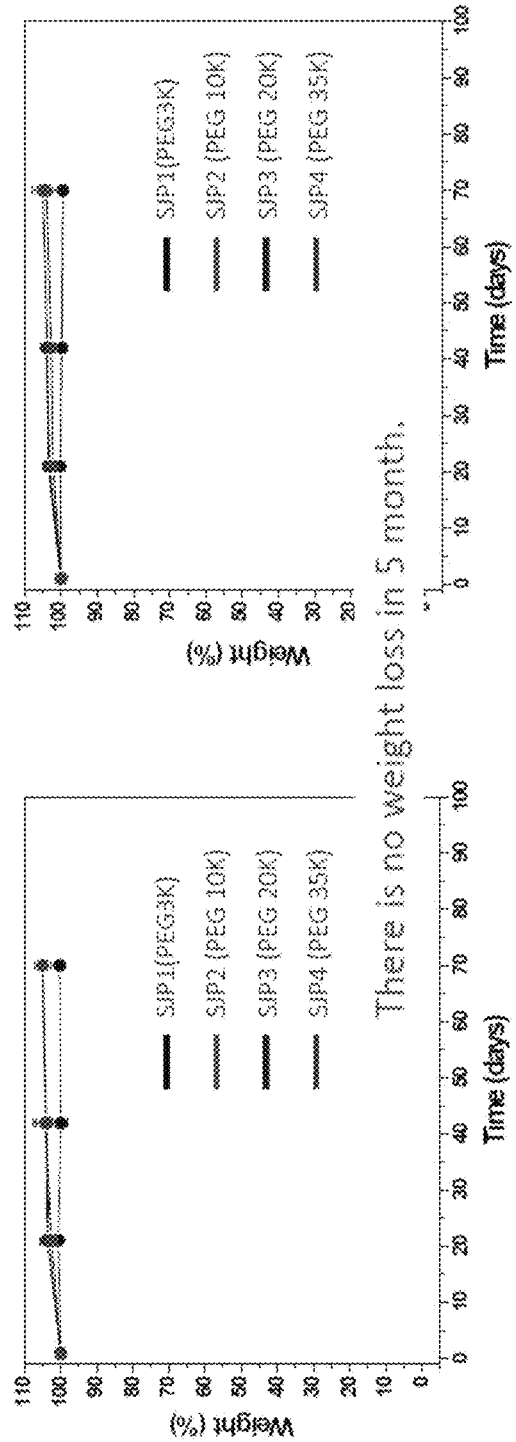
FIG. 69 shows a degradation study of disc shaped depots.

FIG. 69 shows a degradation study of disc shaped depots.

Priorities and Next steps:

Drug X freebase
    Measure the Drug X release of blend system
    Look at release rate with high loading Degradation study
    Depot formed from hexanedithiol and cleavable linker Microparticle
    Preloading through emulsion method
    Postloading through swelling and evaporation method

TABLE 20

Solubility of Drug X fubarate and Drug X Freebase

| | Solubility | | | | | | | |
|---|---|---|---|---|---|---|---|---|
| | THF | EtOH | DMSO | DCM | THF/DMSO (50/50) | EtOH/DMSO (50/50) | DMSO/Water (50/50) | Water |
| Drug X hemi Fumarate | Soluble, but insoluble species exist (5 mg/200 µL) | Soluble, but insoluble species exist (5 mg/200 µL) | Soluble, and transparent (5 mg/100 µL) | N/A | Soluble, and transparent (5 mg/100 µL) | Soluble, and transparent (5 mg/100 µL) | Insoluble (5 mg/200" µL) | Insoluble (5 mg/200" µL) |

TABLE 20-continued

Solubility of Drug X fubarate and Drug X Freebase

| | THF | EtOH | DMSO | DCM | THF/DMSO (50/50) | EtOH/DMSO (50/50) | DMSO/Water (50/50) | Water |
|---|---|---|---|---|---|---|---|---|
| Drug X freebase | Soluble, and transparent (5 mg/100 µL) | Soluble, and transparent (5 mg/100 µL) | Soluble, and transparent (5 mg/100 µL) | Soluble, and transparent (5 mg/100 µL) | Soluble, and transparent (5 mg/100 µL) | N/A | N/A | N/A |

Preparation of Drug X solution and loading in a disc shaped depot:
A solution of Drug X (25 mg) dissolved in a mixture of DMSO/THF (50/50) (0.5 mL)
Swelling and equilibration approach with the prepared solution for Drug X loading
Measurement of Drug X loading capacity and release study to be conducted

TABLE 21

Sustainable Drug X release from blend depot systems

| | | $^1$H-NMR | | GPC | |
|---|---|---|---|---|---|
| Entry. No | Polymer structure | $M_n$ | DP (PEG/PVL/PAVL) | PAVL (%) | $M_n$ | PDI |
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/26 | 10 | 35.7K | 1.14 |
| SJP7 | PVL-co-PAVL | 32K | 0/235/42 | 20 | 24K | 1.48 |

In some embodiments, the crosslinker can be SH—(CH$_2$)$_6$—SH

TABLE 22

Loading of Drug X in polymer blend systems with HDT linker: Blend system consisting of PVL-co-PAVL (SJP7) and PEGylated copolymer (SJP3) with HDT

| | Disc (mg) | Drug (mg) | Disc Loaded (mg) | Drug content (mg) | DLC (%) | DLE (%) | Depot/Drug (w/w) |
|---|---|---|---|---|---|---|---|
| SJP7/SJP3 (50/50)-1 | 25.08 | 25.00 | 31.99 | 6.91 | 21.60 | 27.64 | 1/0.28 |
| SJP7/SJP3 (50/50)-2 | 25.68 | 25.00 | 32.23 | 6.55 | 20.32 | 26.20 | 1/0.26 |
| SJP7/SJP3 (75/25)-1 | 28.05 | 25.00 | 34.47 | 6.42 | 18.62 | 26.68 | 1/0.23 |
| SJP7/SJP3 (75/25)-2 | 27.44 | 25.00 | 33.70 | 6.26 | 18.58 | 25.04 | 1/0.23 |
| SJP7/SJP3 (90/10)-1 | 27.87 | 25.00 | 34.31 | 6.44 | 18.77 | 35.76 | 1/0.23 |
| SJP7/SJP3 (90/10)-2 | 27.24 | 25.00 | 33.53 | 6.29 | 18.76 | 25.16 | 1/0.23 |
| SJP7/SJP3 (95/5)-1 | 28.60 | 25.00 | 35.93 | 7.33 | 20.40 | 29.32 | 1/0.26 |
| SJP7/SJP3 (95/5)-2 | 28.30 | 25.00 | 35.40 | 7.10 | 20.06 | 28.40 | 1/0.25 |
| SJP7/SJP3 (97.5/2.5)-1 | 27.50 | 25.00 | 33.82 | 6.32 | 18.69 | 25.28 | 1/0.23 |
| SJP7/SJP3 (97.5/2.5)-2 | 27.77 | 25.00 | 34.68 | 6.91 | 19.93 | 27.64 | 1/0.25 |
| SJP7/SJP3 (99/1)-1 | 27.43 | 25.00 | 34.29 | 6.89 | 20.01 | 27.44 | 1/0.25 |
| SJP7/SJP3 (99/1)-2 | 28.13 | 25.00 | 34.90 | 6.77 | 19.40 | 28.08 | 1/0.24 |

Figure 70:
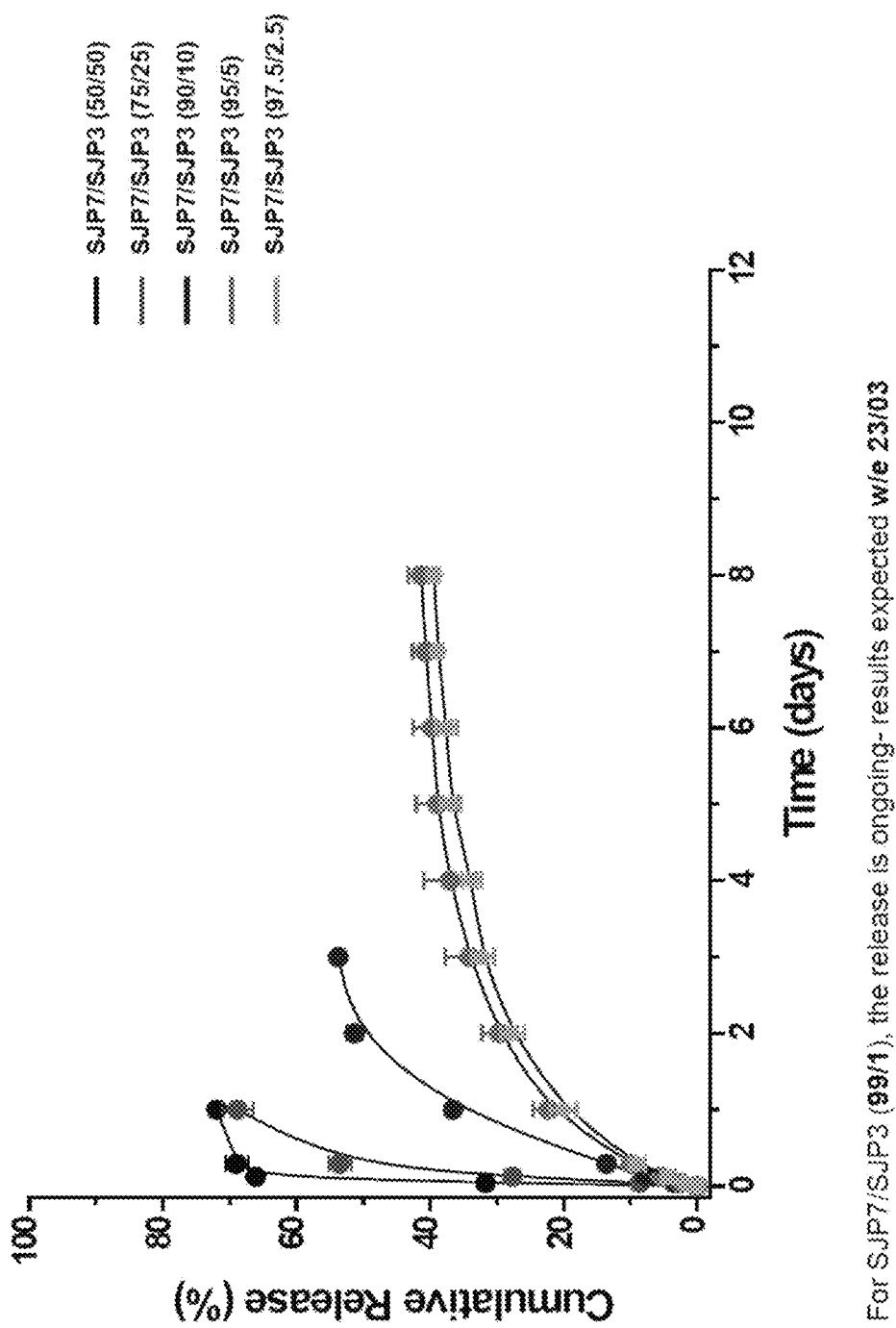
FIG. 70 shows Drug X freebase release of the depot formed from the blend.

FIG. 70 shows Drug X freebase release of the depot formed from the blend.

Figure 71:
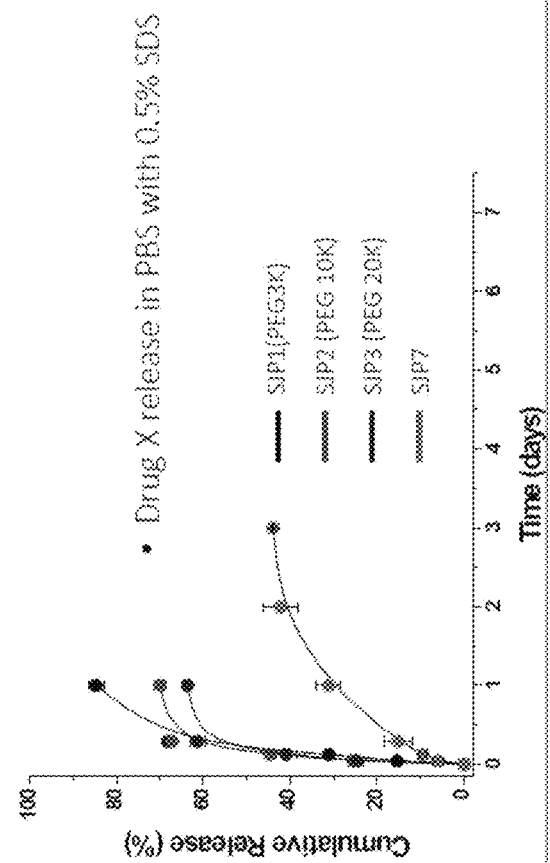
FIG. 71 shows loading and release data of Drug X hemifumarate.

FIG. 71 shows loading and release data of Drug X hemifumarate.

Figure 72:
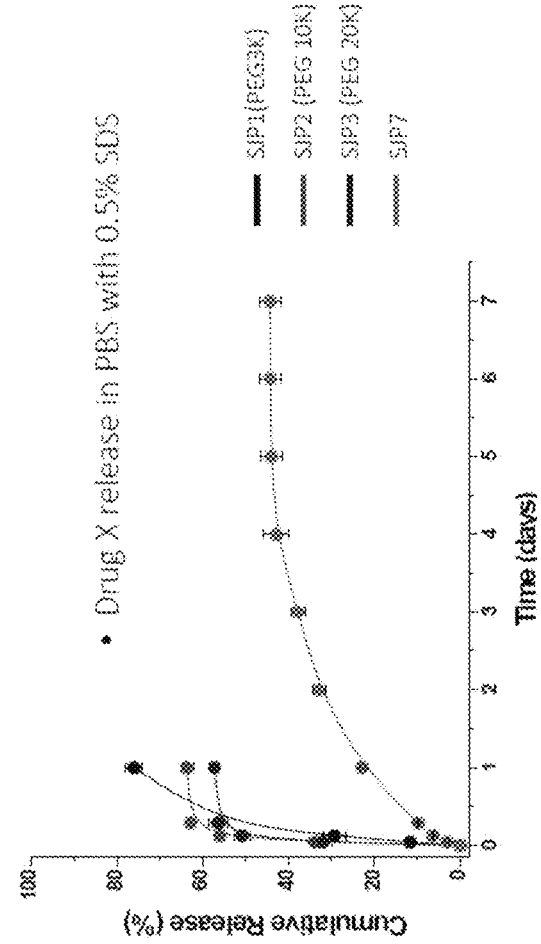
FIG. 72 shows loading and release data of Drug X freebase.

FIG. 72 shows loading and release data of Drug X freebase.

Figure 73:
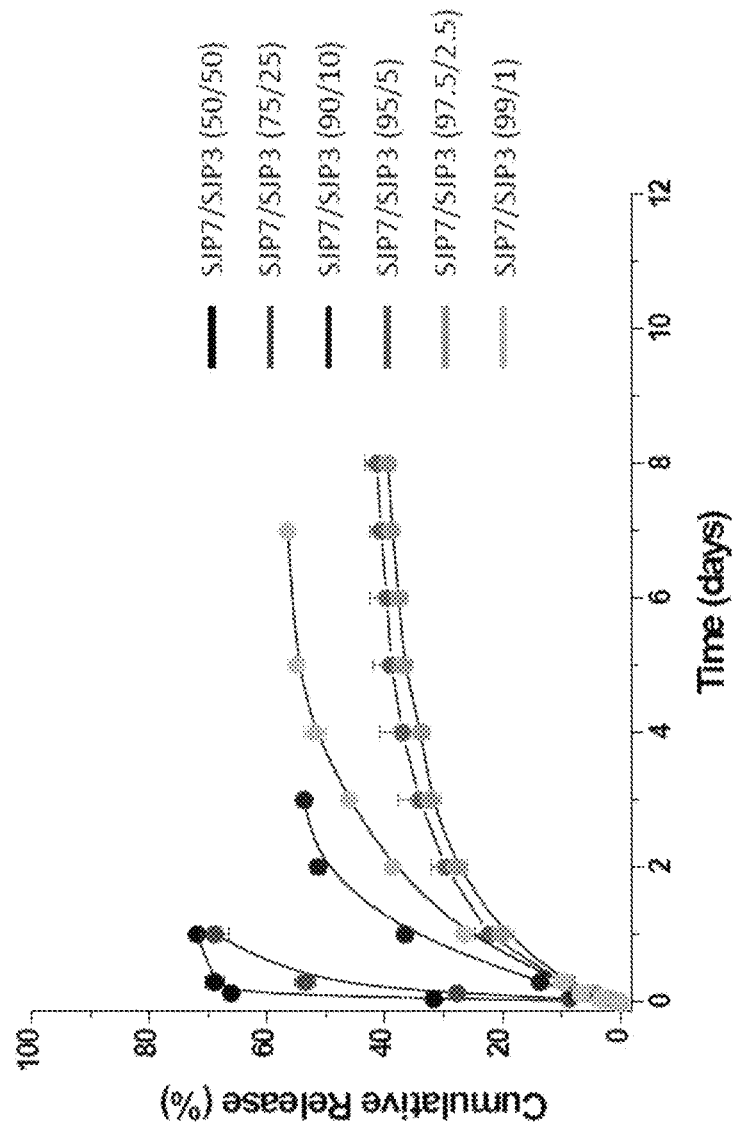
FIG. 73 shows data from a blend system of PVL-co-PAVL (SJP7) and PEGylated copolymer (SJP3) with hexanedithiol.

FIG. 73 shows data from a blend system of PVL-co-PAVL (SJP7) and PEGylated copolymer (SJP3) with hexanedithiol.

TABLE 23

PVL-co-PAVL (SJP7) and blend system (SJP3/SJP7-2.5%) with hexanedithiol

| Drug X | Disc (mg) | Drug (mg) | Disc Loaded (mg) | Drug content (mg) | DLC (%) | DLE (%) | Depot/Drug (w/w) |
|---|---|---|---|---|---|---|---|
| SJP7-1 | 27.82 | 25.00 | 34.08 | 6.26 | 18.37 | 25.04 | 1/0.23 |
| SJP7-2 | 28.55 | 25.00 | 34.94 | 6.39 | 18.29 | 25.56 | 1/0.22 |
| SJP7-1 | 28.44 | 50.00 | 39.22 | 10.78 | 27.49 | 21.56 | 1/0.38 |
| SJP7-2 | 28.43 | 50.00 | 39.27 | 10.84 | 27.60 | 21.68 | 1/0.38 |
| SJP7-1 | 28.43 | 75.00 | 42.24 | 13.81 | 32.69 | 18.41 | 1/0.49 |
| SJP7-2 | 28.54 | 75.00 | 42.57 | 14.03 | 32.96 | 18.71 | 1/0.49 |
| SJP7/SJP3 (97.5/2.5)-1 | 27.94 | 25.00 | 34.80 | 6.86 | 19.71 | 27.44 | 1/0.25 |
| SJP7/SJP3 (97.5/2.5)-2 | 27.77 | 25.00 | 34.82 | 7.05 | 20.25 | 28.20 | 1/0.25 |
| SJP7/SJP3 (97.5/2.5)-1 | 27.93 | 50.00 | 39.02 | 11.09 | 28.42 | 22.18 | 1/0.40 |
| SJP7/SJP3 (97.5/2.5)-2 | 28.46 | 50.00 | 39.35 | 10.89 | 27.67 | 21.78 | 1/0.39 |
| SJP7/SJP3 (97.5/2.5)-1 | 27.86 | 75.00 | 42.37 | 14.51 | 34.25 | 19.35 | 1/0.52 |
| SJP7/SJP3 (97.5/2.5)-2 | 27.99 | 75.00 | 42.72 | 14.73 | 34.48 | 19.64 | 1/0.53 |

Figure 74:
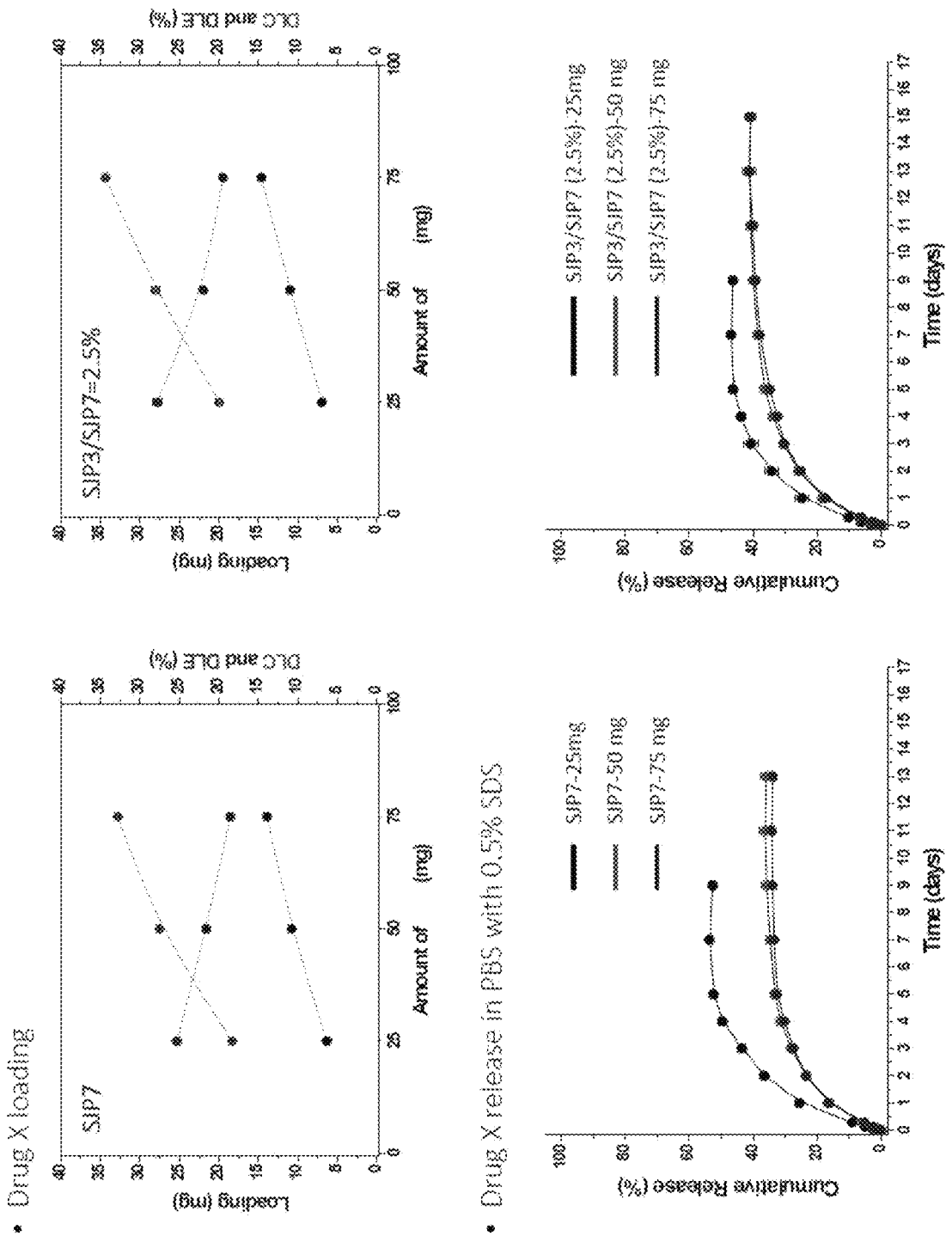
FIG. 74 shows data from PVL-co-PAVL (SJP7) and blend system (SJP3/SJP7-2.5%) with hexanedithiol.

FIG. 74 shows data from PVL-co-PAVL (SJP7) and blend system (SJP3/SJP7-2.5%) with hexanedithiol.

TABLE 24

PVL-co-PAVL (SJP7) and blend system (SJP3/SJP7-2.5%) with cleavable linker

| Drug X | Disc (mg) | Drug (mg) | Disc Loaded (mg) | Drug content (mg) | DLC (%) | DLE (%) | Depot/ Drug (w/w) |
|---|---|---|---|---|---|---|---|
| SJP7-1 | 29.38 | 25.00 | 33.06 | 3.68 | 11.13 | 14.72 | 1/0.13 |
| SJP7-2 | 29.67 | 25.00 | 33.51 | 3.84 | 11.46 | 15.36 | 1/0.13 |
| SJP7-1 | 29.50 | 50.00 | 36.25 | 6.75 | 18.62 | 13.50 | 1/0.23 |
| SJP7-2 | 29.18 | 50.00 | 36.36 | 7.18 | 19.75 | 14.36 | 1/0.25 |
| SJP7-1 | 29.68 | 75.00 | 38.85 | 9.17 | 23.60 | 12.23 | 1/0.31 |
| SJP7-2 | 29.00 | 75.00 | 37.92 | 8.92 | 23.52 | 11.89 | 1/0.31 |
| SJP7/SJP3 (97.5/2.5)-1 | 29.63 | 25.00 | 33.48 | 3.85 | 11.50 | 15.40 | 1/0.13 |
| SJP7/SJP3 (97.5/2.5)-2 | 29.60 | 25.00 | 33.26 | 3.66 | 11.00 | 14.64 | 1/0.12 |
| SJP7/SJP3 (97.5/2.5)-1 | 29.42 | 50.00 | 36.02 | 6.60 | 18.32 | 13.20 | 1/0.22 |
| SJP7/SJP3 (97.5/2.5)-2 | 29.73 | 50.00 | 36.04 | 6.31 | 17.51 | 12.62 | 1/0.2.1 |
| SJP7/SJP3 (97.5/2.5)-1 | 29.75 | 75.00 | 38.82 | 9.07 | 23.36 | 12.09 | 1/0.30 |
| SJP7/SJP3 (97.5/2.5)-2 | 28.82 | 75.00 | 37.12 | 8.30 | 22.36 | 11.07 | 1/0.29 |

Figure 75:
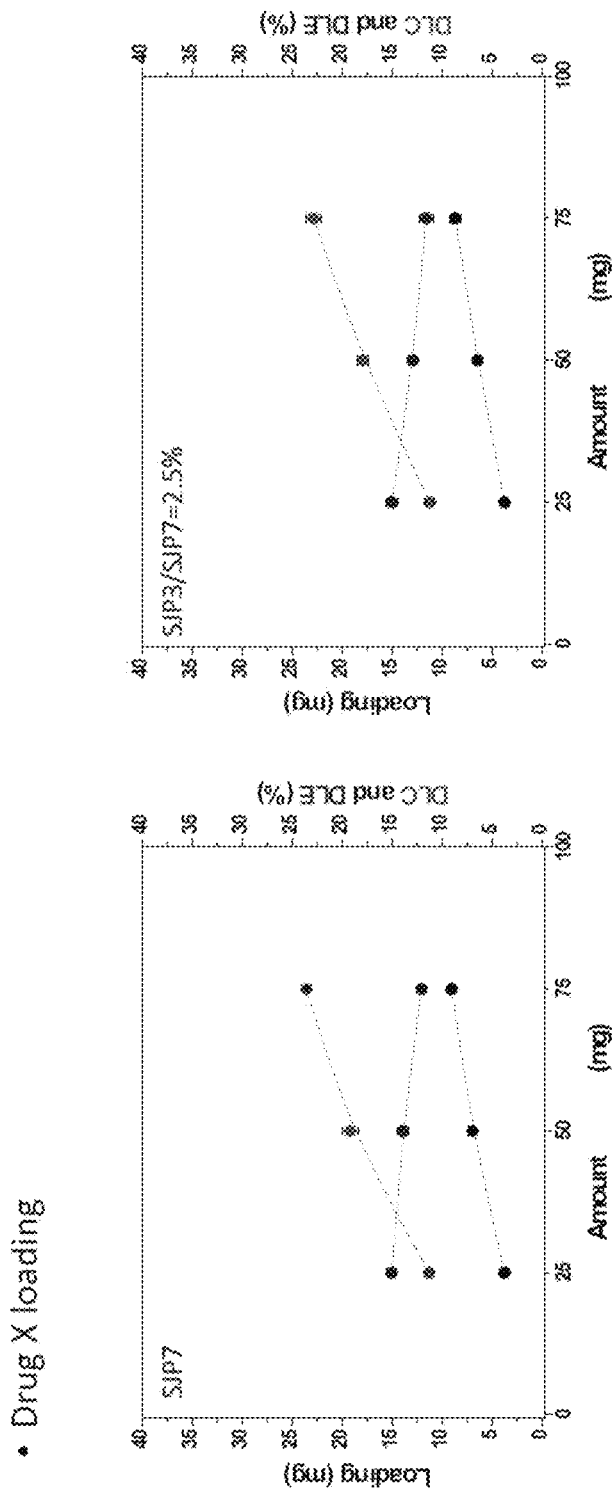
FIG. 75 shows data from PVL-co-PAVL (SJP7) and blend system (SJP3/SJP7-2.5%) with cleavable linker.

FIG. 75 shows data from PVL-co-PAVL (SJP7) and blend system (SJP3/SJP7-2.5%) with cleavable linker.

TABLE 25

PVL-co-PAVL (SJP7) and blend system (SJP3/SJP7-2.5%) with hexanedithiol.

| PTX | Disc (mg) | Drug (mg) | Disc Loaded (mg) | Drug content (mg) | DLC (%) | DLE (%) | Depot/ Drug (w/w) |
|---|---|---|---|---|---|---|---|
| SJP7-1 | 28.38 | 25.00 | 33.84 | 5.46 | 16.13 | 21.84 | 1/0.19 |
| SJP7-2 | 26.27 | 25.00 | 31.87 | 5.60 | 17.57 | 22.40 | 1/0.21 |
| SJP7-1 | 28.30 | 50.00 | 38.70 | 10.40 | 26.87 | 20.80 | 1/0.37 |
| SJP7-2 | 27.72 | 50.00 | 38.06 | 10.34 | 27.17 | 20.68 | 1/0.37 |
| SJP7-1 | 28.62 | 75.00 | 41.24 | 12.62 | 30.60 | 16.83 | 1/0.44 |
| SJP7-2 | 26.11 | 75.00 | 38.45 | 12.34 | 32.09 | 16.45 | 1/0.47 |
| SJP7/SJP3 (97.5/2.5)-1 | 27.63 | 25.00 | 33.33 | 5.70 | 17.10 | 22.80 | 1/0.20 |
| SJP7/SJP3 (97.5/2.5)-2 | 33.11 | 25.00 | 33.11 | 5.63 | 17.00 | 22.52 | 1/0.20 |
| SJP7/SJP3 (97.5/2.5)-1 | 27.98 | 50.00 | 38.38 | 10.40 | 27.10 | 20.80 | 1/0.37 |
| SJP7/SJP3 (97.5/2.5)-2 | 37.99 | 50.00 | 37.99 | 10.08 | 26.53 | 20.16 | 1/0.36 |
| SJP7/SJP3 (97.5/2.5)-1 | 28.29 | 75.00 | 41.54 | 13.25 | 31.90 | 17.67 | 1/0.47 |
| SJP7/SJP3 (97.5/2.5)-2 | 41.23 | 75.00 | 41.23 | 13.16 | 31.92 | 17.55 | 1/0.47 |

Figure 76:
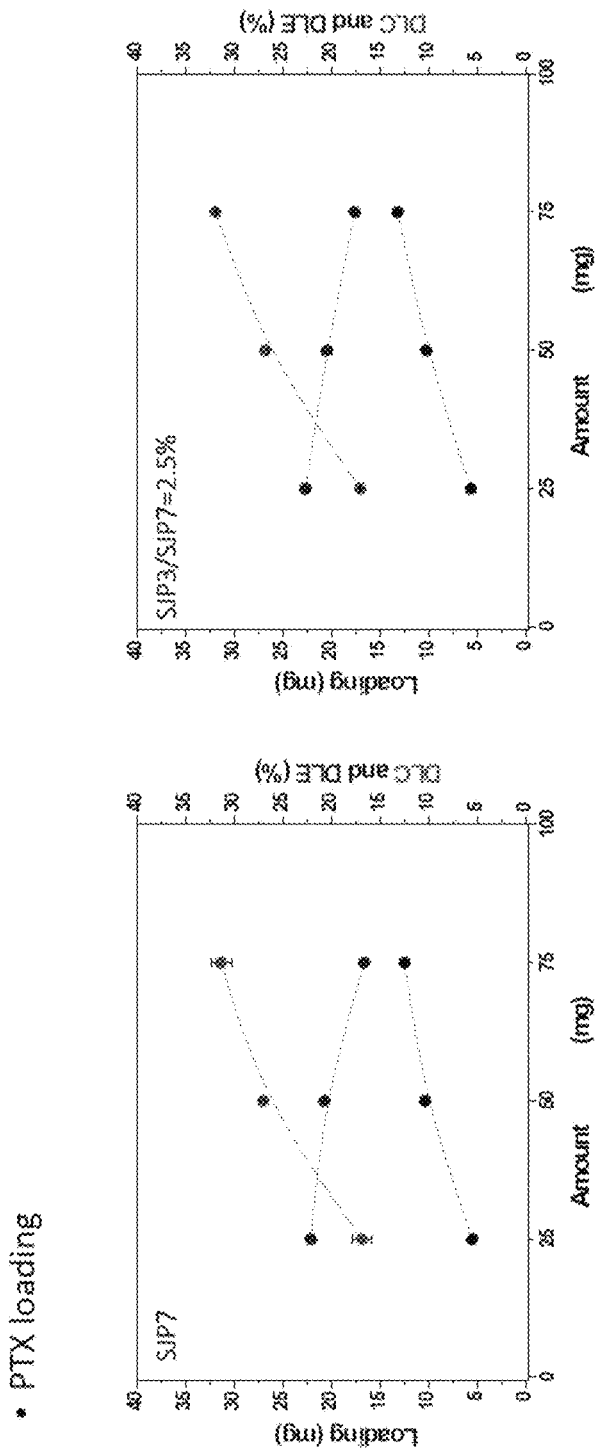
FIG. 76 shows data from PVL-co-PAVL (SJP7) and blend system (SJP3/SJP7-2.5%) with hexanedithiol

FIG. 76 shows data from PVL-co-PAVL (SJP7) and blend system (SJP3/SJP7-2.5%) with hexanedithiol.

FIG. 77 shows a plan of preparation of controlled microparticle by adjusting concentration, according to an embodiment.

Figure 78:
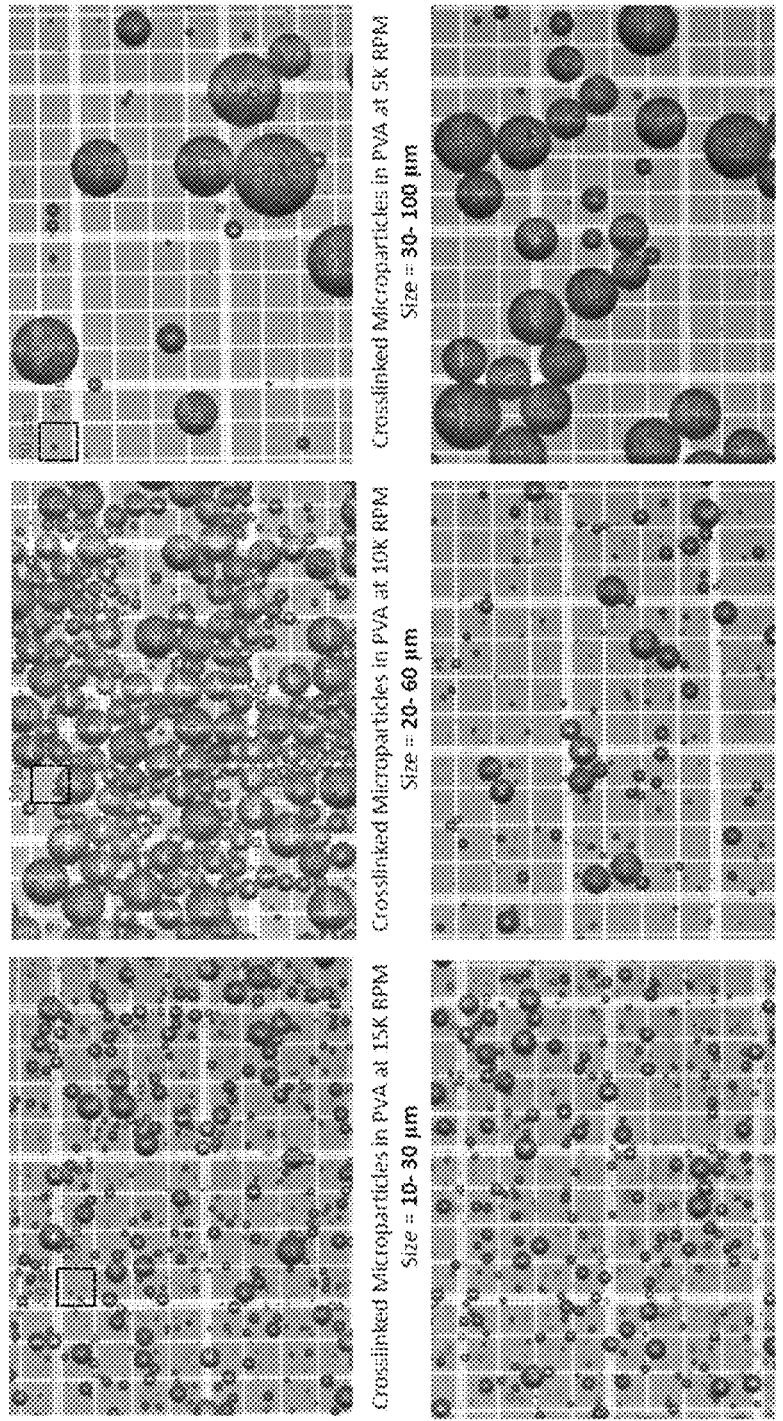
FIG. 78 shows a plan of preparation of controlled microparticle to adjusting speed (RPM), according to an embodiment.

FIG. 78 shows a plan of preparation of controlled microparticle to adjusting speed (RPM), according to an embodiment.

Figure 79:
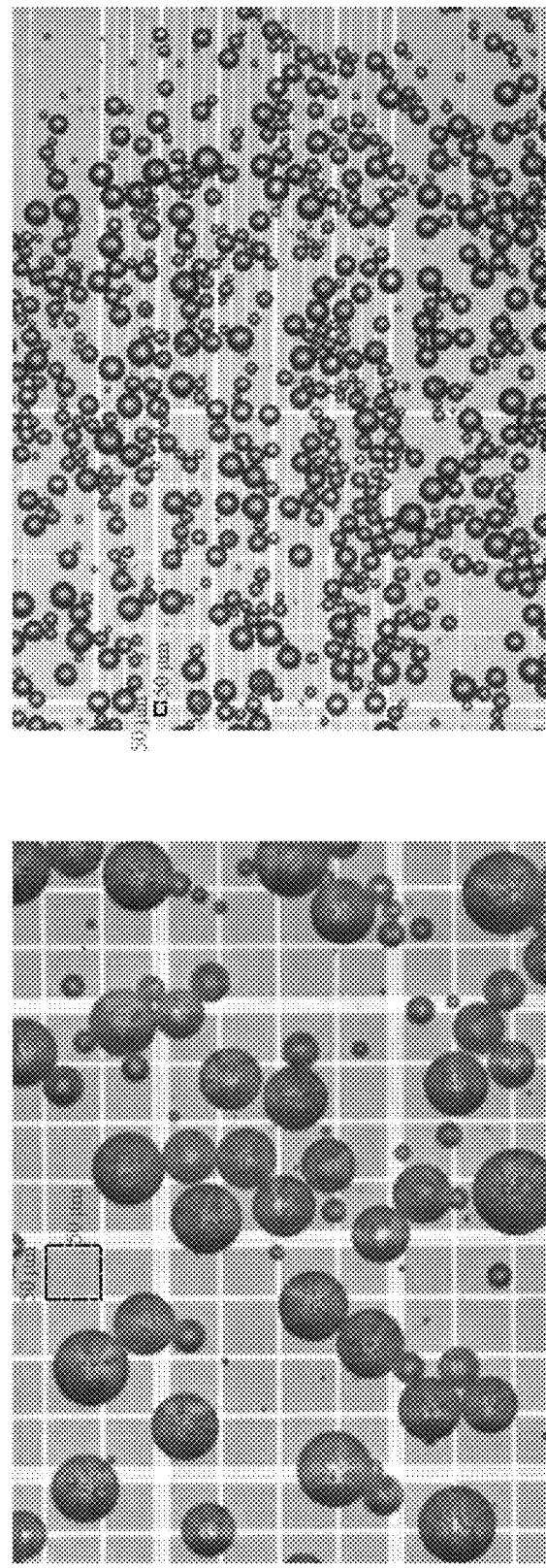
FIG. 79 shows a preparation of a microparticle, according to an embodiment.

FIG. 79 shows a preparation of a microparticle, according to an embodiment.

Figure 80:
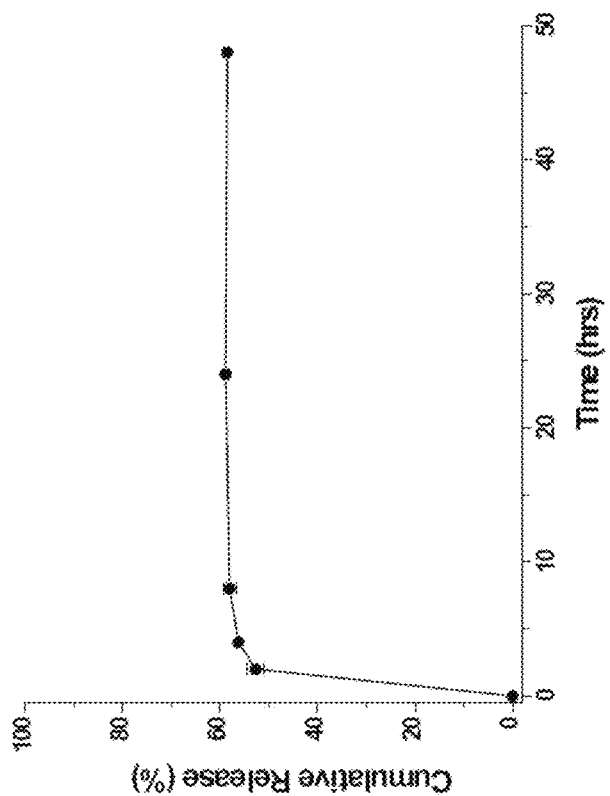
FIG. 80 shows data from loading and release of Drug X freebase.

FIG. 80 shows data from loading and release of Drug X freebase.

Figure 81:
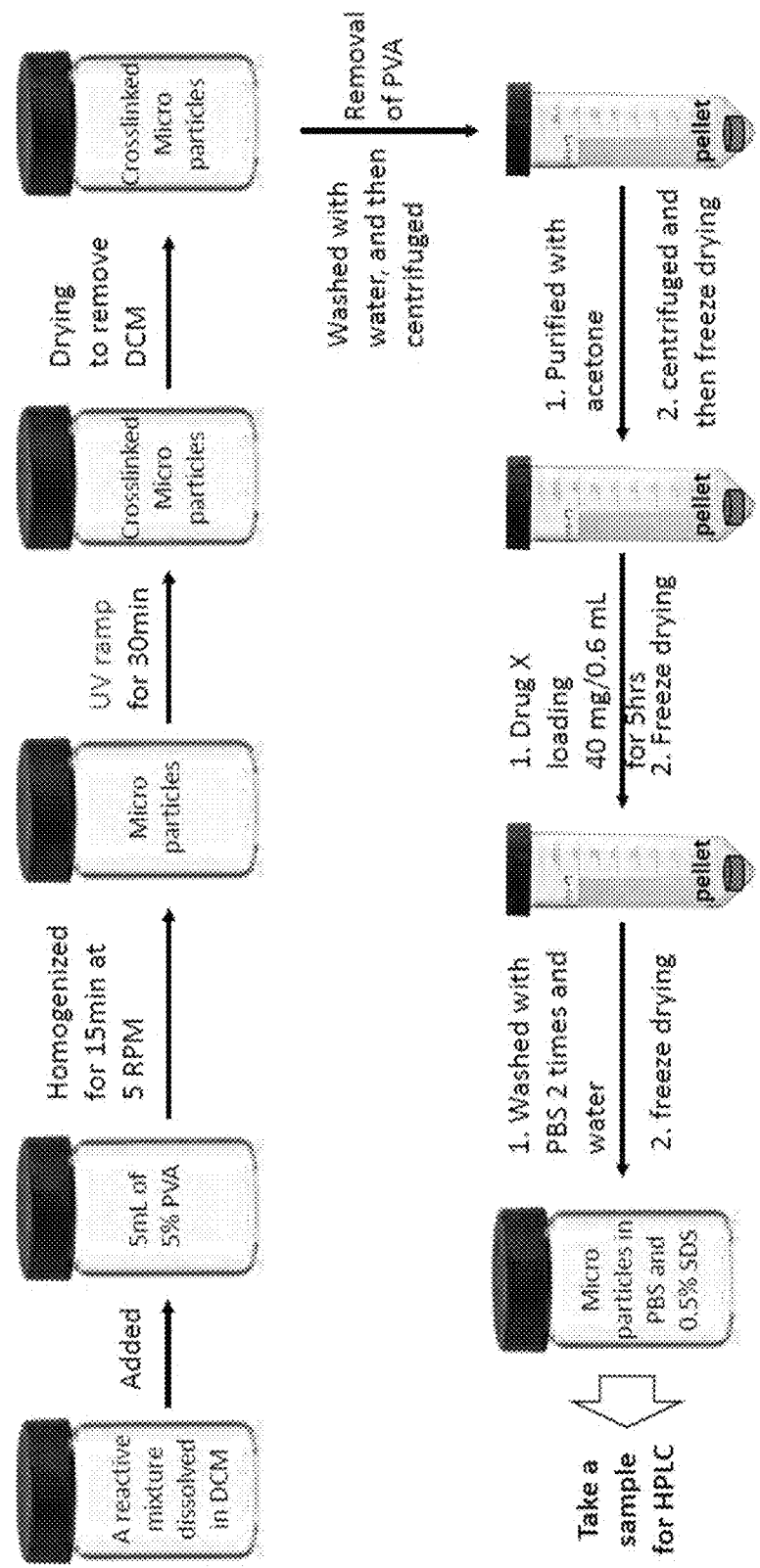
FIG. 81 shows preparation of microparticle and postloading, according to an embodiment.

FIG. 81 shows preparation of microparticle and postloading, according to an embodiment.

Figure 82:
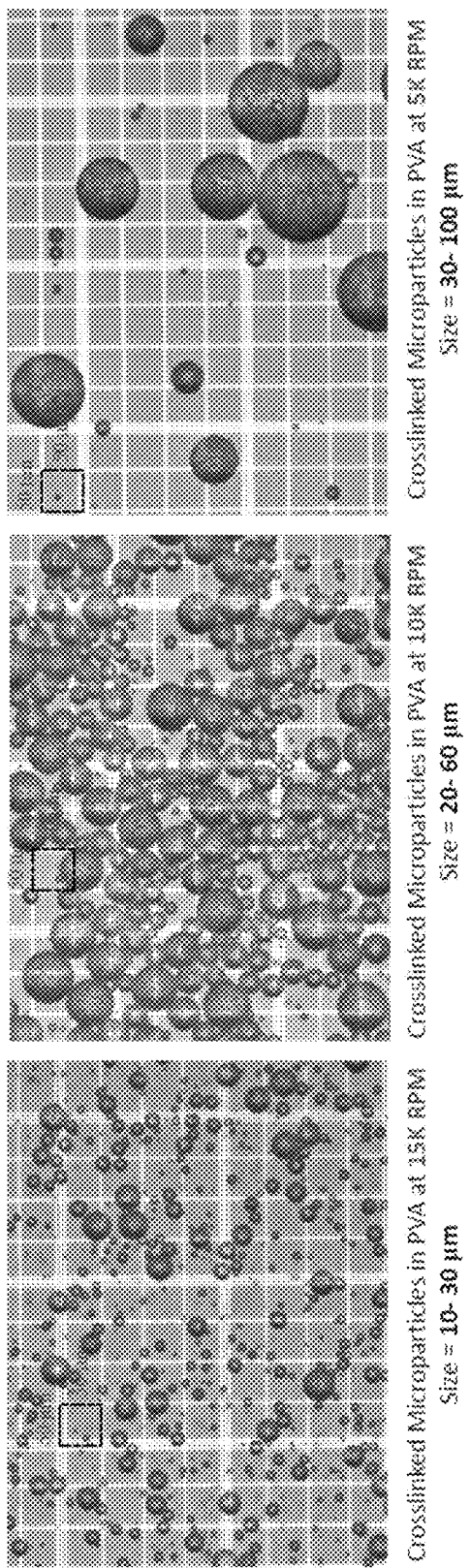
FIG. 82 shows preparation of a controlled microparticle, according to an embodiment.

FIG. 82 shows preparation of a controlled microparticle, according to an embodiment.

Figure 83:
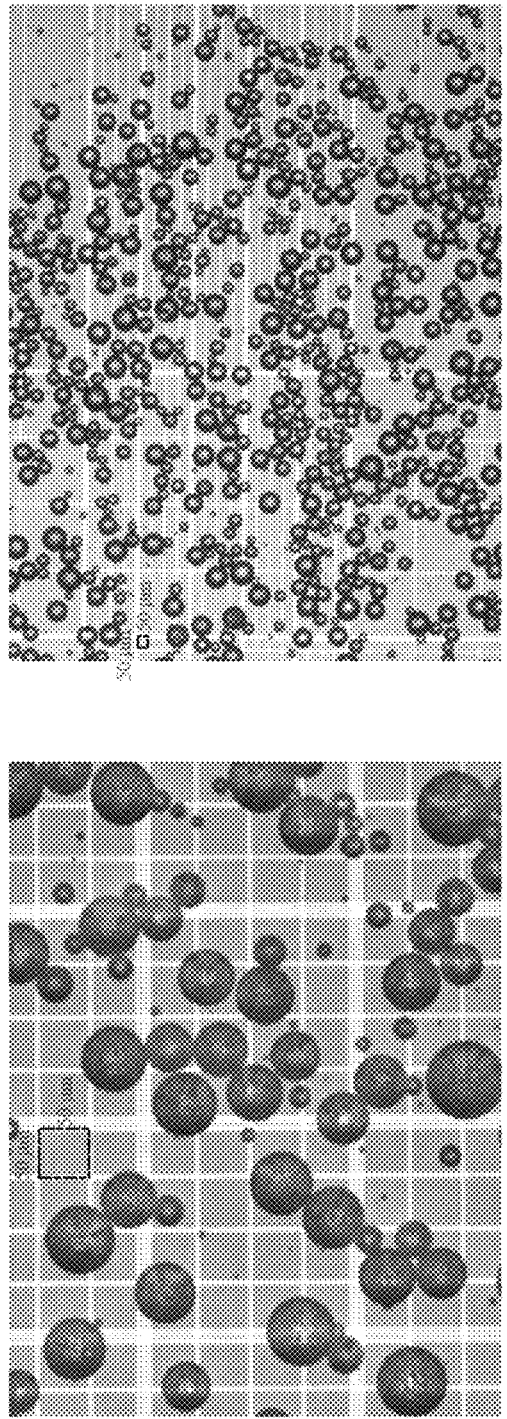
FIG. 83 shows preparation of a microparticle, according to an embodiment.

FIG. 83 shows preparation of a microparticle, according to an embodiment.

Figure 84:
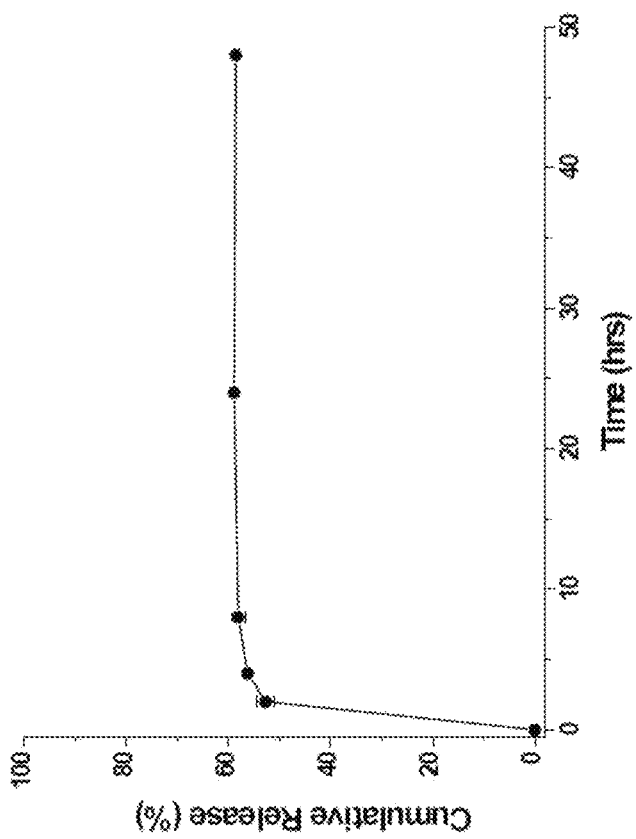
FIG. 84 shows loading and release of Drug X freebase.

FIG. 84 shows loading and release of Drug X freebase. Protocol for degradation:

Prepare a PBS solution (1 mL) containing *pseudomonas* (PS) lipase (0.5 mg/mL, pH 7.5).

Place depots (20-25 mg) in a vial containing 1 mL of the prepared solution at 37° C.

Change enzyme solution everyday or add sodium azide (as antibacterial agent) to avoid proliferation of bacteria.

Samples are withdrawn from the degradation medium, washed thoroughly with distilled water and then freeze-dried.

Measure weight loss of depot.

Sample for degradation study:

SJP7×hexanedithiol

SJP7×cleavable linker

SJP7/SJP3 (2.5%)×hexanedithiol

SJP7/SJP3 (2.5%)×cleavable linker

It has been a week, but no weight loss.

TABLE 26

Loading and Release of Paclitaxel

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7-1 | 28.38 | 25.00 | 33.84 | 5.46 | 16.13 | 21.84 | 1/0.19 |
| SJP7-2 | 26.27 | 25.00 | 31.87 | 5.60 | 17.57 | 22.40 | 1/0.21 |
| SJP7-1 | 28.30 | 50.00 | 38.70 | 10.40 | 26.87 | 20.80 | 1/0.37 |
| SJP7-2 | 27.72 | 50.00 | 38.06 | 10.34 | 27.17 | 20.68 | 1/0.37 |
| SJP7-1 | 28.62 | 75.00 | 41.24 | 12.62 | 30.60 | 16.83 | 1/0.44 |
| SJP7-2 | 26.11 | 75.00 | 38.45 | 12.34 | 32.09 | 16.45 | 1/0.47 |
| SJP7/SJP3 (97.5/2.5)-1 | 27.63 | 25.00 | 33.33 | 5.70 | 17.10 | 22.80 | 1/0.20 |
| SJP7/SJP3 (97.5/2.5)-2 | 27.48 | 25.00 | 33.11 | 5.63 | 17.00 | 22.52 | 1/0.20 |
| SJP7/SJP3 (97.5/2.5)-1 | 27.98 | 50.00 | 38.38 | 10.40 | 27.10 | 20.80 | 1/0.37 |
| SJP7/SJP3 (97.5/2.5)-2 | 27.91 | 50.00 | 37.99 | 10.08 | 26.53 | 20.16 | 1/0.36 |
| SJP7/SJP3 (97.5/2.5)-1 | 28.29 | 75.00 | 41.54 | 13.25 | 31.90 | 17.67 | 1/0.47 |
| SJP7/SJP3 (97.5/2.5)-2 | 28.07 | 75.00 | 41.23 | 13.16 | 31.92 | 17.55 | 1/0.47 |

Figure 85:
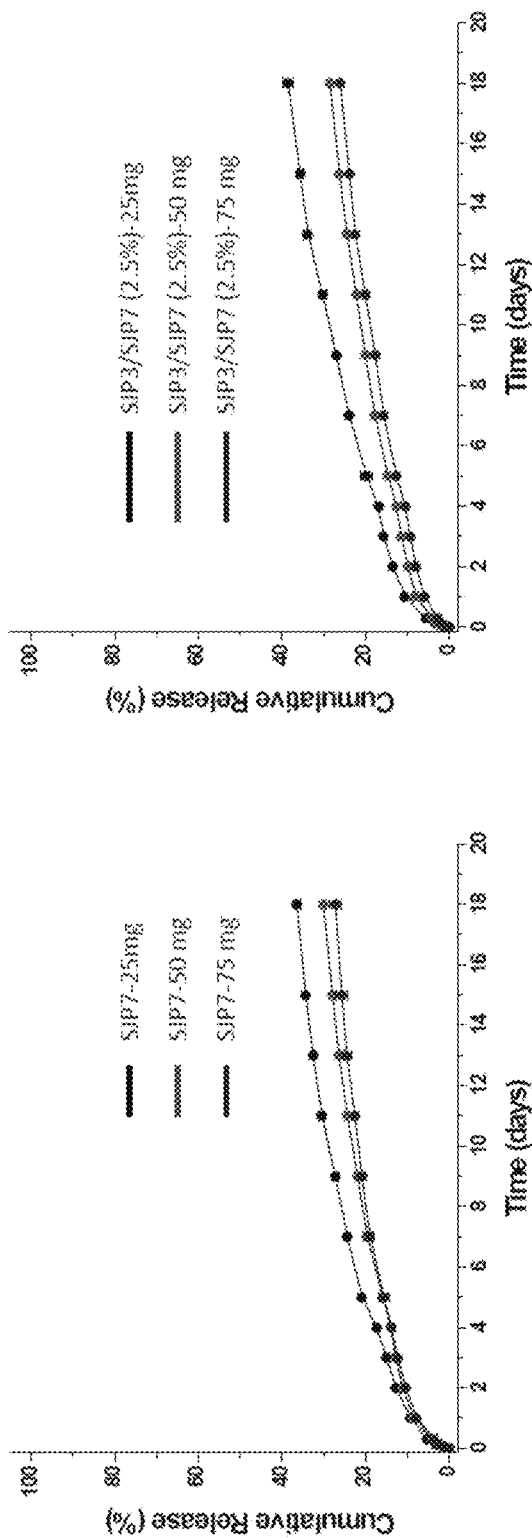
FIG. 85 shows loading and release of Paclitaxel.

FIG. 85 shows loading and release of Paclitaxel.

TABLE 27

Loading and release of Paclitaxel

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7/SJP3 (50/50)-1 | 25.05 | 25.00 | 29.98 | 4.93 | 16.44 | 19.72 | 1/0.20 |
| SJP7/SJP3 (50/50)-2 | 25.36 | 25.00 | 30.67 | 5.31 | 17.31 | 21.24 | 1/0.21 |
| SJP7/SJP3 (75/25)-1 | 27.30 | 25.00 | 32.17 | 4.87 | 15.14 | 19.48 | 1/0.18 |
| SJP7/SJP3 (75/25)-2 | 27.72 | 25.00 | 33.01 | 52.9 | 16.03 | 21.16 | 1/0.19 |
| SJP7/SJP3 (90/10)-1 | 27.99 | 25.00 | 33.03 | 5.04 | 15.26 | 20.16 | 1/0.18 |
| SJP7/SJP3 (90/10)-2 | 27.77 | 25.00 | 32.62 | 4.85 | 14.87 | 19.40 | 1/0.17 |
| SJP7/SJP3 (95/5)-1 | 28.08 | 25.00 | 34.28 | 6.20 | 18.09 | 24.80 | 1/0.22 |
| SJP7/SJP3 (95/5)-2 | 27.92 | 25.00 | 33.99 | 6.07 | 17.86 | 24.28 | 1/0.22 |
| SJP7/SJP3 (97.5/2.5)-1 | 28.07 | 25.00 | 34.12 | 6.05 | 17.73 | 24.20 | 1/0.22 |
| SJP7/SJP3 (97.5/2.5)-2 | 28.46 | 25.00 | 34.39 | 5.93 | 17.24 | 23.72 | 1/0.21 |
| SJP7/SJP3 (99/1)-1 | 27.20 | 25.00 | 32.36 | 5.16 | 15.95 | 20.64 | 1/0.19 |
| SJP7/SJP3 (99/1)-2 | 28.01 | 25.00 | 33.18 | 5.17 | 15.58 | 20.68 | 1/0.18 |

Figure 86:
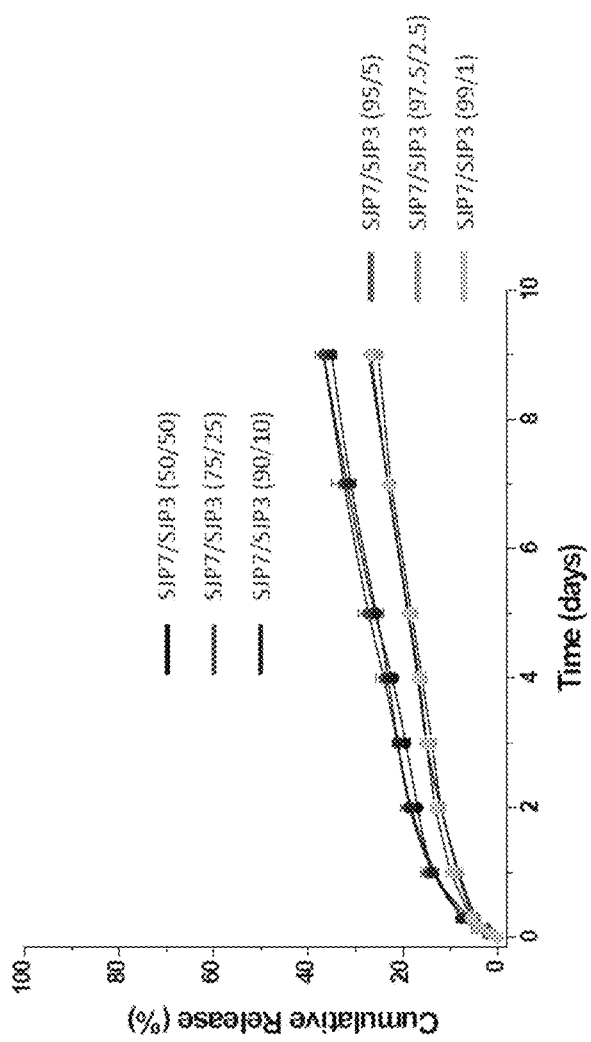
FIG. 86 shows loading and release of Paclitaxel varying amount of PEGylated copolymer.

FIG. 86 shows loading and release of Paclitaxel varying amount of PEGylated copolymer.

Figure 87:
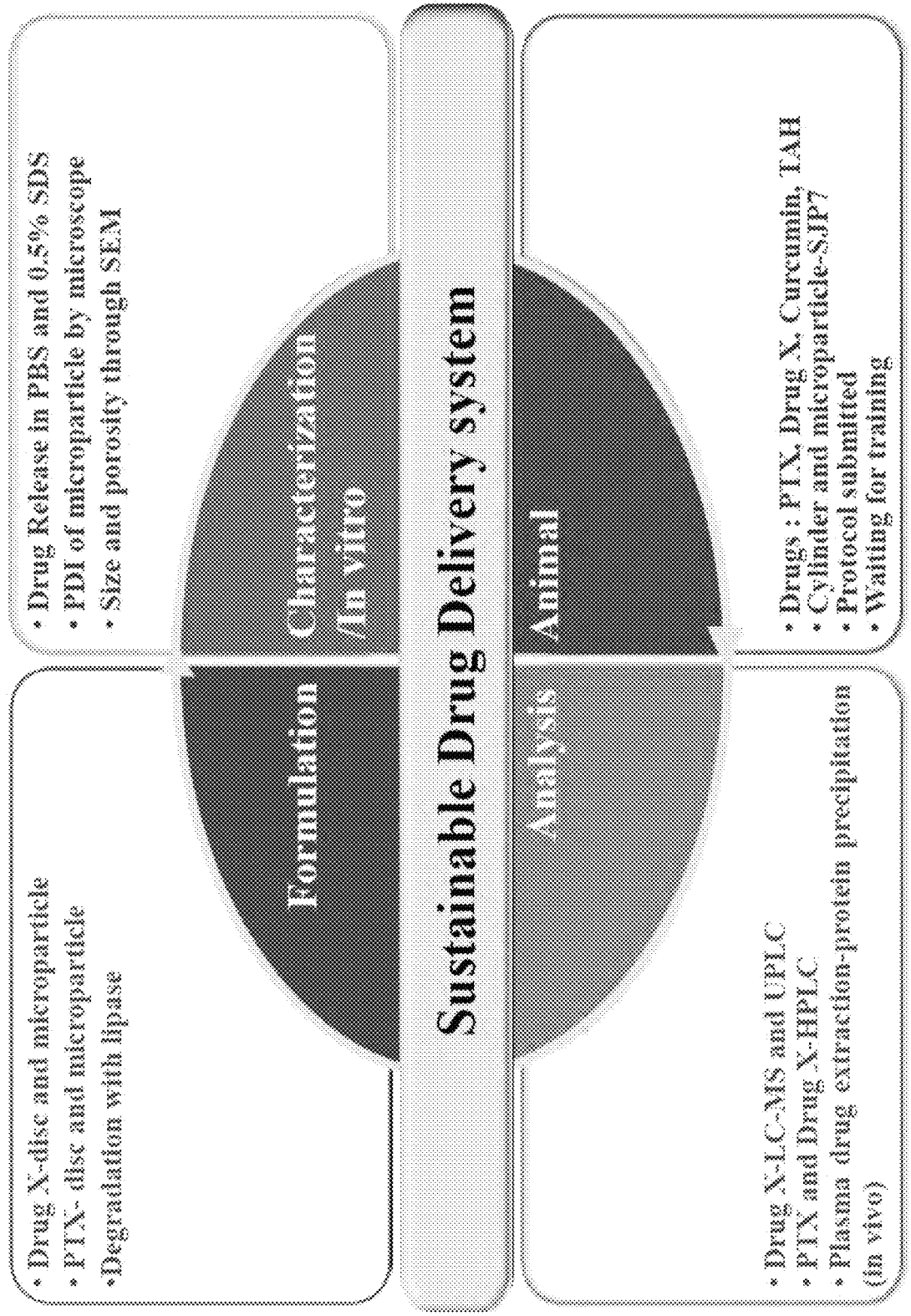
FIG. 87 shows a chart of a sustainable drug delivery system, according to an embodiment.

FIG. 87 shows a chart of a sustainable drug delivery system, according to an embodiment.

Figure 88:
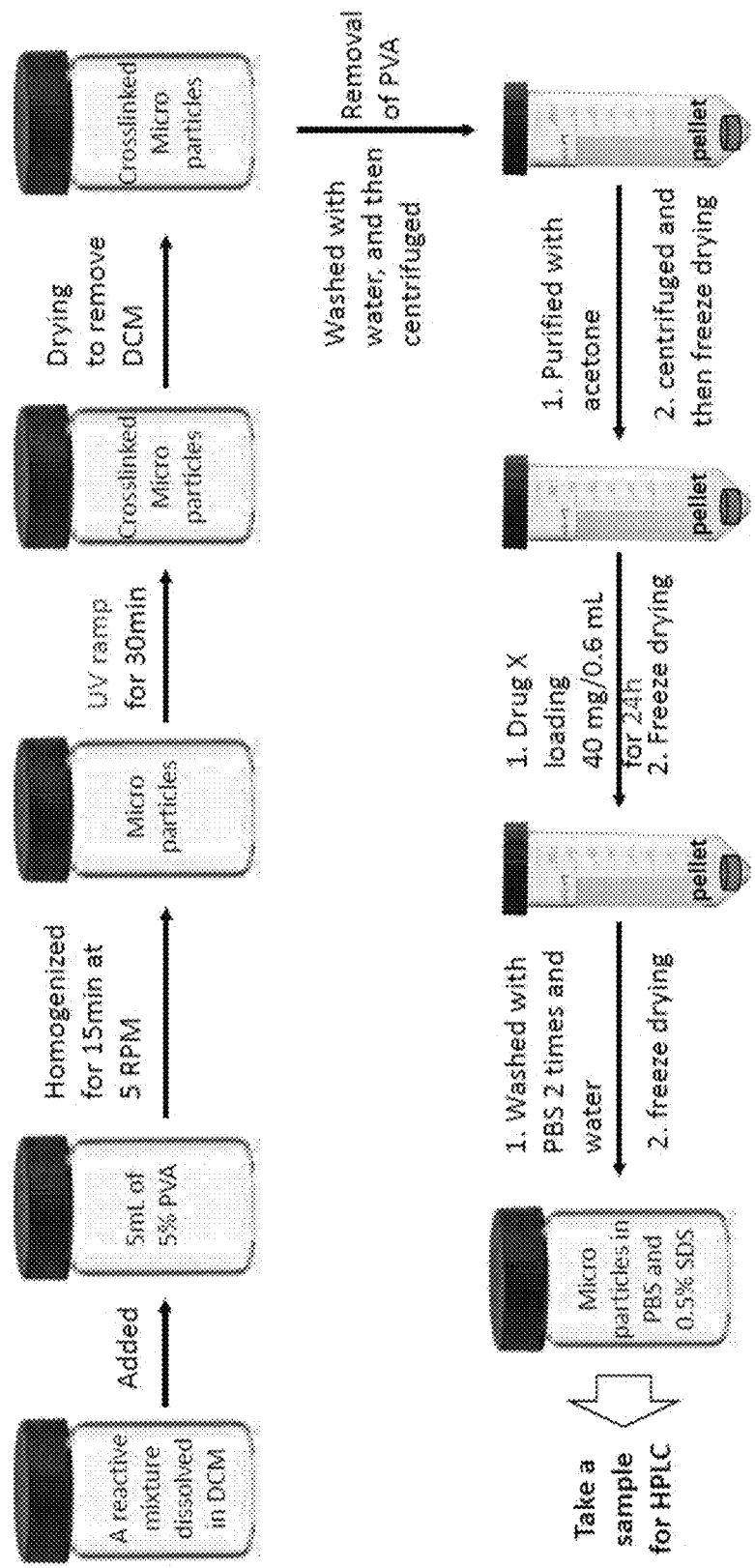
FIG. 88 shows preparation of microparticles and post-loading of a drug, according to an embodiment.

FIG. 88 shows preparation of microparticles and post-loading of a drug, according to an embodiment.

Figure 89:
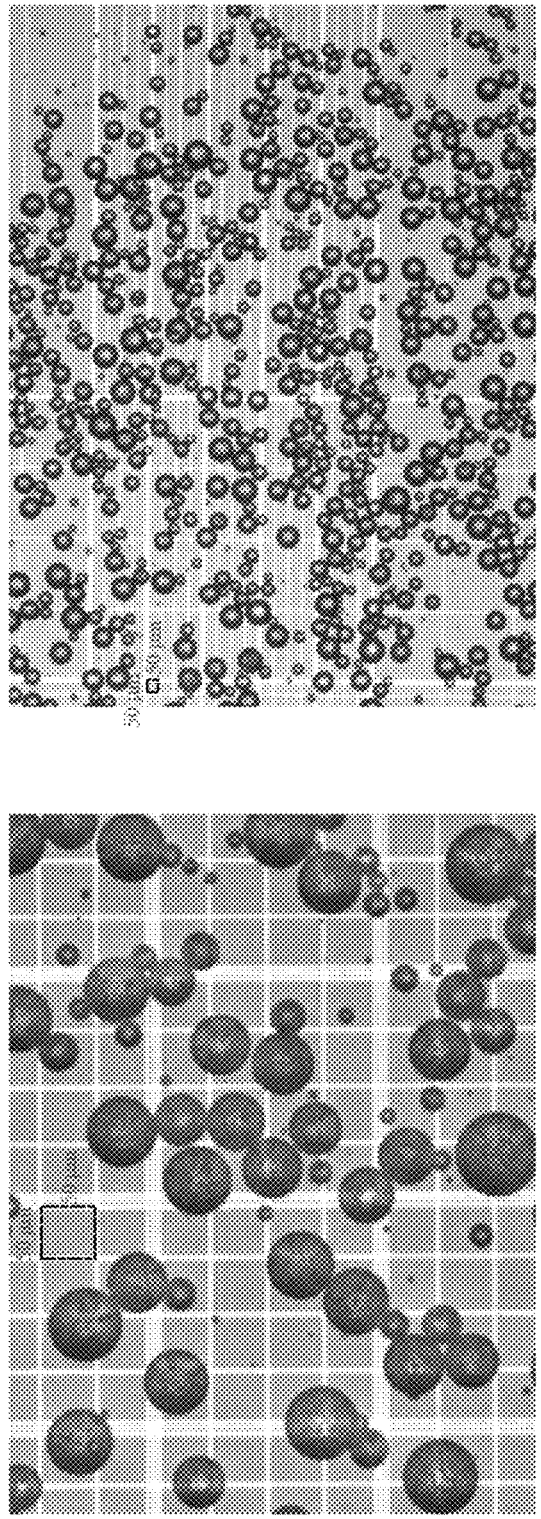
FIG. 89 shows preparation of a microparticle, according to an embodiment.

FIG. 89 shows preparation of a microparticle, according to an embodiment.

Figure 90:
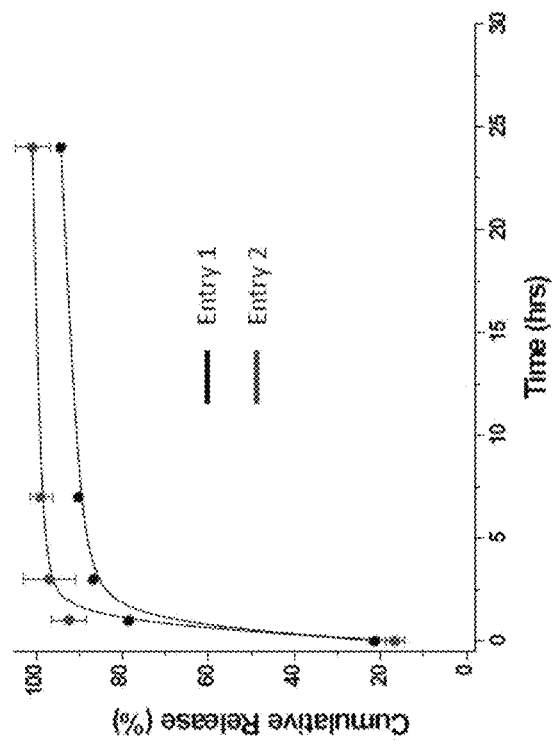
FIG. 90 shows loading and release of Drug X freebase.

FIG. 90 shows loading and release of Drug X freebase.

Figure 91:
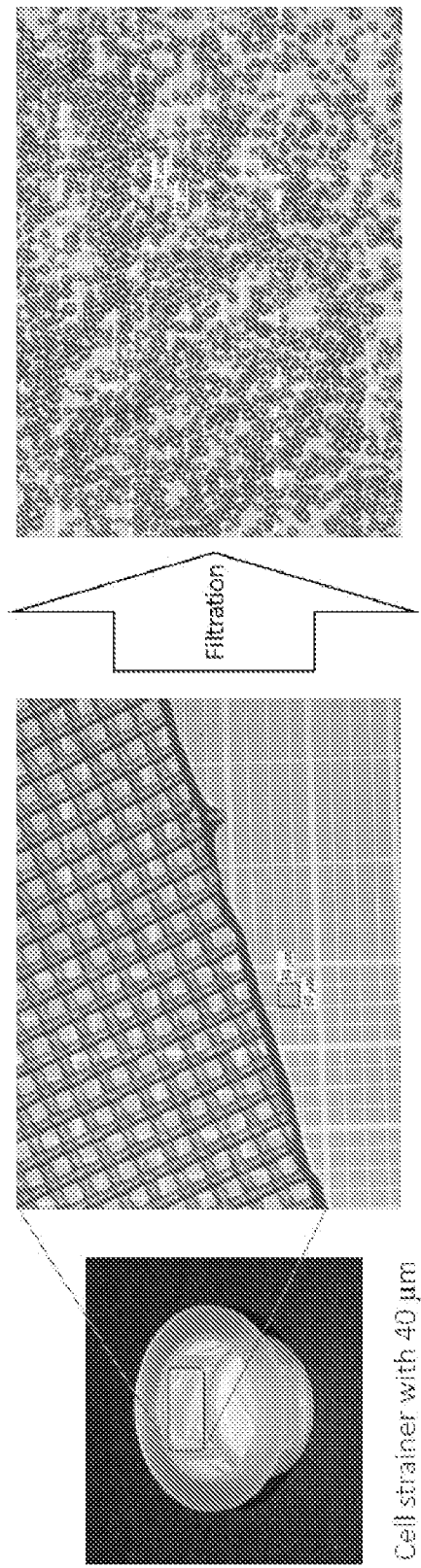
FIG. 91 shows an approach to eliminate centrifugation via microparticle mesh washing, according to an embodiment.

FIG. 91 shows an approach to eliminate centrifugation via microparticle mesh washing, according to an embodiment.

Figure 92:
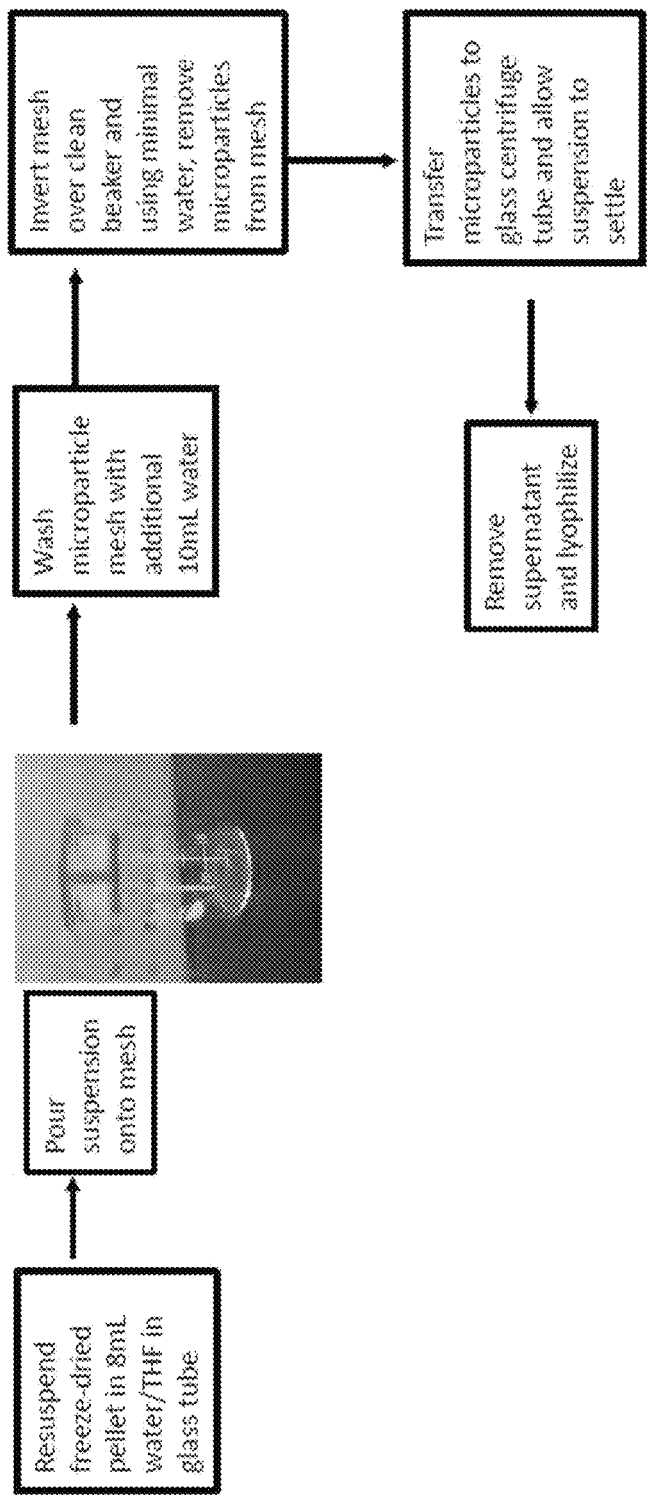
FIG. 92 shows a current mesh washing protocol, according to an embodiment.

FIG. 92 shows a current mesh washing protocol, according to an embodiment.

Figure 93:
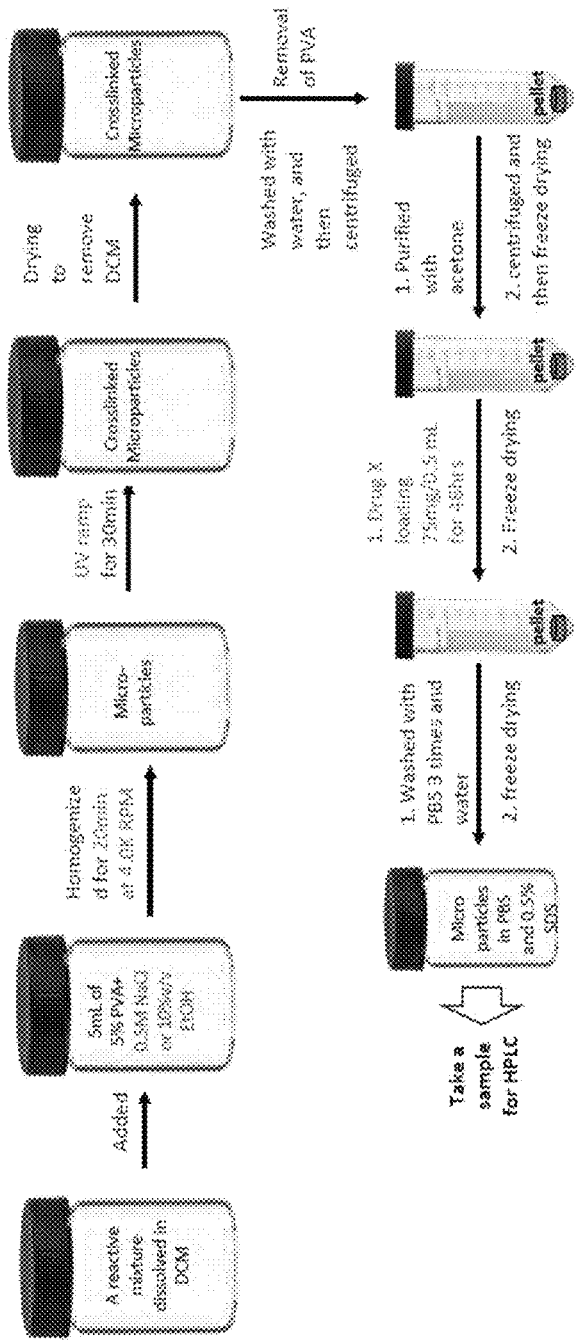
FIG. 93 shows preparation of microparticle and postloading for NaCl MP and EtOH MP.

Why incorporate NaCl or EtOH?
Key parameters affecting the initial release (burst) and encapsulation efficiency of peptide-containing poly(lactide-co-glycolide) microparticles (Luan et at)
General findings
High NaCl concentration (0.5M) in the external aqueous phase delays polymer precipitation and resulted in non-porous microparticles with low initial release
Presence of EtOH in the external aqueous phase result in porous microparticles.
Goal is to control burst release by changing porosity of microparticles FIG. 93 shows preparation of microparticle and postloading for NaCl MP and EtOH MP.

Figure 94:
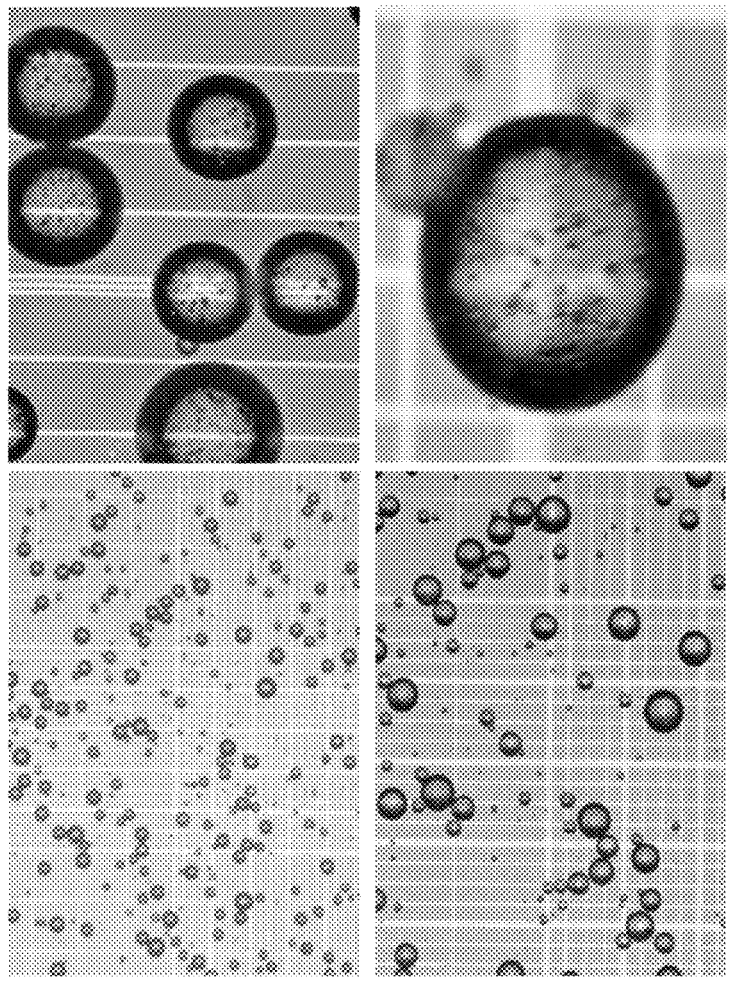
FIG. 94 shows microparticles with NaCl.

FIG. 94 shows microparticles with NaCl.

Figure 95:
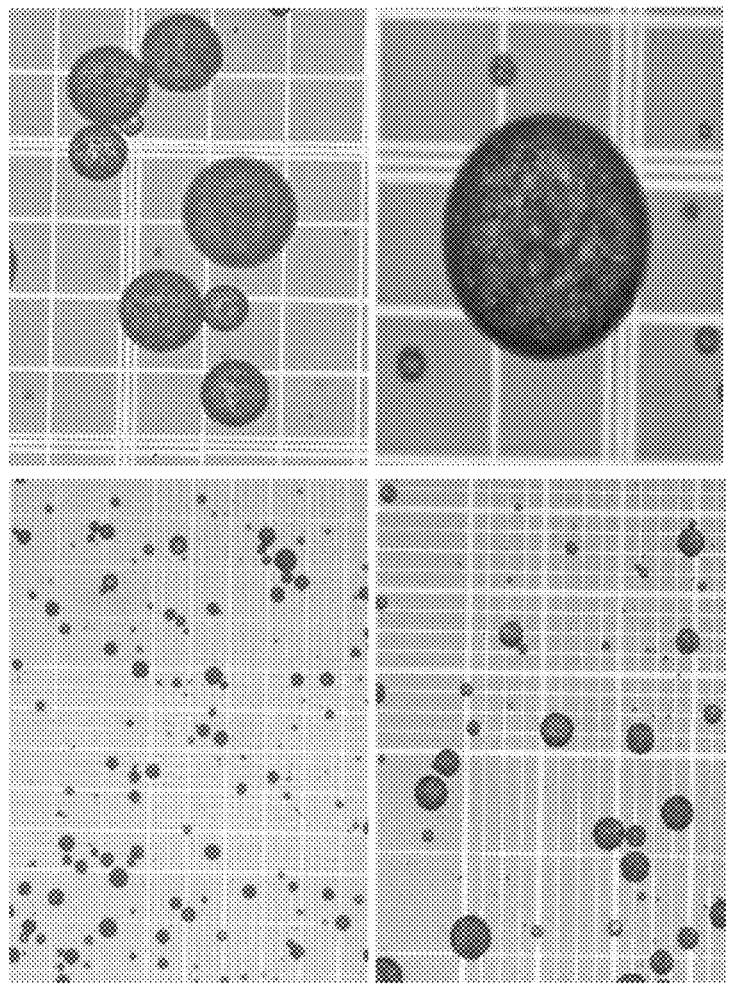
FIG. 95 shows microparticles with EtOH.

FIG. 95 shows microparticles with EtOH.

Figure 96:
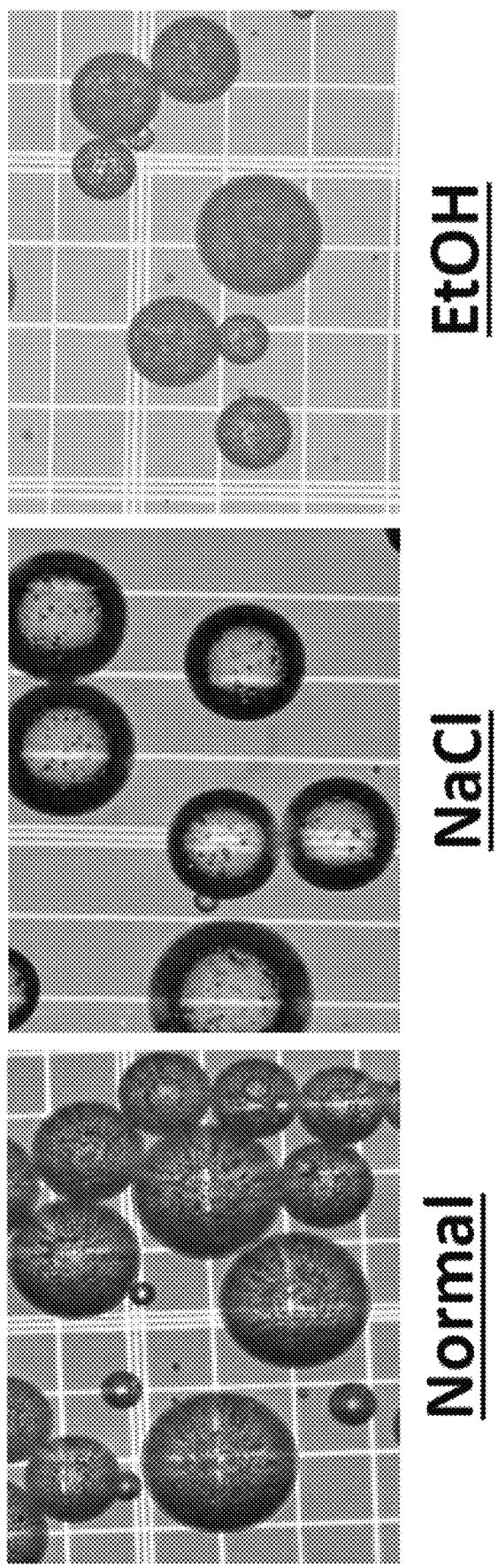
FIG. 96 shows microparticles with NaCl and EtOH.

FIG. 96 shows microparticles with NaCl and EtOH.

Microparticles—Next Steps:
Release study has been started.
Initial release data available next week.
If the release data is good, optimize MP to achieve more uniform size of MPs.
Based on the release data, optimize concentration of NaCl or EtOH to control release rate.
Confirm morphology and surface of MP with SEM.
Load PTX.

TABLE 28

Loading of Drug X in Mesh washed MPs, NaCl MPs, and EtOH MPs

| Entry no | Drug X | Microparticle W/O Drug X loading | Amount of Drug added | Microparticle after Drug X loading | Loaded amount of Drug | DLC (%) | DLE (%) | Drug/ Material (w/w) |
|---|---|---|---|---|---|---|---|---|
| 1 | SJP7-Drug X-1 (Mesh) | 47.00 mg | 70 mg | 37 mg[7] | −10 mg[7] | N/A | N/A | N/A |
|   | SJP7-Drug X-2 (Mesh) | 44.18 mg | 70 mg | 31 mg[7] | −13 mg[7] | N/A | N/A | N/A |
| 2 | SJP7-Drug X-1 (NaCl) | 39.01 mg | 75 mg | 42.68 mg | 3.66 mg[7] | 9.38 | 4.88 | 0.094/1 |
|   | SJP7-Drug X-2 (NaCl) | 37.23 mg | 75 mg | 39.47 mg | 2.25 mg[7] | 6.03 | 2.99 | 0.060/1 |
| 2 | SJP7-Drug X-1 (EtOH) | 32.85 mg | 75 mg | 30.95 mg | −1.9 mg[7] | N/A | N/A | N/A |
|   | SJP7-Drug X-2 (EtOH) | 25.88 mg | 75 mg | 21.18 mg | −2.7 mg[7] | N/A | N/A | N/A |

[7]Lower MP mass after drug loading is due to the loss of MPs during the washing process. If we account for the loss of MP during the washing, we can assume that drug loaded into MPs. We will confirm the drug loading by HPLC release.

Protocol for Degradation:
Prepare a PBS solution (1 mL) containing *pseudomonas* (PS) lipase (0.5 mg/mL, pH 7.5)
Place depots (20-23 mg) in a vial containing 1 mL of the prepared solution at 37° C.
Change enzyme solution everyday to avoid proliferation of bacteria.
Samples are withdrawn from the degradation medium, washed thoroughly with distilled water and then freeze-dried.
Measure weight loss of depot.

Sample for degradation study
SJP7×hexanedithiol
SJP7×cleavable linker
SJP7/SJP3 (2.5%)×hexanedithiol
SJP7/SJP3 (2.5%)×cleavable linker
It has been a month, and 0.2 mg (~1%) decrease for all the samples.
However, cross-linker and a small amount of PEGylated copolymer does not have a significant effect on degradation so far.

TABLE 29

Loading and Release of Paclitaxel

| PTX | Disc (mg) | Drug (mg) | Disc Loaded (mg) | Drug content (mg) | DLC (%) | DLE (%) | Depot/ Drug (w/w) |
|---|---|---|---|---|---|---|---|
| SJP7-1 | 28.38 | 25.00 | 33.84 | 5.46 | 16.13 | 21.84 | 1/0.19 |
| SJP7-2 | 26.27 | 25.00 | 31.87 | 5.60 | 17.57 | 22.40 | 1/0.21 |
| SJP7-1 | 28.30 | 50.00 | 38.70 | 10.40 | 26.87 | 20.80 | 1/0.37 |
| SJP7-2 | 27.72 | 50.00 | 38.06 | 10.34 | 27.17 | 20.68 | 1/0.37 |
| SJP7-1 | 28.62 | 75.00 | 41.24 | 12.62 | 30.60 | 16.83 | 1/0.44 |
| SJP7-2 | 26.11 | 75.00 | 38.45 | 12.34 | 32.09 | 16.45 | 1/0.47 |
| SJP7/SJP3 (97.5/2.5)-1 | 27.63 | 25.00 | 33.33 | 5.70 | 17.10 | 22.80 | 1/0.20 |
| SJP7/SJP3 (97.5/2.5)-2 | 27.48 | 25.00 | 33.11 | 5.63 | 17.00 | 22.52 | 1/0.20 |
| SJP7/SJP3 (97.5/2.5)-1 | 27.98 | 50.00 | 38.38 | 10.40 | 27.10 | 20.80 | 1/0.37 |
| SJP7/SJP3 (97.5/2.5)-2 | 27.91 | 50.00 | 37.99 | 10.08 | 26.53 | 20.16 | 1/0.36 |
| SJP7/SJP3 (97.5/2.5)-1 | 28.29 | 75.00 | 41.54 | 13.25 | 31.90 | 17.67 | 1/0.47 |
| SJP7/SJP3 (97.5/2.5)-2 | 28.07 | 75.00 | 41.23 | 13.16 | 31.92 | 17.55 | 1/0.47 |

Figure 97:
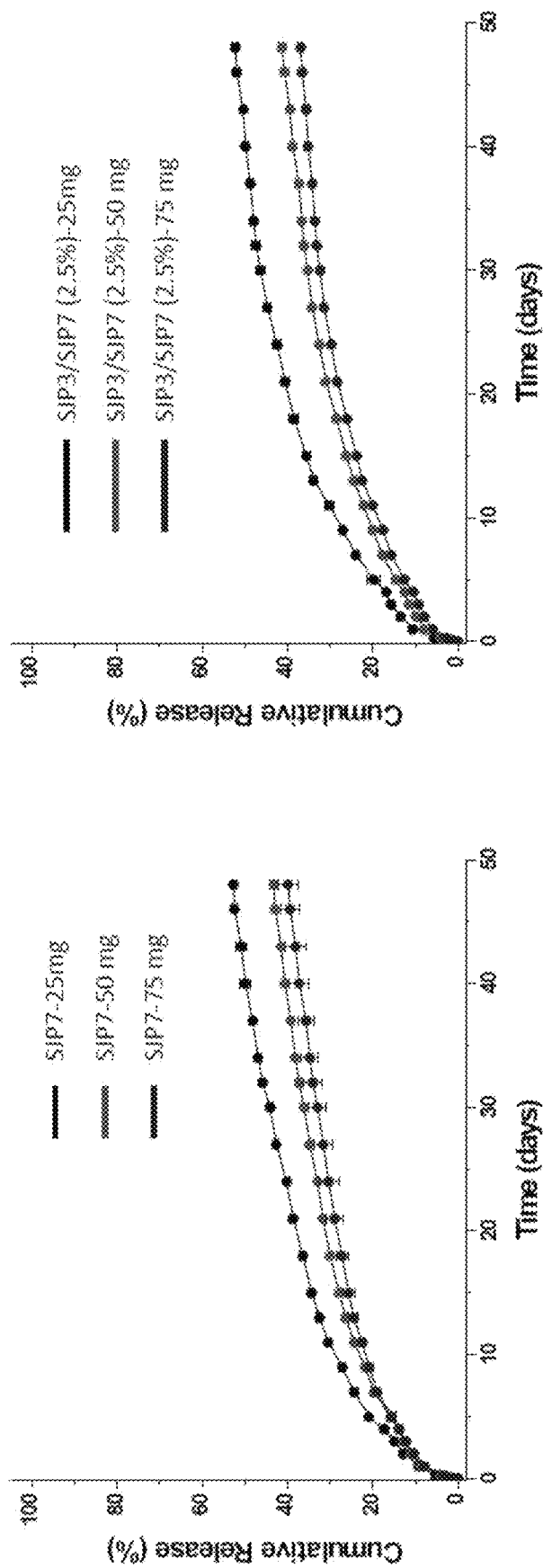
FIG. 97 shows loading and release of Paclitaxel.

FIG. 97 shows loading and release of Paclitaxel.

TABLE 30

Loading and Release of Paclitaxel

| PTX | Disc (mg) | Drug (mg) | Disc Loaded (mg) | Drug content (mg) | DLC (%) | DLE (%) | Depot/ Drug (w/w) |
|---|---|---|---|---|---|---|---|
| SJP7/SJP3 (50/50)-1 | 25.05 | 25.00 | 29.98 | 4.93 | 16.44 | 19.72 | 1/0.20 |
| SJP7/SJP3 (50/50)-2 | 25.36 | 25.00 | 30.67 | 5.31 | 17.31 | 21.24 | 1/0.21 |
| SJP7/SJP3 (75/25)-1 | 27.30 | 25.00 | 32.17 | 4.87 | 15.14 | 19.48 | 1/0.18 |
| SJP7/SJP3 (75/25)-2 | 27.72 | 25.00 | 33.01 | 52.9 | 16.03 | 21.16 | 1/0.19 |
| SJP7/SJP3 (90/10)-1 | 27.99 | 25.00 | 33.03 | 5.04 | 15.26 | 20.16 | 1/0.18 |
| SJP7/SJP3 (90/10)-2 | 27.77 | 25.00 | 32.62 | 4.85 | 14.87 | 19.40 | 1/0.17 |
| SJP7/SJP3 (95/5)-1 | 28.08 | 25.00 | 34.28 | 6.20 | 18.09 | 24.80 | 1/0.22 |

TABLE 30-continued

Loading and Release of Paclitaxel

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7/SJP3 (95/5)-2 | 27.92 | 25.00 | 33.99 | 6.07 | 17.86 | 24.28 | 1/0.22 |
| SJP7/SJP3 (97.5/2.5)-1 | 28.07 | 25.00 | 34.12 | 6.05 | 17.73 | 24.20 | 1/0.22 |
| SJP7/SJP3 (97.5/2.5)-2 | 28.46 | 25.00 | 34.39 | 5.93 | 17.24 | 23.72 | 1/0.21 |
| SJP7/SJP3 (99/1)-1 | 27.20 | 25.00 | 32.36 | 5.16 | 15.95 | 20.64 | 1/0.19 |
| SJP7/SJP3 (99/1)-2 | 28.01 | 25.00 | 33.18 | 5.17 | 15.58 | 20.68 | 1/0.18 |

Figure 98:
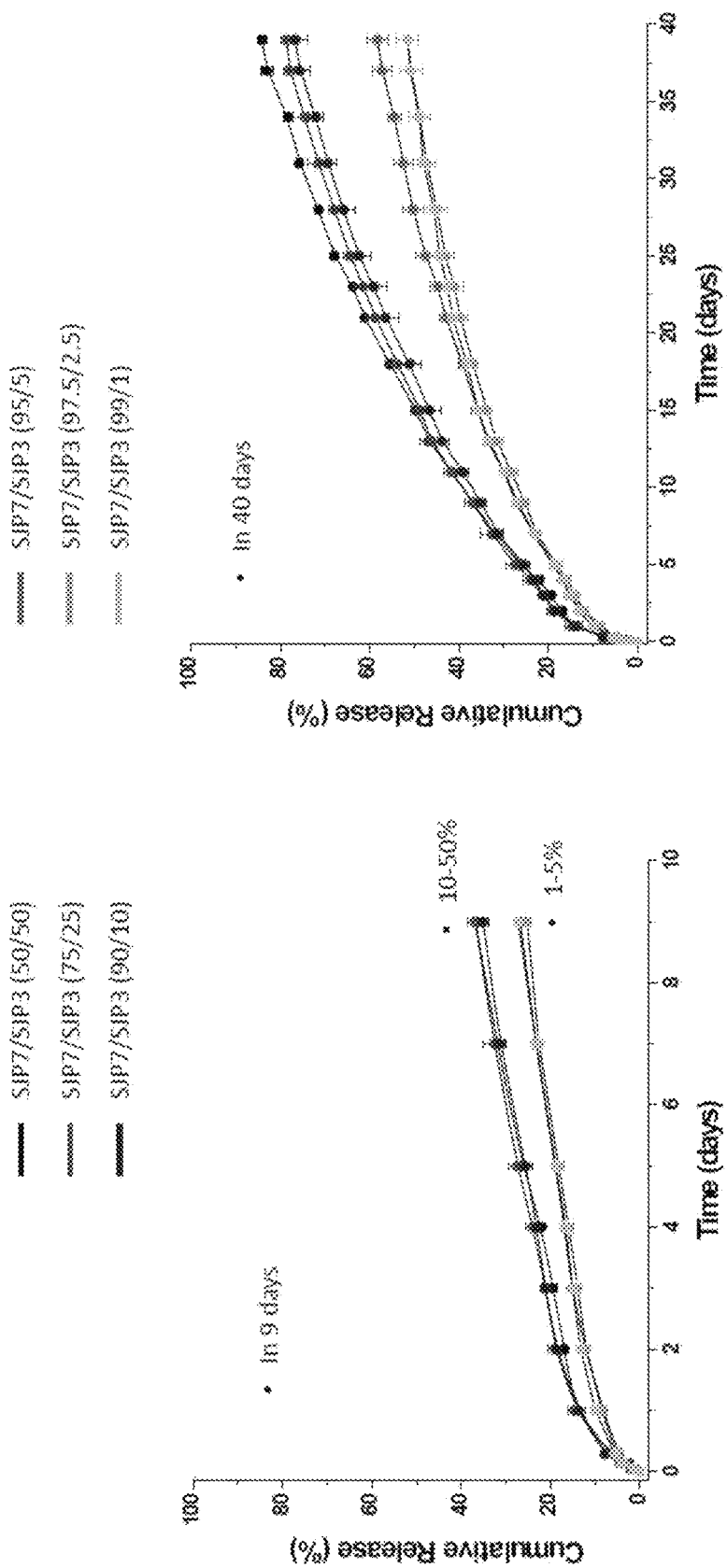
FIG. 98 shows loading and release of Paclitaxel varying amount of PEGylated copolymer.

FIG. 98 shows loading and release of Paclitaxel varying amount of PEGylated copolymer.

Figure 99:
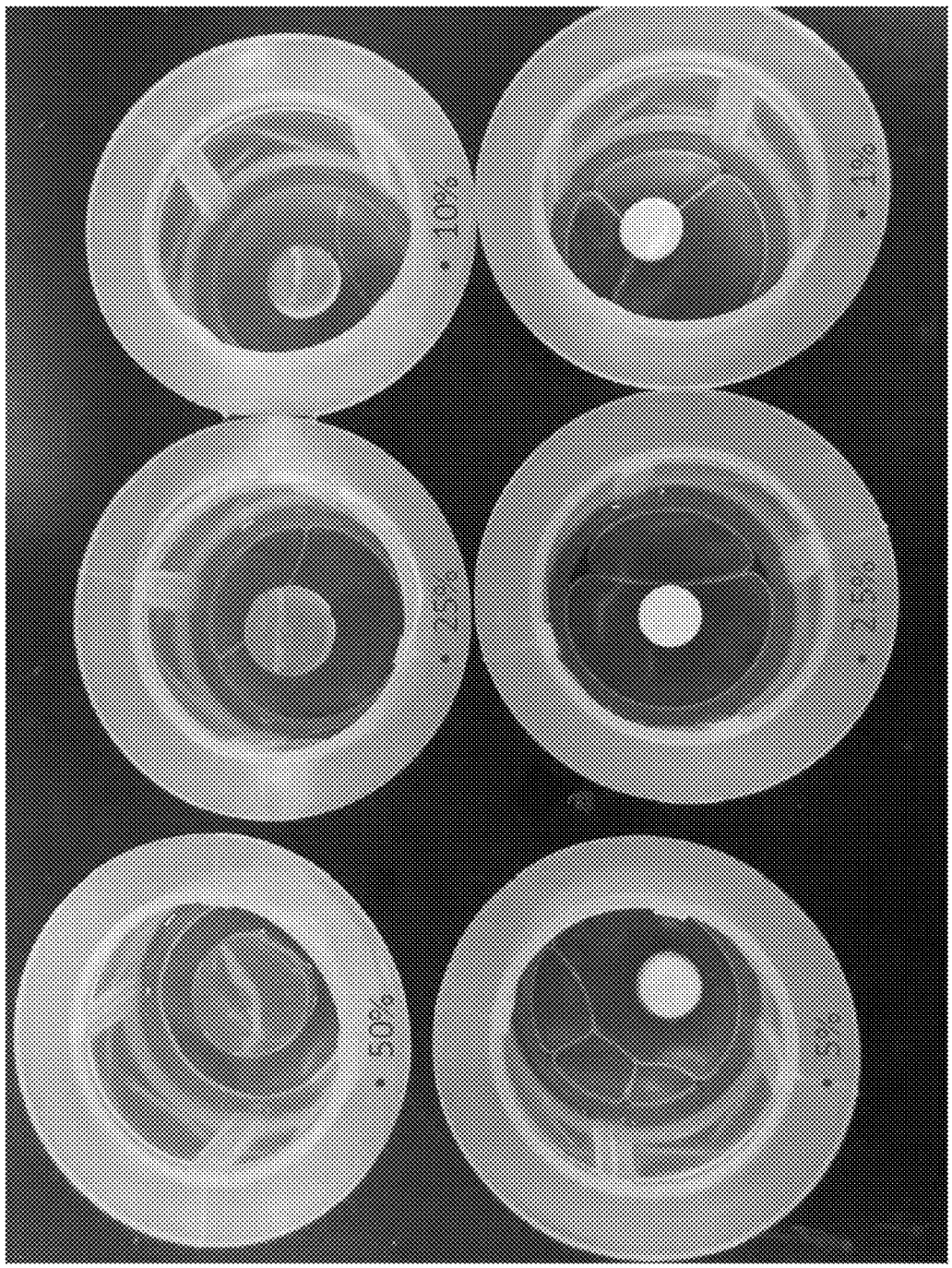
FIG. 99 shows a digital image of a disc during a release experiment.

FIG. 99 shows a digital image of a disc during a release experiment.

Figure 100:
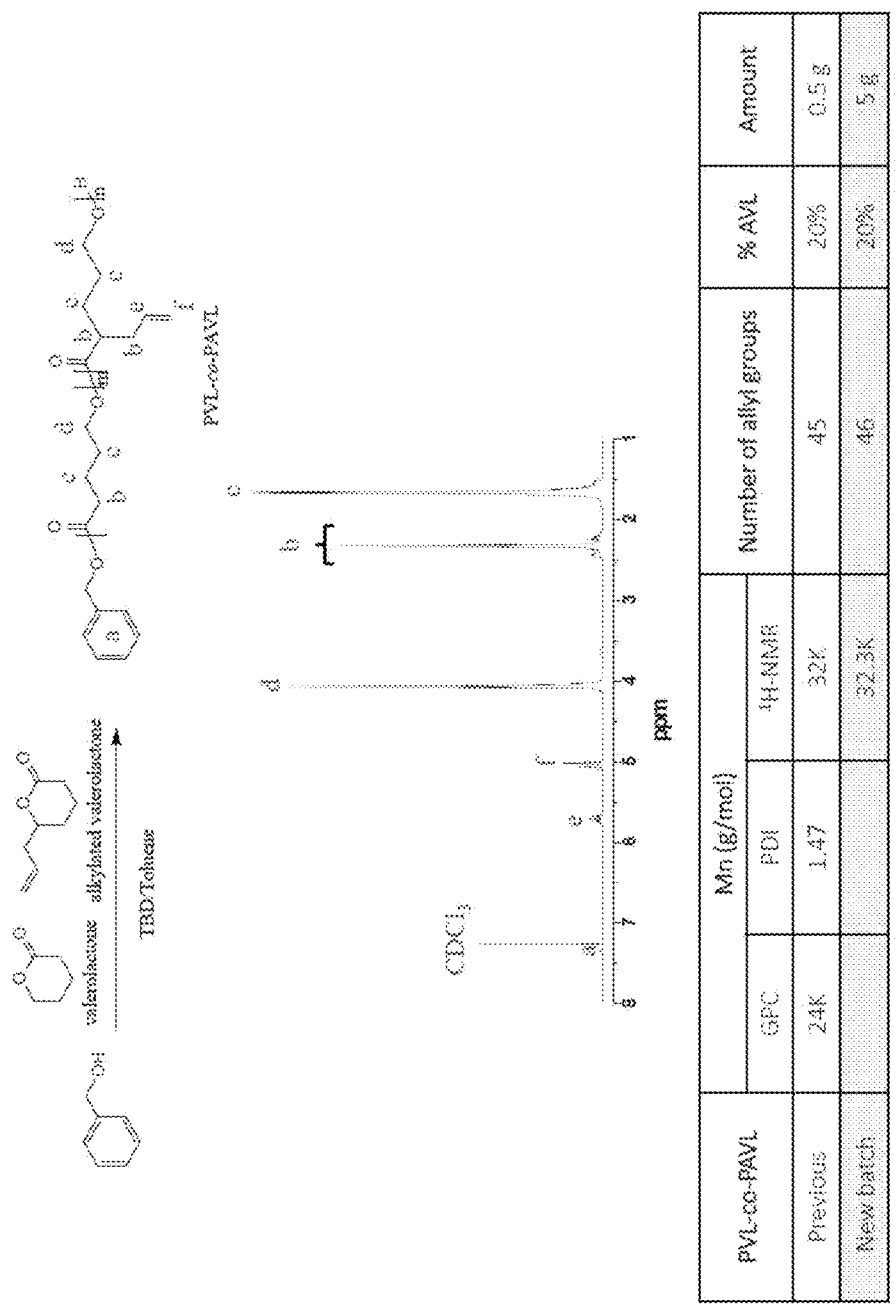
FIG. 100 shows synthesis of PVL-co-PAVL (SJP7), according to an embodiment.

FIG. 100 shows synthesis of PVL-co-PAVL (SJP7), according to an embodiment.

TABLE 31

Loading of Drug X in mesh washed MPs, NaCl MPs and EtOH MPs

| Entry. no | Drug X | Microparticle W/O Drug X loading | Amount of Drug added | Microparticle after Drug X loading | Loaded amount of Drug | DLC (%) | DLE (%) | Drug/Material (w/w) |
|---|---|---|---|---|---|---|---|---|
| 1 | SJP7-Drug X-1 (Mesh) | 47.00 mg | 70 mg | 37 mg[8] | N/M | N/A | N/A | N/A |
|   | SJP7-Drug X-2 (Mesh) | 44.18 mg | 70 mg | 31 mg[8] | N/M | N/A | N/A | N/A |
| 2 | SJP7-Drug X-1 (NaCl) | 39.01 mg | 75 mg | 42.68 mg | 3.66 mg | 9.38 | 4.88 | 0.094/1 |
|   | SJP7-Drug X-2 (NaCl) | 37.23 mg | 75 mg | 39.47 mg | 2.25 mg | 6.03 | 2.99 | 0.060/1 |
| 3 | SJP7-Drug X-1 (EtOH) | 32.85 mg | 75 mg | 30.95 mg | N/M | N/A | N/A | N/A |
|   | SJP7-Drug X-2 (EtOH) | 25.88 mg | 75 mg | 21.18 mg | N/M | N/A | N/A | N/A |

[8]Lower MP mass after drug loading is due to the loss of MPs during the washing process, if we account for the loss of MP during the washing, we can assume that drug loaded into MPs. We will confirm the drug loading by HPLC release.

Figure 101:
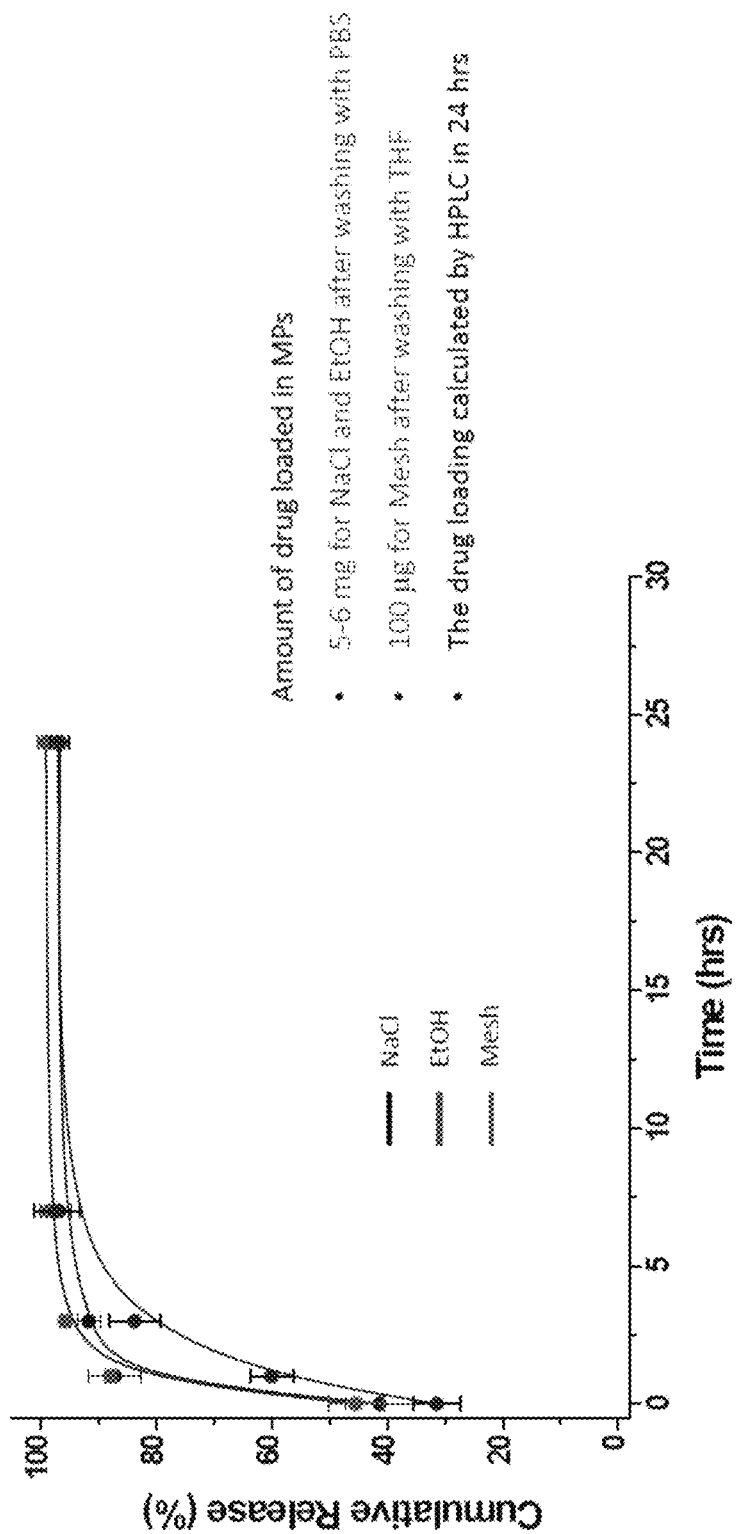
FIG. 101 shows release of Drug X in mesh washed MPs, NaCl MPs and EtOH MPs.

FIG. 101 shows release of Drug X in mesh washed MPs, NaCl MPs and EtOH MPs.

TABLE 32

Drug X loading and release using mesh washed MPs, NaCl MPs and EtOH MPs.

| Entry. no | Drug X | Microparticle before Drug X loading | Amount of Drug added | Microparticle after Drug X loading | Mass difference by Balance | Total amount of drug released | Solution for washing free drug |
|---|---|---|---|---|---|---|---|
| 1 | SJP7-Drug X-1 (Mesh) | 47.00 mg | 70 mg | 37 mg | No measurable due to loss MPs | 0.085 mg | THF |
|   | SJP7-Drug X-2 (Mesh) | 44.18 mg | 70 mg | 31 mg | No measurable due to loss MPs | 0.065 mg | THF |
| 2 | SJP7-Drug X-1 (NaCl) | 39.01 mg | 75 mg | 42.68 mg | 3.66mg | 5.67 mg | PBS |
|   | SJP7-Drug X-2 (NaC1) | 37.23 mg | 75 mg | 39.47 mg | 2.25mg | 6.73 mg | PBS |
| 2 | SJP7-Drug X-1 (EtOH) | 32.85 mg | 75 mg | 30.95 mg | No measurable due to loss MPs | 6.47 mg | PBS |

TABLE 32-continued

Drug X loading and release using mesh washed MPs, NaCl MPs and EtOH MPs.

| Entry. no | Drug X | Microparticle before Drug X loading | Amount of Drug added | Microparticle after Drug X loading | Mass difference by Balance | Total amount of drug released | Solution for washing free drug |
|---|---|---|---|---|---|---|---|
| | SJP7-Drug X-2 (EtOH) | 25.88 mg | 75 mg | 21.18 mg | No measurable due to loss MPs | 5.00 mg | PBS |

Figure 102:
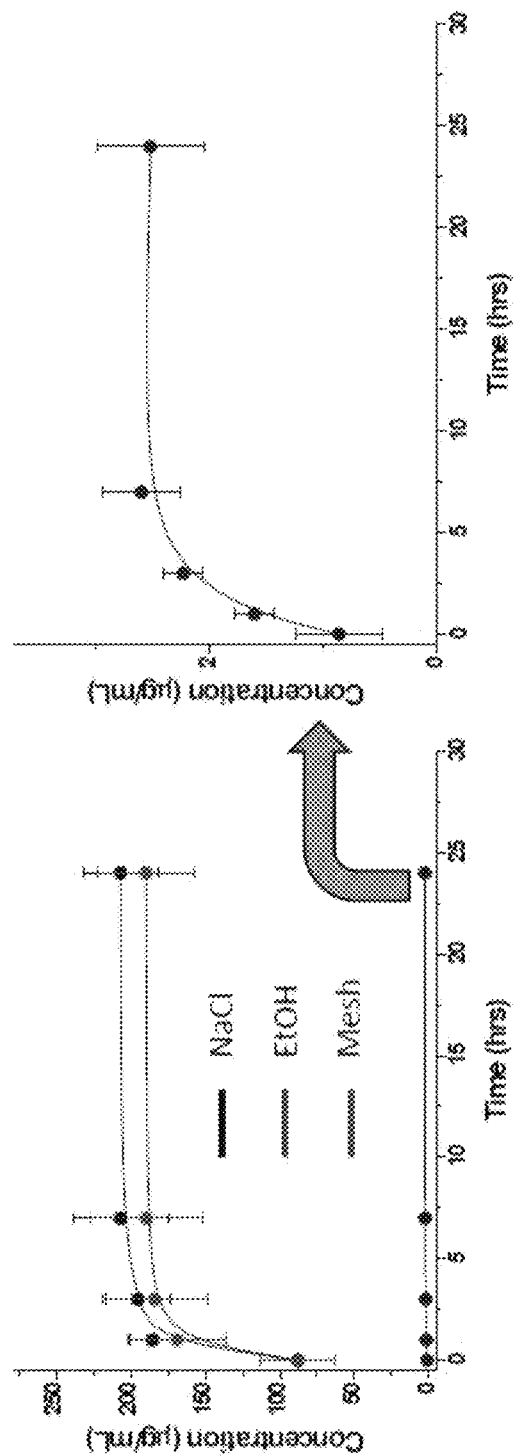
FIG. 102 shows Drug X loading and release using mesh washed MPs, NaCl MPs and EtOH MPs.

FIG. 102 shows Drug X loading and release using mesh washed MPs, NaCl MPs and EtOH MPs. There is no significant difference with Mesh, NaCl, and EtOH for release rate. Drug X loaded MPs show insufficient washing (high t=0) and burst release in a day.

FIG. 103 shows SEM images of MPs before drug loading. NaCl and EtOH does not have significant effect on surface morphology of MPs. MPs including smooth surface and pores exist more randomly. Scale bar will be added.

TABLE 33

Drug X loading and release using Mesh washed MPs NaCl MPs and EtOH MPs

| Entry. no | Drug X | Microparticle before Drug X loading | Amount of Drug added | Microparticle after Drug X loading | Mass difference by Balance | Total amount of drug released | Solution for washing free drug |
|---|---|---|---|---|---|---|---|
| 1 | SJP7-Drug X-1 | 21.14 mg | 50 mg | 25.54 mg | 4.40 mg | 6.4 mg | PBS |
| 2 | SJP7-Drug X-1 | 23.75 mg | 50 mg | 22.54 mg | Most drug washed out | N/A | Mobile Phase |
| | SJP7-Drug X-2 | 23.76 mg | 50 mg | 23.06 mg | Most drug washed out | N/a | Mobile Phase |

Figure 104:
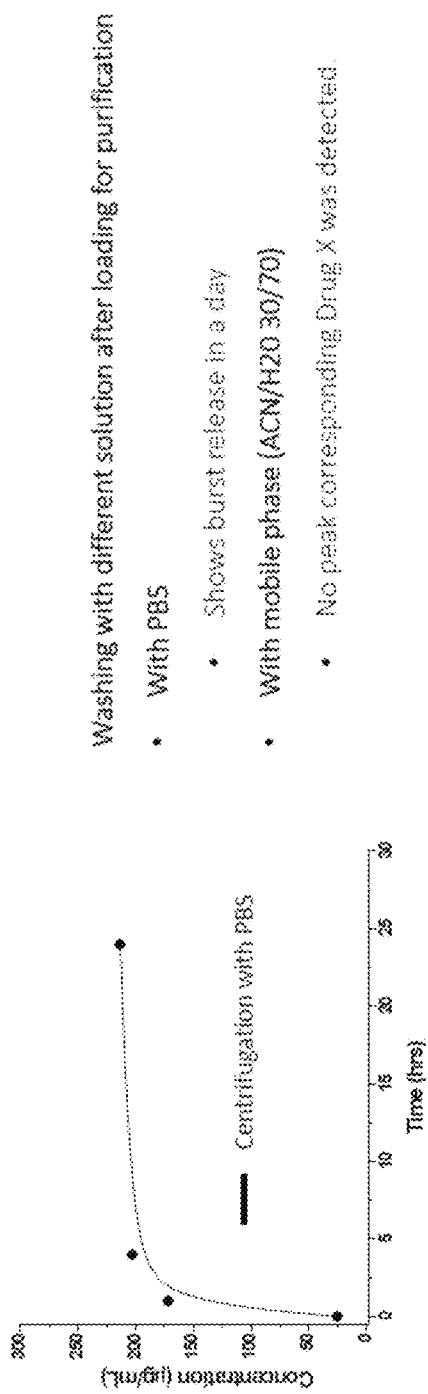
FIG. 104 shows Drug X Loading and release using MPs after washing with different solution.

FIG. 104 shows Drug X Loading and release using MPs after washing with different solution.

TABLE 34

Drug X Loading and release using Mesh washed MPs, NaCl MPs and EtOH MPs.

| Entry. no | Drug X | Microparticle before Drug X loading | Amount of Drug added | Total amount of drug released | Solution for washing free drug | Amount of release media |
|---|---|---|---|---|---|---|
| 1 | SJP7-Drug X-1 | 25.11 mg | 50 mg | 13.3 mg | PBS 10 mL X 2 H$_2$O 10 mL X 1 | 30 mL |
| 2 | SJP7-Drug X-1 | 24.70 mg | 50 mg | 15.4 mg | PBS 10 mL X 2 H$_2$O 10 mL X 1 | 60 mL |

Figure 105:
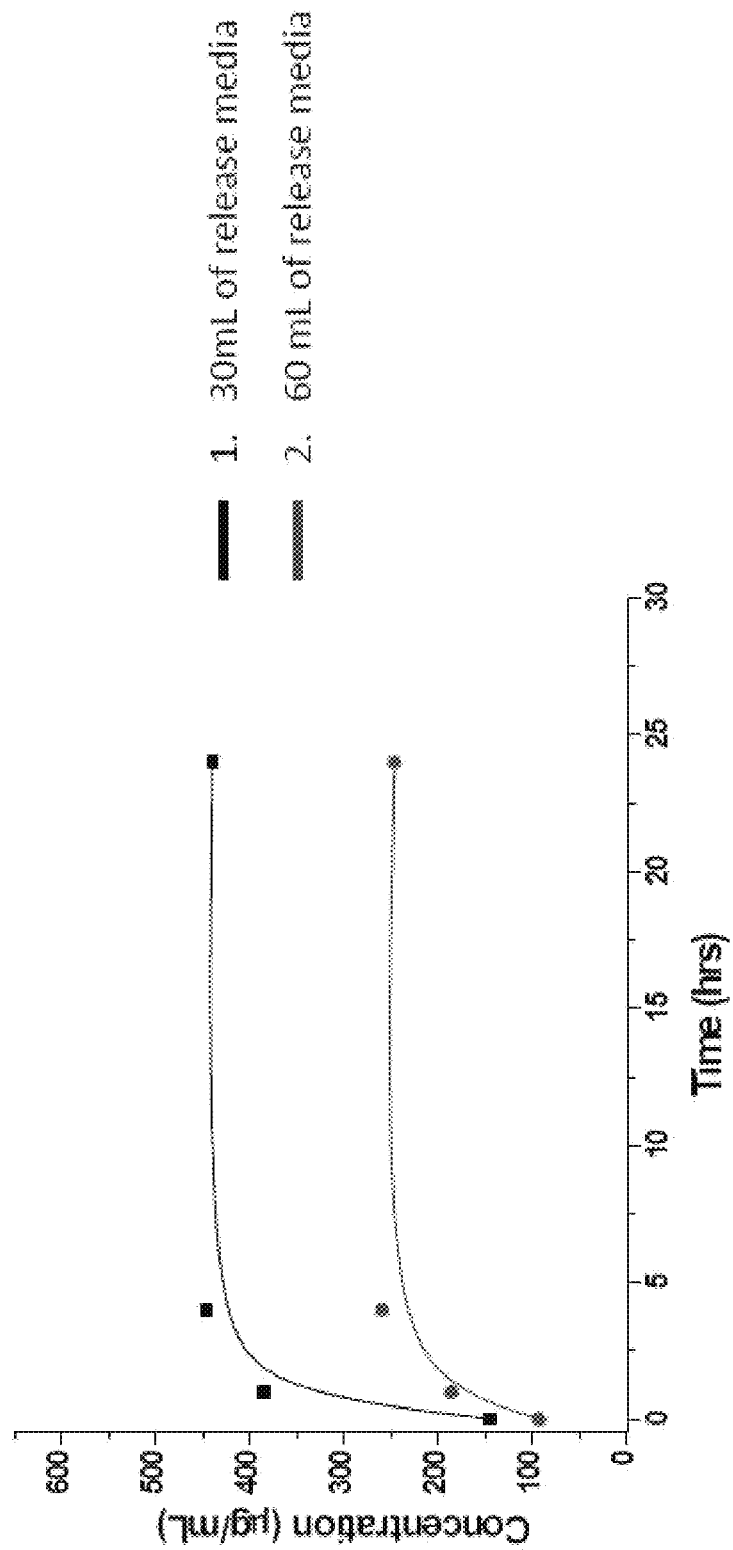

FIG. 105 shows Drug X Loading and release using Mesh washed MPs, NaCl MPs and EtOH MPs. There is no issue of saturation as concentration with 60 mL of release media shows half concentration of 30 mL and the same amount of Drug X release.

Figure 106:
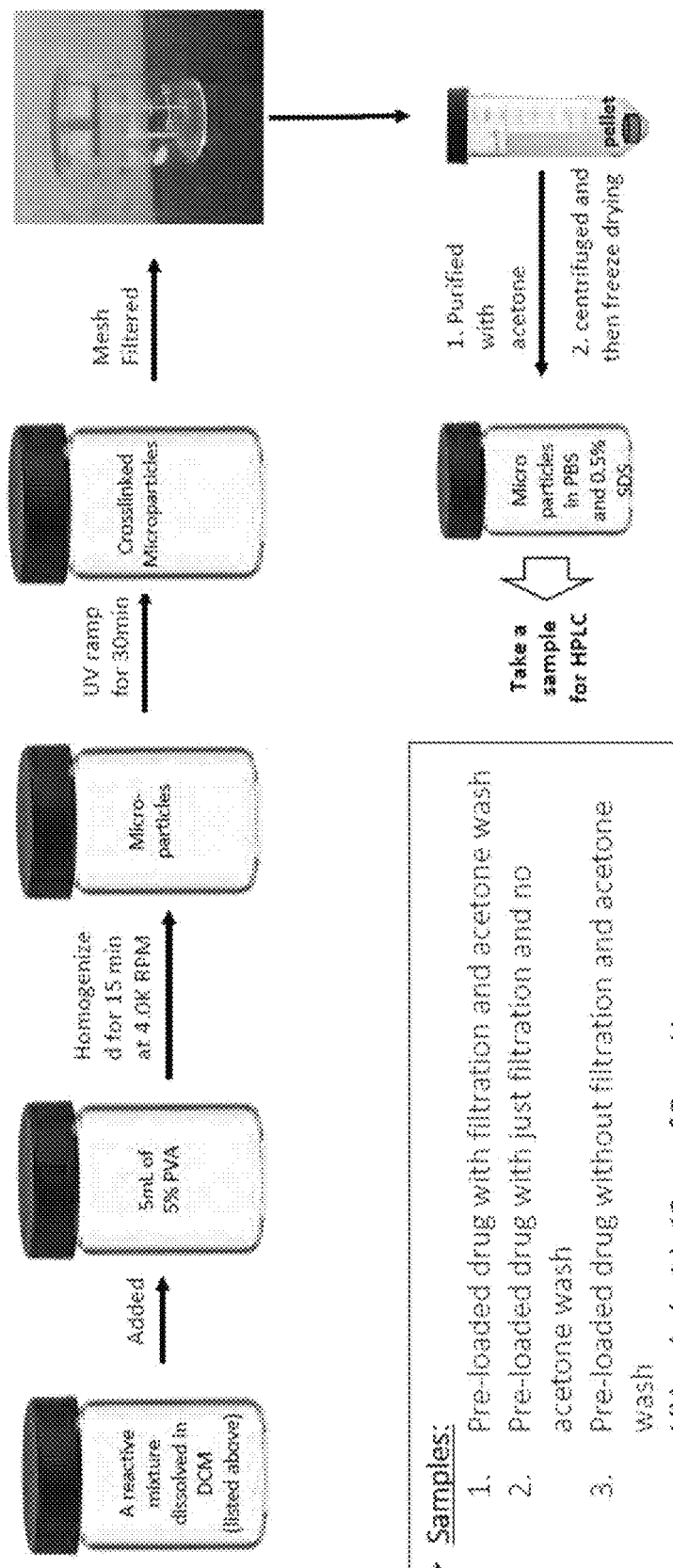

FIG. 106 shows pre-loading of Drug X into a microparticle, according to an embodiment.

Result of Pre-loading MP with Drug X:

None of the samples showed drug peak for the 24 hours release study

Conclusion:

None of the samples, including the non-washed MP, did not show any release after 24 hours. This suggests that the drug might have washed out.

TABLE 35

PTX loading and release using MPs

| Entry. no | PTX | Microparticle before loading (mg) | Amount of Drug added (mg) | Amount of Drug Extracted (mg) | DLC (%) | Solution for washing free drug | Amount of release media |
|---|---|---|---|---|---|---|---|
| 1 | SJP7-PTX-1 | 10.20 | 20.00 | 2.67 (0.7)$^{STD}$ | 20.75 | ACN/H2O (55/45) 10 mL X 1 H$_2$O 10 mL X 1 | 200 mL |
|   | SJP7-PTX-2 | 10.13 | 20.00 | 2.67 (0.7)$^{STD}$ | 20.86 | ACN/H2O (55/45) 10 mL X 1 H$_2$O 10 mL X 1 | 200 mL |
| 2 | SJP7-PTX-1 | 10.10 | 20.00 | 6.19 (0.14)$^{STD}$ | 38.00 | ACN/H2O (55/45) 10 mL X 1 H$_2$O 10 mL X 1 | 200 mL |
|   | SJP7-PTX-2 | 10.06 | 20.00 | 6.19 (0.14)$^{STD}$ | 37.86 | ACN/H2O (55/45) 10 mL X 1 H$_2$O 10 mL X 1 | 200 mL |

Figure 107:
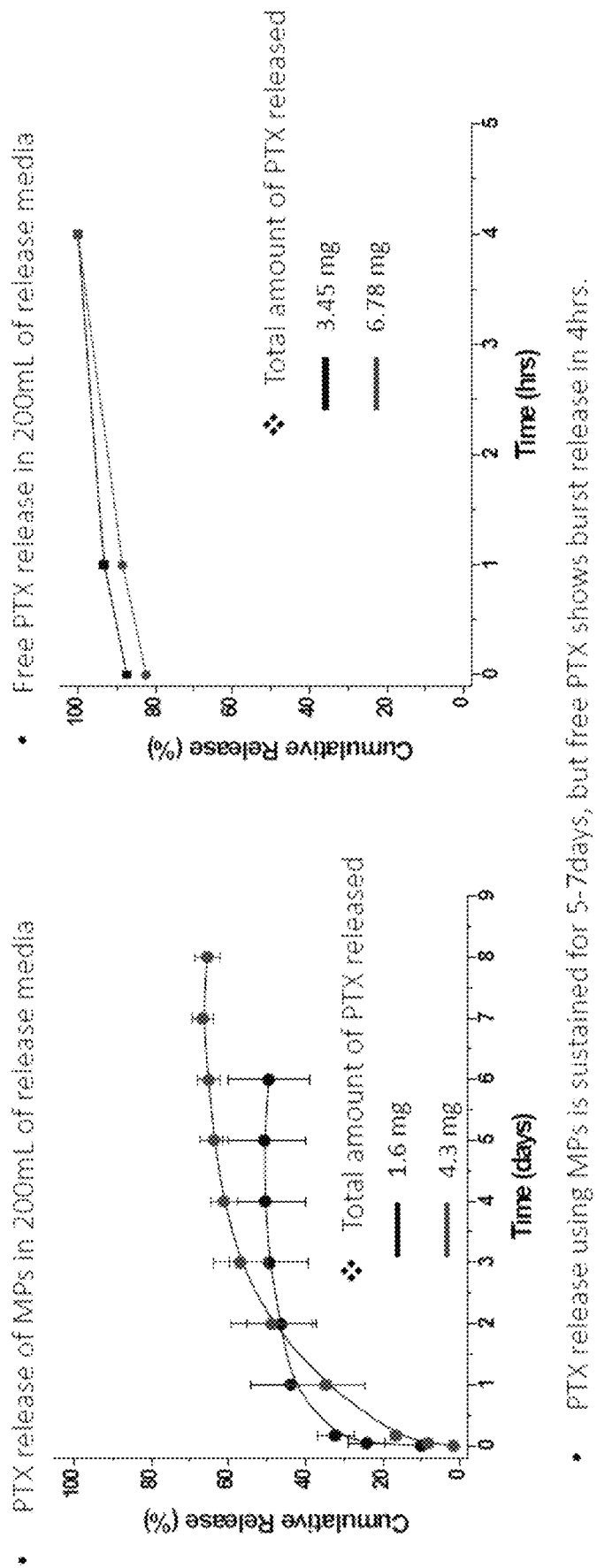

FIG. 107 shows PTX loading and release using MPs.

Pre-loading of MP is not show release. This may be due to drug being washed out during the acetone wash step (to remove unreacted residue) and mesh filtration step. Pre-loading of MP that did not have any washing involved also did not show any drug release. Drug loading of pre-loaded MP to be confirmed with extraction.

Figure 108:
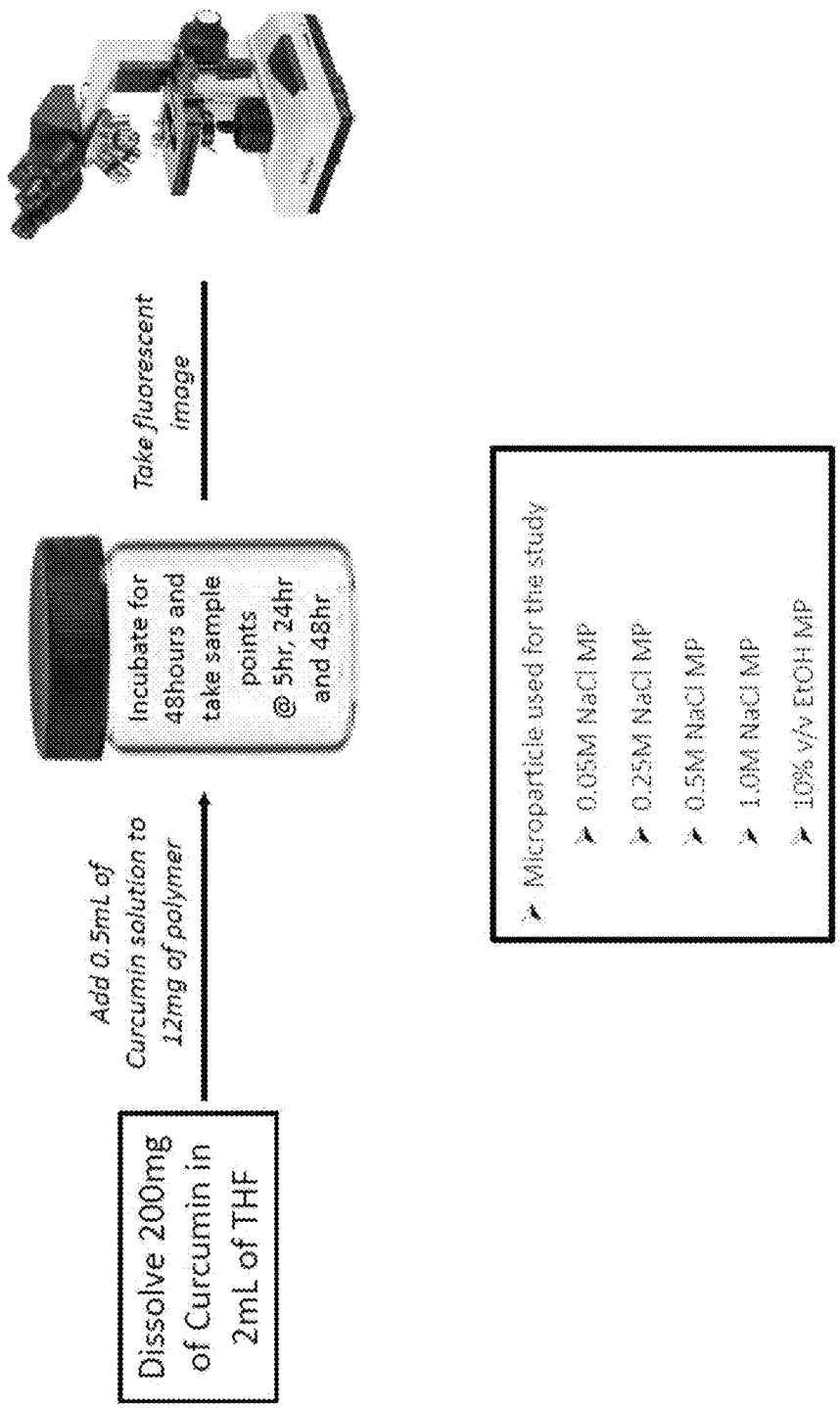

FIG. 108 shows curcumin post-loading protocol for NaCl MP and EtOH MP.

Figure 109:
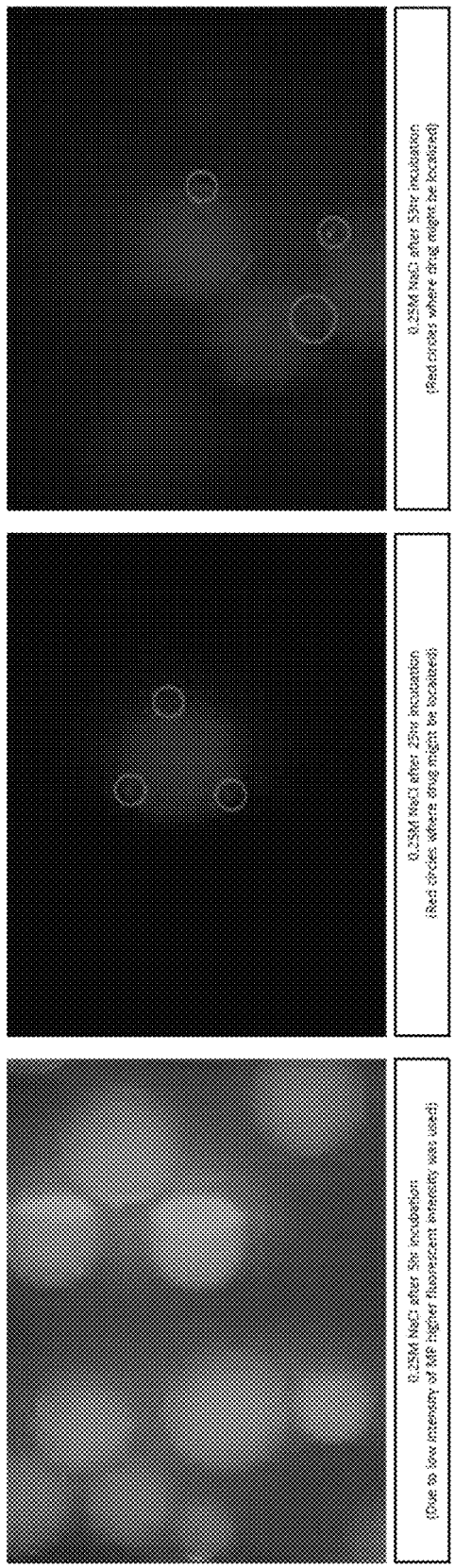

FIG. 109 shows fluorescent Image of Curcumin loaded MP (0.25M NaCl) Different incubation time.

Figure 110:
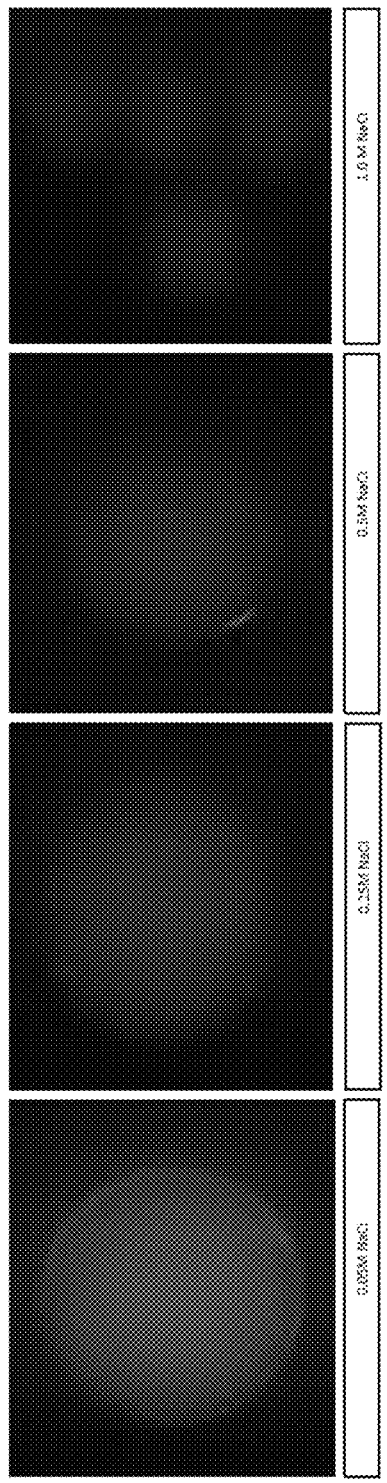

FIG. 110 shows fluorescent image of curcumin loaded MP Different concentration of NaCl and EtOH MP (after 24 hour incubation).

Figure 111:
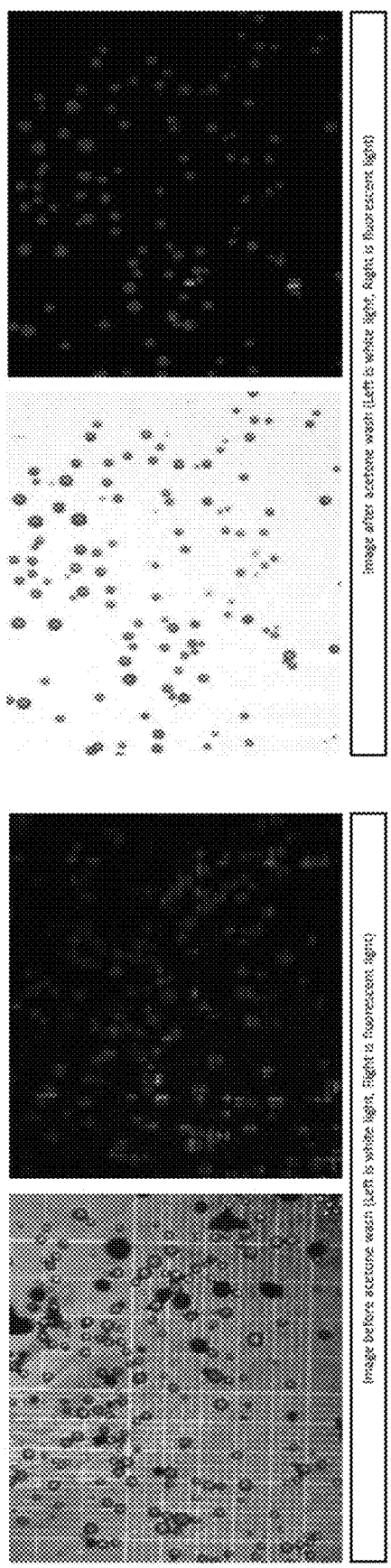

FIG. 111 shows a fluorescent image of curcumin loaded MP before and after wash. There is no difference between before and after washing in terms of fluorescent. The microparticles still retained curcumin even after acetone wash. This suggests that drug is staying inside the microparticle even with organic solvent wash. However, we still cannot determine how much of drug remained inside the microparticle based on the fluorescent image.

Figure 112:
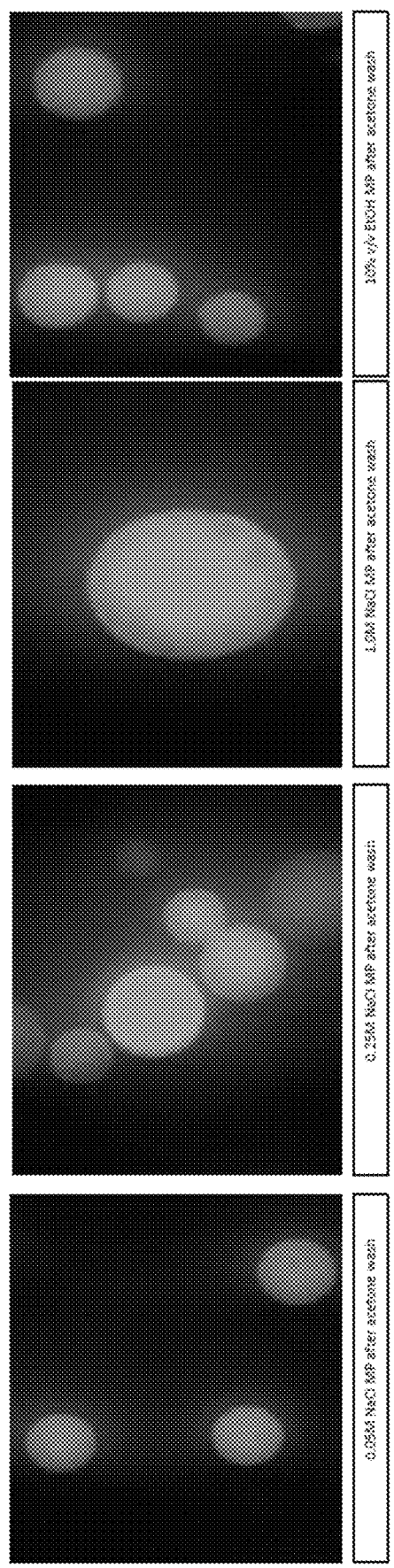

FIG. 112 shows a fluorescent image of curcumin loaded MP before and after wash.

Figure 113:
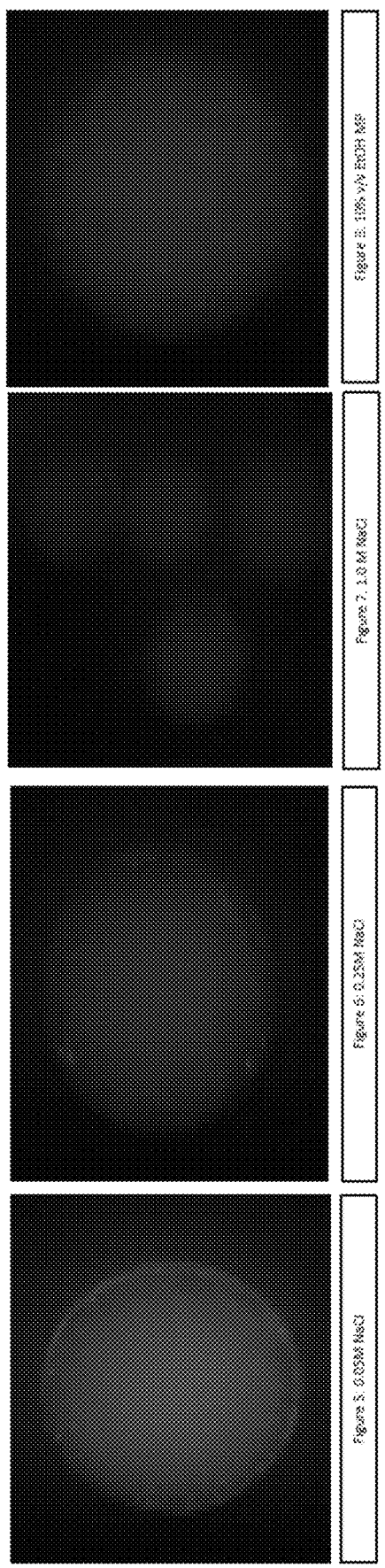

FIG. 113 shows a fluorescent image of curcumin loaded MP before washing. After acetone wash, NaCl or EtOH seem to have no effect on the loading of the drug. After acetone wash, the fluorescent intensity increases, which is probably due to less interference from the background solution after the wash.

Protocol for degradation

Prepare a PBS solution (1 mL) containing *pseudomonas* (PS) lipase (0.5 mg/mL, pH 7.5)

Place depots (20-23 mg) in a vial containing 1 mL of the prepared solution at 37° C.

Change enzyme solution everyday to avoid proliferation of bacteria.

Samples are withdrawn from the degradation medium, washed thoroughly with distilled water for 1 day and then freeze-dried.

Measure weight loss of depot with a analytical balance.

Sample for degradation study
SJP7×HDT
SJP7×ECL
SJP7/SJP3 (2.5%)×HDT
SJP7/SJP3 (2.5%)×ECL

TABLE 36

Mass change by enzymatic degradation

| Entry No. | Sample | Initial weight (mg) | After a week (mg) | A month (mg) | Two month (mg) | Total weight loss (mg) |
|---|---|---|---|---|---|---|
| 1 | SJP7 X HDT-1 | 23.32 | 23.26 | 23.13 | 22.99 | 0.33 |
|   | SJP7 X HDT-2 | 24.18 | 24.12 | 23.99 | 23.86 | 0.32 |
| 2 | SJP7 X ECL-1 | 22.10 | 21.98 | 21.94 | 21.75 | 0.35 |
|   | SJP7 X ECL-2 | 22.92 | 22.67 | 22.55 | 22.44 | 0.48 |
| 3 | SJP7/SJP3 (2.5%) X HDT-1 | 21.96 | 21.83 | 21.72 | 21.67 | 0.29 |
|   | SJP7/SJP3 (2.5%) X HDT-2 | 21.23 | 21.11 | 21.06 | 20.92 | 0.31 |
| 4 | SJP7/SJP3 (2.5%) X HDT-1 | 22.19 | 21.99 | 21.86 | 21.78 | 0.41 |
|   | SJP7/SJP3 (2.5%) X HDT-2 | 22.47 | 22.33 | 22.20 | 22.11 | 0.36 |

It has been two month, and 0.3-0.4 mg (1.5-2%) decrease for all the samples. Cross-linker and a small amount of PEGylated copolymer does not have a significant effect on degradation so far. We will check degradation with higher concentration of lipase solution (1 mg/1 mL). We are also looking at other lipase.

TABLE 37

Blend system consisting of PVL-co-PAVL (SJP7) and PEGylated copolymer (SJP3) with hexanedithiol

| | Disc (mg) | Drug (mg) | Disc Loaded (m) | Drug content (mg) | DLC (%) | DLE (%) | Depot/Drug (w/w) |
|---|---|---|---|---|---|---|---|
| SJP7/SJP3 (50/50)-1 | 25.08 | 25.00 | 31.99 | 6.91 | 21.60 | 27.64 | 1/0.28 |
| SJP7/SJP3 (50/50)-2 | 25.68 | 25.00 | 32.23 | 6.55 | 20.32 | 26.20 | 1/0.26 |
| SJP7/SJP3 (75/25)-1 | 28.05 | 25.00 | 34.47 | 6.42 | 18.62 | 25.68 | 1/0.23 |
| SJP7/SJP3 (75/25)-2 | 27.44 | 25.00 | 33.70 | 6.26 | 18.58 | 25.04 | 1/0.23 |
| SJP7/SJP3 (90/10)-1 | 27.87 | 25.00 | 34.31 | 6.44 | 18.77 | 25.76 | 1/0.23 |
| SJP7/SJP3 (90/10)-2 | 27.24 | 25.00 | 33.53 | 6.29 | 18.76 | 25.16 | 1/0.23 |
| SJP7/SJP3 (95/5)-1 | 28.25 | 25.00 | 35.03 | 6.78 | 19.35 | 27.12 | 1/0.24 |
| SJP7/SJP3 (95/5)-2 | 28.10 | 25.00 | 34.45 | 6.35 | 18.43 | 25.40 | 1/0.22 |
| SJP7/SJP3 (97.5/2.5)-1 | 28.20 | 25.00 | 34.52 | 6.32 | 18.31 | 25.28 | 1/0.22 |
| SJP7/SJP3 (97.5/2.5)-2 | 28.01 | 25.00 | 34.43 | 6.42 | 18.65 | 25.68 | 1/0.23 |
| SJP7/SJP3 (99/1)-1 | 27.72 | 25.00 | 34.12 | 6.40 | 18.76 | 25.60 | 1/0.23 |
| SJP7/SJP3 (99/1)-2 | 27.68 | 25.00 | 34.10 | 6.42 | 18.83 | 25.68 | 1/0.23 |

Figure 114:
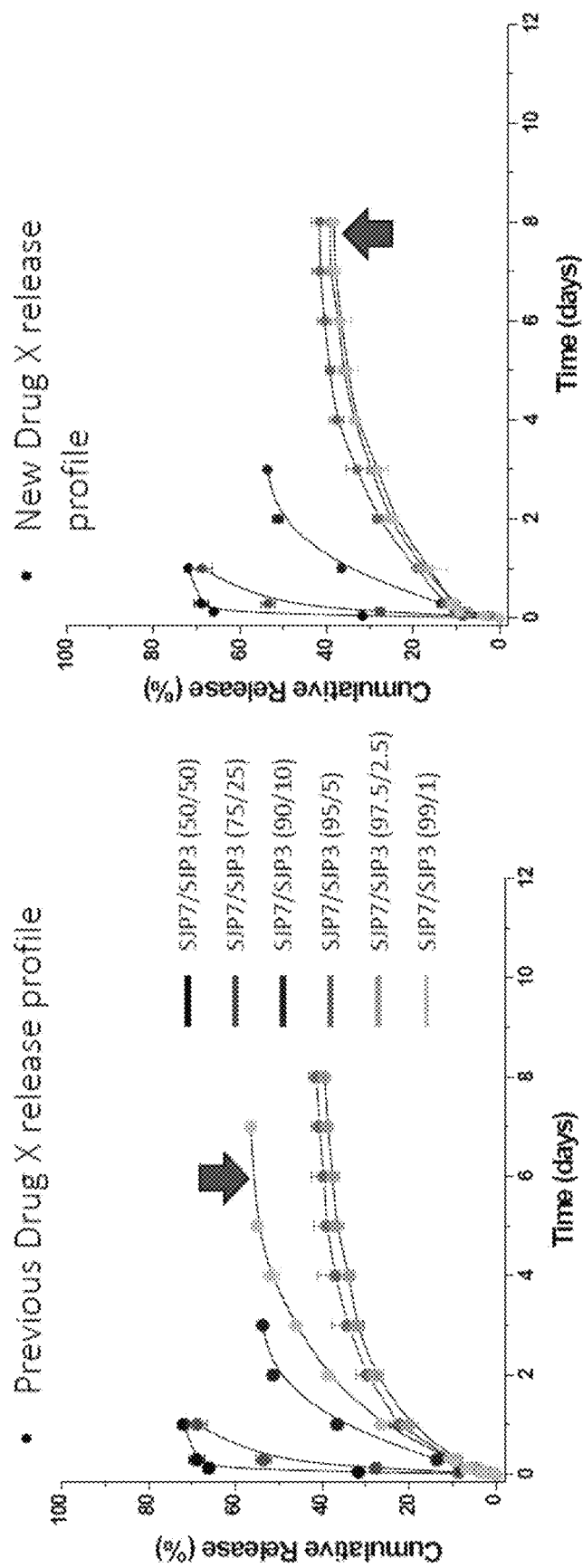

FIG. 114 shows a blend system of SJP7 and SJP3 with hexanedithiol.

TABLE 38

Loading of Paclitaxel varying amount of PEGylated copolymer

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7-1 | 28.38 | 25.00 | 33.84 | 5.46 | 16.13 | 21.84 | 1/0.19 |
| SJP7-2 | 26.27 | 25.00 | 31.87 | 5.60 | 17.57 | 22.40 | 1/0.21 |
| SJP7-1 | 28.30 | 50.00 | 38.70 | 10.40 | 26.87 | 20.80 | 1/0.37 |
| SJP7-2 | 27.72 | 50.00 | 38.06 | 10.34 | 27.17 | 20.68 | 1/0.37 |
| SJP7-1 | 28.62 | 75.00 | 41.24 | 12.62 | 30.60 | 16.83 | 1/0.44 |
| SJP7-2 | 26.11 | 75.00 | 38.45 | 12.34 | 32.09 | 16.45 | 1/0.47 |
| SJP7/SJP3 (97.5/2.5)-1 | 27.63 | 25.00 | 33.33 | 5.70 | 17.10 | 22.80 | 1/0.20 |
| SJP7/SJP3 (97.5/2.5)-2 | 27.48 | 25.00 | 33.11 | 5.63 | 17.00 | 22.52 | 1/0.20 |
| SJP7/SJP3 (97.5/2.5)-1 | 27.98 | 50.00 | 38.38 | 10.40 | 27.10 | 20.80 | 1/0.37 |
| SJP7/SJP3 (97.5/2.5)-2 | 27.91 | 50.00 | 37.99 | 10.08 | 26.53 | 20.16 | 1/0.36 |
| SJP7/SJP3 (97.5/2.5)-1 | 28.29 | 75.00 | 41.54 | 13.25 | 31.90 | 17.67 | 1/0.47 |
| SJP7/SJP3 (97.5/2.5)-2 | 28.07 | 75.00 | 41.23 | 13.16 | 31.92 | 17.55 | 1/0.47 |

Figure 115:
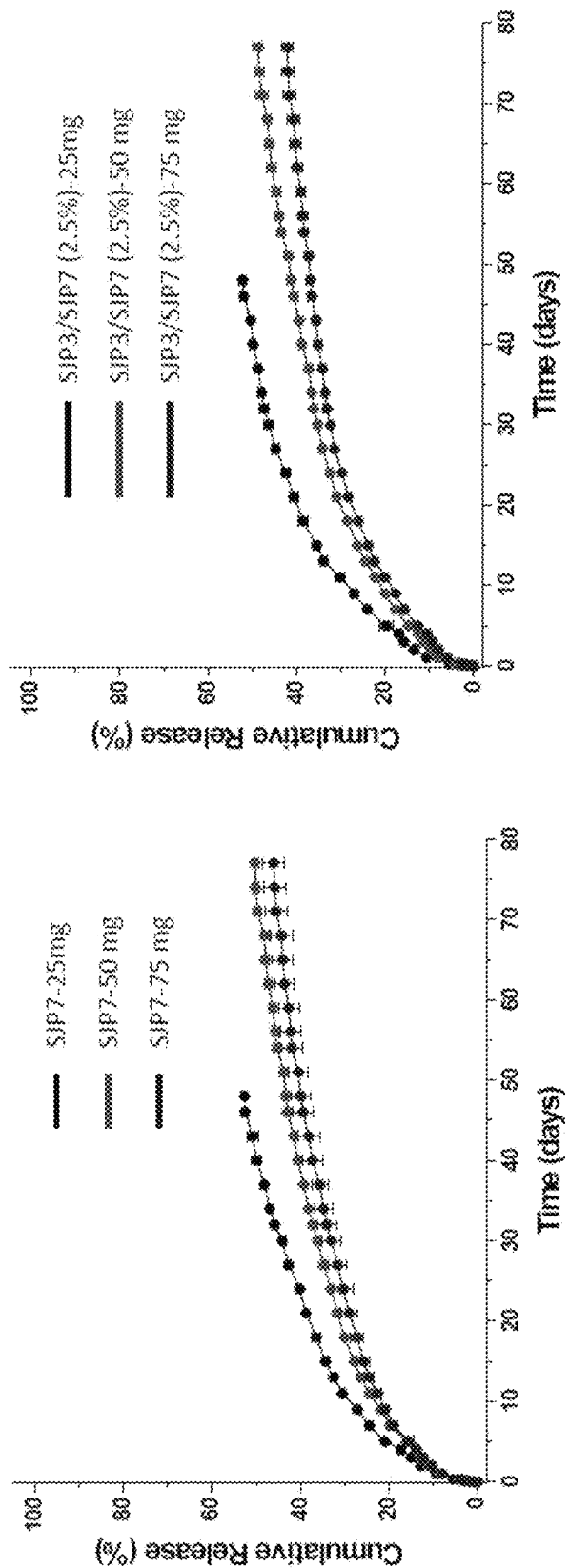

FIG. 115 shows release of Paclitaxel varying amount of PEGylated copolymer. A higher loading yields a slower release. There is no significant difference between SJP7 and its blend with PEGylatec copolymer (2.5%). Release study is done only for loading with 25 mg.

TABLE 39

Loading of Paclitaxel varying amount of PEGylated copolymer

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7/SJP3 (50/50)-1 | 25.05 | 25.00 | 29.98 | 4.93 | 16.44 | 19.72 | 1/0.20 |
| SJP7/SJP3 (50/50)-2 | 25.36 | 25.00 | 30.67 | 531 | 17.31 | 21.24 | 1/0.21 |
| SJP7/SJP3 (75/25)-1 | 27.30 | 25.00 | 32.17 | 4.87 | 15.14 | 19.48 | 1/0.18 |
| SJP7/SJP3 (75/25)-2 | 27.72 | 25.00 | 33.01 | 5.29 | 16.03 | 21.16 | 1/0.19 |
| SJP7/SJP3 (90/10)-1 | 27.99 | 25.00 | 33.03 | 5.04 | 15.26 | 20.16 | 1/0.18 |
| SJP7/SJP3 (90/10)-2 | 27.77 | 25.00 | 32.62 | 4.85 | 14.87 | 19.40 | 1/0.17 |
| SJP7/SJP3 (95/5)-1 | 28.08 | 25.00 | 34.28 | 6.20 | 18.09 | 24.80 | 1/0.22 |
| SJP7/SJP3 (95/5)-2 | 27.92 | 25.00 | 33.99 | 6.07 | 17.86 | 24.28 | 1/0.22 |
| SJP7/SJP3 (97.5/2.5)-1 | 28.07 | 25.00 | 34.12 | 6.05 | 17.73 | 24.20 | 1/0.22 |
| SJP7/SJP3 (97.5/2.5)-2 | 28.46 | 25.00 | 34.39 | 5.93 | 17.24 | 23.72 | 1/0.21 |
| SJP7/SJP3 (99/1)-1 | 27.20 | 25.00 | 32.36 | 5.16 | 15.95 | 20.64 | 1/0.19 |
| SJP7/SJP3 (99/1)-2 | 28.01 | 25.00 | 33.18 | 15.17 | 15.58 | 20.68 | 1/0.18 |

Amount of PTX loaded in disc is similar regardless of amount of PEGylated copolymer.

Figure 116:
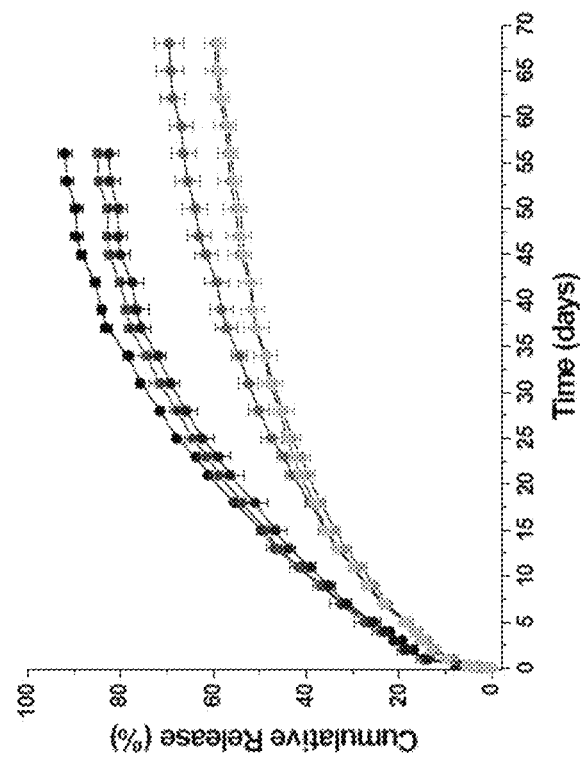

FIG. 116 shows release of Paclitaxel varying amount of PEGylated copolymer.

FIG. 117 shows Drug X loading and release in release media at pH 6.

Protocol for Degradation:
Prepare a PBS solution (1 mL) containing *pseudomonas* (PS) lipase (1 mg/mL, pH 7.5)

Place depots (20-23 mg) in a vial containing 1 mL of the prepared solution at 37° C.

Change enzyme solution everyday to avoid proliferation of bacteria.

Samples are withdrawn from the degradation medium, washed thoroughly with distilled water for 1 day and then freeze-dried.

Measure weight loss of depot with a analytical balance.

TABLE 40

Mass change by enzymatic degradation

| Entry No. | Sample | Initial weight (mg) | After a week (mg) | A month (mg) | Two month (mg) | Three month (mg) | Total weight loss (mg) |
|---|---|---|---|---|---|---|---|
| 1 | SJP7 X HDT-1 | 23.32 | 23.26 | 23.13 | 22.99 | 22.92 | 0.4 |
|   | SJP7 X HDT-2 | 24.18 | 24.12 | 23.99 | 23.86 | 23.57 | 0.61 |
| 2 | SJP7 X ECL-1 | 22.10 | 21.98 | 21.94 | 21.75 | 21.45 | 0.65 |
|   | SJP7 X ECL-2 | 22.92 | 22.67 | 22.55 | 22.44 | 22.08 | 0.84 |
| 3 | SJP7/SJP3 (2.5%) X HDT-1 | 21.96 | 21.83 | 21.72 | 21.67 | 21.61 | 0.35 |
|   | SJP7/SJP3 (2.5%) X HDT-2 | 21.23 | 21.11 | 21.06 | 20.92 | 20.75 | 0.48 |
| 4 | SJP7/SJP3 (2.5%) X HDT-1 | 22.19 | 21.99 | 21.86 | 21.78 | 21.50 | 0.69 |
|   | SJP7/SJP3 (2.5%) X HDT-2 | 22.47 | 22.33 | 22.20 | 22.11 | 21.70 | 0.77 |

TABLE 41

Mass change by enzymatic degradation of blended discs

| Entry No. | Sample (w/w) | Initial weight (mg) | After a week (mg) | Two weeks (mg) | Total weight loss (mg) | Total weight loss (mg) |
|---|---|---|---|---|---|---|
| 1 | SJP3/SJP7-1% x HDT-1 | 19.18 | 18.91 | 18.89 | 0.29 | 1.5 |
|   | SJP3/SJP7-1% x HDT-2 | 19.44 | 19.17 | 19.5 | 0.29 | 1.5 |
| 2 | SJP3/SJP7-2.5% x HDT-1 | 20.12 | 19.94 | 19.90 | 0.22 | 1.1 |
|   | SJP3/SJP7-2.5% x HDT-2 | 19.04 | 18.69 | 18.66 | 0.38 | 2.0 |
| 3 | SJP3/SJP7-5% x HDT-1 | 18.32 | 18.15 | 18.12 | 0.2 | 1.1 |
|   | SJP3/SJP7-5% x HDT-2 | 19.53 | 19.42 | 19.34 | 0.19 | 1.0 |
| 4 | SJP3/SJP7-10% x HDT-1 | 19.42 | 19.19 | 19.06 | 0.36 | 1.9 |
|   | SJP3/SJP7-10% x HDT-2 | 18.20 | 17.91 | 17.83 | 0.37 | 2.0 |
| 5 | SJP3/SJP7-25% x HDT-1 | 19.79 | 17.99 | 16.59 | 3.2 | 16.1 |
|   | SJP3/SJP7-25% x HDT-2 | 21.06 | 19.02 | 17.62 | 3.44 | 16.3 |
| 6 | SJP3/SJP7-50% x HDT-1 | 20.13 | 9.62 | 7.83 | 12.3 | 61.1 |
|   | SJP3/SJP7-50% x HDT-2 | 18.56 | 8.71 | 7.13 | 11.42 | 61.5 |
| 7 | SJP3-100% x HDT-1 | 19.84 | 12.31 | 4.23 | 15.61 | 78.7 |
|   | SJP3-100% x HDT-2 | 21.41 | 11.55 | 4.69 | 16.72 | 78.1 |

FIG. 118 shows enzymatic degradation of blended disc.

FIG. 119 shows an overall procedure used for preparation of disc and Drug X loading and release, according to an embodiment.

TABLE 42

Library of Synthesized copolymer materials

| Entry | | $^1$H-NMR | | GPC | |
|---|---|---|---|---|---|
| No. | Polymer structure | $M_n$ | DP (PEG/PVL/PAVL) | PAVL (%) | $M_n$ | PDI |
| SJP1 | PAVL-b-PVL-b-3KPEG-b-PVL-b-PAVL | 28K | 85/214/22 | 11 | 17.6K | 1.26 |
| SJP2 | PAVL-b-PVL-b-10KPEG-b-PVL-b-PAVL | 25.5K | 300/100/18 | 10 | 15.6K | 1.39 |
| SJP3 | PAVL-b-PVL-b-20KPEG-b-PVL-b-PAVL | 34.5K | 475/100/18 | 10 | 35.7K | 1.14 |
| SJP7 | PVL-co-PAVL | 32K | 0/235/45 | 20 | 24K | 1.48 |

TABLE 43

Solubility of Drug X freebase

| Drug | TFH | EtOH | DMSO | DCM | THF/DMSO (50/50) |
|---|---|---|---|---|---|
| Drug X freebase | Soluble, and transparent (5 mg/100 µl) | Soluble, and transparent (5 mg/100 µl) | Soluble, and transparent (5 mg/100 µl) | Soluble, and transparent (5 mg/100 µl) | Soluble, and transparent (5 mg/100 µl) |

FIG. 120 shows a Drug X freebase loading in disc shaped depot formed from SJP1, SJP2, SJP3, and SJP7.

FIG. 121 shows Drug X release of the depot formed from SJP1, SJP2, SJP3 and SJP7.

TABLE 44

Blend system consisting of PVL-co-PAVL (SJP7) and PEGylated copolymer (SJP3) with hexanedithiol

| Drug X | Disc (mg) | Drug Loaded (mg) | Disc Loaded (mg) | Drug content (mg) | DLC (%) | DLE (%) | Depot/Drug (w/w) |
|---|---|---|---|---|---|---|---|
| SJP7/SJP3 (50/50)-1 | 25.08 | 25.00 | 31.99 | 6.91 | 21.60 | 27.64 | 1/0.28 |
| SJP7/SJP3 (50/50)-2 | 25.68 | 25.00 | 32.23 | 6.55 | 20.32 | 26.20 | 1/0.26 |
| SJP7/SJP3 (75/25)-1 | 28.05 | 25.00 | 34.47 | 6.42 | 18.62 | 25.68 | 1/0.23 |
| SJP7/SJP3 (75/25)-2 | 27.44 | 25.00 | 33.70 | 626 | 18.58 | 25.04 | 1/0.23 |
| SJP7/SJP3 (90/10)-1 | 27.87 | 25.00 | 34.31 | 6.44 | 18.77 | 25.76 | 1/0.23 |
| SJP7/SJP3 (90/10)-2 | 27.24 | 25.00 | 33.53 | 6.29 | 18.76 | 25.16 | 1/0.23 |
| SJP7/SJP3 (95/5)-1 | 28.25 | 25.00 | 35.03 | 6.78 | 19.35 | 27.12 | 1/0.24 |
| SJP7/SJP3 (95/5)-2 | 28.10 | 25.00 | 34.45 | 6.35 | 18.43 | 25.40 | 1/0.22 |
| SJP7/SJP3 (97.5/2.5)-1 | 28.20 | 25.00 | 34.52 | 6.32 | 18.31 | 25.28 | 1/0.22 |
| SJP7/SJP3 (97.5/2.5)-2 | 28.01 | 25.00 | 34.43 | 6.42 | 18.65 | 25.68 | 1/0.23 |
| SJP7/SJP3 (99/1)-1 | 27.72 | 25.00 | 34.12 | 6.40 | 18.76 | 25.60 | 1/0.23 |
| SJP7/SJP3 (99/1)-2 | 27.68 | 25.00 | 34.10 | 6.42 | 18.83 | 25.68 | 1/0.23 |

FIG. 122 shows Drug X release profile for a blend system of SJP7 and SJP3 with hexanedithiol.

TABLE 45

Drug X loading of disc at different concentration of Drug X

| Drug X | Disc (mg) | Drug Loaded (mg) | Disc Loaded (mg) | Dmg content (mg) | DLC (%) | DLE (%) | Depot/Drug (w/w) |
|---|---|---|---|---|---|---|---|
| SJP7-1 | 27.82 | 25.00 | 34.08 | 6.26 | 18.37 | 25.04 | 1/0.23 |
| SJP7-2 | 28.55 | 25.00 | 34.94 | 6.39 | 18.29 | 25.56 | 1/0.22 |
| SJP7-1 | 28.44 | 50.00 | 39.22 | 10.78 | 27.49 | 21.56 | 1/0.38 |
| SJP7-2 | 28.43 | 50.00 | 39.27 | 10.84 | 27.60 | 21.68 | 1/0.38 |
| SJP7-1 | 28.43 | 75.00 | 42.24 | 13.81 | 32.69 | 18.41 | 1/0.49 |
| SJP7-2 | 28.54 | 75.00 | 42.57 | 14.03 | 32.96 | 18.41 | 1/0.49 |
| SJP7/SJP3 (97.5/2.5)-1 | 27.94 | 25.00 | 34.80 | 6.86 | 19.71 | 27.44 | 1/0.25 |
| SJP7/SJP3 (97.5/2.5)-2 | 27.77 | 25.00 | 34.82 | 7.05 | 20.25 | 28.20 | 1/0.25 |
| SJP7/SJP3 (97.5/2.5)-1 | 27.93 | 50.00 | 39.02 | 11.09 | 28.42 | 22.18 | 1/0.40 |
| SJP7/SJP3 (97.5/2.5)-2 | 28.46 | 50.00 | 39.35 | 10.89 | 27.67 | 21.78 | 1/0.39 |
| SJP7/SJP3 (97.5/2.5)-1 | 27.86 | 75.00 | 42.37 | 14.51 | 34.25 | 19.35 | 1/0.25 |
| SJP7/SJP3 (97.5/2.5)-2 | 27.99 | 75.00 | 42.72 | 14.73 | 34.48 | 19.64 | 1/0.53 |

FIG. 123 shows Drug X release of disc prepared from SJP7 and its blend system with SJP3 (2.5%).

Conclusion of Drug X loading and release using disc:

Disc shaped depots (5 mm×0.5 mm) formed from a series of copolymer (SJP1. SJP2, SJP3, SJP7) and HDT as cross-linker used to examine Drug X loading and release in PBS and 0.5% SDS at pH 7.45.

Disc prepared from PVL-co-PAVL (SJP7) shows slower Drug X release compared to PEGylated copolymer (i.e. SJP1, SJP2, SJP3)

Blend system of SJP7 and SJP3 shows controlled Drug X release depending on weight percent (1%-50%) of SJP3 incorporated.

Over 30% Drug X loading is achieved, and Drug X-loaded discs demonstrate sustained release for 15 days.

Drug X degradation did not affect the release data significantly because the release rate was greater than the degradation rate. Concerning the Drug X degradation, the system should release more and for longer period of time than currently presented.

FIG. 124 shows an overall procedure for preparation of a microparticle and post-loading, according to an embodiment.

FIG. 125 shows preparation of a well-controlled microparticle, according to an embodiment.

FIG. 126 shows preparation of a microparticle, according to an embodiment.

FIG. 127 shows loading and release of Drug X freebase.

FIG. 128 shows filtration using mesh to remove small particles.

FIG. 129 shows Drug X Loading and release using NaCl MPs and EtOH MPs.

FIG. 130 shows SEM images of MPs before drug loading.

FIG. 131 shows Drug X loading and release of MPs after washing out with different solution.

FIG. 132 shows Drug X loading and release for ruling out a saturation issue.

FIG. 133 shows Drug X loading and release in release media at pH 6. A peak related to Drug X is not detected. This is due to dissolution of Drug X in PVA (used as water phase) and water (used to remove PVA).

FIG. 134 shows microparticle release in PBS with SDS.

FIG. 135 shows disc release in PBS with SDS.

TABLE 46

HPLC chromatogram of Drug X freebase at different concentration as a function of time

| Concentration (μg/ml) | Time | PBS with SDS | |
|---|---|---|---|
| | | Area ($2^{nd}$) | Peak position ($2^{nd}$) (retention time) |
| 120 | T = 0 | 1849.3 (218.0) | 2.5 (2.08) |
| | 1 hr | 1768.4 (223.0) | 2.7 (2.25) |
| | 3 hrs | 1764.9 (219.47) | 2.7 (2.25) |
| | 7 hrs | 1707.5 (212.8) | 2.7 (2.24) |
| | 1 day | 1613.5 (189.8) | 2.69 (2.25) |
| | 2 days | 1539.2 (193.9) | 2.68 (2.25) |
| | 3 days | 1401.2 (167.5) | 2.67 (2.25) |
| | 4 days | 1318.3 (160.3) | 2.69 (2.27) |
| 60 | T = 0 | 929.6 (73.9) | 2.28 (1.87) |
| | 1 hr | 934.7 (99.6) | 2.67 (2.26) |
| | 3 hrs | 909.05 (85.18) | 2.67 (2.25) |
| | 7 hrs | 906.7 (95.5) | 2.67 (2.25) |
| | 1 day | 867.8 (87.6) | 2.67 (2.25) |
| | 2 days | 783.7 (77.0) | 2.67 (2.25) |
| | 3 days | 712.2 (72.3) | 2.66 (2.25) |
| | 4 days | 677.3 (68.1) | 2.68 (2.27) |
| 12 | T = 0 | 192.6 | 2.1 |
| | 1 hr | 191.5 | 2.67 |
| | 3 hrs | 185.7 | 2.66 |
| | 7 hrs | 182.8 | 2.67 |
| | 1 day | 179.2 | 2.67 |
| | 2 days | 178.7 | 2.67 |
| | 3 days | 155.2 | 2.66 |
| | 4 days | 155.8 | 2.67 |

FIG. 136 shows release in PBS with SDS, at 120 μg/1 mL.

FIG. 137 shows release in PBS with SDS at 60 μg/1 mL.

FIG. 138 shows release in PBS with SDS at 12 μg/1 mL.

TABLE 47

HPLC chromatogram of Drug X freebase at different concentration as a function of time

| Concentration (μg/ml) | Time | PBS with SDS | |
|---|---|---|---|
| | | Area ($2^{nd}$) | Peak position ($2^{nd}$) (retention time) |
| 120 | T = 0 | 1841.8 | 1.66 |
| | 1 hr | 1797.8 | 2.0 |
| | 3 hrs | 1790.0 | 1.7 |
| | 7 hrs | 1687.7 | 1.59 |
| | 1 day | 1319.2 | 1.57 |
| | 2 days | 1023.1 | 1.58 |
| | 3 days | 722.9 | 1.57 |
| | 4 days | 593.4 | 1.59 |
| 60 | T = 0 | 903.4 | 1.87 |
| | 1 hr | 897.8 | 2.14 |
| | 3 hrs | 875.2 | 1.82 |
| | 7 hrs | 850.6 | 1.62 |
| | 1 day | 663.9 | 1.58 |
| | 2 days | 511.8 | 1.58 |
| | 3 days | 361.7 | 1.58 |
| | 4 days | 303.9 | 1.59 |
| 12 | T = 0 | 169.2 | 2.10 |
| | 1 hr | 164.51 | 2.26 |
| | 3 hrs | 162.2 | 1.91 |
| | 7 hrs | 161.0 | 1.67 |
| | 1 day | 132.2 | 1.59 |
| | 2 days | 103.6 | 1.59 |
| | 3 days | 84.2 | 1.59 |
| | 4 days | 57.5 | 1.59 |

FIG. 139 shows release in PBS without SDS at 120 μg/1 mL.

FIG. 140 shows release in PBS without SDS at 60 μg/1 mL.

FIG. 141 shows release in PBS without SDS at 12 μg/1 mL.

FIG. 142 shows Drug X stability in aqueous solution at different concentration of SDS (i.e., 0.5%, 1%, 2.5%, 5% at pH 7.45)—Peak #1 (RT~0.965).

FIG. 143 shows Drug X stability in aqueous solution at different concentration of SDS (i.e., 0.5%, 1%, 2.5%, 5% at pH 7.45)—Peak #2 (RT~1.115).

FIG. 144 shows Drug X stability in aqueous solution at different concentration of SDS (i.e., 0.5%, 1%, 2.5%, 5% at pH 7.45)—Peak #3 (RT~2.915).

FIG. 145 shows Drug X stability in aqueous solution at different concentration of SDS (i.e., 0.5%, 1%, 2.5%, 5% at pH 7.45)—Peak #4 (Drug).

FIG. 146 shows the change in area of drug peak from T=0 to T=7 days.

FIG. 147 shows peaks associated with various mixes of Drug X in SDS.

FIG. 148 shows curcumin post-loading protocol for NaCl MP and EtOH MP.

FIG. 149 shows fluorescent images of curcumin loaded MP (0.25M NaCl) with different incubation times.

FIG. 150 shows fluorescent images of curcumin loaded MP at different concentrations of NaCl and EtOH MP (after 24 hour incubation).

FIG. 151 shows fluorescent images of curcumin loaded MP before and after wash.

FIG. 152 shows fluorescent images of curcumin loaded MP before and after wash.

FIG. 153 shows extent of swelling in organic solvent and PBS.

For PBS with 0.5% SDS:
  Second peak appeared at early time point (2.2-2.3 min) for high concentration (A peak corresponding to Drug X is detected at 2.6-2.7 min). The appearance of second peak correlates with concentration of the drug. At high concentration, the second peak is much more noticeable than at a low concentration.
  Area of the peak corresponding to Drug X freebase is constantly decreased as a function of time.
  All the release sample of disc was measured after dilution to rule out second peak.

For PBS without SDS
  Second peak is not detected, but the peak corresponding to Drug X free base (around 1.5 min) is constantly decreasing as a function of time regardless of concentration.

FIG. 154 shows protocol 1 for PTX loading and release of MPs.

FIG. 155 shows mass change by enzymatic degradation.

Table 48 shows an examination of degradation for 50%, 25%, and 10% at low concentration (0.5 mg or PS/1 mL of PBS) because rate of degradation seems too fast for 50% and 25% of blend system which showed 50% and 10% of weight loss after a week.

TABLE 48

Further degradation study at lower concentration of lipase.

| Entry No. | Sample | Initial weight (mg) | After a week (mg) | Two weeks (mg) | A month (mg) | Total weight loss (mg) | Total weight loss (%) |
|---|---|---|---|---|---|---|---|
| 1 | SJP3/SJP7-10% x HDT-1 | 21.16 | 21.12 | | | 0.04 | 0.2 |
|   | SJP3/SJP7-10% x HDT-2 | 17.50 | 17.36 | | | 0.14 | 0.8 |
| 2 | SJP3/SJP7-25% x HDT-1 | 18.72 | 18.55 | | | 0.17 | 0.9 |
|   | SJP3/SJP7-25% x HDT-2 | 21.53 | 21.31 | | | 0.22 | 1.0 |
| 3 | SJP3/SJP7-50% x HDT-1 | 16.90 | 10.45 | | | 6.45 | 38.2 |
|   | SJP3/SJP7-50% x HDT-2 | 16.88 | 8.55 | | | 8.33 | 49.3 |

Degradation for all series of PEGylated copolymers was examined 0.5 mg in 1 mL of PBS. Therefore, we can develop a bunch of degradable cross-linked depots with different rate of degradation for many biomedical applications.

TABLE 49

Further degradation study at lower concentration of lipase

| Entry No. | Sample (w/w) | Initial weight (mg) | After a week (mg) | Two weeks (mg) | A month (mg) | Total weight loss (mg) | Total weight loss (%) |
|---|---|---|---|---|---|---|---|
| 1 | SJP1 x HDT-1 | 26.34 | 25.02 | | | 1.32 | 5.0 |
|   | SJP1 x HDT-2 | 23.06 | 22.13 | | | 0.93 | 4.0 |
| 2 | SJP2 x HDT-1 | 20.43 | 13.11 | | | 6.89 | 28.8 |
|   | SJP2 x HDT-2 | 21.45 | 14.31 | | | 6.62 | 28.6 |
| 3 | SJP3 x HDT-1 | 23.91 | 17.02 | | | 7.32 | 35.8 |
|   | SJP3 x HDT-2 | 23.13 | 16.51 | | | 7.14 | 33.3 |
| 4 | SJP4 x HDT-1 | 23.30 | 7.76 | | | 15.54 | 66.7 |
|   | SJP4 x HDT-2 | 23.35 | 8.07 | | | 15.28 | 65.4 |

TABLE 50

Loading of Paclitaxel varying amount of PEGylated copolymer

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7-1 | 28.38 | 25.00 | 33.84 | 5.46 | 16.13 | 21.84 | 1/0.19 |
| SJP7-2 | 26.27 | 25.00 | 31.87 | 5.60 | 17.57 | 22.40 | 1/0.21 |
| SJP7-1 | 28.30 | 50.00 | 38.70 | 10.40 | 26.87 | 20.80 | 1/0.37 |
| SJP7-2 | 27.72 | 50.00 | 38.06 | 10.34 | 27.17 | 20.68 | 1/0.37 |
| SJP7-1 | 28.62 | 75.00 | 41.24 | 12.62 | 30.60 | 16.83 | 1/0.44 |
| SJP72 | 26.11 | 75.00 | 38.45 | 12.34 | 32.09 | 16.45 | 1/0.47 |

FIG. 156 shows release of Paclitaxel varying amount of PEGylated copolymer.

TABLE 51

Loading of Paclitaxel varying amount of PEGylated copolymer

| PTX | Disc (mg) | Drug (mg) | Disc Loaded (mg) | Drug content (mg) | DLC (%) | DLE (%) | Depot/Drug (w/w) |
|---|---|---|---|---|---|---|---|
| SJP7/SJP3 (50/50)-1 | 25.05 | 25.00 | 29.98 | 4.93 | 16.44 | 19.72 | 1/0.20 |
| SJP7/SJP3 (50/50)-2 | 25.36 | 25.00 | 30.67 | 5.31 | 17.31 | 21.24 | 1/0.21 |
| SJP7/SJP3 (75/25)-1 | 27.30 | 25.00 | 32.17 | 4.87 | 15.14 | 19.48 | 1/0.18 |
| SJP7/SJP3 (75/25)-2 | 27.72 | 25.00 | 33.01 | 5.29 | 16.03 | 21.16 | 1/0.19 |
| SJP7/SJP3 (90/10)-1 | 27.99 | 25.00 | 33.03 | 5.04 | 15.26 | 20.16 | 1/0.18 |
| SJP7/SJP3 (90/10)-2 | 27.77 | 25.00 | 32.62 | 4.85 | 14.87 | 19.40 | 1/0.17 |
| SJP7/SJP3 (95/5)-1 | 28.08 | 25.00 | 34.28 | 6.20 | 18.09 | 24.80 | 1/0.22 |
| SJP7/SJP3 (95/5)-2 | 27.92 | 25.00 | 33.99 | 6.07 | 17.86 | 24.28 | 1/0.22 |
| SJP7/SJP3 (97.5/2.5)-1 | 28.07 | 25.00 | 34.12 | 6.05 | 17.73 | 24.20 | 1/0.22 |
| SJP7/SJP3 (97.5/2.5)-2 | 28.46 | 25.00 | 34.39 | 5.93 | 17.24 | 23.72 | 1/0.21 |
| SJP7/SJP3 (99/1)-1 | 27.20 | 25.00 | 32.36 | 5.16 | 15.95 | 20.64 | 1/0.19 |
| SJP7/SJP3 (99/1)-2 | 28.01 | 25.00 | 33.18 | 5.17 | 15.58 | 20.68 | 1/0.18 |

FIG. 157 shows release of Paclitaxel varying amount of PEGylated copolymer.

TABLE 52

Confirmation of actual loading capacity of a disc.

| Entry No. | Sample | Initial weight (mg) | After a week (mg) | Total weight loss (mg) |
|---|---|---|---|---|
| 1 | SJP7 X HDT-1 | 23.25 | 23.15 | 0.10 |
|   | SJP7 X HDT-2 | 24.82 | 24.69 | 0.13 |
| 2 | SJP3 X HDT-1 | 26.97 | 26.57 | 0.40 |
|   | SJP3 X HDT-2 | 26.38 | 26.04 | 0.34 |

In Table 52, a study was conducted, in which a disc was placed in 0.5 mL of organic solvent mixture (DIMSO/THF) without drug for 8 hrs which is same condition used for Drug X loading, and then swelled discs were freeze-dried twice for 4 days. Significant mass change of disc was not observed, demonstrating no effect of solvent on loading capacity.

TABLE 53

Drug X loading of disc and extraction efficiency.

| | Disc (mg) | Drug (mg) | Disc Loaded (mg) | Drug content (mg) | DLC (%) | DLE (%) | Extraction efficiency |
|---|---|---|---|---|---|---|---|
| SJP7-1 | 25.05 | 25.00 | 29.98 | 4.93 | 16.44 | 19.72 | 1/0.20 |
| SJP7-2 | 25.36 | 25.00 | 30.67 | 531 | 17.31 | 21.24 | 1/0.21 |

In Table 53, a study was conducted in which a Drug X-loaded disc was placed in 10 mL of dichloromethane (DCM) for 8 hr at room temperature to extract Drug X, and DCM was removed using a rotary evaporator at 25° C. This extraction process was repeated two times. The extracted drug dissolved in a acetonitrile (ACN) was filtered using 0.45 μm a nylon membrane and measured by HPLC for extraction efficiency.

20 mg of Drug X was used for loading 10 mg MP for the release.

Result: After 1 hr, 1 g of Drug X was released from the MP and around 100 μg of Drug X remained inside the MP after extraction. There was no second peak detected in both 1 hr release and extraction. Based on this degradation does not occur at 1 hr time point. Furthermore, since almost all Drug X is release within 1 hr, we need an alterative method to determine if the degradation occur inside the polymer matrix.

Conclusion: Most of Drug X is releasing within 1 hr.

PTX related experiments:

Loaded and purified MP for PTX loading with the blend system

Three MP were prepared:

Standard (SJP7) MP

50% PCL (14K: 50% SJP7 MP

25% PCL (14K): 75% SJP7 MP

FIG. 158 shows a protocol for degradation of a microparticle (SJP7).

TABLE 54

Mass change by enzymatic degradation

| Entry No. | Sample (w/w) | Initial weight (mg) | After 1 week (mg) | 2 weeks (mg) | 3 weeks (mg) | 7 weeks (mg) | Total weight loss (mg) | Total weight loss (%) |
|---|---|---|---|---|---|---|---|---|
| 1 | SJP3/SJP7-1% x HDT-1 | 19.18 | 18.91 | 18.89 | 18.89 | 18.65 | 0.53 | 2.763295 |
|   | SJP3/SJP7-1% x HDT-2 | 19.44 | 19.17 | 19.15 | 19.14 | 18.84 | 0.6 | 3.08642 |
| 2 | SJP3/SJP7-2.5% x HDT-1 | 20.12 | 19.94 | 19.90 | 19.86 | 19.70 | 0.42 | 2.087475 |
|   | SJP3/SJP7-2.5% x HDT-2 | 19.04 | 18.89 | 18.69 | 18.66 | 18.60 | 0.44 | 2.310924 |
| 3 | SJP3/SJP7-(5%) x HDT-1 | 18.32 | 18.15 | 18.12 | 18.09 | 17.90 | 0.42 | 2.292576 |
|   | SJP3/SJP7-(5%) x HDT-2 | 19.53 | 19.42 | 19.34 | 19.27 | 19.17 | 0.36 | 1.843318 |
| 4 | SJP3/SJP7-(10%) x HDT-1 | 19.42 | 19.19 | 19.06 | 19.01 | 18.74 | 0.68 | 3.501545 |
|   | SJP3/SJP7-(10%) x HDT-2 | 18.20 | 17.91 | 17.83 | 17.73 | 17.44 | 0.76 | 4.175824 |
| 5 | SJP3/SJP7-(25%) x HDT-1 | 19.79 | 17.99 | 16.59 | 15.22 | 10.19 | 9.6 | 48.50935 |
|   | SJP3/SJP7-(25%) x HDT-2 | 21.06 | 19.02 | 17.62 | 16.21 | 10.22 | 10.84 | 51.47198 |
| 6 | SJP3/SJP7-(50%) x HDT-1 | 20.13 | 9.62 | 7.83 | 7.28 | 5.84 | 14.29 | 70.98857 |
|   | SJP3/SJP7-(50%) x HDT-2 | 18.56 | 8.71 | 7.13 | 6.55 | 4.58 | 13.98 | 75.32328 |
| 7 | SJP3-(100%) x HDT-1 | 19.84 | 12.31 | 4.23 | 0 | | | |
|   | SJP3- (100%) x HDT-2 | 21.41 | 11.55 | 4.69 | 0 | | | |

Method: We will use a dialysis bag to properly change release media without loss of microparticle. This will prevent accumulation of Drug X degradation over time and allow more accurate release analysis. We will examine release with Drug X-loaded microparticle in different media (i.e. only PBS at pH 7.5).

Result: No Drug X was detected throughout the study. This may be due to two factors:

Drug X is interacting or releasing slowly from the dialysis bag. When we put, free Drug X inside the dialysis bag we did not detect the drug until Day 1 release point time.

The volume of the release media is too large 20 mL) therefore the release drug might be below the limit of detection.

Method: Drug X-loaded microparticle in release media will be taken after 1 hrs and utilized to extract residue Drug X from microparticle. This will demonstrate Drug X stability in polymer matrix if degradants are not detected.

FIG. 159 shows mass change by enzymatic degradation.

FIG. 160 shows a PTX-Discs PK study outline.

FIG. 161 shows Drug X release with and without release media exchange. Drug X did not show longer release duration. However, Drug X did show high drug release. The high drug release is probably due to the influence of concentration gradient created as fresh release media is added every day.

FIG. 162 shows Drug X stability in polymer matrix. During the two-day released ~50% of Drug X and from the extraction we recovered ~35% of Drug X. In total, we recovered ~83%-90% of the encapsulated Drug X. When considering that Drug X extraction efficiency is 85% in the disc, we can conclude we recovered most of drug X encapsulated. This suggests that Drug X is stable inside of a polymer matrix.

FIG. 163 shows Drug X stability in a disc after 2 weeks of release in PBS. We took out a disc after 2 weeks of release and freeze fried it. Then, the residual Drug X remaining in discs was extracted using dichloromethane to confirm Drug X stability in the disc. When considering 88-93% of drug was recovered from the discs (release & extraction), Drug X does not seem to be degrading in polymer matrix.

FIG. 164 shows Drug X related experiments. MPs were made using a mold. However, the hydrogel mold did not dissolve as it should have after crosslinking. This is probably because when SJP7 solution is spread on the mold, there is a thin film that forms, which crosslinks as well.

Using Albumin to slow Drug X release from SJP7: Rationale: Currently Drug X is releasing very quickly from our formulation. Albumin can slow the release. Albumin is the most abundant blood plasma protein. 80% of Drug X bind to blood plasma protein. There is a marketed product, Abraxane, which uses albumin for formulation. Albumin was added before Drug X was post-loaded.

TABLE 55

PTX loading of MPs using blend system with protocol

| Entry. no | Drug | Microparticle before drug loading (mg) | Amount of Drug added (mg) | Amount of Drug Extracted (mg) | DLC (%) | Solution for washing free drug | Amount of release media |
|---|---|---|---|---|---|---|---|
| 1 | SJP7-TAA-1 | 12.02 | 20.00 | 4.45 | 25.74 | MeOH/H$_2$O (80/20) 10 mL X 1 H$_2$O 10 mL X 1 | 100 mL |
| 2 | SJP7-TAH-1 | 12.07 | 20.00 | 5.05 (02)$^{STD}$ | 27.37 | MeOH/H$_2$O (90/10) 10 mL X 1 H$_2$O 10 mL X 1 | 250 mL |
|   | SJP7-TAH-2 | 12.06 | 20.00 | 5.05 (0.2)$^{STD}$ | 27.36 | MeOH/H$_2$O (90/10) 10 mL X 1 H2O 10 mL X 1 | 250 mL |

TAA and TAH can be used for loading and release study with MP (JPP7). This protocol is the same for PTX, TAA and TAH-loaded MPs were washed out with mobile phase used for HPLC assay, respectively, after drug loading.

FIG. 165 shows TAA and TAH release using blend system with protocol.

FIG. 166 shows results from degradation of cross-linked film in enzyme solution at 37.5°.

FIG. 167 shows SEM images of crosslinked films—CoPAVL.

FIG. 168 shows SEM images of blend$_{25}$—CoPAVL/PEG-PAVL (75/25).

FIG. 169 shows SEM images of blend$_{25}$—CoPAVL/PEG-PAVL (50/50).

Drug X related experiments-Albumin:
Two different albumin were used to make the discs with SJP7.
Bovine Serum Albumin
Human Serum Albumin
Due to the poor solubility of albumin in organic solvent, the albumin were physically trapped during the crosslinking.
The idea is that as the albumin dissolves in release media, it will bind to Drug X and slow the release.

TABLE 56

Loading data

| Sample Name | Initial weight (mg) | Weight after loading (mg) | Amount of loaded (mg) | Amount of used (mg) | Loading efficiency (%) |
|---|---|---|---|---|---|
| BSA Loaded #1 | 13.74 | 16.36 | 2.62 | 25 | 10.48 |
| BSA Loaded #2 | 14.37 | 17 | 2.63 | 25 | 10.52 |

TABLE 56-continued

Loading data

| Sample Name | Initial weight (mg) | Weight after loading (mg) | Amount of loaded (mg) | Amount of used (mg) | Loading efficiency (%) |
|---|---|---|---|---|---|
| HSA Loaded #1 | 14.74 | 16.86 | 2.12 | 25 | 8.48 |
| HSA Loaded #1 | 12.54 | 14.53 | 1.99 | 25 | 7.96 |

Bovine Serum Albumin seem to load more Drug X than Human Serum Albumin. Lower Drug X loading compare to normal SJP7 may be due to the albumin taking up space in the matrix.

TABLE 57

Drug X loading and release of SJP7 discs

| | Drug X | Disc (mg) | Drug (mg) | Disc Loaded (mg) | Drug content (mg) | DLC (%) | DLE (%) | Depot/Drug (w/w) | Media |
|---|---|---|---|---|---|---|---|---|---|
| 1 | SJP7-1 | 27.82 | 25.00 | 34.08 | 6.26 | 18.37 | 25.04 | 1/0.23 | PBS |
|   | SJP7-2 | 28.55 | 25.00 | 34.94 | 6.39 | 18.29 | 25.56 | 1/0.22 | and 0.5% SDS |
| 2 | SJP7-1 | 26.11 | 25.00 | 32.41 | 6.30 | 19.44 | 25.20 | 1/0.24 | PBS |
|   | SJP7-2 | 25.97 | 25.00 | 32.53 | 6.56 | 20.17 | 26.24 | 1/0.24 | |

We expected slower release if we can rule out an effect of degradant by release media change. As release media was changed, amount of drug released seems to increase due to the influence of the concentration gradient between disc and fresh media. However, the duration of Drug X release was similar regardless of media change.

TABLE 58

Drug X related experiments-Albumin

| | Drug X | Disc (mg) | Drug (mg) | Disc Loaded (mg) | Drug content (mg) | DLC (%) | DLE (%) | Depot/Drug (w/w) | Media |
|---|---|---|---|---|---|---|---|---|---|
| 1 | BSA-1 | 13.74 | 25.00 | 16.36 | 2.62 | 16.01 | 10.48 | 1/0.19 | PBS |
|   | BSA-2 | 14.37 | 25.00 | 17.00 | 2.63 | 15.47 | 10.52 | 1/0.18 | |
| 2 | HAS-1 | 14.74 | 25.00 | 16.86 | 2.12 | 12.57 | 8.48 | 1/0.14 | PBS |
|   | HSA-2 | 12.54 | 25.00 | 14.53 | 1.99 | 13.70 | 7.96 | 1/0.16 | |

Two different albumin were used to make the discs with SJP7: bovine serum albumin, human serum albumin. Due to the poor solubility of albumin in organic solvent, the albumin were physically trapped during the crosslinking. The idea is that as the albumin dissolves in release media, it will bind to Drug X and slow the release. Bovine serum albumin seem to load more Drug X than human serum albumin. Lower Drug X loading compared to normal SJP7 may be due to the albumin taking up space in the matrix. 18 of Drug X-loaded disc (SJP7) with 10 mg loading. 8 of PTX-loaded disc (SJP7) with 10 mg loading. 8 of PTX-loaded disc (SJP7/SJP3 50/50) with 10 mg loading. 6 of disc as control.

EXAMPLES

Materials

Materials: 6-Valerolactone (VL), 4-(Dimethylamino)pyridine (DMPA), 1,6-hexanedithiol, benzyl alcohol, chloroform-d ($CDCl_3$), acetaminophen (ACM), were purchased from Sigma-Aldrich (Oakville, Calif.), Triamcinolone acetonide (TAA), and paclitaxel (PTX) were obtained from Ark Pharm, curcumin (CCM) from Cayman Chemicals (Ann Arbor, USA) and triamcinolone hexacetonide (TAH) from Spectrum chemicals (New Brunswick, USA) α-Allyl-δ-valerolactone (AVL) was provided by Pendant Biosciences (Toronto, Calif.). Solvents (HPLC grade) including, acetonitrile (ACN), methanol, DMSO, tetrahydrofuran (THF), toluene, dichloromethane ($CH_2Cl_2$), hexane and ethyl ether were purchased from Caledon Laboratories (Georgetown, Calif.) and were used without purification.

Example 1: Polymer Synthesis

Polyester copolymers (PVL-co-PAVL) were prepared as described by Silvers, Chang and Emrick (2012) with some modifications.27 Briefly, in a flame-dried round two-neck flask, the catalyst 1,5,7-triazabicyclo[4.4.0]dec-5-ene (2 mol % TBD 0.273 g) was added and dried under vacuum (e.g. P39K). Anhydrous toluene (4 mL) and benzyl alcohol (m=0.027 g) were then combined in the two-neck flask with TBD under argon and stirred for 30 min. Distilled monomers (VL=9 mL and AVL=1.01 mL) were combined prior to their transfer by cannulation in the reaction vessel under positive pressure of argon. Polymerization was carried out at room temperature for 6 hours. The slurry solution was first precipitated in 2 L cold methanol, re-dissolved in THF (4 mL) and then precipitated in 2 L of a mixture of hexane/ethyl ether (30/70 v/v).

Characterization of the copolymer materials: The infrared spectra of the copolymers, cross-linked materials and drugs were recorded at room temperature on a Nicolet Fourier-transform IR (FT-IR) spectrometer equipped with ATR accessory and normalized for comparison. $^1$H NMR spectra were recorded in $CDCl_3$ on a Bruker AMX400 or Bruker AC300 spectrometer. The molecular weight of each copolymer material was determined by GPC analysis in THF using a Waters 2695 system that includes two PLgel 5 μm Agilent columns and a Waters 2414 RI detector. A calibration curve was constructed using polystyrene standards. DSC measurements were carried out on a Q100 TA series thermal analysis system over different temperature ranges with a common heating rate of 10° C./min under nitrogen (3 cycles).

Example 2: Preparation of Cross-Linked Copolymer Matrices 100 mg of copolymer, 0.25 molar equivalents of DMPA, and 0.5 functional group molar equivalents of 1,6-hexanedithiol were added in dry DMSO and warmed until full dissolution. The solution was drawn into a 1 ml syringe (i.d. 4.7 mm) and the syringe was placed upright (d=5 cm) to allow for UV crosslinking at 365 nm for 20 minutes. The tip of the syringe was removed and the cylindrical cross-linked polymer (CP) was plunged out of the syringe. The swollen cylinder was purified by solvent exchange in THF for a period of ~24 hours to remove any unreacted starting materials (i.e. 50 mL of fresh THF every 2 hours for 8 hours, and in fresh THF (100 mL) overnight) and dried at room temperature for 48 hours.

Solubility parameters: Polymer-solvent compatibility is defined by the evaluation of the cohesive energy density per unit of volume of both components. The Hildebrand solubility parameter is expressed as the square root of the cohesive energy density 1.

$$\delta_{E/V} = \left(\frac{\Delta E_i^v}{vi}\right)^{\frac{1}{2}}$$

The total solubility parameters can be divided into three components including Van der Waals dispersion forces ($\delta_d$), dipole-dipole interactions ($\delta_p$) and hydrogen bonding ($\delta_h$) 2. Total Hildebrand solubility ($\delta_t$) of the copolymers and the drugs have been determined by the group contribution method (GCM) 3. Hancock, B. C.; York, P.; Rowe, R. C. The use of solubility parameters in pharmaceutical dosage form design. *International journal of Pharmaceutics* 1997, 148, 1, 1-21.; Van Krevelen., D. W.; Te Nijenhuis, K., Chapter 7—Cohesive Properties and Solubility. In *Properties of Polymers (Fourth Edition)*, Elsevier: Amsterdam, 2009; pp 189-227.

$$\delta_d = \frac{\sum F_{di}}{V},$$

$$\delta_p = \frac{\sqrt{\sum F_{pi}^2}}{V},$$

$$\delta_h = \sqrt{\frac{\sum E_{hi}}{V}}$$

$$\delta_t = \sqrt{\delta_t^2 + \delta_p^2 + \delta_h^2}$$

Example 3: Drug Loading in CPs

All drugs were post-loaded within the cross-linked matrices using swelling/equilibration of dried CPs in saturated drug solution Briefly, THF was chosen as the drug loading, solvent. CPs (~15 mg±2 mg) were equilibrated in 0.5 ml of THF (drug concentration 30 mg/mL) for four hours followed by a brief rinse in fresh THF (10 seconds) to remove surface adsorbed drug. The drug loaded CPs are then dried for 48 hours at room temperature (e.g. the necessary time for solvent evaporation). The drug loaded CPs were then weighed on an analytical balance (0.1 mg precision) to determine the drug loading content (DLC % w/w). DLC (% w/w) was also confirmed by HPLC analysis of drug removed from the CPs by extraction using THF. Briefly, drug loaded CPs were immersed in 4 mL of THF for three hours with constant shaking. The solvent was then removed for analysis and the process repeated once again. Similar DLC values were obtained using the two methods. (i.e S.D<5%).

Example 4: In Vitro Drug Release

CPs were placed in a floating basket and added to beakers containing 100 ml of PBS, pH=7.4 (±0.3), and containing either 0.1% Tween 80 or 0.1 to 0.5% SDS to enhance the solubility of the poorly water-soluble drugs in the release media. The CPs were incubated at 37° C. under constant stirring and at pre-determined time points, a 1 ml aliquot was removed and replaced with 1 mL of fresh media and the samples were immediately frozen at −20° C. for storage prior to HPLC analysis. Sink conditions were maintained throughout the entire release experiment by replacement of the release media with fresh PBS every 4-5 days (maximum release ≤15 μg/mL of drug released). The remaining drug content in CPs was extracted as follows: TFIF (3 mL) was added to the CPs with shaking for 4 hours. The THF was then removed and evaporated by rotary evaporation at 45° C. Drug extraction was repeated twice. The drug was reconstituted in 1 ml of the HPLC mobile phase and analyzed to correct the DLC and release curves.

Mathematical modeling of drug release: Fitting curves and $R^2_{adjusted}$ (first order, higuchi, korsemeyer-peppas and peppas-sahlin) from the release data point were obtained using ddsolver add-on on excel (FIG. 8). R Project for Mac (Version 3.3.3) was used for fitting the mathematical model using the non-linear minimization (NLM) fitting routine based on the analytical solution to Fick's second law of diffusion ( Table 3) $M_t$ and $M_{oo}$ denote the absolute cumulative amounts of drug released at time t and infinite time, respectively; $q_n$ are the positive zeros of the Bessel J function of order 0, meaning that $J_0(q_n)=0$ for all n; R and H denote the radius and height of the cylinder; and D represents the diffusion coefficient of the drug within the system.

Drug solubility in different release media: An excess of drug (≥1 mg/ML) was added to the release media (e.g. PBS with Tween or SDS at 0.1, 0.5 or 1% w/v) and incubated at 37° C. for 48 hours under magnetic stirring. The solutions were centrifuged at 8000 rpm for 10 minutes, and a 1 ml aliquot was withdrawn, filtered through a 0.45 um nylon membrane, and analyzed by HPLC.

Scanning electron microscopy (SEM): The morphology of the surface and the cross-section of freeze dried and air dried samples of cross-linked materials were examined by SEM on a Hitachi S-3400N scanning electron microscope. Briefly, freeze-dried samples were prepared as follows; CPs were swollen in THF for 4 hours, immersed in liquid nitrogen for 5 minutes and placed rapidly (swollen) in the freeze drier for 24 h. For cross-section analysis, a small incision was made in the swollen samples (e.g. THF) prior to liquid nitrogen treatment. For samples dried at room temperature, only liquid nitrogen prior to the freeze drying process was performed.

Degradation and cytotoxicity studies: In vitro stability of the CPs was assessed by incubating samples in PBS pH 7.4 over months. At pre-determined time points, the CPs were removed, blotted dry, weighed and the pH of the surrounding media was measured. (FIG. 15). The cytotoxicities of the cross-linked matrices were evaluated in L929 mouse fibroblast cells using the extraction dilution method (FIG. 16). Baek, H. S.; Yoo, J. Y.; Rah, D. K.; Han, D.-W.; Lee, D. H.; Kwon, O.-H.; Park, J.-C. Evaluation of the Extraction Method for the Cytotoxicity Testing of Latex Gloves. *Yonsei Medical Journal* 2005, 46, (4), 579-583.

Investigation of buffer diffusion within the matrices: To evaluate the aqueous penetration and permeability of the CPs, hollow cylinders were prepared. Prior cross-linking reaction (described above), a cylindrical stainless steel bar was pushed into the center of the syringe (L=5 cm D=1 mm) and maintained at a distance of 0.5 mm from the base of the syringe (see FIG. 13B). Once cross-linked and washed (as describe above), the cavity (D=1040 μm±60 m) of the hollow cylinder was filled with 10 μL of 0.1M PBS pH 7.4 containing 25 mg/ml sulforhodamine B (e.g. hydrophilic probe), Then, diffusion within the matrices was monitored by analysis of the external media (PBS pH 7.4 SDS 0.5% w/v). At pre-determined time points, a 1 ml aliquot was removed and replaced with 1 mL of fresh media and the samples were immediately frozen at −20° C. for storage prior to analysis. Absorbance of the samples was measured at a wavelength of 540 nm using a Spectra Max Plus microplate reader (Molecular Devices, CA, USA).

Example 5: Synthesis of Pentablock Copolymer

A series of pentablock copolymers was prepared via ring opening polymerization of VL and AVL in the presence of PEG (polyethylene glycol) as the macroinitiator and TBD (1, 5, 7-triazabicyclo[4.4.0]dec-5-ene) as the catalyst. For the synthesis of PAVL-b-AVL-b-PEG 20K-b-PVL-b-PAVL as a typical example, PEG 20K (1 g, 0.1 mmol of OH group) in round two-neck flask was carefully flame-dried to melt PEG down and remove residue water under vacuum. After cooling down to room temperature, TBD (25 mg, 0.18 mmol) was added and dried again under vacuum. The reaction mixture was dissolved in anhydrous toluene (20 mL) and stirred at room temperature for 30 min. Then, purified VL (0.5 mL, 5.0 mmol, target repeating unit=100) was transfer to the reaction mixture by cannulation to start polymerization and followed by stirring at room temperature for 3 hrs. For block copolymerization, AVL (0.17 mL, 1.25 mmol, target repeating unit is 25) as second monomer was injected into the reactive mixture by cannulation, and the resulting mixture was further stirred at room temperature for 4 hrs. The as-synthesized polymer solution was precipitated from a mixture of Ethyl ether and Hexane (70/30 v/v) for purification, and residues were dried in a vacuum oven at room temperature overnight.

Example 6: Experiments with Depots Formed from Higher Concentration of Copolymer Procedure:
SJP2 with concentration listed below was used to make the depot
   300 mg/ml (30% w/v)
   400 mg/ml (40% w/v)
   500 mg/ml(50% w/v)
All depots were crosslinked for 8 minutes and washed with acetone (24 hr)→water (24 hr)→Lyophilized (24 hr)
Depot with dimension of 0.5 cm by 0.12 cm were pre-weighted and placed in to 100 uL of 200 mg/ml Albumin solution (5% FITC-albumin) for 4 hrs and 24 hrs. Their swollen weight was recorded.
The swollen depots were lyophilized overnight and the dried weight was recorded to determined the albumin loading.

Example 7: Experiments with Depots Formed from Higher Concentrations of SJP4 Copolymer Procedure:
SJP 4 with concentration listed below was used to make the depot
300 mg/ml (30% w/v)
400 mg/ml (40% w/v)
500 mg/ml (50% w/v)
All depots were crosslinked for 8 minutes and washed with acetone (24 hr) water (24 hr) Lyophilized (24 hr)
Depot with dimension of 0.5 cm by 0.12 cm were pre-weighted and placed in to 100 uL of 200 mg/ml Albumin solution (5% FITC-albumin) for 4 hrs and 24 hrs. Their swollen weight was recorded.
The swollen depots were lyophilized overnight and the dried weight was recorded to determined the albumin loading.

Example 8: Preparation of Drug X Solution and Loading in a Disc Shaped Depot Procedure:
A solution of Drug X (25 mg) dissolved in a mixture of DMSO/THF (50/50) or DMSO (0.5 mL)
Swelling and equilibration approach with the prepared solution for Drug X loading
Measurement of Drug X loading capacity and release study to be conducted

Example 9: Protocol for Degradation

Procedure:
Prepare a PBS solution (1 mL) containing *pseudomonas* (PS) lipase (0.5 mg/mL, pH 7.5).
Place depots (20-25 mg) in a vial containing 1 mL of the prepared solution at 37° C.
Change enzyme solution everyday or add sodium azide (as antibacterial agent) to avoid proliferation of bacteria.
Samples are withdrawn from the degradation medium, washed thoroughly with distilled water and then freeze-dried.
Measure weight loss of depot.
Sample for degradation study:
SJP7×hexanedithiol
SJP7×cleavable linker
SJP7/SJP3 (2.5%)×hexanedithiol
SJP7/SJP3 (2.5%)×cleavable linker

Example 10: Protocol for Degradation

Procedure:
Prepare a PBS solution (1 mL) containing *pseudomonas* (PS) lipase (0.5 mg/mL, pH 7.5)
Place depots (20-23 mg) in a vial containing 1 mL of the prepared solution at 37° C.
Change enzyme solution everyday to avoid proliferation of bacteria.
Samples are withdrawn from the degradation medium, washed thoroughly with distilled water and then freeze-dried.
Measure weight loss of depot.
Sample for degradation study
 SJP7×hexanedithiol
 SJP7×cleavable linker
 SJP7/SJP3 (2.5%)×hexanedithiol
 SJP7/SJP3 (2.5%)×cleavable linker
It has been a month, and 0.2 mg (~1%) decrease for all the samples.
However, cross-linker and a small amount of PEGylated copolymer does not have a significant effect on degradation so far.

Example 11: Protocol for Degradation

Procedure:
Prepare a PBS solution (1 mL) containing *pseudomonas* (PS) lipase (0.5 mg/mL, pH 7.5)
Place depots (20-23 mg) in a vial containing 1 mL of the prepared solution at 37° C.
Change enzyme solution everyday to avoid proliferation of bacteria.
Samples are withdrawn from the degradation medium, washed thoroughly with distilled water for 1 day and then freeze-dried.
Measure weight loss of depot with a analytical balance.
Sample for degradation study
 SJP7×HDT
 SJP7×ECL
 SJP7/SJP3 (2.5%)×HDT
 SJP7/SJP3 (2.5%)×ECL

Example 12: Protocol for Degradation

Procedure:
Prepare a PBS solution (1 mL) containing *pseudomonas* (PS) lipase (1 mg/mL, pH 7.5)
Place depots (20-23 mg) in a vial containing 1 mL of the prepared solution at 37° C.
Change enzyme solution everyday to avoid proliferation of bacteria.
Samples are withdrawn from the degradation medium, washed thoroughly with distilled water for 1 day and then freeze-dried.
Measure weight loss of depot with an analytical balance.

REFERENCES

1. Athanasiou, K. A.; Niederauer, G. G.; Agrawal, C. M. Sterilization, toxicity, biocompatibility and clinical applications of polylactic acid/polyglycolic acid copolymers. *Biomaterials* 1996, 17, 2, 93-102.
2. Wang, J.; Jiang, A.; Joshi, M.; Christoforidis, J. Drug Delivery Implants in the Treatment of Vitreous Inflammation. *Mediators of Inflammation* 2013, 2013, 8.
3. Kohane, D. S. Microparticles and nanoparticles for drug delivery. *Biotechnology and Bioengineering* 2007, 96, 2, 203-209.
4. Pinto, F. C. H.; Da Silva-Cunha Junior, A.; Oréfice, R. L.; Ayres, E.; Andrade, S. P.; Lima, L. D. C.; Lima Moura, S. A.; Da Silva, G. R. Controlled release of triamcinolone acetonide from polyurethane implantable devices: application for inhibition of inflammatory-angiogenesis. *Journal of Materials Science: Materials in Medicine* 2012, 23, (6), 1431-1445.
5. Silva, G. R. d.; Fialho, S. L.; Siqueira, R. C.; Jorge, R.; Cunha Júnior, A. d. S. Implants as drug delivery devices for the treatment of eye diseases. *Brazilian Journal of Pharmaceutical Sciences* 2010, 46, 585-595.
6. Folkman, J.; Long, D. M. The use of silicone rubber as a carrier for prolonged drug therapy. *Journal of Surgical Research* 1964, 4, 3, 139-142.

7. Kleiner, L. W.; Wright, J. C.; Wang, Y. Evolution of implantable and insertable drug delivery systems. *Journal of Controlled Release* 2014, 181, 1-10.

8. Kulkarni., R. K.; Pani, K. C.; Neuman, C. C.; Leonard, F. F. Polylactic acid for surgical implants. *Archives of Surgery* 1966, 93, (5), 839-843.

9. Sun, H.; Mei, L.; Song, C.; Cui, X.; Wang., P. The in vivo degradation, absorption and excretion of PCL-based implant. *Biomaterials* 2006, 27, (9), 1735-1740.

10. Faisant, N.; Siepmann, J.; Benoit, J. P. PLGA-based microparticles: elucidation of mechanisms and a new, simple mathematical model quantifying drug release. *European Journal of Pharmaceutical Sciences* 2002, 15, (4), 355-366.

11. Jain, R. A. The manufacturing techniques of various drug loaded biodegradable poly(lactide-co-glycolide) (PLGA) devices. *Biomaterials* 2000, 21, (23), 2475-2490.

12. Ramchandani, M.; Robinson, D. In vitro and in vivo release of ciprofloxacin from PLGA 50:50 implants. *Journal of Controlled Release* 1998, 54, 2, 167-175.

13. Yerragunta, B.; Jogala, S.; Chinnala, K.; Aukunuru, J. Development of a novel 3-month drug releasing risperidone microspheres. *Journal of Pharmacy And Bioallied Sciences* 2015, 7, 1, 37-44.

14. Citrin, D. L.; Resnick, M. I.; Guinan, P.; Al-Bussam, N.; Scott, M.; Gau, T. C.; Kennealey, G. T. A comparison of Zoladex® and DES in the treatment of advanced prostate cancer: Results of a randomized, multicenter trial. *The Prostate* 1991, 18, 2, 139-146.

15. Peeling, W. B. Phase III studies to compare goserelin (zoladex) with orchiectomy and with diethylstilbestrol in treatment of prostatic carcinoma. *Urology* 1989, 33, (5, Supplement), 45-52.

16. https://http://www.zoladex.com/ Zoladex 10.8 and 3.6 mg implants.

17. Attenello, F. J.; Mukherjee, D.; Datoo, G.; McGirt, M. J.; Bohan, E.; Weingart, J. D.; Olivi, A.; Quinones-Hinojosa, A.; Brem, L I. Use of Gliadel (BCNU) Wafer in the Surgical Treatment of Malignant Glioma: A 10-Year Institutional Experience. *Annals of Surgical Oncology* 2008, 15, (10), 2887.

18. Dordunoo, S. K.; Oktaba, A. M. C.; Hunter, W.; Min, W.; Cruz, T.; Burt, H. M. Release of taxol from poly(ε-caprolactone) pastes: effect of water-soluble additives. *Journal of Controlled Release* 1997, 44, 1, 87-94.

19. Coombes, A. G. A.; Rizzi, S. C.; Williamson, M.; Barralet, J. E.; Downes, S.; Wallace, W. A. Precipitation casting of polycaprolactone for applications in tissue engineering and drug delivery. *Biomaterials* 2004, 25, 2, 315-325.

20. Fialho, S. L.; Behar-Cohen, F.; Silva-Cunha, A. Dexarnethasone-loaded poly(ε-caprolactone) intravitreal implants: A pilot study. *European Journal of Pharmaceutics and Biopharmaceutics* 2008, 68, 3, 637-646.

21. Khor, H. L; Ng, K. W.; Schantz, J. T.; Phan, T.-T.; Lim, T. C.; Teoh., S. H.; Hutmacher., D. W. Poly(ε-caprolactone) films as a potential substrate for tissue engineering an epidermal equivalent. *Materials Science and Engineering: C* 2002, 20, (1-2), 71-75.

22. Cheng, L.; Guo, S.; Wu, W. Characterization and in vitro release of praziquantel from poly(ε-caprolactone) implants. *International Journal of Pharmaceutics* 2009, 377, (1-2), 112-119.

23. Woodruff, M. A.; Hutmacher, D. W. The return of a forgotten polymer-Polycaprolactone in the 21st century. *Progress in Polymer Science* 2010, 35, (10), 1217-1256.

24. C. G. Pitt, A. S., *Capronor—a biodegradable delivery system for levonorgestrel*. Philadelphia, 1984; Vol. Long-acting contraceptive delivery systems, Harper and Row.

25. Ma, G.; Song, C.; Sun, H.; Yang, J.; Leng, X. A biodegradable levonorgestrel-releasing implant made of PCL/F68 compound as tested in rats and dogs. *Contraception* 2006, 74, 2, 141-147.

26. Löfgren, A.; Albertsson, A.-C.; Dubois, P.; Jérôme, R. Recent Advances in Ring-Opening Polymerization of Lactones and Related Compounds. *Journal of Macromolecular Science, Part C* 1995, 35, 3, 379-418.

27. Silvers, A. L.; Chang, C.-C.; Emrick, T. Functional aliphatic polyesters and nanoparticles prepared by organocatalysis and orthogonal grafting chemistry. *Journal of Polymer Science Part A: Polymer Chemistry* 2012, 50, (17), 3517-3529.

28. Parrish, B.; Quansah, J. K.; Emrick, T. Functional polyesters prepared by polymerization of α-allyl(valerolactone) and its copolymerization with ε-caprolactone and δ-valerolactone. *Journal of Polymer Science Part A: Polymer Chemistry* 2002, 40, (12), 1983-1990.

29. Huang, Y.; Pan, Y.; Fu, J.; Huang, X.; Tang, X. Study of crosslinking of polyphosphazene with allyl pendant groups initiated by benzoyl peroxide. *Journal of Applied Polymer Science* 2009, 113, (4), 2353-2360.

30. Mecerreyes, D.; Miller, R. D.; Hedrick, J. L.; Detrembleur, C.; Jérôme, R. Ring-opening polymerization of 6-hydroxynon-8-enoic acid lactone: Novel biodegradable copolymers containing allyl pendent groups. *Journal of Polymer Science Part A: Polymer Chemistry* 2000, 38, (5), 870-875.

31. Darcos, V.; Antoniacomi, S.; Paniagua, C.; Coudane, J. Cationic polyesters hearing pendent amino groups prepared by thiol-ene chemistry. *Polymer Chemistry* 2012, 3, 2, 362-368.

32. Lou, X.; Detrembleur, C.; Jérôme, R. Living Cationic Polymerization of 6-Valerolactone and Synthesis of High Molecular Weight Homopolymer and Asymmetric Telechelic and Block Copolymer. *Macromolecules* 2002, 35, (4), 1190-1195.

33. Lee, H.; Zeng, F.; Dunne, M.; Allen, C. Methoxy Poly(ethylene glycol)-block-Poly(δ-valerolactone) Copolymer Micelles for Formulation of Hydrophobic Drugs. *Biomacromolecules* 2005, 6, (6), 3119-3128.

34. Zeng, F.; Lee, H.; Chidiac, M.; Allen, C. Synthesis and Characterization of Six-Arm Star Poly(δ-valerolactone)-block-Methoxy Poly(ethylene glycol) Copolymers. *Biomacromolecules* 2005, 6, (4), 2140-2149.

35. Zeng, F.; Lee, H.; Allen, C. Epidermal Growth Factor-Conjugated Poly(ethylene glycol)-block-Poly(δ-valerolactone) Copolymer Micelles for Targeted Delivery of Chemotherapeutics. *Bioconjugate Chemistry* 2006, 17, 2, 399-409.

36. Hancock, B. C.; York, P.; Rowe, R. C. The use of solubility parameters in pharmaceutical dosage form design. *International journal of Pharmaceutics* 1997, 148, 1, 1-21.

37. Van Krevelen., D. W.; Te Nijenhuis, K., Chapter 7—Cohesive Properties and Solubility. In *Properties of Polymers (Fourth Edition)*, Elsevier: Amsterdam, 2009; pp 189-227.

38. Baek, H. S.; Yoo, J. Y.; Rah, D. K.; Han, D.-W.; Lee, D. H.; Kwon, O.-H.; Park, J.-C. Evaluation of the Extraction Method for the Cytotoxicity Testing of Latex Gloves. *Yonsei Medical Journal* 2005, 46, (4), 579-583.

39. Aubin, M.; Prud'homme, R. E. Preparation and properties of poly(valerolactone). *Polymer* 1981, 22, (9), 1223-1226.
40. Keroack, D.; Zhao, Y.; Prud'homme, R. E. Molecular orientation in crystalline miscible blends. *Polymer* 1999, 40, 1, 243-251.
41. Jenkins, M. J.; Harrison, K. L. The effect of molecular weight on the crystallization kinetics of polycaprolactone. *Polymers for Advanced Technologies* 2006, 17, (6), 474-478.
42. Elzein, T.; Nasser-Eddine, M.; Delaite., C.; Bistac, S.; Dumas, P. FTIR study of polycaprolactone chain organization at interfaces. *Journal of Colloid and Interface Science* 2004, 273, 2, 381-387.
43. Kazumichi, I.; Masaru, Y.; Hironobu, F.; Masaharu, A.; Minoru, K.; Tohoru, M.; Hidetoshi, Y.; Tsuneji, N. A new biodegradable implant consisting of waxy-type poly($\varepsilon$-caprolactone-co-$\delta$-valerolactone) and estramustine. *International Journal of Pharmaceutics* 1991, 68, 1, 87-95.
44. Murphy, S. H.; Leeke, G. A.; Jenkins, M. J. A Comparison of the use of FTIR spectroscopy with DSC in the characterisation of melting and crystallisation in polycaprolactone. *Journal of Thermal Analysis and Calorimetry* 2012, 107, 2, 669-674.
45. Zange, R.; Kissel, T. Comparative in vitro biocompatibility testing of polycyanoacrylates and -poly(d,l-lactide-co-glycolide) using different mouse fibroblast (L929) biocompatibility test models. *European Journal of Pharmaceutics and Biopharmaceutics* 1997, 44, 2, 149-157.
46. Boire, T. C.; Gupta, M. K.; Zachman, A. L.; Lee, S. H.; Balikov, D. A.; Kim, K.; Bellan, L. M.; Sung, H.-J. Pendant allyl crosslinking as a tunable shape memory actuator for vascular applications. *Acta Biomaterialia* 2015, 24, 53-63.
47. Yeo, M.; Jung, W.-K.; Kim, G. Fabrication, characterisation and biological activity of phlorotannin-conjugated PCL/[small beta]-TCP composite scaffolds for bone tissue regeneration. *Journal of Materials Chemistry* 2012, 22, (8), 3568-3577.
48. Lyu, S.; Untereker, D. Degradability of Polymers for Implantable Biomedical Devices. *International Journal of Molecular Sciences* 2009, 10, (9), 4033-4065.
49. Sung, H.-J.; Meredith, C.; Johnson, C.; Galis, Z. S. The effect of scaffold degradation rate on three-dimensional cell growth and angiogenesis. *Biomaterials* 2004, 25, (26), 5735-5742.
50. Toncheva, V.; Van Den Bulcke, A.; Schacht, E.; Mergaert., J.; Swings, J. Synthesis and environmental degradation of polyesters based on poly ($\varepsilon$-caprolactone). *Journal of environmental polymer degradation* 1996, 4, 2, 71-83.
51. Liu, J.; Xiao, Y.; Allen, C. Polymer-drug compatibility: A guide to the development of delivery systems for the anticancer agent, ellipticine. *Journal of Pharmaceutical Sciences* 2004, 93, 1, 132-143.
52. Jouyban., A., *Handbook of Solubility Data for Pharmaceuticals*. CRC Press: 2009.
53. OECD. Guidelines for Testing of Chemicals. Section 1, Physical Chemical properties. 1995, 107.
54. Mikkelsen, L. M., Enzyme solubility in liquid detergent and use of detergent composition. Google Patents: 2014.
55. Samaha, M. W.; Naggar, V. F. Micellar properties of non-ionic surfactants in relation to their solubility parameters. *International Journal of Pharmaceutics* 1988, 42, 1, 1-9.
56. Crotts, G.; Park, T. G. Protein delivery from poly(lactic-co-glycolic acid) biodegradable microspheres: Release kinetics and stability issues. *Journal of Microencapsulation* 1998, 15, (6), 699-713.
57. FDA. Guidance for Industry: Dissolution Testing of Immediate Release Solid Oral Dosage Forms, Office of Training and Communications, Rockville, Md., 1997, pp. A1- A2. 1997.
58. M. Vasanthavada; W.-Q. Tong; Serajuddin, A., *Water-Insoluble Drug Formulation, Second Edition*. CRC press: 2008.
59. Egawa, H.; Maeda, S.; Yonemochi, E.; Oguchi, T.; Yamamoto, K.; Nakai, Y. Solubility Parameter and Dissolution Behavior of Cefalexin Powders with Different Crystallinity. *CHEMICAL & PHARMACEUTICAL BULLETIN* 1992, 40, 3, 819-820.
60. da Silva-Junior, A. A.; de Matos, J. R.; Formariz, T. P.; Rossanezi, G.; Scarpa, M. V.; do Egito, E. S. T.; de Oliveira, A. G. Thermal behavior arid stability of biodegradable spray-dried microparticles containing triamcinolone. *International journal of Pharmaceutics* 2009, 368, 1, 45-55.
61. Marsac, P. J.; Shamblin, S. L.; Taylor, L. S. Theoretical and Practical Approaches for Prediction of Drug-Polymer Miscibility and Solubility. *Pharmaceutical Research* 2006, 23, (10), 2417.
62. Greenhalgh, D. J.; Williams, A. C.; Timmins, P.; York, P. Solubility parameters as predictors of miscibility in solid dispersions. *Journal of Pharmaceutical Sciences* 1999, 88, (11), 1182-1190.
63. D'Souza, S. S.; DeLuca, P. P. Methods to Assess in vitro Drug Release from Injectable Polymeric Particulate Systems. *Pharmaceutical Research* 2006, 23, 3, 460-474.
64. Siepmann, J.; Siepmann, F. Mathematical modeling of drug delivery. *International Journal of Pharmaceutics* 2008, 364, 2, 328-343.
65. Zhang, Y.; Huo, M.; Zhou, J.; Zou, A.; Li, W.; Yao, C.; Xie, S. DDSolver: An Add-In Program for Modeling and Comparison of Drug Dissolution Profiles. *The AAPS Journal* 2010, 12, 3, 263-271.
66. Peppas, N. A.; Sahlin, J. J. A simple equation for the description of solute release. III. Coupling of diffusion and relaxation. *International Journal of Pharmaceutics* 1989, 57, 2, 169-172.
67. Higuchi, T. Rate of Release of Medicaments from Ointment Bases Containing Drugs in Suspension. *Journal of Pharmaceutical Sciences* 1961, 50, (10), 874-875.
68. Korsmeyer, R. W.; Gurny, R.; Doelker, E.; Burl, P.; Peppas, N. A. Mechanisms of solute release from porous hydrophilic polymers. *International Journal of Pharmaceutics* 1983, 15, 1, 25-35.
69. Ritger, P. L.; Peppas, N. A. A simple equation for description of solute release 1. Fickian and non-fickian release from non-swellable devices in the form of slabs, spheres, cylinders or discs. *Journal of Controlled Release* 1987, 5, 1, 23-36.
70. Vergnaud, J. M., Controlled drug release of oral dosage forms. E. Horwood: New York:, 1993.
71. Guse, C.; Koennings, S.; Kreye, F.; Siepmann, F.; Goepferich, A.; Siepmann, J. Drug release from lipid-based implants: Elucidation of the underlying mass transport mechanisms. *International Journal of Pharmaceutics* 2006, 314, 2, 137-144.
72. Nair, R.; Nyamweya, N.; Gönen, S.; Martinez-Miranda, L. J.; Hoag, S. W. Influence of various drugs on the glass transition temperature of poly(vinylpyrrolidone): a thermodynamic and spectroscopic investigation. *International Journal of Pharmaceutics* 2001, 225, 1, 83-96.
73. Klose, D.; Siepmann, F.; Elkharraz, K.; Krenzlin, S.; Siepmann, J. How porosity and size affect the drug release mechanisms from PLGA-based microparticles. *International Journal of Pharmaceutics* 2006, 314, 2, 198-206.
74. Miyajima., M.; Koshika, A.; Okada, J. i.; Ikeda, M.; Nishimura, K. Effect of polymer crystallinity on papaverine release from poly (l-lactic acid) matrix. *Journal of Controlled Release* 1997, 49, (2-3), 207-215.
75. Jeong, J.-C.; Lee, J.; Cho, K. Effects of crystalline microstructure on drug release behavior of poly(ε-caprolactone) microspheres. *Journal of Controlled Release* 2003, 92, 3, 249-258.
76. Fetters, L. J.; Lohse, D. J.; Richter, D.; Witten, T. A.; Zirkel, A. Connection between Polymer Molecular Weight, Density, Chain Dimensions, and Melt Viscoelastic Properties. *Macromolecules* 1994, 27, (17), 4639-4647.
77. Nsereko, S.; Amiji, N I. Localized delivery of paclitaxel in solid tumors from biodegradable chitin microparticle formulations. *Biomaterials* 2002, 23, (13), 2723-2731.
78. Suh, H.; Jeong, B.; Rathi, R.; Kim, S. W. Regulation of smooth muscle cell proliferation using paclitaxel-loaded poly(ethylene oxide)-poly(lactide/glycolide) nanospheres. *Journal of Biomedical Materials Research* 1998, 42, 2, 331-338.
79. Doty, A. C.; Hirota, K.; Olsen, K. F.; Sakamoto, N.; Ackermann, R.; Feng, M. R.; Wang, Y.; Choi, S.; Qu, W.; Schwendeman, A.; Schwendeman, S. P. Validation of a cage implant system for assessing in vivo performance of long-acting release microspheres. *Biomaterials* 2016, 109, 88-96.
80. Yang, H.-y.; van Dijk, M.; Licht, R.; Beekhuizen, M.; van Rijen, M.; Janstil, M. K.; Oner, F. C.; Dhert, W. J. A.; Schumann, D.; Creemers, L. B. Applicability of a Newly Developed Bioassay for Determining Bioactivity of Anti-Inflammatory Compounds in Release Studies—Celecoxib and Triamcinolone Acetonide Released from Novel PLGA-Based Microspheres. *Pharmaceutical Research* 2015, 32, 2, 680-690.
81. Toshiro, H.; Hiroaki, O.; Yasuaki, O.; Hajime, T. Factors influencing the profiles of TRH release from copoly(d,l-lactic/glycolic acid) microspheres. *International Journal of Pharmaceutics* 1991, 72, 3, 199-205.
82. Omelczuk, M. O.; McGinity, J. W. The influence of Polymer Glass Transition Temperature and Molecular Weight on Drug Release from Tablets Containing Poly (PL-lactic Acid). *Pharmaceutical Research* 1992, 9, 1, 26-32.
83. Nishi, C.; Nakajima, N.; Ikada, Y., In vitro evaluation of diepoxy compounds used for biomaterial modification. Journal of Biomedical Materials Research 1995, 29, 829-834.
84. Serrano, M. C.; Pagani, R.; Vallet-Regi, M.; Pena, J.; Ramila, A.; Izquierdo, I.; Portoles, M. T., In vitro biocompatibility assessment of poly(epsilon-caprolactone) films using L929 mouse fibroblasts. Biomaterials 2004, 25 (25), 5603-11.
85. Du Z, Zhang Y, Xu H, Lang M. Functionalized Pluronic-b-poly(ε-caprolactone) based nanocarriers of paclitaxel solubilization, antiproliferative efficacy and in vivo pharmaceutic kinetics. Journal of Materials Chemistry B 2015; 3:3685-94.
86. Barra J, Lescure F, Doetker E, Bustarnante P. The Expanded Hansen Approach to Solubility Parameters. Paracetamol and Citric Acid in Individual Solvents. Journal of Pharmacy and Pharmacology 1997; 49:644-51.
87. Jones M D, Buckton G. Comparison of the cohesion-adhesion balance approach to colloidal probe atomic force microscopy and the measurement of Hansen partial solubility parameters by inverse gas chromatography for the prediction of dry powder inhalation performance. International Journal of Pharmaceutics 2016; 509:419-30.
88. F. Salaün IV. Curcumin loaded nanocapsules: formulation and Influence of the nanoencapsulation processes variables on the physico-chemical characteristics of the particles. Int J Chem Reactor Eng 2009; 7:A55.
89. Varshochian, R., et al. (2013). "The protective effect of albumin on bevacizumab activity and stability in PLGA nanoparticles intended for retinal and choroidal neovascularization treatments." *European Journal of Pharmaceutical Sciences* 503: 341-352.
90. Varshochian, R., et al. (2015). "Albuminated PLGA nanoparticles containing bevacizumab intended for ocular neovascularization treatment." *Journal of Biomedical Materials Research Part A* 103(10): 3148-3156.
91. Yandrapu, S. K., et al. (2013). "Nanoparticles in Porous Microparticles Prepared by Supercritical Infusion and Pressure Quench Technology for Sustained Delivery of Bevacizumab." *Molecular Pharmaceutics* 10(12): 4676-4686.
92. Fialho, S. L., et al. (2007). "Biodegradable implants for ocular delivery of anti-inflammatory drug." *Journal of Drug Delivery Science and Technology* 171: 93-97.

The invention claimed is:
1. A compound or a pharmaceutically acceptable salt thereof, comprising:
a poly(allylvalerolactone)-co-polyethylene glycol (PEG) copolymer;
wherein at least a portion of allylvalerolactone residues within the copolymer are crosslinked with a crosslinker;
wherein the copolymer has a number average molecular weight of less than 10 kDa; and
wherein the copolymer has a polydispersity index of less than or equal to 1.5.
2. The compound of claim 1, wherein the copolymer comprises poly(allylvalerolactone)-b-3K-polyethylene glycol-b-poly(allylvalerolactone).
3. The compound of claim 2, wherein the copolymer has a number average molecular weight of 6.2 kDa.
4. The compound of claim 1, wherein the copolymer comprises poly(valerolactone) residues.
5. The compound of claim 4, wherein the copolymer comprises poly(allylvalerolactone)-co-poly(valerolactone)-3K-polyethylene glycol-poly(allylvalerolactone)-co-poly(valerolactone).
6. The compound of claim 5, wherein the copolymer has a number average molecular weight of 8.5 kDa.
7. The compound of claim 1, wherein the crosslinker comprises a dithiol moiety.
8. The compound of claim 7, wherein the crosslinker is 1,6-hexanedithiol.
9. The compound of claim 1, wherein the compound is loaded with a drug.
10. The compound of claim 9, wherein the drug includes at least one of paclitaxel, triamcinolone acetonide, triamcinolone hexacetonide, acetaminophen, and curcumin.

* * * * *